United States Patent
Xiao et al.

(10) Patent No.: US 11,161,913 B2
(45) Date of Patent: Nov. 2, 2021

(54) CHIMERIC ANTIGEN RECEPTOR CELLS FOR TREATING SOLID TUMOR

(71) Applicants: Innovative Cellular Therapeutics Holdings, Ltd., Grand Cayman (KY); Innovative Cellular Therapeutics, Inc., Rockville, MD (US)

(72) Inventors: Lei Xiao, Rockville, MD (US); He Sun, Shanghai (CN); Zhiyuan Cao, Shanghai (CN); Wensheng Wang, Shanghai (CN); Chengfei Pu, Shanghai (CN); Li Mao, Shanghai (CN)

(73) Assignees: Innovative Cellular Therapeutics Holdings, Ltd., Grand Cayman (KY); Innovative Cellular Therapeutics, Inc., Rockville, MD (US)

( * ) Notice: Subject to any disclaimer, the term of this patent is extended or adjusted under 35 U.S.C. 154(b) by 0 days.

(21) Appl. No.: 17/220,387

(22) Filed: Apr. 1, 2021

(65) Prior Publication Data

US 2021/0230308 A1 Jul. 29, 2021

Related U.S. Application Data

(63) Continuation of application No. 17/270,571, filed as application No. PCT/US2019/048890 on Aug. 29, 2019.

(60) Provisional application No. 62/848,984, filed on May 16, 2019, provisional application No. 62/842,936, filed on May 3, 2019, provisional application No. 62/807,482, filed on Feb. 19, 2019, provisional application No. 62/754,175, filed on Nov. 1, 2018, provisional application No. 62/731,079, filed on Sep. 13, 2018, provisional application No. 62/725,025, filed on Aug. 30, 2018.

(51) Int. Cl.
| C07K 16/00 | (2006.01) |
| C07K 16/40 | (2006.01) |
| A61K 47/68 | (2017.01) |

(52) U.S. Cl.
CPC .......... C07K 16/40 (2013.01); A61K 47/6801 (2017.08); C07K 2317/622 (2013.01)

(58) Field of Classification Search
None
See application file for complete search history.

(56) References Cited

U.S. PATENT DOCUMENTS

| 9,388,237 B2 | 7/2016 | Govindan |
| 9,572,837 B2 | 2/2017 | Wu |
| 9,932,405 B2 | 4/2018 | Xiao et al. |
| 10,561,686 B2 | 2/2020 | Xiao et al. |
| 2002/0052027 A1 | 5/2002 | Chen et al. |
| 2002/0192183 A1 | 12/2002 | Jensen |
| 2005/0079170 A1 | 4/2005 | Le Gall et al. |
| 2013/0287748 A1 | 10/2013 | June et al. |
| 2014/0050708 A1 | 2/2014 | Powell et al. |
| 2014/0227237 A1 | 8/2014 | June et al. |
| 2014/0271635 A1 | 9/2014 | Brogdon et al. |
| 2015/0037356 A1 | 2/2015 | Elvin et al. |
| 2015/0038684 A1 | 2/2015 | Jensen |
| 2016/0024175 A1 | 1/2016 | Chow et al. |
| 2016/0250258 A1 | 9/2016 | Delaney et al. |
| 2016/0256488 A1 | 9/2016 | Wu |
| 2016/0362472 A1 | 12/2016 | Bitter et al. |
| 2017/0015746 A1 | 1/2017 | Jensen |
| 2017/0096638 A1 | 4/2017 | Wu |
| 2017/0136063 A1 | 5/2017 | Perez et al. |
| 2017/0137783 A1 | 5/2017 | Bedoya et al. |
| 2017/0145094 A1 | 5/2017 | Galetto |
| 2017/0145108 A1 | 5/2017 | Schreiber et al. |
| 2017/0209492 A1 | 7/2017 | June et al. |
| 2017/0218337 A1 | 8/2017 | Friedman |
| 2017/0224798 A1 | 8/2017 | Cooper et al. |
| 2017/0319638 A1 | 11/2017 | Conner et al. |
| 2017/0335281 A1 | 11/2017 | Loew et al. |
| 2017/0362325 A1 | 12/2017 | Jung et al. |
| 2017/0368098 A1 | 12/2017 | Chen et al. |
| 2018/0028631 A1 | 2/2018 | Chen |
| 2018/0153977 A1 | 6/2018 | Wu et al. |
| 2018/0179289 A1 | 6/2018 | Xiao et al. |
| 2018/0222995 A1 | 8/2018 | Xiao et al. |
| 2018/0223255 A1 | 8/2018 | Wu et al. |
| 2018/0243340 A1 | 8/2018 | Varadarajan et al. |
| 2018/0346876 A1 | 12/2018 | Xiao et al. |
| 2019/0000878 A1 | 1/2019 | Xiao et al. |
| 2019/0185817 A1 | 6/2019 | Melton et al. |
| 2019/0216851 A1 | 7/2019 | Xiao et al. |
| 2019/0314411 A1 | 10/2019 | Xiao et al. |
| 2020/0155598 A1 | 5/2020 | Xiao et al. |

(Continued)

FOREIGN PATENT DOCUMENTS

| WO | WO2008131445 | 10/2008 |
| WO | WO2012050374 | 4/2012 |

(Continued)

OTHER PUBLICATIONS

Rizzardi et al. (BMC Cancer, 2014, 14:244) (Year: 2014).*
"Anti-ACPP Product Datasheet", Atlas Antibodies, retrieved on Oct. 31, 2019 from https://www.atlasantibodies.com/api/print_datasheet/HPA004335.pdf, Dec. 2012 1 page.
"Anti-UPK2 Product Datasheet", Atlas Antibodies, retrieved on Oct. 31, 2019 from https://www.atlasantibodies.com/api/print_datasheet/HPA061106.pdf, Dec. 2012, 1 page.
Invitation to Pay Additional Fees mailed on Nov. 13, 2019 for PCT Application PCT/US19/48890, 3 Pages.
International Preliminary Report on Patentability dated Mar. 11, 2021 for PCT Application No. PCT/US19/48890, 8 pages.

(Continued)

*Primary Examiner* — Meera Natarajan
(74) *Attorney, Agent, or Firm* — Lee & Hayes, P.C.

(57) ABSTRACT

The compositions and methods described herein are directed to treating solid tumor using CAR T therapy. The compositions include CAR comprising an extracellular domain that binds a siglec protein or a receptor that binds the peptide hormone kisspeptin.

13 Claims, 26 Drawing Sheets

Specification includes a Sequence Listing.

(56) References Cited

U.S. PATENT DOCUMENTS

| | | |
|---|---|---|
| 2021/0060069 A1 | 3/2021 | Xiao et al. |
| 2021/0077532 A1 | 3/2021 | Xiao et al. |
| 2021/0100841 A1 | 4/2021 | Xiao et al. |
| 2021/0137983 A1 | 5/2021 | Xiao et al. |
| 2021/0161961 A1 | 6/2021 | Xiao et al. |
| 2021/0252059 A1 | 8/2021 | Pu et al. |

FOREIGN PATENT DOCUMENTS

| | | |
|---|---|---|
| WO | WO2012079000 A1 | 6/2012 |
| WO | WO2014011984 | 1/2014 |
| WO | WO2015157384 A1 | 10/2015 |
| WO | WO2015157432 A1 | 10/2015 |
| WO | WO2016-070136 | 5/2016 |
| WO | WO2016090034 A2 | 6/2016 |
| WO | WO2016090190 A1 | 6/2016 |
| WO | WO2016113203 | 7/2016 |
| WO | WO2016210293 | 12/2016 |
| WO | WO2017011804 A1 | 1/2017 |
| WO | WO2017027291 A1 | 2/2017 |
| WO | WO2017050884 | 3/2017 |
| WO | WO2017040324 | 9/2017 |
| WO | WO2017149515 | 9/2017 |
| WO | WO2017167217 A1 | 10/2017 |
| WO | WO2017172981 | 10/2017 |
| WO | WO2017173403 | 10/2017 |
| WO | WO2017177137 | 10/2017 |
| WO | WO2018013918 | 1/2018 |
| WO | WO2018018958 | 2/2018 |
| WO | WO2018023976 A1 | 2/2018 |
| WO | WO2018049418 | 3/2018 |
| WO | WO2018067697 | 4/2018 |
| WO | WO2018106732 A1 | 6/2018 |
| WO | WO2018111763 A1 | 6/2018 |
| WO | WO2019091478 | 5/2019 |
| WO | WO2019140100 A1 | 7/2019 |
| WO | WO2019178576 A1 | 9/2019 |

OTHER PUBLICATIONS

PCT Search Report and Written Opinion dated Feb. 7, 2020 for PCT Application No. PCT/US19/48890, 15 pages.

Chen, et al., "CAR T-cell intrinsic PD-1 checkpoint blockade: a two-in-one approach for solid tumor immunotherapy," Feb. 2017, Oncolmmunology, 6:2, e1273302, DOI: 10.1080/2162402X.2016. 1273302. 4 pages.

Extended European Search Report dated Nov. 25, 2019 in EP Application No. 19180127.3, Xiao et al., a corresponding foreign application of U.S. Appl. No. 16/146,218, 11 pages.

Fang et al., "Stable antibody expression at therapeutic levels using the 2A peptide," May 2005, Nature Biotechnology. 23(5):584-590.

PCT Communication Invitation to Pay Fees dated Mar. 30, 2020 for PCT Application No. PCT/US20/13099, "Modified Cell Expansion and Uses Thereof", 2 pages.

Jernberg-Wiklund, et al., "Recombinant interferon-gamma inhibits the growth of IL-6-dependent human multiple myeloma cell lines in vitro," 1991. Eur J Haematol, 46:231-239.

Lee et al., "T cells expressing CD19 chimeric antigen receptors for acute lymphoblastic leukemia in children and young adults: a phase 1 dose-escalation trial," Oct. 2014. The Lancet, 385(9967): 517-528.

Maude et al., "Chimeric antigen receptor T cells for sustained remissions in leukemia," Oct. 2014. N Engl J Med. 371(16): 1507-1517.

Milone, et al., "Chimeric receptors containing CD137 signal transduction domains mediate enhanced survival of T cells and increased antileukemic efficacy in vivo," Apr. 2009. Molecular Therapy, 17(8): 1453-1464.

Partial European Search Report dated Nov. 4, 2019 in EP Application No. 19180127.3, Xiao et al., a corresponding foreign application of U.S. Appl. No. 16/146,218, 18 pages.

International Search Report and Written Opinion dated Jun. 17, 2019 for PCT Application No. PCT/US19/13068, 14 pages.

International Search Report and Written Opinion dated Feb. 20, 2020 for PCT Application No. PCT/US19/62417, 14 pages.

International Search Report and Written Opinion dated Jun. 4, 2020 for PCT Application No. PCT/US2020/013099, 13 pages.

Qin et al., "Incorporation of a hinge domain improves the expansion of chimeric antigen receptor T cells," 2017, Journal of Hematology & Oncology, 10:68, 11 pages.

Sahm et al, "Expression of IL-15 in NK Cells Results in Rapid Enrichment and Selective Cytotoxicity of Gene-Modified Effectors That Carry a Tumor-Specific Antigen Receptor," Sep. 2012, Cancer Immunol Immunother, 61(9): 1451-1461.

Supplemental European Search Report dated Jan. 13, 2020 in EP Application No. 19700326, Xiao et al., a corresponding foreign application of U.S. Appl. No. 16/146,218, 7 pages.

Takahashi, et al, "Expression of MUC1 on myeloma cells and induction of HJLA-unrestricted CTL against MUC1 from a multiple myeloma patient," 1994. J Immunol, 153:2102-2109.

Wilkie, et al. "Retargeting of human T cells to tumor-associated MUC1: The evolution of a chimeric antigen receptor," 2008, J. Immunol., 180:4901-4909.

Xiao et al., "Pre-clinical experiments of cart cells identifying tshr as a potential target against metastatic thyroid cancer," May 2018. Database EMBASE [Online] Elsevier Science Publishers, Database Accession No. EMB-623339571, 1 page.

You et al., "Phase 1 clinical trial demonstrated that MUC1 positive metastatic seminal vesicle cancer can be effectively eradicated y modified Anti-MUC1 chimeric antigen receptor transduced T cells", Apr. 2016, Science China: Life Sciences, 59(4): 386-397.

U.S. Appl. No. 16/146,218, filed Sep. 28, 2018, US-2019-0216851-A1, U.S. Pat. No. 10,561,686, Issued.

U.S. Appl. No. 16/961,418, filed Jul. 10, 2020, Pending.

U.S. Appl. No. 17/270,571, filed Feb. 23, 2021, Pending.

U.S. Appl. No. 17/220,387, filed Apr. 1, 2021, Pending.

U.S. Appl. No. 16/445,965, filed Jun. 19, 2019, US-2020-0155598-A1, U.S. Pat. No. 10,918,667, Issued.

U.S. Appl. No. 17/144,800, filed Jan. 8, 2021, Pending.

U.S. Appl. No. 16/387,166, filed Apr. 17, 2019, US 2019-0314411 A1, U.S. Pat. No. 10,869,888, Issued.

U.S. Appl. No. 17/091,741, filed Nov. 6, 2020, Pending.

U.S. Appl. No. 17/108,076, filed Dec. 1, 2020, US 2021-0077532 A1, Pending.

U.S. Appl. No. 17/123,732, filed Dec. 16, 2020, Pending.

U.S. Appl. No. 17/173,504, filed Feb. 11, 2021, Pending.

U.S. Appl. No. 16/996,237, filed Aug. 18, 2020, US 2021-0060069 A1, Pending.

U.S. Appl. No. 16/999,357, filed Aug. 21, 2020, Pending.

International Preliminary Report on Patentability dated Jul. 22, 2021 in PCT Application No. PCT/US2020/013099, 9 pages.

Brischwein et al. "Strictly Target Cell-dependent Activation of T cells by Bispecific Single-chain Antibody Constructs of the BiTE Class," Nov. 2007. J Immunother, 30(8): 798-807.

International Search Report & Written Opinion dated Aug. 13, 2021 in PCT Application No. PCT/2021/028429, 12 pages.

Wong et al. "Blinatumomab Induces Autologous T-cell Killing of Chronic Lymphocytic Leukemia Cells," Jun. 2013. Haematologica, vol. 98 (12): 1930-1938.

Chmielewski, "Of CARs and TRUCKs: Chimeric Antigen Receptor (CAR) T Cells Engineered with an Inducible Cytokine to Modulate the Tumor Stroma," Jan. 2014. Imunological Reviews, 257(1): 83-90.

European Search Report dated Aug. 31, 2021 in European Application No. 21275039.2, a foreign corresponding application of U.S. Appl. No. 16/999,357, 13 pages.

Huang et al., "Interleukin-Armed Chimeric Antigen Receptor-Modified T Cells for Cancer Immunotherapy," Sep. 2017. Gene Therapy, 25(3): 192-197.

Lee et al., "Use of a Single CAR T Cell and Several Bispecific Adapters Facilitates Eradication of Multiple Antigenically Different Solid Tumors," Nov. 2018. Cancer Research, 79(2): 387-396.

* cited by examiner

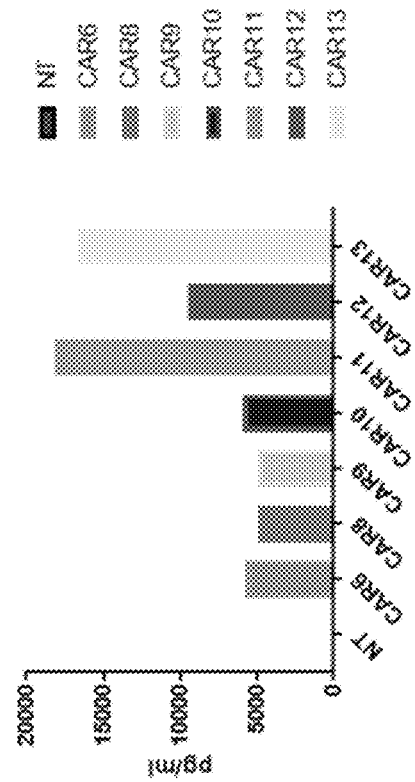
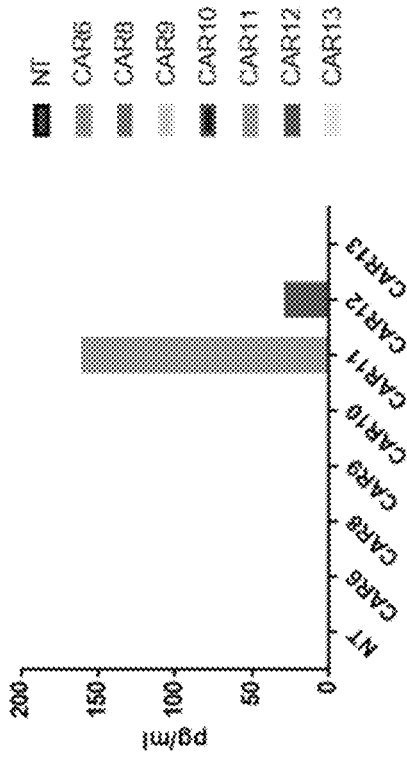
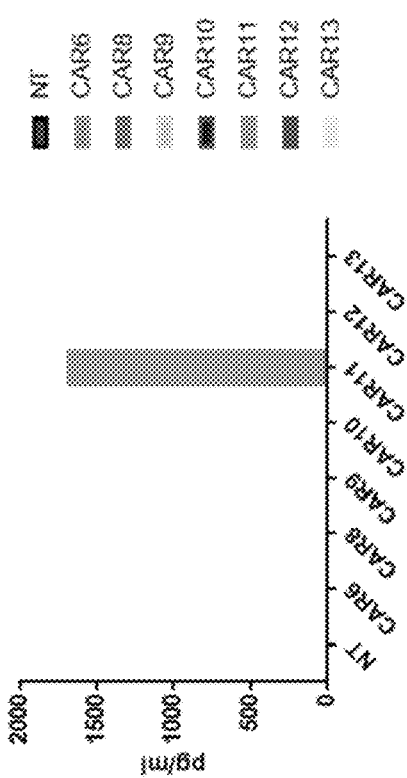
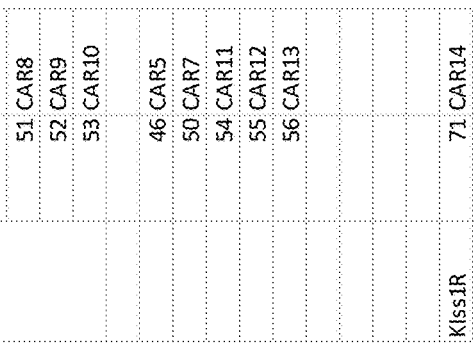
FIG. 4

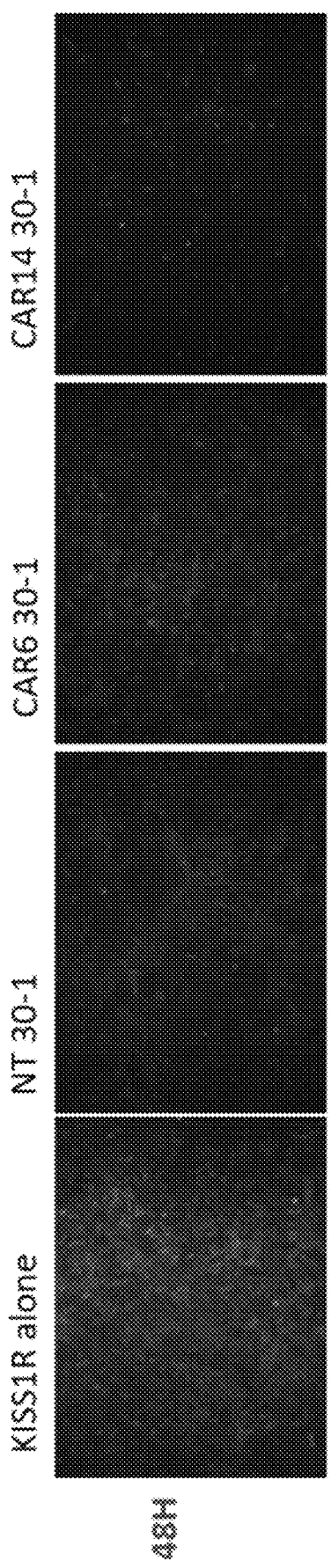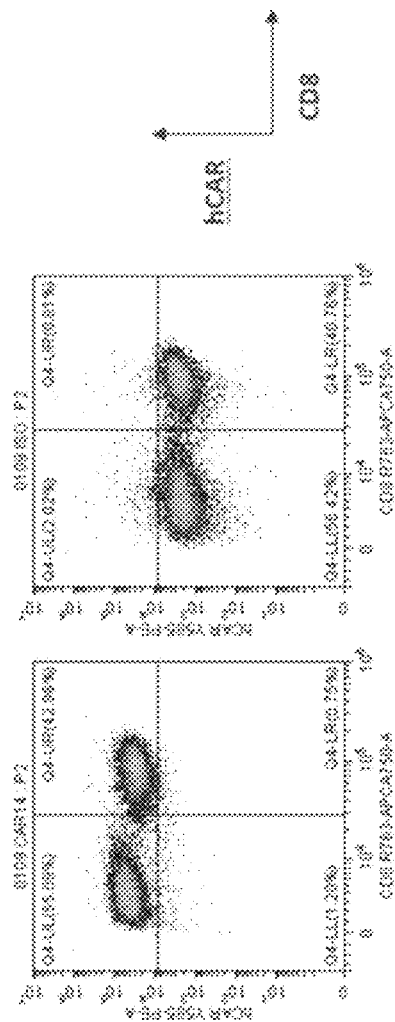
FIG. 6

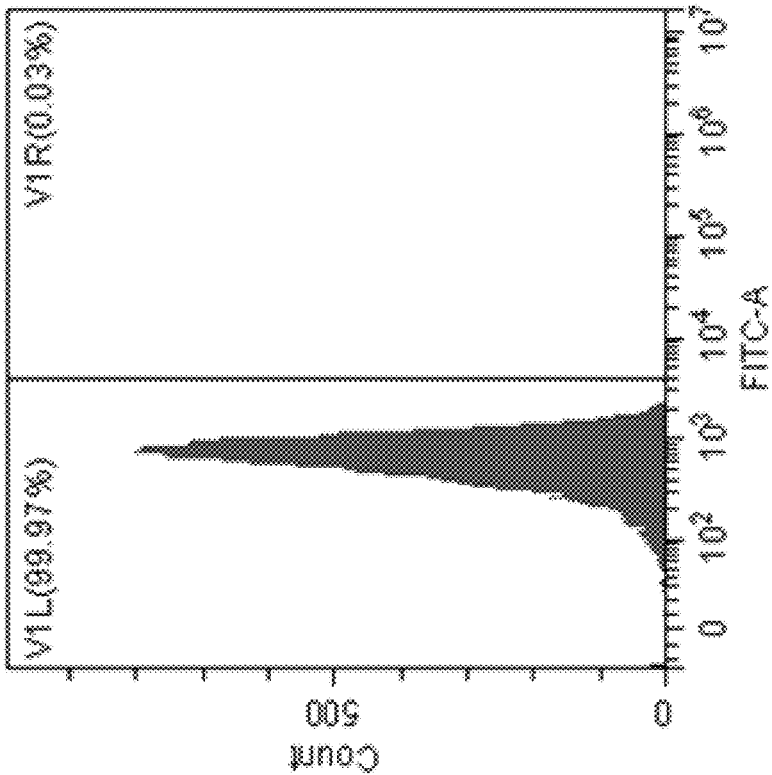
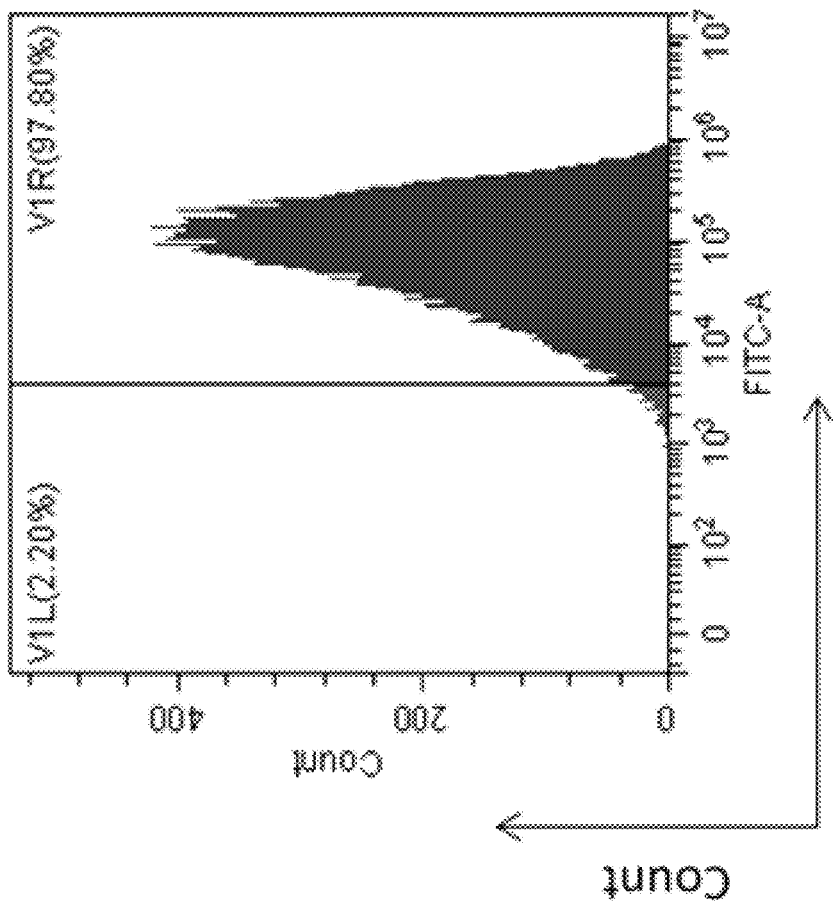
FIG. 12

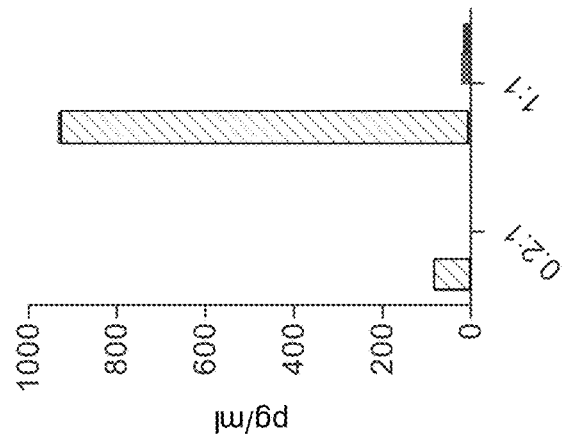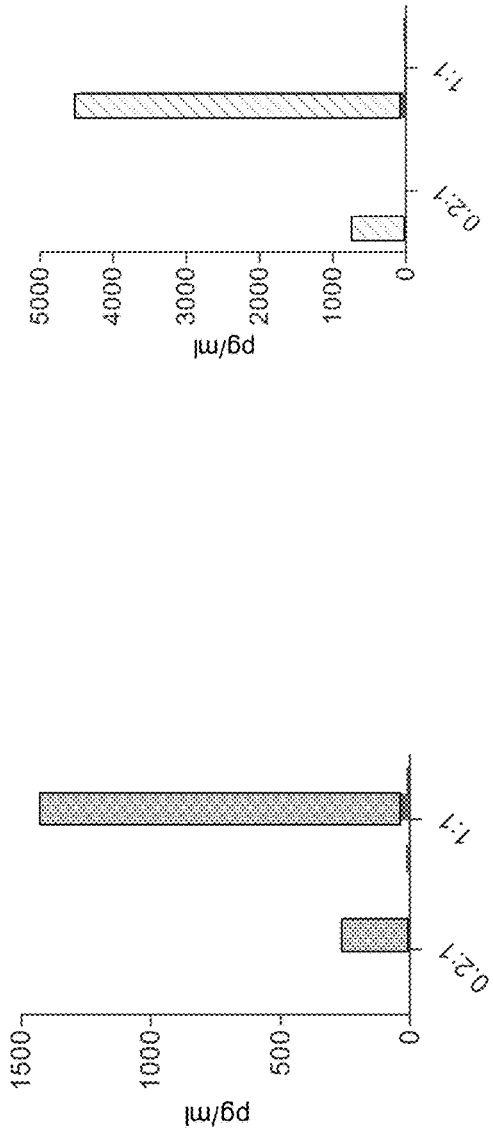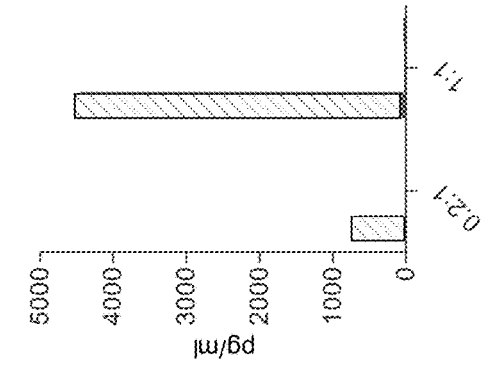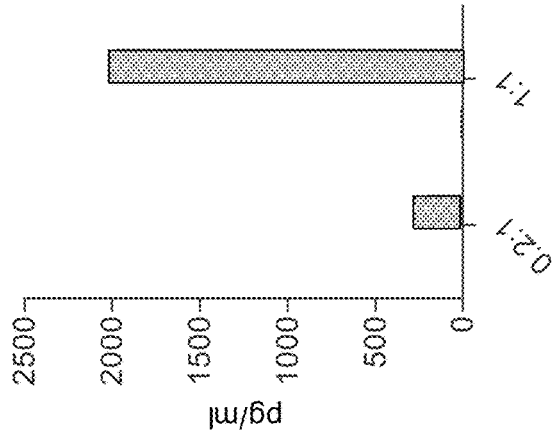
FIG. 17

| Antigen | Gene | Cancer Types |
|---|---|---|
| PRLR | Prolactin receptor | Breast cancer |
| GUCY2C | Guanylate cyclase 2C | Colorectal cancer |
| Muc17 | Mucin 17 | Gastric Cancer |
| CD207 | CD207 | Bladder Cancer |
| FZD10 | Frizzled family receptor 10 | Ovary tumor |
| TSHR | Thyroid stimulating hormone receptor | Thyroid Tumor |

FIG. 25

CHIMERIC ANTIGEN RECEPTOR CELLS FOR TREATING SOLID TUMOR

CROSS REFERENCE TO RELATED APPLICATIONS

This application is a continuation of co-pending U.S. patent application Ser. No. 17/270,571 filed Feb. 23, 2021, which is a U.S. National Phase Application of International Application No. PCT/US2019/048890, filed on Aug. 29, 2019, which claims the benefit of U.S. Provisional Patent Application 62/725,025, filed on Aug. 30, 2018; U.S. Provisional Patent Application 62/731,079, filed on Sep. 13, 2018; U.S. Provisional Patent Application 62/754,175, filed on Nov. 1, 2018; U.S. Provisional Patent Application 62/807,482, filed on Feb. 19, 2019; U.S. Provisional Patent Application 62/842,936, filed on May 3, 2019; and U.S. Provisional Patent Application 62/848,984, filed on May 16, 2019; which are hereby incorporated by reference in their entirety.

SEQUENCE LISTING INFORMATION

A computer readable textfile, entitled "SDS1.0053PCT 8-29-2019_ST25.txt," created on or about Aug. 29, 2019 with a file size of about 533 KB, contains the sequence listing for this application and is hereby incorporated by reference in its entirety.

TECHNICAL FIELD

The present disclosure relates to modified cells and uses, in particular to compositions and methods for treating cancer using Chimeric Antigen Receptor (CAR) cells.

BACKGROUND

Most existing cancer treatment programs include surgery, radiotherapy, and chemotherapy, targeted therapy and immunotherapy. The drawbacks of the existing programs include poor treatment of advanced patients, side effects, patients with poor quality of life. For example, treatment of renal cancer includes resection, targeted therapy (anti-VEGF and mTOR inhibitor, etc.) and immunotherapy (IL-2, PD1 antibody, etc.). Treatment of pancreatic cancer includes surgical resection, radiotherapy, and chemotherapy. Treatment of urothelial carcinoma includes surgical resection, chemoradiation, targeted therapy, and immunotherapy. Treatment of breast cancer includes surgical resection, chemoradiation, targeted therapy, and immunotherapy. Treatment of ovarian cancer includes surgical resection, radiotherapy, chemotherapy, and targeted therapy. Treatment of prostate cancer includes surgical resection, chemoradiation, targeted therapy, and Immunotherapy. Treatment of esophageal cancer includes surgical resection, radiotherapy, and chemotherapy. Treatment of colorectal cancer includes surgical resection, radiotherapy, chemotherapy, and targeted therapy. Treatment of endometrial cancer: surgical resection, radiotherapy, chemotherapy, and targeted therapy.

SUMMARY

Embodiments relate to a discovery that some antigen have relatively low expression on tumor cells, as compared to the expression on normal tissues. Further, while expressed in normal tissues, some other antigens are specifically expressed in a certain tissue (e.g., a group of cells or an organ), and the killing of normal cells of the tissue does not cause a life-threatening event (e.g., complications) to the subject. Examples of the nonessential tissues include organs such as prostate, breast, or melanocyte. Accordingly, the embodiments of the present disclosure relate to a chimeric antigen receptor (CAR) including an extracellular domain that binds at least one of these antigens and treating the cancer using cells including the CAR.

Embodiments relate to compositions and methods for treating cancer using CAR cells. Embodiments relate to an isolated nucleic acid sequence encoding a CAR, wherein the CAR comprises an extracellular domain, a transmembrane domain, and an intracellular domain, wherein the extracellular domain of the CAR binds an antigen of a solid tumor. The antigen may comprise SIGLEC15, SLC6A3, KISS1R, QRFPR, GPR119, CLDN6, UPK2, ADAM12, SLC45A3, ACPP, MUC21, MUC16, MS4A12, ALPP, SLC2A14, GS1-259H13.2, ERVFRD-1, ADGRG2, ECEL1, CHRNA2, GP2, or PSG9.

This Summary is not intended to identify key features or essential features of the claimed subject matter, nor is it intended to be used to limit the scope of the claimed subject matter.

BRIEF DESCRIPTION OF THE DRAWINGS

The Detailed Description is described with reference to the accompanying figures. The use of the same reference numbers in different figures indicates similar or identical items.

FIGS. 4 and 5 show results of cytokine release assays of anti-SIGLEC15 CAR.

FIG. 6 shows results of a killing assay of KISSR CAR.

FIG. 12 shows 293T cells expressing ACPP.

FIG. 17 shows cytokine release assay of anti-ACPP CAR T cells.

FIG. 25 shows a table of markers and the uses thereof.

DETAILED DESCRIPTION

Figure 1:
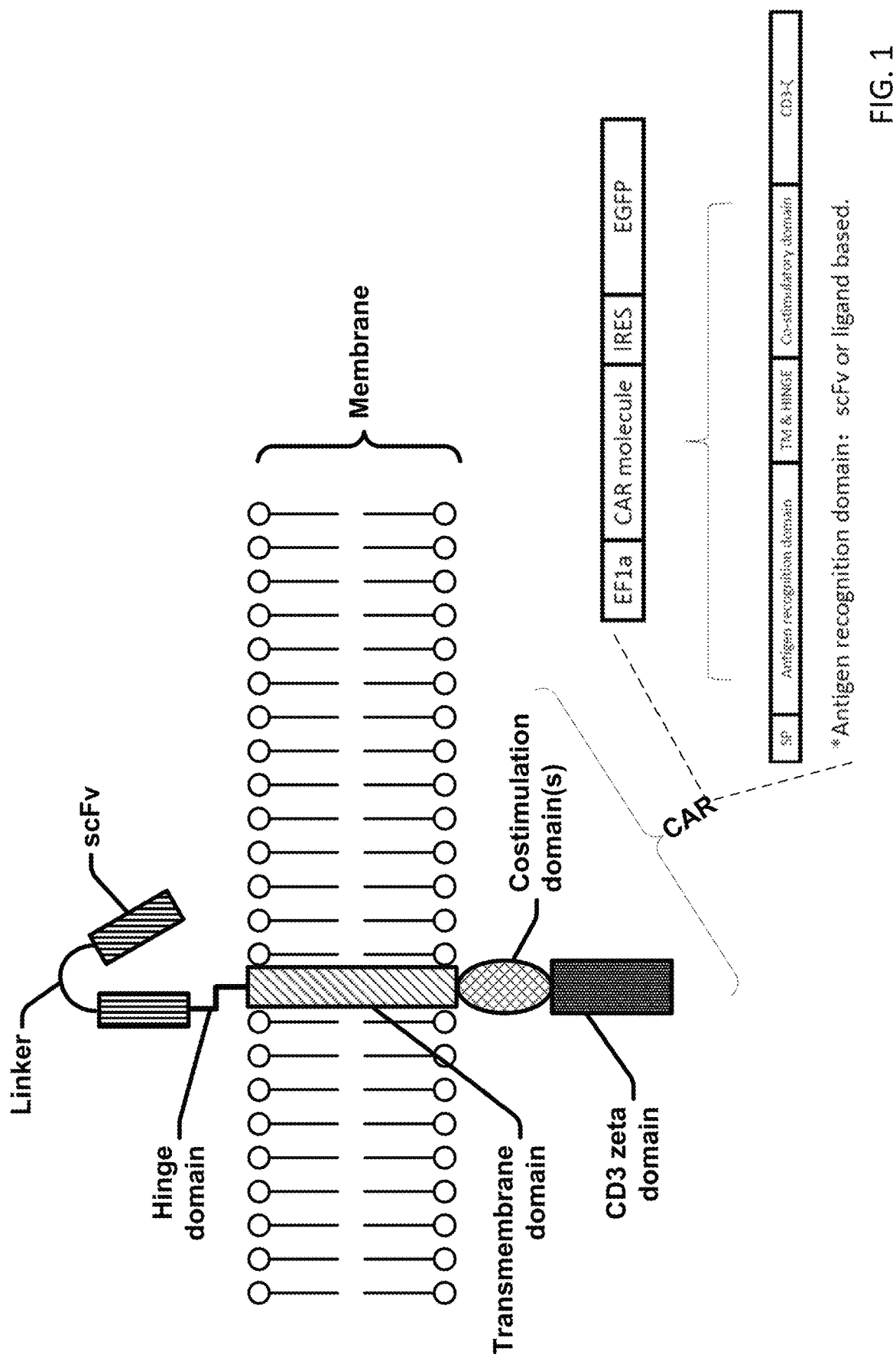
FIG. 1 shows a schematic diagram illustrating an example of a CAR structure.

Unless defined otherwise, all technical and scientific terms used herein have the same meaning as commonly understood by those of ordinary skill in the art to which the disclosure belongs. Although any method and material similar or equivalent to those described herein can be used in the practice or testing of the present disclosure, preferred methods and materials are described. For the purposes of the present disclosure, the following terms are defined below.

The articles "a" and "an" are used herein to refer to one or to more than one (i.e., to at least one) of the grammatical object of the article. By way of example, "an element" means one element or more than one element.

By "about" is meant a quantity, level, value, number, frequency, percentage, dimension, size, amount, weight or length that varies by as much as 20, 15, 10, 9, 8, 7, 6, 5, 4, 3, 2 or 1% to a reference quantity, level, value, number, frequency, percentage, dimension, size, amount, weight or length.

The term "activation," as used herein, refers to the state of a cell that has been sufficiently stimulated to induce detectable cellular proliferation. Activation can also be associated with induced cytokine production and detectable effector functions. The term "activated T cells" refers to, among other things, T cells that are undergoing cell division.

The term "antibody" is used in the broadest sense and refers to monoclonal antibodies (including full length monoclonal antibodies), polyclonal antibodies, multi-specific antibodies (e.g., bispecific antibodies), and antibody fragments so long as they exhibit the desired biological activity or function. The antibodies in the present disclosure may exist in a variety of forms including, for example, polyclonal antibodies, monoclonal antibodies, Fv, Fab and F(ab)$_2$, as well as single chain antibodies and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

The term "antibody fragments" refers to a portion of a full length antibody, for example, the antigen binding or variable region of the antibody. Other examples of antibody fragments include Fab, Fab', F(ab')2, and Fv fragments; diabodies; linear antibodies; single-chain antibody molecules; and multi-specific antibodies formed from antibody fragments.

The term "Fv" refers to the minimum antibody fragment which contains a complete antigen-recognition and -binding site. This fragment consists of a dimer of one heavy- and one light-chain variable region domain in tight, non-covalent association. From the folding of these two domains emanates six hypervariable loops (3 loops each from the H and L chain) that contribute the amino acid residues for antigen binding and confer antigen binding specificity to the antibody. However, even a single variable domain (or half of a Fv including only three complementarity determining regions (CDRs) specific for an antigen) has the ability to recognize and bind antigen, although at a lower affinity than the entire binding site (the dimer).

An "antibody heavy chain," as used herein, refers to the larger of the two types of polypeptide chains present in all antibody molecules in their naturally occurring conformations. An "antibody light chain," as used herein, refers to the smaller of the two types of polypeptide chains present in all antibody molecules in their naturally occurring conformations. K and A light chains refer to the two major antibody light chain isotypes.

The term "synthetic antibody" refers to an antibody which is generated using recombinant DNA technology, such as, for example, an antibody expressed by a bacteriophage. The term also includes an antibody which has been generated by the synthesis of a DNA molecule encoding the antibody and the expression of the DNA molecule to obtain the antibody, or to obtain an amino acid encoding the antibody. The synthetic DNA is obtained using technology that is available and well known in the art.

The term "antigen" refers to a molecule that provokes an immune response, which may involve either antibody production, or the activation of specific immunologically-competent cells, or both. Antigens include any macromolecule, including all proteins or peptides, or molecules derived from recombinant or genomic DNA. For example, DNA including a nucleotide sequence or a partial nucleotide sequence encoding a protein or peptide that elicits an immune response, and therefore, encodes an "antigen" as the term is used herein. An antigen need not be encoded solely by a full-length nucleotide sequence of a gene. An antigen can be generated, synthesized or derived from a biological sample including a tissue sample, a tumor sample, a cell, or a biological fluid.

The term "anti-tumor effect" as used herein, refers to a biological effect associated with a decrease in tumor volume, a decrease in the number of tumor cells, a decrease in the number of metastases, decrease in tumor cell proliferation, decrease in tumor cell survival, an increase in life expectancy of a subject having tumor cells, or amelioration of various physiological symptoms associated with the cancerous condition. An "anti-tumor effect" can also be manifested by the ability of the peptides, polynucleotides, cells, and antibodies in the prevention of the occurrence of tumor in the first place.

The term "auto-antigen" refers to an antigen mistakenly recognized by the immune system as being foreign. Auto-antigens include cellular proteins, phosphoproteins, cellular surface proteins, cellular lipids, nucleic acids, glycoproteins, including cell surface receptors.

The term "autologous" is used to describe a material derived from a subject which is subsequently re-introduced into the same subject.

The term "allogeneic" is used to describe a graft derived from a different subject of the same species. As an example, a donor subject may be a related or unrelated or recipient subject, but the donor subject has immune system markers which are similar to the recipient subject.

The term "xenogeneic" is used to describe a graft derived from a subject of a different species. As an example, the donor subject is from a different species than a recipient subject and the donor subject and the recipient subject can be genetically and immunologically incompatible.

The term "cancer" refers to a disease characterized by the rapid and uncontrolled growth of aberrant cells. Cancer cells can spread locally or through the bloodstream and lymphatic system to other parts of the body. Examples of various cancers include breast cancer, prostate cancer, ovarian cancer, cervical cancer, skin cancer, pancreatic cancer, colorectal cancer, renal cancer, liver cancer, brain cancer, lymphoma, leukemia, lung cancer, and the like.

Cancers that may be treated include tumors that are not vascularized, or not yet substantially vascularized, as well as vascularized tumors. The cancers may include non-solid tumors (such as hematological tumors, for example, leukemias and lymphomas) or may include solid tumors. Types of cancers to be treated with the CARs of the disclosure include, but are not limited to, carcinoma, blastoma, and sarcoma, and certain leukemia or lymphoid malignancies, benign and malignant tumors, and malignancies, e.g., sarcomas, carcinomas, and melanomas. Adult tumors/cancers and pediatric tumors/cancers are also included.

Hematologic cancers are cancers of the blood or bone marrow. Examples of hematological (or hematogenous) cancers include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, include fibrosarcoma, myxosarcoma, liposarcoma, chondrosarcoma, osteosarcoma, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme), astrocytoma, CNS lymphoma, germinoma, medulloblastoma, Schwannoma craniopharyngioma, ependymoma, pinealoma, hemangioblastoma, acoustic neuroma, oligodendroglioma, meningioma, neuroblastoma, retinoblastoma, and brain metastases).

A solid tumor antigen is an antigen expressed on a solid tumor. In embodiments, solid tumor antigens are also expressed at low levels on healthy tissue. Examples of solid tumor antigens and their related disease tumors are provided in Table 1.

TABLE 1

| Solid Tumor antigen | Disease tumor |
| --- | --- |
| PRLR | Breast Cancer |
| CLCA1 | colorectal Cancer |
| MUC12 | colorectal Cancer |
| GUCY2C | colorectal Cancer |
| GPR35 | colorectal Cancer |
| CR1L | Gastric Cancer |
| MUC 17 | Gastric Cancer |

TABLE 1-continued

| Solid Tumor antigen | Disease tumor |
| --- | --- |
| TMPRSS11B | esophageal Cancer |
| MUC21 | esophageal Cancer |
| TMPRSS11E | esophageal Cancer |
| CD207 | bladder Cancer |
| SLC30A8 | pancreatic Cancer |
| CFC1 | pancreatic Cancer |
| SLC12A3 | Cervical Cancer |
| SSTR1 | Cervical tumor |
| GPR27 | Ovary tumor |
| FZD10 | Ovary tumor |
| TSHR | Thyroid Tumor |
| SIGLEC15 | Urothelial cancer |
| SLC6A3 | Renal cancer |
| KISS1R | Renal cancer |
| QRFPR | Renal cancer: |
| GPR119 | Pancreatic cancer |
| CLDN6 | Endometrial cancer/Urothelial cancer |
| UPK2 | Urothelial cancer (including bladder cancer) |
| ADAM12 | Breast cancer, pancreatic cancer and the like |
| SLC45A3 | Prostate cancer |
| ACPP | Prostate cancer |
| MUC21 | Esophageal cancer |
| MUC16 | Ovarian cancer |
| MS4A12 | Colorectal cancer |
| ALPP | Endometrial cancer |
| CEA | Colorectal carcinoma |
| EphA2 | Glioma |
| FAP | Mesothelioma |
| GPC3 | Lung squamous cell carcinoma |
| IL13-Rα2 | Glioma |
| Mesothelin | Metastatic cancer |
| PSMA | Prostate cancer |
| ROR1 | Breast lung carcinoma |
| VEGFR-II | Metastatic cancer |
| GD2 | Neuroblastoma |
| FR-α | Ovarian carcinoma |
| ErbB2 | Carcinomas |
| EpCAM | Carcinomas |
| EGFRvIII | Glioma-Glioblastoma |
| EGFR | Glioma-NSCL cancer |
| tMUC 1 | Cholangiocarcinoma, Pancreatic cancer, Breast |
| PSCA | pancreas, stomach, or prostate cancer |

Throughout this specification, unless the context requires otherwise, the words "comprise," "includes" and "including" will be understood to imply the inclusion of a stated step or element (ingredients or components) or group of steps or elements (ingredients or components) but not the exclusion of any other step or element or group of steps or elements.

The phrase "consisting of" is meant to include, and is limited to, whatever follows the phrase "consisting of." Thus, the phrase "consisting of" indicates that the listed elements are required or mandatory and that no other elements may be present.

The phrase "consisting essentially of" is meant to include any element listed after the phrase and can include other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

The terms "complementary" and "complementarity" refer to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules or there may be "complete" or "total" complementarity between the nucleic acids. The degree of complementarity between nucleic acid strands has significant effects on the efficiency and strength of hybridization between nucleic acid strands.

The term "corresponds to" or "corresponding to" refers to (a) a polynucleotide having a nucleotide sequence that is substantially identical or complementary to all or a portion of a reference polynucleotide sequence or encoding an amino acid sequence identical to an amino acid sequence in a peptide or protein; or (b) a peptide or polypeptide having an amino acid sequence that is substantially identical to a sequence of amino acids in a reference peptide or protein.

The term "costimulatory ligand" refers to a molecule on an antigen presenting cell (e.g., an APC, dendritic cell, B cell, and the like) that specifically binds a cognate costimulatory molecule on a T cell, thereby providing a signal which, in addition to the primary signal provided by, for instance, binding of a TCR/CD3 complex with an MHC molecule loaded with peptide, mediates a T cell response, including at least one of proliferation, activation, differentiation, and other cellular responses. A costimulatory ligand can include B7-1 (CD80), B7-2 (CD86), PD-L1, PD-L2, 4-1BBL, OX40L, inducible co-stimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, a ligand for CD7, an agonist or antibody that binds the Toll ligand receptor and a ligand that specifically binds with B7-H3. A co-stimulatory ligand also includes, inter alia, an agonist or an antibody that specifically binds with a co-stimulatory molecule present on a T cell, such as CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds CD83.

The term "co-stimulatory molecule" refers to the cognate binding partner on a T cell that specifically binds with a co-stimulatory ligand, thereby mediating a co-stimulatory response by the T cell, such as proliferation. Co-stimulatory molecules include an MHC class I molecule, BTLA, and a Toll-like receptor.

The term "co-stimulatory signal" refers to a signal, which in combination with a primary signal, such as TCR/CD3 ligation, leads to T cell proliferation and/or upregulation or downregulation of key molecules. The terms "disease" and "condition" may be used interchangeably or may be different in that the particular malady or condition may not have a known causative agent (so that etiology has not yet been worked out), and it is therefore not yet recognized as a disease but only as an undesirable condition or syndrome, wherein a more or less specific set of symptoms have been identified by clinicians. The term "disease" is a state of health of a subject wherein the subject cannot maintain homeostasis, and wherein if the disease is not ameliorated then the subject's health continues to deteriorate. In contrast, a "disorder" in a subject is a state of health in which the animal is able to maintain homeostasis, but in which the animal's state of health is less favorable than it would be in the absence of the disorder. Left untreated, a disorder does not necessarily cause a further decrease in the animal's state of health.

The term "effective" refers to adequate to accomplish a desired, expected, or intended result. For example, an "effective amount" in the context of treatment may be an amount of a compound sufficient to produce a therapeutic or prophylactic benefit.

The term "encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence (except that a "T" is replaced by a "U") and is usually provided in sequence listings, and the non-coding strand, used as the template for transcription of a gene or cDNA, can be referred to as encoding the protein or other product of that gene or cDNA.

The term "exogenous" refers to a molecule that does not naturally occur in a wild-type cell or organism but is typically introduced into the cell by molecular biological techniques. Examples of exogenous polynucleotides include vectors, plasmids, and/or man-made nucleic acid constructs encoding the desired protein. With regard to polynucleotides and proteins, the term "endogenous" or "native" refers to naturally-occurring polynucleotide or amino acid sequences that may be found in a given wild-type cell or organism. Also, a particular polynucleotide sequence that is isolated from a first organism and transferred to a second organism by molecular biological techniques is typically considered an "exogenous" polynucleotide or amino acid sequence with respect to the second organism. In specific embodiments, polynucleotide sequences can be "introduced" by molecular biological techniques into a microorganism that already contains such a polynucleotide sequence, for instance, to create one or more additional copies of an otherwise naturally-occurring polynucleotide sequence, and thereby facilitate overexpression of the encoded polypeptide.

The term "expression" refers to the transcription and/or translation of a particular nucleotide sequence driven by its promoter.

The term "expression vector" refers to a vector including a recombinant polynucleotide including expression control sequences operably linked to a nucleotide sequence to be expressed. An expression vector includes sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

The term "homologous" refers to sequence similarity or sequence identity between two polypeptides or between two polynucleotides when a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared ×100. For example, if 6 of 10 of the positions in two sequences are matched or homologous then the two sequences are 60% homologous. By way of example, the DNA sequences ATTGCC and TATGGC share 50% homology. A comparison is made when two sequences are aligned to give maximum homology.

The term "immunoglobulin" or "Ig," refers to a class of proteins, which function as antibodies. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses, and is important in defense against bacteria and viruses. IgD is the immunoglobulin that has no known antibody function but may serve as an antigen receptor. IgE is the immunoglobulin that mediates immediate hypersensitivity by causing the release of mediators from mast cells and basophils upon exposure to the allergen.

The term "isolated" refers to a material that is substantially or essentially free from components that normally accompany it in its native state. The material can be a cell or a macromolecule such as a protein or nucleic acid. For example, an "isolated polynucleotide," as used herein, refers to a polynucleotide, which has been purified from the sequences which flank it in a naturally-occurring state, e.g., a DNA fragment which has been removed from the sequences that are normally adjacent to the fragment. Alternatively, an "isolated peptide" or an "isolated polypeptide" and the like, as used herein, refer to in vitro isolation and/or purification of a peptide or polypeptide molecule from its natural cellular environment, and from association with other components of the cell.

The term "substantially purified" refers to a material that is substantially frr from components that normally associated with it in its native state. For example, a substantially purified cell refers to a cell that has been separated from other cell types with which it is normally associated in its naturally occurring or native state. In some instances, a population of substantially purified cells refers to a homogenous population of cells. In other instances, this term refers simply to a cell that has been separated from the cells with which they are naturally associated in their natural state. In embodiments, the cells are cultured in vitro. In embodiments, the cells are not cultured in vitro.

In the context of the present disclosure, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "lentivirus" refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. Moreover, the use of lentiviruses enables integration of the genetic information into the host chromosome resulting in stably transduced genetic information. HIV, SIV, and FIV are all examples of lentiviruses. Vectors derived from lentiviruses offer the means to achieve significant levels of gene transfer in vivo.

The term "modulating," refers to mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation.

The term "under transcriptional control" refers to a promoter being operably linked to and in the correct location and orientation in relation to a polynucleotide to control the initiation of transcription by RNA polymerase and expression of the polynucleotide.

The term "overexpressed" tumor antigen or "overexpression" of the tumor antigen is intended to indicate an abnormal level of expression of the tumor antigen in a cell from a disease area such as a solid tumor within a specific tissue or organ of the patient relative to the level of expression in a normal cell from that tissue or organ. Patients having solid tumors or a hematological malignancy characterized by overexpression of the tumor antigen can be determined by standard assays known in the art.

The term "parenteral administration" of a composition includes, e.g., subcutaneous (s.c.), intravenous (i.v.), intramuscular (i.m.), intrasternal injection, or infusion techniques.

The terms "patient," "subject," and "individual," and the like are used interchangeably herein, and refer to any human, animal, or living organism, amenable to the methods described herein. In certain non-limiting embodiments, the patient, subject, or individual is a human or animal. In embodiments, the term "subject" is intended to include living organisms in which an immune response can be elicited (e.g., mammals). Examples of subjects include humans, and animals such as dogs, cats, mice, rats, and transgenic species thereof.

A subject in need of treatment or in need thereof includes a subject having a disease, condition, or disorder that needs to be treated. A subject in need thereof also includes a subject that needs treatment for prevention of a disease, condition, or disorder. In embodiments, the disease is cancer.

The term "polynucleotide" or "nucleic acid" refers to mRNA, RNA, cRNA, rRNA, cDNA or DNA. The term typically refers to a polymeric form of nucleotides of at least 10 bases in length, either ribonucleotides or deoxynucleotides or a modified form of either type of nucleotide. The term includes all forms of nucleic acids including single and double stranded forms of nucleic acids.

The terms "polynucleotide variant" and "variant" and the like refer to polynucleotides displaying substantial sequence identity with a reference polynucleotide sequence or polynucleotides that hybridize with a reference sequence under stringent conditions that are defined hereinafter. These terms also encompass polynucleotides that are distinguished from a reference polynucleotide by the addition, deletion or substitution of at least one nucleotide. Accordingly, the terms "polynucleotide variant" and "variant" include polynucleotides in which one or more nucleotides have been added or deleted or replaced with different nucleotides. In this regard, it is well understood in the art that certain alterations inclusive of mutations, additions, deletions, and substitutions can be made to a reference polynucleotide whereby the altered polynucleotide retains the biological function or activity of the reference polynucleotide or has increased activity in relation to the reference polynucleotide (i.e., optimized). Polynucleotide variants include, for example, polynucleotides having at least 50% (and at least 51% to at least 99% and all integer percentages in between, e.g., 90%, 95%, or 98%) sequence identity with a reference polynucleotide sequence described herein. The terms "polynucleotide variant" and "variant" also include naturally-occurring allelic variants and orthologs.

The terms "polypeptide," "polypeptide fragment," "peptide," and "protein" are used interchangeably herein to refer to a polymer of amino acid residues and to variants and synthetic analogues of the same. Thus, these terms apply to amino acid polymers in which one or more amino acid residues are synthetic non-naturally occurring amino acids, such as a chemical analogue of a corresponding naturally occurring amino acid, as well as to naturally-occurring amino acid polymers. In certain aspects, polypeptides may include enzymatic polypeptides, or "enzymes," which typically catalyze (i.e., increase the rate of) various chemical reactions.

The term "polypeptide variant" refers to polypeptides that are distinguished from a reference polypeptide sequence by the addition, deletion, or substitution of at least one amino acid residue. In embodiments, a polypeptide variant is distinguished from a reference polypeptide by one or more substitutions, which may be conservative or non-conservative. In embodiments, the polypeptide variant comprises conservative substitutions and, in this regard, it is well understood in the art that some amino acids may be changed to others with broadly similar properties without changing the nature of the activity of the polypeptide. Polypeptide variants also encompass polypeptides in which one or more amino acids have been added or deleted or replaced with different amino acid residues.

The term "promoter" refers to a DNA sequence recognized by the synthetic machinery of the cell or introduced synthetic machinery, required to initiate the specific transcription of a polynucleotide sequence. The term "expression control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

The term "bind," "binds," or "interacts with" refers to a molecule recognizing and adhering to a second molecule in a sample or organism but does not substantially recognize or adhere to other structurally unrelated molecules in the sample. The term "specifically binds," as used herein with respect to an antibody, refers to an antibody which recognizes a specific antigen, but does not substantially recognize or bind other molecules in a sample. For example, an antibody that specifically binds an antigen from one species may also bind that antigen from one or more species. But, such cross-species reactivity does not itself alter the classification of an antibody as specific. In another example, an antibody that specifically binds an antigen may also bind different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds a specific protein structure rather than to any protein. If an antibody is specific for epitope "A," the presence of a molecule containing epitope A (or free, unlabeled A), in a reaction containing labeled "A" and the antibody, will reduce the amount of labeled A bound to the antibody.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding, and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

Zinc finger binding domains can be "engineered" to bind to a predetermined nucleotide sequence, for example via engineering (altering one or more amino acids) of the recognition helix region of a naturally occurring zinc finger protein. Further, a Zinc finger binding domain may be fused a DNA-cleavage domain to form a Zinc finger nuclease (ZFN) targeting a specific desired DNA sequence. For example, a pair of ZFNs (e.g., a ZFN-left arm and a ZFN-right arm) may be engineered to target and cause modifications of specific desired DNA sequences (e.g., TRAC genes).

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In embodiments, fusion polypeptides are used for targeted double-stranded DNA cleavage.

A "target site" or "target sequence" is a nucleic acid sequence that defines a portion of a nucleic acid to which a binding molecule will bind, provided sufficient conditions for binding exist. For example, the sequence 5' GAATTC 3' is a target site for the Eco RI restriction endonuclease.

A "fusion" molecule is a molecule in which two or more subunit molecules are linked, preferably covalently. The subunit molecules can be the same chemical type of molecule or can be different chemical types of molecules. Examples of the first type of fusion molecule include, but are not limited to, fusion proteins (for example, a fusion between a ZFP DNA-binding domain and one or more activation domains) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage, and polypeptide ligation can also be involved in the expression of the protein in a cell. Methods for polynucleotide and polypeptide delivery to cells are presented elsewhere in this disclosure.

"Modulation" of gene expression refers to a change in the activity of a gene. Modulation of expression can include but is not limited to, gene activation and gene repression. Genome editing (e.g., cleavage, alteration, inactivation, random mutation) can be used to modulate expression. Gene inactivation refers to any reduction in gene expression as compared to a cell that does not include a ZFP as described herein. Thus, gene inactivation may be partial or complete.

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

By "statistically significant," it is meant that the result was unlikely to have occurred by chance. Statistical significance can be determined by any method known in the art. Commonly used measures of significance include the p-value, which is the frequency or probability with which the observed event would occur if the null hypothesis were true. If the obtained p-value is smaller than the significance level, then the null hypothesis is rejected. In simple cases, the significance level is defined at a p-value of 0.05 or less. A "decreased" or "reduced" or "lesser" amount is typically a "statistically significant" or a physiologically significant amount, and may include a decrease that is about 1.1, 1.2, 1.3, 1.4, 1.5, 1.6 1.7, 1.8, 1.9, 2, 2.5, 3, 3.5, 4, 4.5, 5, 6, 7, 8, 9, 10, 15, 20, 30, 40, or 50 or more times (e.g., 100, 500, 1000 times) (including all integers and decimal points in between and above 1, e.g., 1.5, 1.6, 1.7. 1.8, etc.) an amount or level described herein.

The term "stimulation," refers to a primary response induced by binding of a stimulatory molecule (e.g., a TCR/CD3 complex) with its cognate ligand thereby mediating a signal transduction event, such as signal transduction via the TCR/CD3 complex. Stimulation can mediate altered expression of certain molecules, such as downregulation of TGF-β, and/or reorganization of cytoskeletal structures. CD3 zeta is not the only suitable primary signaling domain for a CAR construct with respect to the primary response. For example, back in 1993, both CD3 zeta and FcR gamma were shown as functional primary signaling domains of CAR molecules. Eshhar et al., "Specific activation and targeting of cytotoxic lymphocytes through chimeric single chains consisting of antibody-binding domains and the gamma or zeta subunits of the immunoglobulin and T cell receptors" PNAS, 1993 Jan. 15; 90(2):720-4, showed that two CAR constructs in which an scFv was fused to "either the FcR gamma chain or the CD3 complex chain" triggered T cell activation and target cell.

Notably, as demonstrated in Eshhar et al., CAR constructs containing only the primary signaling domain CD3 zeta or FcR gamma are functional without the co-presence of co-stimulatory domains. Additional non-CD3 zeta based CAR constructs have been developed over the years. For example, Wang et al. ("A Chimeric Antigen Receptor (CARs) Based Upon a Killer Immunoglobulin-Like Receptor (KIR) Triggers Robust Cytotoxic Activity in Solid Tumors" Molecular Therapy, vol. 22, no. Suppl. 1, May 2014, page S57) tested a CAR molecule in which an scFv was fused to "the transmembrane and cytoplasmic domain of" a killer immunoglobulin-like receptor (KIR). Wang et al. reported that, "a KIR-based CAR targeting mesothelin (SS 1-KIR) triggers antigen-specific cytotoxic activity and cytokine production that is comparable to CD3~-based CARs." A second publication from the same group, Wang et al. ("Generation of Potent T-cell Immunotherapy for Cancer Using DAP12-Based, Multichain, Chimeric Immunoreceptors" Cancer Immunol Res. 2015 July; 3(7):815-26) showed that a CAR molecule in which "a single-chain variable fragment for antigen recognition was fused to the transmembrane and cytoplasmic domains of KIR2DS2, a stimulatory killer immunoglobulin-like receptor (KIR)" functioned both in vitro and in vivo "when introduced into human T cells with DAP12, an immunotyrosine-based activation motifs-containing adaptor."

The term "stimulatory molecule" refers to a molecule on a T cell that specifically binds a cognate stimulatory ligand present on an antigen presenting cell. For example, a functional signaling domain derived from a stimulatory molecule is the zeta chain associated with the T cell receptor complex.

The term "stimulatory ligand" refers to a ligand that when present on an antigen presenting cell (e.g., an APC, a dendritic cell, a B-cell, and the like.) can specifically bind with a cognate binding partner (referred to herein as a "stimulatory molecule") on a cell, for example a T cell, thereby mediating a primary response by the T cell, including activation, initiation of an immune response, proliferation, and similar processes. Stimulatory ligands are well-known in the art and encompass, inter alia, an MHC Class I molecule loaded with a peptide, an anti-CD3 antibody, a superagonist anti-CD28 antibody, and a superagonist anti-CD2 antibody.

The term "therapeutic" refers to a treatment and/or prophylaxis. A therapeutic effect is obtained by suppression, remission, or eradication of a disease state or alleviating the symptoms of a disease state.

The term "therapeutically effective amount" refers to the amount of the subject compound that will elicit the biological or medical response of a tissue, system, or subject that is being sought by the researcher, veterinarian, medical doctor or another clinician. The term "therapeutically effective amount" includes that amount of a compound that, when administered, is sufficient to prevent the development of, or alleviate to some extent, one or more of the signs or symptoms of the disorder or disease being treated. The therapeutically effective amount will vary depending on the compound, the disease and its severity and the age, weight, etc., of the subject to be treated.

The term "treat a disease" refers to the reduction of the frequency or severity of at least one sign or symptom of a disease or disorder experienced by a subject.

The term "transfected" or "transformed" or "transduced" refers to a process by which an exogenous nucleic acid is transferred or introduced into the host cell. A "transfected" or "transformed" or "transduced" cell is one which has been transfected, transformed, or transduced with exogenous nucleic acid. The cell includes the primary subject cell and its progeny.

The term "vector" refers to a polynucleotide that comprises an isolated nucleic acid and which can be used to deliver the isolated nucleic acid to the interior of a cell in vitro and in vivo (in a subject). Numerous vectors are known in the art including linear polynucleotides, polynucleotides associated with ionic or amphiphilic compounds, plasmids, and viruses. Thus, the term "vector" includes an autonomously replicating plasmid or a virus. The term also includes non-plasmid and non-viral compounds which facilitate transfer of nucleic acid into cells, such as, for example, polylysine compounds, liposomes, and the like. Examples of viral vectors include, adenoviral vectors, adeno-associated virus vectors, retroviral vectors, and others. For example, lentiviruses are complex retroviruses, which, in addition to the common retroviral genes gag, pol, and env, contain other genes with regulatory or structural function. Lentiviral vectors are well known in the art. Some examples of lentivirus include the Human Immunodeficiency Viruses: HIV-1, HIV-2, and the Simian Immunodeficiency Virus: SIV. Lentiviral vectors have been generated by multiply attenuating the HIV virulence genes, for example, the genes env, vif, vpr, vpu, and nef are deleted making the vector biologically safe.

Ranges: throughout this disclosure, various aspects of the disclosure can be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Embodiments of the present disclosure relate to treating cancer using chimeric antigen receptor (CAR) cells. Embodiments relate to an isolated nucleic acid encoding a CAR, wherein the CAR comprises an extracellular domain, a transmembrane domain, and an intracellular domain, wherein the extracellular domain of the CAR binds an antigen of a solid tumor. For example, transcriptional data shows that expression of antigens such as SLC6A3, KISS1R, QRFPR in normal tissues is very low, but expression of such antigens in cells related to renal cancer is high. Information of some of the antigens is provided below in Table 2.

TABLE 2

| Gene name | Subcellular localization | Organ mainly expressing | Target Tumor | Target SEQ ID NO. |
| --- | --- | --- | --- | --- |
| SIGLEC15 | Plasma membrane | Expression in all normal tissues is very low | Urothelial cancer | 17 |

TABLE 2-continued

| Gene name | Subcellular localization | Organ mainly expressing | Target Tumor | Target SEQ ID NO. |
| --- | --- | --- | --- | --- |
| SLC6A3 | Plasma membrane | Expression in all normal tissues is very low | Renal cancer | 18 |
| KISS1R | Plasma membrane | Expression in all normal tissues is very low | Renal cancer | 19 |
| QRFPR | Plasma membrane | Expression in all normal tissues is very low | Renal cancer: | 20 |
| GPR119 | Plasma membrane | Expression in all normal tissues is very low | Pancreatic cancer | 21 |
| CLDN6 | Plasma membrane | Expression in all normal tissues is very low | Endometrial cancer/ Urothelial cancer | 22 |
| UPK2 | Plasma membrane | Urethra/ bladder | Urothelial cancer (including bladder cancer) | 1 |
| ADAM12 | Plasma membrane | placenta | Breast cancer, pancreatic cancer and the like | 2 |
| SLC45A3 | Plasma membrane | prostate | Prostate cancer | 3 |
| ACPP | Plasma membrane | prostate | Prostate cancer | 4 |
| MUC21 | Plasma membrane | esophagus | Esophageal cancer | 5 |
| MUC16 | Plasma membrane | Cervical/ Fallopian tube | Ovarian cancer | 6 |
| MS4A12 | Plasma membrane | the large intestine | Colorectal cancer | 7 |
| ALPP | Plasma membrane | Placenta/ cervix | Endometrial cancer | 8 |
| SLC2A14 | Plasma membrane | testis | Testicular cancer | 9 |
| GS1-259H13.2 | Plasma membrane | testis | Thyroid cancer or glioma or testicular cancer and other | 10 |
| ERVFRD-1 | Plasma membrane | Placenta or parathyroid | Kidney cancer or Urethral cancer and many others | 11 |
| ADGRG2 | Plasma membrane | Epididymis | Ovarian cancer | 12 |
| ECEL1 | Plasma membrane | Ovary | Endometrial cancer | 13 |
| CHRNA2 | Plasma membrane | Prostate or cortex | Prostate cancer | 14 |
| GP2 | Plasma membrane | pancreas | Pancreatic cancer | 15 |
| PSG9 | Plasma membrane | placenta | Kidney cancer or liver cancer | 16 |

In embodiments, the extracellular domain of the CAR binds SIGLEC15. SIGLEC15 is a receptor protein expressed on the cell membrane, which recognizes sialylated glycans. Transcriptional data predict that it is overexpressed in urothelial cancer cells and is expressed at a low level in normal tissues. It is mainly found in spleen and lymph nodes, and other immune organs have a certain amount of low expression. For example, the extracellular domain of the CAR binds SIGLEC15 having the amino acid sequence of SEQ ID NO: 17. In embodiments, the extracellular domain comprises one of the amino acid sequences of SEQ ID NOs: 45-56. Embodiments relate to a method of eliciting and/or enhancing T cell response in a subject having the solid tumor or treating the solid tumor of the subject, the method comprising administering an effective amount of T cell comprising the CAR to the subject. In embodiments, the tumor is associated with urothelial cancer.

The T cell response in a subject refers to cell-mediated immunity associated with a helper, killer, regulatory, and other types T cells. For example, T cell response may include activities such as assistance to other white blood cells in immunologic processes and identifying and destroying virus-infected cells and tumor cells. T cell response in the subject may be measured via various indicators such as a number of virus-infected cells and/or tumor cells that T cells kill, an amount of cytokines that T cells release in co-culturing with virus-infected cells and/or tumor cells, a level of proliferation of T cells in the subject, a phenotype change of T cells (e.g., changes to memory T cells), and a level longevity or lifetime of T cells in the subject.

In embodiments, in vitro killing assay may be performed by measuring the killing efficacy of CAR T cells by co-culturing CAR T cells with antigen-positive cells. CAR T cells may be considered to have killing effect on the corresponding antigen-positive cells by showing a decrease in the number of corresponding antigen-positive cells co-cultured with CAR T cells and an increase in the release of IFNγ, TNFα, etc. as compared to control cells that do not express the corresponding antigen. Further, in vivo antitumor activity of the CAR T cells may be tested. For example, xenograft models may be established using the antigens described herein in immunodeficient mice. Heterotransplantation of human cancer cells or tumor biopsies into immunodeficient rodents (xenograft models) has, for the past two decades, constituted the major preclinical screen for the development of novel cancer therapeutics (Song et al., Cancer Res. PMC 2014 Aug. 21, and Morton et al., Nature Protocols, 2, -247-250 (2007)). To evaluate the anti-tumor activity of CAR T cells in vivo, immunodeficient mice bearing tumor xenografts were evaluated for CAR T cell anti-tumor activity (e.g., a decrease in mouse tumors and mouse blood IFNγ, TNFα, et al.).

The term "chimeric antigen receptor" or alternatively a "CAR" refers to a recombinant polypeptide construct comprising at least an extracellular antigen binding domain, a transmembrane domain and an intracellular signaling domain (e.g., cytoplasmic domain). In embodiments, the domains in the CAR polypeptide construct are on the same polypeptide chain (e.g., comprising a chimeric fusion protein). In embodiments, the domains of the CAR polypeptide are not on the same molecule, e.g. not contiguous with each other or are on different polypeptide chains.

In embodiments, the intracellular signaling domain may include a functional signaling domain derived from a stimulatory molecule and/or a co-stimulatory molecule as described herein. In embodiments, the intracellular signaling domain includes a functional signaling domain derived from a primary signaling domain (e.g., a primary signaling domain of CD3-zeta). In embodiments, the intracellular signaling domain further includes one or more functional signaling domains derived from at least one co-stimulatory molecule. The co-stimulatory signaling region refers to a portion of the CAR including the intracellular domain of a co-stimulatory molecule. Co-stimulatory molecules can include cell surface molecules for inducing an efficient response from the lymphocytes (in response to an antigen).

Between the extracellular domain and the transmembrane domain of the CAR, there may be incorporated a spacer domain. As used herein, the term "spacer domain" generally means any oligo- or polypeptide that functions to link the transmembrane domain to the extracellular domain and/or the cytoplasmic domain in the polypeptide chain. A spacer domain may include up to 300 amino acids, 10 to 100 amino acids, or 25 to 50 amino acids.

The extracellular domain of a CAR may include an antigen binding domain (e.g., a scFv, a single domain antibody, or TCR, such as a TCR alpha binding domain or a TCR beta binding domain) that targets a specific tumor marker (e.g., a tumor antigen). Tumor antigens are proteins that are produced by tumor cells that elicit an immune response, particularly T cell mediated immune responses. Tumor antigens are well known in the art and include, for example, a glioma-associated antigen, carcinoembryonic antigen (CEA), β-human chorionic gonadotropin, alphafetoprotein (AFP), lectin-reactive AFP, thyroglobulin, RAGE-1, MN-CA IX, human telomerase reverse transcriptase, RU1, RU2 (AS), intestinal carboxyl esterase, mut hsp70-2, M-CSF, prostase, prostate-specific antigen (PSA), PAP, NY-ESO-1, LACE-1a, p53, prostein, PSMA, Her2/neu, survivin and telomerase, prostate-carcinoma tumor antigen-1 (PCTA-1), MAGE, ELF2M, neutrophil elastase, ephrinB2, CD22, insulin growth factor (IGF)-I, IGF-II, IGF-I receptor and mesothelin. For example, when the antigen that the CAR binds is CD19, the CAR thereof is referred to as CD19CAR.

In embodiments, the extracellular ligand-binding domain comprises a scFv comprising the light chain variable (VL) region and the heavy chain variable (VH) region of a target antigen-specific monoclonal antibody joined by a flexible linker. Single chain variable region fragments are made by linking light and/or heavy chain variable regions by using a short linking peptide (Bird et al., Science 242:423-426, 1988). An example of a linking peptide is the GS linker having the amino acid sequence (GGGGS)3 (SEQ ID: 24), which bridges approximately 3.5 nm between the carboxy terminus of one variable region and the amino terminus of the other variable region. Linkers of other sequences have been designed and used (Bird et al., 1988, supra). In general, linkers can be short, flexible polypeptides comprising about 20 or fewer amino acid residues. Linkers can in turn be modified for additional functions, such as attachment of drugs or attachment to solid supports. The single chain variants can be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or prokaryotic, such as E. coli. Polynucleotides encoding the scFv of interest can be made by routine manipulations such as ligation of polynucleotides. The resultant scFv can be isolated using standard protein purification techniques known in the art.

In embodiments, the tumor antigen includes HER2, CD19, CD20, CD22, Kappa or light chain, CD30, CD33, CD123, CD38, ROR1, ErbB3/4, EGFR, EGFRvIII, EphA2, FAP, carcinoembryonic antigen, EGP2, EGP40, mesothelin, TAG72, PSMA, NKG2D ligands, B7-H6, IL-13 receptor a 2, IL-11 receptor a, MUC1, MUC16, CA9, GD2, GD3, HMW-MAA, CD171, Lewis Y, G250/CAIX, HLA-A1 MAGE A1, HLA-A2 NY-ESO-1, PSC1, folate receptor-α, CD44v7/8, 8H9, NCAM, VEGF receptors, 5T4, Fetal AchR, NKG2D ligands, CD44v6, TEM1, TEM8, or viral-associated antigens expressed by a tumor. In embodiments, the binding element of the CAR may include any antigen binding moiety that when bound to its cognate antigen, affects a tumor cell such that the tumor cell fails to grow, or is promoted to die or diminish.

In embodiments, the extracellular domain of the CAR binds KISS1R. KISS1R is a galanin-like G protein-coupled receptor that binds Kisspeptin (metastin), a peptide encoded by the metastasis suppressor gene KISS1. KISS1 R may be involved in the regulation of endocrine function. For example, the extracellular domain of the CAR binds KISS1R having the amino acid sequence of SEQ ID NO: 19. In embodiments, the extracellular domain of the CAR comprises one of the amino acid sequences of SEQ ID NOs: 71 and 72. Embodiments relate to a method of eliciting and/or enhancing T cell response in a subject having a solid tumor or treating a solid tumor in the subject, wherein the method comprises administering an effective amount of T cells comprising the CAR. In embodiments, the solid tumor is associated with renal cancer.

In embodiments, the extracellular domain of the CAR binds CLDN6. CLDN6 is a component of tight junction strands, which is a member of the claudin family, an integral membrane protein. Transcriptional data predict high expression in endometrial cancer, urothelial cancer, whereas expression in normal tissues is a component of tight junction strands, which are members of the claudin family Low volume. For example, the extracellular domain of the CAR binds CLDN6 having the amino acid sequence of SEQ ID NO: 22. In embodiments, the extracellular domain of the CAR comprises one of the amino acid sequences of SEQ ID NOs: 29-44. Embodiments relate to a method of eliciting and/or enhancing T-cell response in a subject having a solid tumor or treating a solid tumor in the subject, wherein the method comprises administering an effective amount of T cells comprising the CAR. In embodiments, the solid tumor is associated with endometrial cancer and/or urothelial cancer.

In embodiments, the extracellular domain of the CAR bindsMUC16. MUC21 and MUC16 are large membrane-bound glycoproteins, which belong to mucin family. Mucins are 0-glycosylated proteins that play an essential role in forming protective mucous barriers on epithelial surfaces. MUC21 has restricted expression toward esophagus, for esophageal cancer. MUC16 has low expression in normal tissues and low expression in the endometrium. In ovarian cancer, MUC16 is highly expressed. For example, the extracellular domain of the CAR binds MUC16 having the amino acid sequence of SEQ ID NO: 6. In embodiments, the extracellular domain of the CAR comprises one of the amino acid sequences of SEQ ID NOs: 63-70. Embodiments relate to a method of eliciting and/or enhancing T cell response in a subject having a solid tumor or treating a solid tumor in the subject, wherein the method comprises administering an effective amount of T cells comprising the CAR. In embodiments, the solid tumor is associated with ovarian cancer.

In embodiments, the extracellular domain of the CAR binds SLC6A3. SLC6A3 is a dopamine transporter, a member of the sodium- and chloride-dependent neurotransmitter transporter family. For example, the extracellular domain of the CAR binds SLC6A3 having the amino acid sequence of SEQ ID NO: 18. Embodiments include a method of eliciting and/or enhancing T-cell response in a subject having a solid tumor or treating a solid tumor in the subject, wherein the method comprises administering an effective amount of T cells comprising the CAR. In embodiments, the tumor comprises renal cancer.

In embodiments, the extracellular domain of the CAR binds QRFPR. QRFPR is pyroglutamylated RFamide peptide receptor and may be involved in adipogenesis with its ligand, QRFP. For example, the extracellular domain of the CAR binds QRFPR having the amino acid sequence of SEQ ID NO: 20. Embodiments relate to a method of eliciting and/or enhancing T-cell response in a subject having a solid tumor or treating a solid tumor in the subject, wherein the method comprises administering an effective amount of T cells comprising the CAR. In embodiments, the solid tumor is associated with renal cancer.

In embodiments, the extracellular domain of the CAR binds GPR119. GPR119 is a member of the rhodopsin subfamily of G-protein-coupled receptors, has low expression in the pancreas and gastrointestinal tract, and may be involved in glucose homeostasis. Transcriptional data predict high expression in pancreatic cancer. For example, the extracellular domain of the CAR binds GPR119 having the amino acid sequence of SEQ ID NO: 21. Embodiments relate to a method of eliciting and/or enhancing T-cell response in a subject having a solid tumor or treating a solid tumor of the subject, wherein the method comprises administering an effective amount of T cells comprising the CAR. In embodiments, the tumor is associated with pancreatic cancer.

In embodiments, the extracellular domain of the CAR bindsUPK2. UPK2 is one of the proteins of the highly conserved urothelium-specific integral membrane proteins of the asymmetric unit membrane, expressed primarily in urinary bladder in normal tissues and urothelial carcinoma, including bladder cancer. For example, the extracellular domain of the CAR binds UPK2 having the amino acid sequence of SEQ ID NO: 1. Embodiments relate to a method of eliciting and/or enhancing T-cell response in a subject having a solid tumor or treating a solid tumor in the subject, wherein the method comprises administering an effective amount of T cells comprising the CAR. In embodiments, the solid tumor is associated with urothelial cancer and/or bladder cancer.

In embodiments, the extracellular domain of the CAR binds ADAM12. ADAM12 is a member of a family of proteins that are structurally related to snake venom disintegrins, involved in cell-cell and cell-matrix interactions, and is highly expressed in tumors such as placenta and breast/pancreatic cancer. For example, the extracellular domain of the CAR binds ADAM12 having the amino acid sequence of SEQ ID NO: 2. Embodiments relate to a method of eliciting and/or enhancing T-cell response in a subject having a solid tumor or treating a solid tumor in the subject, wherein the method comprises administering an effective amount of T cells comprising the CAR. In embodiments, the solid tumor is associated with breast cancer and/or pancreatic cancer.

In embodiments, the extracellular domain of the CAR binds SLC45A3. SLC45A3 is a plasma membrane protein, normal tissue is mainly expressed in prostate, for prostate cancer. For example, the extracellular domain of the CAR binds SLC45A3 having the amino acid sequence of SEQ ID NO: 3. Embodiments relate to a method of eliciting and/or enhancing T-cell response in a subject having a solid tumor or treating a solid tumor in the subject, wherein the method comprises administering an effective amount of T cells comprising the CAR. In embodiments, the solid tumor is associated with prostate cancer.

In embodiments, the extracellular domain of the CAR binds ACPP. ACPP is an enzyme that catalyzes the conversion of orthophosphoric monoester to alcohol and orthophosphate, contains a transmembrane domain and localized in the plasma membrane-endosomal-lysosomal pathway. Normal tissue is specifically expressed in the prostate for prostate cancer. For example, the extracellular domain of the CAR binds ACPP having the amino acid sequence of SEQ ID NO: 4. Embodiments relate to a method of eliciting and/or enhancing T-cell response in a subject having a solid tumor or treating a solid tumor in the subject, wherein the method comprises administering an effective amount of T cells comprising the CAR. In embodiments, the solid tumor is associated with prostate cancer.

In embodiments, the extracellular domain of the CAR binds MUC21. MUC21 and MUC16 are large membrane-bound glycoproteins, which belong to mucin family. Mucins are 0-glycosylated proteins that play an essential role in forming protective mucous barriers on epithelial surfaces. MUC21 has restricted expression toward esophagus, when the subject has esophageal cancer. For example, the extracellular domain of the CAR binds MUC21 having the amino acid sequence of SEQ ID NO: 5. Embodiments relate to a method of eliciting and/or enhancing T-cell response in a subject having a solid tumor or treating a solid tumor in the subject, wherein the method comprises administering an effective amount of T cells comprising the CAR. In embodiments, the solid tumor is associated with esophageal cancer.

In embodiments, the extracellular domain of the CAR binds MS4A12. MS4A12 is a cell surface protein found in the apical membrane of colonocytes, restricted expression on colon, and may be used against colorectal cancer. For example, the extracellular domain of the CAR binds MS4A12 having the amino acid sequence of SEQ ID NO: 7. Embodiments relate to a method of eliciting and/or enhancing T-cell response in a subject having a solid tumor or treating a solid tumor in the subject, wherein the method comprises administering an effective amount of T cells comprising the CAR. In embodiments, the solid tumor is associated with colorectal cancer.

In embodiments, the extracellular domain of the CAR binds ALPP. ALPP is an alkaline phosphatase, a metalloenzyme that catalyzes the hydrolysis of phosphoric acid monoesters. The expression of ALPP is restricted to the placenta, Strong ectopic expression of ALPP has been detected in ovarian adenocarcinoma, serous cystadenocarcinoma, and other ovarian cancer cells. For example, the extracellular domain of the CAR binds ALPP having the amino acid sequence of SEQ ID NO: 8. Embodiments relate to a method of eliciting and/or enhancing T-cell response in a subject having a solid tumor or treating a solid tumor in the subject, wherein the method comprises administering an effective amount of T cells comprising he CAR. In embodiments, the solid tumor is associated with endometrial cancer.

In embodiments, the extracellular domain of the CAR binds SLC2A14. For example, the extracellular domain of the CAR binds SLC2A14 having the amino acid sequence of SEQ ID NO: 9. Embodiments relate to a method of eliciting and/or enhancing T-cell response in a subject having a solid tumor or treating a solid tumor in the subject, wherein the method comprises administering an effective amount of T cells comprising the CAR. In embodiments, the tumor is associated with testicular cancer.

In embodiments, the extracellular domain of the CAR binds GS1-259H13.2. For example, the extracellular domain of the CAR binds GS1-259H13.2 having the amino acid sequence of SEQ ID NO: 10. Embodiments relate to a method of eliciting and/or enhancing T-cell response in a subject having a solid tumor or treating a solid tumor of the subject, wherein the method comprises administering an effective amount of T cells comprising the CAR. In embodiments, the tumor is associated with thyroid cancer or glioma, or testicular cancer.

In embodiments, the extracellular domain of the CAR binds ERVFRD-1. For example, the extracellular domain of the CAR binds ERVFRD-1 having the amino acid sequence of SEQ ID NO: 11. Embodiments relate to a method of eliciting and/or enhancing T-cell response in a subject having a solid tumor or treating a solid tumor in the subject, wherein the method comprises administering an effective amount of T cells comprising the CAR. In embodiments, the tumor is associated with kidney cancer or Urethral cancer.

In embodiments, the extracellular domain of the CAR binds ADGRG2. For example, the extracellular domain of the CAR binds ADGRG2 having the amino acid sequence of SEQ ID NO: 12. Embodiments relate to a method of eliciting and/or enhancing T-cell response in a subject having a solid tumor or treating a solid tumor in the subject, wherein the method comprises administering an effective amount of T cells comprising the CAR. In embodiments, the tumor is associated with ovarian cancer.

In embodiments, the extracellular domain of the CAR binds ECEL1. For example, the extracellular domain of the CAR binds ECEL1 having the amino acid sequence of SEQ ID NO: 13. Embodiments relate to a method of eliciting and/or enhancing T-cell response in a subject having a solid tumor or treating a solid tumor in the subject, wherein the method comprises administering an effective amount of T cells comprising the CAR. In embodiments, the tumor is associated with endometrial cancer.

In embodiments, the extracellular domain of the CAR binds CHRNA2. For example, the extracellular domain of the CAR binds CHRNA2 having the amino acid sequence of SEQ ID NO: 14. Embodiments relate to a method of eliciting and/or enhancing T-cell response in a subject having a solid tumor or treating a solid tumor in the subject, wherein the method comprises administering an effective amount of T cells comprising the CAR. In embodiments, the tumor is associated with prostate cancer.

In embodiments, the extracellular domain of the CAR binds GP2. For example, the extracellular domain of the CAR binds GP2 having the amino acid sequence of SEQ ID NO: 15. Embodiments relate to a method of eliciting and/or enhancing T-cell response in a subject having a solid tumor or treating a solid tumor in the subject, wherein the method comprises administering an effective amount of T cells comprising the CAR. In embodiments, the tumor is associated with pancreatic cancer.

In embodiments, the extracellular domain of the CAR binds PSG9. For example, the extracellular domain of the CAR binds PSG9 having the amino acid sequence of SEQ ID NO: 16. Embodiments relate to a method of eliciting and/or enhancing T-cell response in a subject having a solid tumor or treating a solid tumor in the subject, wherein the method comprises administering an effective amount of T cells comprising the CAR. In embodiments, the tumor is associated with Kidney cancer or liver cancer.

Figure 26:
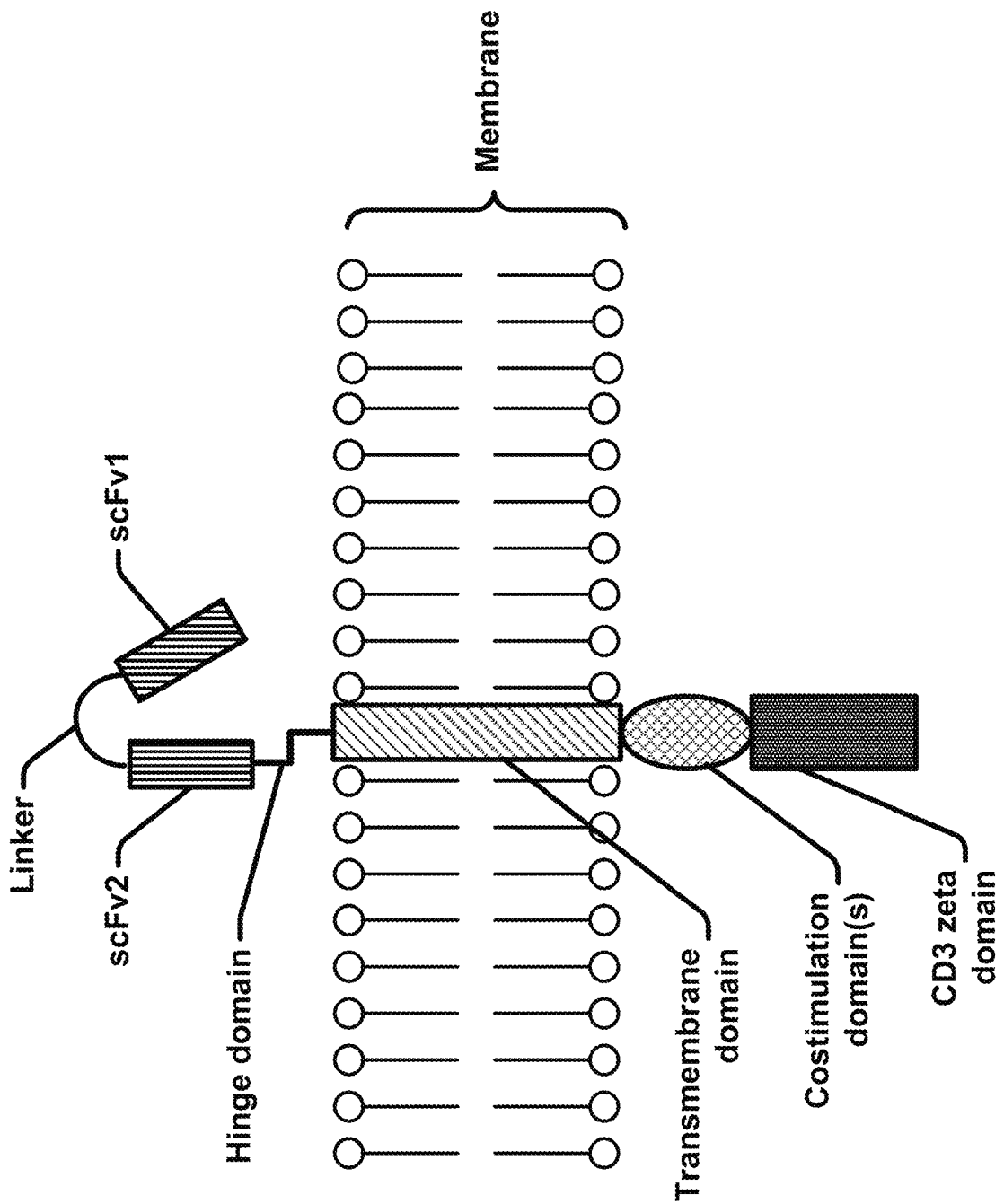
FIG. 26 shows an exemplary structure of a CAR.

The present disclosure also relates to a bispecific chimeric antigen receptor (See FIG. 26), a polynucleotide encoding the bispecific chimeric antigen receptor, and/or a modified cell comprising the polynucleotide, wherein the bispecific chimeric antigen receptor comprises a first antigen binding domain, a second antigen binding domain, a cytoplasmic domain, and a transmembrane domain, and wherein the first antigen binding domain recognizes a first antigen, and the second antigen binding domain recognize a second antigen. In embodiments, the first antigen is an antigen associated with a white blood cell, and the second antigen is a solid tumor antigen. In embodiments, the first and second antigens are identical or different. In embodiments, the first and second antigens are both solid tumor antigens. For example, the first antigen is a tumor associated MUC1, and the second antigen is selected from one of the antigens of SEQ ID NO: 1-22. In embodiments, the first binding domain and the second binding domain are connected via a linker (e.g., SEQ ID NO: 188).

In embodiments, the intracellular domain of the CAR comprises a co-stimulatory signaling region that comprises an intracellular domain of a co-stimulatory molecule selected from the group consisting of CD27, CD28, 4-1BB, OX40, CD30, CD40, PD-1, ICOS, lymphocyte function-associated antigen-1 (LFA-1), CD2, CD7, LIGHT, NKG2C, B7-H3, and any combination thereof.

In embodiments, the intracellular domain comprises a CD3 zeta signaling domain. Embodiments relate to a vector comprising the isolated nucleic acid sequence described herein. Embodiments relate to an isolated cell comprising the isolated nucleic acid sequence described herein.

Embodiments relate to a composition comprising a population of cells including T cells comprising the CAR described herein. Embodiments relate to a CAR encoded by the isolated nucleic acid sequence described herein.

The cells, including CAR cells and modified cells, described herein can be derived from a stem cell. The stem cells may be adult stem cells, embryonic stem cells, or non-human stem cells, cord blood stem cells, progenitor cells, bone marrow stem cells, induced pluripotent stem cells, totipotent stem cells, or hematopoietic stem cells. The cells can also be a dendritic cell, a NK-cell, a B-cell, or a T cell selected from the group consisting of inflammatory T lymphocytes, cytotoxic T lymphocytes, regulatory T lymphocytes, and helper T lymphocytes. In embodiments, the cells can be derived from the group consisting of CD4+ T-lymphocytes and CD8+ T-lymphocytes. Prior to expansion and genetic modification of the cells described herein, a source of cells may be obtained from a subject through a variety of non-limiting methods. T cells may be obtained from a number of non-limiting sources, including peripheral blood mononuclear cells, bone marrow, lymph node tissue, cord blood, thymus tissue, tissue from a site of infection, ascites, pleural effusion, spleen tissue, and tumors. In embodiments, any number of T cell lines available and known to those skilled in the art, can be used. In embodiments, the cells may be derived from a healthy donor, from a patient diagnosed with cancer or from a patient diagnosed with an infection. In embodiments, the cells are part of a mixed population of cells which present different phenotypic characteristics.

The term "stem cell" refers to any type of cell which has the capacity for self-renewal and the ability to differentiate into other kind(s) of cell. For example, a stem cell gives rise either to two daughter stem cells (as occurs in vitro with embryonic stem cells in culture) or to one stem cell and a cell that undergoes differentiation (as occurs e.g. in hematopoietic stem cells, which give rise to blood cells). Different categories of stem cells may be distinguished on the basis of their origin and/or on the extent of their capacity for differentiation into other types of cell. Stem cells can include embryonic stem (ES) cells (i.e., pluripotent stem cells), somatic stem cells, induced pluripotent stem cells, and any other types stem cells.

Pluripotent embryonic stem cells can be found in the inner cell mass of a blastocyst and have high innate capacity for differentiation. For example, pluripotent embryonic stem cells have the potential to form any type of cell in the body. When grown in vitro for long periods of time, ES cells maintain pluripotency, and progeny cells retain the potential for multilineage differentiation.

Somatic stem cells can include fetal stem cells (from the fetus) and adult stem cells (found in various tissues, such as bone marrow). These cells have been regarded as having a capacity for differentiation lower than that of the pluripotent ES cells—with the capacity of fetal stem cells being greater than that of adult stem cells; they apparently differentiate into only a limited number of different types of cells and have been described as multipotent. "Tissue-specific" stem cells normally give rise to only one type of cell. For example, embryonic stem cells can differentiate into blood stem cells (e.g., Hematopoietic stem cells (HSCs)), which can further differentiate into various blood cells (e.g., red blood cells, platelets, white blood cells, etc.).

Induced pluripotent stem cells (iPS cells or iPSCs) can include a type of pluripotent stem cell artificially derived from a non-pluripotent cell (e.g., an adult somatic cell) by inducing expression of specific genes. Induced pluripotent stem cells are similar to naturally occurring pluripotent stem cells, such as embryonic stem (ES) cells, in many aspects, such as the expression of certain stem cell genes and proteins, chromatin methylation patterns, doubling time, embryoid body formation, teratoma formation, viable chimera formation, and potency and differentiability. Induced pluripotent cells can be isolated from adult stomach, liver, skin cells, and blood cells.

In embodiments, the CAR cells, the modified cell, or the cell is a T cell, a NK cell, a macrophage or a dendritic cell. For example, the CAR cells, the modified cell, or the cell is a T cell.

In embodiments, the antigen binding molecule is a T Cell Receptor (TCR). In embodiments, the TCR is modified TCR. In embodiments, the TCR is derived from spontaneously occurring tumor-specific T cells in patients. In embodiments, the TCR binds a tumor antigen. In embodiments, the tumor antigen comprises CEA, gp100, MART-1, p53, MAGE-A3, or NY-ESO-1. In embodiments, the TCR comprises TCRγ and TCRδ chains or TCRα and TCRβ chains. In embodiments, a T cell clone that expresses a TCR with high affinity for the target antigen may be isolated. In embodiments, tumor-infiltrating lymphocytes (TILs) or peripheral blood mononuclear cells (PBMCs) may be cultured in the presence of antigen-presenting cells (APCs) pulsed with a peptide representing an epitope known to elicit a dominant T cell response when presented in the context of a defined HLA allele. High-affinity clones may be then selected on the basis of MHC-peptide tetramer staining and/or the ability to recognize and lyse target cells pulsed with low titrated concentrations of cognate peptide antigen. After the clone has been selected, the TCRα and TCRβ chains or TCRγ and TCRδ chains are identified and isolated by molecular cloning. For example, for TCRα and TCRβ chains, the TCRα and TCRβ gene sequences are then used to generate an expression construct that ideally promotes stable, high-level expression of both TCR chains in human T cells. The transduction vehicle (e.g., a gammaretrovirus or lentivirus) may be then generated and tested for functionality (antigen specificity and functional avidity) and used to produce a clinical lot of the vector. An aliquot of the final product is then used to transduce the target T cell population (generally purified from patient PBMCs), which is expanded before infusion into the subject.

In embodiments, the binding element of the CAR may include any antigen binding moiety that when bound to its cognate antigen, affects a tumor cell for example, it kills the tumor cell, inhibits the growth of the tumor cell, or promotes death of the tumor cell.

The nucleic acid sequences coding for the desired molecules can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

The embodiments of the present disclosure further relate to vectors in which a DNA of the present disclosure is inserted. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity.

Viruses can be used to deliver nucleic acids into a cell in vitro and in vivo (in a subject). Examples of viruses useful for delivery of nucleic acids into cells include retrovirus, adenovirus, herpes simplex virus, vaccinia virus, and adeno-associated virus.

There also exist non-viral methods for deliverying nucleic acids into a cell, for example, electroporation, gene gun, sonoporation, magnetofection, and the use of oligonucleotides, lipoplexes, dendrimers, and inorganic nanoparticles.

The expression of natural or synthetic nucleic acids encoding CARs is typically achieved by operably linking a nucleic acid encoding the CAR polypeptide or portions thereof to one or more promoters and incorporating the construct into an expression vector. The vectors can be suitable for replication and integration into eukaryotes. Typical cloning vectors contain transcription and translation terminators, initiation sequences, and promoters useful for regulation of the expression of the desired nucleic acid sequence.

Additional information related to expression of synthetic nucleic acids encoding CARs and gene transfer into mammalian cells is provided in U.S. Pat. No. 8,906,682, incorporated by reference in its entirety.

Pharmaceutical compositions of the present disclosure may be administered in a manner appropriate to the disease to be treated (or prevented). The quantity and frequency of administration will be determined by such factors as the condition of the patient, and the type and severity of the patient's disease, although appropriate dosages may be determined by clinical trials.

When "an immunologically effective amount", "an anti-tumor effective amount", "a tumor-inhibiting effective amount", or "therapeutic amount" is indicated, the precise amount of the compositions of the present disclosure to be administered can be determined by a physician with consideration of individual differences in age, weight, tumor size, extent of infection or metastasis, and condition of the patient (subject). It can be stated that a pharmaceutical composition comprising the T cells described herein may be administered at a dosage of $10^4$ to $10^9$ cells/kg body weight, preferably $10^9$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly. In embodiments, it may be desired to administer activated T cells to a subject and then subsequently redraw the blood (or have apheresis performed), collect the activated and expanded T cells, and reinfuse the patient with these activated and expanded T cells. This process can be carried out multiple times every few weeks. In embodiments, T cells can be activated from blood draws of from 10 cc to 400 cc. In embodiments, T cells are activated from blood draws of 20 cc, 30 cc, 40 cc, 50 cc, 60 cc, 70 cc, 80 cc, 90 cc, or 100 cc. Not to be bound by theory, using this multiple blood draw/multiple reinfusion protocols, certain populations of T cells may be selected.

The administration of the pharmaceutical compositions described herein may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous (i. v.) injection, or intraperitoneally. In embodiments, the T cell compositions of the present disclosure are administered to a patient by intradermal or subcutaneous injection. In embodiments, the T cell compositions of the present disclosure are preferably administered by i.v. injection. The compositions of T cells may be injected directly into a tumor, lymph node, or site of infection. In embodiments of the present disclosure, cells activated and expanded using the methods described herein, or other methods known in the art where T cells are expanded to therapeutic levels, are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or natalizumab treatment for MS patients or efalizumab treatment for psoriasis patients or other treatments for PML patients. In further embodiments, the T cells of the present disclosure may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, FK506, rapamycin, mycophenolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin). (Liu et al., Cell 66:807-815, 1991; Henderson et al., Immun 73:316-321, 1991; Bierer et al., Curr. Opin. Immun 5:763-773, 1993; Isoniemi (supra)). In embodiments, the cell compositions of the present disclosure are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH. In embodiments, the cell compositions of the present disclosure are administered following B-cell ablative therapy such as agents that react with CD20, e.g., Rituxan. For example, subjects may undergo standard treatment with high dose chemotherapy followed by peripheral blood stem cell transplantation. In embodiments, following the transplant, subjects receive an infusion of the expanded immune cells of the present disclosure. In embodiments, expanded cells are administered before or following surgery.

The dosage of the above treatments to be administered to a patient will vary with the precise nature of the condition being treated and the recipient of the treatment. The scaling of dosages for human administration can be performed according to art-accepted practices by a physician depending on various factors.

Additional information on the methods of cancer treatment using engineered or modified T cells is provided in U.S. Pat. No. 8,906,682, incorporated by reference in its entirety.

In embodiments, the population of cells described herein is used in autologous CAR T cell therapy. In embodiments, the CAR T cell therapy is allogenic CAR T cell therapy, TCR T cell therapy, and NK cell therapy.

Embodiments relate to an in vitro method for preparing modified cells. The method may include obtaining a sample of cells from the subject. For example, the sample may include T cells or T cell progenitors. The method may further include transfecting the cells with a DNA encoding at least a CAR, culturing the population of CAR cells ex vivo in a medium that selectively enhances proliferation of CAR-expressing T cells.

In embodiments, the sample is a cryopreserved sample. In embodiments, the sample of cells is from umbilical cord blood or a peripheral blood sample from the subject. In embodiments, the sample of cells is obtained by apheresis or venipuncture. In embodiments, the sample of cells is a subpopulation of T cells.

Embodiments of the present disclosure relate to treating cancer using Chimeric Antigen Receptor (CAR) cells using a molecule associated with a gene fusion. Embodiments relate to an isolated nucleic acid sequence encoding a chimeric antigen receptor (CAR), wherein the CAR comprises an extracellular domain, a transmembrane domain, and an intracellular domain, wherein the extracellular domain binds a gene fusion antigen of a gene fusion.

As used herein, the term "gene fusion" refers to the fusion of at least a portion of a gene to at least a portion of an additional gene. The gene fusion need not include entire genes or exons of genes. In some instances, gene fusion is associated with alternations in cancer. A gene fusion product refers to a chimeric genomic DNA, a chimeric messenger RNA, a truncated protein or a chimeric protein resulting from a gene fusion. The gene fusion product may be detected by various methods described in U.S. Pat. No. 9,938,582, which is incorporated as a reference herein. A "gene fusion antigen" refers to a truncated protein or a chimeric protein that results from a gene fusion. In embodiments, an epitope of a gene fusion antigen may include a part of the gene fusion antigen or an immunogenic part of another antigen caused by the gene fusion. In embodiments, the gene fusion antigen interacts with, or is part of, cell membranes.

In embodiments, the gene fusion comprises a fusion of at least a portion of a first gene to at least a portion of a second gene. In embodiments, the first gene and the second gene comprise a first gene and a second gene of a fusion listed in Table 3. In embodiments, the gene fusion antigen is associated with a condition listed in the Table 3.

In embodiments, detection of mRNA and protein expression levels of the target molecules (listed in Table 2) in human cells may be performed using experimental methods such as qPCR and FACS. Further, target molecules specifically expressed in the corresponding tumor cells with very low expression or undetectable expression in normal tissue cells may be identified.

In embodiments, In Vitro Killer Assay as well as killing experiment of CAR T Cells Co-Cultured with Antigen-Positive Cells may be performed. CAR T cells may exhibit a killing effect on the corresponding antigen-positive cells, a decrease in the number of corresponding antigen-positive cells co-cultured with CAR T cells, and an increase in the release of IFNγ, TNFα, etc. as compared to control cells that did not express the corresponding antigen.

In embodiments, In Vivo Killer Assay may be performed. For example, mice may be transplanted with corresponding antigen tumor cells, and tumorigenic, transfusion of CAR T cells, and a decrease in mouse tumors and mouse blood IFNγ, TNFα, and other signals may be defected.

Embodiments relate to a method of eliciting and/or enhancing T cell response in a subject having a solid tumor or treating a solid tumor in the subject, the method comprising administering an effective amount of T cells comprising the CAR described herein. In embodiments, the intracellular domain of the CAR comprises a co-stimulatory signaling region that comprises an intracellular domain of a co-stimulatory molecule selected from the group consisting of CD27, CD28, 4-1BB, OX40, CD30, CD40, PD-1, ICOS, lymphocyte function-associated antigen-1 (LFA-1), CD2, CD7, LIGHT, NKG2C, B7-H3, and any combination thereof. In embodiments, the intracellular domain comprises a CD3 zeta signaling domain.

Embodiments relate to a vector comprising the isolated nucleic acid described herein.

Embodiments relate to an isolated cell comprising the isolated nucleic acid sequence described herein. Embodiments relate to a composition comprising a population of T cells comprising the CAR described herein. Embodiments relate to a CAR encoded by the isolated nucleic acid sequence described herein. Embodiments relate to a method of eliciting and/or enhancing T-cell response in a subject or treating a tumor of the subject, the method comprising: administering an effective amount of T cell comprising the CAR described herein.

TABLE 3

| Conditions | Type | Fusion | First gene | Gene description | sublocation | Second Gene | Gene description | sublocation |
| --- | --- | --- | --- | --- | --- | --- | --- | --- |
| breast invasive carcinoma | BRCA | GNAS--NECTIN2 | GNAS | GNAS complex locus | Plasma membrane | NECTIN2 | Nectin cell adhesion molecule 2 | Plasma membrane |
| breast invasive carcinoma | BRCA | FGFR1--ADAM18 | FGFR1 | Fibroblast growth factor receptor 1 | Plasma membrane | ADAM18 | ADAM metallopeptidase domain 18 | Plasma membrane |
| cervical squamous cell carcinoma and endocervical adenocarcinoma | CESC | WHRN--TNC | WHRN | Whirlin | Cytoplasm; Plasma membrane | TNC | Tenascin C | Extracellular; Plasma membrane |

TABLE 3-continued

| Conditions | Type | Fusion | First gene | Gene description | sublocation | Second Gene | Gene description | sublocation |
|---|---|---|---|---|---|---|---|---|
| head and neck squamous cell carcinoma | HNSC | PQLC1--HSBP1L1 | PQLC1 | PQ loop repeat containing 1 | Plasma membrane | HSBP1L1 | Heat shock factor binding protein 1 like 1 | Plasma membrane |
| kidney renal papillary cell carcinoma | KIRP | FNDC3B--BCHE | FNDC3B | Fibronectin type III domain containing 3B | Plasma membrane | BCHE | Butyrylcholinesterase | Plasma membrane |
| brain lower grade glioma | LGG | GRIA4--NAALAD2 | GRIA4 | Glutamate ionotropic receptor AMPA type subunit 4 | Plasma membrane | NAALAD2 | N-acetylated alpha-linked acidic dipeptidase 2 | Plasma membrane |
| brain lower grade glioma | LGG | EPHB2--PDZD4 | EPHB2 | EPH receptor B2 | Plasma membrane | PDZD4 | PDZ domain containing 4 | Cytoplasm; Plasma membrane |
| brain lower grade glioma | LGG | SEC24A--KCNK7 | SEC24A | SEC24 homolog A, COPII coat complex component | Plasma membrane | KCNK7 | Potassium two pore domain channel subfamily K member 7 | Plasma membrane |
| liver hepatocellular carcinoma | LIHC | ACVR1B--ACVRL1 | ACVR1B | Activin A receptor type 1B | Plasma membrane | ACVRL1 | Activin A receptor like type 1 | Plasma membrane |
| liver hepatocellular carcinoma | LIHC | ABCC2--CTNNA3 | ABCC2 | ATP binding cassette subfamily C member 2 | Plasma membrane | CTNNA3 | Catenin alpha 3 | Cytoplasm; Cytoskeleton; Plasma membrane |
| liver hepatocellular carcinoma | LIHC | EFNA1--ADAM15 | EFNA1 | Ephrin A1 | Extracellular; Plasma membrane | ADAM15 | ADAM metallopeptidase domain 15 | Plasma membrane |
| lung adenocarcinoma | LUAD | CPNE8--CADM2 | CPNE8 | Copine 8 | Plasma membrane | CADM2 | Cell adhesion molecule 2 | Plasma membrane |
| lung adenocarcinoma | LUAD | NOTCH2--ADAM30 | NOTCH2 | Notch 2 | Plasma membrane | ADAM30 | ADAM metallopeptidase domain 30 | Plasma membrane |
| lung adenocarcinoma | LUAD | CELSR1--CD52 | CELSR1 | Cadherin EGF LAG seven-pass G-type receptor 1 | Plasma membrane | CD52 | CD52 molecule | Plasma membrane |
| lung adenocarcinoma | LUAD | ILVBL--SLC1A6 | ILVBL | IlvB acetolactate synthase like | Plasma membrane | SLC1A6 | Solute carrier family 1 member 6 | Plasma membrane |
| lung adenocarcinoma | LUAD | F11R--NOS1AP | F11R | F11 receptor | Plasma membrane | NOS1AP | Nitric oxide synthase 1 adaptor protein | Cytoplasm; Plasma membrane |
| lung squamous cell carcinoma | LUSC | CELSR1--SEZ6L | CELSR1 | Cadherin EGF LAG seven-pass G-type receptor 1 | Plasma membrane | SEZ6L | Seizure related 6 homolog like | Plasma membrane |
| lung squamous cell carcinoma | LUSC | KIRREL--CD1A | KIRREL | Kin of IRRE like (Drosophila) | Plasma membrane | CD1A | CD1a molecule | Endosome; Golgi apparatus; Plasma membrane |
| lung squamous cell carcinoma | LUSC | ATP10D--GABRA2 | ATP10D | ATPase phospholipid transporting 10D (putative) | Plasma membrane | GABRA2 | Gamma-aminobutyric acid type A receptor alpha2 subunit | Plasma membrane |
| pancreatic adenocarcinoma | PAAD | ORAI2--SLC47A2 | ORAI2 | ORAI calcium release-activated calcium modulator 2 | Plasma membrane | SLC47A2 | Solute carrier family 47 member 2 | Plasma membrane |
| pheochromocytoma and paraganglioma | PCPG | ADCYAP1R1--GHRHR | ADCYAP1R1 | ADCYAP receptor type I | Plasma membrane | GHRHR | Growth hormone releasing hormone receptor | Plasma membrane |
| pheochromocytoma and paraganglioma | PCPG | TMEM178B--DPP6 | TMEM178B | Transmembrane protein 178B | Plasma membrane | DPP6 | Dipeptidyl peptidase like 6 | Plasma membrane |
| prostate adenocarcinoma | PRAD | ADAM9--RGS20 | ADAM9 | ADAM metallopeptidase domain 9 | Plasma membrane | RGS20 | Regulator of G-protein signaling 20 | Plasma membrane |
| prostate adenocarcinoma | PRAD | FAM16061--VTI1A | FAM160B1 | Family with sequence similarity 160 member B1 | Plasma membrane | VTI1A | Vesicle transport through interaction with t-SNAREs 1A | Plasma membrane |
| prostate adenocarcinoma | PRAD | TMPRSS2--PDE9A | TMPRSS2 | Transmembrane protease, serine 2 | Plasma membrane | PDE9A | Phosphodiesterase 9A | Plasma membrane |
| prostate adenocarcinoma | PRAD | PDE9A--TMPRSS2 | PDE9A | Phosphodiesterase 9A | Plasma membrane | TMPRSS2 | Transmembrane protease, serine 2 | Plasma membrane |
| rectum adenocarcinoma | READ | LHFPL2--PTPRK | LHFPL2 | Lipoma HMGIC fusion partner-like 2 | Plasma membrane | PTPRK | Protein tyrosine phosphatase, receptor type K | Plasma membrane |

TABLE 3-continued

| Conditions | Type | Fusion | First gene | Gene description | sublocation | Second Gene | Gene description | sublocation |
|---|---|---|---|---|---|---|---|---|
| sarcoma | SARC | TM7SF3--KCNC2 | TM7SF3 | Transmembrane 7 superfamily member 3 | Plasma membrane | KCNC2 | Potassium voltage-gated channel subfamily C member 2 | Plasma membrane |
| sarcoma | SARC | MPZL1--TNFSF4 | MPZL1 | Myelin protein zero like 1 | Plasma membrane | TNFSF4 | Tumor necrosis factor superfamily member 4 | Plasma membrane |
| sarcoma | SARC | GNG7--PAQR5 | GNG7 | G protein subunit gamma 7 | Plasma membrane | PAQR5 | Progestin and adipoQ receptor family member 5 | Plasma membrane |
| sarcoma | SARC | KIRREL--CD1A | KIRREL | Kin of IRRE like (Drosophila) | Plasma membrane | CD1A | CD1a molecule | Endosome; Golgi apparatus; Plasma membrane |
| sarcoma | SARC | P2RX5--TRPV1 | P2RX5 | Purinergic receptor P2X 5 | Plasma membrane | TRPV1 | Transient receptor potential cation channel subfamily V member 1 | Plasma membrane |
| skin cutaneous melanoma | SKCM | PTPRG--SYNPR | PTPRG | Protein tyrosine phosphatase, receptor type G | Plasma membrane | SYNPR | Synaptoporin | Plasma membrane |

In embodiments, the CAR molecules described herein comprise one or more complementarity-determining regions (CDRs) for binding an antigen of interest. CDRs are part of the variable domains in immunoglobulins and T cell receptors for binding a specific antigen. There are three CDRs for each variable domain. Since there is a variable heavy domain and a variable light domain, there are six CDRs for binding an antigen. Further since an antibody has two heavy chains and two light chains, an antibody has twelve CDRs altogether for binding antigens. In embodiments, the CAR molecules comprise one or more CDRs of SIGLEC15, SLC6A3, KISS1R, QRFPR, GPR119, CLDN6, UPK2, ADAM12, SLC45A3, ACPP, MUC21, MUC16, MS4A12, or ALPP.

The present disclosure describes modified cells that include one or more different antigen binding domains. The modified cells can include at least two different antigen binding domains: a first antigen binding domain for expanding and/or maintaining the genetically modified cells, and a second antigen binding domain for killing a target cell, such as a tumor cell. For example, the first antigen binding domain binds a surface marker, such as a cell surface molecule of a white blood cell (WBC) (e.g., CD19), and the second antigen binding domain binds a target antigen on tumor cells. In embodiments, the cell surface molecule is a surface antigen of a WBC. In embodiments, the target antigen on tumor cells comprise one or more of SIGLEC15, SLC6A3, KISS1R, QRFPR, GPR119, CLDN6, UPK2, ADAM12, SLC45A3, ACPP, MUC21, MUC16, MS4A12, or ALPP. The at least two antigen binding domains may be located on the same or different modified cells. For example, the modified cells may include a modified cell including a CAR binding CD19, a modified cell including a CAR binding to ACPP, a modified cell including a CAR binding CD19 and ACPP, and/or a modified cell including two CARs that respectively bind CD19 and ACPP. In embodiments, the modified cells may be used to treat a subject having cancer.

In embodiments, the modified cells described herein includes a CAR molecule comprising at least two different antigen binding domains. The CAR molecule can be a bispecific CAR molecule. For example, the two antigen binding domains can be on the same CAR molecule, on different CAR molecules, or on a CAR molecule and T cell receptor (TCR). A single CAR can include at least two different antigen binding domains, or the two different antigen binding domains are each on a separate CAR molecule. The at least two different antigen binding domains can be on the same CAR molecule or different CAR molecules, but in the same modified cell. Moreover, the at least two different antigen binding domains can be on a CAR molecule and a T cell receptor in the same modified cell. In embodiments, the bispecific CAR molecule may include a binding domain binding an antigen of WBC (e.g., CD19) and a binding domain binding a solid tumor antigen. In embodiments, the bispecific CAR molecule may include two binding domains binding two different solid tumor antigens.

In embodiments, the at least two different antigen binding domains are on different CAR molecules which are expressed by different modified cells. Further, the one or more different antigen binding domains are on a CAR molecule and a T cell receptor, which are expressed by different modified cells.

Related sequences are provided in this Application and Innovative Cellular Therapeutics' PCT Patent Applications Nos: PCT/CN2016/075061, PCT/CN2018/08891, and PCT/US19/13068, which are incorporated by reference in their entirety.

The present disclosure is further described by reference to the following exemplary embodiments and examples. These exemplary embodiments and examples are provided for purposes of illustration only and are not intended to be limiting unless otherwise specified. Thus, the present disclosure should in no way be construed as being limited to the following exemplary embodiments and examples, but rather, should be construed to encompass any and all variations which become evident as a result of the teaching provided herein.

EXEMPLARY EMBODIMENTS

The following are exemplary embodiments:
1. An isolated nucleic acid sequence encoding a chimeric antigen receptor (CAR), wherein the CAR comprises an extracellular domain, a transmembrane domain, and an intracellular domain, wherein the extracellular domain binds an antigen of a solid tumor.

2. The isolated nucleic acid sequence of embodiment 1, wherein the extracellular domain binds SIGLEC15.
3. The isolated nucleic acid sequence of embodiment 1, wherein the extracellular domain binds SIGLEC15 having the amino acid sequence of SEQ ID NO: 17.
4. The isolated nucleic acid sequence of embodiment 1, wherein the extracellular domain comprises one of the amino acid sequences of SEQ ID NOs: 45-56.
5. A method of eliciting and/or enhancing T-cell response in a subject having a solid tumor or treating a solid tumor in the subject, the method comprising administering an effective amount of T cells comprising the CAR of any one of embodiments 2-4.
6. The isolated nucleic acid sequence or the method of any one of embodiments 1-5, wherein the tumor is associated with urothelial cancer.
7. The isolated nucleic acid sequence of embodiment 1, wherein the extracellular domain binds KISS1R.
8. The isolated nucleic acid sequence of embodiment 1, wherein the extracellular domain binds KISS1R having the amino acid sequence of SEQ ID NO: 19.
9. The isolated nucleic acid sequence of embodiment 1, wherein the extracellular domain comprises one of the amino acid sequences of SEQ ID NOs: 71 and 72.
10. A method of eliciting and/or enhancing T-cell response in a subject having the solid tumor or treating the solid tumor of the subject, the method comprising administering an effective amount of T cell comprising the CAR of any one of embodiments 7-9.
11. The isolated nucleic acid sequence or the method of any one of embodiments 1 and 7-10, wherein the tumor is associated with renal cancer.
12. The isolated nucleic acid sequence of embodiment 1, wherein the extracellular domain binds CLDN6.
13. The isolated nucleic acid sequence of embodiment 1, wherein the extracellular domain binds CLDN6 having the amino acid sequence of SEQ ID NO: 22.
14. The isolated nucleic acid sequence of embodiment 1, wherein the extracellular domain comprises one of the amino acid sequences of SEQ ID NOs: 29-44.
15. A method of eliciting and/or enhancing T cell response in a subject having a solid tumor or treating a solid tumor in the subject, the method comprising administering an effective amount of T cells comprising the CAR of any one of embodiments 12-15.
16. The isolated nucleic acid sequence or the method of any one of embodiments 1 and 12-16, wherein the tumor is associated with endometrial cancer and/or urothelial cancer.
17. The isolated nucleic acid sequence of embodiment 1, wherein the extracellular domain binds MUC16.
18. The isolated nucleic acid sequence of embodiment 1, wherein the extracellular domain binds MUC16 having the amino acid sequence of SEQ ID NO: 6.
19. The isolated nucleic acid sequence of embodiment 1, wherein the extracellular domain comprises one of the amino acid sequences of SEQ ID NOs: 63-70.
20. A method of eliciting and/or enhancing T-cell response in a subject having the solid tumor or treating the solid tumor of the subject, the method comprising administering an effective amount of T cell comprising the CAR of any one of embodiments 17-19.
21. The isolated nucleic acid sequence or the method of any one of embodiments 1 and 17-20, wherein the tumor is associated with ovarian cancer.
22. The isolated nucleic acid sequence of embodiment 1, wherein the extracellular domain binds SLC6A3.
23. The isolated nucleic acid sequence of embodiment 1, wherein the extracellular domain binds SLC6A3 having the amino acid sequence of SEQ ID NO: 18.
24. A method of eliciting and/or enhancing T-cell response in a subject having the solid tumor or treating the solid tumor of the subject, the method comprising administering an effective amount of T cell comprising the CAR of any one of embodiments 22 and 23.
25. The isolated nucleic acid sequence or the method of any one of embodiments 1 and 22-24, wherein the tumor is associated with renal cancer.
26. The isolated nucleic acid sequence of embodiment 1, wherein the extracellular domain binds QRFPR.
27 The isolated nucleic acid sequence of embodiment 1, wherein the extracellular domain binds QRFPR having the amino acid sequence of SEQ ID NO: 20.
28. A method of eliciting and/or enhancing T-cell response in a subject having the solid tumor or treating the solid tumor of the subject, the method comprising administering an effective amount of T cell comprising the CAR of any one of embodiments 26 and 27.
29. The isolated nucleic acid sequence or the method of any one of embodiments 1 and 26-28, wherein the tumor is associated with renal cancer.
30. The isolated nucleic acid sequence of embodiment 1, wherein the extracellular domain binds GPR119.
31 The isolated nucleic acid sequence of embodiment 1, wherein the extracellular domain binds GPR119 having the amino acid sequence of SEQ ID NO: 21.
32. A method of eliciting and/or enhancing T-cell response in a subject having the solid tumor or treating the solid tumor of the subject, the method comprising administering an effective amount of T cell comprising the CAR of any one of embodiments 30 and 31.
33. The isolated nucleic acid sequence or the method of any one of embodiments 1 and 30-32, wherein the tumor is associated with pancreatic cancer.
34. The isolated nucleic acid sequence of embodiment 1, wherein the extracellular domain binds UPK2.
35 The isolated nucleic acid sequence of embodiment 1, wherein the extracellular domain binds UPK2 having the amino acid sequence of SEQ ID NO: 1.
36. A method of eliciting and/or enhancing T-cell response in a subject having the solid tumor or treating the solid tumor of the subject, the method comprising administering an effective amount of T cell comprising the CAR of any one of embodiments 34 and 35.
37. The isolated nucleic acid sequence or the method of any one of embodiments 1 and 34-36, wherein the tumor is associated with urothelial cancer and/or bladder cancer.
38. The isolated nucleic acid sequence of embodiment 1, wherein the extracellular domain binds ADAM12.
39 The isolated nucleic acid sequence of embodiment 1, wherein the extracellular domain binds ADAM12 having the amino acid sequence of SEQ ID NO: 2.
40. A method of eliciting and/or enhancing T-cell response in a subject having the solid tumor or treating the solid tumor of the subject, the method comprising administering an effective amount of T cell comprising the CAR of any one of embodiments 38 and 39.
41. The isolated nucleic acid sequence or the method of any one of embodiments 1 and 38-40, wherein the tumor is associated with breast cancer and/or pancreatic cancer.
42. The isolated nucleic acid sequence of embodiment 1, wherein the extracellular domain binds SLC45A3.

43. The isolated nucleic acid sequence of embodiment 1, wherein the extracellular domain binds SLC45A3 having the amino acid sequence of SEQ ID NO: 3.

44. A method of eliciting and/or enhancing T-cell response in a subject having the solid tumor or treating the solid tumor of the subject, the method comprising administering an effective amount of T cell comprising the CAR of any one of embodiments 42 and 43.

45. The isolated nucleic acid sequence or the method of any one of embodiments 1 and 42-44, wherein the tumor is associated with prostate cancer.

46. The isolated nucleic acid sequence of embodiment 1, wherein the extracellular domain binds ACPP.

47. The isolated nucleic acid sequence of embodiment 1, wherein the extracellular domain binds ACPP having the amino acid sequence of SEQ ID NO: 4.

48. A method of eliciting and/or enhancing T-cell response in a subject having the solid tumor or treating the solid tumor of the subject, the method comprising administering an effective amount of T cell comprising the CAR of any one of embodiments 46 and 47.

49. The isolated nucleic acid sequence or the method of any one of embodiments 1 and 46-48, wherein the tumor is associated with prostate cancer.

50. The isolated nucleic acid sequence of embodiment 1, wherein the extracellular domain binds MUC21.

51. The isolated nucleic acid sequence of embodiment 1, wherein the extracellular domain binds MUC21 having the amino acid sequence of SEQ ID NO: 5.

52. A method of eliciting and/or enhancing T-cell response in a subject having the solid tumor or treating the solid tumor of the subject, the method comprising administering an effective amount of T cell comprising the CAR of any one of embodiments 50 and 51.

53. The isolated nucleic acid sequence or the method of any one of embodiments 1 and 50-52, wherein the tumor is associated with esophageal cancer.

54. The isolated nucleic acid sequence of embodiment 1, wherein the extracellular domain binds MS4A12.

55. The isolated nucleic acid sequence of embodiment 1, wherein the extracellular domain binds MS4A12 having the amino acid sequence of SEQ ID NO: 7.

56. A method of eliciting and/or enhancing T-cell response in a subject having the solid tumor or treating the solid tumor of the subject, the method comprising administering an effective amount of T cell comprising the CAR of any one of embodiments 54 and 55.

57. The isolated nucleic acid sequence or the method of any one of embodiments 1 and 54-56, wherein the tumor is associated with colorectal cancer.

58. The isolated nucleic acid sequence of embodiment 1, wherein the extracellular domain binds ALPP.

59. The isolated nucleic acid sequence of embodiment 1, wherein the extracellular domain binds ALPP having the amino acid sequence of SEQ ID NO: 8.

60. A method of eliciting and/or enhancing T-cell response in a subject having the solid tumor or treating the solid tumor of the subject, the method comprising administering an effective amount of T cell comprising the CAR of any one of embodiments 58 and 59.

61. The isolated nucleic acid sequence or the method of any one of embodiments 1 and 58-60, wherein the tumor is associated with endometrial cancer.

62. The isolated nucleic acid sequence of embodiment 1, wherein the extracellular domain binds SLC2A14.

63. The isolated nucleic acid sequence of embodiment 1, wherein the extracellular domain binds SLC2A14 having the amino acid sequence of SEQ ID NO: 9.

64. A method of eliciting and/or enhancing T-cell response in a subject having the solid tumor or treating the solid tumor of the subject, the method comprising administering an effective amount of T cell comprising the CAR of any one of embodiments 62 and 63.

65. The isolated nucleic acid sequence or the method of any one of embodiments 1 and 62-64, wherein the tumor is associated with testicular cancer.

66. The isolated nucleic acid sequence of embodiment 1, wherein the extracellular domain binds GS1-259H13.2.

67. The isolated nucleic acid sequence of embodiment 1, wherein the extracellular domain binds GS1-259H13.2 having the amino acid sequence of SEQ ID NO: 10.

68. A method of eliciting and/or enhancing T-cell response in a subject having the solid tumor or treating the solid tumor of the subject, the method comprising administering an effective amount of T cell comprising the CAR of any one of embodiments 66 and 67.

69. The isolated nucleic acid sequence or the method of any one of embodiments 1 and 66-69, wherein the tumor is associated with thyroid cancer or glioma, or testicular cancer.

70. The isolated nucleic acid sequence of embodiment 1, wherein the extracellular domain binds ERVFRD-1.

71. The isolated nucleic acid sequence of embodiment 1, wherein the extracellular domain binds ERVFRD-1 having the amino acid sequence of SEQ ID NO: 11.

72. A method of eliciting and/or enhancing T-cell response in a subject having the solid tumor or treating the solid tumor of the subject, the method comprising administering an effective amount of T cell comprising the CAR of any one of embodiments 70 and 71.

73. The isolated nucleic acid sequence or the method of any one of embodiments 1 and 70-72, wherein the tumor is associated with kidney cancer or Urethral cancer.

74. The isolated nucleic acid sequence of embodiment 1, wherein the extracellular domain binds ADGRG2.

75. The isolated nucleic acid sequence of embodiment 1, wherein the extracellular domain binds ADGRG2 having the amino acid sequence of SEQ ID NO: 12.

76. A method of eliciting and/or enhancing T-cell response in a subject having the solid tumor or treating the solid tumor of the subject, the method comprising administering an effective amount of T cell comprising the CAR of any one of embodiments 74 and 75.

77. The isolated nucleic acid sequence or the method of any one of embodiments 1 and 74-76, wherein the tumor is associated with ovarian cancer.

78. The isolated nucleic acid sequence of embodiment 1, wherein the extracellular domain binds ECEL1.

79. The isolated nucleic acid sequence of embodiment 1, wherein the extracellular domain binds ECEL1 having the amino acid sequence of SEQ ID NO: 13.

80. A method of eliciting and/or enhancing T-cell response in a subject having the solid tumor or treating the solid tumor of the subject, the method comprising administering an effective amount of T cell comprising the CAR of any one of embodiments 78 and 29.

81. The isolated nucleic acid sequence or the method of any one of embodiments 1 and 78-80, wherein the tumor is associated with endometrial cancer.

82. The isolated nucleic acid sequence of embodiment 1, wherein the extracellular domain binds CHRNA2.

83 The isolated nucleic acid sequence of embodiment 1, wherein the extracellular domain binds CHRNA2 having the amino acid sequence of SEQ ID NO: 14.
84. A method of eliciting and/or enhancing T-cell response in a subject having the solid tumor or treating the solid tumor of the subject, the method comprising administering an effective amount of T cell comprising the CAR of any one of embodiments 82 and 83.
85. The isolated nucleic acid sequence or the method of any one of embodiments 1 and 82-84, wherein the tumor is associated with prostate cancer.
86. The isolated nucleic acid sequence of embodiment 1, wherein the extracellular domain binds GP2.
87 The isolated nucleic acid sequence of embodiment 1, wherein the extracellular domain binds GP2 having the amino acid sequence of SEQ ID NO: 15.
88. A method of eliciting and/or enhancing T-cell response in a subject having the solid tumor or treating the solid tumor of the subject, the method comprising administering an effective amount of T cell comprising the CAR of any one of embodiments 86 and 87.
89. The isolated nucleic acid sequence or the method of any one of embodiments 1 and 86-88, wherein the tumor is associated with pancreatic cancer.
90. The isolated nucleic acid sequence of embodiment 1, wherein the extracellular domain binds PSG9.
91 The isolated nucleic acid sequence of embodiment 1, wherein the extracellular domain binds PSG9 having the amino acid sequence of SEQ ID NO: 16.
92. A method of eliciting and/or enhancing T-cell response in a subject having the solid tumor or treating the solid tumor of the subject, the method comprising administering an effective amount of T cell comprising the CAR of any one of embodiments 90 and 91.
93. The isolated nucleic acid sequence or the method of any one of embodiments 1 and 90-92, wherein the tumor is associated with Kidney cancer or liver cancer.
94. The isolated nucleic acid sequence or the method of any one of embodiments 1-93, wherein the intracellular domain comprising a co-stimulatory signaling region that comprises an intracellular domain of a co-stimulatory molecule selected from the group consisting of CD27, CD28, 4-1BB, OX40, CD30, CD40, PD-1, ICOS, lymphocyte function-associated antigen-1 (LFA-1), CD2, CD7, LIGHT, NKG2C, B7-H3, and any combination thereof.
95. The isolated nucleic acid sequence or the method of any one of embodiments 1-93, wherein the intracellular domain comprises a CD3 zeta signaling domain.
96. A vector comprising the isolated nucleic acid sequence of any one of embodiments 1-93.
97. An isolated cell comprising the isolated nucleic acid sequence of any one of embodiments 1-93.
98. A composition comprising a population of T cells comprising the CAR of any one of embodiments 96 or 97.
99. A CAR encoded by the isolated nucleic acid sequence of any one of embodiments 1-93.
100. An isolated nucleic acid sequence encoding a chimeric antigen receptor (CAR), wherein the CAR comprises an extracellular domain, a transmembrane domain, and an intracellular domain, wherein the extracellular domain binds a gene fusion antigen of a gene fusion.
101. The isolated nucleic acid sequence of claim 100, wherein the gene fusion comprises a fusion of at least a portion of a first gene to at least a portion of a second gene.
102. The isolated nucleic acid sequence of embodiment 101, wherein the first gene and the second gene comprise a first gene and a second gene of a fusion listed in Table 5.
103. The isolated nucleic acid sequence of embodiment 102, wherein the gene fusion antigen is associated with a condition listed in the Table 3.
104. A method of eliciting and/or enhancing T-cell response in a subject having the solid tumor or treating the solid tumor of the subject, the method comprising administering an effective amount of T cell comprising the CAR of any of embodiments 100-103.
105. The isolated nucleic acid sequence or the method of any one of embodiments 100-103, wherein the intracellular domain comprising a co-stimulatory signaling region that comprises an intracellular domain of a co-stimulatory molecule selected from the group consisting of CD27, CD28, 4-1BB, OX40, CD30, CD40, PD-1, ICOS, lymphocyte function-associated antigen-1 (LFA-1), CD2, CD7, LIGHT, NKG2C, B7-H3, and any combination thereof.
106. The isolated nucleic acid sequence or the method of any one of embodiments 100-103, wherein the intracellular domain comprises a CD3 zeta signaling domain.
107. A vector comprising the isolated nucleic acid sequence of any one of embodiments 100-106.
108. An isolated cell comprising the isolated nucleic acid sequence of any one of embodiments 100-106.
109. A composition comprising a population of T cells comprising the CAR of any one of embodiments 8 or 9.
110. A CAR encoded by the isolated nucleic acid sequence of any one of embodiments 100-106.
111. The isolated nucleic acid sequence, modified T cell or the method of one of embodiments 1-110, wherein the cell or modified cell is a T cell derived from a healthy donor or a subject having cancer, and the modified T cell comprises a dominant negative form of a receptor associated with an immune checkpoint inhibitor.
112. The isolated nucleic acid sequence, modified T cell or the method of one of embodiments 1-110, wherein the immune checkpoint inhibitor is selected from the group consisting of programmed death 1 (PD-1), cytotoxic T lymphocyte antigen-4 (CTLA-4), B- and T-lymphocyte attenuator (BTLA), T cell immunoglobulin mucin-3 (TIM-3), lymphocyte-activation protein 3 (LAG-3), T cell immunoreceptor with Ig and ITIM domains (TIGIT), leukocyte-associated immunoglobulin-like receptor 1 (LAIRI), natural killer cell receptor 2B4 (2B4), and CD 160.
113. The isolated nucleic acid sequence, modified T cell or the method of embodiment 112, wherein immune checkpoint inhibitor is modified PD-1.
114. The isolated nucleic acid sequence, modified T cell or the method of embodiment 112, wherein the modified PD-1 lacks a functional PD-1 intracellular domain for PD-1 signal transduction, interferes with a pathway between PD-1 of a human T cell of the human cells and PD-L1 of a certain cell, comprises or is a PD-1 extracellular domain or a PD-1 transmembrane domain, or a combination thereof, or a modified PD-1 intracellular domain comprising a substitution or deletion as compared to a wild-type PD-1 intracellular domain, or comprises or is a soluble receptor comprising a PD-1 extracellular domain that binds PD-L1 of a certain cell.
115. The isolated nucleic acid sequence, modified T cell or the method of embodiment 112, wherein an inhibitory effect of PD-L1 on cytokine production of the human T cells of the population is less than an inhibitory effect of PD-L1 on cytokine production of human T cells that do not comprise at least a part of the nucleic acid sequence that encodes the modified PD-1.
116. The isolated nucleic acid sequence, modified T cell or the method of one of embodiments 1-104, wherein the modified T cell is engineered to express and secrete a therapeutic agent such as a cytokine.

117. The isolated nucleic acid sequence, modified T cell or the method of embodiment 116, wherein the therapeutic agent that is or comprises IFN-γ.

118. The isolated nucleic acid sequence, modified T cell or the method of embodiment 116, wherein the therapeutic agent is or comprises at least one of IL-6 or IFN-γ, IL-17, and CCL19.

119. The isolated nucleic acid sequence, modified T cell or the method of embodiment 116, wherein the therapeutic agent that is or comprises IL-15 or IL-12, or a combination thereof.

120. The isolated nucleic acid sequence, modified T cell or the method of embodiment 116, wherein the small protein or the therapeutic agent is or comprises a recombinant or native cytokine.

121. The isolated nucleic acid sequence, modified T cell or the method of embodiment 116, wherein the therapeutic agent comprises a FC fusion protein associated with a small protein.

122. The isolated nucleic acid sequence, modified T cell or the method of embodiment 116, wherein the small protein is or comprises IL-12, IL-15, IL-6 or IFN-γ.

123. The isolated nucleic acid sequence, modified T cell or the method of embodiment 116, wherein the therapeutic agent is regulated by Hif1a, NFAT, FOXP3, and/or NFkB.

124. The isolated nucleic acid sequence, modified T cell or the method of embodiment 116, wherein the small protein or the therapeutic agent is or comprises two or more recombinant or native cytokines are collected via 2A or/IRES component.

125. The isolated nucleic acid sequence, modified T cell or the method of one of embodiments 1-124, wherein the modified T cell comprises a first targeting vector and a second targeting vector, the first targeting vector comprising a nucleic acid sequence encoding a CAR binding a blood antigen and the therapeutic agent, and the second targeting vector comprises a nucleic acid sequence encoding a CAR biding solid tumor antigen and a dominant negative form of the immune checkpoint molecule.

126. The isolated nucleic acid sequence, modified T cell or the method of one of embodiments 1-124, wherein the modified T cell comprises a first targeting vector and a second targeting vector, the first targeting vector comprising a nucleic acid sequence encoding a CAR binding CD19 and the therapeutic agent, and the second targeting vector comprises a nucleic acid sequence encoding a CAR biding UPK2, ACPP, SIGLEC15 or KISS1R and a dominant negative form of PD-1.

127. The isolated nucleic acid sequence, modified T cell or the method of one of embodiments 1-124, wherein the modified T cell comprises a first targeting vector and a second targeting vector, the first targeting vector comprising a nucleic acid sequence encoding a CAR binding a blood antigen, and the second targeting vector comprises a nucleic acid sequence encoding a CAR biding solid tumor antigen.

128. The isolated nucleic acid sequence, modified T cell or the method of one of embodiments 1-124, wherein the modified T cell comprises a first targeting vector and a second targeting vector, the first targeting vector comprising a nucleic acid sequence encoding a CAR binding a B cell antigen, and the second targeting vector comprises a nucleic acid sequence encoding a CAR biding solid tumor antigen.

129. The isolated nucleic acid sequence, modified T cell or the method of embodiment 128, wherein the solid tumor antigen is at least one of antigens listed in Table 2, and/or the B cell antigen is CD19, CD20, CD22, or BCMA.

130. The isolated nucleic acid sequence, modified T cell or the method of embodiment 128, wherein the solid tumor antigen comprises at least one of antigens listed in Table 2.

131. A method of eliciting and/or enhancing T cell expansion in a subject in need thereof, 0 the method comprising administering an effective amount of the composition of T cells of embodiment 130 to the subject, the subject having a higher level of T cell expansion as compared with a subject that is administered an effective amount of the CAR T cells that do not have the CAR binding the B cell antigen.

132. The isolated nucleic acid sequence, modified T cell or the method of one of embodiments 1-131, wherein the modified T cell comprises a nucleic acid sequence encoding hTERT, SV40LT, or a combination thereof.

133. The isolated nucleic acid sequence, modified T cell or the method of embodiment 132, wherein the modified T cell is more proliferable than T cells without nucleic acid sequence.

134. The isolated nucleic acid sequence, modified T cell or the method of embodiment 133, wherein the proliferable cell remains functions of normal T cells/CAR T cells such as cell therapy functions.

135. The isolated nucleic acid sequence, modified T cell or the method of embodiment 133, wherein the T cell comprises a CAR and is cultured in the presence of an agent that is recognized by the extracellular domain of the CAR, thereby producing a modified CAR cell.

136. The isolated nucleic acid sequence, modified T cell or the method of one of embodiments 1-135, wherein integration of the nucleic acid sequence encoding hTERT, the nucleic acid encoding SV40LT, or a combination thereof includes genomic integration of the nucleic acid sequence encoding hTERT, a nucleic acid encoding SV40LT, or a combination thereof and constitutive expression of hTERT, SV40LT, or a combination thereof.

137. The isolated nucleic acid sequence, modified T cell or the method of one of embodiments 1-136, wherein expression of hTERT, SV40LT, or a combination thereof, is regulated by an inducible expression system such as a rtTA-TRE system.

138. The isolated nucleic acid sequence, modified T cell or the method of one of embodiments 1-136, wherein modified T cell comprises a nucleic acid sequence encoding a suicide gene such as a an HSV-TK system.

139. The isolated nucleic acid sequence, modified T cell or the method of one of embodiments 1-138, wherein the cell has a reduced graft-versus-host disease (GVHD) response in a bioincompatible human recipient as compared to the GVHD response of the primary human T cell.

140. The isolated nucleic acid sequence, modified T cell or the method of one of embodiments 1-138, wherein the cell has a reduced expression of endogenous TRAC gene.

141. A antibody that binds ACPP, wherein the antibody comprises a heavy chain variable region (HVR) sequence comprising the amino acid sequence of SEQ ID NO: 83, 87, 89, or 85 and a light chain variable region (LVR) sequence comprising the amino acid sequences of SEQ ID NO: 82, 86, 88, or 84.

142. The antibody of embodiment 141, wherein the HVR comprises the amino acid sequences of SEQ ID NO: 82, and the comprises the amino acid sequence of SEQ ID NO: 83.

143. The antibody of embodiment 141, wherein the HVR comprises the amino acid sequences of SEQ ID NO: 86, and the HVR comprises the amino acid sequence of SEQ ID NO: 87.

144. The antibody of embodiment 141, wherein the HVR comprises the amino acid sequences of SEQ ID NO: 88, and the HVR comprises the amino acid sequence of SEQ ID NO: 89.

145. The antibody of embodiment 141, wherein the HVR comprises the amino acid sequences of SEQ ID NO: 84, and the HVR comprises the amino acid sequence of SEQ ID NO: 85.

146. The antibody of one of embodiments 141-145, wherein the antibody is a scFv comprising the LVR, a linker, and the HVR.

147. The antibody of one of embodiments 141-146, wherein the HVR is joined to a human IgG chain constant region.

148. The antibody of embodiment 147, wherein the human IgG is IgG1 or IgG3.

149. The antibody of one of embodiments 141-146, wherein the antibody is a conjugated to a cytotoxic agent.

150. The antibody of one of embodiments 141-146, wherein the cytotoxic agent is a radioactive isotope or a toxin.

151. The antibody of one of embodiments 141-146, wherein the antibody is conjugated to a sequence derived from 4-1BB or CD28, or a combination thereof.

152. The antibody of one of embodiments 141-146, wherein the antibody or fragment is produced in HEK293 cells.

153. A composition comprising the antibody or fragment of one of embodiments 141-152 and a pharmaceutically acceptable carrier.

154. An article of manufacture comprising a container and a composition contained therein, wherein the composition comprises the antibody or fragment of one of embodiments 141-152.

155. A polynucleotide that encodes the antibody or fragment of one of embodiments 141-152.

156. An expression vector encoding the antibody or fragment of one of embodiments 141-152.

157. A host cell comprising a nucleic acid of one of embodiments 155 and 156.

158. A method of treating a subject with cancer, comprising administering to the subject a therapeutically effective amount of the antibody or fragment of one of embodiments 141-152.

159. A method of treating a subject having prostate cancer, comprising administering to the subject a therapeutically effective amount of the antibody or fragment of one of embodiments 141-152.

160. A modified cell comprising a chimeric antigen receptor (CAR) comprising an antigen recognition domain comprising the antibody or fragment of one of embodiments 141-152 and an intracellular domain.

161. A method for treating a subject having cancer, the method comprising: administering a modified cell to the subject, wherein the modified cell comprises an antigen recognition domain comprising the antibody or fragment of one of embodiments 141-152 and an intracellular domain.

162. The modified cell or the method of one of embodiments 160 and 161, wherein the modified cell comprises at least one of a B cell, a T cell, an NK cell, an embryonic cell, a dendritic cell or a macrophage.

163. The method of embodiment 162, wherein the genetically modified cell replicates in vivo.

164. The method of embodiment 161, wherein the modified cell forms memory cells in the subject.

165. The method of embodiment 161, wherein the modified cells are administered intravenously to the subject.

166. The method of embodiment 161, wherein the modified cells persist in the subject.

167. The method of embodiment 161, wherein the modified cell is an autologous T cell.

168. A modified cell comprising a nucleic acid sequence encoding a chimeric antigen receptor (CAR), wherein the CAR comprises an ACPP antigen binding domain comprising the amino acid sequence of SEQ ID NO:83 and 82, 87 and 86, 89 and 88, or 85 and 84.

169. The modified cell of embodiment 168, wherein the CAR further comprises a transmembrane domain, and an intracellular domain and a signaling domain of a co-stimulatory molecule.

170. The modified cell of embodiment 169, wherein the intracellular domain comprising a CD3-zeta signaling domain 171. The modified cell of embodiment 169, wherein the antigen binding fragment is a scFv.

172. The modified cell of embodiment 169, wherein the scFv comprises the amino acid sequence of SEQ ID NO:83 and 82.

173. The modified cell of embodiment 169, wherein the scFv comprises the amino acid sequence of SEQ ID NO:87 and 86.

174. The modified cell of embodiment 169, wherein the scFv comprises the amino acid sequence of SEQ ID NO:89 and 88.

175. The human T cell of embodiment 169, wherein the scFv comprises the amino acid sequence of SEQ ID NO:85 and 84.

176. The modified cell of embodiment 167, wherein the T cell comprises a vector that comprises the nucleic acid sequence.

177. The modified cell of embodiment 176, wherein the vector is a lentiviral vector.

178. The modified cell of one of embodiments 168-177, wherein the modified cell comprises an additional CAR, and the additional CAR binds an antigen of a white blood cell.

179. The modified cell of embodiment 178, wherein the antigen of the white blood cell is a B cell antigen.

180. The modified cell of embodiment 179, wherein the antigen of the B cell antigen is CD19, CD20, CD22, or BCMA.

181. The modified cell of one of embodiments 168-180, wherein the modified cell comprises a dominant negative PD-1.

182. The modified cell one of embodiments 168-180, wherein the modified cell comprises a modified PD-1 lacking a functional PD-1 intracellular domain.

183. The modified cell of one of embodiments 168-180, wherein the intracellular domain comprises a co-stimulatory signaling region that comprises an intracellular domain of a co-stimulatory molecule selected from the group consisting of CD27, CD28, 4-1BB, OX40, CD30, CD40, PD-1, ICOS, lymphocyte function-associated antigen-1 (LFA-1), CD2, CD7, LIGHT, NKG2C, B7-H3, and any combination thereof.

184. The modified cell of embodiment 183, wherein the antigen is Epidermal growth factor receptor (EGFR), Variant III of the epidermal growth factor receptor (EGFRvIII), Human epidermal growth factor receptor 2 (HER2), Mesothelin (MSLN), Prostate-specific membrane antigen (PSMA), Carcinoembryonic antigen (CEA), Disialoganglioside 2 (GD2), Interleukin-13Ra2 (IL13 Ra2), Glypican-3 (GPC3), Carbonic anhydrase IX (CAIX), L1 cell adhesion molecule (L1-CAM), Cancer antigen 125 (CA125), Cluster of differentiation 133 (CD133), Fibroblast activation protein (FAP), Cancer/testis antigen 1B (CTAG1B), Mucin 1 (MUC1), Folate receptor-α (FR-α), CD19, FZD10, TSHR, PRLR, Muc 17, GUCY2C, CD207, CD3, CD5, B-Cell Maturation Antigen (BCMA), or CD4.

185. The modified cell of one of embodiment 168-184, wherein the modified cell is a T cell, NK cell, or dendritic cells.

186. The modified cell of one of embodiment 168-185, wherein the modified cell further comprises a nucleic acid sequence encoding a therapeutic agent 187. The modified cell of embodiment 186, wherein the therapeutic agent is present in the modified cell in a recombinant DNA construct, in an mRNA, or in a viral vector.

188. The modified cell of embodiment 186, wherein the modified cell comprises a therapeutic agent mRNA encoding the therapeutic agent, and the mRNA is not integrated into the genome of the modified cell.

189. The modified cell of embodiment 186, wherein the modified cell comprises a nucleic acid sequence comprising or the isolated nucleic acid sequence comprises a promoter comprising a binding site for a transcription modulator that modulates the expression and/or secretion of the therapeutic agent in the cell.

190. The modified cell of embodiment 189, wherein the transcription modulator is or includes Hif1a, NFAT, FOXP3, and/or NFkB.

191. The modified cell of embodiment 189, wherein the promoter is responsive to the transcription modulator.

192. The modified cell of embodiment 189, wherein the promoter is operably linked to the nucleic acid sequence encoding the therapeutic agent such that the promoter drives expression and/or secretion of the therapeutic agent in the cell.

193. A pharmaceutical composition comprising the modified cell of one of embodiments 168-53.

194. A method of eliciting and/or enhancing a T cell response in a subject in need thereof and/or treating a tumor of the subject, the method comprising administering an effective amount of the composition of embodiment 193 to the subject.

195. An antibody or antibody fragment that binds UPK2, wherein the antibody or antibody fragment comprises a heavy chain variable region (HVR) sequence comprising the amino acid sequence of SEQ ID NO: 94, 98, 102, 106, 110, 114, 118, or 122 and a light chain variable region (LVR) sequence comprising the amino acid sequences of SEQ ID NO: 93, 97, 101, 105, 109, 113, 117, or 121.

196. The antibody or antibody fragment of embodiment 195, wherein the HVR comprises the amino acid sequences of SEQ ID NO: 93, and HVR comprises the amino acid sequences of SEQ ID NO: 94.

197. The antibody or antibody fragment of embodiment 195, wherein the HVR comprises the amino acid sequences of SEQ ID NO: 97, and HVR comprises the amino acid sequences of SEQ ID NO: 98.

198. The antibody or antibody fragment of embodiment 195, wherein the HVR comprises the amino acid sequences of SEQ ID NO: 101, and HVR comprises the amino acid sequences of SEQ ID NO: 102.

199. The antibody or antibody fragment of embodiment 195, wherein the HVR comprises the amino acid sequences of SEQ ID NO: 105, and HVR comprises the amino acid sequences of SEQ ID NO: 106.

200. The antibody or antibody fragment of embodiment 195, wherein the HVR comprises the amino acid sequences of SEQ ID NO: 109, and HVR comprises the amino acid sequences of SEQ ID NO: 110.

201. The antibody or antibody fragment of embodiment 195, wherein the HVR comprises the amino acid sequences of SEQ ID NO: 113, and HVR comprises the amino acid sequences of SEQ ID NO: 114.

202. The antibody or antibody fragment of embodiment 195, wherein the HVR comprises the amino acid sequences of SEQ ID NO: 117, and HVR comprises the amino acid sequences of SEQ ID NO: 118.

203. The antibody or antibody fragment of embodiment 195, wherein the HVR comprises the amino acid sequences of SEQ ID NO: 121, and HVR comprises the amino acid sequences of SEQ ID NO: 122.

204. The antibody or antibody fragment of one of embodiments 195-203, wherein the HVR is joined to a human IgG chain constant region.

205. The antibody or antibody fragment of embodiment 204, wherein the human IgG is IgG1 or IgG3.

206. The antibody or antibody fragment of one of embodiments 195-205, wherein the antibody or antibody fragment is a conjugated to a cytotoxic agent.

207. The antibody or antibody fragment of 12, wherein the cytotoxic agent is a radioactive isotope or a toxin.

208. The antibody or antibody fragment of one of embodiments 195-207, wherein the antibody or antibody fragment is conjugated to a sequence derived from 4-1 BB or CD28, or a combination thereof.

209. The antibody or antibody fragment of one of embodiments 195-208, wherein the antibody or fragment is produced in HEK293 cells.

210. The antibody or antibody fragment of one of embodiments 195-209, wherein the antibody is a scFv.

211. The antibody or antibody fragment of embodiment 210, wherein the scFv comprises or is the SEQ ID NO: 92, 96, 100, 104, 108, 112, 116, or 120.

212. The antibody or antibody fragment of embodiment 210, wherein the antibody or antibody fragment comprises the SEQ ID NO: 92, 96, 100, 104, 108, 112, 116, or 120.

213. A composition comprising the antibody or fragment of one of embodiments 195-212 and a pharmaceutically acceptable carrier.

214. An article of manufacture comprising a container and a composition contained therein, wherein the composition comprises the antibody or fragment of one of embodiments 195-212.

215. A polynucleotide that encodes the antibody or fragment of one of embodiments 195-212.

216. An expression vector encoding the antibody or fragment of one of embodiments 195-212.

217. A host cell comprising a nucleic acid of any one of embodiments 21 or 216.

218. A method of treating a subject having a UPK2 positive tumor (e.g., urothelial cancer and bladder cancer), comprising administering to the subject a therapeutically effective amount of the antibody or fragment of one of embodiments 195-212.

219. A method of treating a subject having urothelial cancer or bladder cancer, comprising administering to the subject a therapeutically effective amount of the antibody or fragment of one of embodiments 195-212.

220. A chimeric antigen receptor (CAR) comprising an antigen binding domain comprising the antibody or fragment of one of embodiments 195-212

221. A polynucleotide that encodes the CAR of embodiment 220.

222. A modified cell comprising a nucleic acid sequence encoding a chimeric antigen receptor (CAR), wherein the CAR comprises an UPK2 antigen binding domain comprising the antibody or fragment of one of embodiments 195-212.

223. The modified cell of embodiment 222, wherein the CAR further comprises a transmembrane domain, and an intracellular domain and a signaling domain of a co-stimulatory molecule.

224. The modified cell of embodiment 223, wherein the intracellular domain comprising a CD3-zeta signaling domain 225. The modified cell of one of embodiments 222-224, wherein the antigen binding fragment is a scFv.

226. The modified cell of one of embodiments 222-224, wherein the scFv comprises the amino acid sequence of SEQ ID NO: 92. 96, 100, 104, 108, 112, 116, or 120.

227. The modified cell of one of embodiments 222-224, wherein the modified cell comprises a vector that comprises a nucleic acid sequence comprising the SEQ ID NO: 91, 95, 99, 103, 107, 111, 115, or 119.

228. The modified cell of embodiment 227, wherein the vector is a lentiviral vector.

229. The modified cell of one of embodiments 222-228, wherein the modified cell is a T cell derived from a primary human T cell isolated from a patient.

230. The modified cell of one of embodiments 222-228, wherein the modified cell is a T cell derived from a primary human T cell isolated from a human donor.

231. The modified cell of embodiment 229, wherein the cell has a reduced expression of endogenous TRAC gene.

232. The modified cell of one of embodiments 222-231, wherein the modified cell comprises an additional CAR, and the additional CAR binds an antigen of a white blood cell.

233. The modified cell of embodiment 232, wherein the antigen of the white blood cell is a B cell antigen.

234. The modified cell of embodiment 233, wherein the antigen of the B cell antigen is CD19, CD20, CD22, or BCMA.

235. The modified cell of one of embodiments 222-234, wherein the modified cell comprises a dominant negative PD-1.

236. The modified cell one of embodiments 222-234, wherein the modified cell comprises a modified PD-1 lacking a functional PD-1 intracellular domain.

237. The modified cell of one of embodiments 222-234, wherein the intracellular domain comprises a co-stimulatory signaling region that comprises an intracellular domain of a co-stimulatory molecule selected from the group consisting of CD27, CD28, 4-1BB, OX40, CD30, CD40, PD-1, ICOS, lymphocyte function-associated antigen-1 (LFA-1), CD2, CD7, LIGHT, NKG2C, B7-H3, and any combination thereof.

238. The modified cell of embodiment 237, wherein the antigen is Epidermal growth factor receptor (EGFR), Variant III of the epidermal growth factor receptor (EGFRvIII), Human epidermal growth factor receptor 2 (HER2), Mesothelin (MSLN), Prostate-specific membrane antigen (PSMA), Carcinoembryonic antigen (CEA), Disialoganglioside 2 (GD2), Interleukin-13Ra2 (IL13 Ra2), Glypican-3 (GPC3), Carbonic anhydrase IX (CAIX), L1 cell adhesion molecule (L1-CAM), Cancer antigen 125 (CA125), Cluster of differentiation 133 (CD133), Fibroblast activation protein (FAP), Cancer/testis antigen 1B (CTAG1B), Mucin 1 (MUC1), Folate receptor-α (FR-α), CD19, FZD10, TSHR, PRLR, Muc 17, GUCY2C, CD207, CD3, CD5, B-Cell Maturation Antigen (BCMA), or CD4.

239. The modified cell of one of embodiment 222-238, wherein the modified cell is a T cell, NK cell, or dendritic cells.

240. The modified cell of one of embodiment 222-239, wherein the modified cell further comprises a nucleic acid sequence encoding a therapeutic agent 241. The modified cell of embodiment 240, wherein the therapeutic agent is present in the modified cell in a recombinant DNA construct, in an mRNA, or in a viral vector.

242. The modified cell of embodiment 240, wherein the modified cell comprises a therapeutic agent mRNA encoding the therapeutic agent, and the mRNA is not integrated into the genome of the modified cell.

243. The modified cell of embodiment 240, wherein the modified cell comprises a nucleic acid sequence comprising or the isolated nucleic acid sequence comprises a promoter comprising a binding site for a transcription modulator that modulates the expression and/or secretion of the therapeutic agent in the cell.

244. The modified cell of embodiment 243, wherein the transcription modulator is or includes Hif1a, NFAT, FOXP3, and/or NFkB.

245. The modified cell of embodiment 243, wherein the promoter is responsive to the transcription modulator.

246. The modified cell of embodiment 243, wherein the promoter is operably linked to the nucleic acid sequence encoding the therapeutic agent such that the promoter drives expression and/or secretion of the therapeutic agent in the cell.

247. A pharmaceutical composition comprising the modified cell of one of embodiments 168-53.

248. A method of eliciting and/or enhancing T cell response in a subject in need thereof and/or treating a tumor of the subject, the method comprising administering an effective amount of the composition of embodiment 247 to the subject.

249. An isolated nucleic acid sequence encoding a binding molecule comprising a first and a second binding domain, wherein the first binding domain binds an antigen, and the second binding domain binds the T cell CD3 receptor complex.

250. The isolated nucleic acid of embodiment 249, wherein the antigen is Epidermal growth factor receptor (EGFR), Variant III of the epidermal growth factor receptor (EGFRvIII), Human epidermal growth factor receptor 2 (HER2), Mesothelin (MSLN), Prostate-specific membrane antigen (PSMA), Carcinoembryonic antigen (CEA), Disialoganglioside 2 (GD2), Interleukin-13Ra2 (IL13 Ra2), Glypican-3 (GPC3), Carbonic anhydrase IX (CAIX), L1 cell adhesion molecule (L1-CAM), Cancer antigen 125 (CA125), Cluster of differentiation 133 (CD133), Fibroblast activation protein (FAP), Cancer/testis antigen 1B (CTAG1B), Mucin 1 (MUC1), Folate receptor-α (FR-α), CD19, FZD10, TSHR, PRLR, Muc 17, GUCY2C, CD207, CD3, CD5, B-Cell Maturation Antigen (BCMA), or CD4.

251. The isolated nucleic acid sequence of embodiment 249, wherein the second binding domain binds CD3 epsilon, and/or the first binding domain comprises one of acid sequence of SEQ ID NO: 30, 34, 38, 42, 46, 64, 68, 92, 96, 100, 104, 108, 112, 116, 120, and 136-172.

252. The isolated nucleic acid sequence of embodiment 249, wherein the first binding domain binds tn-Muc1, TSHR, FZD10, PRLR, Muc 16, Muc 17, GUCY2C, CD207, CLDN18.2, CLDN6, or SIGL1C.

253. The isolated nucleic acid sequence of embodiment 249, wherein the isolated nucleic acid sequence encodes a polypeptide comprising one of the amino acid sequences of SEQ ID NO: 123-135.

254. A vector comprising a nucleic acid sequence as defined in any one of embodiments 249-253.

255. A host cell transformed or transfected with the nucleic acid sequence as defined in any one of embodiments 1-5 or with the vector as defined in embodiment 254.

256. A method for the production of a binding molecule according to any one of embodiments 1 to 4, the method comprising culturing a host cell as defined in embodiment 254 under conditions allowing the expression of the binding molecule as defined in any one of embodiments 1 to 4 and recovering the produced binding molecule from the culture.

257. A pharmaceutical composition comprising a binding molecule according to any one of embodiments 1 to 4 or produced according to the method of embodiment 256.

258. A kit comprising a binding molecule as defined in any one of embodiments 1 to 4, a nucleic acid molecule as defined in any one of embodiments 1-4, a vector as defined in embodiment 253, and/or a host cell as defined in embodiment 7.

259. A method for the treatment or amelioration of a disease, comprising administering to a subject in need thereof the binding molecule according to any one of embodiments 1 to 4, or method according to the method of embodiment 256.

260. The method of embodiment 259, further comprising: administering to the subject in need thereof an effective amount of T cell comprising an antigen binding molecule that binds a cell surface molecule of a white cell, wherein the cell surface molecule of the white cell is CD19, CD22, CD20, BCMA, CD5, CD7, CD2, CD16, CD56, CD30, CD14, CD68, CD11 b, CD18, CD169, CD1c, CD33, CD38, CD138, or CD13.

261. The method of embodiment 260, wherein the antigen binding molecule comprises the antigen binding domain, a transmembrane domain, a co-stimulatory signaling region, and a CD3 zeta signaling domain.

262. The method of embodiment 261, wherein the T cell has an additional CAR binding the antigen.

263. An isolated nucleic acid sequence encoding a chimeric antigen receptor (CAR), wherein the CAR comprises an extracellular domain, a transmembrane domain, and an intracellular domain, the extracellular domain comprising at least two binding domains binding a tumor antigen.

264. The isolated nucleic acid sequence of embodiment 263, wherein the at least two binding domains are scFv binding ta-Muc1 and not ta-Muc1 antigen, respectively.

265. The isolated nucleic acid sequence of embodiment 263, wherein the least two binding domains comprise an antigen binding domain binding ta-Muc1, and an additional antigen biding domain binding an antigen different from ta-Muc1.

266. The isolated nucleic acid sequence of embodiment 265, wherein the antigen different from ta-Muc1 is Epidermal growth factor receptor (EGFR), Variant III of the epidermal growth factor receptor (EGFRvIII), Human epidermal growth factor receptor 2 (HER2), Mesothelin (MSLN), Prostate-specific membrane antigen (PSMA), Carcinoembryonic antigen (CEA), Disialoganglioside 2 (GD2), Interleukin-13Ra2 (IL13 Ra2), Glypican-3 (GPC3), Carbonic anhydrase IX (CAIX), L1 cell adhesion molecule (L1-CAM), Cancer antigen 125 (CA125), Cluster of differentiation 133 (CD133), Fibroblast activation protein (FAP), Cancer/testis antigen 1B (CTAG1B), Folate receptor-α (FR-α), CD19, FZD10, TSHR, PRLR, Muc 17, GUCY2C, CD207, CD3, CD5, B-Cell Maturation Antigen (BCMA), or CD4.

267. The isolated nucleic acid sequence of embodiment 263, wherein the intracellular domain comprises a co-stimulatory signaling region that comprises an intracellular domain of a co-stimulatory molecule selected from the group consisting of CD27, CD28, 4-1BB, OX40, CD30, CD40, PD-1, ICOS, lymphocyte function-associated antigen-1 (LFA-1), CD2, CD7, LIGHT, NKG2C, B7-H3, and any combination thereof.

268. The isolated nucleic acid sequence of embodiment 263, wherein the at least two binding domains comprise SEQ ID NO: 135 and one of SEQ ID NO: 30, 34, 38, 42, 46, 64, 68, 92, 96, 100, 104, 108, 112, 116, 120, and 136-172.

269. The isolated nucleic acid sequence of embodiment 15, wherein the at least two binding domains comprise SEQ ID NO: 70 and one of SEQ ID NO: 59-84.

270. A population of CAR cells comprising the isolated nucleic acid sequence of any one of embodiments 249-253 and 263-268.

271. A pharmaceutical composition comprising the population of the CAR cells of embodiment 270.

272. A method of eliciting and/or enhancing T cell response, eliciting or causing T cell response in a subject in need thereof and/or treating a tumor of the subject, the method comprising administering an effective amount of the composition of embodiment 271 to the subject.

273. One or more modified cells including two or more different antigen binding domains, wherein at least a first antigen binding domain binds a cell surface marker and the second antigen binding domain binds tumor antigen.

274. The one or more modified cells of embodiment 273, wherein the cell surface marker includes the cell surface marker of a white blood cell.

275. The one or more modified cells of embodiment 273 or 274, wherein the tumor antigen includes one or more of SIGLEC15, SLC6A3, KISS1R, QRFPR, GPR119, CLDN6, UPK2, ADAM12, SLC45A3, ACPP, MUC21, MUC16, MS4A12, or ALPP.

276. The one or more modified cells of any one of embodiments 273-275, wherein the antigen binding domains are on the same CAR molecule, different CAR molecules, or on a CAR molecule and a T cell receptor.

277. The one or more modified cells of any one of embodiments 273-276, wherein the two or more different antigen binding domains are on different CAR molecules on different modified cells.

278. The one or more modified cells of any one of embodiments 273-277, wherein the two or more different antigen binding domains are on a CAR molecule and a T cell receptor which are on different modified cells.

279. A population of cells comprising the one or more modified cells of any one of embodiments 273-278.

280. Use of the nucleic acid sequences, the CAR molecules, the antibodies, the vectors, the cells, the population of cells, the compositions, the pharmaceutical compositions, the kit, or the methods of any one of embodiments 1-279 for use in a method of treating a subject's body by therapy.

281. The use of embodiment 280, wherein the subject is a human or animal.

282. The use of embodiment 280 or 281, wherein the subject is suffering from cancer.

283. The use of any one of embodiments 280-282, wherein the use elicits and/or enhances a T cell response in the subject.

284. Use of the nucleic acid sequences, the CAR molecules, the antibodies, the vectors, the cells, the population of cells, the compositions, the pharmaceutical compositions, the kit, or the methods of any one of embodiments 1-279 for use in a method of eliciting and/or enhancing a T cell response in a subject.

285. The use of embodiment 284, wherein the subject is a human or animal.

286. The use of embodiment 284 or 285, wherein the subject is suffering from cancer.

EXAMPLES

The present disclosure is further described by reference to the following examples. These examples are provided for purposes of illustration only and are not intended to be limiting unless otherwise specified. Thus, the present disclosure should in no way be construed as being limited to the following examples, but rather, should be construed to encompass any and all variations which become evident as a result of the teaching provided herein.

Expression of CAR on T Cells

Lentiviral vectors that encode a CAR were generated (see Chimeric Receptors Containing CD137 Signal Transduction Domains Mediate Enhanced Survival of T Cells and Increased Antileukemic Efficacy In Vivo Molecular Therapy vol. 17 no. 8, 1453-1464 August 2009 incorporated herein by reference) and were introduced into human T cells.

Figure 2:
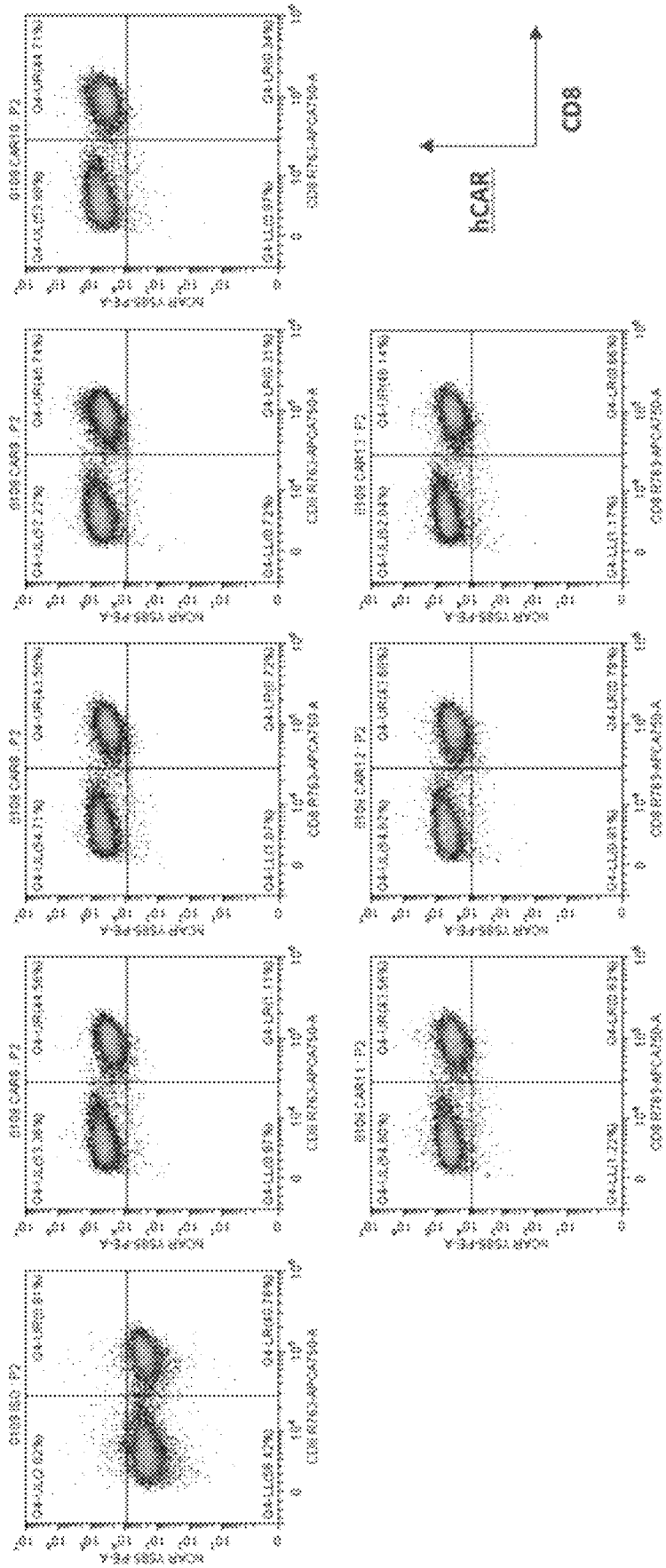
FIG. 2 shows flow cytometry analysis of T cells expressing CARs.

Primary T cells were obtained from patients. The obtained primary T cells were transduced with lentiviral vectors to obtain modified T cells. Flow-cytometry was performed and analyzed to confirm the expression of CARs in primary T cells (FIG. 2). Techniques related to cell cultures, construction of lentiviral vectors, and flow cytometry may be found in Control of large, established tumor xenografts with genetically retargeted human T cells containing CD28 and CD137 domains. 3360-3365 PNAS Mar. 3, 2009, vol. 106 no. 9, which is incorporated herein by reference.

Expression of Antigens and Related Tumor Analysis

Detection of mRNA and protein expression levels of target molecules in human cells using experimental methods such as qPCR and FACS were performed. It has been shown that some of the target molecules listed below are specifically expressed in the corresponding tumor cells with relatively low expression or undetectable expression in normal tissue. For example, eight genes were localized in normal tissues and overexpressed in tumor cells. The target point and the corresponding relationship between the tumor are provided in the Table 4. Various assays (e.g., killing) were perform, and results are shown in FIGS. 3-7. Techniques related to cell cultures, construction of cytotoxic T-lymphocyte assay may be found in "Control of large, established tumor xenografts with genetically retargeted human T cells containing CD28 and CD137 domains," PNAS, Mar. 3, 2009, vol. 106 no. 9, 3360-3365, which is incorporated herein by reference in its entirety.

TABLE 4

| Gene name | Subcellular localization | Organ mainly expressing | Target Tumor | Target SEQ ID NO. |
|---|---|---|---|---|
| SIGLEC15 | Plasma membrane | Expression in all normal tissues but very low | Urothelial cancer | 17 |
| SLC6A3 | Plasma membrane | Expression in all normal tissues but very low | Renal cancer | 18 |

TABLE 4-continued

| Gene name | Subcellular localization | Organ mainly expressing | Target Tumor | Target SEQ ID NO. |
|---|---|---|---|---|
| KISS1R | Plasma membrane | Expression in all normal tissues but very low | Renal cancer | 19 |
| QRFPR | Plasma membrane | Expression in all normal tissues but very low | Renal cancer: | 20 |
| GPR119 | Plasma membrane | Expression in all normal tissues but very low | Pancreatic cancer | 21 |
| CLDN6 | Plasma membrane | Expression in all normal tissues but very low | Endometrial cancer/ Urothelial cancer | 22 |
| UPK2 | Plasma membrane | Urethra/bladder | Urothelial cancer (including bladder cancer) | 1 |
| ADAM12 | Plasma membrane | placenta | Breast cancer, pancreatic cancer and the like | 2 |
| SLC45A3 | Plasma membrane | prostate | Prostate cancer | 3 |
| ACPP | Plasma membrane | prostate | Prostate cancer | 4 |
| MUC21 | Plasma membrane | esophagus | Esophageal cancer | 5 |
| MUC16 | Plasma membrane | Cervical/ Fallopian tube | Ovarian cancer | 6 |
| MS4A12 | Plasma membrane | the large intestine | Colorectal cancer | 7 |
| ALPP | Plasma membrane | Placenta/cervix | Endometrial cancer | 8 |

Identifying Gene Fusion Antigens

Databases (e.g., TCGA) were analyzed to identify gene fusion products and gene fusion antigens. Hundreds of gene fusion products were identified and determined to be associated with cancer. Among these hundreds of gene fusion products, 33 gene fusion antigen groups were further identified based on predetermined criteria. For example, these gene fusion products were found to be expressed in tumor cells, and both fusion proteins of the fusion genes were located in the cytoplasmic membrane. Information of these 33 gene fusion antigen groups are listed in Table 5. Samples corresponding to each row of Table 5 include TCGA-D8-A1XJ-01A-11R-A14M-07, TCGA-E2-A574-01A-11R-A29R-07, TCGA-FU-A3TX-01A-11R-A22U-07, TCGA-CV-7434-01A-11R-2132-07, TCGA-G7-6793-01A-11R-1965-07, TCGA-DB-5277-01A-01R-1470-07, TCGA-KT-A7W1-01A-11R-A34F-07, TCGA-VM-A8CD-01A-11R-A36H-07, TCGA-DD-A3A5-01A-11R-A22L-07, TCGA-DD-AAEA-01A-11R-A41C-07, TCGA-ZS-A9CF-01A-11R-A38B-07, TCGA-44-7670-01A-11R-2066-07, TCGA-55-7281-01A-11R-2039-07, TCGA-62-8394-01A-11R-2326-07, TCGA-78-7143-01A-11R-2039-07, TCGA-78-7146-01A-11R-2039-07, TCGA-46-6025-01A-11R-1820-07, TCGA-85-7710-01A-11R-2125-07, TCGA-02-A52V-01A-31R-A262-07, TCGA-FB-AAPZ-01A-11R-A41B-07, TCGA-P8-A5KC-01A-11R-A35K-07, TCGA-WB-A81D-01A-11R-A35L-07, TCGA-EJ-5510-01A-01R-1580-07, TCGA-EJ-A46G-01A-31R-A26U-07, TCGA-ZG-A9L2-01A-31R-A41O-07, TCGA-ZG-A9L2-01A-31R-A41O-07, TCGA-EI-7002-01A-11R-1928-07, TCGA-DX-A1KZ-01A-11R-A24X-07, TCGA-DX-A2J0-01A-11R-A21T-07, TCGA-DX-A3UF-01A-11R-A30C-07, TCGA-DX-AB2V-01A-11R-A411-07, TCGA-K1-A6RU-01A-11R-A32Q-07, and TCGA-EB-A24D-01A-11R-A18T-07, each representing a barcode in TCGA database. TCGA barcodes, represents the metadata of the participants and their samples in TCGA database.

TALBE 5

| Cancer | Cancer_type | Fusion | Junction | Spanning | Breakpoint 1 | Breakpoint 2 | gene1 |
|---|---|---|---|---|---|---|---|
| breast invasive carcinoma | BRCA | GNAS--NECTIN2 | 23 | 51 | chr20:58895684:+ | chr19:44882211:+ | GNAS |
| breast invasive carcinoma | BRCA | FGFR1--ADAM18 | 9 | 42 | chr8:38457356:− | chr8:39606307:+ | FGFR1 |
| cervical squamous cell carcinoma and endocervical adenocarcinoma | CESC | WHRN--TNC | 1000 | 1000 | chr9:114403306:− | chr9:115035229:− | WHRN |
| head and neck squamous cell carcinoma | HNSC | PQLC1--HSBP1L1 | 28 | 210 | chr18:79943329:− | chr18:79966612:+ | PQLC1 |
| kidney renal papillary cell carcinoma | KIRP | FNDC3B--BCHE | 91 | 307 | chr3:172133546:+ | chr3:165786311:− | FNDC3B |
| brain lower grade glioma | LGG | GRIA4--NAALAD2 | 28 | 113 | chr11:105862208:+ | chr11:90173824:+ | GRIA4 |
| brain lower grade glioma | LGG | EPHB2--PDZD4 | 6 | 29 | chr1:22785076:+ | chrX:153808595:− | EPHB2 |
| brain lower grade glioma | LGG | SEC24A--KCNK7 | 11 | 140 | chr5:134649173:+ | chr11:65593874:− | SEC24A |
| liver hepatocellular carcinoma | LIHC | ACVR1B--ACVRL1 | 6 | 43 | chr12:51951 834:+ | chr12:51912 470:+ | ACVR1B |
| liver hepatocellular carcinoma | LIHC | ABCC2--CTNNA3 | 192 | 315 | chr10:99784781:+ | chr10:65920617:− | ABCC2 |
| liver hepatocellular carcinoma | LIHC | EFNA1--ADAM15 | 5 | 17 | chr1:155131634:+ | chr1:155062460:− | EFNA1 |
| lung adenocarcinoma | LUAD | CPNE8--CADM2 | 16 | 74 | chr12:38905437:− | chr3:85802047:+ | CPNE8 |
| lung adenocarcinoma | LUAD | NOTCH2--ADAM30 | 1000 | 1000 | chr1:119935472:− | chr1:119894596:− | NOTCH2 |
| lung adenocarcinoma | LUAD | CELSR1--CD52 | 81 | 308 | chr22:46463707:− | chr1:26320171:+ | CELSR1 |
| lung adenocarcinoma | LUAD | ILVBL--SLC1A6 | 27 | 67 | chr19:15122693:− | chr19:14950390:− | ILVBL |
| lung adenocarcinoma | LUAD | F11R--NOS1AP | 29 | 220 | chr1:161021010:− | chr1:162355187:− | F11R |
| lung squamous cell carcinoma | LUSC | CELSR1--SEZ6L | 137 | 521 | chr22:46533627:− | chr22:26292406:+ | CELSR1 |
| lung squamous cell carcinoma | LUSC | KIRREL--CD1A | 10 | 64 | chr1:157993728:+ | chr1:158255084:+ | KIRREL |
| lung squamous cell carcinoma | LUSC | ATP10D--GABRA2 | 20 | 79 | chr4:47525642:+ | chr4:46250604:− | ATP10D |
| pancreatic adenocarcinoma | PAAD | ORAI2--SLC47A2 | 7 | 17 | chr7:102439181:+ | chr17:19681670:− | ORAI2 |
| pheochromocytoma and paraganglioma | PCPG | ADCYAP1R1--GHRHR | 5 | 25 | chr7:31100210:+ | chr7:30974971:+ | ADCYAP1R1 |
| pheochromocytoma and paraganglioma | PCPG | TMEM178B--DPP6 | 15 | 107 | chr7:141212704:+ | chr7:154769417:+ | TMEM178B |
| prostate adenocarcinoma | PRAD | ADAM9--RGS20 | 5 | 28 | chr8:38997160:+ | chr8:53879258:+ | ADAM9 |

TALBE 5-continued

| | | | | | | | |
|---|---|---|---|---|---|---|---|
| prostate adenocarcinoma | PRAD | FAM160B1--VTI1A | 10 | 35 | chr10:114836246:+ | chr10:112668218:+ | FAM160B1 |
| prostate adenocarcinoma | PRAD | TMPRSS2--PDE9A | 22 | 56 | chr21:41494356:− | chr21:42743776:+ | TMPRSS2 |
| prostate adenocarcinoma | PRAD | PDE9A--TMPRSS2 | 17 | 40 | chr21:42733426:+ | chr21:41498189:− | PDE9A |
| rectum adenocarcinoma | READ | LHFPL2--PTPRK | 8 | 62 | chr5:78509784:− | chr6:128089992:− | LHFPL2 |
| sarcoma | SARC | TM7SF3--KCNC2 | 13 | 82 | chr12:26990450:− | chr12:75051317:− | TM7SF3 |
| sarcoma | SARC | MPZL1--TNFSF4 | 16 | 175 | chr1:167776166:+ | chr1:173188569:− | MPZL1 |
| sarcoma | SARC | GNG7--PAQR5 | 5 | 6 | chr19:2520608:− | chr15:69399974:+ | GNG7 |
| sarcoma | SARC | KIRREL--CD1A | 1000 | 1000 | chr1:157993728:+ | chr1:158256786:+ | KIRREL |
| sarcoma | SARC | P2RX5--TRPV1 | 28 | 103 | chr17:3679590:− | chr17:3572249:− | P2RX5 |
| skin cutaneous melanoma | SKCM | PTPRG--SYNPR | 6 | 55 | chr3:61748982:+ | chr3:63480832:+ | PTPRG |

| Cancer | Gene description | sublocation | gene2 | Gene description2 | sublocation3 |
|---|---|---|---|---|---|
| breast invasive carcinoma | GNAS complex locus | Plasma membrane | NECTIN2 | Nectin cell adhesion molecule 2 | Plasma membrane |
| breast invasive carcinoma | Fibroblast growth factor receptor 1 | Plasma membrane | ADAM18 | ADAM metallopeptidase domain 18 | Plasma membrane |
| cervical squamous cell carcinoma and endocervical adenocarcinoma | Whirlin | Cytoplasm; Plasma membrane | TNC | Tenascin C | Extracellular; Plasma membrane |
| head and neck squamous cell carcinoma | PQ loop repeat containing 1 | Plasma membrane | HSBP1L1 | Heat shock factor binding protein 1 like 1 | Plasma membrane |
| kidney renal papillary cell carcinoma | Fibronectin type III domain containing 3B | Plasma membrane | BCHE | Butyrylcholinesterase | Plasma membrane |
| brain lower grade glioma | Glutamate ionotropic receptor AMPA type subunit 4 | Plasma membrane | NAALAD2 | N-acetylated alpha-linked acidic dipeptidase 2 | Plasma membrane |
| brain lower grade glioma | EPH receptor B2 | Plasma membrane | PDZD4 | PDZ domain containing 4 | Cytoplasm; Plasma membrane |
| brain lower grade glioma | SEC24 homolog A, COPII coat complex component | Plasma membrane | KCNK7 | Potassium two pore domain channel subfamily K member 7 | Plasma membrane |
| liver hepatocellular carcinoma | Activin A receptor type 1B | Plasma membrane | ACVRL1 | Activin A receptor like type 1 | Plasma membrane |
| liver hepatocellular carcinoma | ATP binding cassette subfamily C member 2 | Plasma membrane | CTNNA3 | Catenin alpha 3 | Cytoplasm; Cytoskeleton; Plasma membrane |
| liver hepatocellular carcinoma | Ephrin A1 | Extracellular; Plasma membrane | ADAM15 | ADAM metallopeptidase domain 15 | Plasma membrane |
| lung adenocarcinoma | Copine 8 | Plasma membrane | CADM2 | Cell adhesion molecule 2 | Plasma membrane |
| lung adenocarcinoma | Notch 2 | Plasma membrane | ADAM30 | ADAM metallopeptidase domain 30 | Plasma membrane |

TALBE 5-continued

| | | | | | |
|---|---|---|---|---|---|
| lung adenocarcinoma | Cadherin EGF LAG seven-pass G-type receptor 1 | Plasma membrane | CD52 | CD52 molecule | Plasma membrane |
| lung adenocarcinoma | IlvB acetolactate synthase like | Plasma membrane | SLC1A6 | Solute carrier family 1 member 6 | Plasma membrane |
| lung adenocarcinoma | F11 receptor | Plasma membrane | NOS1AP | Nitric oxide synthase 1 adaptor protein | Cytoplasm; Plasma membrane |
| lung squamous cell carcinoma | Cadherin EGF LAG seven-pass G-type receptor 1 | Plasma membrane | SEZ6L | Seizure related 6 homolog like | Plasma membrane |
| lung squamous cell carcinoma | Kin of IRRE like (Drosophila) | Plasma membrane | CD1A | CD1a molecule | Endosome; Golgi apparatus; Plasma membrane |
| lung squamous cell carcinoma | ATPase phospholipid transporting 10D (putative) | Plasma membrane | GABRA2 | Gamma-aminobutyric acid type A receptor alpha2 subunit | Plasma membrane |
| pancreatic adenocarcinoma | ORAI calcium release-activated calcium modulator 2 | Plasma membrane | SLC47A2 | Solute carrier family 47 member 2 | Plasma membrane |
| pheochromocytoma and paraganglioma | ADCYAP receptor type I | Plasma membrane | GHRHR | Growth hormone releasing hormone receptor | Plasma membrane |
| pheochromocytoma and paraganglioma | Transmembrane protein 178B | Plasma membrane | DPP6 | Dipeptidyl peptidase like 6 | Plasma membrane |
| prostate adenocarcinoma | ADAM metallopeptidase domain 9 | Plasma membrane | RGS20 | Regulator of G-protein signaling 20 | Plasma membrane |
| prostate adenocarcinoma | Family with sequence similarity 160 member B1 | Plasma membrane | VTI1A | Vesicle transport through interaction with t-SNAREs 1A | Plasma membrane |
| prostate adenocarcinoma | Transmembrane protease, serine 2 | Plasma membrane | PDE9A | Phosphodiesterase 9A | Plasma membrane |
| prostate adenocarcinoma | Phosphodiesterase 9A | Plasma membrane | TMPRSS2 | Transmembrane protease, serine 2 | Plasma membrane |
| rectum adenocarcinoma | Lipoma HMGIC fusion partner-like 2 | Plasma membrane | PTPRK | Protein tyrosine phosphatase, receptor type K | Plasma membrane |
| sarcoma | Transmembrane 7 superfamily member 3 | Plasma membrane | KCNC2 | Potassium voltage-gated channel subfamily C member 2 | Plasma membrane |
| sarcoma | Myelin protein zero like 1 | Plasma membrane | TNFSF4 | Tumor necrosis factor superfamily member 4 | Plasma membrane |
| sarcoma | G protein subunit gamma 7 | Plasma membrane | PAQR5 | Progestin and adipoQ receptor family member 5 | Plasma membrane |

TABLE 5-continued

| | | | | | | |
|---|---|---|---|---|---|---|
| | sarcoma | Kin of IRRE like (Drosophila) | Plasma membrane | CD1A | CD1a molecule | Endosome; Golgi apparatus; Plasma membrane |
| | sarcoma | Purinergic receptor P2X 5 | Plasma membrane | TRPV1 | Transient receptor potential cation channel subfamily V member 1 | Plasma membrane |
| | skin cutaneous melanoma | Protein tyrosine phosphatase, receptor type G | Plasma membrane | SYNPR | Synaptoporin | Plasma membrane |

TABLE 6

Identifier and related Sequences

| Identifier | SEQ ID NO: | Identifier | SEQ ID NO: | Identifier | SEQ ID NO: |
|---|---|---|---|---|---|
| UPK2 | 1 | Hinge | 25 | VL1 VH1 SIGLEC-15-CAR-2 | 49 |
| ADAM12 | 2 | TM | 26 | VL1 VH2 SIGLEC-15-CAR-3 | 50 |
| SLC45A3 | 3 | 4-1BB | 27 | VL1 VH3 SIGLEC-15-CAR-4 | 51 |
| ACPP | 4 | CD3 zeta | 28 | VL1 VH 4 SIGLEC-15-CAR-5 | 52 |
| MUC21 | 5 | CLDN6-CAR-1 | 29 | VL2 VH 1 SIGLEC-15-CAR-6 | 53 |
| MUC16 | 6 | ScFv CLDN6-CAR-1 | 30 | VL2 VH2 SIGLEC-15-CAR-7 | 54 |
| MS4A12 | 7 | ScFv VL CLDN6-CAR-1 | 31 | VL2 VH3 SIGLEC-15-CAR-8 | 55 |
| ALPP | 8 | ScFv VH CLDN6-CAR-1 | 32 | VL2 VH4 SIGLEC-15-CAR-9 | 56 |
| SLC2A14 | 9 | CLDN6-CAR-2 | 33 | VL1 SIGLEC-15-CAR | 57 |
| GS1-259H13.2 | 10 | ScFv CLDN6-CAR-2 | 34 | VL2 SIGLEC-15-CAR | 58 |
| ERVFRD-1 | 11 | ScFv VL CLDN6-CAR-2 | 35 | VH1 SIGLEC-15-CAR | 59 |
| ADGRG2 | 12 | ScFv VH CLDN6-CAR-2 | 36 | VH2 SIGLEC-15-CAR | 60 |
| ECEL1 | 13 | CLDN6-CAR-3 | 37 | VH3 SIGLEC-15-CAR | 61 |
| CHRNA2 | 14 | scFv CLDN6-CAR-3 | 38 | VH4 SIGLEC-15-CAR | 62 |
| GP2 | 15 | scFv VL CLDN6-CAR-3 | 39 | MUC16-CAR-1 | 63 |
| PSG9 | 16 | scFv VH CLDN6-CAR-3 | 40 | scFv MUC16-CAR-1 | 64 |
| SIGLEC15 | 17 | CLDN6-CAR-4 | 41 | scFv VL MUC16-CAR-1 | 65 |
| SLC6A3 | 18 | scFv CLDN6-CAR-4 | 42 | scFv VH MUC16-CAR-1 | 66 |
| KISS1R | 19 | scFv VL CLDN6-CAR-4 | 43 | MUC16-CAR-2 | 67 |
| QRFPR | 20 | scFv VH CLDN6-CAR-4 | 44 | scFv MUC16-CAR-2 | 68 |
| GPR119 | 21 | SIGLEC-15-CAR-1 | 45 | scFv VL MUC16-CAR-2 | 69 |
| CLDN6 | 22 | scFv SIGLEC-15-CAR-1 | 46 | scFv VH MUC16-CAR-2 | 70 |
| SP | 23 | scFv VL SIGLEC-15-CAR-1 | 47 | KISS1R-CAR | 71 |
| Linker | 24 | scFv VH SIGLEC-15-CAR-1 | 48 | Ligent peptide KISS1R-CAR | 72 |
| 6503 S5D1 VL NA | 73 | 6503 S5D1 VL aa | 82 | scFv UPK2-S3D10 NA | 107 |
| 6503 S5D1 VH NA | 74 | 6503 S5D1 VH aa | 83 | scFv UPK2-S3D10 aa | 108 |
| 6504 55F2 VL NA | 75 | 6504 55F2 VL aa | 84 | VL UPK2-S3D10 aa | 109 |
| 6504 S5F2 VH NA | 76 | 6504 S5F2 VH aa | 85 | VH UPK2-S3D10 aa | 110 |
| 6502 S12E9 VL NA | 77 | 6502 S12E9 VL aa | 86 | scFv UPK2-S7F9 NA | 111 |
| 6502 S12E9 VH NA | 78 | 6502 S12E9 VH aa | 87 | scFv UPK2-S7F9 aa | 112 |
| 6501 S10E12 VL NA | 79 | 6501 S10E12 VL aa | 88 | VL UPK2-S7F9 aa | 113 |
| 6501 S10E12 VH NA | 80 | 6501 S10E12 VH aa | 89 | VH UPK2-S7F9 aa | 114 |
| 3xGGGGS NA | 81 | 3xGGGGS aa | 90 | scFv UPK2-S7F11 NA | 115 |
| scFv UPK2-S2B7 NA | 91 | scFv UPK2-S3A4 NA | 99 | scFv UPK2-S7F11 aa | 116 |

TABLE 6-continued

Identifier and related Sequences

| Identifier | SEQ ID NO: | Identifier | SEQ ID NO: | Identifier | SEQ ID NO: |
|---|---|---|---|---|---|
| scFv UPK2-S2B7 aa | 92 | scFv UPK2-S3A4 AA | 100 | VL UPK2-S7F11 aa | 117 |
| VH UPK2-S2B7 aa | 93 | VL UPK2-S3A4 AA | 101 | VH UPK2-S7F11 aa | 118 |
| VL UPK2-S2B7 aa | 94 | VH UPK2-S3A4 AA | 102 | scFv UPK2-S7F11 NA | 119 |
| scFv UPK2-S2E2 NA | 95 | scFv UPK2-S3C10 NA | 103 | scFv UPK2-S7F11 aa | 120 |
| scFv UPK2-S2E2 aa | 96 | scFv UPK2-S3C10 AA | 104 | VL UPK2-S7F11 aa | 121 |
| VL UPK2-S2E2 aa | 97 | VL UPK2-S3C10 AA | 105 | VH UPK2-S7F11 aa | 122 |
| VH UPK2-S2E2 aa | 98 | VH UPK2-S3C10 AA | 106 | MUC1-1 HL CD3 HL | 123 |
| MUC1-2 HL CD3 HL | 124 | FZD10 HL CD3 HL | 125 | TSHR HL CD3 HL | 126 |
| PRLR HL CD3 HL | 127 | MUC17 HL CD3 HL | 128 | GUCY2C HL CD3 HL | 129 |
| CD207 HL CD3 | 130 | CLDN18.2 HL CD3 HL | 131 | CLDN6 HL CD3HL HL | 132 |
| SIGL1C-15 HL CD3 HL | 133 | muc16 HL cd3 HL | 134 | Cd3 HL | 135 |
| scFv TSHR | 136 | scFv PRLR | 137 | scFv Muc 17 | 138 |
| scFv GUCY2C | 139 | scFv CD207 | 140 | Prolactin (ligand) | 141 |
| scFv CD3 | 142 | scFv CD4 | 143 | scFv CD4-2 | 144 |
| scFv CD5 | 145 | scfv CD33 | 146 | scfv CD123 | 147 |
| scfv ROR1 | 148 | scfv CD70 | 149 | scfv CD133 | 150 |
| scfv GPC3 | 151 | scfv EpCAM | 152 | scfv CD20 | 153 |
| scfv CD22 | 154 | scfv CD30 | 155 | scfv CD5 | 156 |
| scfv Her2 | 157 | scfv CEA | 158 | scfv PSCA | 159 |
| scfv TAG-72 | 160 | scfv CD38 | 161 | scfv EGFRV III | 162 |
| scfv EphA2 | 163 | scfv FAP | 164 | scfv GD2 | 165 |
| scfv GD3 | 166 | scfv IL13R-2a | 167 | scfv NKG2D | 168 |
| scfv PSMA | 169 | scfv survivin | 170 | Tumor associated MUC1 scFv | 171 |
| scfv Mesothelin | 172 | scFv 6503 S5D1 | 173 | scFv 6504 S5F2 | 174 |
| scFv 6502 S12E9 | 175 | scFv 6501 S10E12 | 176 | scFv S4C7 | 177 |
| scFv S12D4 | 178 | scFv S9F5 | 179 | 6502 S12E9 VL | 180 |
| 6502 S12E9 VH | 181 | S4C7VH | 182 | S4C7VL | 183 |
| S12D4VH | 184 | S12D4VL | 185 | S9F5VH | 186 |
| S9F5VL | 187 | 4xGGGGS | 188 | PmCGR | 189 |
| PmCKR | 190 | | | | | scFv: Signal peptide + V L + 3xGGGGS +VH

Anti-SINGLEC-15 CAR and Anti-KISSR CAR

FIG. 2 shows flow cytometry analysis of T cells expressing CARs. On Day 1, CD3 positive T cells were sorted. On Day 3, the T cells were infected with lentivirus encoding CAR (multiplicity of infection (MOI): 50:1), On Day 5-6, expression assay was performed. On Day 6, T cells were cultured with 3T3-antigen-mcherry-SC with ratio 30:1. Sequences and corresponding references listed in FIGS. 2-7 are listed in Table 7.

Figure 3:
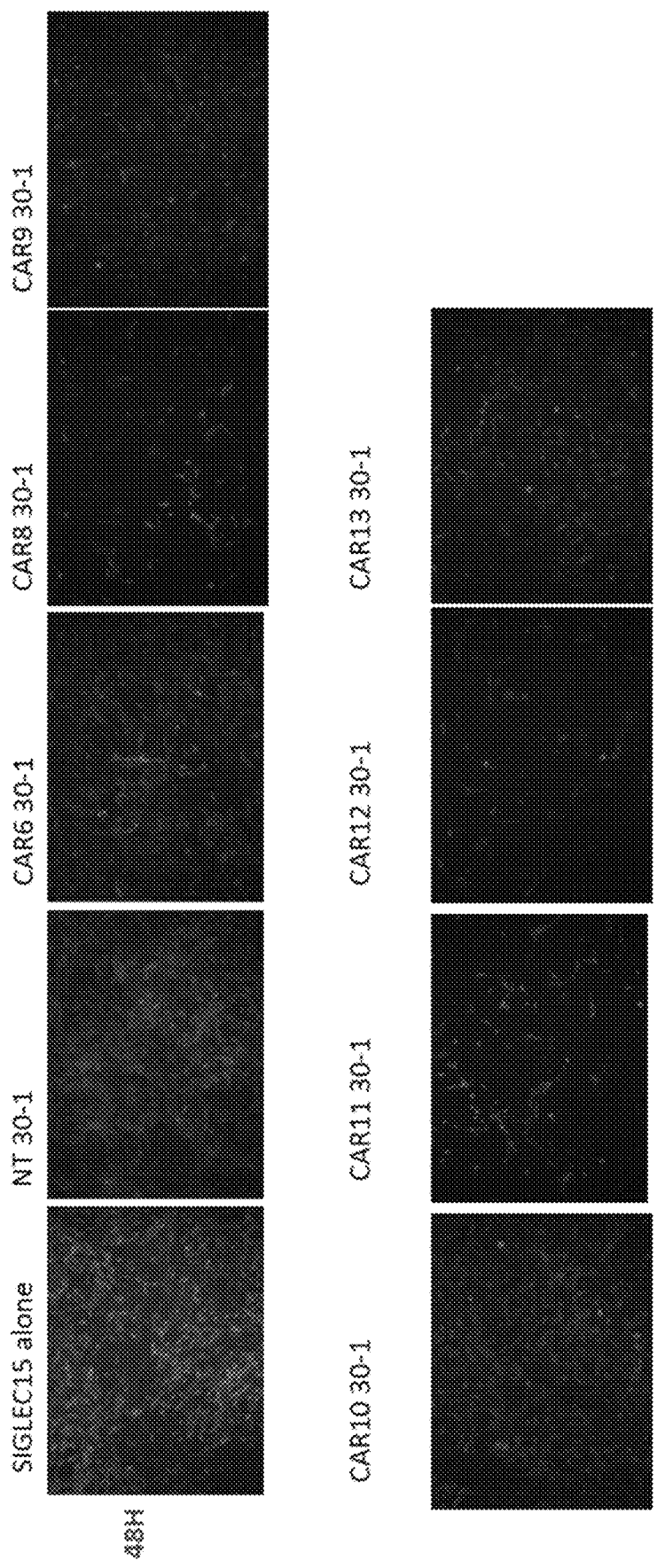
FIG. 3 shows results of a killing assay of anti-SIGLEC15 CAR.
Figure 5:
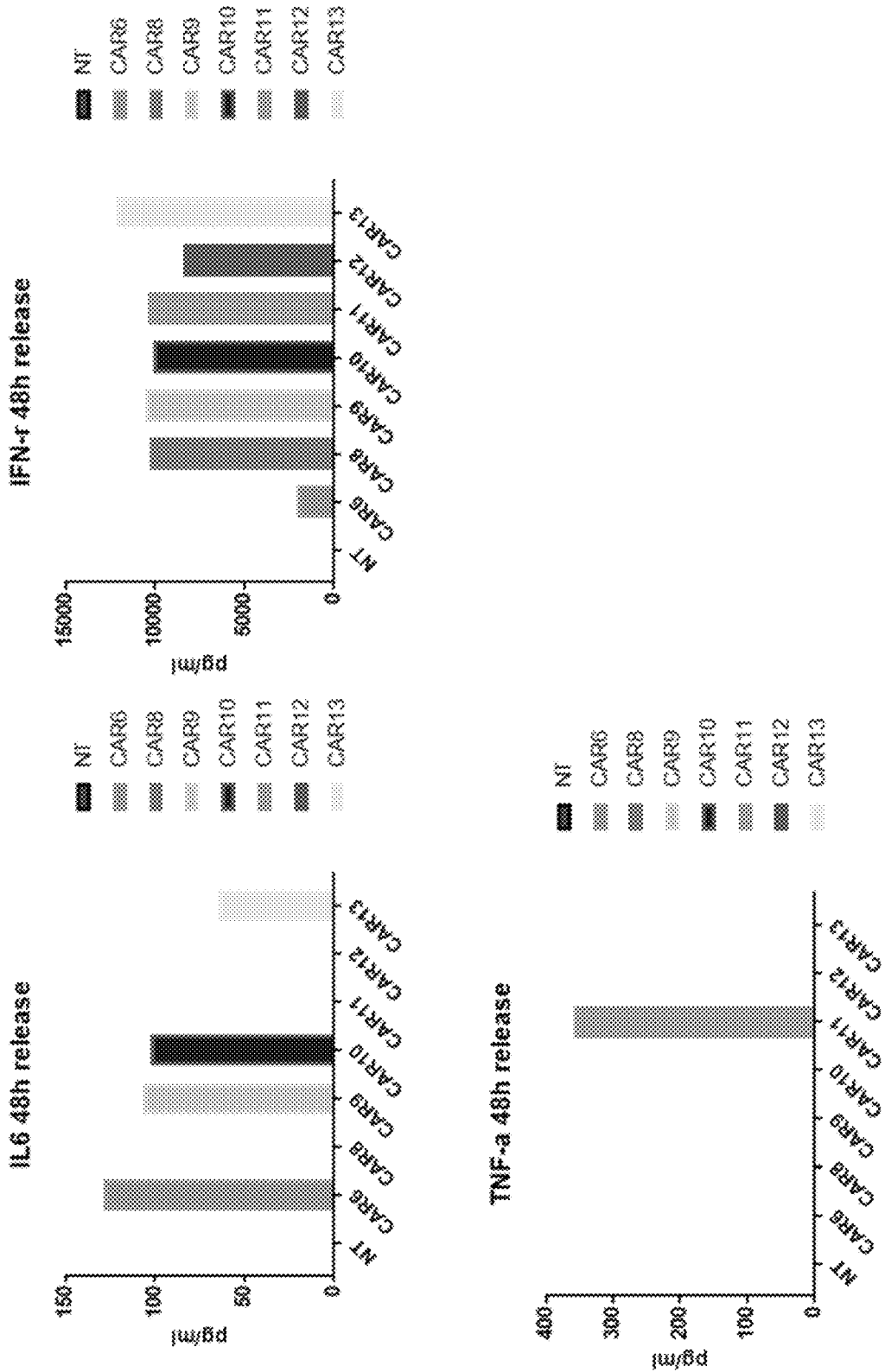

FIG. 3 shows results of a killing assay of anti-SIGLEC15 CAR (SIGLEC15-CAR SEQ ID NO: 46, 50, 51, and 52). It was observed that anti-SIGLEC15 CART cells killed the substrate cells. The negative control SIGLEC15 alone group was the group without the added anti-SIGLEC 15 CART cells, and the NT group was added to non-transfected T cells. FIGS. 4 and 5 show results of cytokine release assays of anti-SIGLEC15 CAR cocultured with the substrate cells.

TABLE 7

| Target | Seq ID | ID |
|---|---|---|
| SIGLEC 15 | 49 | CAR6 |
| | 51 | CAR8 |
| | 52 | CAR9 |
| | 53 | CAR10 |
| | 46 | CAR5 |
| | 50 | CAR7 |
| | 54 | CAR11 |
| | 55 | CAR12 |
| | 56 | CAR13 |
| KIss1R | 71 | CAR14 |

Figure 7:
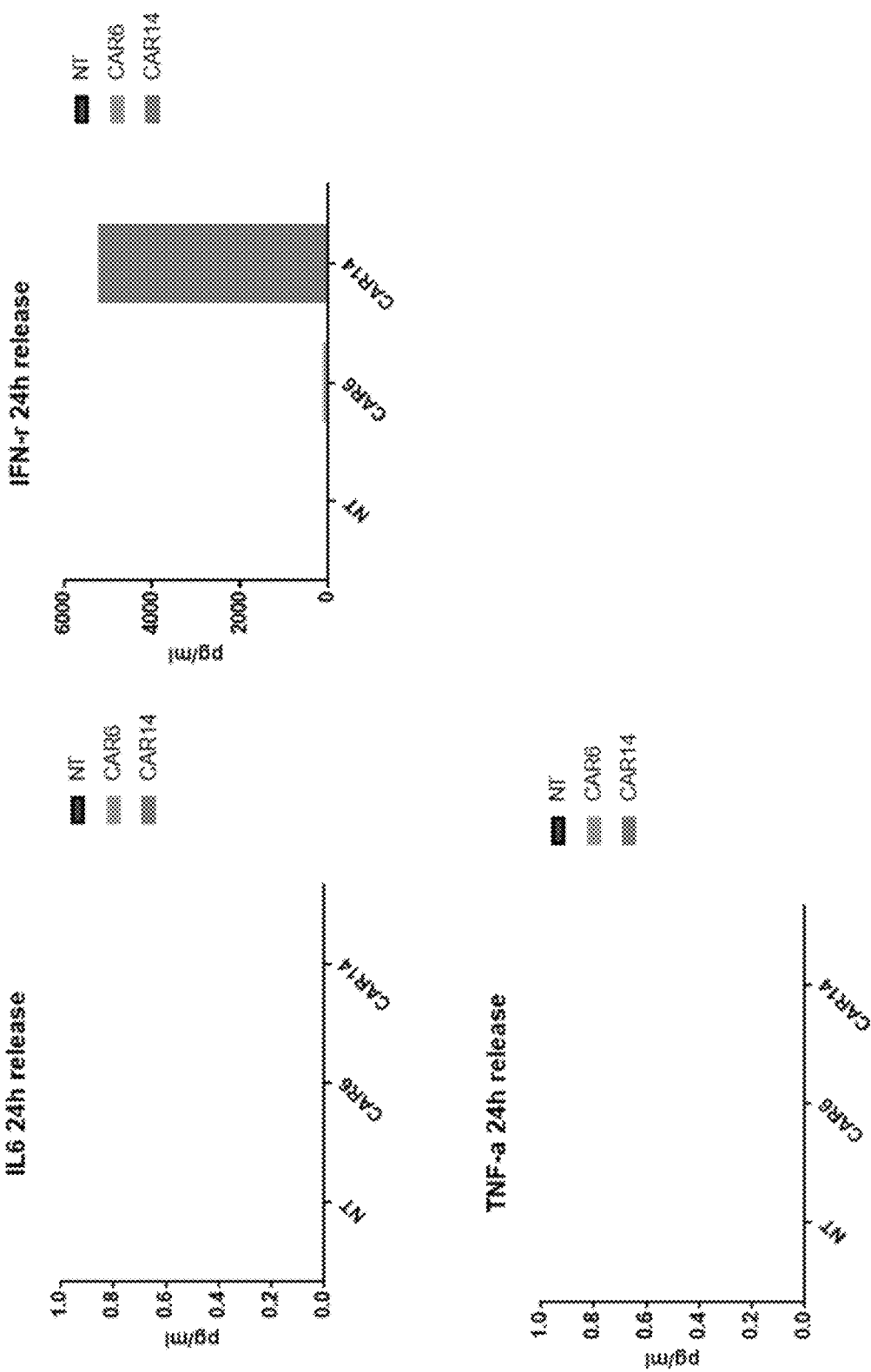
FIG. 7 show results of a cytokine release assay of anti-KISSR CAR.

FIG. 6 shows results of a killing assay of anti-KISSR CAR (KISSR-CAR: SEQ ID NO: 71). It was observed that anti-KISS1R CAR T cells killed the substrate cells. The NT group was added to non-transfected T cells. FIG. 7 show results of cytokine release assays of anti-KISSR CAR T cells co-cultured with the substrate cells.

ACPP Antibody Preparation and Anti-ACPP CAR

Figure 8:
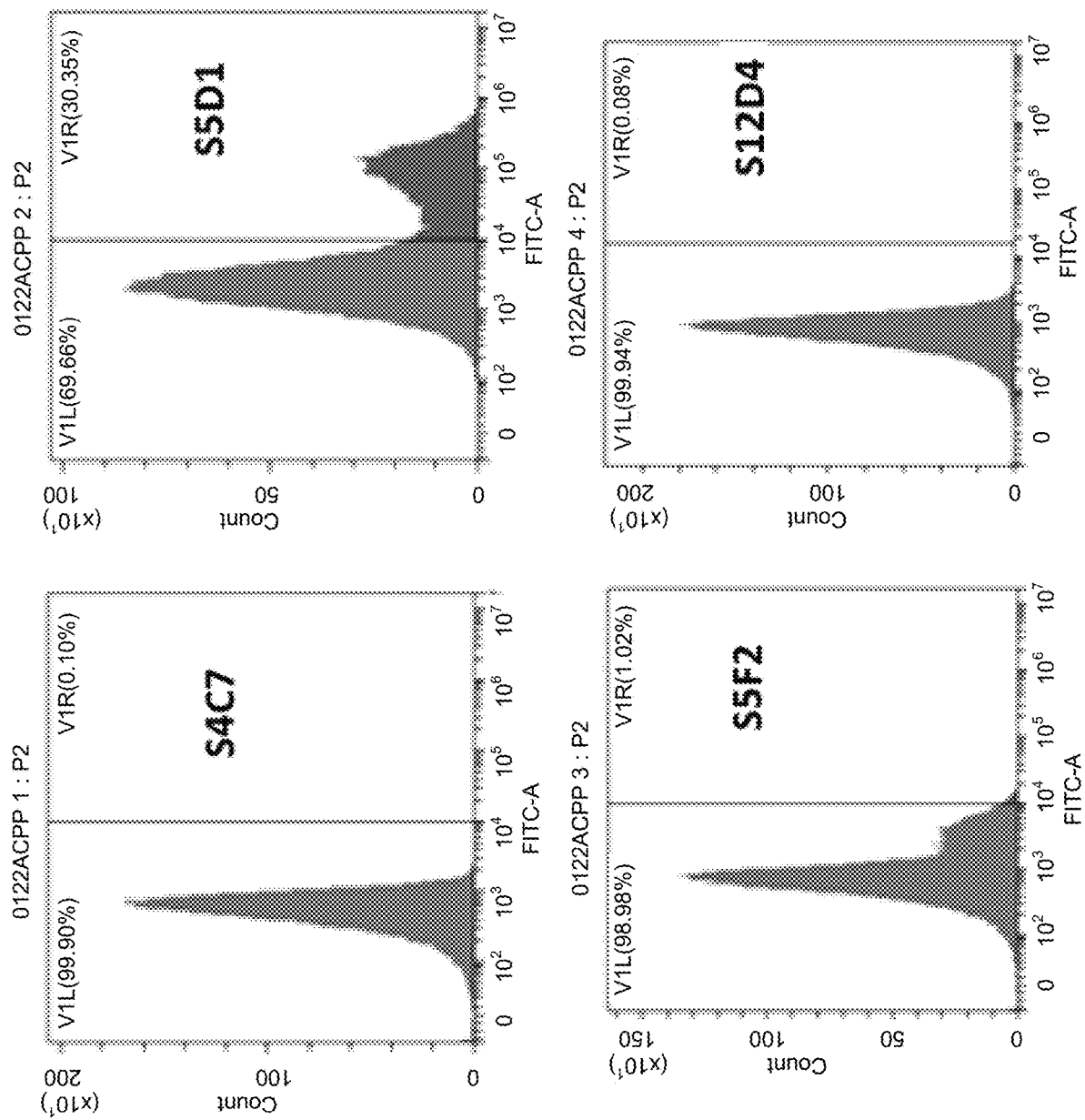
FIGS. 8, 9, and 10 show flow cytometry assay for ACPP antibodies.
Figure 9:
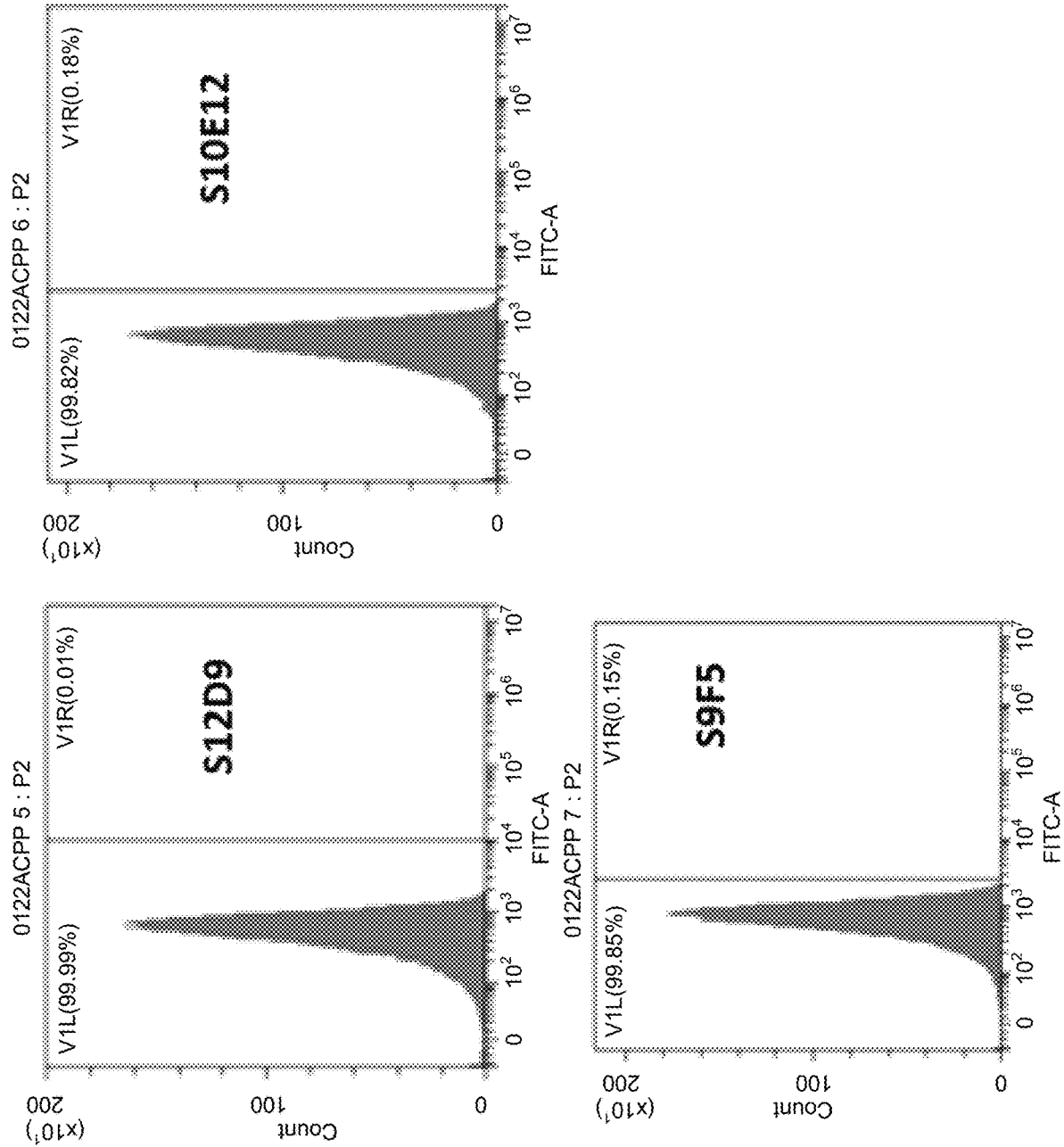
Figure 10:
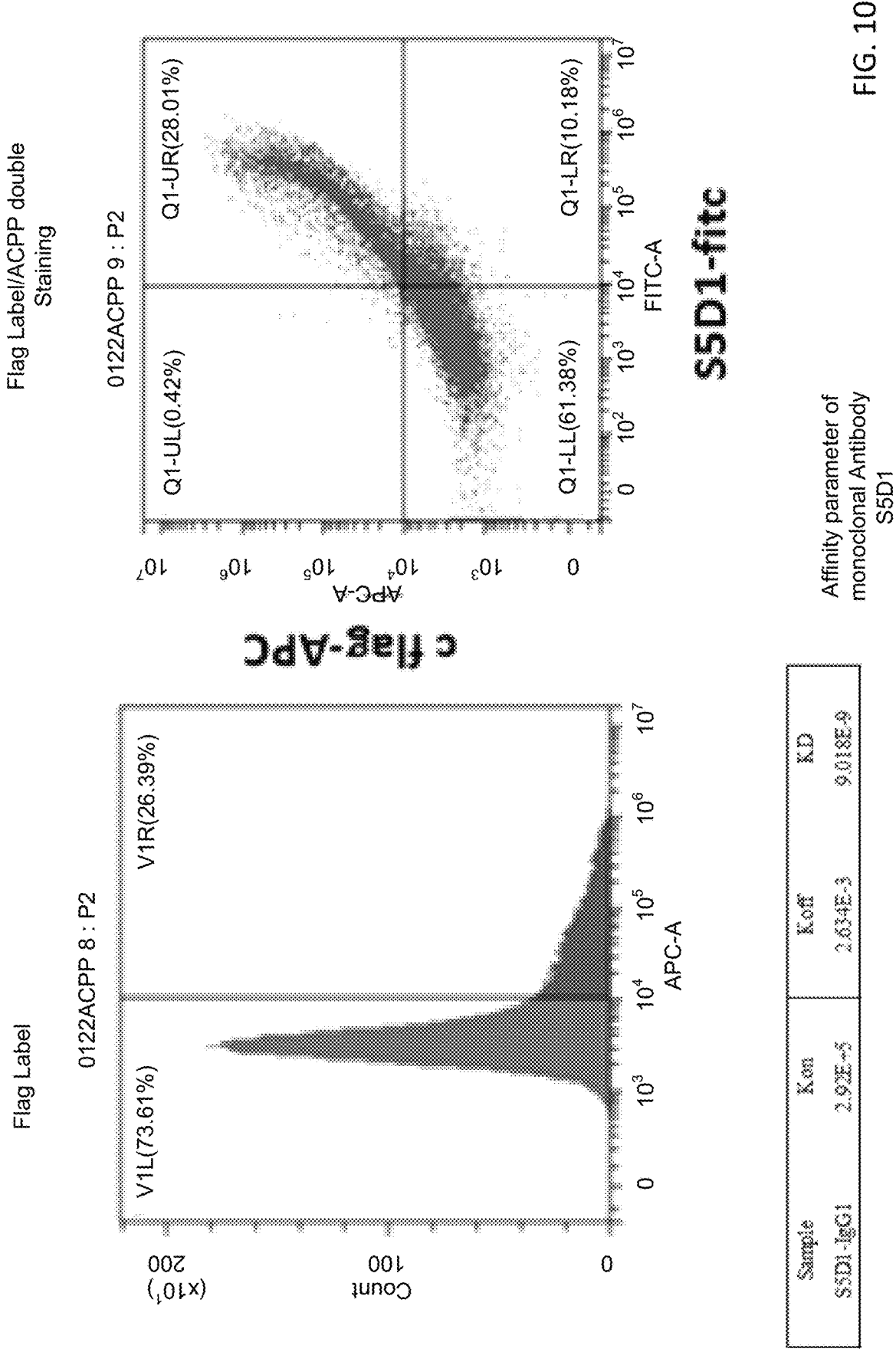

FIGS. 8-10 show flow cytometry assay for ACPP antibodies. 293T cells were transfected with the pcDNA-ACPP-flag plasmid to express the C-terminal flag-tagged ACPP protein. After 2 days, staining was detected using 7 ACPP antibodies and flag tag antibody staining. ACPP single staining does not break the membrane staining, first add ACPP primary antibody, then use goat anti human-FITC secondary antibody. When the flag label is single-dyed, APC direct-labeled primary antibody is used and the membrane is stained. Flag/ACPP double staining when ruptured. The Flag tag antibody detected 26.39% of the cells expressing the antigen. The S5D1 antibody detected 30.35% of cells expressing ACPP antigen. The double staining results showed that the positive cells had the same ACPP and flag expression levels. The staining results are specific. S5F2 also has a weaker binding, and the rest of the antibody flow has no signal. The transfected plasmid was able to express a C-terminal flag-tagged ACPP transmembrane protein on 293T cells. Flow cytometry experiments demonstrated that ACPP antibody S5D1 has good binding ability to antigen expressed on cell membrane. Flag labeling confirmed the normal expression of the protein.

For the affinity assay in FIG. 10, the affinity of two monoclonal antibodies, S5D1 and S5F2, was analyzed using GE's BIAcore X-100 Biomolecular Interaction Analyzer. Affinity analysis was performed using a conventional procedure. The human monoclonal antibody S5D1 or S5F2 was captured using an anti-human antibody coated on a chip. Affinity analysis was then performed using different concentrations of recombinantly expressed PAP as the mobile phase. The affinity of the monoclonal antibody S5D1 is about 9 nM. It is speculated that the affinity of S5F2 is lower than 100 nM. S5D1 has a higher affinity for ACPP antigen. The sequences of the antibodies are listed in Table 6.

The ACPP antibodies were generated by cloning and expressing the selected serum prostatic acid phosphatase (PAP) antigen and screening using the prepared PAP antigen of the phage display human antibody library (humanphage-display). The ACPP gene sequence was cloned into the recombinant antigen expression vector PTSE-His. The constructed recombinant plasmid was transfected into HEK293 cells. The recombinant protein was purified using GE's Histrap FF affinity chromatography column. The human single-chain antibody library was screened using ACPP-His as an antigen with reference to a classical solid-phase screening strategy. The single-chain antibody library consists of a total of 12 sub-libraries of fully synthetic human single-chain antibody, natural human single-chain antibody and semi-synthetic-semi-natural single-chain antibody library. The total library capacity exceeds 10E9, and the correct rate is about 75%. Three rounds of routine screening were performed using solid phase coated antigens. After the second round of screening and after the third round of screening, 600 monoclonal clones (1200 monoclonal clones) were randomly selected for monoclonal identification. Approximately 40 positive monoclonal capable of specifically binding to PAP were obtained. Sequence analysis was performed on all monoclonal. The results showed that these positive clones shared 7 different antibody sequences. Representative clones are S4C7, S5D1, S5F2, S9F5, S10E12, 512D4 and 512D9, respectively (Sequences are listed in Table 6). The genes of the heavy and light chain variable region of the above seven scFvs were cloned into the eukaryotic expression vectors pTSEG1n and pTSEK, respectively. Seven human full antibodies were prepared using the HEK293 cell transient expression system. The recombinantly expressed whole antibody was purified using a Protein A affinity chromatography column.

Figure 11:
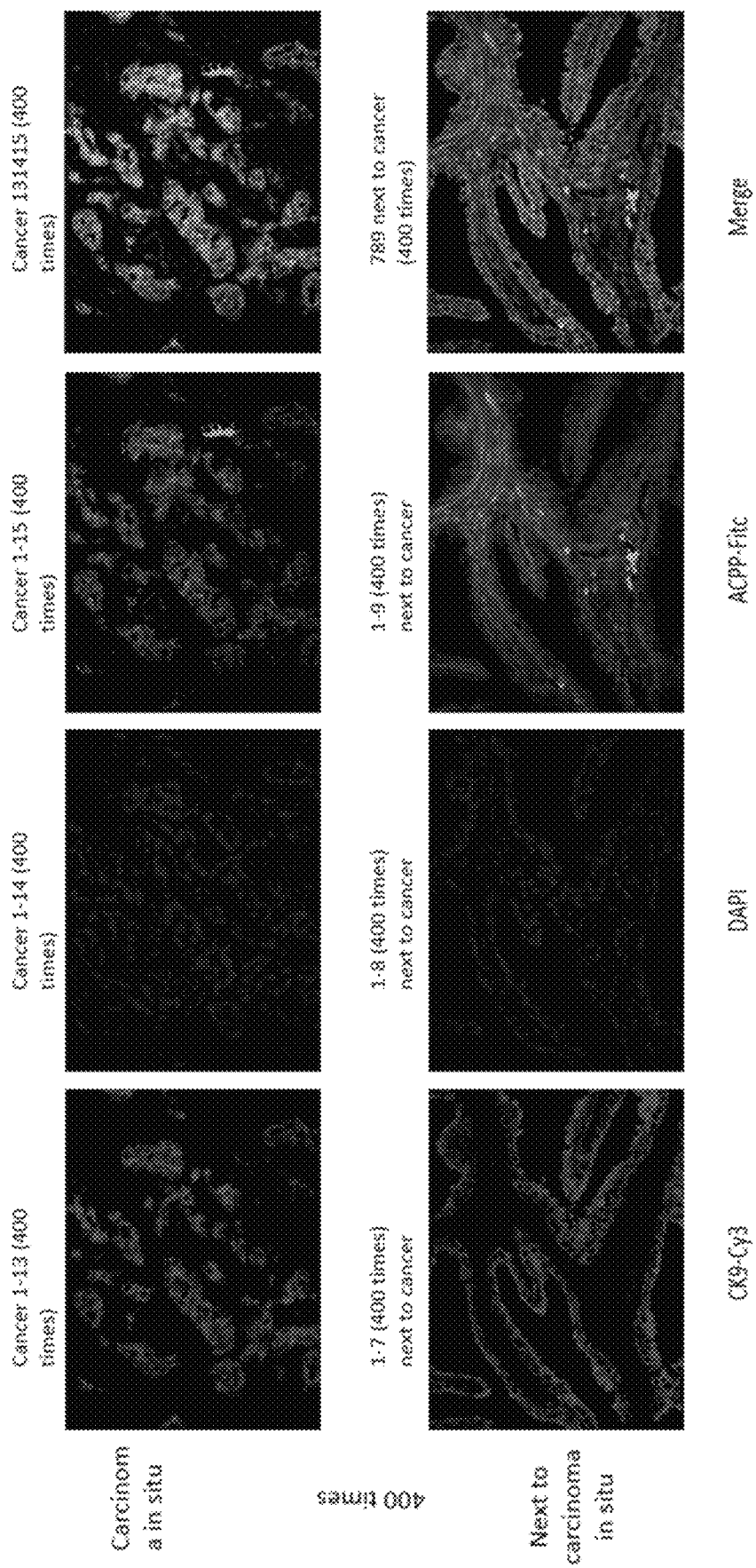
FIG. 11 shows immunofluorescence staining of paraffin sections of prostate cancer.

FIG. 11 shows immunofluorescence staining of paraffin sections of prostate cancer. The corresponding method includes: 1. tissue dehydration; 2. tissue transparency; 3. dipping wax; 4. embedding; 5. slicing and baking the slices; 6. sectioning and dewaxing; 7. antigen retrieval; 8. serum blocking; 9. adding primary antibody; 10. adding fluorescent secondary antibody; 11. serum blocking protecting from light; 12. adding primary antibody; 13. adding fluorescent secondary antibody; 14. complex dye core; and 15. collecting image. As shown, prostate cancer in situ and tissues adjacent to carcinoma in situ have higher ACPP expression. At the same time, the ACPP antibody used for the staining was S5D1, indicating that the antibody can specifically recognize ACPP. S5D1 was selected for further experiments below. The expression of ACPP in tumor tissue sections can be visualized by immunofluorescence staining, and it can also reflect the specificity and sensitivity of the antibody.

FIG. 12 shows 293T cells expressing ACPP. On day 0, the 293T-WT cells were digested and placed on a 6-well plate. On day 1, the cells were infected with the ACPP-lentivirus expression vector. On day 2, the medium was changed to remove the lentivirus, and fresh medium was added. The cells were digested and analyzed by flow cytometry. The antibody for flow cytometry was S5D1 and the antibody usage was 1 ug/100 ul. The flow results showed that the ACPP expression of 293T-ACPP cells was 97.80%. It can be used as an ACPP positive cell in subsequent experiments. ACPP can be overexpressed in 293T cells as an ACPP positive cell for experiments to assess the function of ACPP CART cells.

Figure 13:
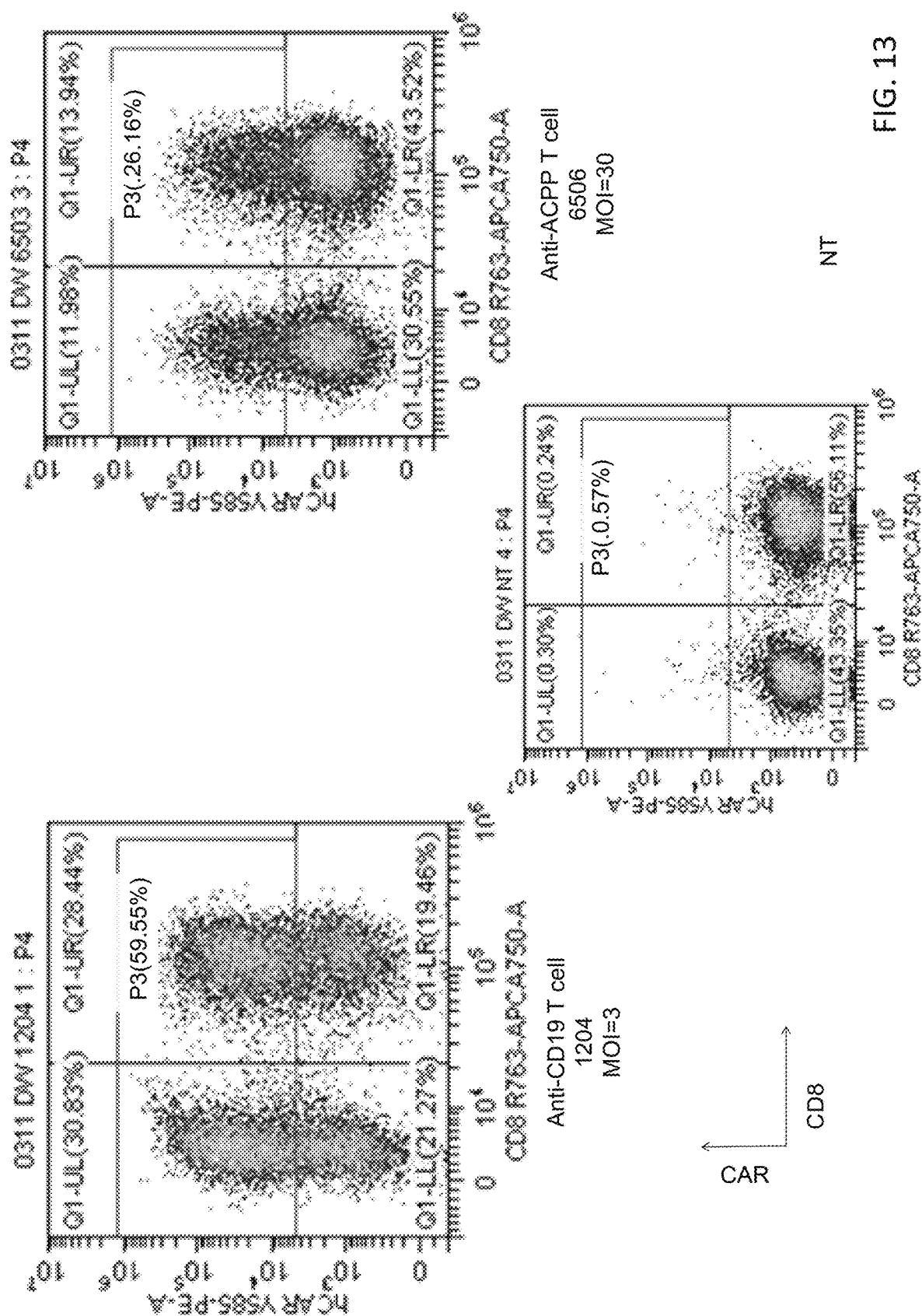
FIG. 13 shows cytometry assay of T cells expressing ACPP CAR.

FIG. 13 shows flow cytometry assay of T cells expressing anti-ACPP CAR (anti-ACPP scFv: SEQ ID: 173). On day 0, peripheral blood from healthy volunteers was drawn; CD3+ T cells were sorted; and CD3/CD28 Dynabeads were added at a 1:1 ratio. On Day 1, T cells were transduced with vectors. CD19CAR T cells were obtained according to the infection ratio of MOI=13; ACPP CART cells were obtained according to the infection ratio of MOI=130. On day 2, culturing media were changed, and lentivirus was removed. The cells were then resuspended using fresh medium.

On day 6, flow cytometry was used to detect CAR expression. Since both CD19CAR and ACPP CAR include humanized antibodies, human CAR antibodies are used for detection. As a result, the expression of CD19 CAR in infected T cells was 59.55%, and the expression of ACPP CAR in infected T cells was 26.16%. Since both CD19CAR and ACPP CAR are humanized antibodies, the CAR expression was measured by using human CAR antibody for flow detection.

Figure 14:
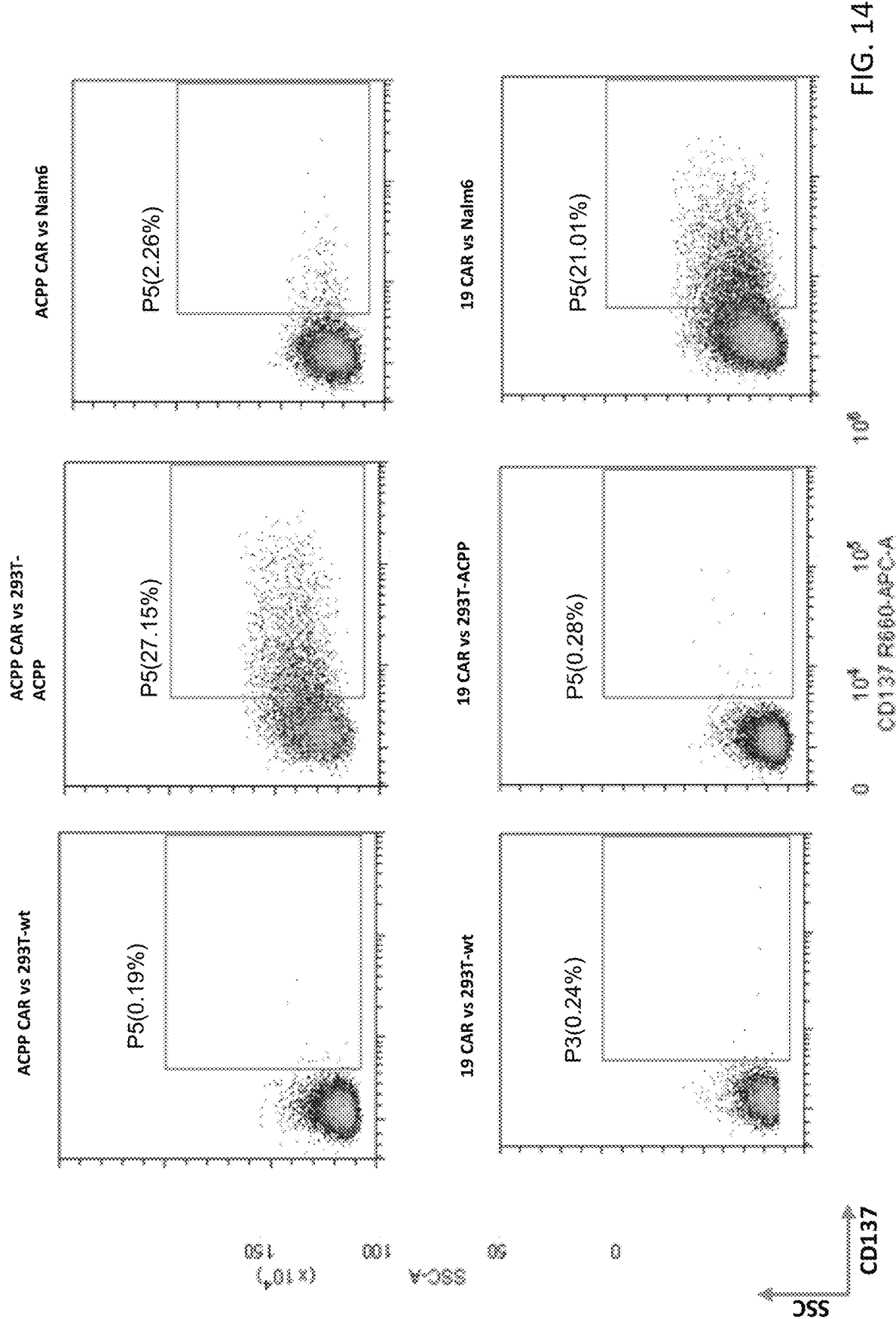
FIG. 14 shows results of co-culturing assay.

FIG. 14 shows results of co-culturing assay. The CAR ratio of ACPP CART cells and CD19CAR T cells was normalized with NT cells. $10^4$ CAR+ cells and $10^4$ 293T-WT or 293T-ACPP or Nalm-6 cells were co-cultured. CD137 expression of CAR positive CD8 positive cells was detected by flow cytometry after 48 hrs. The left column is the CD137 expression of CAR T cells co-cultured with 293T-WT cells, and the CD137 expression is absent in both the CD19CAR group and the ACPP CAR group. This indicates that CAR T cells cannot be activated due to the absence of specific antigen expression in 293T. In the middle column, CAR T cells were co-cultured with 293T or 293T-ACPP cells overexpressing ACPP. The expression of CD137 in the ACPP CAR group was 27.15%, and that CD137 was not expressed in the CD19CAR group. This indicates that ACPP-CAR T Cells recognized and were activated by ACPP. The right column is a co-culture of CAR T cells with Nalm-6 cells, which are CD19-positive cells that are specifically recognized and activated by CD19CAR T cells. The results showed that the expression of CD137 in the CD19CAR group was 21.01%, and that CD137 was not expressed in the ACPP CAR group. The results are in line with expectations. Taken together, it was demonstrated that ACPP CAR T cells specifically recognize and can be activated by the ACPP antigen. CD137 is a marker protein for the activation of T cells, so the level of CD137 up-regulation of CAR T cells after co-culture with CAR T cells and substrate target cells can be used to determine whether CAR T cells are activated.

Figure 15:
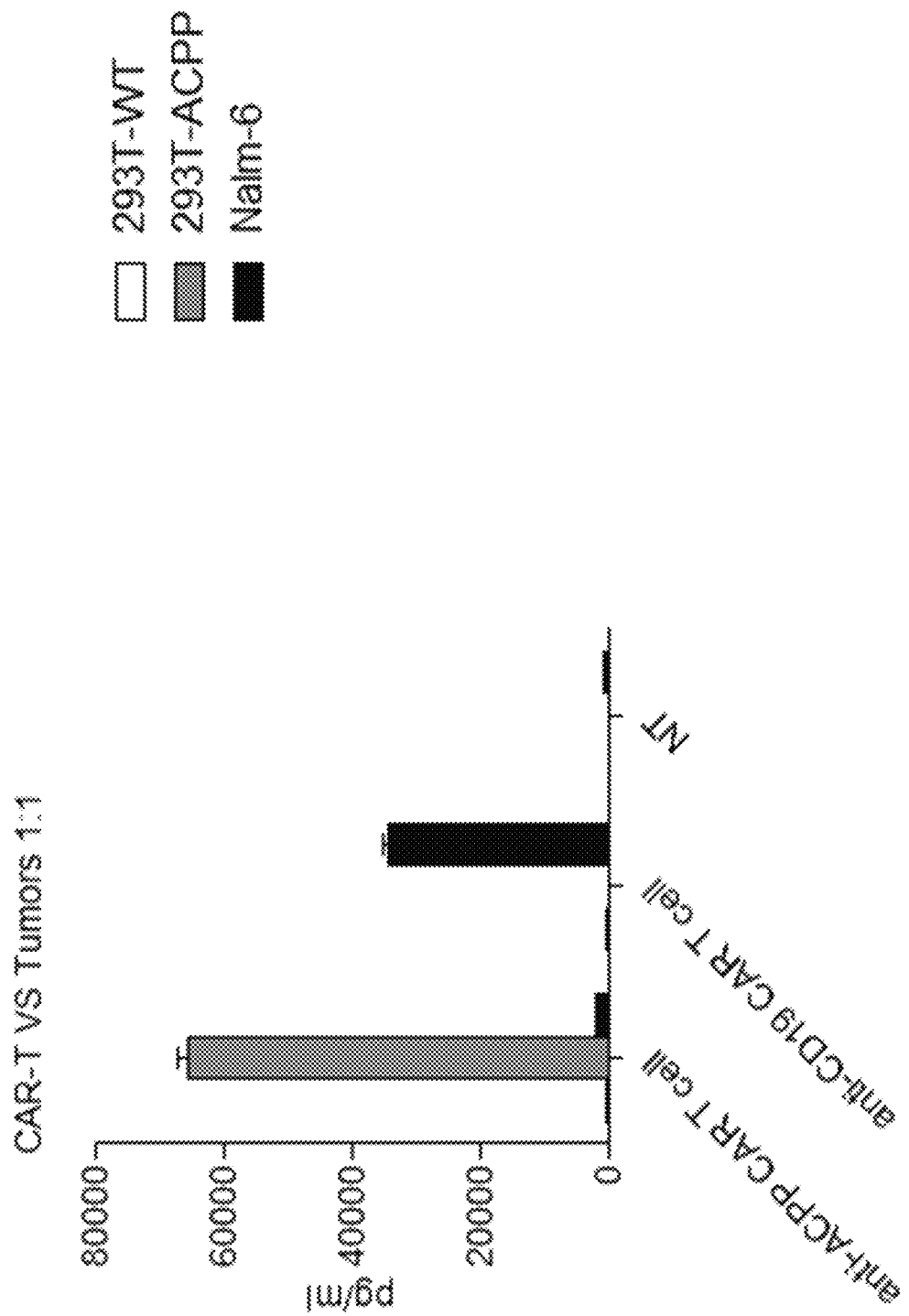
FIG. 15 shows IFN-γ release of anti-ACPP CART cells in response to ACPP.

FIG. 15 shows IFN-γ release by ACPP CART cells in response to ACPP. The CAR ratio of ACPP CART cells and CD19 CART cells was normalized with NT cells. The experiment was carried out by co-culturing 0.2 or $10^4$ CAR+ cells and $10^4$ 293T-WT or 293T-ACPP or Nalm-6 cells. After 24 hr, the supernatant was collected and the amount of IFN-γ released was examined. Nalm-6 is a CD19 positive cell, and 293T-ACPP is a 293T cell overexpressing ACPP. FIG. 15 is a graph showing the results of CAR T cells: substrate cells of 1:1. ACPP CAR T cells exhibit significant IFN-γ release when co-cultured with 293T-ACPP, indicating that 293T-ACPP can be recognized by ACPP CAR T cells and release IFN-γ to kill target cells. At the same time, Nalm-6 can also be recognized by CD19CAR T cells and release IFN-γ to kill target cells. Furthermore, Nalm-6 did not stimulate the release of IFN-γ by ACPP CAR T cells. CD19 CAR T cells were also unable to stimulate IFN-γ release by 293T-ACPP. In sum, ACPP CAR T cells can specifically recognize ACPP-positive target cells and release IFN-γ to kill target cells under their stimulation. During the process of killing target cells by T cells, a large amount of cytokines such as IFN-γ are usually released to enhance the killing ability. Therefore, whether the CAR T cell has the ability to kill the target cell can be determined by the amount of IFN-γ released when the CAR T cell is co-cultured with the substrate target cell.

Figure 16:
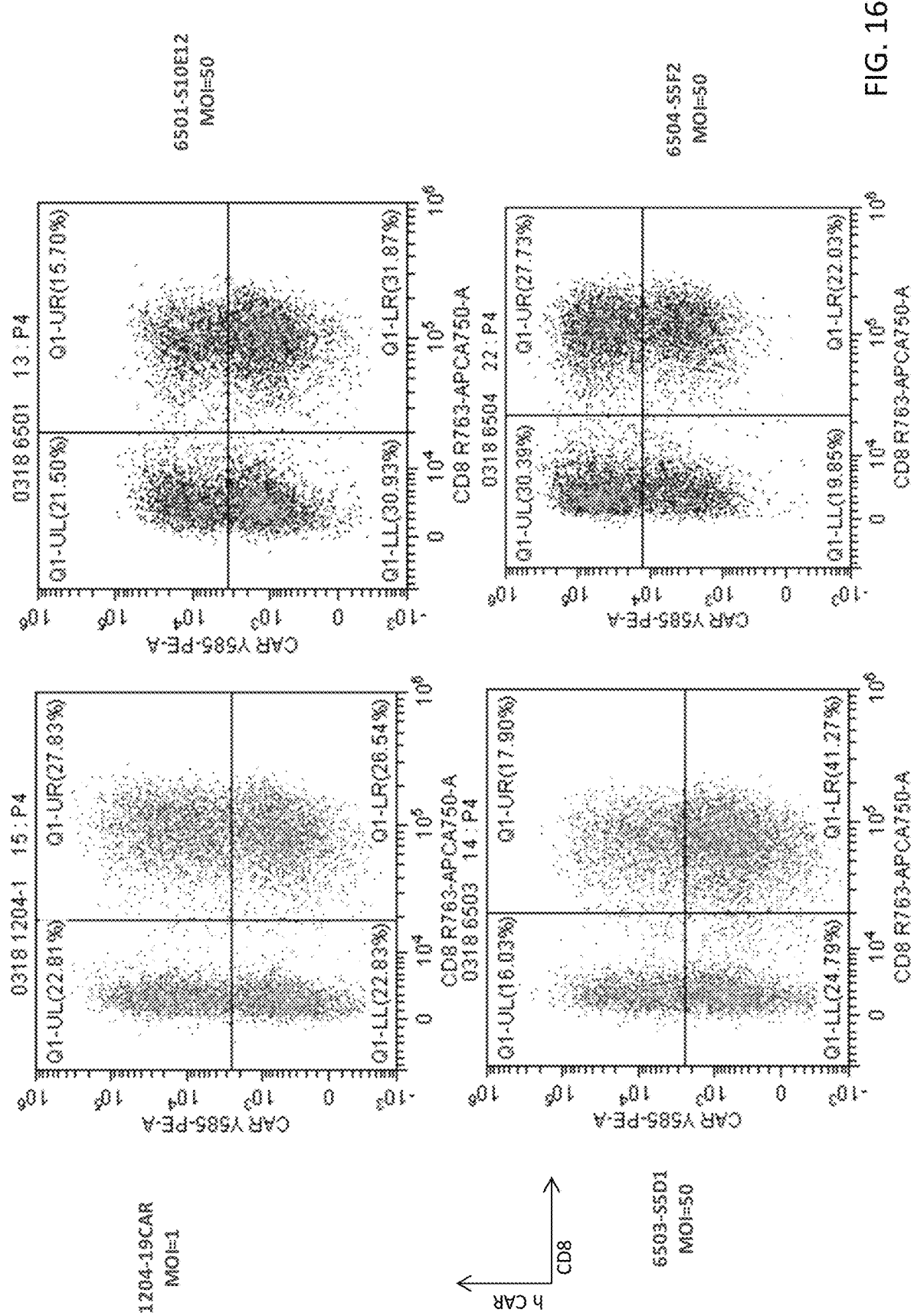
FIG. 16 shows that CAR expression of anti-ACPP CAR on T cells can be measured by detecting human CAR antibody.

FIG. 16 shows that CAR expression of ACPP CAR on T cells can be measured by detecting human CAR antibody. On day 0, peripheral blood from healthy volunteers was drawn; CD3+ T cells were sorted; and CD3/CD28 Dynabeads were added in a 1:1 ratio. On Day 1, T cells were transducted with vectors. CD19CAR T cells were obtained according to the infection ratio of MOI=1; ACPP CAR T cells were obtained according to the infection ratio of MOI=50. On day 2, culturing media were changed and lentivirus was removed. The cells were then resuspended using fresh medium. On day 6, flow cytometry was used to detect CAR expression. Since both CD19CAR and ACPP CAR are humanized antibodies, human CAR antibodies are used for detection. The results are shown in the figure. The expression of CD19CAR in CD19CAR T cells was 50.64%, and the expression of ACPP in ACPP CAR T cells (6501) was 37.2%, in ACPP CAR T cells (6503) was 33.93%, and in ACPP CART cells (6504) was 45.63%. Since both 19CAR and ACPP CAR are humanized antibodies, the CAR expression level can be obtained by using human CAR antibody for flow detection.

FIG. 17 shows cytokine release by ACPP CAR T cells in response to ACPP. The CAR ratio of ACPP CART cells and CD19 CART cells was normalized with NT cells. The experiment was carried out with 0.2 or $1 \times 10^4$ CAR+ cells co-cultured with $1 \times 10^4$ 293T-ACPP or Nalm-6 cells, and the supernatant was collected after 24 hrs to detect IFN-γ and IL2. Nalm-6 is a CD19 positive cell, and 293T-ACPP is a 293T cell overexpressing ACPP. FIG. 17 shows that ACPP CAR T 6503 exhibits significant increased release of IFN-γ and IL2 when co-cultured with 293T-ACPP, indicating that ACPP CAR T 6503 cells recognize 293T-ACPP and activate the release of IFN-γ and IL2. In contrast, ACPP CAR T 6501 and 6504 cells could not activate the release of IFN-γ and IL2. At the same time, CD19CAR T cells were able to recognize Nalm-6 and activate the release of IFN-γ and IL2. Furthermore, Nalm-6 failed to activate ACPP CART cells to release IFN-γ. At the same time, CD19CAR T cells could not be activated by 293T-ACPP to release IFN-γ. This indicates that the two targeted CAR T cells are specific. During the process of killing the target cells by T cells, a large amount of cytokines such as IFN-γ and IL2 are usually released to enhance the killing ability. Therefore, whether the CAR T cells have a killing ability against the target cells can be determined by the release amount of IFN-γ and IL2 when the CAR T cells are co-cultured with the substrate target cells.

Figure 18:
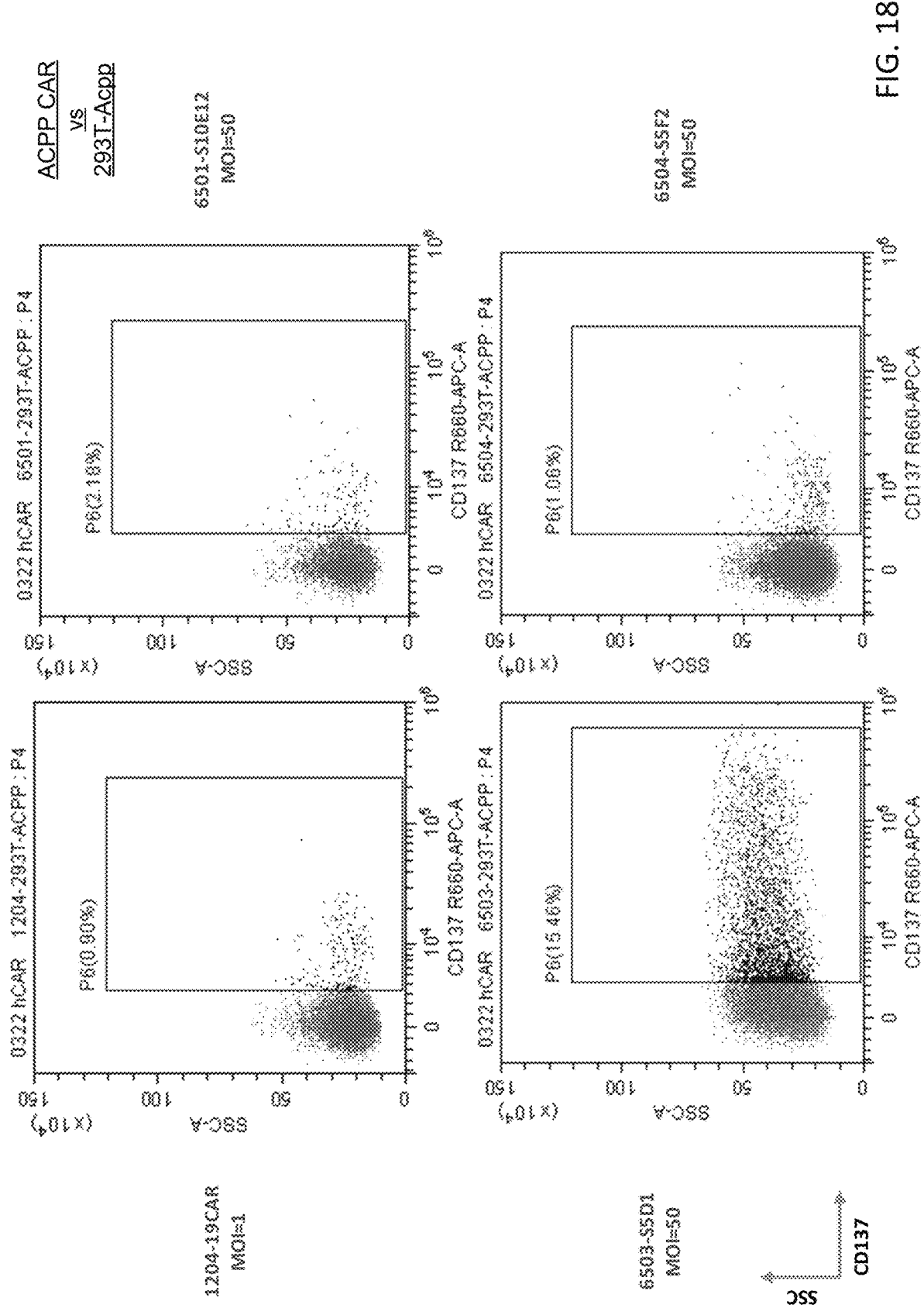
FIGS. 18 and 19 show CD137 expression in various conditions.
Figure 19:
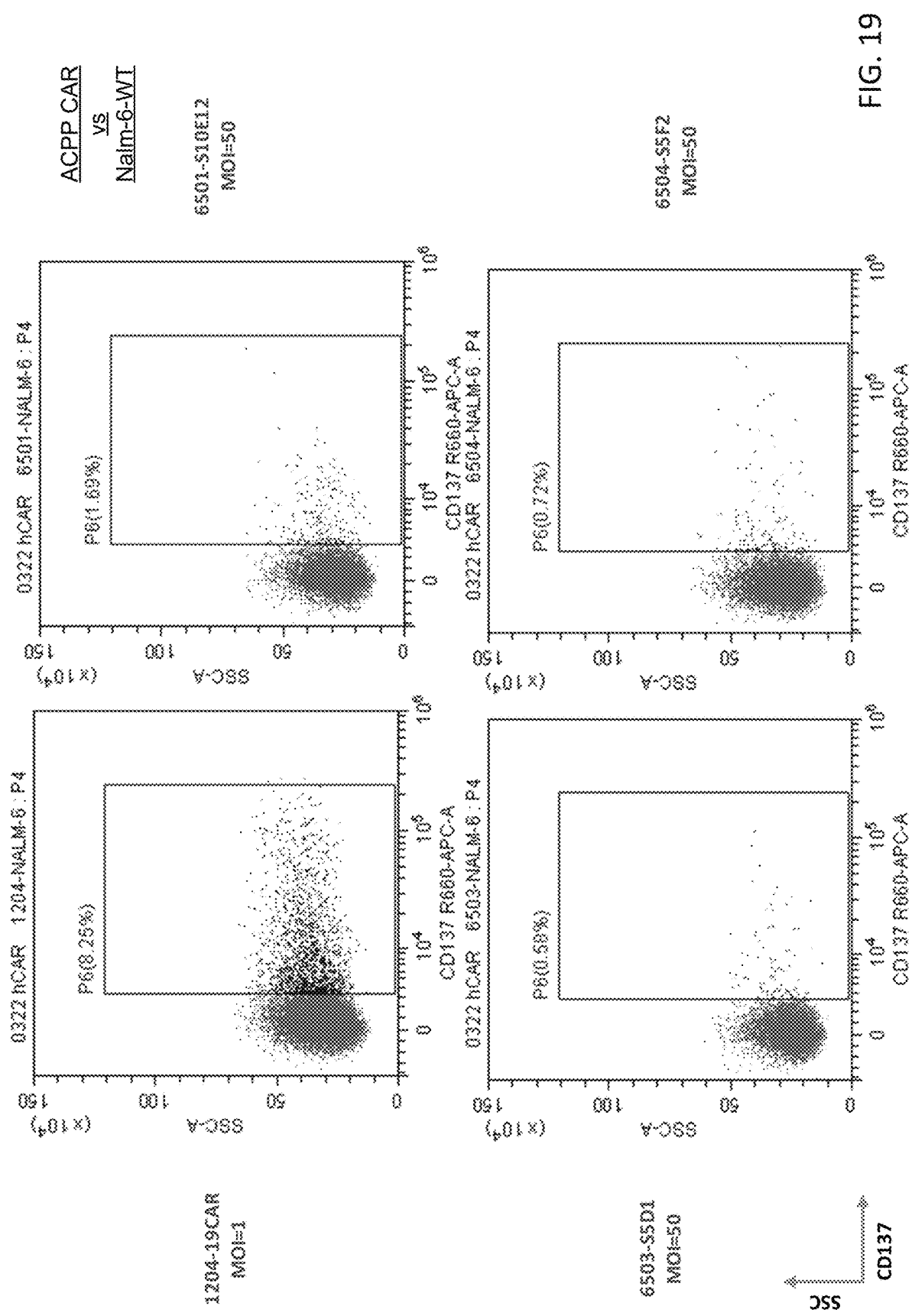

FIGS. 18 and 19 show CD137 expression in various conditions. CAR 1204 is a human-derived CD19CAR, which can be labeled with human CAR antibody and CD137 antibody. The CAR ratio of ACPP CART cells and CD19CAR T cells was normalized with NT cells. $10^4$ CAR+ cells were co-cultured with $10^4$ 293T-ACPP or Nalm-6 cells, and CD137 expression of CD8 positive cells was detected by flow cytometry after 24 hrs. The first row is the result of co-culture of CAR T cells and 293T-ACPP. CD19CAR T cells were not activated by 293T-ACPP to express CD137. ACPP CART 6503 cells were activated by 293T-ACPP to express CD137. ACPP CART 6501 and 6504 cells were not activated by 293T-ACPP to express CD137. The second row is the result of co-culture of CAR T cells and the CD19 positive cell line Nalm6. CD19CAR T cells can be activated by Nalm6 to express CD137. All ACPP CAR T cells could not be activated by Nalm6 to express CD137, indicating that CD19CAR T and ACPP CAR T cells are specific. CD137 is a marker protein for the activation of T cells. Thus, it is determined that CAR T cells are activated by detecting the expression of CD137 in CAR T cells after co-culture of CAR T cells and substrate target cells.

UPK2 Antibody Preparation

Figure 20:
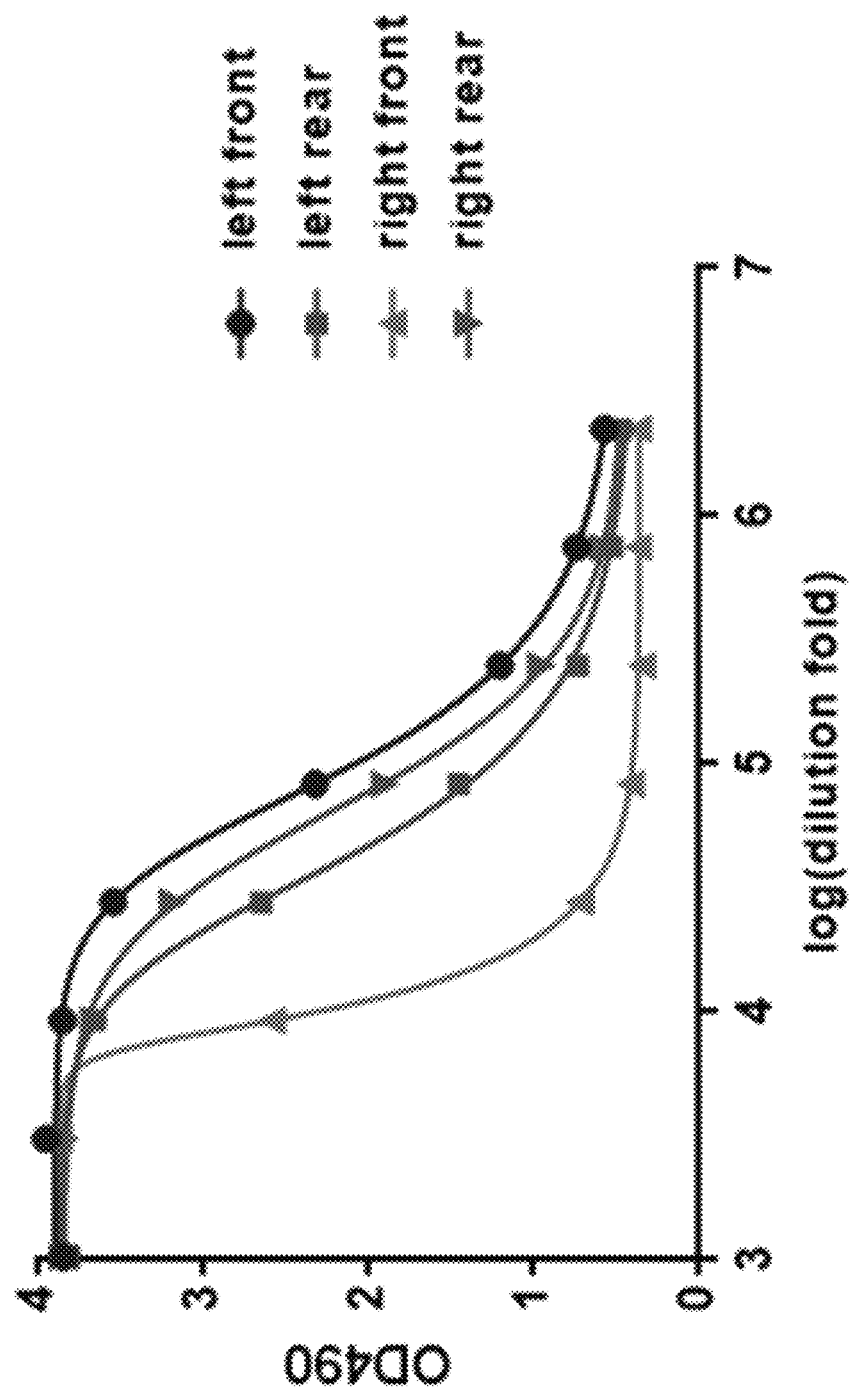
FIG. 20 shows antibody titer against UPK2-His in mouse serum after ELISA assay.

The recombinant UPK2 extracellular domain (UPK2-His) was prepared using *E. coli* expression system. BALB/c mice of 6-8 weeks old were taken, and the mice were subjected to tail vein blood sampling to leave the background serum before immunization. The UPK2-His recombinant antigen was immunized for the first time and emulsified with complete Freund's adjuvant. Each mouse was intraperitoneally injected with 50 μg of recombinant antigen. The immunization was boosted at intervals of two weeks, and UPK2-His recombinant antigen was emulsified by incomplete adjuvant. Each mouse was intraperitoneally injected with 50 μg of recombinant antigen for three booster immunizations. The tail vein blood collection was performed before the third booster immunization to analyze the serum UPK2 antibody titer. The results showed that the antibody titer of UPK2 in the serum of three of the four mice reached $10^6$ or more (FIG. 20), indicating that the immunization was successful.

The fifth immunization was changed to shock the immunization, and the UPK2-His recombinant antigen without adjuvant was used as the immunogen. Each mouse was intraperitoneally injected with 50 μg of recombinant antigen, and the mice were sacrificed 3 days after the immunization. Spleen cells were collected from mice and labeled as "left front" in the graph shown in FIG. 20.

The mouse spleen lymphocytes were separated using mouse lymphocyte separation solution (Dakko, CAT #DKW33-R0100), and the isolated lymphocytes were totaled using the total RNA extraction kit (Tiangen, CAT #DP430). RNA extraction. Using the extracted total RNA as a template, the first strand cDNA synthesis kit (Thermo scientific, CAT #K1621) was used to synthesize the heavy chain variable region and the light chain variable region, respectively. The reverse transcription primers were gene-specific primers, and the primer pairing was performed. The regions are located in the antibody heavy chain constant region and the antibody light chain constant region, respectively, and the specific sequences are PmCGR: TGCATTT-GAACTCCTTGCC (SEQ ID NO: 189) and PmCKR: CCATCAATCTTCCACTTGAC (SEQ ID NO: 190), respectively. The synthesized cDNA was immediately stored at −70° C. for storage. Then, the cDNA was obtained by reverse transcription and used as a template to obtain the primers (Journal of Immunological Methods, 201 (1997), 35-55), and the murine antibodies VH and VK were amplified by PCR, respectively. The overlap extension PCR technique was used to construct a single chain antibody (scFv). Finally, the prepared mouse single-chain antibody gene was cloned into the vector pADSCFV-S to construct a ScFv library. The library capacity of this antibody library reached $1.6 \times 10^8$, and the correct rate was 41.5%.

Figure 21:
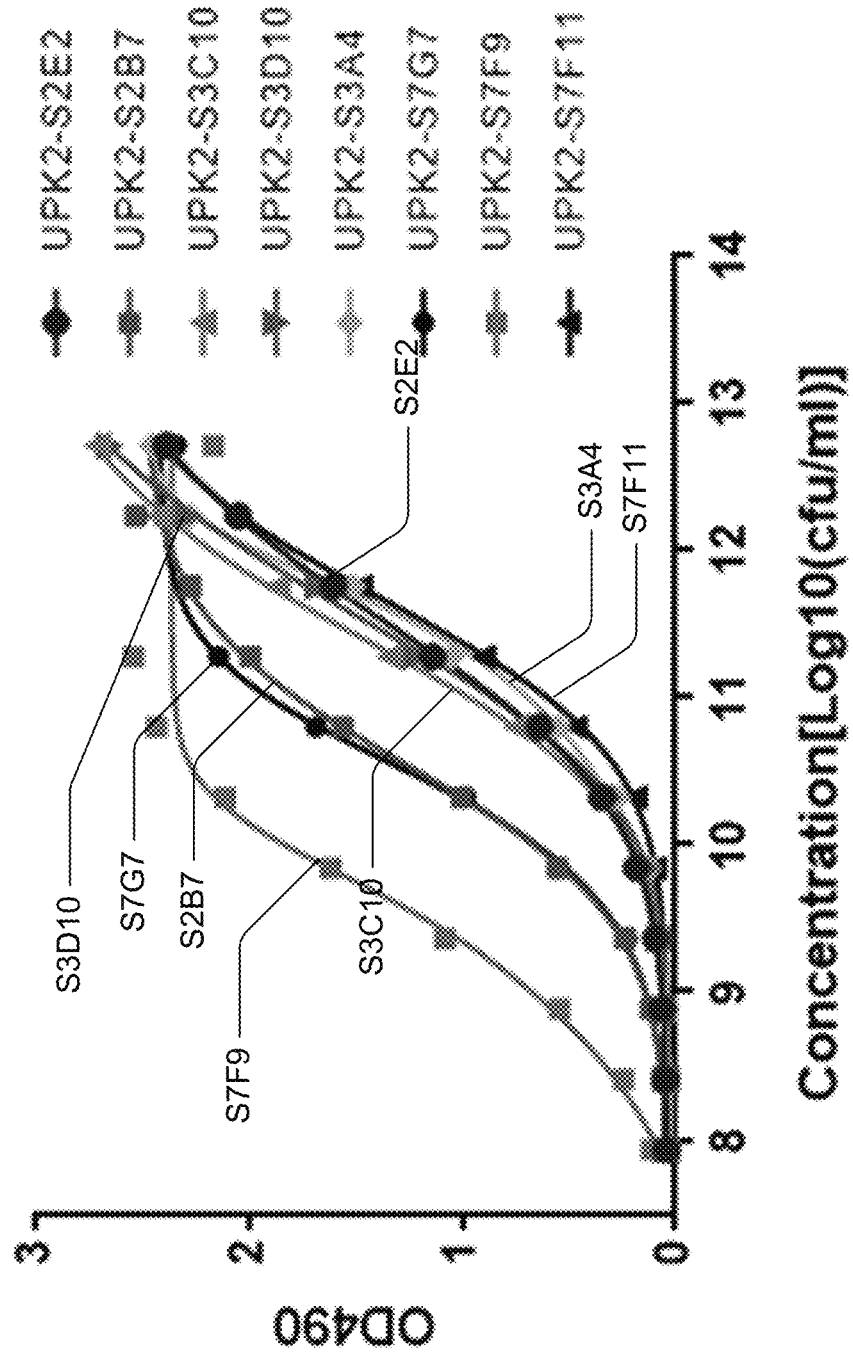
FIG. 21 shows analysis of binding of 8 phage display antibodies to UPK2-His based on Phage-ELISA.

Using recombinant UPK2-his as the antigen, the mouse single-chain antibody library was screened by reference to the classical solid-phase screening strategy, and three rounds of screening were performed by means of binding, elution, neutralization, infection and amplification, in the second round. After the third round of screening, about 700 monoclonal clones were identified by phage ELISA. Sixty clones with high positive ELISA signal were selected for sequence analysis to obtain eight strains with different sequences that bind to UPK2-His. The eight antibodies are: clone S2B7, S2E2, S3A4, S3C10, S3D10, S7F9, S7F11 and S7G7 (FIG. 21). The heavy and light chain variable region sequences (scFv) of the eight monoclonal antibodies are shown in Table 6.

The heavy and light chain variable region genes of the above eight scFvs were cloned into the eukaryotic expression vectors pTSEG1n and pTSEK, respectively, and eight murine-human chimeric antibodies (murine antibody variable regions) were prepared using the company's HEK293 cell transient expression system. Human antibody constant region). The recombinant whole antibody was purified by Protein A affinity chromatography column, and SDS-PAGE showed. These eight antibodies were normally expressed, and their purity met the level for protein identification.

Figure 22:
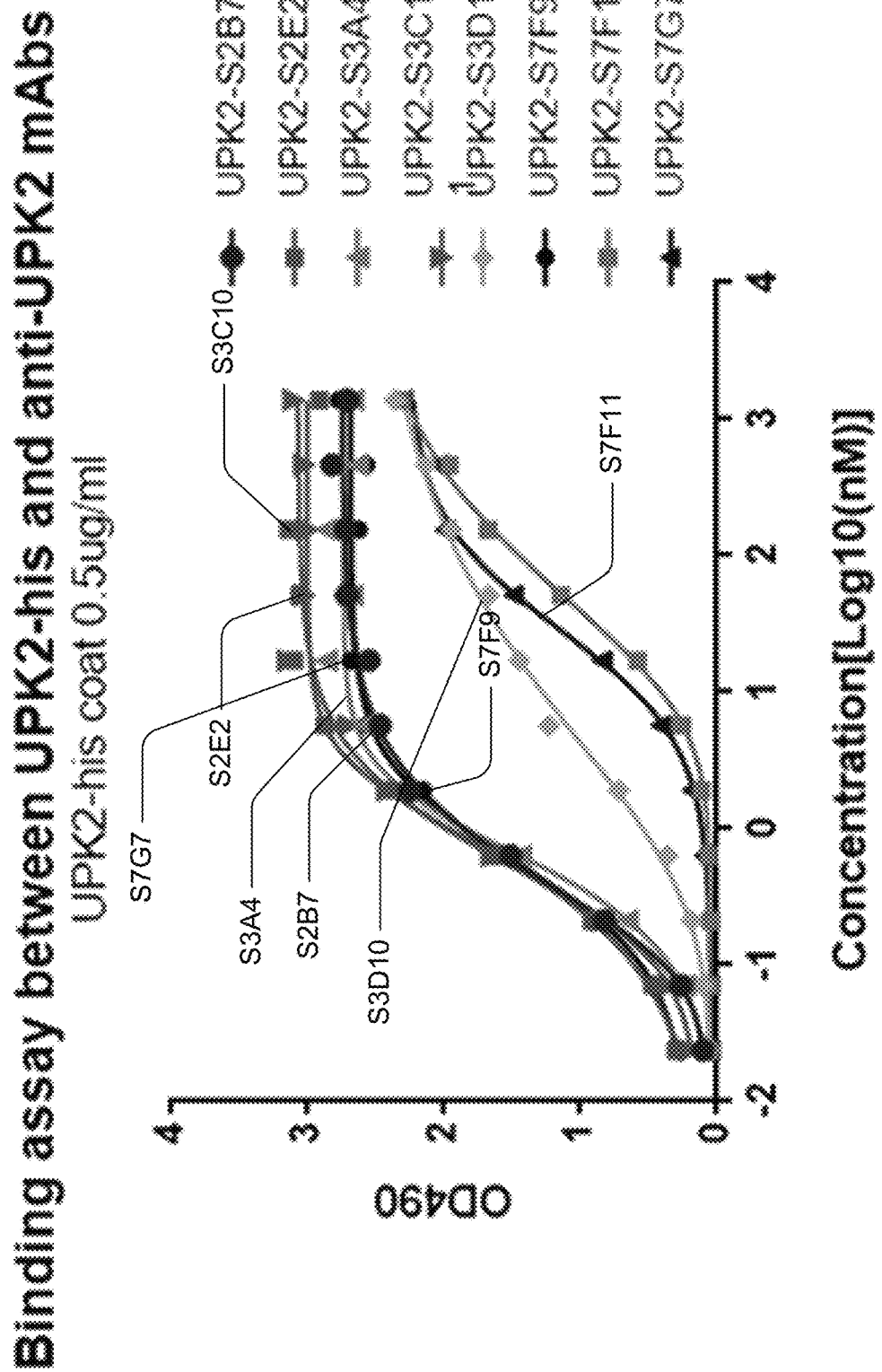
FIG. 22 shows ELISA analysis of the binding of recombinant monoclonal antibodies to recombinant UPK2-His.

The ability of recombinant whole antibodies to bind antigen UPK2-His was analyzed using a classical ELISA method. The results are shown in FIG. 22. As shown in FIG. 22, all 8 antibodies can bind to the antigen UPK2-His.

Figure 23:
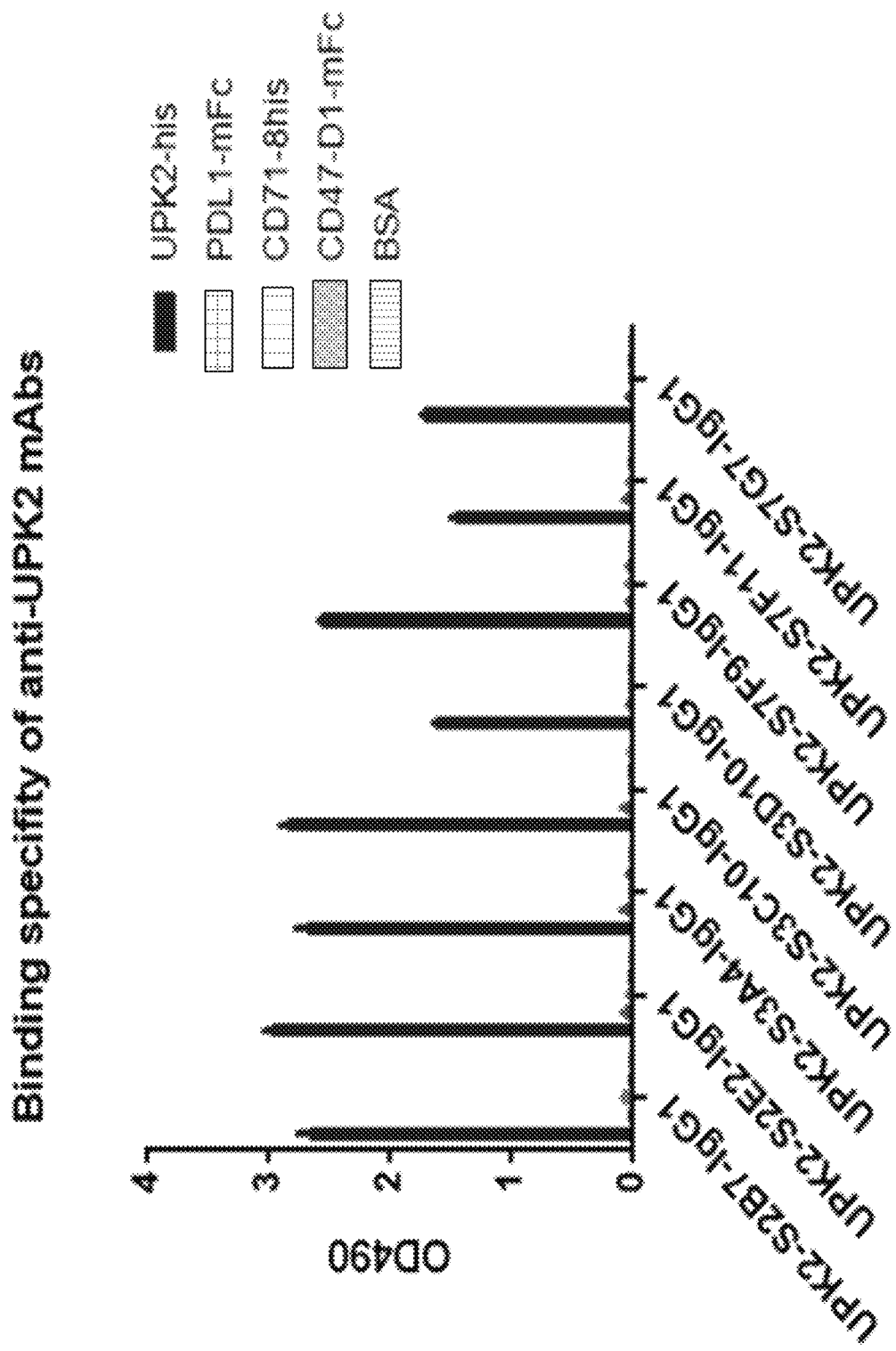
FIG. 23 shows ELISA analysis of the specificity of recombinant anti-UPK2 mAb.
Figure 24:
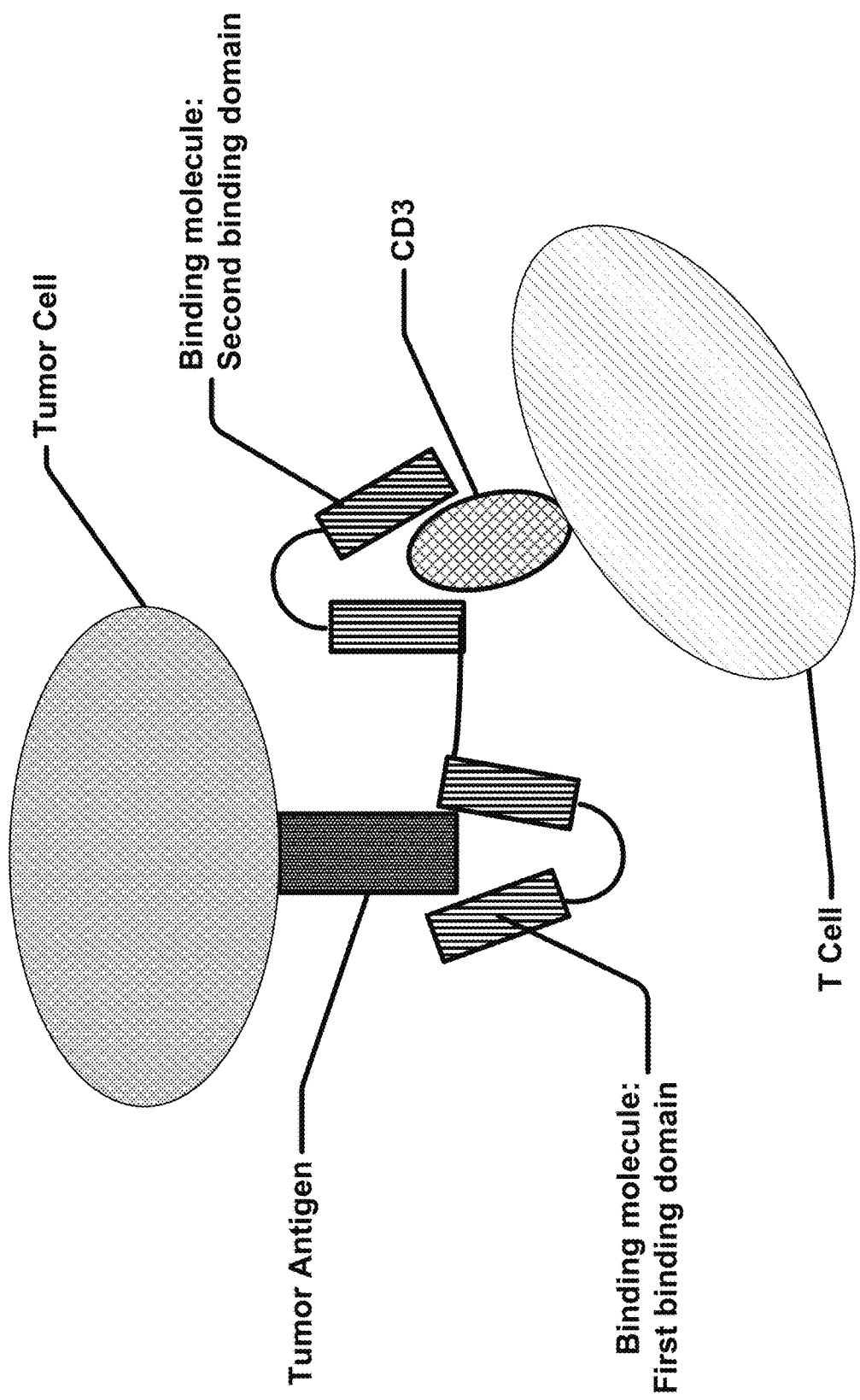
FIG. 24 shows an exemplary structure of a binding molecule.

At the same time, the specificity of the prepared monoclonal antibody was analyzed by a similar ELISA method. As shown in FIG. 23, the eight recombinant antibodies can specifically recognize the recombinant UPK2-His, and there are no obvious non-specific bindings of various unrelated antigens.

The affinity of the eight monoclonal antibodies was analyzed using GE's BIAcore X-100. Affinity analysis was performed using a conventional procedure by first capturing the human monoclonal antibody with an anti-human antibody coated on a chip, and then using different concentrations of recombinant UPK2-His as the mobile phase for affinity analysis. As shown in Table 8, the affinity (KD) of these recombinant antibodies is mostly between 0.1 nM and 10 nM. Among them, the binding and dissociation of S7F11/S7G7 were slow, and the binding of S3D10 was too slow. When the three monoclonal antibodies were analyzed by BIAcore X-100 for affinity analysis, the automatic fitting of KD was poor, and the data was for reference only.

TABLE 8

Recombinant anti-UPK2 monoclonal antibody affinity parameters determined by BIAcore

| Monoclonal antibody | Kon | Koff | KD | Remarks |
| --- | --- | --- | --- | --- |
| S2B7 | $1.493 \times 10^5$ | $3.495 \times 10^{-3}$ | $2.34 \times 10^8$ | |
| S3A4 | $1.125 \times 10^5$ | $3.05 \times 10^{-3}$ | $2.712 \times 10^{-8}$ | |
| S7F9 | $1.4 \times 10^5$ | $2.344 \times 10^{-3}$ | $1.674 \times 10^{-8}$ | |
| S2E2 | $1.381 \times 10^6$ | $3.894 \times 10^{-3}$ | $2.82 \times 10^{-9}$ | |
| S3C10 | $1.226 \times 10^6$ | $1.117 \times 10^{-3}$ | $9.109 \times 10^{-10}$ | |
| S7F11 | $3.504 \times 10^3$ | $8.126 \times 10^{-6}$ | $2.319 \times 10^{-9}$ | Kd overrun |
| S7G7 | $5.049 \times 10^4$ | $1.202 \times 10^{-6}$ | $2.381 \times 10^{-11}$ | Kd overrun |
| S3D10 | $6.431 \times 10^2$ | $2.614 \times 10^{-3}$ | $4.064 \times 10^{-6}$ | U-value = 15 |

In this study, the recombinant UPK2 extracellular domain (UPK2-His) was used to complete the immunization of mice, the construction, screening and monoclonal identification of the murine immune library. Eight murine monoclonal antibodies (S2B7, S2E2, S3A4, S3C10, S3D10, S7F9, S7F11 and S7G7), with different sequences and capable of binding recombinant UPK2 were obtained. and preliminary specificity analysis showed that these monoclonal antibodies specifically bind to recombinant UPK2-his. Affinity analysis based on BIAcore showed that the affinity of these recombinant anti-UPK2 antibodies was mostly between 0.1 nM and 10 nM.

All publications, patents and patent applications cited in this specification are incorporated herein by reference in their entireties as if each individual publication, patent or patent application were specifically and individually indicated to be incorporated by reference. While the foregoing has been described in terms of various embodiments, the skilled artisan will appreciate that various modifications, substitutions, omissions, and changes may be made without departing from the spirit thereof.

What is claimed is:

1. An antibody that binds ACPP, wherein the antibody comprises a heavy chain variable region (HVR) comprising amino acid sequence SEQ ID NO: 83 and a light chain variable region (LVR) comprising amino acid sequence SEQ ID NO: 82.

2. The antibody of claim 1, wherein the HVR is joined to a human IgG chain constant region.

3. The antibody of claim 2, wherein the human IgG comprises IgG1 or IgG3.

4. The antibody of claim 1, wherein the antibody is conjugated to a cytotoxic agent.

5. The antibody of claim 4, wherein the cytotoxic agent comprises a radioactive isotope or a toxin.

6. The antibody of claim 1, wherein SEQ ID NO: 83 and SEQ ID NO: 82 are joined by a linker.

7. The antibody of claim 6, wherein the linker comprises SEQ ID NO: 24 or SEQ ID NO: 184.

8. The antibody of claim 1, wherein the antibody comprises a scFv.

9. The antibody of claim 8, wherein the scFv comprises a linker joining SEQ ID NO: 82 and SEQ ID NO: 83.

10. The antibody of claim 8, wherein the scFv comprises amino acid sequence SEQ ID NO: 173.

11. The antibody of claim 8, wherein the antibody is conjugated to a cytotoxic agent.

12. The antibody of claim 11, wherein the cytotoxic agent comprises a radioactive isotope or a toxin.

13. The antibody of claim 9, wherein the linker comprises SEQ ID NO: 24 or SEQ ID NO: 184.

* * * * *

SEQUENCE LISTING

<160> NUMBER OF SEQ ID NOS: 190

<210> SEQ ID NO 1
<211> LENGTH: 184
<212> TYPE: PRT
<213> ORGANISM: Homo sapiens

<400> SEQUENCE: 1

```
Met Ala Pro Leu Leu Pro Ile Arg Thr Leu Pro Leu Ile Leu Ile Leu
1               5                   10                  15

Leu Ala Leu Leu Ser Pro Gly Ala Ala Asp Phe Asn Ile Ser Ser Leu
            20                  25                  30

Ser Gly Leu Leu Ser Pro Ala Leu Thr Glu Ser Leu Leu Val Ala Leu
        35                  40                  45

Pro Pro Cys His Leu Thr Gly Gly Asn Ala Thr Leu Met Val Arg Arg
    50                  55                  60

Ala Asn Asp Ser Lys Val Val Thr Ser Ser Phe Val Val Pro Pro Cys
65                  70                  75                  80

Arg Gly Arg Arg Glu Leu Val Ser Val Val Asp Ser Gly Ala Gly Phe
```

```
                    85                  90                  95
Thr Val Thr Arg Leu Ser Ala Tyr Gln Val Thr Asn Leu Val Pro Gly
                100                 105                 110

Thr Lys Phe Tyr Ile Ser Tyr Leu Val Lys Lys Gly Thr Ala Thr Glu
            115                 120                 125

Ser Ser Arg Glu Ile Pro Met Ser Thr Leu Pro Arg Arg Asn Met Glu
        130                 135                 140

Ser Ile Gly Leu Gly Met Ala Arg Thr Gly Gly Met Val Val Ile Thr
145                 150                 155                 160

Val Leu Leu Ser Val Ala Met Phe Leu Leu Val Leu Gly Phe Ile Ile
                165                 170                 175

Ala Leu Ala Leu Gly Ser Arg Lys
                180

<210> SEQ ID NO 2
<211> LENGTH: 909
<212> TYPE: PRT
<213> ORGANISM: Homo sapiens

<400> SEQUENCE: 2

Met Ala Ala Arg Pro Leu Pro Val Ser Pro Ala Arg Ala Leu Leu Leu
1               5                   10                  15

Ala Leu Ala Gly Ala Leu Leu Ala Pro Cys Glu Ala Arg Gly Val Ser
            20                  25                  30

Leu Trp Asn Gln Gly Arg Ala Asp Glu Val Val Ser Ala Ser Val Gly
        35                  40                  45

Ser Gly Asp Leu Trp Ile Pro Val Lys Ser Phe Asp Ser Lys Asn His
    50                  55                  60

Pro Glu Val Leu Asn Ile Arg Leu Gln Arg Glu Ser Lys Glu Leu Ile
65                  70                  75                  80

Ile Asn Leu Glu Arg Asn Glu Gly Leu Ile Ala Ser Ser Phe Thr Glu
                85                  90                  95

Thr His Tyr Leu Gln Asp Gly Thr Asp Val Ser Leu Ala Arg Asn Tyr
            100                 105                 110

Thr Val Ile Leu Gly His Cys Tyr Tyr His Gly His Val Arg Gly Tyr
        115                 120                 125

Ser Asp Ser Ala Val Ser Leu Ser Thr Cys Ser Gly Leu Arg Gly Leu
    130                 135                 140

Ile Val Phe Glu Asn Glu Ser Tyr Val Leu Glu Pro Met Lys Ser Ala
145                 150                 155                 160

Thr Asn Arg Tyr Lys Leu Phe Pro Ala Lys Lys Leu Lys Ser Val Arg
                165                 170                 175

Gly Ser Cys Gly Ser His His Asn Thr Pro Asn Leu Ala Ala Lys Asn
            180                 185                 190

Val Phe Pro Pro Ser Gln Thr Trp Ala Arg Arg His Lys Arg Glu
        195                 200                 205

Thr Leu Lys Ala Thr Lys Tyr Val Glu Leu Val Ile Val Ala Asp Asn
    210                 215                 220

Arg Glu Phe Gln Arg Gln Gly Lys Asp Leu Glu Lys Val Lys Gln Arg
225                 230                 235                 240

Leu Ile Glu Ile Ala Asn His Val Asp Lys Phe Tyr Arg Pro Leu Asn
                245                 250                 255

Ile Arg Ile Val Leu Val Gly Val Glu Val Trp Asn Asp Met Asp Lys
            260                 265                 270
```

```
Cys Ser Val Ser Gln Asp Pro Phe Thr Ser Leu His Glu Phe Leu Asp
            275                 280                 285

Trp Arg Lys Met Lys Leu Leu Pro Arg Lys Ser His Asp Asn Ala Gln
290                 295                 300

Leu Val Ser Gly Val Tyr Phe Gln Gly Thr Thr Ile Gly Met Ala Pro
305                 310                 315                 320

Ile Met Ser Met Cys Thr Ala Asp Gln Ser Gly Gly Ile Val Met Asp
                325                 330                 335

His Ser Asp Asn Pro Leu Gly Ala Ala Val Thr Leu Ala His Glu Leu
                340                 345                 350

Gly His Asn Phe Gly Met Asn His Asp Thr Leu Asp Arg Gly Cys Ser
            355                 360                 365

Cys Gln Met Ala Val Glu Lys Gly Gly Cys Ile Met Asn Ala Ser Thr
        370                 375                 380

Gly Tyr Pro Phe Pro Met Val Phe Ser Ser Cys Ser Arg Lys Asp Leu
385                 390                 395                 400

Glu Thr Ser Leu Glu Lys Gly Met Gly Val Cys Leu Phe Asn Leu Pro
                405                 410                 415

Glu Val Arg Glu Ser Phe Gly Gly Gln Lys Cys Gly Asn Arg Phe Val
            420                 425                 430

Glu Glu Gly Glu Glu Cys Asp Cys Gly Glu Pro Glu Glu Cys Met Asn
        435                 440                 445

Arg Cys Cys Asn Ala Thr Thr Cys Thr Leu Lys Pro Asp Ala Val Cys
    450                 455                 460

Ala His Gly Leu Cys Cys Glu Asp Cys Gln Leu Lys Pro Ala Gly Thr
465                 470                 475                 480

Ala Cys Arg Asp Ser Ser Asn Ser Cys Asp Leu Pro Glu Phe Cys Thr
                485                 490                 495

Gly Ala Ser Pro His Cys Pro Ala Asn Val Tyr Leu His Asp Gly His
            500                 505                 510

Ser Cys Gln Asp Val Asp Gly Tyr Cys Tyr Asn Gly Ile Cys Gln Thr
        515                 520                 525

His Glu Gln Gln Cys Val Thr Leu Trp Gly Pro Gly Ala Lys Pro Ala
530                 535                 540

Pro Gly Ile Cys Phe Glu Arg Val Asn Ser Ala Gly Asp Pro Tyr Gly
545                 550                 555                 560

Asn Cys Gly Lys Val Ser Lys Ser Ser Phe Ala Lys Cys Glu Met Arg
                565                 570                 575

Asp Ala Lys Cys Gly Lys Ile Gln Cys Gln Gly Gly Ala Ser Arg Pro
            580                 585                 590

Val Ile Gly Thr Asn Ala Val Ser Ile Glu Thr Asn Ile Pro Leu Gln
        595                 600                 605

Gln Gly Gly Arg Ile Leu Cys Arg Gly Thr His Val Tyr Leu Gly Asp
    610                 615                 620

Asp Met Pro Asp Pro Gly Leu Val Leu Ala Gly Thr Lys Cys Ala Asp
625                 630                 635                 640

Gly Lys Ile Cys Leu Asn Arg Gln Cys Gln Asn Ile Ser Val Phe Gly
                645                 650                 655

Val His Glu Cys Ala Met Gln Cys His Gly Arg Gly Val Cys Asn Asn
            660                 665                 670

Arg Lys Asn Cys His Cys Glu Ala His Trp Ala Pro Pro Phe Cys Asp
        675                 680                 685

Lys Phe Gly Phe Gly Gly Ser Thr Asp Ser Gly Pro Ile Arg Gln Ala
```

-continued

```
                690                 695                 700
Asp Asn Gln Gly Leu Thr Ile Gly Ile Leu Val Thr Ile Leu Cys Leu
705                 710                 715                 720

Leu Ala Ala Gly Phe Val Val Tyr Leu Lys Arg Lys Thr Leu Ile Arg
                725                 730                 735

Leu Leu Phe Thr Asn Lys Lys Thr Thr Ile Glu Lys Leu Arg Cys Val
                740                 745                 750

Arg Pro Ser Arg Pro Pro Arg Gly Phe Gln Pro Cys Gln Ala His Leu
                755                 760                 765

Gly His Leu Gly Lys Gly Leu Met Arg Lys Pro Pro Asp Ser Tyr Pro
                770                 775                 780

Pro Lys Asp Asn Pro Arg Arg Leu Leu Gln Cys Gln Asn Val Asp Ile
785                 790                 795                 800

Ser Arg Pro Leu Asn Gly Leu Asn Val Pro Gln Pro Gln Ser Thr Gln
                805                 810                 815

Arg Val Leu Pro Pro Leu His Arg Ala Pro Arg Ala Pro Ser Val Pro
                820                 825                 830

Ala Arg Pro Leu Pro Ala Lys Pro Ala Leu Arg Gln Ala Gln Gly Thr
                835                 840                 845

Cys Lys Pro Asn Pro Pro Gln Lys Pro Leu Pro Ala Asp Pro Leu Ala
                850                 855                 860

Arg Thr Thr Arg Leu Thr His Ala Leu Ala Arg Thr Pro Gly Gln Trp
865                 870                 875                 880

Glu Thr Gly Leu Arg Leu Ala Pro Leu Arg Pro Ala Pro Gln Tyr Pro
                885                 890                 895

His Gln Val Pro Arg Ser Thr His Thr Ala Tyr Ile Lys
                900                 905

<210> SEQ ID NO 3
<211> LENGTH: 553
<212> TYPE: PRT
<213> ORGANISM: Homo sapiens

<400> SEQUENCE: 3

Met Val Gln Arg Leu Trp Val Ser Arg Leu Leu Arg His Arg Lys Ala
1               5                   10                  15

Gln Leu Leu Leu Val Asn Leu Leu Thr Phe Gly Leu Glu Val Cys Leu
                20                  25                  30

Ala Ala Gly Ile Thr Tyr Val Pro Pro Leu Leu Leu Glu Val Gly Val
                35                  40                  45

Glu Glu Lys Phe Met Thr Met Val Leu Gly Ile Gly Pro Val Leu Gly
                50                  55                  60

Leu Val Cys Val Pro Leu Leu Gly Ser Ala Ser Asp His Trp Arg Gly
65                  70                  75                  80

Arg Tyr Gly Arg Arg Arg Pro Phe Ile Trp Ala Leu Ser Leu Gly Ile
                85                  90                  95

Leu Leu Ser Leu Phe Leu Ile Pro Arg Ala Gly Trp Leu Ala Gly Leu
                100                 105                 110

Leu Cys Pro Asp Pro Arg Pro Leu Glu Leu Ala Leu Leu Ile Leu Gly
                115                 120                 125

Val Gly Leu Leu Asp Phe Cys Gly Gln Val Cys Phe Thr Pro Leu Glu
                130                 135                 140

Ala Leu Leu Ser Asp Leu Phe Arg Asp Pro Asp His Cys Arg Gln Ala
145                 150                 155                 160
```

Tyr Ser Val Tyr Ala Phe Met Ile Ser Leu Gly Gly Cys Leu Gly Tyr
            165                 170                 175

Leu Leu Pro Ala Ile Asp Trp Asp Thr Ser Ala Leu Ala Pro Tyr Leu
            180                 185                 190

Gly Thr Gln Glu Glu Cys Leu Phe Gly Leu Leu Thr Leu Ile Phe Leu
            195                 200                 205

Thr Cys Val Ala Ala Thr Leu Leu Val Ala Glu Ala Ala Leu Gly
210                 215                 220

Pro Thr Glu Pro Ala Glu Gly Leu Ser Ala Pro Ser Leu Ser Pro His
225                 230                 235                 240

Cys Cys Pro Cys Arg Ala Arg Leu Ala Phe Arg Asn Leu Gly Ala Leu
            245                 250                 255

Leu Pro Arg Leu His Gln Leu Cys Cys Arg Met Pro Arg Thr Leu Arg
            260                 265                 270

Arg Leu Phe Val Ala Glu Leu Cys Ser Trp Met Ala Leu Met Thr Phe
            275                 280                 285

Thr Leu Phe Tyr Thr Asp Phe Val Gly Glu Gly Leu Tyr Gln Gly Val
            290                 295                 300

Pro Arg Ala Glu Pro Gly Thr Glu Ala Arg Arg His Tyr Asp Glu Gly
305                 310                 315                 320

Val Arg Met Gly Ser Leu Gly Leu Phe Leu Gln Cys Ala Ile Ser Leu
            325                 330                 335

Val Phe Ser Leu Val Met Asp Arg Leu Val Gln Arg Phe Gly Thr Arg
            340                 345                 350

Ala Val Tyr Leu Ala Ser Val Ala Ala Phe Pro Val Ala Ala Gly Ala
            355                 360                 365

Thr Cys Leu Ser His Ser Val Ala Val Val Thr Ala Ser Ala Ala Leu
            370                 375                 380

Thr Gly Phe Thr Phe Ser Ala Leu Gln Ile Leu Pro Tyr Thr Leu Ala
385                 390                 395                 400

Ser Leu Tyr His Arg Glu Lys Gln Val Phe Leu Pro Lys Tyr Arg Gly
            405                 410                 415

Asp Thr Gly Gly Ala Ser Ser Glu Asp Ser Leu Met Thr Ser Phe Leu
            420                 425                 430

Pro Gly Pro Lys Pro Gly Ala Pro Phe Pro Asn Gly His Val Gly Ala
            435                 440                 445

Gly Gly Ser Gly Leu Leu Pro Pro Pro Ala Leu Cys Gly Ala Ser
            450                 455                 460

Ala Cys Asp Val Ser Val Arg Val Val Gly Glu Pro Thr Glu Ala
465                 470                 475                 480

Arg Val Val Pro Gly Arg Gly Ile Cys Leu Asp Leu Ala Ile Leu Asp
            485                 490                 495

Ser Ala Phe Leu Leu Ser Gln Val Ala Pro Ser Leu Phe Met Gly Ser
            500                 505                 510

Ile Val Gln Leu Ser Gln Ser Val Thr Ala Tyr Met Val Ser Ala Ala
            515                 520                 525

Gly Leu Gly Leu Val Ala Ile Tyr Phe Ala Thr Gln Val Val Phe Asp
            530                 535                 540

Lys Ser Asp Leu Ala Lys Tyr Ser Ala
545                 550

<210> SEQ ID NO 4
<211> LENGTH: 418
<212> TYPE: PRT

<213> ORGANISM: Homo sapiens

<400> SEQUENCE: 4

```
Met Arg Ala Ala Pro Leu Leu Leu Ala Arg Ala Ala Ser Leu Ser Leu
1               5                   10                  15

Gly Phe Leu Phe Leu Leu Phe Phe Trp Leu Asp Arg Ser Val Leu Ala
            20                  25                  30

Lys Glu Leu Lys Phe Val Thr Leu Val Phe Arg His Gly Asp Arg Ser
        35                  40                  45

Pro Ile Asp Thr Phe Pro Thr Asp Pro Ile Lys Glu Ser Ser Trp Pro
    50                  55                  60

Gln Gly Phe Gly Gln Leu Thr Gln Leu Gly Met Glu Gln His Tyr Glu
65                  70                  75                  80

Leu Gly Glu Tyr Ile Arg Lys Arg Tyr Arg Lys Phe Leu Asn Glu Ser
                85                  90                  95

Tyr Lys His Glu Gln Val Tyr Ile Arg Ser Thr Asp Val Asp Arg Thr
            100                 105                 110

Leu Met Ser Ala Met Thr Asn Leu Ala Ala Leu Phe Pro Pro Glu Gly
        115                 120                 125

Val Ser Ile Trp Asn Pro Ile Leu Leu Trp Gln Pro Ile Pro Val His
    130                 135                 140

Thr Val Pro Leu Ser Glu Asp Gln Leu Leu Tyr Leu Pro Phe Arg Asn
145                 150                 155                 160

Cys Pro Arg Phe Gln Glu Leu Glu Ser Glu Thr Leu Lys Ser Glu Glu
                165                 170                 175

Phe Gln Lys Arg Leu His Pro Tyr Lys Asp Phe Ile Ala Thr Leu Gly
            180                 185                 190

Lys Leu Ser Gly Leu His Gly Gln Asp Leu Phe Gly Ile Trp Ser Lys
        195                 200                 205

Val Tyr Asp Pro Leu Tyr Cys Glu Ser Val His Asn Phe Thr Leu Pro
    210                 215                 220

Ser Trp Ala Thr Glu Asp Thr Met Thr Lys Leu Arg Glu Leu Ser Glu
225                 230                 235                 240

Leu Ser Leu Leu Ser Leu Tyr Gly Ile His Lys Gln Lys Glu Lys Ser
                245                 250                 255

Arg Leu Gln Gly Gly Val Leu Val Asn Glu Ile Leu Asn His Met Lys
            260                 265                 270

Arg Ala Thr Gln Ile Pro Ser Tyr Lys Lys Leu Ile Met Tyr Ser Ala
        275                 280                 285

His Asp Thr Thr Val Ser Gly Leu Gln Met Ala Leu Asp Val Tyr Asn
    290                 295                 300

Gly Leu Leu Pro Pro Tyr Ala Ser Cys His Leu Thr Glu Leu Tyr Phe
305                 310                 315                 320

Glu Lys Gly Glu Tyr Phe Val Glu Met Tyr Tyr Arg Asn Glu Thr Gln
                325                 330                 335

His Glu Pro Tyr Pro Leu Met Leu Pro Gly Cys Ser Pro Ser Cys Pro
            340                 345                 350

Leu Glu Arg Phe Ala Glu Leu Val Gly Pro Val Ile Pro Gln Asp Trp
        355                 360                 365

Ser Thr Glu Cys Met Thr Thr Asn Ser His Gln Val Leu Lys Val Ile
    370                 375                 380

Phe Ala Val Ala Phe Cys Leu Ile Ser Ala Val Leu Met Val Leu Leu
385                 390                 395                 400

Phe Ile His Ile Arg Arg Gly Leu Cys Trp Gln Arg Glu Ser Tyr Gly
                405                 410                 415
```

Asn Ile

<210> SEQ ID NO 5
<211> LENGTH: 560
<212> TYPE: PRT
<213> ORGANISM: Homo sapiens

<400> SEQUENCE: 5

Met Lys Met Gln Lys Gly Asn Val Leu Leu Met Phe Gly Leu Leu Leu
1               5                   10                  15

His Leu Glu Ala Ala Thr Asn Ser Asn Glu Thr Ser Thr Ser Ala Asn
            20                  25                  30

Thr Gly Ser Ser Val Ile Ser Ser Gly Ala Ser Thr Ala Thr Asn Ser
        35                  40                  45

Gly Ser Ser Val Thr Ser Ser Gly Val Ser Thr Ala Thr Ile Ser Gly
    50                  55                  60

Ser Ser Val Thr Ser Asn Gly Val Ser Ile Val Thr Asn Ser Glu Phe
65                  70                  75                  80

His Thr Thr Ser Ser Gly Ile Ser Thr Ala Thr Asn Ser Glu Phe Ser
                85                  90                  95

Thr Val Ser Ser Gly Ile Ser Ile Ala Thr Asn Ser Glu Ser Ser Thr
            100                 105                 110

Thr Ser Ser Gly Ala Ser Thr Ala Thr Asn Ser Glu Ser Ser Thr Pro
        115                 120                 125

Ser Ser Gly Ala Ser Thr Ala Thr Asn Ser Asp Ser Ser Thr Thr Ser
    130                 135                 140

Ser Gly Ala Ser Thr Ala Thr Asn Ser Asp Ser Ser Thr Thr Ser Ser
145                 150                 155                 160

Glu Ala Ser Thr Ala Thr Asn Ser Glu Ser Ser Thr Thr Ser Ser Gly
                165                 170                 175

Ala Ser Thr Ala Thr Asn Ser Glu Ser Ser Thr Val Ser Ser Arg Ala
            180                 185                 190

Ser Thr Ala Thr Asn Ser Glu Ser Ser Thr Thr Ser Ser Gly Ala Ser
        195                 200                 205

Thr Ala Thr Asn Ser Glu Ser Arg Thr Thr Ser Asn Gly Ala Gly Thr
    210                 215                 220

Ala Thr Asn Ser Glu Ser Ser Thr Thr Ser Ser Gly Ala Ser Thr Ala
225                 230                 235                 240

Thr Asn Ser Glu Ser Ser Thr Pro Ser Ser Gly Ala Gly Thr Ala Thr
                245                 250                 255

Asn Ser Glu Ser Ser Thr Thr Ser Ser Gly Ala Gly Thr Ala Thr Asn
            260                 265                 270

Ser Glu Ser Ser Thr Val Ser Ser Gly Ile Ser Thr Val Thr Asn Ser
        275                 280                 285

Glu Ser Ser Thr Pro Ser Ser Gly Ala Asn Thr Ala Thr Asn Ser Glu
    290                 295                 300

Ser Ser Thr Thr Ser Ser Gly Ala Asn Thr Ala Thr Asn Ser Asp Ser
305                 310                 315                 320

Ser Thr Thr Ser Ser Gly Ala Ser Thr Ala Thr Asn Ser Glu Ser Ser
                325                 330                 335

Thr Thr Ser Ser Gly Ala Ser Thr Ala Thr Asn Ser Glu Ser Ser Thr
            340                 345                 350

Thr Ser Ser Gly Ala Ser Thr Ala Thr Asn Ser Gly Ser Ser Thr Thr
        355                 360                 365

```
Ser Ser Gly Thr Ser Thr Ala Thr Asn Ser Glu Ser Ser Thr Val Ser
    370                 375                 380

Ser Gly Ala Ser Thr Ala Thr Thr Ser Glu Ser Ser Thr Thr Ser Ser
385                 390                 395                 400

Gly Ala Ser Thr Ala Thr Asn Ser Glu Ser Ser Thr Val Ser Ser Gly
                405                 410                 415

Ala Ser Thr Ala Thr Asn Ser Glu Ser Ser Thr Thr Ser Ser Gly Ala
                420                 425                 430

Asn Thr Ala Thr Asn Ser Gly Ser Ser Val Thr Ser Ala Gly Ser Gly
            435                 440                 445

Thr Ala Ala Leu Thr Gly Met His Thr Thr Ser His Ser Ala Ser Thr
    450                 455                 460

Ala Val Ser Glu Ala Lys Pro Gly Gly Ser Leu Val Pro Trp Glu Ile
465                 470                 475                 480

Phe Leu Ile Thr Leu Val Ser Val Val Ala Val Gly Leu Phe Ala
                485                 490                 495

Gly Leu Phe Phe Cys Val Arg Asn Ser Leu Ser Leu Arg Asn Thr Phe
                500                 505                 510

Asn Thr Ala Val Tyr His Pro His Gly Leu Asn His Gly Leu Gly Pro
                515                 520                 525

Gly Pro Gly Gly Asn His Gly Ala Pro His Arg Pro Arg Trp Ser Pro
            530                 535                 540

Asn Trp Phe Trp Arg Arg Pro Val Ser Ser Ile Ala Met Glu Met Ser
545                 550                 555                 560

<210> SEQ ID NO 6
<211> LENGTH: 14507
<212> TYPE: PRT
<213> ORGANISM: Homo sapiens

<400> SEQUENCE: 6

Met Leu Lys Pro Ser Gly Leu Pro Gly Ser Ser Pro Thr Arg Ser
1               5                   10                  15

Leu Met Thr Gly Ser Arg Ser Thr Lys Ala Thr Pro Glu Met Asp Ser
            20                  25                  30

Gly Leu Thr Gly Ala Thr Leu Ser Pro Lys Thr Ser Thr Gly Ala Ile
        35                  40                  45

Val Val Thr Glu His Thr Leu Pro Phe Thr Ser Pro Asp Lys Thr Leu
    50                  55                  60

Ala Ser Pro Thr Ser Ser Val Val Gly Arg Thr Thr Gln Ser Leu Gly
65                  70                  75                  80

Val Met Ser Ser Ala Leu Pro Glu Ser Thr Ser Arg Gly Met Thr His
                85                  90                  95

Ser Glu Gln Arg Thr Ser Pro Ser Leu Ser Pro Gln Val Asn Gly Thr
            100                 105                 110

Pro Ser Arg Asn Tyr Pro Ala Thr Ser Met Val Ser Gly Leu Ser Ser
        115                 120                 125

Pro Arg Thr Arg Thr Ser Thr Glu Gly Asn Phe Thr Lys Glu Ala
            130                 135                 140

Ser Thr Tyr Thr Leu Thr Val Glu Thr Thr Ser Gly Pro Val Thr Glu
145                 150                 155                 160

Lys Tyr Thr Val Pro Thr Glu Thr Ser Thr Thr Glu Gly Asp Ser Thr
                165                 170                 175

Glu Thr Pro Trp Asp Thr Arg Tyr Ile Pro Val Lys Ile Thr Ser Pro
```

-continued

```
                180                 185                 190
Met Lys Thr Phe Ala Asp Ser Thr Ala Ser Lys Glu Asn Ala Pro Val
            195                 200                 205
Ser Met Thr Pro Ala Glu Thr Val Thr Asp Ser His Thr Pro Gly
    210                 215                 220
Arg Thr Asn Pro Ser Phe Gly Thr Leu Tyr Ser Ser Phe Leu Asp Leu
225                 230                 235                 240
Ser Pro Lys Gly Thr Pro Asn Ser Arg Gly Glu Thr Ser Leu Glu Leu
                245                 250                 255
Ile Leu Ser Thr Thr Gly Tyr Pro Phe Ser Ser Pro Glu Pro Gly Ser
            260                 265                 270
Ala Gly His Ser Arg Ile Ser Thr Ser Ala Pro Leu Ser Ser Ser Ala
        275                 280                 285
Ser Val Leu Asp Asn Lys Ile Ser Glu Thr Ser Ile Phe Ser Gly Gln
    290                 295                 300
Ser Leu Thr Ser Pro Leu Ser Pro Gly Val Pro Glu Ala Arg Ala Ser
305                 310                 315                 320
Thr Met Pro Asn Ser Ala Ile Pro Phe Ser Met Thr Leu Ser Asn Ala
                325                 330                 335
Glu Thr Ser Ala Glu Arg Val Arg Ser Thr Ile Ser Ser Leu Gly Thr
            340                 345                 350
Pro Ser Ile Ser Thr Lys Gln Thr Ala Glu Thr Ile Leu Thr Phe His
        355                 360                 365
Ala Phe Ala Glu Thr Met Asp Ile Pro Ser Thr His Ile Ala Lys Thr
    370                 375                 380
Leu Ala Ser Glu Trp Leu Gly Ser Pro Gly Thr Leu Gly Gly Thr Ser
385                 390                 395                 400
Thr Ser Ala Leu Thr Thr Thr Ser Pro Ser Thr Thr Leu Val Ser Glu
                405                 410                 415
Glu Thr Asn Thr His His Ser Ser Ser Gly Lys Glu Thr Glu Gly Thr
            420                 425                 430
Leu Asn Thr Ser Met Thr Pro Leu Glu Thr Ser Ala Pro Gly Glu Glu
        435                 440                 445
Ser Glu Met Thr Ala Thr Leu Val Pro Thr Leu Gly Phe Thr Thr Leu
    450                 455                 460
Asp Ser Lys Ile Arg Ser Pro Ser Gln Val Ser Ser His Pro Thr
465                 470                 475                 480
Arg Glu Leu Arg Thr Thr Gly Ser Thr Ser Gly Arg Gln Ser Ser Ser
                485                 490                 495
Thr Ala Ala His Gly Ser Ser Asp Ile Leu Arg Ala Thr Thr Ser Ser
            500                 505                 510
Thr Ser Lys Ala Ser Ser Trp Thr Ser Glu Ser Thr Ala Gln Gln Phe
        515                 520                 525
Ser Glu Pro Gln His Thr Gln Trp Val Glu Thr Ser Pro Ser Met Lys
    530                 535                 540
Thr Glu Arg Pro Pro Ala Ser Thr Ser Val Ala Ala Pro Ile Thr Thr
545                 550                 555                 560
Ser Val Pro Ser Val Val Ser Gly Phe Thr Thr Leu Lys Thr Ser Ser
                565                 570                 575
Thr Lys Gly Ile Trp Leu Glu Glu Thr Ser Ala Asp Thr Leu Ile Gly
            580                 585                 590
Glu Ser Thr Ala Gly Pro Thr Thr His Gln Phe Ala Val Pro Thr Gly
        595                 600                 605
```

-continued

```
Ile Ser Met Thr Gly Gly Ser Thr Arg Gly Ser Gln Gly Thr Thr
    610                 615                 620
His Leu Leu Thr Arg Ala Thr Ala Ser Ser Glu Thr Ser Ala Asp Leu
625                 630                 635                 640
Thr Leu Ala Thr Asn Gly Val Pro Val Ser Val Ser Pro Ala Val Ser
                645                 650                 655
Lys Thr Ala Ala Gly Ser Ser Pro Pro Gly Gly Thr Lys Pro Ser Tyr
                660                 665                 670
Thr Met Val Ser Ser Val Ile Pro Glu Thr Ser Ser Leu Gln Ser Ser
            675                 680                 685
Ala Phe Arg Glu Gly Thr Ser Leu Gly Leu Thr Pro Leu Asn Thr Arg
690                 695                 700
His Pro Phe Ser Ser Pro Glu Pro Asp Ser Ala Gly His Thr Lys Ile
705                 710                 715                 720
Ser Thr Ser Ile Pro Leu Leu Ser Ser Ala Ser Val Leu Glu Asp Lys
                725                 730                 735
Val Ser Ala Thr Ser Thr Phe Ser His His Lys Ala Thr Ser Ser Ile
                740                 745                 750
Thr Thr Gly Thr Pro Glu Ile Ser Thr Lys Thr Lys Pro Ser Ser Ala
            755                 760                 765
Val Leu Ser Ser Met Thr Leu Ser Asn Ala Ala Thr Ser Pro Glu Arg
770                 775                 780
Val Arg Asn Ala Thr Ser Pro Leu Thr His Pro Ser Pro Ser Gly Glu
785                 790                 795                 800
Glu Thr Ala Gly Ser Val Leu Thr Leu Ser Thr Ser Ala Glu Thr Thr
                805                 810                 815
Asp Ser Pro Asn Ile His Pro Thr Gly Thr Leu Thr Ser Glu Ser Ser
                820                 825                 830
Glu Ser Pro Ser Thr Leu Ser Leu Pro Ser Val Ser Gly Val Lys Thr
            835                 840                 845
Thr Phe Ser Ser Ser Thr Pro Ser Thr His Leu Phe Thr Ser Gly Glu
850                 855                 860
Glu Thr Glu Glu Thr Ser Asn Pro Ser Val Ser Gln Pro Glu Thr Ser
865                 870                 875                 880
Val Ser Arg Val Arg Thr Thr Leu Ala Ser Thr Ser Val Pro Thr Pro
                885                 890                 895
Val Phe Pro Thr Met Asp Thr Trp Pro Thr Arg Ser Ala Gln Phe Ser
                900                 905                 910
Ser Ser His Leu Val Ser Glu Leu Arg Ala Thr Ser Ser Thr Ser Val
            915                 920                 925
Thr Asn Ser Thr Gly Ser Ala Leu Pro Lys Ile Ser His Leu Thr Gly
930                 935                 940
Thr Ala Thr Met Ser Gln Thr Asn Arg Asp Thr Phe Asn Asp Ser Ala
945                 950                 955                 960
Ala Pro Gln Ser Thr Thr Trp Pro Glu Thr Ser Pro Arg Phe Lys Thr
                965                 970                 975
Gly Leu Pro Ser Ala Thr Thr Val Ser Ser Ala Thr Ser Leu
                980                 985                 990
Ser Ala Thr Val Met Val Ser Lys Phe Thr Ser Pro Ala Thr Ser Ser
            995                 1000                1005
Met Glu Ala Thr Ser Ile Arg Glu Pro Ser Thr Thr Ile Leu Thr
    1010                1015                1020
```

```
Thr Glu Thr Thr Asn Gly Pro Gly Ser Met Ala Val Ala Ser Thr
    1025                1030                1035

Asn Ile Pro Ile Gly Lys Gly Tyr Ile Thr Glu Gly Arg Leu Asp
    1040                1045                1050

Thr Ser His Leu Pro Ile Gly Thr Thr Ala Ser Ser Glu Thr Ser
    1055                1060                1065

Met Asp Phe Thr Met Ala Lys Glu Ser Val Ser Met Ser Val Ser
    1070                1075                1080

Pro Ser Gln Ser Met Asp Ala Ala Gly Ser Ser Thr Pro Gly Arg
    1085                1090                1095

Thr Ser Gln Phe Val Asp Thr Phe Ser Asp Asp Val Tyr His Leu
    1100                1105                1110

Thr Ser Arg Glu Ile Thr Ile Pro Arg Asp Gly Thr Ser Ser Ala
    1115                1120                1125

Leu Thr Pro Gln Met Thr Ala Thr His Pro Pro Ser Pro Asp Pro
    1130                1135                1140

Gly Ser Ala Arg Ser Thr Trp Leu Gly Ile Leu Ser Ser Ser Pro
    1145                1150                1155

Ser Ser Pro Thr Pro Lys Val Thr Met Ser Ser Thr Phe Ser Thr
    1160                1165                1170

Gln Arg Val Thr Thr Ser Met Ile Met Asp Thr Val Glu Thr Ser
    1175                1180                1185

Arg Trp Asn Met Pro Asn Leu Pro Ser Thr Thr Ser Leu Thr Pro
    1190                1195                1200

Ser Asn Ile Pro Thr Ser Gly Ala Ile Gly Lys Ser Thr Leu Val
    1205                1210                1215

Pro Leu Asp Thr Pro Ser Pro Ala Thr Ser Leu Glu Ala Ser Glu
    1220                1225                1230

Gly Gly Leu Pro Thr Leu Ser Thr Tyr Pro Glu Ser Thr Asn Thr
    1235                1240                1245

Pro Ser Ile His Leu Gly Ala His Ala Ser Ser Glu Ser Pro Ser
    1250                1255                1260

Thr Ile Lys Leu Thr Met Ala Ser Val Val Lys Pro Gly Ser Tyr
    1265                1270                1275

Thr Pro Leu Thr Phe Pro Ser Ile Glu Thr His Ile His Val Ser
    1280                1285                1290

Thr Ala Arg Met Ala Tyr Ser Ser Gly Ser Ser Pro Glu Met Thr
    1295                1300                1305

Ala Pro Gly Glu Thr Asn Thr Gly Ser Thr Trp Asp Pro Thr Thr
    1310                1315                1320

Tyr Ile Thr Thr Thr Asp Pro Lys Asp Thr Ser Ser Ala Gln Val
    1325                1330                1335

Ser Thr Pro His Ser Val Arg Thr Leu Arg Thr Thr Glu Asn His
    1340                1345                1350

Pro Lys Thr Glu Ser Ala Thr Pro Ala Ala Tyr Ser Gly Ser Pro
    1355                1360                1365

Lys Ile Ser Ser Ser Pro Asn Leu Thr Ser Pro Ala Thr Lys Ala
    1370                1375                1380

Trp Thr Ile Thr Asp Thr Thr Glu His Ser Thr Gln Leu His Tyr
    1385                1390                1395

Thr Lys Leu Ala Glu Lys Ser Ser Gly Phe Glu Thr Gln Ser Ala
    1400                1405                1410

Pro Gly Pro Val Ser Val Val Ile Pro Thr Ser Pro Thr Ile Gly
```

```
            1415                1420                1425

Ser  Ser  Thr  Leu  Glu  Leu  Thr  Ser  Asp  Val  Pro  Gly  Glu  Pro  Leu
     1430                1435                1440

Val  Leu  Ala  Pro  Ser  Glu  Gln  Thr  Thr  Ile  Thr  Leu  Pro  Met  Ala
     1445                1450                1455

Thr  Trp  Leu  Ser  Thr  Ser  Leu  Thr  Glu  Glu  Met  Ala  Ser  Thr  Asp
     1460                1465                1470

Leu  Asp  Ile  Ser  Ser  Pro  Ser  Ser  Pro  Met  Ser  Thr  Phe  Ala  Ile
     1475                1480                1485

Phe  Pro  Pro  Met  Ser  Thr  Pro  Ser  His  Glu  Leu  Ser  Lys  Ser  Glu
     1490                1495                1500

Ala  Asp  Thr  Ser  Ala  Ile  Arg  Asn  Thr  Asp  Ser  Thr  Thr  Leu  Asp
     1505                1510                1515

Gln  His  Leu  Gly  Ile  Arg  Ser  Leu  Gly  Arg  Thr  Gly  Asp  Leu  Thr
     1520                1525                1530

Thr  Val  Pro  Ile  Thr  Pro  Leu  Thr  Thr  Thr  Trp  Thr  Ser  Val  Ile
     1535                1540                1545

Glu  His  Ser  Thr  Gln  Ala  Gln  Asp  Thr  Leu  Ser  Ala  Thr  Met  Ser
     1550                1555                1560

Pro  Thr  His  Val  Thr  Gln  Ser  Leu  Lys  Asp  Gln  Thr  Ser  Ile  Pro
     1565                1570                1575

Ala  Ser  Ala  Ser  Pro  Ser  His  Leu  Thr  Glu  Val  Tyr  Pro  Glu  Leu
     1580                1585                1590

Gly  Thr  Gln  Gly  Arg  Ser  Ser  Ser  Glu  Ala  Thr  Thr  Phe  Trp  Lys
     1595                1600                1605

Pro  Ser  Thr  Asp  Thr  Leu  Ser  Arg  Glu  Ile  Glu  Thr  Gly  Pro  Thr
     1610                1615                1620

Asn  Ile  Gln  Ser  Thr  Pro  Pro  Met  Asp  Asn  Thr  Thr  Thr  Gly  Ser
     1625                1630                1635

Ser  Ser  Ser  Gly  Val  Thr  Leu  Gly  Ile  Ala  His  Leu  Pro  Ile  Gly
     1640                1645                1650

Thr  Ser  Ser  Pro  Ala  Glu  Thr  Ser  Thr  Asn  Met  Ala  Leu  Glu  Arg
     1655                1660                1665

Arg  Ser  Ser  Thr  Ala  Thr  Val  Ser  Met  Ala  Gly  Thr  Met  Gly  Leu
     1670                1675                1680

Leu  Val  Thr  Ser  Ala  Pro  Gly  Arg  Ser  Ile  Ser  Gln  Ser  Leu  Gly
     1685                1690                1695

Arg  Val  Ser  Ser  Val  Leu  Ser  Glu  Ser  Thr  Thr  Glu  Gly  Val  Thr
     1700                1705                1710

Asp  Ser  Ser  Lys  Gly  Ser  Ser  Pro  Arg  Leu  Asn  Thr  Gln  Gly  Asn
     1715                1720                1725

Thr  Ala  Leu  Ser  Ser  Ser  Leu  Glu  Pro  Ser  Tyr  Ala  Glu  Gly  Ser
     1730                1735                1740

Gln  Met  Ser  Thr  Ser  Ile  Pro  Leu  Thr  Ser  Ser  Pro  Thr  Thr  Pro
     1745                1750                1755

Asp  Val  Glu  Phe  Ile  Gly  Gly  Ser  Thr  Phe  Trp  Thr  Lys  Glu  Val
     1760                1765                1770

Thr  Thr  Val  Met  Thr  Ser  Asp  Ile  Ser  Lys  Ser  Ser  Ala  Arg  Thr
     1775                1780                1785

Glu  Ser  Ser  Ser  Ala  Thr  Leu  Met  Ser  Thr  Ala  Leu  Gly  Ser  Thr
     1790                1795                1800

Glu  Asn  Thr  Gly  Lys  Glu  Lys  Leu  Arg  Thr  Ala  Ser  Met  Asp  Leu
     1805                1810                1815
```

-continued

Pro Ser Pro Thr Pro Ser Met Glu Val Thr Pro Trp Ile Ser Leu
    1820            1825                1830

Thr Leu Ser Asn Ala Pro Asn Thr Thr Asp Ser Leu Asp Leu Ser
    1835            1840                1845

His Gly Val His Thr Ser Ser Ala Gly Thr Leu Ala Thr Asp Arg
    1850            1855                1860

Ser Leu Asn Thr Gly Val Thr Arg Ala Ser Arg Leu Glu Asn Gly
    1865            1870                1875

Ser Asp Thr Ser Ser Lys Ser Leu Ser Met Gly Asn Ser Thr His
    1880            1885                1890

Thr Ser Met Thr Tyr Thr Glu Lys Ser Glu Val Ser Ser Ser Ile
    1895            1900                1905

His Pro Arg Pro Glu Thr Ser Ala Pro Gly Ala Glu Thr Thr Leu
    1910            1915                1920

Thr Ser Thr Pro Gly Asn Arg Ala Ile Ser Leu Thr Leu Pro Phe
    1925            1930                1935

Ser Ser Ile Pro Val Glu Glu Val Ile Ser Thr Gly Ile Thr Ser
    1940            1945                1950

Gly Pro Asp Ile Asn Ser Ala Pro Met Thr His Ser Pro Ile Thr
    1955            1960                1965

Pro Pro Thr Ile Val Trp Thr Ser Thr Gly Thr Ile Glu Gln Ser
    1970            1975                1980

Thr Gln Pro Leu His Ala Val Ser Ser Glu Lys Val Ser Val Gln
    1985            1990                1995

Thr Gln Ser Thr Pro Tyr Val Asn Ser Val Ala Val Ser Ala Ser
    2000            2005                2010

Pro Thr His Glu Asn Ser Val Ser Ser Gly Ser Ser Thr Ser Ser
    2015            2020                2025

Pro Tyr Ser Ser Ala Ser Leu Glu Ser Leu Asp Ser Thr Ile Ser
    2030            2035                2040

Arg Arg Asn Ala Ile Thr Ser Trp Leu Trp Asp Leu Thr Thr Ser
    2045            2050                2055

Leu Pro Thr Thr Thr Trp Pro Ser Thr Ser Leu Ser Glu Ala Leu
    2060            2065                2070

Ser Ser Gly His Ser Gly Val Ser Asn Pro Ser Ser Thr Thr Thr
    2075            2080                2085

Glu Phe Pro Leu Phe Ser Ala Ala Ser Thr Ser Ala Ala Lys Gln
    2090            2095                2100

Arg Asn Pro Glu Thr Glu Thr His Gly Pro Gln Asn Thr Ala Ala
    2105            2110                2115

Ser Thr Leu Asn Thr Asp Ala Ser Ser Val Thr Gly Leu Ser Glu
    2120            2125                2130

Thr Pro Val Gly Ala Ser Ile Ser Ser Glu Val Pro Leu Pro Met
    2135            2140                2145

Ala Ile Thr Ser Arg Ser Asp Val Ser Gly Leu Thr Ser Glu Ser
    2150            2155                2160

Thr Ala Asn Pro Ser Leu Gly Thr Ala Ser Ser Ala Gly Thr Lys
    2165            2170                2175

Leu Thr Arg Thr Ile Ser Leu Pro Thr Ser Glu Ser Leu Val Ser
    2180            2185                2190

Phe Arg Met Asn Lys Asp Pro Trp Thr Val Ser Ile Pro Leu Gly
    2195            2200                2205

```
Ser His Pro Thr Thr Asn Thr Glu Thr Ser Ile Pro Val Asn Ser
    2210             2215             2220

Ala Gly Pro Pro Gly Leu Ser Thr Val Ala Ser Asp Val Ile Asp
2225             2230             2235

Thr Pro Ser Asp Gly Ala Glu Ser Ile Pro Thr Val Ser Phe Ser
    2240             2245             2250

Pro Ser Pro Asp Thr Glu Val Thr Thr Ile Ser His Phe Pro Glu
2255             2260             2265

Lys Thr Thr His Ser Phe Arg Thr Ile Ser Ser Leu Thr His Glu
    2270             2275             2280

Leu Thr Ser Arg Val Thr Pro Ile Pro Gly Asp Trp Met Ser Ser
2285             2290             2295

Ala Met Ser Thr Lys Pro Thr Gly Ala Ser Pro Ser Ile Thr Leu
    2300             2305             2310

Gly Glu Arg Arg Thr Ile Thr Ser Ala Ala Pro Thr Thr Ser Pro
2315             2320             2325

Ile Val Leu Thr Ala Ser Phe Thr Glu Thr Ser Thr Val Ser Leu
    2330             2335             2340

Asp Asn Glu Thr Thr Val Lys Thr Ser Asp Ile Leu Asp Ala Arg
2345             2350             2355

Lys Thr Asn Glu Leu Pro Ser Asp Ser Ser Ser Ser Ser Asp Leu
    2360             2365             2370

Ile Asn Thr Ser Ile Ala Ser Ser Thr Met Asp Val Thr Lys Thr
2375             2380             2385

Ala Ser Ile Ser Pro Thr Ser Ile Ser Gly Met Thr Ala Ser Ser
    2390             2395             2400

Ser Pro Ser Leu Phe Ser Ser Asp Arg Pro Gln Val Pro Thr Ser
2405             2410             2415

Thr Thr Glu Thr Asn Thr Ala Thr Ser Pro Ser Val Ser Ser Asn
    2420             2425             2430

Thr Tyr Ser Leu Asp Gly Gly Ser Asn Val Gly Gly Thr Pro Ser
2435             2440             2445

Thr Leu Pro Pro Phe Thr Ile Thr His Pro Val Glu Thr Ser Ser
    2450             2455             2460

Ala Leu Leu Ala Trp Ser Arg Pro Val Arg Thr Phe Ser Thr Met
2465             2470             2475

Val Ser Thr Asp Thr Ala Ser Gly Glu Asn Pro Thr Ser Ser Asn
    2480             2485             2490

Ser Val Val Thr Ser Val Pro Ala Pro Gly Thr Trp Thr Ser Val
2495             2500             2505

Gly Ser Thr Thr Asp Leu Pro Ala Met Gly Phe Leu Lys Thr Ser
    2510             2515             2520

Pro Ala Gly Glu Ala His Ser Leu Leu Ala Ser Thr Ile Glu Pro
2525             2530             2535

Ala Thr Ala Phe Thr Pro His Leu Ser Ala Ala Val Val Thr Gly
    2540             2545             2550

Ser Ser Ala Thr Ser Glu Ala Ser Leu Leu Thr Thr Ser Glu Ser
2555             2560             2565

Lys Ala Ile His Ser Ser Pro Gln Thr Pro Thr Thr Pro Thr Ser
    2570             2575             2580

Gly Ala Asn Trp Glu Thr Ser Ala Thr Pro Glu Ser Leu Leu Val
2585             2590             2595

Val Thr Glu Thr Ser Asp Thr Thr Leu Thr Ser Lys Ile Leu Val
```

```
                  2600                2605                2610
Thr Asp Thr Ile Leu Phe Ser Thr Val Ser Thr Pro Pro Ser Lys
    2615                2620                2625
Phe Pro Ser Thr Gly Thr Leu Ser Gly Ala Ser Phe Pro Thr Leu
    2630                2635                2640
Leu Pro Asp Thr Pro Ala Ile Pro Leu Thr Ala Thr Glu Pro Thr
    2645                2650                2655
Ser Ser Leu Ala Thr Ser Phe Asp Ser Thr Pro Leu Val Thr Ile
    2660                2665                2670
Ala Ser Asp Ser Leu Gly Thr Val Pro Glu Thr Thr Leu Thr Met
    2675                2680                2685
Ser Glu Thr Ser Asn Gly Asp Ala Leu Val Leu Lys Thr Val Ser
    2690                2695                2700
Asn Pro Asp Arg Ser Ile Pro Gly Ile Thr Ile Gln Gly Val Thr
    2705                2710                2715
Glu Ser Pro Leu His Pro Ser Ser Thr Ser Pro Ser Lys Ile Val
    2720                2725                2730
Ala Pro Arg Asn Thr Thr Tyr Glu Gly Ser Ile Thr Val Ala Leu
    2735                2740                2745
Ser Thr Leu Pro Ala Gly Thr Thr Gly Ser Leu Val Phe Ser Gln
    2750                2755                2760
Ser Ser Glu Asn Ser Glu Thr Thr Ala Leu Val Asp Ser Ser Ala
    2765                2770                2775
Gly Leu Glu Arg Ala Ser Val Met Pro Leu Thr Thr Gly Ser Gln
    2780                2785                2790
Gly Met Ala Ser Ser Gly Gly Ile Arg Ser Gly Ser Thr His Ser
    2795                2800                2805
Thr Gly Thr Lys Thr Phe Ser Ser Leu Pro Leu Thr Met Asn Pro
    2810                2815                2820
Gly Glu Val Thr Ala Met Ser Glu Ile Thr Thr Asn Arg Leu Thr
    2825                2830                2835
Ala Thr Gln Ser Thr Ala Pro Lys Gly Ile Pro Val Lys Pro Thr
    2840                2845                2850
Ser Ala Glu Ser Gly Leu Leu Thr Pro Val Ser Ala Ser Ser Ser
    2855                2860                2865
Pro Ser Lys Ala Phe Ala Ser Leu Thr Thr Ala Pro Pro Thr Trp
    2870                2875                2880
Gly Ile Pro Gln Ser Thr Leu Thr Phe Glu Phe Ser Glu Val Pro
    2885                2890                2895
Ser Leu Asp Thr Lys Ser Ala Ser Leu Pro Thr Pro Gly Gln Ser
    2900                2905                2910
Leu Asn Thr Ile Pro Asp Ser Asp Ala Ser Thr Ala Ser Ser Ser
    2915                2920                2925
Leu Ser Lys Ser Pro Glu Lys Asn Pro Arg Ala Arg Met Met Thr
    2930                2935                2940
Ser Thr Lys Ala Ile Ser Ala Ser Ser Phe Gln Ser Thr Gly Phe
    2945                2950                2955
Thr Glu Thr Pro Glu Gly Ser Ala Ser Pro Ser Met Ala Gly His
    2960                2965                2970
Glu Pro Arg Val Pro Thr Ser Gly Thr Gly Asp Pro Arg Tyr Ala
    2975                2980                2985
Ser Glu Ser Met Ser Tyr Pro Asp Pro Ser Lys Ala Ser Ser Ala
    2990                2995                3000
```

-continued

```
Met Thr Ser Thr Ser Leu Ala Ser Lys Leu Thr Thr Leu Phe Ser
3005                3010                3015

Thr Gly Gln Ala Ala Arg Ser Gly Ser Ser Ser Pro Ile Ser
3020                3025                3030

Leu Ser Thr Glu Lys Glu Thr Ser Phe Leu Ser Pro Thr Ala Ser
3035                3040                3045

Thr Ser Arg Lys Thr Ser Leu Phe Leu Gly Pro Ser Met Ala Arg
3050                3055                3060

Gln Pro Asn Ile Leu Val His Leu Gln Thr Ser Ala Leu Thr Leu
3065                3070                3075

Ser Pro Thr Ser Thr Leu Asn Met Ser Gln Glu Glu Pro Pro Glu
3080                3085                3090

Leu Thr Ser Ser Gln Thr Ile Ala Glu Glu Glu Gly Thr Thr Ala
3095                3100                3105

Glu Thr Gln Thr Leu Thr Phe Thr Pro Ser Glu Thr Pro Thr Ser
3110                3115                3120

Leu Leu Pro Val Ser Ser Pro Thr Glu Pro Thr Ala Arg Arg Lys
3125                3130                3135

Ser Ser Pro Glu Thr Trp Ala Ser Ser Ile Ser Val Pro Ala Lys
3140                3145                3150

Thr Ser Leu Val Glu Thr Thr Asp Gly Thr Leu Val Thr Thr Ile
3155                3160                3165

Lys Met Ser Ser Gln Ala Ala Gln Gly Asn Ser Thr Trp Pro Ala
3170                3175                3180

Pro Ala Glu Glu Thr Gly Ser Ser Pro Ala Gly Thr Ser Pro Gly
3185                3190                3195

Ser Pro Glu Met Ser Thr Thr Leu Lys Ile Met Ser Ser Lys Glu
3200                3205                3210

Pro Ser Ile Ser Pro Glu Ile Arg Ser Thr Val Arg Asn Ser Pro
3215                3220                3225

Trp Lys Thr Pro Glu Thr Thr Val Pro Met Glu Thr Thr Val Glu
3230                3235                3240

Pro Val Thr Leu Gln Ser Thr Ala Leu Gly Ser Gly Ser Thr Ser
3245                3250                3255

Ile Ser His Leu Pro Thr Gly Thr Thr Ser Pro Thr Lys Ser Pro
3260                3265                3270

Thr Glu Asn Met Leu Ala Thr Glu Arg Val Ser Leu Ser Pro Ser
3275                3280                3285

Pro Pro Glu Ala Trp Thr Asn Leu Tyr Ser Gly Thr Pro Gly Gly
3290                3295                3300

Thr Arg Gln Ser Leu Ala Thr Met Ser Ser Val Ser Leu Glu Ser
3305                3310                3315

Pro Thr Ala Arg Ser Ile Thr Gly Thr Gly Gln Gln Ser Ser Pro
3320                3325                3330

Glu Leu Val Ser Lys Thr Thr Gly Met Glu Phe Ser Met Trp His
3335                3340                3345

Gly Ser Thr Gly Gly Thr Thr Gly Asp Thr His Val Ser Leu Ser
3350                3355                3360

Thr Ser Ser Asn Ile Leu Glu Asp Pro Val Thr Ser Pro Asn Ser
3365                3370                3375

Val Ser Ser Leu Thr Asp Lys Ser Lys His Lys Thr Glu Thr Trp
3380                3385                3390
```

```
Val Ser Thr Thr Ala Ile Pro Ser Thr Val Leu Asn Asn Lys Ile
    3395            3400                3405

Met Ala Ala Glu Gln Gln Thr Ser Arg Ser Val Asp Glu Ala Tyr
    3410            3415                3420

Ser Ser Thr Ser Ser Trp Ser Asp Gln Thr Ser Gly Ser Asp Ile
    3425            3430                3435

Thr Leu Gly Ala Ser Pro Asp Val Thr Asn Thr Leu Tyr Ile Thr
    3440            3445                3450

Ser Thr Ala Gln Thr Thr Ser Leu Val Ser Leu Pro Ser Gly Asp
    3455            3460                3465

Gln Gly Ile Thr Ser Leu Thr Asn Pro Ser Gly Gly Lys Thr Ser
    3470            3475                3480

Ser Ala Ser Ser Val Thr Ser Pro Ser Ile Gly Leu Glu Thr Leu
    3485            3490                3495

Arg Ala Asn Val Ser Ala Val Lys Ser Asp Ile Ala Pro Thr Ala
    3500            3505                3510

Gly His Leu Ser Gln Thr Ser Ser Pro Ala Glu Val Ser Ile Leu
    3515            3520                3525

Asp Val Thr Thr Ala Pro Thr Pro Gly Ile Ser Thr Thr Ile Thr
    3530            3535                3540

Thr Met Gly Thr Asn Ser Ile Ser Thr Thr Pro Asn Pro Glu
    3545            3550                3555

Val Gly Met Ser Thr Met Asp Ser Thr Pro Ala Thr Glu Arg Arg
    3560            3565                3570

Thr Thr Ser Thr Glu His Pro Ser Thr Trp Ser Ser Thr Ala Ala
    3575            3580                3585

Ser Asp Ser Trp Thr Val Thr Asp Met Thr Ser Asn Leu Lys Val
    3590            3595                3600

Ala Arg Ser Pro Gly Thr Ile Ser Thr Met His Thr Thr Ser Phe
    3605            3610                3615

Leu Ala Ser Ser Thr Glu Leu Asp Ser Met Ser Thr Pro His Gly
    3620            3625                3630

Arg Ile Thr Val Ile Gly Thr Ser Leu Val Thr Pro Ser Ser Asp
    3635            3640                3645

Ala Ser Ala Val Lys Thr Glu Thr Ser Thr Ser Glu Arg Thr Leu
    3650            3655                3660

Ser Pro Ser Asp Thr Thr Ala Ser Thr Pro Ile Ser Thr Phe Ser
    3665            3670                3675

Arg Val Gln Arg Met Ser Ile Ser Val Pro Asp Ile Leu Ser Thr
    3680            3685                3690

Ser Trp Thr Pro Ser Ser Thr Glu Ala Glu Asp Val Pro Val Ser
    3695            3700                3705

Met Val Ser Thr Asp His Ala Ser Thr Lys Thr Asp Pro Asn Thr
    3710            3715                3720

Pro Leu Ser Thr Phe Leu Phe Asp Ser Leu Ser Thr Leu Asp Trp
    3725            3730                3735

Asp Thr Gly Arg Ser Leu Ser Ser Ala Thr Ala Thr Thr Ser Ala
    3740            3745                3750

Pro Gln Gly Ala Thr Thr Pro Gln Glu Leu Thr Leu Glu Thr Met
    3755            3760                3765

Ile Ser Pro Ala Thr Ser Gln Leu Pro Phe Ser Ile Gly His Ile
    3770            3775                3780

Thr Ser Ala Val Thr Pro Ala Ala Met Ala Arg Ser Ser Gly Val
```

```
              3785                3790                3795
Thr Phe Ser Arg Pro Asp Pro Thr Ser Lys Lys Ala Glu Gln Thr
    3800                3805                3810
Ser Thr Gln Leu Pro Thr Thr Thr Ser Ala His Pro Gly Gln Val
    3815                3820                3825
Pro Arg Ser Ala Ala Thr Thr Leu Asp Val Ile Pro His Thr Ala
    3830                3835                3840
Lys Thr Pro Asp Ala Thr Phe Gln Arg Gln Gly Gln Thr Ala Leu
    3845                3850                3855
Thr Thr Glu Ala Arg Ala Thr Ser Asp Ser Trp Asn Glu Lys Glu
    3860                3865                3870
Lys Ser Thr Pro Ser Ala Pro Trp Ile Thr Glu Met Met Asn Ser
    3875                3880                3885
Val Ser Glu Asp Thr Ile Lys Glu Val Thr Ser Ser Ser Ser Val
    3890                3895                3900
Leu Arg Thr Leu Asn Thr Leu Asp Ile Asn Leu Glu Ser Gly Thr
    3905                3910                3915
Thr Ser Ser Pro Ser Trp Lys Ser Ser Pro Tyr Glu Arg Ile Ala
    3920                3925                3930
Pro Ser Glu Ser Thr Thr Asp Lys Glu Ala Ile His Pro Ser Thr
    3935                3940                3945
Asn Thr Val Glu Thr Thr Gly Trp Val Thr Ser Ser Glu His Ala
    3950                3955                3960
Ser His Ser Thr Ile Pro Ala His Ser Ala Ser Ser Lys Leu Thr
    3965                3970                3975
Ser Pro Val Val Thr Thr Ser Thr Arg Glu Gln Ala Ile Val Ser
    3980                3985                3990
Met Ser Thr Thr Thr Trp Pro Glu Ser Thr Arg Ala Arg Thr Glu
    3995                4000                4005
Pro Asn Ser Phe Leu Thr Ile Glu Leu Arg Asp Val Ser Pro Tyr
    4010                4015                4020
Met Asp Thr Ser Ser Thr Thr Gln Thr Ser Ile Ile Ser Ser Pro
    4025                4030                4035
Gly Ser Thr Ala Ile Thr Lys Gly Pro Arg Thr Glu Ile Thr Ser
    4040                4045                4050
Ser Lys Arg Ile Ser Ser Ser Phe Leu Ala Gln Ser Met Arg Ser
    4055                4060                4065
Ser Asp Ser Pro Ser Glu Ala Ile Thr Arg Leu Ser Asn Phe Pro
    4070                4075                4080
Ala Met Thr Glu Ser Gly Gly Met Ile Leu Ala Met Gln Thr Ser
    4085                4090                4095
Pro Pro Gly Ala Thr Ser Leu Ser Ala Pro Thr Leu Asp Thr Ser
    4100                4105                4110
Ala Thr Ala Ser Trp Thr Gly Thr Pro Leu Ala Thr Thr Gln Arg
    4115                4120                4125
Phe Thr Tyr Ser Glu Lys Thr Thr Leu Phe Ser Lys Gly Pro Glu
    4130                4135                4140
Asp Thr Ser Gln Pro Ser Pro Pro Ser Val Glu Glu Thr Ser Ser
    4145                4150                4155
Ser Ser Ser Leu Val Pro Ile His Ala Thr Thr Ser Pro Ser Asn
    4160                4165                4170
Ile Leu Leu Thr Ser Gln Gly His Ser Pro Ser Ser Thr Pro Pro
    4175                4180                4185
```

```
Val Thr Ser Val Phe Leu Ser     Glu Thr Ser Gly Leu     Gly Lys Thr
    4190            4195                4200

Thr Asp Met Ser Arg Ile Ser     Leu Glu Pro Gly Thr     Ser Leu Pro
    4205            4210                4215

Pro Asn Leu Ser Ser Thr Ala     Gly Glu Ala Leu Ser     Thr Tyr Glu
    4220            4225                4230

Ala Ser Arg Asp Thr Lys Ala     Ile His His Ser Ala     Asp Thr Ala
    4235            4240                4245

Val Thr Asn Met Glu Ala Thr     Ser Ser Glu Tyr Ser     Pro Ile Pro
    4250            4255                4260

Gly His Thr Lys Pro Ser Lys     Ala Thr Ser Pro Leu     Val Thr Ser
    4265            4270                4275

His Ile Met Gly Asp Ile Thr     Ser Ser Thr Ser Val     Phe Gly Ser
    4280            4285                4290

Ser Glu Thr Thr Glu Ile Glu     Thr Val Ser Ser Val     Asn Gln Gly
    4295            4300                4305

Leu Gln Glu Arg Ser Thr Ser     Gln Val Ala Ser Ser     Ala Thr Glu
    4310            4315                4320

Thr Ser Thr Val Ile Thr His     Val Ser Ser Gly Asp     Ala Thr Thr
    4325            4330                4335

His Val Thr Lys Thr Gln Ala     Thr Phe Ser Ser Gly     Thr Ser Ile
    4340            4345                4350

Ser Ser Pro His Gln Phe Ile     Thr Ser Thr Asn Thr     Phe Thr Asp
    4355            4360                4365

Val Ser Thr Asn Pro Ser Thr     Ser Leu Ile Met Thr     Glu Ser Ser
    4370            4375                4380

Gly Val Thr Ile Thr Thr Gln     Thr Gly Pro Thr Gly     Ala Ala Thr
    4385            4390                4395

Gln Gly Pro Tyr Leu Leu Asp     Thr Ser Thr Met Pro     Tyr Leu Thr
    4400            4405                4410

Glu Thr Pro Leu Ala Val Thr     Pro Asp Phe Met Gln     Ser Glu Lys
    4415            4420                4425

Thr Thr Leu Ile Ser Lys Gly     Pro Lys Asp Val Ser     Trp Thr Ser
    4430            4435                4440

Pro Pro Ser Val Ala Glu Thr     Ser Tyr Pro Ser Ser     Leu Thr Pro
    4445            4450                4455

Phe Leu Val Thr Thr Ile Pro     Pro Ala Thr Ser Thr     Leu Gln Gly
    4460            4465                4470

Gln His Thr Ser Ser Pro Val     Ser Ala Thr Ser Val     Leu Thr Ser
    4475            4480                4485

Gly Leu Val Lys Thr Thr Asp     Met Leu Asn Thr Ser     Met Glu Pro
    4490            4495                4500

Val Thr Asn Ser Pro Gln Asn     Leu Asn Asn Pro Ser     Asn Glu Ile
    4505            4510                4515

Leu Ala Thr Leu Ala Ala Thr     Thr Asp Ile Glu Thr     Ile His Pro
    4520            4525                4530

Ser Ile Asn Lys Ala Val Thr     Asn Met Gly Thr Ala     Ser Ser Ala
    4535            4540                4545

His Val Leu His Ser Thr Leu     Pro Val Ser Ser Glu     Pro Ser Thr
    4550            4555                4560

Ala Thr Ser Pro Met Val Pro     Ala Ser Ser Met Gly     Asp Ala Leu
    4565            4570                4575
```

```
Ala Ser Ile Ser Ile Pro Gly Ser Glu Thr Thr Asp Ile Glu Gly
    4580            4585                4590

Glu Pro Thr Ser Ser Leu Thr Ala Gly Arg Lys Glu Asn Ser Thr
    4595            4600                4605

Leu Gln Glu Met Asn Ser Thr Thr Glu Ser Asn Ile Ile Leu Ser
    4610            4615                4620

Asn Val Ser Val Gly Ala Ile Thr Glu Ala Thr Lys Met Glu Val
    4625            4630                4635

Pro Ser Phe Asp Ala Thr Phe Ile Pro Thr Pro Ala Gln Ser Thr
    4640            4645                4650

Lys Phe Pro Asp Ile Phe Ser Val Ala Ser Ser Arg Leu Ser Asn
    4655            4660                4665

Ser Pro Pro Met Thr Ile Ser Thr His Met Thr Thr Gln Thr
    4670            4675                4680

Gly Ser Ser Gly Ala Thr Ser Lys Ile Pro Leu Ala Leu Asp Thr
    4685            4690                4695

Ser Thr Leu Glu Thr Ser Ala Gly Thr Pro Ser Val Val Thr Glu
    4700            4705                4710

Gly Phe Ala His Ser Lys Ile Thr Thr Ala Met Asn Asn Asp Val
    4715            4720                4725

Lys Asp Val Ser Gln Thr Asn Pro Pro Phe Gln Asp Glu Ala Ser
    4730            4735                4740

Ser Pro Ser Ser Gln Ala Pro Val Leu Val Thr Thr Leu Pro Ser
    4745            4750                4755

Ser Val Ala Phe Thr Pro Gln Trp His Ser Thr Ser Ser Pro Val
    4760            4765                4770

Ser Met Ser Ser Val Leu Thr Ser Ser Leu Val Lys Thr Ala Gly
    4775            4780                4785

Lys Val Asp Thr Ser Leu Glu Thr Val Thr Ser Ser Pro Gln Ser
    4790            4795                4800

Met Ser Asn Thr Leu Asp Asp Ile Ser Val Thr Ser Ala Ala Thr
    4805            4810                4815

Thr Asp Ile Glu Thr Thr His Pro Ser Ile Asn Thr Val Val Thr
    4820            4825                4830

Asn Val Gly Thr Thr Gly Ser Ala Phe Glu Ser His Ser Thr Val
    4835            4840                4845

Ser Ala Tyr Pro Glu Pro Ser Lys Val Thr Ser Pro Asn Val Thr
    4850            4855                4860

Thr Ser Thr Met Glu Asp Thr Thr Ile Ser Arg Ser Ile Pro Lys
    4865            4870                4875

Ser Ser Lys Thr Thr Arg Thr Glu Thr Glu Thr Ser Ser Leu
    4880            4885                4890

Thr Pro Lys Leu Arg Glu Thr Ser Ile Ser Gln Glu Ile Thr Ser
    4895            4900                4905

Ser Thr Glu Thr Ser Thr Val Pro Tyr Lys Glu Leu Thr Gly Ala
    4910            4915                4920

Thr Thr Glu Val Ser Arg Thr Asp Val Thr Ser Ser Ser Ser Thr
    4925            4930                4935

Ser Phe Pro Gly Pro Asp Gln Ser Thr Val Ser Leu Asp Ile Ser
    4940            4945                4950

Thr Glu Thr Asn Thr Arg Leu Ser Thr Ser Pro Ile Met Thr Glu
    4955            4960                4965

Ser Ala Glu Ile Thr Ile Thr Thr Gln Thr Gly Pro His Gly Ala
```

-continued

```
                 4970                4975                4980
Thr Ser Gln Asp Thr Phe Thr Met Asp Pro Ser Asn Thr Thr Pro
    4985                4990                4995
Gln Ala Gly Ile His Ser Ala Met Thr His Gly Phe Ser Gln Leu
    5000                5005                5010
Asp Val Thr Thr Leu Met Ser Arg Ile Pro Gln Asp Val Ser Trp
    5015                5020                5025
Thr Ser Pro Pro Ser Val Asp Lys Thr Ser Pro Ser Ser Phe
    5030                5035                5040
Leu Ser Ser Pro Ala Met Thr Thr Pro Ser Leu Ile Ser Ser Thr
    5045                5050                5055
Leu Pro Glu Asp Lys Leu Ser Ser Pro Met Thr Ser Leu Leu Thr
    5060                5065                5070
Ser Gly Leu Val Lys Ile Thr Asp Ile Leu Arg Thr Arg Leu Glu
    5075                5080                5085
Pro Val Thr Ser Ser Leu Pro Asn Phe Ser Ser Thr Ser Asp Lys
    5090                5095                5100
Ile Leu Ala Thr Ser Lys Asp Ser Lys Asp Thr Lys Glu Ile Phe
    5105                5110                5115
Pro Ser Ile Asn Thr Glu Glu Thr Asn Val Lys Ala Asn Asn Ser
    5120                5125                5130
Gly His Glu Ser His Ser Pro Ala Leu Ala Asp Ser Glu Thr Pro
    5135                5140                5145
Lys Ala Thr Thr Gln Met Val Ile Thr Thr Val Gly Asp Pro
    5150                5155                5160
Ala Pro Ser Thr Ser Met Pro Val His Gly Ser Ser Glu Thr Thr
    5165                5170                5175
Asn Ile Lys Arg Glu Pro Thr Tyr Phe Leu Thr Pro Arg Leu Arg
    5180                5185                5190
Glu Thr Ser Thr Ser Gln Glu Ser Ser Phe Pro Thr Asp Thr Ser
    5195                5200                5205
Phe Leu Leu Ser Lys Val Pro Thr Gly Thr Ile Thr Glu Val Ser
    5210                5215                5220
Ser Thr Gly Val Asn Ser Ser Lys Ile Ser Thr Pro Asp His
    5225                5230                5235
Asp Lys Ser Thr Val Pro Pro Asp Thr Phe Thr Gly Glu Ile Pro
    5240                5245                5250
Arg Val Phe Thr Ser Ser Ile Lys Thr Lys Ser Ala Glu Met Thr
    5255                5260                5265
Ile Thr Thr Gln Ala Ser Pro Pro Glu Ser Ala Ser His Ser Thr
    5270                5275                5280
Leu Pro Leu Asp Thr Ser Thr Thr Leu Ser Gln Gly Gly Thr His
    5285                5290                5295
Ser Thr Val Thr Gln Gly Phe Pro Tyr Ser Glu Val Thr Thr Leu
    5300                5305                5310
Met Gly Met Gly Pro Gly Asn Val Ser Trp Met Thr Thr Pro Pro
    5315                5320                5325
Val Glu Glu Thr Ser Ser Val Ser Ser Leu Met Ser Ser Pro Ala
    5330                5335                5340
Met Thr Ser Pro Ser Pro Val Ser Ser Thr Ser Pro Gln Ser Ile
    5345                5350                5355
Pro Ser Ser Pro Leu Pro Val Thr Ala Leu Pro Thr Ser Val Leu
    5360                5365                5370
```

-continued

| | | | | | | | | | | | |
|---|---|---|---|---|---|---|---|---|---|---|---|
|Val|Thr|Thr|Thr|Asp|Val|Leu|Gly|Thr|Ser|Pro|Glu|Ser|Val|
|5375| | | | |5380| | | |5385| | | | |

Val Thr Thr Thr Asp Val Leu Gly Thr Ser Pro Glu Ser Val
    5375                5380              5385

Thr Ser Ser Pro Pro Asn Leu Ser Ser Ile Thr His Glu Arg Pro
    5390                5395              5400

Ala Thr Tyr Lys Asp Thr Ala His Thr Glu Ala Ala Met His His
    5405                5410              5415

Ser Thr Asn Thr Ala Val Thr Asn Val Gly Thr Ser Gly Ser Gly
    5420                5425              5430

His Lys Ser Gln Ser Ser Val Leu Ala Asp Ser Glu Thr Ser Lys
    5435                5440              5445

Ala Thr Pro Leu Met Ser Thr Thr Ser Thr Leu Gly Asp Thr Ser
    5450                5455              5460

Val Ser Thr Ser Thr Pro Asn Ile Ser Gln Thr Asn Gln Ile Gln
    5465                5470              5475

Thr Glu Pro Thr Ala Ser Leu Ser Pro Arg Leu Arg Glu Ser Ser
    5480                5485              5490

Thr Ser Glu Lys Thr Ser Ser Thr Thr Glu Thr Asn Thr Ala Phe
    5495                5500              5505

Ser Tyr Val Pro Thr Gly Ala Ile Thr Gln Ala Ser Arg Thr Glu
    5510                5515              5520

Ile Ser Ser Ser Arg Thr Ser Ile Ser Asp Leu Asp Arg Pro Thr
    5525                5530              5535

Ile Ala Pro Asp Ile Ser Thr Gly Met Ile Thr Arg Leu Phe Thr
    5540                5545              5550

Ser Pro Ile Met Thr Lys Ser Ala Glu Met Thr Val Thr Thr Gln
    5555                5560              5565

Thr Thr Thr Pro Gly Ala Thr Ser Gln Gly Ile Leu Pro Trp Asp
    5570                5575              5580

Thr Ser Thr Thr Leu Phe Gln Gly Gly Thr His Ser Thr Val Ser
    5585                5590              5595

Gln Gly Phe Pro His Ser Glu Ile Thr Thr Leu Arg Ser Arg Thr
    5600                5605              5610

Pro Gly Asp Val Ser Trp Met Thr Thr Pro Pro Val Glu Glu Thr
    5615                5620              5625

Ser Ser Gly Phe Ser Leu Met Ser Pro Ser Met Thr Ser Pro Ser
    5630                5635              5640

Pro Val Ser Ser Thr Ser Pro Glu Ser Ile Pro Ser Ser Pro Leu
    5645                5650              5655

Pro Val Thr Ala Leu Leu Thr Ser Val Leu Val Thr Thr Thr Asn
    5660                5665              5670

Val Leu Gly Thr Thr Ser Pro Glu Pro Val Thr Ser Ser Pro Pro
    5675                5680              5685

Asn Leu Ser Ser Pro Thr Gln Glu Arg Leu Thr Thr Tyr Lys Asp
    5690                5695              5700

Thr Ala His Thr Glu Ala Met His Ala Ser Met His Thr Asn Thr
    5705                5710              5715

Ala Val Ala Asn Val Gly Thr Ser Ile Ser Gly His Glu Ser Gln
    5720                5725              5730

Ser Ser Val Pro Ala Asp Ser His Thr Ser Lys Ala Thr Ser Pro
    5735                5740              5745

Met Gly Ile Thr Phe Ala Met Gly Asp Thr Ser Val Ser Thr Ser
    5750                5755              5760

```
Thr Pro Ala Phe Phe Glu Thr Arg Ile Gln Thr Glu Ser Thr Ser
    5765            5770            5775

Ser Leu Ile Pro Gly Leu Arg Asp Thr Arg Thr Ser Glu Glu Ile
    5780            5785            5790

Asn Thr Val Thr Glu Thr Ser Thr Val Leu Ser Glu Val Pro Thr
    5795            5800            5805

Thr Thr Thr Thr Glu Val Ser Arg Thr Glu Val Ile Thr Ser Ser
    5810            5815            5820

Arg Thr Thr Ile Ser Gly Pro Asp His Ser Lys Met Ser Pro Tyr
    5825            5830            5835

Ile Ser Thr Glu Thr Ile Thr Arg Leu Ser Thr Phe Pro Phe Val
    5840            5845            5850

Thr Gly Ser Thr Glu Met Ala Ile Thr Asn Gln Thr Gly Pro Ile
    5855            5860            5865

Gly Thr Ile Ser Gln Ala Thr Leu Thr Leu Asp Thr Ser Ser Thr
    5870            5875            5880

Ala Ser Trp Glu Gly Thr His Ser Pro Val Thr Gln Arg Phe Pro
    5885            5890            5895

His Ser Glu Glu Thr Thr Thr Met Ser Arg Ser Thr Lys Gly Val
    5900            5905            5910

Ser Trp Gln Ser Pro Pro Ser Val Glu Glu Thr Ser Ser Pro Ser
    5915            5920            5925

Ser Pro Val Pro Leu Pro Ala Ile Thr Ser His Ser Ser Leu Tyr
    5930            5935            5940

Ser Ala Val Ser Gly Ser Ser Pro Thr Ser Ala Leu Pro Val Thr
    5945            5950            5955

Ser Leu Leu Thr Ser Gly Arg Arg Lys Thr Ile Asp Met Leu Asp
    5960            5965            5970

Thr His Ser Glu Leu Val Thr Ser Ser Leu Pro Ser Ala Ser Ser
    5975            5980            5985

Phe Ser Gly Glu Ile Leu Thr Ser Glu Ala Ser Thr Asn Thr Glu
    5990            5995            6000

Thr Ile His Phe Ser Glu Asn Thr Ala Glu Thr Asn Met Gly Thr
    6005            6010            6015

Thr Asn Ser Met His Lys Leu His Ser Ser Val Ser Ile His Ser
    6020            6025            6030

Gln Pro Ser Gly His Thr Pro Pro Lys Val Thr Gly Ser Met Met
    6035            6040            6045

Glu Asp Ala Ile Val Ser Thr Ser Thr Pro Gly Ser Pro Glu Thr
    6050            6055            6060

Lys Asn Val Asp Arg Asp Ser Thr Ser Pro Leu Thr Pro Glu Leu
    6065            6070            6075

Lys Glu Asp Ser Thr Ala Leu Val Met Asn Ser Thr Thr Glu Ser
    6080            6085            6090

Asn Thr Val Phe Ser Ser Val Ser Leu Asp Ala Ala Thr Glu Val
    6095            6100            6105

Ser Arg Ala Glu Val Thr Tyr Tyr Asp Pro Thr Phe Met Pro Ala
    6110            6115            6120

Ser Ala Gln Ser Thr Lys Ser Pro Asp Ile Ser Pro Glu Ala Ser
    6125            6130            6135

Ser Ser His Ser Asn Ser Pro Pro Leu Thr Ile Ser Thr His Lys
    6140            6145            6150

Thr Ile Ala Thr Gln Thr Gly Pro Ser Gly Val Thr Ser Leu Gly
```

```
                6155                    6160                    6165

Gln Leu Thr Leu Asp Thr Ser Thr Ile Ala Thr Ser Ala Gly Thr
                6170                    6175                    6180

Pro Ser Ala Arg Thr Gln Asp Phe Val Asp Ser Glu Thr Thr Ser
                6185                    6190                    6195

Val Met Asn Asn Asp Leu Asn Asp Val Leu Lys Thr Ser Pro Phe
                6200                    6205                    6210

Ser Ala Glu Glu Ala Asn Ser Leu Ser Ser Gln Ala Pro Leu Leu
                6215                    6220                    6225

Val Thr Thr Ser Pro Ser Pro Val Thr Ser Thr Leu Gln Glu His
                6230                    6235                    6240

Ser Thr Ser Ser Leu Val Ser Val Thr Ser Val Pro Thr Pro Thr
                6245                    6250                    6255

Leu Ala Lys Ile Thr Asp Met Asp Thr Asn Leu Glu Pro Val Thr
                6260                    6265                    6270

Arg Ser Pro Gln Asn Leu Arg Asn Thr Leu Ala Thr Ser Glu Ala
                6275                    6280                    6285

Thr Thr Asp Thr His Thr Met His Pro Ser Ile Asn Thr Ala Val
                6290                    6295                    6300

Ala Asn Val Gly Thr Thr Ser Ser Pro Asn Glu Phe Tyr Phe Thr
                6305                    6310                    6315

Val Ser Pro Asp Ser Asp Pro Tyr Lys Ala Thr Ser Ala Val Val
                6320                    6325                    6330

Ile Thr Ser Thr Ser Gly Asp Ser Ile Val Ser Thr Ser Met Pro
                6335                    6340                    6345

Arg Ser Ser Ala Met Lys Lys Ile Glu Ser Glu Thr Thr Phe Ser
                6350                    6355                    6360

Leu Ile Phe Arg Leu Arg Glu Thr Ser Thr Ser Gln Lys Ile Gly
                6365                    6370                    6375

Ser Ser Ser Asp Thr Ser Thr Val Phe Asp Lys Ala Phe Thr Ala
                6380                    6385                    6390

Ala Thr Thr Glu Val Ser Arg Thr Glu Leu Thr Ser Ser Ser Arg
                6395                    6400                    6405

Thr Ser Ile Gln Gly Thr Glu Lys Pro Thr Met Ser Pro Asp Thr
                6410                    6415                    6420

Ser Thr Arg Ser Val Thr Met Leu Ser Thr Phe Ala Gly Leu Thr
                6425                    6430                    6435

Lys Ser Glu Glu Arg Thr Ile Ala Thr Gln Thr Gly Pro His Arg
                6440                    6445                    6450

Ala Thr Ser Gln Gly Thr Leu Thr Trp Asp Thr Ser Ile Thr Thr
                6455                    6460                    6465

Ser Gln Ala Gly Thr His Ser Ala Met Thr His Gly Phe Ser Gln
                6470                    6475                    6480

Leu Asp Leu Ser Thr Leu Thr Ser Arg Val Pro Glu Tyr Ile Ser
                6485                    6490                    6495

Gly Thr Ser Pro Pro Ser Val Glu Lys Thr Ser Ser Ser Ser Ser
                6500                    6505                    6510

Leu Leu Ser Leu Pro Ala Ile Thr Ser Pro Ser Pro Val Pro Thr
                6515                    6520                    6525

Thr Leu Pro Glu Ser Arg Pro Ser Ser Pro Val His Leu Thr Ser
                6530                    6535                    6540

Leu Pro Thr Ser Gly Leu Val Lys Thr Thr Asp Met Leu Ala Ser
                6545                    6550                    6555
```

-continued

Val Ala Ser Leu Pro Pro Asn Leu Gly Ser Thr Ser His Lys Ile
6560           6565                6570

Pro Thr Thr Ser Glu Asp Ile Lys Asp Thr Glu Lys Met Tyr Pro
6575           6580                6585

Ser Thr Asn Ile Ala Val Thr Asn Val Gly Thr Thr Thr Ser Glu
6590           6595                6600

Lys Glu Ser Tyr Ser Ser Val Pro Ala Tyr Ser Glu Pro Pro Lys
6605           6610                6615

Val Thr Ser Pro Met Val Thr Ser Phe Asn Ile Arg Asp Thr Ile
6620           6625                6630

Val Ser Thr Ser Met Pro Gly Ser Ser Glu Ile Thr Arg Ile Glu
6635           6640                6645

Met Glu Ser Thr Phe Ser Leu Ala His Gly Leu Lys Gly Thr Ser
6650           6655                6660

Thr Ser Gln Asp Pro Ile Val Ser Thr Glu Lys Ser Ala Val Leu
6665           6670                6675

His Lys Leu Thr Thr Gly Ala Thr Glu Thr Ser Arg Thr Glu Val
6680           6685                6690

Ala Ser Ser Arg Arg Thr Ser Ile Pro Gly Pro Asp His Ser Thr
6695           6700                6705

Glu Ser Pro Asp Ile Ser Thr Glu Val Ile Pro Ser Leu Pro Ile
6710           6715                6720

Ser Leu Gly Ile Thr Glu Ser Ser Asn Met Thr Ile Ile Thr Arg
6725           6730                6735

Thr Gly Pro Pro Leu Gly Ser Thr Ser Gln Gly Thr Phe Thr Leu
6740           6745                6750

Asp Thr Pro Thr Thr Ser Ser Arg Ala Gly Thr His Ser Met Ala
6755           6760                6765

Thr Gln Glu Phe Pro His Ser Glu Met Thr Thr Val Met Asn Lys
6770           6775                6780

Asp Pro Glu Ile Leu Ser Trp Thr Ile Pro Pro Ser Ile Glu Lys
6785           6790                6795

Thr Ser Phe Ser Ser Ser Leu Met Pro Ser Pro Ala Met Thr Ser
6800           6805                6810

Pro Pro Val Ser Ser Thr Leu Pro Lys Thr Ile His Thr Thr Pro
6815           6820                6825

Ser Pro Met Thr Ser Leu Leu Thr Pro Ser Leu Val Met Thr Thr
6830           6835                6840

Asp Thr Leu Gly Thr Ser Pro Glu Pro Thr Thr Ser Ser Pro Pro
6845           6850                6855

Asn Leu Ser Ser Thr Ser His Glu Ile Leu Thr Thr Asp Glu Asp
6860           6865                6870

Thr Thr Ala Ile Glu Ala Met His Pro Ser Thr Ser Thr Ala Ala
6875           6880                6885

Thr Asn Val Glu Thr Thr Ser Ser Gly His Gly Ser Gln Ser Ser
6890           6895                6900

Val Leu Ala Asp Ser Glu Lys Thr Lys Ala Thr Ala Pro Met Asp
6905           6910                6915

Thr Thr Ser Thr Met Gly His Thr Thr Val Ser Thr Ser Met Ser
6920           6925                6930

Val Ser Ser Glu Thr Thr Lys Ile Lys Arg Glu Ser Thr Tyr Ser
6935           6940                6945

| | | | | | | | | | | | |
|---|---|---|---|---|---|---|---|---|---|---|---|
|Leu|Thr|Pro|Gly|Leu|Arg|Glu|Thr|Ser|Ile|Ser|Gln|Asn|Ala|Ser|
|6950| | | | |6955| | | | |6960| | | | |

Leu Thr Pro Gly Leu Arg Glu Thr Ser Ile Ser Gln Asn Ala Ser
6950                6955                6960

Phe Ser Thr Asp Thr Ser Ile Val Leu Ser Glu Val Pro Thr Gly
6965                6970                6975

Thr Thr Ala Glu Val Ser Arg Thr Glu Val Thr Ser Ser Gly Arg
6980                6985                6990

Thr Ser Ile Pro Gly Pro Ser Gln Ser Thr Val Leu Pro Glu Ile
6995                7000                7005

Ser Thr Arg Thr Met Thr Arg Leu Phe Ala Ser Pro Thr Met Thr
7010                7015                7020

Glu Ser Ala Glu Met Thr Ile Pro Thr Gln Thr Gly Pro Ser Gly
7025                7030                7035

Ser Thr Ser Gln Asp Thr Leu Thr Leu Asp Thr Ser Thr Thr Lys
7040                7045                7050

Ser Gln Ala Lys Thr His Ser Thr Leu Thr Gln Arg Phe Pro His
7055                7060                7065

Ser Glu Met Thr Thr Leu Met Ser Arg Gly Pro Gly Asp Met Ser
7070                7075                7080

Trp Gln Ser Ser Pro Ser Leu Glu Asn Pro Ser Ser Leu Pro Ser
7085                7090                7095

Leu Leu Ser Leu Pro Ala Thr Thr Ser Pro Pro Ile Ser Ser
7100                7105                7110

Thr Leu Pro Val Thr Ile Ser Ser Ser Pro Leu Pro Val Thr Ser
7115                7120                7125

Leu Leu Thr Ser Ser Pro Val Thr Thr Thr Asp Met Leu His Thr
7130                7135                7140

Ser Pro Glu Leu Val Thr Ser Ser Pro Pro Lys Leu Ser His Thr
7145                7150                7155

Ser Asp Glu Arg Leu Thr Thr Gly Lys Asp Thr Thr Asn Thr Glu
7160                7165                7170

Ala Val His Pro Ser Thr Asn Thr Ala Ala Ser Asn Val Glu Ile
7175                7180                7185

Pro Ser Ser Gly His Glu Ser Pro Ser Ser Ala Leu Ala Asp Ser
7190                7195                7200

Glu Thr Ser Lys Ala Thr Ser Pro Met Phe Ile Thr Ser Thr Gln
7205                7210                7215

Glu Asp Thr Thr Val Ala Ile Ser Thr Pro His Phe Leu Glu Thr
7220                7225                7230

Ser Arg Ile Gln Lys Glu Ser Ile Ser Ser Leu Ser Pro Lys Leu
7235                7240                7245

Arg Glu Thr Gly Ser Ser Val Glu Thr Ser Ser Ala Ile Glu Thr
7250                7255                7260

Ser Ala Val Leu Ser Glu Val Ser Ile Gly Ala Thr Thr Glu Ile
7265                7270                7275

Ser Arg Thr Glu Val Thr Ser Ser Ser Arg Thr Ser Ile Ser Gly
7280                7285                7290

Ser Ala Glu Ser Thr Met Leu Pro Glu Ile Ser Thr Thr Arg Lys
7295                7300                7305

Ile Ile Lys Phe Pro Thr Ser Pro Ile Leu Ala Glu Ser Ser Glu
7310                7315                7320

Met Thr Ile Lys Thr Gln Thr Ser Pro Pro Gly Ser Thr Ser Glu
7325                7330                7335

Ser Thr Phe Thr Leu Asp Thr Ser Thr Thr Pro Ser Leu Val Ile

```
                7340                7345                7350
Thr His Ser Thr Met Thr Gln Arg Leu Pro His Ser Glu Ile Thr
    7355                7360                7365

Thr Leu Val Ser Arg Gly Ala Gly Asp Val Pro Arg Pro Ser Ser
    7370                7375                7380

Leu Pro Val Glu Glu Thr Ser Pro Pro Ser Ser Gln Leu Ser Leu
    7385                7390                7395

Ser Ala Met Ile Ser Pro Ser Pro Val Ser Ser Thr Leu Pro Ala
    7400                7405                7410

Ser Ser His Ser Ser Ser Ala Ser Val Thr Ser Leu Leu Thr Pro
    7415                7420                7425

Gly Gln Val Lys Thr Thr Glu Val Leu Asp Ala Ser Ala Glu Pro
    7430                7435                7440

Glu Thr Ser Ser Pro Pro Ser Leu Ser Ser Thr Ser Val Glu Ile
    7445                7450                7455

Leu Ala Thr Ser Glu Val Thr Thr Asp Thr Glu Lys Ile His Pro
    7460                7465                7470

Phe Ser Asn Thr Ala Val Thr Lys Val Gly Thr Ser Ser Ser Gly
    7475                7480                7485

His Glu Ser Pro Ser Ser Val Leu Pro Asp Ser Glu Thr Thr Lys
    7490                7495                7500

Ala Thr Ser Ala Met Gly Thr Ile Ser Ile Met Gly Asp Thr Ser
    7505                7510                7515

Val Ser Thr Leu Thr Pro Ala Leu Ser Asn Thr Arg Lys Ile Gln
    7520                7525                7530

Ser Glu Pro Ala Ser Ser Leu Thr Thr Arg Leu Arg Glu Thr Ser
    7535                7540                7545

Thr Ser Glu Glu Thr Ser Leu Ala Thr Glu Ala Asn Thr Val Leu
    7550                7555                7560

Ser Lys Val Ser Thr Gly Ala Thr Thr Glu Val Ser Arg Thr Glu
    7565                7570                7575

Ala Ile Ser Phe Ser Arg Thr Ser Met Ser Gly Pro Glu Gln Ser
    7580                7585                7590

Thr Met Ser Gln Asp Ile Ser Ile Gly Thr Ile Pro Arg Ile Ser
    7595                7600                7605

Ala Ser Ser Val Leu Thr Glu Ser Ala Lys Met Thr Ile Thr Thr
    7610                7615                7620

Gln Thr Gly Pro Ser Glu Ser Thr Leu Glu Ser Thr Leu Asn Leu
    7625                7630                7635

Asn Thr Ala Thr Thr Pro Ser Trp Val Glu Thr His Ser Ile Val
    7640                7645                7650

Ile Gln Gly Phe Pro His Pro Glu Met Thr Thr Ser Met Gly Arg
    7655                7660                7665

Gly Pro Gly Gly Val Ser Trp Pro Ser Pro Pro Phe Val Lys Glu
    7670                7675                7680

Thr Ser Pro Pro Ser Ser Pro Leu Ser Leu Pro Ala Val Thr Ser
    7685                7690                7695

Pro His Pro Val Ser Thr Thr Phe Leu Ala His Ile Pro Pro Ser
    7700                7705                7710

Pro Leu Pro Val Thr Ser Leu Leu Thr Ser Gly Pro Ala Thr Thr
    7715                7720                7725

Thr Asp Ile Leu Gly Thr Ser Thr Glu Pro Gly Thr Ser Ser Ser
    7730                7735                7740
```

-continued

```
Ser Ser Leu Ser Thr Thr Ser His Glu Arg Leu Thr Thr Tyr Lys
    7745             7750                 7755

Asp Thr Ala His Thr Glu Ala Val His Pro Ser Thr Asn Thr Gly
    7760             7765                 7770

Gly Thr Asn Val Ala Thr Thr Ser Ser Gly Tyr Lys Ser Gln Ser
    7775             7780                 7785

Ser Val Leu Ala Asp Ser Ser Pro Met Cys Thr Thr Ser Thr Met
    7790             7795                 7800

Gly Asp Thr Ser Val Leu Thr Ser Thr Pro Ala Phe Leu Glu Thr
    7805             7810                 7815

Arg Arg Ile Gln Thr Glu Leu Ala Ser Ser Leu Thr Pro Gly Leu
    7820             7825                 7830

Arg Glu Ser Ser Gly Ser Glu Gly Thr Ser Ser Gly Thr Lys Met
    7835             7840                 7845

Ser Thr Val Leu Ser Lys Val Pro Thr Gly Ala Thr Thr Glu Ile
    7850             7855                 7860

Ser Lys Glu Asp Val Thr Ser Ile Pro Gly Pro Ala Gln Ser Thr
    7865             7870                 7875

Ile Ser Pro Asp Ile Ser Thr Arg Thr Val Ser Trp Phe Ser Thr
    7880             7885                 7890

Ser Pro Val Met Thr Glu Ser Ala Glu Ile Thr Met Asn Thr His
    7895             7900                 7905

Thr Ser Pro Leu Gly Ala Thr Thr Gln Gly Thr Ser Thr Leu Asp
    7910             7915                 7920

Thr Ser Ser Thr Thr Ser Leu Thr Met Thr His Ser Thr Ile Ser
    7925             7930                 7935

Gln Gly Phe Ser His Ser Gln Met Ser Thr Leu Met Arg Arg Gly
    7940             7945                 7950

Pro Glu Asp Val Ser Trp Met Ser Pro Pro Leu Leu Glu Lys Thr
    7955             7960                 7965

Arg Pro Ser Phe Ser Leu Met Ser Ser Pro Ala Thr Thr Ser Pro
    7970             7975                 7980

Ser Pro Val Ser Ser Thr Leu Pro Glu Ser Ile Ser Ser Ser Pro
    7985             7990                 7995

Leu Pro Val Thr Ser Leu Leu Thr Ser Gly Leu Ala Lys Thr Thr
    8000             8005                 8010

Asp Met Leu His Lys Ser Ser Glu Pro Val Thr Asn Ser Pro Ala
    8015             8020                 8025

Asn Leu Ser Ser Thr Ser Val Glu Ile Leu Ala Thr Ser Glu Val
    8030             8035                 8040

Thr Thr Asp Thr Glu Lys Thr His Pro Ser Ser Asn Arg Thr Val
    8045             8050                 8055

Thr Asp Val Gly Thr Ser Ser Ser Gly His Glu Ser Thr Ser Phe
    8060             8065                 8070

Val Leu Ala Asp Ser Gln Thr Ser Lys Val Thr Ser Pro Met Val
    8075             8080                 8085

Ile Thr Ser Thr Met Glu Asp Thr Ser Val Ser Thr Ser Thr Pro
    8090             8095                 8100

Gly Phe Phe Glu Thr Ser Arg Ile Gln Thr Glu Pro Thr Ser Ser
    8105             8110                 8115

Leu Thr Leu Gly Leu Arg Lys Thr Ser Ser Ser Glu Gly Thr Ser
    8120             8125                 8130
```

-continued

```
Leu Ala Thr Glu Met Ser Thr Val Leu Ser Gly Val Pro Thr Gly
    8135            8140            8145

Ala Thr Ala Glu Val Ser Arg Thr Glu Val Thr Ser Ser Ser Arg
    8150            8155            8160

Thr Ser Ile Ser Gly Phe Ala Gln Leu Thr Val Ser Pro Glu Thr
    8165            8170            8175

Ser Thr Glu Thr Ile Thr Arg Leu Pro Thr Ser Ser Ile Met Thr
    8180            8185            8190

Glu Ser Ala Glu Met Met Ile Lys Thr Gln Thr Asp Pro Pro Gly
    8195            8200            8205

Ser Thr Pro Glu Ser Thr His Thr Val Asp Ile Ser Thr Thr Pro
    8210            8215            8220

Asn Trp Val Glu Thr His Ser Thr Val Thr Gln Arg Phe Ser His
    8225            8230            8235

Ser Glu Met Thr Thr Leu Val Ser Arg Ser Pro Gly Asp Met Leu
    8240            8245            8250

Trp Pro Ser Gln Ser Ser Val Glu Glu Thr Ser Ser Ala Ser Ser
    8255            8260            8265

Leu Leu Ser Leu Pro Ala Thr Thr Ser Pro Ser Pro Val Ser Ser
    8270            8275            8280

Thr Leu Val Glu Asp Phe Pro Ser Ala Ser Leu Pro Val Thr Ser
    8285            8290            8295

Leu Leu Asn Pro Gly Leu Val Ile Thr Thr Asp Arg Met Gly Ile
    8300            8305            8310

Ser Arg Glu Pro Gly Thr Ser Ser Thr Ser Asn Leu Ser Ser Thr
    8315            8320            8325

Ser His Glu Arg Leu Thr Thr Leu Glu Asp Thr Val Asp Thr Glu
    8330            8335            8340

Asp Met Gln Pro Ser Thr His Thr Ala Val Thr Asn Val Arg Thr
    8345            8350            8355

Ser Ile Ser Gly His Glu Ser Gln Ser Ser Val Leu Ser Asp Ser
    8360            8365            8370

Glu Thr Pro Lys Ala Thr Ser Pro Met Gly Thr Thr Tyr Thr Met
    8375            8380            8385

Gly Glu Thr Ser Val Ser Ile Ser Thr Ser Asp Phe Phe Glu Thr
    8390            8395            8400

Ser Arg Ile Gln Ile Glu Pro Thr Ser Ser Leu Thr Ser Gly Leu
    8405            8410            8415

Arg Glu Thr Ser Ser Ser Glu Arg Ile Ser Ser Ala Thr Glu Gly
    8420            8425            8430

Ser Thr Val Leu Ser Glu Val Pro Ser Gly Ala Thr Thr Glu Val
    8435            8440            8445

Ser Arg Thr Glu Val Ile Ser Ser Arg Gly Thr Ser Met Ser Gly
    8450            8455            8460

Pro Asp Gln Phe Thr Ile Ser Pro Asp Ile Ser Thr Glu Ala Ile
    8465            8470            8475

Thr Arg Leu Ser Thr Ser Pro Ile Met Thr Glu Ser Ala Glu Ser
    8480            8485            8490

Ala Ile Thr Ile Glu Thr Gly Ser Pro Gly Ala Thr Ser Glu Gly
    8495            8500            8505

Thr Leu Thr Leu Asp Thr Ser Thr Thr Thr Phe Trp Ser Gly Thr
    8510            8515            8520

His Ser Thr Ala Ser Pro Gly Phe Ser His Ser Glu Met Thr Thr
```

```
            8525                8530                8535
Leu Met Ser Arg Thr Pro Gly Asp Val Pro Trp Pro Ser Leu Pro
            8540                8545                8550
Ser Val Glu Glu Ala Ser Ser Val Ser Ser Leu Ser Ser Pro
            8555                8560                8565
Ala Met Thr Ser Thr Ser Phe Phe Ser Thr Leu Pro Glu Ser Ile
            8570                8575                8580
Ser Ser Ser Pro His Pro Val Thr Ala Leu Leu Thr Leu Gly Pro
            8585                8590                8595
Val Lys Thr Thr Asp Met Leu Arg Thr Ser Ser Glu Pro Glu Thr
            8600                8605                8610
Ser Ser Pro Pro Asn Leu Ser Ser Thr Ser Ala Glu Ile Leu Ala
            8615                8620                8625
Thr Ser Glu Val Thr Lys Asp Arg Glu Lys Ile His Pro Ser Ser
            8630                8635                8640
Asn Thr Pro Val Val Asn Val Gly Thr Val Ile Tyr Lys His Leu
            8645                8650                8655
Ser Pro Ser Ser Val Leu Ala Asp Leu Val Thr Thr Lys Pro Thr
            8660                8665                8670
Ser Pro Met Ala Thr Thr Ser Thr Leu Gly Asn Thr Ser Val Ser
            8675                8680                8685
Thr Ser Thr Pro Ala Phe Pro Glu Thr Met Met Thr Gln Pro Thr
            8690                8695                8700
Ser Ser Leu Thr Ser Gly Leu Arg Glu Ile Ser Thr Ser Gln Glu
            8705                8710                8715
Thr Ser Ser Ala Thr Glu Arg Ser Ala Ser Leu Ser Gly Met Pro
            8720                8725                8730
Thr Gly Ala Thr Thr Lys Val Ser Arg Thr Glu Ala Leu Ser Leu
            8735                8740                8745
Gly Arg Thr Ser Thr Pro Gly Pro Ala Gln Ser Thr Ile Ser Pro
            8750                8755                8760
Glu Ile Ser Thr Glu Thr Ile Thr Arg Ile Ser Thr Pro Leu Thr
            8765                8770                8775
Thr Thr Gly Ser Ala Glu Met Thr Ile Thr Pro Lys Thr Gly His
            8780                8785                8790
Ser Gly Ala Ser Ser Gln Gly Thr Phe Thr Leu Asp Thr Ser Ser
            8795                8800                8805
Arg Ala Ser Trp Pro Gly Thr His Ser Ala Ala Thr His Arg Ser
            8810                8815                8820
Pro His Ser Gly Met Thr Thr Pro Met Ser Arg Gly Pro Glu Asp
            8825                8830                8835
Val Ser Trp Pro Ser Arg Pro Ser Val Glu Lys Thr Ser Pro Pro
            8840                8845                8850
Ser Ser Leu Val Ser Leu Ser Ala Val Thr Ser Pro Ser Pro Leu
            8855                8860                8865
Tyr Ser Thr Pro Ser Glu Ser His Ser Ser Pro Leu Arg Val
            8870                8875                8880
Thr Ser Leu Phe Thr Pro Val Met Met Lys Thr Thr Asp Met Leu
            8885                8890                8895
Asp Thr Ser Leu Glu Pro Val Thr Thr Ser Pro Pro Ser Met Asn
            8900                8905                8910
Ile Thr Ser Asp Glu Ser Leu Ala Thr Ser Lys Ala Thr Met Glu
            8915                8920                8925
```

```
Thr Glu Ala Ile Gln Leu Ser Glu Asn Thr Ala Val Thr Gln Met
    8930            8935            8940

Gly Thr Ile Ser Ala Arg Gln Glu Phe Tyr Ser Ser Tyr Pro Gly
    8945            8950            8955

Leu Pro Glu Pro Ser Lys Val Thr Ser Pro Val Val Thr Ser Ser
    8960            8965            8970

Thr Ile Lys Asp Ile Val Ser Thr Thr Ile Pro Ala Ser Ser Glu
    8975            8980            8985

Ile Thr Arg Ile Glu Met Glu Ser Thr Ser Thr Leu Thr Pro Thr
    8990            8995            9000

Pro Arg Glu Thr Ser Thr Ser Gln Glu Ile His Ser Ala Thr Lys
    9005            9010            9015

Pro Ser Thr Val Pro Tyr Lys Ala Leu Thr Ser Ala Thr Ile Glu
    9020            9025            9030

Asp Ser Met Thr Gln Val Met Ser Ser Ser Arg Gly Pro Ser Pro
    9035            9040            9045

Asp Gln Ser Thr Met Ser Gln Asp Ile Ser Thr Glu Val Ile Thr
    9050            9055            9060

Arg Leu Ser Thr Ser Pro Ile Lys Thr Glu Ser Thr Glu Met Thr
    9065            9070            9075

Ile Thr Thr Gln Thr Gly Ser Pro Gly Ala Thr Ser Arg Gly Thr
    9080            9085            9090

Leu Thr Leu Asp Thr Ser Thr Thr Phe Met Ser Gly Thr His Ser
    9095            9100            9105

Thr Ala Ser Gln Gly Phe Ser His Ser Gln Met Thr Ala Leu Met
    9110            9115            9120

Ser Arg Thr Pro Gly Asp Val Pro Trp Leu Ser His Pro Ser Val
    9125            9130            9135

Glu Glu Ala Ser Ser Ala Ser Phe Ser Leu Ser Ser Pro Val Met
    9140            9145            9150

Thr Ser Ser Ser Pro Val Ser Ser Thr Leu Pro Asp Ser Ile His
    9155            9160            9165

Ser Ser Ser Leu Pro Val Thr Ser Leu Leu Thr Ser Gly Leu Val
    9170            9175            9180

Lys Thr Thr Glu Leu Leu Gly Thr Ser Ser Glu Pro Glu Thr Ser
    9185            9190            9195

Ser Pro Pro Asn Leu Ser Ser Thr Ser Ala Glu Ile Leu Ala Ile
    9200            9205            9210

Thr Glu Val Thr Thr Asp Thr Glu Lys Leu Glu Met Thr Asn Val
    9215            9220            9225

Val Thr Ser Gly Tyr Thr His Glu Ser Pro Ser Ser Val Leu Ala
    9230            9235            9240

Asp Ser Val Thr Thr Lys Ala Thr Ser Ser Met Gly Ile Thr Tyr
    9245            9250            9255

Pro Thr Gly Asp Thr Asn Val Leu Thr Ser Thr Pro Ala Phe Ser
    9260            9265            9270

Asp Thr Ser Arg Ile Gln Thr Lys Ser Lys Leu Ser Leu Thr Pro
    9275            9280            9285

Gly Leu Met Glu Thr Ser Ile Ser Glu Glu Thr Ser Ser Ala Thr
    9290            9295            9300

Glu Lys Ser Thr Val Leu Ser Ser Val Pro Thr Gly Ala Thr Thr
    9305            9310            9315
```

| | | | | | | | | | | | |
|---|---|---|---|---|---|---|---|---|---|---|---|
|Glu|Val|Ser|Arg|Thr|Glu|Ala|Ile|Ser|Ser|Ser|Arg|Thr|Ser|Ile|
| |9320| | | |9325| | | |9330| | | | | |

Glu Val Ser Arg Thr Glu Ala Ile Ser Ser Ser Arg Thr Ser Ile
    9320            9325            9330

Pro Gly Pro Ala Gln Ser Thr Met Ser Ser Asp Thr Ser Met Glu
    9335            9340            9345

Thr Ile Thr Arg Ile Ser Thr Pro Leu Thr Arg Lys Glu Ser Thr
    9350            9355            9360

Asp Met Ala Ile Thr Pro Lys Thr Gly Pro Ser Gly Ala Thr Ser
    9365            9370            9375

Gln Gly Thr Phe Thr Leu Asp Ser Ser Ser Thr Ala Ser Trp Pro
    9380            9385            9390

Gly Thr His Ser Ala Thr Thr Gln Arg Phe Pro Gln Ser Val Val
    9395            9400            9405

Thr Thr Pro Met Ser Arg Gly Pro Glu Asp Val Ser Trp Pro Ser
    9410            9415            9420

Pro Leu Ser Val Glu Lys Asn Ser Pro Pro Ser Ser Leu Val Ser
    9425            9430            9435

Ser Ser Ser Val Thr Ser Pro Ser Pro Leu Tyr Ser Thr Pro Ser
    9440            9445            9450

Gly Ser Ser His Ser Ser Pro Val Pro Val Thr Ser Leu Phe Thr
    9455            9460            9465

Ser Ile Met Met Lys Ala Thr Asp Met Leu Asp Ala Ser Leu Glu
    9470            9475            9480

Pro Glu Thr Thr Ser Ala Pro Asn Met Asn Ile Thr Ser Asp Glu
    9485            9490            9495

Ser Leu Ala Ala Ser Lys Ala Thr Thr Glu Thr Glu Ala Ile His
    9500            9505            9510

Val Phe Glu Asn Thr Ala Ala Ser His Val Glu Thr Thr Ser Ala
    9515            9520            9525

Thr Glu Glu Leu Tyr Ser Ser Pro Gly Phe Ser Glu Pro Thr
    9530            9535            9540

Lys Val Ile Ser Pro Val Val Thr Ser Ser Ser Ile Arg Asp Asn
    9545            9550            9555

Met Val Ser Thr Thr Met Pro Gly Ser Ser Gly Ile Thr Arg Ile
    9560            9565            9570

Glu Ile Glu Ser Met Ser Ser Leu Thr Pro Gly Leu Arg Glu Thr
    9575            9580            9585

Arg Thr Ser Gln Asp Ile Thr Ser Ser Thr Glu Thr Ser Thr Val
    9590            9595            9600

Leu Tyr Lys Met Pro Ser Gly Ala Thr Pro Glu Val Ser Arg Thr
    9605            9610            9615

Glu Val Met Pro Ser Ser Arg Thr Ser Ile Pro Gly Pro Ala Gln
    9620            9625            9630

Ser Thr Met Ser Leu Asp Ile Ser Asp Glu Val Val Thr Arg Leu
    9635            9640            9645

Ser Thr Ser Pro Ile Met Thr Glu Ser Ala Glu Ile Thr Ile Thr
    9650            9655            9660

Thr Gln Thr Gly Tyr Ser Leu Ala Thr Ser Gln Val Thr Leu Pro
    9665            9670            9675

Leu Gly Thr Ser Met Thr Phe Leu Ser Gly Thr His Ser Thr Met
    9680            9685            9690

Ser Gln Gly Leu Ser His Ser Glu Met Thr Asn Leu Met Ser Arg
    9695            9700            9705

Gly Pro Glu Ser Leu Ser Trp Thr Ser Pro Arg Phe Val Glu Thr

```
            9710                9715                9720
Thr Arg Ser Ser Ser Ser Leu Thr Ser Leu Pro Leu Thr Thr Ser
            9725                9730                9735
Leu Ser Pro Val Ser Ser Thr Leu Leu Asp Ser Ser Pro Ser Ser
            9740                9745                9750
Pro Leu Pro Val Thr Ser Leu Ile Leu Pro Gly Leu Val Lys Thr
            9755                9760                9765
Thr Glu Val Leu Asp Thr Ser Ser Glu Pro Lys Thr Ser Ser Ser
            9770                9775                9780
Pro Asn Leu Ser Ser Thr Ser Val Glu Ile Pro Ala Thr Ser Glu
            9785                9790                9795
Ile Met Thr Asp Thr Glu Lys Ile His Pro Ser Ser Asn Thr Ala
            9800                9805                9810
Val Ala Lys Val Arg Thr Ser Ser Ser Val His Glu Ser His Ser
            9815                9820                9825
Ser Val Leu Ala Asp Ser Glu Thr Thr Ile Thr Ile Pro Ser Met
            9830                9835                9840
Gly Ile Thr Ser Ala Val Asp Asp Thr Thr Val Phe Thr Ser Asn
            9845                9850                9855
Pro Ala Phe Ser Glu Thr Arg Arg Ile Pro Thr Glu Pro Thr Phe
            9860                9865                9870
Ser Leu Thr Pro Gly Phe Arg Glu Thr Ser Thr Glu Glu Thr
            9875                9880                9885
Thr Ser Ile Thr Glu Thr Ser Ala Val Leu Tyr Gly Val Pro Thr
            9890                9895                9900
Ser Ala Thr Thr Glu Val Ser Met Thr Glu Ile Met Ser Ser Asn
            9905                9910                9915
Arg Ile His Ile Pro Asp Ser Asp Gln Ser Thr Met Ser Pro Asp
            9920                9925                9930
Ile Ile Thr Glu Val Ile Thr Arg Leu Ser Ser Ser Ser Met Met
            9935                9940                9945
Ser Glu Ser Thr Gln Met Thr Ile Thr Thr Gln Lys Ser Ser Pro
            9950                9955                9960
Gly Ala Thr Ala Gln Ser Thr Leu Thr Leu Ala Thr Thr Thr Ala
            9965                9970                9975
Pro Leu Ala Arg Thr His Ser Thr Val Pro Pro Arg Phe Leu His
            9980                9985                9990
Ser Glu Met Thr Thr Leu Met Ser Arg Ser Pro Glu Asn Pro Ser
            9995                10000               10005
Trp Lys Ser Ser Leu Phe Val Glu Lys Thr Ser Ser Ser Ser Ser
            10010               10015               10020
Leu Leu Ser Leu Pro Val Thr Thr Ser Pro Ser Val Ser Ser Thr
            10025               10030               10035
Leu Pro Gln Ser Ile Pro Ser Ser Ser Phe Ser Val Thr Ser Leu
            10040               10045               10050
Leu Thr Pro Gly Met Val Lys Thr Thr Asp Thr Ser Thr Glu Pro
            10055               10060               10065
Gly Thr Ser Leu Ser Pro Asn Leu Ser Gly Thr Ser Val Glu Ile
            10070               10075               10080
Leu Ala Ala Ser Glu Val Thr Thr Asp Thr Glu Lys Ile His Pro
            10085               10090               10095
Ser Ser Ser Met Ala Val Thr Asn Val Gly Thr Thr Ser Ser Gly
            10100               10105               10110
```

His Glu Leu Tyr Ser Ser Val   Ser Ile His Ser Glu   Pro Ser Lys
    10115           10120                10125

Ala Thr Tyr Pro Val Gly Thr   Pro Ser Ser Met Ala   Glu Thr Ser
    10130           10135                10140

Ile Ser Thr Ser Met Pro Ala   Asn Phe Glu Thr Thr   Gly Phe Glu
    10145           10150                10155

Ala Glu Pro Phe Ser His Leu   Thr Ser Gly Phe Arg   Lys Thr Asn
    10160           10165                10170

Met Ser Leu Asp Thr Ser Ser   Val Thr Pro Thr Asn   Thr Pro Ser
    10175           10180                10185

Ser Pro Gly Ser Thr His Leu   Leu Gln Ser Ser Lys   Thr Asp Phe
    10190           10195                10200

Thr Ser Ser Ala Lys Thr Ser   Ser Pro Asp Trp Pro   Pro Ala Ser
    10205           10210                10215

Gln Tyr Thr Glu Ile Pro Val   Asp Ile Ile Thr Pro   Phe Asn Ala
    10220           10225                10230

Ser Pro Ser Ile Thr Glu Ser   Thr Gly Ile Thr Ser   Phe Pro Glu
    10235           10240                10245

Ser Arg Phe Thr Met Ser Val   Thr Glu Ser Thr His   His Leu Ser
    10250           10255                10260

Thr Asp Leu Leu Pro Ser Ala   Glu Thr Ile Ser Thr   Gly Thr Val
    10265           10270                10275

Met Pro Ser Leu Ser Glu Ala   Met Thr Ser Phe Ala   Thr Thr Gly
    10280           10285                10290

Val Pro Arg Ala Ile Ser Gly   Ser Gly Ser Pro Phe   Ser Arg Thr
    10295           10300                10305

Glu Ser Gly Pro Gly Asp Ala   Thr Leu Ser Thr Ile   Ala Glu Ser
    10310           10315                10320

Leu Pro Ser Ser Thr Pro Val   Pro Phe Ser Ser Ser   Thr Phe Thr
    10325           10330                10335

Thr Thr Asp Ser Ser Thr Ile   Pro Ala Leu His Glu   Ile Thr Ser
    10340           10345                10350

Ser Ser Ala Thr Pro Tyr Arg   Val Asp Thr Ser Leu   Gly Thr Glu
    10355           10360                10365

Ser Ser Thr Thr Glu Gly Arg   Leu Val Met Val Ser   Thr Leu Asp
    10370           10375                10380

Thr Ser Ser Gln Pro Gly Arg   Thr Ser Ser Ser Pro   Ile Leu Asp
    10385           10390                10395

Thr Arg Met Thr Glu Ser Val   Glu Leu Gly Thr Val   Thr Ser Ala
    10400           10405                10410

Tyr Gln Val Pro Ser Leu Ser   Thr Arg Leu Thr Arg   Thr Asp Gly
    10415           10420                10425

Ile Met Glu His Ile Thr Lys   Ile Pro Asn Glu Ala   Ala His Arg
    10430           10435                10440

Gly Thr Ile Arg Pro Val Lys   Gly Pro Gln Thr Ser   Thr Ser Pro
    10445           10450                10455

Ala Ser Pro Lys Gly Leu His   Thr Gly Gly Thr Lys   Arg Met Glu
    10460           10465                10470

Thr Thr Thr Thr Ala Leu Lys   Thr Thr Thr Thr Ala   Leu Lys Thr
    10475           10480                10485

Thr Ser Arg Ala Thr Leu Thr   Thr Ser Val Tyr Thr   Pro Thr Leu
    10490           10495                10500

| | | | | | | | | | | | |
|---|---|---|---|---|---|---|---|---|---|---|---|
| Gly | Thr 10505 | Leu | Thr | Pro | Leu 10510 | Asn | Ala | Ser | Met | Gln 10515 | Met | Ala | Ser | Thr |
| Ile | Pro 10520 | Thr | Glu | Met | Met 10525 | Ile | Thr | Thr | Pro | Tyr 10530 | Val | Phe | Pro | Asp |
| Val | Pro 10535 | Glu | Thr | Thr | Ser 10540 | Ser | Leu | Ala | Thr | Ser 10545 | Leu | Gly | Ala | Glu |
| Thr | Ser 10550 | Thr | Ala | Leu | Pro 10555 | Arg | Thr | Thr | Pro | Ser 10560 | Val | Phe | Asn | Arg |
| Glu | Ser 10565 | Glu | Thr | Thr | Ala 10570 | Ser | Leu | Val | Ser | Arg 10575 | Ser | Gly | Ala | Glu |
| Arg | Ser 10580 | Pro | Val | Ile | Gln 10585 | Thr | Leu | Asp | Val | Ser 10590 | Ser | Ser | Glu | Pro |
| Asp | Thr 10595 | Thr | Ala | Ser | Trp 10600 | Val | Ile | His | Pro | Ala 10605 | Glu | Thr | Ile | Pro |
| Thr | Val 10610 | Ser | Lys | Thr | Thr 10615 | Pro | Asn | Phe | Phe | His 10620 | Ser | Glu | Leu | Asp |
| Thr | Val 10625 | Ser | Ser | Thr | Ala 10630 | Thr | Ser | His | Gly | Ala 10635 | Asp | Val | Ser | Ser |
| Ala | Ile 10640 | Pro | Thr | Asn | Ile 10645 | Ser | Pro | Ser | Glu | Leu 10650 | Asp | Ala | Leu | Thr |
| Pro | Leu 10655 | Val | Thr | Ile | Ser 10660 | Gly | Thr | Asp | Thr | Ser 10665 | Thr | Thr | Phe | Pro |
| Thr | Leu 10670 | Thr | Lys | Ser | Pro 10675 | His | Glu | Thr | Glu | Thr 10680 | Arg | Thr | Thr | Trp |
| Leu | Thr 10685 | His | Pro | Ala | Glu 10690 | Thr | Ser | Ser | Thr | Ile 10695 | Pro | Arg | Thr | Ile |
| Pro | Asn 10700 | Phe | Ser | His | His 10705 | Glu | Ser | Asp | Ala | Thr 10710 | Pro | Ser | Ile | Ala |
| Thr | Ser 10715 | Pro | Gly | Ala | Glu 10720 | Thr | Ser | Ser | Ala | Ile 10725 | Pro | Ile | Met | Thr |
| Val | Ser 10730 | Pro | Gly | Ala | Glu 10735 | Asp | Leu | Val | Thr | Ser 10740 | Gln | Val | Thr | Ser |
| Ser | Gly 10745 | Thr | Asp | Arg | Asn 10750 | Met | Thr | Ile | Pro | Thr 10755 | Leu | Thr | Leu | Ser |
| Pro | Gly 10760 | Glu | Pro | Lys | Thr 10765 | Ile | Ala | Ser | Leu | Val 10770 | Thr | His | Pro | Glu |
| Ala | Gln 10775 | Thr | Ser | Ser | Ala 10780 | Ile | Pro | Thr | Ser | Thr 10785 | Ile | Ser | Pro | Ala |
| Val | Ser 10790 | Arg | Leu | Val | Thr 10795 | Ser | Met | Val | Thr | Ser 10800 | Leu | Ala | Ala | Lys |
| Thr | Ser 10805 | Thr | Thr | Asn | Arg 10810 | Ala | Leu | Thr | Asn | Ser 10815 | Pro | Gly | Glu | Pro |
| Ala | Thr 10820 | Thr | Val | Ser | Leu 10825 | Val | Thr | His | Pro | Ala 10830 | Gln | Thr | Ser | Pro |
| Thr | Val 10835 | Pro | Trp | Thr | Thr 10840 | Ser | Ile | Phe | Phe | His 10845 | Ser | Lys | Ser | Asp |
| Thr | Thr 10850 | Pro | Ser | Met | Thr 10855 | Thr | Ser | His | Gly | Ala 10860 | Glu | Ser | Ser | Ser |
| Ala | Val 10865 | Pro | Thr | Pro | Thr 10870 | Val | Ser | Thr | Glu | Val 10875 | Pro | Gly | Val | Val |
| Thr | Pro 10880 | Leu | Val | Thr | Ser 10885 | Ser | Arg | Ala | Val | Ile 10890 | Ser | Thr | Thr | Ile |
| Pro | Ile | Leu | Thr | Leu | Ser | Pro | Gly | Glu | Pro | Glu | Thr | Thr | Pro | Ser |

```
                10895               10900               10905

Met Ala Thr Ser His Gly Glu   Glu Ala Ser Ser Ala   Ile Pro Thr
            10910               10915               10920

Pro Thr Val Ser Pro Gly Val   Pro Gly Val Val Thr   Ser Leu Val
            10925               10930               10935

Thr Ser Ser Arg Ala Val Thr   Ser Thr Thr Ile Pro   Ile Leu Thr
            10940               10945               10950

Phe Ser Leu Gly Glu Pro Glu   Thr Thr Pro Ser Met   Ala Thr Ser
            10955               10960               10965

His Gly Thr Glu Ala Gly Ser   Ala Val Pro Thr Val   Leu Pro Glu
            10970               10975               10980

Val Pro Gly Met Val Thr Ser   Leu Val Ala Ser Ser   Arg Ala Val
            10985               10990               10995

Thr Ser Thr Thr Leu Pro Thr   Leu Thr Leu Ser Pro   Gly Glu Pro
            11000               11005               11010

Glu Thr Thr Pro Ser Met Ala   Thr Ser His Gly Ala   Glu Ala Ser
            11015               11020               11025

Ser Thr Val Pro Thr Val Ser   Pro Glu Val Pro Gly   Val Val Thr
            11030               11035               11040

Ser Leu Val Thr Ser Ser Ser   Gly Val Asn Ser Thr   Ser Ile Pro
            11045               11050               11055

Thr Leu Ile Leu Ser Pro Gly   Glu Leu Glu Thr Thr   Pro Ser Met
            11060               11065               11070

Ala Thr Ser His Gly Ala Glu   Ala Ser Ser Ala Val   Pro Thr Pro
            11075               11080               11085

Thr Val Ser Pro Gly Val Ser   Gly Val Val Thr Pro   Leu Val Thr
            11090               11095               11100

Ser Ser Arg Ala Val Thr Ser   Thr Thr Ile Pro Ile   Leu Thr Leu
            11105               11110               11115

Ser Ser Ser Glu Pro Glu Thr   Thr Pro Ser Met Ala   Thr Ser His
            11120               11125               11130

Gly Val Glu Ala Ser Ser Ala   Val Leu Thr Val Ser   Pro Glu Val
            11135               11140               11145

Pro Gly Met Val Thr Ser Leu   Val Thr Ser Ser Arg   Ala Val Thr
            11150               11155               11160

Ser Thr Thr Ile Pro Thr Leu   Thr Ile Ser Ser Asp   Glu Pro Glu
            11165               11170               11175

Thr Thr Thr Ser Leu Val Thr   His Ser Glu Ala Lys   Met Ile Ser
            11180               11185               11190

Ala Ile Pro Thr Leu Ala Val   Ser Pro Thr Val Gln   Gly Leu Val
            11195               11200               11205

Thr Ser Leu Val Thr Ser Ser   Gly Ser Glu Thr Ser   Ala Phe Ser
            11210               11215               11220

Asn Leu Thr Val Ala Ser Ser   Gln Pro Glu Thr Ile   Asp Ser Trp
            11225               11230               11235

Val Ala His Pro Gly Thr Glu   Ala Ser Ser Val Val   Pro Thr Leu
            11240               11245               11250

Thr Val Ser Thr Gly Glu Pro   Phe Thr Asn Ile Ser   Leu Val Thr
            11255               11260               11265

His Pro Ala Glu Ser Ser Ser   Thr Leu Pro Arg Thr   Thr Ser Arg
            11270               11275               11280

Phe Ser His Ser Glu Leu Asp   Thr Met Pro Ser Thr   Val Thr Ser
            11285               11290               11295
```

```
Pro Glu Ala Glu Ser Ser Ala Ile Ser Thr Thr Ile Ser Pro
    11300           11305             11310
Gly Ile Pro Gly Val Leu Thr Ser Leu Val Thr Ser Gly Arg
    11315           11320             11325
Asp Ile Ser Ala Thr Phe Pro Thr Val Pro Glu Ser Pro His Glu
    11330           11335             11340
Ser Glu Ala Thr Ala Ser Trp Val Thr His Pro Ala Val Thr Ser
    11345           11350             11355
Thr Thr Val Pro Arg Thr Thr Pro Asn Tyr Ser His Ser Glu Pro
    11360           11365             11370
Asp Thr Thr Pro Ser Ile Ala Thr Ser Pro Gly Ala Glu Ala Thr
    11375           11380             11385
Ser Asp Phe Pro Thr Ile Thr Val Ser Pro Asp Val Pro Asp Met
    11390           11395             11400
Val Thr Ser Gln Val Thr Ser Ser Gly Thr Asp Thr Ser Ile Thr
    11405           11410             11415
Ile Pro Thr Leu Thr Leu Ser Ser Gly Glu Pro Glu Thr Thr Thr
    11420           11425             11430
Ser Phe Ile Thr Tyr Ser Glu Thr His Thr Ser Ser Ala Ile Pro
    11435           11440             11445
Thr Leu Pro Val Ser Pro Gly Ala Ser Lys Met Leu Thr Ser Leu
    11450           11455             11460
Val Ile Ser Ser Gly Thr Asp Ser Thr Thr Thr Phe Pro Thr Leu
    11465           11470             11475
Thr Glu Thr Pro Tyr Glu Pro Glu Thr Thr Ala Ile Gln Leu Ile
    11480           11485             11490
His Pro Ala Glu Thr Asn Thr Met Val Pro Arg Thr Thr Pro Lys
    11495           11500             11505
Phe Ser His Ser Lys Ser Asp Thr Thr Leu Pro Val Ala Ile Thr
    11510           11515             11520
Ser Pro Gly Pro Glu Ala Ser Ser Ala Val Ser Thr Thr Thr Ile
    11525           11530             11535
Ser Pro Asp Met Ser Asp Leu Val Thr Ser Leu Val Pro Ser Ser
    11540           11545             11550
Gly Thr Asp Thr Ser Thr Thr Phe Pro Thr Leu Ser Glu Thr Pro
    11555           11560             11565
Tyr Glu Pro Glu Thr Thr Ala Thr Trp Leu Thr His Pro Ala Glu
    11570           11575             11580
Thr Ser Thr Thr Val Ser Gly Thr Ile Pro Asn Phe Ser His Arg
    11585           11590             11595
Gly Ser Asp Thr Ala Pro Ser Met Val Thr Ser Pro Gly Val Asp
    11600           11605             11610
Thr Arg Ser Gly Val Pro Thr Thr Thr Ile Pro Pro Ser Ile Pro
    11615           11620             11625
Gly Val Val Thr Ser Gln Val Thr Ser Ser Ala Thr Asp Thr Ser
    11630           11635             11640
Thr Ala Ile Pro Thr Leu Thr Pro Ser Pro Gly Glu Pro Glu Thr
    11645           11650             11655
Thr Ala Ser Ser Ala Thr His Pro Gly Thr Gln Thr Gly Phe Thr
    11660           11665             11670
Val Pro Ile Arg Thr Val Pro Ser Ser Glu Pro Asp Thr Met Ala
    11675           11680             11685
```

Ser Trp Val Thr His Pro Pro Gln Thr Ser Thr Pro Val Ser Arg
11690                    11695               11700

Thr Thr Ser Ser Phe Ser His Ser Ser Pro Asp Ala Thr Pro Val
11705                    11710               11715

Met Ala Thr Ser Pro Arg Thr Glu Ala Ser Ser Ala Val Leu Thr
11720                    11725               11730

Thr Ile Ser Pro Gly Ala Pro Glu Met Val Thr Ser Gln Ile Thr
11735                    11740               11745

Ser Ser Gly Ala Ala Thr Ser Thr Thr Val Pro Thr Leu Thr His
11750                    11755               11760

Ser Pro Gly Met Pro Glu Thr Thr Ala Leu Leu Ser Thr His Pro
11765                    11770               11775

Arg Thr Glu Thr Ser Lys Thr Phe Pro Ala Ser Thr Val Phe Pro
11780                    11785               11790

Gln Val Ser Glu Thr Thr Ala Ser Leu Thr Ile Arg Pro Gly Ala
11795                    11800               11805

Glu Thr Ser Thr Ala Leu Pro Thr Gln Thr Thr Ser Ser Leu Phe
11810                    11815               11820

Thr Leu Leu Val Thr Gly Thr Ser Arg Val Asp Leu Ser Pro Thr
11825                    11830               11835

Ala Ser Pro Gly Val Ser Ala Lys Thr Ala Pro Leu Ser Thr His
11840                    11845               11850

Pro Gly Thr Glu Thr Ser Thr Met Ile Pro Thr Ser Thr Leu Ser
11855                    11860               11865

Leu Gly Leu Leu Glu Thr Thr Gly Leu Leu Ala Thr Ser Ser Ser
11870                    11875               11880

Ala Glu Thr Ser Thr Ser Thr Leu Thr Leu Thr Val Ser Pro Ala
11885                    11890               11895

Val Ser Gly Leu Ser Ser Ala Ser Ile Thr Thr Asp Lys Pro Gln
11900                    11905               11910

Thr Val Thr Ser Trp Asn Thr Glu Thr Ser Pro Ser Val Thr Ser
11915                    11920               11925

Val Gly Pro Pro Glu Phe Ser Arg Thr Val Thr Gly Thr Thr Met
11930                    11935               11940

Thr Leu Ile Pro Ser Glu Met Pro Thr Pro Pro Lys Thr Ser His
11945                    11950               11955

Gly Glu Gly Val Ser Pro Thr Thr Ile Leu Arg Thr Thr Met Val
11960                    11965               11970

Glu Ala Thr Asn Leu Ala Thr Thr Gly Ser Ser Pro Thr Val Ala
11975                    11980               11985

Lys Thr Thr Thr Phe Asn Thr Leu Ala Gly Ser Leu Phe Thr
11990                    11995               12000

Pro Leu Thr Thr Pro Gly Met Ser Thr Leu Ala Ser Glu Ser Val
12005                    12010               12015

Thr Ser Arg Thr Ser Tyr Asn His Arg Ser Trp Ile Ser Thr Thr
12020                    12025               12030

Ser Ser Tyr Asn Arg Arg Tyr Trp Thr Pro Ala Thr Ser Thr Pro
12035                    12040               12045

Val Thr Ser Thr Phe Ser Pro Gly Ile Ser Thr Ser Ser Ile Pro
12050                    12055               12060

Ser Ser Thr Ala Ala Thr Val Pro Phe Met Val Pro Phe Thr Leu
12065                    12070               12075

Asn Phe Thr Ile Thr Asn Leu Gln Tyr Glu Glu Asp Met Arg His

```
            12080              12085              12090

Pro Gly Ser Arg Lys Phe Asn  Ala Thr Glu Arg Glu  Leu Gln Gly
        12095                    12100                12105

Leu Leu Lys Pro Leu Phe Arg  Asn Ser Ser Leu Glu  Tyr Leu Tyr
        12110                    12115                12120

Ser Gly Cys Arg Leu Ala Ser  Leu Arg Pro Glu Lys  Asp Ser Ser
        12125                    12130                12135

Ala Thr Ala Val Asp Ala Ile  Cys Thr His Arg Pro  Asp Pro Glu
        12140                    12145                12150

Asp Leu Gly Leu Asp Arg Glu  Arg Leu Tyr Trp Glu  Leu Ser Asn
        12155                    12160                12165

Leu Thr Asn Gly Ile Gln Glu  Leu Gly Pro Tyr Thr  Leu Asp Arg
        12170                    12175                12180

Asn Ser Leu Tyr Val Asn Gly  Phe Thr His Arg Ser  Ser Met Pro
        12185                    12190                12195

Thr Thr Ser Thr Pro Gly Thr  Ser Thr Val Asp Val  Gly Thr Ser
        12200                    12205                12210

Gly Thr Pro Ser Ser Ser Pro  Ser Pro Thr Thr Ala  Gly Pro Leu
        12215                    12220                12225

Leu Met Pro Phe Thr Leu Asn  Phe Thr Ile Thr Asn  Leu Gln Tyr
        12230                    12235                12240

Glu Glu Asp Met Arg Arg Thr  Gly Ser Arg Lys Phe  Asn Thr Met
        12245                    12250                12255

Glu Ser Val Leu Gln Gly Leu  Leu Lys Pro Leu Phe  Lys Asn Thr
        12260                    12265                12270

Ser Val Gly Pro Leu Tyr Ser  Gly Cys Arg Leu Thr  Leu Leu Arg
        12275                    12280                12285

Pro Glu Lys Asp Gly Ala Ala  Thr Gly Val Asp Ala  Ile Cys Thr
        12290                    12295                12300

His Arg Leu Asp Pro Lys Ser  Pro Gly Leu Asn Arg  Glu Gln Leu
        12305                    12310                12315

Tyr Trp Glu Leu Ser Lys Leu  Thr Asn Asp Ile Glu  Glu Leu Gly
        12320                    12325                12330

Pro Tyr Thr Leu Asp Arg Asn  Ser Leu Tyr Val Asn  Gly Phe Thr
        12335                    12340                12345

His Gln Ser Ser Val Ser Thr  Thr Ser Thr Pro Gly  Thr Ser Thr
        12350                    12355                12360

Val Asp Leu Arg Thr Ser Gly  Thr Pro Ser Ser Leu  Ser Ser Pro
        12365                    12370                12375

Thr Ile Met Ala Ala Gly Pro  Leu Leu Val Pro Phe  Thr Leu Asn
        12380                    12385                12390

Phe Thr Ile Thr Asn Leu Gln  Tyr Gly Glu Asp Met  Gly His Pro
        12395                    12400                12405

Gly Ser Arg Lys Phe Asn Thr  Thr Glu Arg Val Leu  Gln Gly Leu
        12410                    12415                12420

Leu Gly Pro Ile Phe Lys Asn  Thr Ser Val Gly Pro  Leu Tyr Ser
        12425                    12430                12435

Gly Cys Arg Leu Thr Ser Leu  Arg Ser Glu Lys Asp  Gly Ala Ala
        12440                    12445                12450

Thr Gly Val Asp Ala Ile Cys  Ile His His Leu Asp  Pro Lys Ser
        12455                    12460                12465

Pro Gly Leu Asn Arg Glu Arg  Leu Tyr Trp Glu Leu  Ser Gln Leu
        12470                    12475                12480
```

-continued

```
Thr Asn Gly Ile Lys Glu Leu Gly Pro Tyr Thr Leu Asp Arg Asn
    12485           12490           12495

Ser Leu Tyr Val Asn Gly Phe Thr His Arg Thr Ser Val Pro Thr
    12500           12505           12510

Ser Ser Thr Pro Gly Thr Ser Thr Val Asp Leu Gly Thr Ser Gly
    12515           12520           12525

Thr Pro Phe Ser Leu Pro Ser Pro Ala Thr Ala Gly Pro Leu Leu
    12530           12535           12540

Val Leu Phe Thr Leu Asn Phe Thr Ile Thr Asn Leu Lys Tyr Glu
    12545           12550           12555

Glu Asp Met His Arg Pro Gly Ser Arg Lys Phe Asn Thr Thr Glu
    12560           12565           12570

Arg Val Leu Gln Thr Leu Leu Gly Pro Met Phe Lys Asn Thr Ser
    12575           12580           12585

Val Gly Leu Leu Tyr Ser Gly Cys Arg Leu Thr Leu Leu Arg Ser
    12590           12595           12600

Glu Lys Asp Gly Ala Ala Thr Gly Val Asp Ala Ile Cys Thr His
    12605           12610           12615

Arg Leu Asp Pro Lys Ser Pro Gly Val Asp Arg Glu Gln Leu Tyr
    12620           12625           12630

Trp Glu Leu Ser Gln Leu Thr Asn Gly Ile Lys Glu Leu Gly Pro
    12635           12640           12645

Tyr Thr Leu Asp Arg Asn Ser Leu Tyr Val Asn Gly Phe Thr His
    12650           12655           12660

Trp Ile Pro Val Pro Thr Ser Ser Thr Pro Gly Thr Ser Thr Val
    12665           12670           12675

Asp Leu Gly Ser Gly Thr Pro Ser Ser Leu Pro Ser Pro Thr Thr
    12680           12685           12690

Ala Gly Pro Leu Leu Val Pro Phe Thr Leu Asn Phe Thr Ile Thr
    12695           12700           12705

Asn Leu Lys Tyr Glu Glu Asp Met His Cys Pro Gly Ser Arg Lys
    12710           12715           12720

Phe Asn Thr Thr Glu Arg Val Leu Gln Ser Leu Leu Gly Pro Met
    12725           12730           12735

Phe Lys Asn Thr Ser Val Gly Pro Leu Tyr Ser Gly Cys Arg Leu
    12740           12745           12750

Thr Leu Leu Arg Ser Glu Lys Asp Gly Ala Ala Thr Gly Val Asp
    12755           12760           12765

Ala Ile Cys Thr His Arg Leu Asp Pro Lys Ser Pro Gly Val Asp
    12770           12775           12780

Arg Glu Gln Leu Tyr Trp Glu Leu Ser Gln Leu Thr Asn Gly Ile
    12785           12790           12795

Lys Glu Leu Gly Pro Tyr Thr Leu Asp Arg Asn Ser Leu Tyr Val
    12800           12805           12810

Asn Gly Phe Thr His Gln Thr Ser Ala Pro Asn Thr Ser Thr Pro
    12815           12820           12825

Gly Thr Ser Thr Val Asp Leu Gly Thr Ser Gly Thr Pro Ser Ser
    12830           12835           12840

Leu Pro Ser Pro Thr Ser Ala Gly Pro Leu Leu Val Pro Phe Thr
    12845           12850           12855

Leu Asn Phe Thr Ile Thr Asn Leu Gln Tyr Glu Glu Asp Met His
    12860           12865           12870
```

```
His Pro Gly Ser Arg Lys Phe Asn Thr Thr Glu Arg     Val Leu Gln
    12875               12880               12885

Gly Leu Leu Gly Pro Met Phe Lys Asn Thr Ser Val     Gly Leu Leu
    12890               12895               12900

Tyr Ser Gly Cys Arg Leu Thr Leu Leu Arg Pro Glu     Lys Asn Gly
    12905               12910               12915

Ala Ala Thr Gly Met Asp Ala Ile Cys Ser His Arg     Leu Asp Pro
    12920               12925               12930

Lys Ser Pro Gly Leu Asn Arg Glu Gln Leu Tyr Trp     Glu Leu Ser
    12935               12940               12945

Gln Leu Thr His Gly Ile Lys Glu Leu Gly Pro Tyr     Thr Leu Asp
    12950               12955               12960

Arg Asn Ser Leu Tyr Val Asn Gly Phe Thr His Arg     Ser Ser Val
    12965               12970               12975

Ala Pro Thr Ser Thr Pro Gly Thr Ser Thr Val Asp     Leu Gly Thr
    12980               12985               12990

Ser Gly Thr Pro Ser Ser Leu Pro Ser Pro Thr Thr     Ala Val Pro
    12995               13000               13005

Leu Leu Val Pro Phe Thr Leu Asn Phe Thr Ile Thr     Asn Leu Gln
    13010               13015               13020

Tyr Gly Glu Asp Met Arg His Pro Gly Ser Arg Lys     Phe Asn Thr
    13025               13030               13035

Thr Glu Arg Val Leu Gln Gly Leu Leu Gly Pro Leu     Phe Lys Asn
    13040               13045               13050

Ser Ser Val Gly Pro Leu Tyr Ser Gly Cys Arg Leu     Ile Ser Leu
    13055               13060               13065

Arg Ser Glu Lys Asp Gly Ala Ala Thr Gly Val Asp     Ala Ile Cys
    13070               13075               13080

Thr His His Leu Asn Pro Gln Ser Pro Gly Leu Asp     Arg Glu Gln
    13085               13090               13095

Leu Tyr Trp Gln Leu Ser Gln Met Thr Asn Gly Ile     Lys Glu Leu
    13100               13105               13110

Gly Pro Tyr Thr Leu Asp Arg Asn Ser Leu Tyr Val     Asn Gly Phe
    13115               13120               13125

Thr His Arg Ser Ser Gly Leu Thr Thr Ser Thr Pro     Trp Thr Ser
    13130               13135               13140

Thr Val Asp Leu Gly Thr Ser Gly Thr Pro Ser Pro     Val Pro Ser
    13145               13150               13155

Pro Thr Thr Thr Gly Pro Leu Leu Val Pro Phe Thr     Leu Asn Phe
    13160               13165               13170

Thr Ile Thr Asn Leu Gln Tyr Glu Glu Asn Met Gly     His Pro Gly
    13175               13180               13185

Ser Arg Lys Phe Asn Ile Thr Glu Ser Val Leu Gln     Gly Leu Leu
    13190               13195               13200

Lys Pro Leu Phe Lys Ser Thr Ser Val Gly Pro Leu     Tyr Ser Gly
    13205               13210               13215

Cys Arg Leu Thr Leu Leu Arg Pro Glu Lys Asp Gly     Val Ala Thr
    13220               13225               13230

Arg Val Asp Ala Ile Cys Thr His Arg Pro Asp Pro     Lys Ile Pro
    13235               13240               13245

Gly Leu Asp Arg Gln Gln Leu Tyr Trp Glu Leu Ser     Gln Leu Thr
    13250               13255               13260

His Ser Ile Thr Glu Leu Gly Pro Tyr Thr Leu Asp     Arg Asp Ser
```

```
       13265               13270               13275
Leu Tyr Val Asn Gly Phe Thr Gln Arg Ser Ser Val Pro Thr Thr
       13280               13285               13290
Ser Thr Pro Gly Thr Phe Thr Val Gln Pro Glu Thr Ser Glu Thr
       13295               13300               13305
Pro Ser Ser Leu Pro Gly Pro Thr Ala Thr Gly Pro Val Leu Leu
       13310               13315               13320
Pro Phe Thr Leu Asn Phe Thr Ile Thr Asn Leu Gln Tyr Glu Glu
       13325               13330               13335
Asp Met Arg Arg Pro Gly Ser Arg Lys Phe Asn Thr Thr Glu Arg
       13340               13345               13350
Val Leu Gln Gly Leu Leu Met Pro Leu Phe Lys Asn Thr Ser Val
       13355               13360               13365
Ser Ser Leu Tyr Ser Gly Cys Arg Leu Thr Leu Leu Arg Pro Glu
       13370               13375               13380
Lys Asp Gly Ala Ala Thr Arg Val Asp Ala Val Cys Thr His Arg
       13385               13390               13395
Pro Asp Pro Lys Ser Pro Gly Leu Asp Arg Glu Arg Leu Tyr Trp
       13400               13405               13410
Lys Leu Ser Gln Leu Thr His Gly Ile Thr Glu Leu Gly Pro Tyr
       13415               13420               13425
Thr Leu Asp Arg His Ser Leu Tyr Val Asn Gly Phe Thr His Gln
       13430               13435               13440
Ser Ser Met Thr Thr Thr Arg Thr Pro Asp Thr Ser Thr Met His
       13445               13450               13455
Leu Ala Thr Ser Arg Thr Pro Ala Ser Leu Ser Gly Pro Met Thr
       13460               13465               13470
Ala Ser Pro Leu Leu Val Leu Phe Thr Ile Asn Phe Thr Ile Thr
       13475               13480               13485
Asn Leu Arg Tyr Glu Glu Asn Met His His Pro Gly Ser Arg Lys
       13490               13495               13500
Phe Asn Thr Thr Glu Arg Val Leu Gln Gly Leu Leu Arg Pro Val
       13505               13510               13515
Phe Lys Asn Thr Ser Val Gly Pro Leu Tyr Ser Gly Cys Arg Leu
       13520               13525               13530
Thr Leu Leu Arg Pro Lys Lys Asp Gly Ala Ala Thr Lys Val Asp
       13535               13540               13545
Ala Ile Cys Thr Tyr Arg Pro Asp Pro Lys Ser Pro Gly Leu Asp
       13550               13555               13560
Arg Glu Gln Leu Tyr Trp Glu Leu Ser Gln Leu Thr His Ser Ile
       13565               13570               13575
Thr Glu Leu Gly Pro Tyr Thr Leu Asp Arg Asp Ser Leu Tyr Val
       13580               13585               13590
Asn Gly Phe Thr Gln Arg Ser Ser Val Pro Thr Thr Ser Ile Pro
       13595               13600               13605
Gly Thr Pro Thr Val Asp Leu Gly Thr Ser Gly Thr Pro Val Ser
       13610               13615               13620
Lys Pro Gly Pro Ser Ala Ala Ser Pro Leu Leu Val Leu Phe Thr
       13625               13630               13635
Leu Asn Phe Thr Ile Thr Asn Leu Arg Tyr Glu Glu Asn Met Gln
       13640               13645               13650
His Pro Gly Ser Arg Lys Phe Asn Thr Thr Glu Arg Val Leu Gln
       13655               13660               13665
```

```
Gly Leu Leu Arg Ser Leu Phe Lys Ser Thr Ser Val Gly Pro Leu
    13670            13675                13680

Tyr Ser Gly Cys Arg Leu Thr Leu Leu Arg Pro Glu Lys Asp Gly
    13685            13690                13695

Thr Ala Thr Gly Val Asp Ala Ile Cys Thr His His Pro Asp Pro
    13700            13705                13710

Lys Ser Pro Arg Leu Asp Arg Glu Gln Leu Tyr Trp Glu Leu Ser
    13715            13720                13725

Gln Leu Thr His Asn Ile Thr Glu Leu Gly Pro Tyr Ala Leu Asp
    13730            13735                13740

Asn Asp Ser Leu Phe Val Asn Gly Phe Thr His Arg Ser Ser Val
    13745            13750                13755

Ser Thr Thr Ser Thr Pro Gly Thr Pro Thr Val Tyr Leu Gly Ala
    13760            13765                13770

Ser Lys Thr Pro Ala Ser Ile Phe Gly Pro Ser Ala Ala Ser His
    13775            13780                13785

Leu Leu Ile Leu Phe Thr Leu Asn Phe Thr Ile Thr Asn Leu Arg
    13790            13795                13800

Tyr Glu Glu Asn Met Trp Pro Gly Ser Arg Lys Phe Asn Thr Thr
    13805            13810                13815

Glu Arg Val Leu Gln Gly Leu Leu Arg Pro Leu Phe Lys Asn Thr
    13820            13825                13830

Ser Val Gly Pro Leu Tyr Ser Gly Cys Arg Leu Thr Leu Leu Arg
    13835            13840                13845

Pro Glu Lys Asp Gly Glu Ala Thr Gly Val Asp Ala Ile Cys Thr
    13850            13855                13860

His Arg Pro Asp Pro Thr Gly Pro Gly Leu Asp Arg Glu Gln Leu
    13865            13870                13875

Tyr Leu Glu Leu Ser Gln Leu Thr His Ser Ile Thr Glu Leu Gly
    13880            13885                13890

Pro Tyr Thr Leu Asp Arg Asp Ser Leu Tyr Val Asn Gly Phe Thr
    13895            13900                13905

His Arg Ser Ser Val Pro Thr Thr Ser Thr Gly Val Val Ser Glu
    13910            13915                13920

Glu Pro Phe Thr Leu Asn Phe Thr Ile Asn Asn Leu Arg Tyr Met
    13925            13930                13935

Ala Asp Met Gly Gln Pro Gly Ser Leu Lys Phe Asn Ile Thr Asp
    13940            13945                13950

Asn Val Met Gln His Leu Leu Ser Pro Leu Phe Gln Arg Ser Ser
    13955            13960                13965

Leu Gly Ala Arg Tyr Thr Gly Cys Arg Val Ile Ala Leu Arg Ser
    13970            13975                13980

Val Lys Asn Gly Ala Glu Thr Arg Val Asp Leu Leu Cys Thr Tyr
    13985            13990                13995

Leu Gln Pro Leu Ser Gly Pro Gly Leu Pro Ile Lys Gln Val Phe
    14000            14005                14010

His Glu Leu Ser Gln Gln Thr His Gly Ile Thr Arg Leu Gly Pro
    14015            14020                14025

Tyr Ser Leu Asp Lys Asp Ser Leu Tyr Leu Asn Gly Tyr Asn Glu
    14030            14035                14040

Pro Gly Pro Asp Glu Pro Pro Thr Thr Pro Lys Pro Ala Thr Thr
    14045            14050                14055
```

-continued

| | | | | | | | | | | | |
|---|---|---|---|---|---|---|---|---|---|---|---|
|Phe|Leu|Pro|Pro|Leu|Ser|Glu|Ala|Thr|Thr|Ala|Met|Gly|Tyr|His|
| |14060| | | |14065| | | |14070| | | | | |
|Leu|Lys|Thr|Leu|Thr|Leu|Asn|Phe|Thr|Ile|Ser|Asn|Leu|Gln|Tyr|
| |14075| | | |14080| | | |14085| | | | | |
|Ser|Pro|Asp|Met|Gly|Lys|Gly|Ser|Ala|Thr|Phe|Asn|Ser|Thr|Glu|
| |14090| | | |14095| | | |14100| | | | | |
|Gly|Val|Leu|Gln|His|Leu|Leu|Arg|Pro|Leu|Phe|Gln|Lys|Ser|Ser|
| |14105| | | |14110| | | |14115| | | | | |
|Met|Gly|Pro|Phe|Tyr|Leu|Gly|Cys|Gln|Leu|Ile|Ser|Leu|Arg|Pro|
| |14120| | | |14125| | | |14130| | | | | |
|Glu|Lys|Asp|Gly|Ala|Ala|Thr|Gly|Val|Asp|Thr|Thr|Cys|Thr|Tyr|
| |14135| | | |14140| | | |14145| | | | | |
|His|Pro|Asp|Pro|Val|Gly|Pro|Gly|Leu|Asp|Ile|Gln|Gln|Leu|Tyr|
| |14150| | | |14155| | | |14160| | | | | |
|Trp|Glu|Leu|Ser|Gln|Leu|Thr|His|Gly|Val|Thr|Gln|Leu|Gly|Phe|
| |14165| | | |14170| | | |14175| | | | | |
|Tyr|Val|Leu|Asp|Arg|Asp|Ser|Leu|Phe|Ile|Asn|Gly|Tyr|Ala|Pro|
| |14180| | | |14185| | | |14190| | | | | |
|Gln|Asn|Leu|Ser|Ile|Arg|Gly|Glu|Tyr|Gln|Ile|Asn|Phe|His|Ile|
| |14195| | | |14200| | | |14205| | | | | |
|Val|Asn|Trp|Asn|Leu|Ser|Asn|Pro|Asp|Pro|Thr|Ser|Ser|Glu|Tyr|
| |14210| | | |14215| | | |14220| | | | | |
|Ile|Thr|Leu|Leu|Arg|Asp|Ile|Gln|Asp|Lys|Val|Thr|Thr|Leu|Tyr|
| |14225| | | |14230| | | |14235| | | | | |
|Lys|Gly|Ser|Gln|Leu|His|Asp|Thr|Phe|Arg|Phe|Cys|Leu|Val|Thr|
| |14240| | | |14245| | | |14250| | | | | |
|Asn|Leu|Thr|Met|Asp|Ser|Val|Leu|Val|Thr|Val|Lys|Ala|Leu|Phe|
| |14255| | | |14260| | | |14265| | | | | |
|Ser|Ser|Asn|Leu|Asp|Pro|Ser|Leu|Val|Glu|Gln|Val|Phe|Leu|Asp|
| |14270| | | |14275| | | |14280| | | | | |
|Lys|Thr|Leu|Asn|Ala|Ser|Phe|His|Trp|Leu|Gly|Ser|Thr|Tyr|Gln|
| |14285| | | |14290| | | |14295| | | | | |
|Leu|Val|Asp|Ile|His|Val|Thr|Glu|Met|Glu|Ser|Ser|Val|Tyr|Gln|
| |14300| | | |14305| | | |14310| | | | | |
|Pro|Thr|Ser|Ser|Ser|Thr|Gln|His|Phe|Tyr|Leu|Asn|Phe|Thr|
| |14315| | | |14320| | | |14325| | | | | |
|Ile|Thr|Asn|Leu|Pro|Tyr|Ser|Gln|Asp|Lys|Ala|Gln|Pro|Gly|Thr|
| |14330| | | |14335| | | |14340| | | | | |
|Thr|Asn|Tyr|Gln|Arg|Asn|Lys|Arg|Asn|Ile|Glu|Asp|Ala|Leu|Asn|
| |14345| | | |14350| | | |14355| | | | | |
|Gln|Leu|Phe|Arg|Asn|Ser|Ser|Ile|Lys|Ser|Tyr|Phe|Ser|Asp|Cys|
| |14360| | | |14365| | | |14370| | | | | |
|Gln|Val|Ser|Thr|Phe|Arg|Ser|Val|Pro|Asn|Arg|His|His|Thr|Gly|
| |14375| | | |14380| | | |14385| | | | | |
|Val|Asp|Ser|Leu|Cys|Asn|Phe|Ser|Pro|Leu|Ala|Arg|Arg|Val|Asp|
| |14390| | | |14395| | | |14400| | | | | |
|Arg|Val|Ala|Ile|Tyr|Glu|Glu|Phe|Leu|Arg|Met|Thr|Arg|Asn|Gly|
| |14405| | | |14410| | | |14415| | | | | |
|Thr|Gln|Leu|Gln|Asn|Phe|Thr|Leu|Asp|Arg|Ser|Ser|Val|Leu|Val|
| |14420| | | |14425| | | |14430| | | | | |
|Asp|Gly|Tyr|Ser|Pro|Asn|Arg|Asn|Glu|Pro|Leu|Thr|Gly|Asn|Ser|
| |14435| | | |14440| | | |14445| | | | | |
|Asp|Leu|Pro|Phe|Trp|Ala|Val|Ile|Leu|Ile|Gly|Leu|Ala|Gly|Leu|

```
                14450              14455              14460

Leu Gly    Val Ile Thr Cys Leu    Ile Cys Gly Val Leu    Val Thr Thr
        14465              14470                     14475

Arg Arg    Arg Lys Lys Glu Gly    Glu Tyr Asn Val Gln    Gln Gln Cys
        14480              14485                     14490

Pro Gly    Tyr Tyr Gln Ser His    Leu Asp Leu Glu Asp    Leu Gln
        14495              14500                     14505

<210> SEQ ID NO 7
<211> LENGTH: 267
<212> TYPE: PRT
<213> ORGANISM: Homo sapiens

<400> SEQUENCE: 7

Met Met Ser Ser Lys Pro Thr Ser His Ala Glu Val Asn Glu Thr Ile
1               5                   10                  15

Pro Asn Pro Tyr Pro Pro Ser Ser Phe Met Ala Pro Gly Phe Gln Gln
            20                  25                  30

Pro Leu Gly Ser Ile Asn Leu Glu Asn Gln Ala Gln Gly Ala Gln Arg
        35                  40                  45

Ala Gln Pro Tyr Gly Ile Thr Ser Pro Gly Ile Phe Ala Ser Ser Gln
    50                  55                  60

Pro Gly Gln Gly Asn Ile Gln Met Ile Asn Pro Ser Val Gly Thr Ala
65                  70                  75                  80

Val Met Asn Phe Lys Glu Glu Ala Lys Ala Leu Gly Val Ile Gln Ile
                85                  90                  95

Met Val Gly Leu Met His Ile Gly Phe Gly Ile Val Leu Cys Leu Ile
            100                 105                 110

Ser Phe Ser Phe Arg Glu Val Leu Gly Phe Ala Ser Thr Ala Val Ile
        115                 120                 125

Gly Gly Tyr Pro Phe Trp Gly Gly Leu Ser Phe Ile Ile Ser Gly Ser
    130                 135                 140

Leu Ser Val Ser Ala Ser Lys Glu Leu Ser Arg Cys Leu Val Lys Gly
145                 150                 155                 160

Ser Leu Gly Met Asn Ile Val Ser Ser Ile Leu Ala Phe Ile Gly Val
                165                 170                 175

Ile Leu Leu Leu Val Asp Met Cys Ile Asn Gly Val Ala Gly Gln Asp
            180                 185                 190

Tyr Trp Ala Val Leu Ser Gly Lys Gly Ile Ser Ala Thr Leu Met Ile
        195                 200                 205

Phe Ser Leu Leu Glu Phe Phe Val Ala Cys Ala Thr Ala His Phe Ala
    210                 215                 220

Asn Gln Ala Asn Thr Thr Thr Asn Met Ser Val Leu Ile Pro Asn
225                 230                 235                 240

Met Tyr Glu Ser Asn Pro Val Thr Pro Ala Ser Ser Ala Pro Pro
                245                 250                 255

Arg Cys Asn Asn Tyr Ser Ala Asn Ala Pro Lys
            260                 265

<210> SEQ ID NO 8
<211> LENGTH: 535
<212> TYPE: PRT
<213> ORGANISM: Homo sapiens

<400> SEQUENCE: 8

Met Leu Gly Pro Cys Met Leu Leu Leu Leu Leu Leu Leu Gly Leu Arg
```

-continued

```
1               5                   10                  15
Leu Gln Leu Ser Leu Gly Ile Ile Pro Val Glu Glu Asn Pro Asp
            20                  25                  30
Phe Trp Asn Arg Glu Ala Ala Glu Ala Leu Gly Ala Ala Lys Lys Leu
            35                  40                  45
Gln Pro Ala Gln Thr Ala Ala Lys Asn Leu Ile Ile Phe Leu Gly Asp
            50                  55                  60
Gly Met Gly Val Ser Thr Val Thr Ala Ala Arg Ile Leu Lys Gly Gln
65                  70                  75                  80
Lys Lys Asp Lys Leu Gly Pro Glu Ile Pro Leu Ala Met Asp Arg Phe
                85                  90                  95
Pro Tyr Val Ala Leu Ser Lys Thr Tyr Asn Val Asp Lys His Val Pro
                100                 105                 110
Asp Ser Gly Ala Thr Ala Thr Ala Tyr Leu Cys Gly Val Lys Gly Asn
                115                 120                 125
Phe Gln Thr Ile Gly Leu Ser Ala Ala Ala Arg Phe Asn Gln Cys Asn
            130                 135                 140
Thr Thr Arg Gly Asn Glu Val Ile Ser Val Met Asn Arg Ala Lys Lys
145                 150                 155                 160
Ala Gly Lys Ser Val Gly Val Val Thr Thr Thr Arg Val Gln His Ala
                165                 170                 175
Ser Pro Ala Gly Thr Tyr Ala His Thr Val Asn Arg Asn Trp Tyr Ser
                180                 185                 190
Asp Ala Asp Val Pro Ala Ser Ala Arg Gln Glu Gly Cys Gln Asp Ile
            195                 200                 205
Ala Thr Gln Leu Ile Ser Asn Met Asp Ile Asp Val Ile Leu Gly Gly
210                 215                 220
Gly Arg Lys Tyr Met Phe Arg Met Gly Thr Pro Asp Pro Glu Tyr Pro
225                 230                 235                 240
Asp Asp Tyr Ser Gln Gly Gly Thr Arg Leu Asp Gly Lys Asn Leu Val
                245                 250                 255
Gln Glu Trp Leu Ala Lys Arg Gln Gly Ala Arg Tyr Val Trp Asn Arg
                260                 265                 270
Thr Glu Leu Met Gln Ala Ser Leu Asp Pro Ser Val Thr His Leu Met
            275                 280                 285
Gly Leu Phe Glu Pro Gly Asp Met Lys Tyr Glu Ile His Arg Asp Ser
            290                 295                 300
Thr Leu Asp Pro Ser Leu Met Glu Met Thr Glu Ala Ala Leu Arg Leu
305                 310                 315                 320
Leu Ser Arg Asn Pro Arg Gly Phe Phe Leu Phe Val Glu Gly Gly Arg
                325                 330                 335
Ile Asp His Gly His His Glu Ser Arg Ala Tyr Arg Ala Leu Thr Glu
            340                 345                 350
Thr Ile Met Phe Asp Asp Ala Ile Glu Arg Ala Gly Gln Leu Thr Ser
            355                 360                 365
Glu Glu Asp Thr Leu Ser Leu Val Thr Ala Asp His Ser His Val Phe
            370                 375                 380
Ser Phe Gly Gly Tyr Pro Leu Arg Gly Ser Ser Ile Phe Gly Leu Ala
385                 390                 395                 400
Pro Gly Lys Ala Arg Asp Arg Lys Ala Tyr Thr Val Leu Leu Tyr Gly
                405                 410                 415
Asn Gly Pro Gly Tyr Val Leu Lys Asp Gly Ala Arg Pro Asp Val Thr
            420                 425                 430
```

```
Glu Ser Glu Ser Gly Ser Pro Glu Tyr Arg Gln Gln Ser Ala Val Pro
            435                 440                 445

Leu Asp Glu Glu Thr His Ala Gly Glu Asp Val Ala Val Phe Ala Arg
        450                 455                 460

Gly Pro Gln Ala His Leu Val His Gly Val Gln Glu Gln Thr Phe Ile
465                 470                 475                 480

Ala His Val Met Ala Phe Ala Ala Cys Leu Glu Pro Tyr Thr Ala Cys
                485                 490                 495

Asp Leu Ala Pro Pro Ala Gly Thr Thr Asp Ala Ala His Pro Gly Arg
            500                 505                 510

Ser Val Val Pro Ala Leu Leu Pro Leu Leu Ala Gly Thr Leu Leu Leu
        515                 520                 525

Leu Glu Thr Ala Thr Ala Pro
530                 535

<210> SEQ ID NO 9
<211> LENGTH: 520
<212> TYPE: PRT
<213> ORGANISM: Homo sapiens

<400> SEQUENCE: 9

Met Glu Phe His Asn Gly Gly His Val Ser Gly Ile Gly Gly Phe Leu
1               5                   10                  15

Val Ser Leu Thr Ser Arg Met Lys Pro His Thr Leu Ala Val Thr Pro
            20                  25                  30

Ala Leu Ile Phe Ala Ile Thr Val Ala Thr Ile Gly Ser Phe Gln Phe
        35                  40                  45

Gly Tyr Asn Thr Gly Val Ile Asn Ala Pro Glu Thr Ile Ile Lys Glu
50                  55                  60

Phe Ile Asn Lys Thr Leu Thr Asp Lys Ala Asn Ala Pro Pro Ser Glu
65                  70                  75                  80

Val Leu Leu Thr Asn Leu Trp Ser Leu Ser Val Ala Ile Phe Ser Val
                85                  90                  95

Gly Gly Met Ile Gly Ser Phe Ser Val Gly Leu Phe Val Asn Arg Phe
            100                 105                 110

Gly Arg Arg Asn Ser Met Leu Ile Val Asn Leu Leu Ala Ala Thr Gly
        115                 120                 125

Gly Cys Leu Met Gly Leu Cys Lys Ile Ala Glu Ser Val Glu Met Leu
130                 135                 140

Ile Leu Gly Arg Leu Val Ile Gly Leu Phe Cys Gly Leu Cys Thr Gly
145                 150                 155                 160

Phe Val Pro Met Tyr Ile Gly Glu Ile Ser Pro Thr Ala Leu Arg Gly
                165                 170                 175

Ala Phe Gly Thr Leu Asn Gln Leu Gly Ile Val Ile Gly Ile Leu Val
            180                 185                 190

Ala Gln Ile Phe Gly Leu Glu Leu Ile Leu Gly Ser Glu Glu Leu Trp
        195                 200                 205

Pro Val Leu Leu Gly Phe Thr Ile Leu Pro Ala Ile Leu Gln Ser Ala
210                 215                 220

Ala Leu Pro Cys Cys Pro Glu Ser Pro Arg Phe Leu Leu Ile Asn Arg
225                 230                 235                 240

Lys Lys Glu Glu Asn Ala Thr Arg Ile Leu Gln Arg Leu Trp Gly Thr
                245                 250                 255

Gln Asp Val Ser Gln Asp Ile Gln Glu Met Lys Asp Glu Ser Ala Arg
```

```
                    260                 265                 270
Met Ser Gln Glu Lys Gln Val Thr Val Leu Glu Leu Phe Arg Val Ser
            275                 280                 285

Ser Tyr Arg Gln Pro Ile Ile Ile Ser Ile Val Leu Gln Leu Ser Gln
        290                 295                 300

Gln Leu Ser Gly Ile Asn Ala Val Phe Tyr Tyr Ser Thr Gly Ile Phe
305                 310                 315                 320

Lys Asp Ala Gly Val Gln Gln Pro Ile Tyr Ala Thr Ile Ser Ala Gly
                325                 330                 335

Val Val Asn Thr Ile Phe Thr Leu Leu Ser Leu Phe Leu Val Glu Arg
            340                 345                 350

Ala Gly Arg Arg Thr Leu His Met Ile Gly Leu Gly Gly Met Ala Phe
        355                 360                 365

Cys Ser Thr Leu Met Thr Val Ser Leu Leu Lys Asn His Tyr Asn
370                 375                 380

Gly Met Ser Phe Val Cys Ile Gly Ala Ile Leu Val Phe Val Ala Cys
385                 390                 395                 400

Phe Glu Ile Gly Pro Gly Pro Ile Pro Trp Phe Ile Val Ala Glu Leu
                405                 410                 415

Phe Ser Gln Gly Pro Arg Pro Ala Ala Met Ala Val Ala Gly Cys Ser
            420                 425                 430

Asn Trp Thr Ser Asn Phe Leu Val Gly Leu Leu Phe Pro Ser Ala Ala
        435                 440                 445

Tyr Tyr Leu Gly Ala Tyr Val Phe Ile Ile Phe Thr Gly Phe Leu Ile
    450                 455                 460

Thr Phe Leu Ala Phe Thr Phe Phe Lys Val Pro Glu Thr Arg Gly Arg
465                 470                 475                 480

Thr Phe Glu Asp Ile Thr Arg Ala Phe Glu Gly Gln Ala His Gly Ala
                485                 490                 495

Asp Arg Ser Gly Lys Asp Gly Val Met Gly Met Asn Ser Ile Glu Pro
            500                 505                 510

Ala Lys Glu Thr Thr Thr Asn Val
        515                 520

<210> SEQ ID NO 10
<211> LENGTH: 221
<212> TYPE: PRT
<213> ORGANISM: Homo sapiens

<400> SEQUENCE: 10

Met Leu Thr Leu Glu Asp Lys Asp Met Lys Gly Phe Ser Trp Ala Ile
1               5                   10                  15

Val Pro Ala Leu Thr Ser Leu Gly Tyr Leu Ile Ile Leu Val Val Ser
            20                  25                  30

Ile Phe Pro Phe Trp Val Arg Leu Thr Asn Glu Glu Ser His Glu Val
        35                  40                  45

Phe Phe Ser Gly Leu Phe Glu Asn Cys Phe Asn Ala Lys Cys Trp Lys
    50                  55                  60

Pro Arg Pro Leu Ser Ile Tyr Ile Ile Leu Gly Arg Val Phe Leu Leu
65                  70                  75                  80

Ser Ala Val Phe Leu Ala Phe Val Thr Thr Phe Ile Met Met Pro Phe
                85                  90                  95

Ala Ser Glu Phe Phe Pro Arg Thr Trp Lys Gln Asn Phe Val Leu Ala
            100                 105                 110
```

```
Cys Ile Ser Phe Phe Thr Gly Ala Cys Ala Phe Leu Ala Leu Val Leu
            115                 120                 125

His Ala Leu Glu Ile Lys Ala Leu Arg Met Lys Leu Gly Pro Leu Gln
130                 135                 140

Phe Ser Val Leu Trp Pro Tyr Val Leu Gly Phe Gly Ile Phe Leu
145                 150                 155                 160

Phe Ile Val Ala Gly Thr Ile Cys Leu Ile Gln Glu Met Val Cys Pro
                165                 170                 175

Cys Trp His Leu Leu Ser Thr Ser Gln Ser Met Glu Glu Asp His Gly
                180                 185                 190

Ser Leu Tyr Leu Asp Asn Leu Glu Ser Leu Gly Gly Glu Pro Ser Ser
            195                 200                 205

Val Gln Lys Glu Thr Gln Val Thr Ala Glu Thr Val Ile
210                 215                 220

<210> SEQ ID NO 11
<211> LENGTH: 538
<212> TYPE: PRT
<213> ORGANISM: Homo sapiens

<400> SEQUENCE: 11

Met Gly Leu Leu Leu Val Leu Ile Leu Thr Pro Ser Leu Ala Ala
1               5                   10                  15

Tyr Arg His Pro Asp Phe Pro Leu Leu Glu Lys Ala Gln Gln Leu Leu
                20                  25                  30

Gln Ser Thr Gly Ser Pro Tyr Ser Thr Asn Cys Trp Leu Cys Thr Ser
            35                  40                  45

Ser Ser Thr Glu Thr Pro Gly Thr Ala Tyr Pro Ala Ser Pro Arg Glu
50                  55                  60

Trp Thr Ser Ile Glu Ala Glu Leu His Ile Ser Tyr Arg Trp Asp Pro
65                  70                  75                  80

Asn Leu Lys Gly Leu Met Arg Pro Ala Asn Ser Leu Leu Ser Thr Val
                85                  90                  95

Lys Gln Asp Phe Pro Asp Ile Arg Gln Lys Pro Pro Ile Phe Gly Pro
            100                 105                 110

Ile Phe Thr Asn Ile Asn Leu Met Gly Ile Ala Pro Ile Cys Val Met
            115                 120                 125

Ala Lys Arg Lys Asn Gly Thr Asn Val Gly Thr Leu Pro Ser Thr Val
130                 135                 140

Cys Asn Val Thr Phe Thr Val Asp Ser Asn Gln Gln Thr Tyr Gln Thr
145                 150                 155                 160

Tyr Thr His Asn Gln Phe Arg His Gln Pro Arg Phe Pro Lys Pro Pro
                165                 170                 175

Asn Ile Thr Phe Pro Gln Gly Thr Leu Leu Asp Lys Ser Ser Arg Phe
            180                 185                 190

Cys Gln Gly Arg Pro Ser Ser Cys Ser Thr Arg Asn Phe Trp Phe Arg
        195                 200                 205

Pro Ala Asp Tyr Asn Gln Cys Leu Gln Ile Ser Asn Leu Ser Ser Thr
210                 215                 220

Ala Glu Trp Val Leu Leu Asp Gln Thr Arg Asn Ser Leu Phe Trp Glu
225                 230                 235                 240

Asn Lys Thr Lys Gly Ala Asn Gln Ser Gln Thr Pro Cys Val Gln Val
                245                 250                 255

Leu Ala Gly Met Thr Ile Ala Thr Ser Tyr Leu Gly Ile Ser Ala Val
            260                 265                 270
```

```
Ser Glu Phe Phe Gly Thr Ser Leu Thr Pro Leu Phe His Phe His Ile
            275                 280                 285

Ser Thr Cys Leu Lys Thr Gln Gly Ala Phe Tyr Ile Cys Gly Gln Ser
    290                 295                 300

Ile His Gln Cys Leu Pro Ser Asn Trp Thr Gly Thr Cys Thr Ile Gly
305                 310                 315                 320

Tyr Val Thr Pro Asp Ile Phe Ile Ala Pro Gly Asn Leu Ser Leu Pro
                325                 330                 335

Ile Pro Ile Tyr Gly Asn Ser Pro Leu Pro Arg Val Arg Arg Ala Ile
            340                 345                 350

His Phe Ile Pro Leu Leu Ala Gly Leu Gly Ile Leu Ala Gly Thr Gly
        355                 360                 365

Thr Gly Ile Ala Gly Ile Thr Lys Ala Ser Leu Thr Tyr Ser Gln Leu
    370                 375                 380

Ser Lys Glu Ile Ala Asn Asn Ile Asp Thr Met Ala Lys Ala Leu Thr
385                 390                 395                 400

Thr Met Gln Glu Gln Ile Asp Ser Leu Ala Ala Val Val Leu Gln Asn
                405                 410                 415

Arg Arg Gly Leu Asp Met Leu Thr Ala Ala Gln Gly Gly Ile Cys Leu
            420                 425                 430

Ala Leu Asp Glu Lys Cys Cys Phe Trp Val Asn Gln Ser Gly Lys Val
        435                 440                 445

Gln Asp Asn Ile Arg Gln Leu Leu Asn Gln Ala Ser Ser Leu Arg Glu
    450                 455                 460

Arg Ala Thr Gln Gly Trp Leu Asn Trp Glu Gly Thr Trp Lys Trp Phe
465                 470                 475                 480

Ser Trp Val Leu Pro Leu Thr Gly Pro Leu Val Ser Leu Leu Leu Leu
                485                 490                 495

Leu Leu Phe Gly Pro Cys Leu Leu Asn Leu Ile Thr Gln Phe Val Ser
            500                 505                 510

Ser Arg Leu Gln Ala Ile Lys Leu Gln Thr Asn Leu Ser Ala Gly Arg
        515                 520                 525

His Pro Arg Asn Ile Gln Glu Ser Pro Phe
    530                 535

<210> SEQ ID NO 12
<211> LENGTH: 1017
<212> TYPE: PRT
<213> ORGANISM: Homo sapiens

<400> SEQUENCE: 12

Met Val Phe Ser Val Arg Gln Cys Gly His Val Gly Arg Thr Glu Glu
1               5                   10                  15

Val Leu Leu Thr Phe Lys Ile Phe Leu Val Ile Cys Leu His Val
            20                  25                  30

Val Leu Val Thr Ser Leu Glu Glu Asp Thr Asp Asn Ser Ser Leu Ser
        35                  40                  45

Pro Pro Pro Ala Lys Leu Ser Val Val Ser Phe Ala Pro Ser Ser Asn
    50                  55                  60

Gly Thr Pro Glu Val Glu Thr Thr Ser Leu Asn Asp Val Thr Leu Ser
65                  70                  75                  80

Leu Leu Pro Ser Asn Glu Thr Glu Lys Thr Lys Ile Thr Ile Val Lys
                85                  90                  95

Thr Phe Asn Ala Ser Gly Val Lys Pro Gln Arg Asn Ile Cys Asn Leu
```

```
            100                 105                 110
Ser Ser Ile Cys Asn Asp Ser Ala Phe Phe Arg Gly Glu Ile Met Phe
            115                 120                 125
Gln Tyr Asp Lys Glu Ser Thr Val Pro Gln Asn Gln His Ile Thr Asn
            130                 135                 140
Gly Thr Leu Thr Gly Val Leu Ser Leu Ser Glu Leu Lys Arg Ser Glu
145                 150                 155                 160
Leu Asn Lys Thr Leu Gln Thr Leu Ser Glu Thr Tyr Phe Ile Met Cys
                    165                 170                 175
Ala Thr Ala Glu Ala Gln Ser Thr Leu Asn Cys Thr Phe Thr Ile Lys
                    180                 185                 190
Leu Asn Asn Thr Met Asn Ala Cys Ala Val Ile Ala Ala Leu Glu Arg
                    195                 200                 205
Val Lys Ile Arg Pro Met Glu His Cys Cys Ser Val Arg Ile Pro
210                 215                 220
Cys Pro Ser Ser Pro Glu Glu Leu Glu Lys Leu Gln Cys Asp Leu Gln
225                 230                 235                 240
Asp Pro Ile Val Cys Leu Ala Asp His Pro Arg Gly Pro Pro Phe Ser
                    245                 250                 255
Ser Ser Gln Ser Ile Pro Val Val Pro Arg Ala Thr Val Leu Ser Gln
                    260                 265                 270
Val Pro Lys Ala Thr Ser Phe Ala Glu Pro Pro Asp Tyr Ser Pro Val
                    275                 280                 285
Thr His Asn Val Pro Ser Pro Ile Gly Glu Ile Gln Pro Leu Ser Pro
            290                 295                 300
Gln Pro Ser Ala Pro Ile Ala Ser Ser Pro Ala Ile Asp Met Pro Pro
305                 310                 315                 320
Gln Ser Glu Thr Ile Ser Ser Pro Met Pro Gln Thr His Val Ser Gly
                    325                 330                 335
Thr Pro Pro Pro Val Lys Ala Ser Phe Ser Ser Pro Thr Val Ser Ala
                    340                 345                 350
Pro Ala Asn Val Asn Thr Thr Ser Ala Pro Pro Val Gln Thr Asp Ile
            355                 360                 365
Val Asn Thr Ser Ser Ile Ser Asp Leu Glu Asn Gln Val Leu Gln Met
            370                 375                 380
Glu Lys Ala Leu Ser Leu Gly Ser Leu Glu Pro Asn Leu Ala Gly Glu
385                 390                 395                 400
Met Ile Asn Gln Val Ser Arg Leu Leu His Ser Pro Pro Asp Met Leu
                    405                 410                 415
Ala Pro Leu Ala Gln Arg Leu Leu Lys Val Val Asp Asp Ile Gly Leu
                    420                 425                 430
Gln Leu Asn Phe Ser Asn Thr Ile Ser Leu Thr Ser Pro Ser Leu
                    435                 440                 445
Ala Leu Ala Val Ile Arg Val Asn Ala Ser Ser Phe Asn Thr Thr Thr
            450                 455                 460
Phe Val Ala Gln Asp Pro Ala Asn Leu Gln Val Ser Leu Glu Thr Gln
465                 470                 475                 480
Ala Pro Glu Asn Ser Ile Gly Thr Ile Thr Leu Pro Ser Leu Met
                    485                 490                 495
Asn Asn Leu Pro Ala His Asp Met Glu Leu Ala Ser Arg Val Gln Phe
            500                 505                 510
Asn Phe Phe Glu Thr Pro Ala Leu Phe Gln Asp Pro Ser Leu Glu Asn
            515                 520                 525
```

```
Leu Ser Leu Ile Ser Tyr Val Ile Ser Ser Val Ala Asn Leu Thr
        530                 535                 540
Val Arg Asn Leu Thr Arg Asn Val Thr Val Thr Leu Lys His Ile Asn
545                 550                 555                 560
Pro Ser Gln Asp Glu Leu Thr Val Arg Cys Val Phe Trp Asp Leu Gly
                565                 570                 575
Arg Asn Gly Gly Arg Gly Gly Trp Ser Asp Asn Gly Cys Ser Val Lys
            580                 585                 590
Asp Arg Arg Leu Asn Glu Thr Ile Cys Thr Cys Ser His Leu Thr Ser
        595                 600                 605
Phe Gly Val Leu Leu Asp Leu Ser Arg Thr Ser Val Leu Pro Ala Gln
        610                 615                 620
Met Met Ala Leu Thr Phe Ile Thr Tyr Ile Gly Cys Gly Leu Ser Ser
625                 630                 635                 640
Ile Phe Leu Ser Val Thr Leu Val Thr Tyr Ile Ala Phe Glu Lys Ile
                645                 650                 655
Arg Arg Asp Tyr Pro Ser Lys Ile Leu Ile Gln Leu Cys Ala Ala Leu
                660                 665                 670
Leu Leu Leu Asn Leu Val Phe Leu Leu Asp Ser Trp Ile Ala Leu Tyr
        675                 680                 685
Lys Met Gln Gly Leu Cys Ile Ser Val Ala Val Phe Leu His Tyr Phe
690                 695                 700
Leu Leu Val Ser Phe Thr Trp Met Gly Leu Glu Ala Phe His Met Tyr
705                 710                 715                 720
Leu Ala Leu Val Lys Val Phe Asn Thr Tyr Ile Arg Lys Tyr Ile Leu
                725                 730                 735
Lys Phe Cys Ile Val Gly Trp Gly Val Pro Ala Val Val Val Thr Ile
                740                 745                 750
Ile Leu Thr Ile Ser Pro Asp Asn Tyr Gly Leu Gly Ser Tyr Gly Lys
            755                 760                 765
Phe Pro Asn Gly Ser Pro Asp Asp Phe Cys Trp Ile Asn Asn Asn Ala
770                 775                 780
Val Phe Tyr Ile Thr Val Val Gly Tyr Phe Cys Val Ile Phe Leu Leu
785                 790                 795                 800
Asn Val Ser Met Phe Ile Val Val Leu Val Gln Leu Cys Arg Ile Lys
                805                 810                 815
Lys Lys Lys Gln Leu Gly Ala Gln Arg Lys Thr Ser Ile Gln Asp Leu
            820                 825                 830
Arg Ser Ile Ala Gly Leu Thr Phe Leu Leu Gly Ile Thr Trp Gly Phe
        835                 840                 845
Ala Phe Phe Ala Trp Gly Pro Val Asn Val Thr Phe Met Tyr Leu Phe
        850                 855                 860
Ala Ile Phe Asn Thr Leu Gln Gly Phe Phe Ile Phe Ile Phe Tyr Cys
865                 870                 875                 880
Val Ala Lys Glu Asn Val Arg Lys Gln Trp Arg Arg Tyr Leu Cys Cys
                885                 890                 895
Gly Lys Leu Arg Leu Ala Glu Asn Ser Asp Trp Ser Lys Thr Ala Thr
            900                 905                 910
Asn Gly Leu Lys Lys Gln Thr Val Asn Gln Gly Val Ser Ser Ser Ser
        915                 920                 925
Asn Ser Leu Gln Ser Ser Asn Ser Thr Asn Ser Thr Thr Leu Leu
        930                 935                 940
```

-continued

```
Val Asn Asn Asp Cys Ser Val His Ala Ser Gly Asn Ala Ser
945                 950                 955                 960

Thr Glu Arg Asn Gly Val Ser Phe Ser Val Gln Asn Gly Asp Val Cys
                965                 970                 975

Leu His Asp Phe Thr Gly Lys Gln His Met Phe Asn Glu Lys Glu Asp
                980                 985                 990

Ser Cys Asn Gly Lys Gly Arg Met Ala Leu Arg Arg Thr Ser Lys Arg
            995                1000                1005

Gly Ser Leu His Phe Ile Glu Gln Met
        1010                1015

<210> SEQ ID NO 13
<211> LENGTH: 775
<212> TYPE: PRT
<213> ORGANISM: Homo sapiens

<400> SEQUENCE: 13

Met Glu Pro Pro Tyr Ser Leu Thr Ala His Tyr Asp Glu Phe Gln Glu
1                   5                  10                  15

Val Lys Tyr Val Ser Arg Cys Gly Ala Gly Gly Ala Arg Gly Ala Ser
                20                  25                  30

Leu Pro Pro Gly Phe Pro Leu Gly Ala Ala Arg Ser Ala Thr Gly Ala
            35                  40                  45

Arg Ser Gly Leu Pro Arg Trp Asn Arg Arg Glu Val Cys Leu Leu Ser
50                  55                  60

Gly Leu Val Phe Ala Ala Gly Leu Cys Ala Ile Leu Ala Ala Met Leu
65                  70                  75                  80

Ala Leu Lys Tyr Leu Gly Pro Val Ala Ala Gly Gly Ala Cys Pro
                85                  90                  95

Glu Gly Cys Pro Glu Arg Lys Ala Phe Ala Arg Ala Ala Arg Phe Leu
            100                 105                 110

Ala Ala Asn Leu Asp Ala Ser Ile Asp Pro Cys Gln Asp Phe Tyr Ser
            115                 120                 125

Phe Ala Cys Gly Gly Trp Leu Arg Arg His Ala Ile Pro Asp Asp Lys
130                 135                 140

Leu Thr Tyr Gly Thr Ile Ala Ala Ile Gly Glu Gln Asn Glu Glu Arg
145                 150                 155                 160

Leu Arg Arg Leu Leu Ala Arg Pro Gly Gly Pro Gly Gly Ala Ala
                165                 170                 175

Gln Arg Lys Val Arg Ala Phe Phe Arg Ser Cys Leu Asp Met Arg Glu
            180                 185                 190

Ile Glu Arg Leu Gly Pro Arg Pro Met Leu Glu Val Ile Glu Asp Cys
            195                 200                 205

Gly Gly Trp Asp Leu Gly Gly Ala Glu Glu Arg Pro Gly Val Ala Ala
        210                 215                 220

Arg Trp Asp Leu Asn Arg Leu Leu Tyr Lys Ala Gln Gly Val Tyr Ser
225                 230                 235                 240

Ala Ala Ala Leu Phe Ser Leu Thr Val Ser Leu Asp Asp Arg Asn Ser
                245                 250                 255

Ser Arg Tyr Val Ile Arg Ile Asp Gln Asp Gly Leu Thr Leu Pro Glu
            260                 265                 270

Arg Thr Leu Tyr Leu Ala Gln Asp Glu Asp Ser Glu Lys Ile Leu Ala
            275                 280                 285

Ala Tyr Arg Val Phe Met Glu Arg Val Leu Ser Leu Leu Gly Ala Asp
            290                 295                 300
```

-continued

```
Ala Val Glu Gln Lys Ala Gln Glu Ile Leu Gln Val Glu Gln Gln Leu
305                 310                 315                 320

Ala Asn Ile Thr Val Ser Glu His Asp Asp Leu Arg Arg Asp Val Ser
                325                 330                 335

Ser Met Tyr Asn Lys Val Thr Leu Gly Gln Leu Gln Lys Ile Thr Pro
            340                 345                 350

His Leu Arg Trp Lys Trp Leu Leu Asp Gln Ile Phe Gln Glu Asp Phe
        355                 360                 365

Ser Glu Glu Glu Val Val Leu Leu Ala Thr Asp Tyr Met Gln Gln
370                 375                 380

Val Ser Gln Leu Ile Arg Ser Thr Pro His Arg Val Leu His Asn Tyr
385                 390                 395                 400

Leu Val Trp Arg Val Val Val Leu Ser Glu His Leu Ser Pro Pro
                405                 410                 415

Phe Arg Glu Ala Leu His Glu Leu Ala Gln Glu Met Glu Gly Ser Asp
            420                 425                 430

Lys Pro Gln Glu Leu Ala Arg Val Cys Leu Gly Gln Ala Asn Arg His
        435                 440                 445

Phe Gly Met Ala Leu Gly Ala Leu Phe Val His Glu His Phe Ser Ala
450                 455                 460

Ala Ser Lys Ala Lys Val Gln Gln Leu Val Glu Asp Ile Lys Tyr Ile
465                 470                 475                 480

Leu Gly Gln Arg Leu Glu Glu Leu Asp Trp Met Asp Ala Glu Thr Arg
                485                 490                 495

Ala Ala Ala Arg Ala Lys Leu Gln Tyr Met Met Val Met Val Gly Tyr
            500                 505                 510

Pro Asp Phe Leu Leu Lys Pro Asp Ala Val Asp Lys Glu Tyr Glu Phe
        515                 520                 525

Glu Val His Glu Lys Thr Tyr Phe Lys Asn Ile Leu Asn Ser Ile Arg
530                 535                 540

Phe Ser Ile Gln Leu Ser Val Lys Lys Ile Arg Gln Glu Val Asp Lys
545                 550                 555                 560

Ser Thr Trp Leu Leu Pro Pro Gln Ala Leu Asn Ala Tyr Tyr Leu Pro
                565                 570                 575

Asn Lys Asn Gln Met Val Phe Pro Ala Gly Ile Leu Gln Pro Thr Leu
            580                 585                 590

Tyr Asp Pro Asp Phe Pro Gln Ser Leu Asn Tyr Gly Gly Ile Gly Thr
        595                 600                 605

Ile Ile Gly His Glu Leu Thr His Gly Tyr Asp Asp Trp Gly Gly Gln
610                 615                 620

Tyr Asp Arg Ser Gly Asn Leu Leu His Trp Trp Thr Glu Ala Ser Tyr
625                 630                 635                 640

Ser Arg Phe Leu Arg Lys Ala Glu Cys Ile Val Arg Leu Tyr Asp Asn
                645                 650                 655

Phe Thr Val Tyr Asn Gln Arg Val Asn Gly Lys His Thr Leu Gly Glu
            660                 665                 670

Asn Ile Ala Asp Met Gly Gly Leu Lys Leu Ala Tyr His Ala Tyr Gln
        675                 680                 685

Lys Trp Val Arg Glu His Gly Pro Glu His Pro Leu Pro Arg Leu Lys
690                 695                 700

Tyr Thr His Asp Gln Leu Phe Phe Ile Ala Phe Ala Gln Asn Trp Cys
705                 710                 715                 720
```

-continued

```
Ile Lys Arg Arg Ser Gln Ser Ile Tyr Leu Gln Val Leu Thr Asp Lys
                725                 730                 735

His Ala Pro Glu His Tyr Arg Val Leu Gly Ser Val Ser Gln Phe Glu
            740                 745                 750

Glu Phe Gly Arg Ala Phe His Cys Pro Lys Asp Ser Pro Met Asn Pro
        755                 760                 765

Ala His Lys Cys Ser Val Trp
    770                 775

<210> SEQ ID NO 14
<211> LENGTH: 529
<212> TYPE: PRT
<213> ORGANISM: Homo sapiens

<400> SEQUENCE: 14

Met Gly Pro Ser Cys Pro Val Phe Leu Ser Phe Thr Lys Leu Ser Leu
1               5                   10                  15

Trp Trp Leu Leu Leu Thr Pro Ala Gly Gly Glu Glu Ala Lys Arg Pro
                20                  25                  30

Pro Pro Arg Ala Pro Gly Asp Pro Leu Ser Ser Pro Ser Pro Thr Ala
            35                  40                  45

Leu Pro Gln Gly Gly Ser His Thr Glu Thr Glu Asp Arg Leu Phe Lys
        50                  55                  60

His Leu Phe Arg Gly Tyr Asn Arg Trp Ala Arg Pro Val Pro Asn Thr
65                  70                  75                  80

Ser Asp Val Val Ile Val Arg Phe Gly Leu Ser Ile Ala Gln Leu Ile
                85                  90                  95

Asp Val Asp Glu Lys Asn Gln Met Met Thr Thr Asn Val Trp Leu Lys
                100                 105                 110

Gln Glu Trp Ser Asp Tyr Lys Leu Arg Trp Asn Pro Thr Asp Phe Gly
            115                 120                 125

Asn Ile Thr Ser Leu Arg Val Pro Ser Glu Met Ile Trp Ile Pro Asp
        130                 135                 140

Ile Val Leu Tyr Asn Asn Ala Asp Gly Glu Phe Ala Val Thr His Met
145                 150                 155                 160

Thr Lys Ala His Leu Phe Ser Thr Gly Thr Val His Trp Val Pro Pro
                165                 170                 175

Ala Ile Tyr Lys Ser Ser Cys Ser Ile Asp Val Thr Phe Phe Pro Phe
            180                 185                 190

Asp Gln Gln Asn Cys Lys Met Lys Phe Gly Ser Trp Thr Tyr Asp Lys
        195                 200                 205

Ala Lys Ile Asp Leu Glu Gln Met Glu Gln Thr Val Asp Leu Lys Asp
    210                 215                 220

Tyr Trp Glu Ser Gly Glu Trp Ala Ile Val Asn Ala Thr Gly Thr Tyr
225                 230                 235                 240

Asn Ser Lys Lys Tyr Asp Cys Cys Ala Glu Ile Tyr Pro Asp Val Thr
                245                 250                 255

Tyr Ala Phe Val Ile Arg Arg Leu Pro Leu Phe Tyr Thr Ile Asn Leu
            260                 265                 270

Ile Ile Pro Cys Leu Leu Ile Ser Cys Leu Thr Val Leu Val Phe Tyr
        275                 280                 285

Leu Pro Ser Asp Cys Gly Glu Lys Ile Thr Leu Cys Ile Ser Val Leu
    290                 295                 300

Leu Ser Leu Thr Val Phe Leu Leu Leu Ile Thr Glu Ile Ile Pro Ser
305                 310                 315                 320
```

```
Thr Ser Leu Val Ile Pro Leu Ile Gly Glu Tyr Leu Leu Phe Thr Met
            325                 330                 335

Ile Phe Val Thr Leu Ser Ile Val Ile Thr Val Phe Val Leu Asn Val
            340                 345                 350

His His Arg Ser Pro Ser Thr His Thr Met Pro His Trp Val Arg Gly
            355                 360                 365

Ala Leu Leu Gly Cys Val Pro Arg Trp Leu Leu Met Asn Arg Pro Pro
            370                 375                 380

Pro Pro Val Glu Leu Cys His Pro Leu Arg Leu Lys Leu Ser Pro Ser
385                 390                 395                 400

Tyr His Trp Leu Glu Ser Asn Val Asp Ala Glu Arg Glu Val Val
                405                 410                 415

Val Glu Glu Asp Arg Trp Ala Cys Ala Gly His Val Ala Pro Ser
            420                 425                 430

Val Gly Thr Leu Cys Ser His Gly His Leu His Ser Gly Ala Ser Gly
            435                 440                 445

Pro Lys Ala Glu Ala Leu Leu Gln Glu Gly Glu Leu Leu Leu Ser Pro
    450                 455                 460

His Met Gln Lys Ala Leu Glu Gly Val His Tyr Ile Ala Asp His Leu
465                 470                 475                 480

Arg Ser Glu Asp Ala Asp Ser Ser Val Lys Glu Asp Trp Lys Tyr Val
                485                 490                 495

Ala Met Val Ile Asp Arg Ile Phe Leu Trp Leu Phe Ile Val Cys
            500                 505                 510

Phe Leu Gly Thr Ile Gly Leu Phe Leu Pro Pro Phe Leu Ala Gly Met
            515                 520                 525

Ile

<210> SEQ ID NO 15
<211> LENGTH: 537
<212> TYPE: PRT
<213> ORGANISM: Homo sapiens

<400> SEQUENCE: 15

Met Pro His Leu Met Glu Arg Met Val Gly Ser Gly Leu Leu Trp Leu
1               5                   10                  15

Ala Leu Val Ser Cys Ile Leu Thr Gln Ala Ser Ala Val Gln Arg Gly
            20                  25                  30

Tyr Gly Asn Pro Ile Glu Ala Ser Ser Tyr Gly Leu Asp Leu Asp Cys
            35                  40                  45

Gly Ala Pro Gly Thr Pro Glu Ala His Val Cys Phe Asp Pro Cys Gln
    50                  55                  60

Asn Tyr Thr Leu Leu Asp Glu Pro Phe Arg Thr Glu Asn Ser Ala
65                  70                  75                  80

Gly Ser Gln Gly Cys Asp Lys Asn Met Ser Gly Trp Tyr Arg Phe Val
            85                  90                  95

Gly Glu Gly Gly Val Arg Met Ser Glu Thr Cys Val Gln Val His Arg
            100                 105                 110

Cys Gln Thr Asp Ala Pro Met Trp Leu Asn Gly Thr His Pro Ala Leu
            115                 120                 125

Gly Asp Gly Ile Thr Asn His Thr Ala Cys Ala His Trp Ser Gly Asn
    130                 135                 140

Cys Cys Phe Trp Lys Thr Glu Val Leu Val Lys Ala Cys Pro Gly Gly
145                 150                 155                 160
```

Tyr His Val Tyr Arg Leu Glu Gly Thr Pro Trp Cys Asn Leu Arg Tyr
165 170 175

Cys Thr Val Pro Arg Asp Pro Ser Thr Val Glu Asp Lys Cys Glu Lys
180 185 190

Ala Cys Arg Pro Glu Glu Cys Leu Ala Leu Asn Ser Thr Trp Gly
195 200 205

Cys Phe Cys Arg Gln Asp Leu Asn Ser Ser Asp Val His Ser Leu Gln
210 215 220

Pro Gln Leu Asp Cys Gly Pro Arg Glu Ile Lys Val Lys Val Asp Lys
225 230 235 240

Cys Leu Leu Gly Gly Leu Gly Leu Gly Glu Glu Val Ile Ala Tyr Leu
245 250 255

Arg Asp Pro Asn Cys Ser Ser Ile Leu Gln Thr Glu Glu Arg Asn Trp
260 265 270

Val Ser Val Thr Ser Pro Val Gln Ala Ser Ala Cys Arg Asn Ile Leu
275 280 285

Glu Arg Asn Gln Thr His Ala Ile Tyr Lys Asn Thr Leu Ser Leu Val
290 295 300

Asn Asp Phe Ile Ile Arg Asp Thr Ile Leu Asn Ile Asn Phe Gln Cys
305 310 315 320

Ala Tyr Pro Leu Asp Met Lys Val Ser Leu Gln Ala Ala Leu Gln Pro
325 330 335

Ile Val Ser Ser Leu Asn Val Ser Val Asp Gly Asn Gly Glu Phe Ile
340 345 350

Val Arg Met Ala Leu Phe Gln Asp Gln Asn Tyr Thr Asn Pro Tyr Glu
355 360 365

Gly Asp Ala Val Glu Leu Ser Val Glu Ser Val Leu Tyr Val Gly Ala
370 375 380

Ile Leu Glu Gln Gly Asp Thr Ser Arg Phe Asn Leu Val Leu Arg Asn
385 390 395 400

Cys Tyr Ala Thr Pro Thr Glu Asp Lys Ala Asp Leu Val Lys Tyr Phe
405 410 415

Ile Ile Arg Asn Ser Cys Ser Asn Gln Arg Asp Ser Thr Ile His Val
420 425 430

Glu Glu Asn Gly Gln Ser Ser Glu Ser Arg Phe Ser Val Gln Met Phe
435 440 445

Met Phe Ala Gly His Tyr Asp Leu Val Phe Leu His Cys Glu Ile His
450 455 460

Leu Cys Asp Ser Leu Asn Glu Gln Cys Gln Pro Ser Cys Ser Arg Ser
465 470 475 480

Gln Val Arg Ser Glu Val Pro Ala Ile Asp Leu Ala Arg Val Leu Asp
485 490 495

Leu Gly Pro Ile Thr Arg Arg Gly Ala Gln Ser Pro Gly Val Met Asn
500 505 510

Gly Thr Pro Ser Thr Ala Gly Phe Leu Val Ala Trp Pro Met Val Leu
515 520 525

Leu Thr Val Leu Leu Ala Trp Leu Phe
530 535

<210> SEQ ID NO 16
<211> LENGTH: 426
<212> TYPE: PRT
<213> ORGANISM: Homo sapiens

<400> SEQUENCE: 16

```
Met Gly Pro Leu Pro Ala Pro Ser Cys Thr Gln Arg Ile Thr Trp Lys
1               5                   10                  15

Gly Leu Leu Leu Thr Ala Ser Leu Leu Asn Phe Trp Asn Pro Pro Thr
                20                  25                  30

Thr Ala Glu Val Thr Ile Glu Ala Gln Pro Pro Lys Val Ser Glu Gly
            35                  40                  45

Lys Asp Val Leu Leu Val His Asn Leu Pro Gln Asn Leu Pro Gly
    50                  55                  60

Tyr Phe Trp Tyr Lys Gly Glu Met Thr Asp Leu Tyr His Tyr Ile Ile
65                  70                  75                  80

Ser Tyr Ile Val Asp Gly Lys Ile Ile Ile Tyr Gly Pro Ala Tyr Ser
                85                  90                  95

Gly Arg Glu Thr Val Tyr Ser Asn Ala Ser Leu Leu Ile Gln Asn Val
                100                 105                 110

Thr Arg Lys Asp Ala Gly Thr Tyr Thr Leu His Ile Ile Lys Arg Gly
            115                 120                 125

Asp Glu Thr Arg Glu Glu Ile Arg His Phe Thr Phe Thr Leu Tyr Leu
130                 135                 140

Glu Thr Pro Lys Pro Tyr Ile Ser Ser Ser Asn Leu Asn Pro Arg Glu
145                 150                 155                 160

Ala Met Glu Ala Val Arg Leu Ile Cys Asp Pro Glu Thr Leu Asp Ala
                165                 170                 175

Ser Tyr Leu Trp Trp Met Asn Gly Gln Ser Leu Pro Val Thr His Arg
                180                 185                 190

Leu Gln Leu Ser Lys Thr Asn Arg Thr Leu Tyr Leu Phe Gly Val Thr
            195                 200                 205

Lys Tyr Ile Ala Gly Pro Tyr Glu Cys Glu Ile Arg Asn Pro Val Ser
210                 215                 220

Ala Ser Arg Ser Asp Pro Val Thr Leu Asn Leu Leu Pro Lys Leu Pro
225                 230                 235                 240

Ile Pro Tyr Ile Thr Ile Asn Asn Leu Asn Pro Arg Glu Asn Lys Asp
                245                 250                 255

Val Leu Ala Phe Thr Cys Glu Pro Lys Ser Glu Asn Tyr Thr Tyr Ile
                260                 265                 270

Trp Trp Leu Asn Gly Gln Ser Leu Pro Val Ser Pro Gly Val Lys Arg
            275                 280                 285

Pro Ile Glu Asn Arg Ile Leu Ile Leu Pro Ser Val Thr Arg Asn Glu
290                 295                 300

Thr Gly Pro Tyr Gln Cys Glu Ile Arg Asp Arg Tyr Gly Gly Leu Arg
305                 310                 315                 320

Ser Asn Pro Val Ile Leu Asn Val Leu Tyr Gly Pro Asp Leu Pro Arg
                325                 330                 335

Ile Tyr Pro Ser Phe Thr Tyr Tyr Arg Ser Gly Glu Asn Leu Asp Leu
                340                 345                 350

Ser Cys Phe Thr Glu Ser Asn Pro Pro Ala Glu Tyr Phe Trp Thr Ile
            355                 360                 365

Asn Gly Lys Phe Gln Gln Ser Gly Gln Lys Leu Phe Ile Pro Gln Ile
            370                 375                 380

Thr Arg Asn His Ser Gly Leu Tyr Ala Cys Ser Val His Asn Ser Ala
385                 390                 395                 400

Thr Gly Lys Glu Ile Ser Lys Ser Met Thr Val Lys Val Ser Gly Pro
                405                 410                 415
```

-continued

Cys His Gly Asp Leu Thr Glu Ser Gln Ser
            420                 425

<210> SEQ ID NO 17
<211> LENGTH: 328
<212> TYPE: PRT
<213> ORGANISM: Homo sapiens

<400> SEQUENCE: 17

Met Glu Lys Ser Ile Trp Leu Leu Ala Cys Leu Ala Trp Val Leu Pro
1               5                   10                  15

Thr Gly Ser Phe Val Arg Thr Lys Ile Asp Thr Thr Glu Asn Leu Leu
            20                  25                  30

Asn Thr Glu Val His Ser Ser Pro Ala Gln Arg Trp Ser Met Gln Val
        35                  40                  45

Pro Pro Glu Val Ser Ala Glu Ala Gly Asp Ala Ala Val Leu Pro Cys
    50                  55                  60

Thr Phe Thr His Pro His Arg His Tyr Asp Gly Pro Leu Thr Ala Ile
65                  70                  75                  80

Trp Arg Ala Gly Glu Pro Tyr Ala Gly Pro Gln Val Phe Arg Cys Ala
                85                  90                  95

Ala Ala Arg Gly Ser Glu Leu Cys Gln Thr Ala Leu Ser Leu His Gly
            100                 105                 110

Arg Phe Arg Leu Leu Gly Asn Pro Arg Arg Asn Asp Leu Ser Leu Arg
        115                 120                 125

Val Glu Arg Leu Ala Leu Ala Asp Asp Arg Arg Tyr Phe Cys Arg Val
130                 135                 140

Glu Phe Ala Gly Asp Val His Asp Arg Tyr Glu Ser Arg His Gly Val
145                 150                 155                 160

Arg Leu His Val Thr Ala Ala Pro Arg Ile Val Asn Ile Ser Val Leu
                165                 170                 175

Pro Ser Pro Ala His Ala Phe Arg Ala Leu Cys Thr Ala Glu Gly Glu
            180                 185                 190

Pro Pro Pro Ala Leu Ala Trp Ser Gly Pro Ala Leu Gly Asn Ser Leu
        195                 200                 205

Ala Ala Val Arg Ser Pro Arg Glu Gly His Gly His Leu Val Thr Ala
210                 215                 220

Glu Leu Pro Ala Leu Thr His Asp Gly Arg Tyr Thr Cys Thr Ala Ala
225                 230                 235                 240

Asn Ser Leu Gly Arg Ser Glu Ala Ser Val Tyr Leu Phe Arg Phe His
                245                 250                 255

Gly Ala Ser Gly Ala Ser Thr Val Ala Leu Leu Leu Gly Ala Leu Gly
            260                 265                 270

Phe Lys Ala Leu Leu Leu Leu Gly Val Leu Ala Ala Arg Ala Ala Arg
        275                 280                 285

Arg Arg Pro Glu His Leu Asp Thr Pro Asp Thr Pro Pro Arg Ser Gln
290                 295                 300

Ala Gln Glu Ser Asn Tyr Glu Asn Leu Ser Gln Met Asn Pro Arg Ser
305                 310                 315                 320

Pro Pro Ala Thr Met Cys Ser Pro
                325

<210> SEQ ID NO 18
<211> LENGTH: 620
<212> TYPE: PRT

<213> ORGANISM: Homo sapiens

<400> SEQUENCE: 18

```
Met Ser Lys Ser Lys Cys Ser Val Gly Leu Met Ser Val Val Ala
1               5                   10                  15

Pro Ala Lys Glu Pro Asn Ala Val Gly Pro Lys Glu Val Glu Leu Ile
            20                  25                  30

Leu Val Lys Glu Gln Asn Gly Val Gln Leu Thr Ser Ser Thr Leu Thr
            35                  40                  45

Asn Pro Arg Gln Ser Pro Val Glu Ala Gln Asp Arg Glu Thr Trp Gly
        50                  55                  60

Lys Lys Ile Asp Phe Leu Leu Ser Val Ile Gly Phe Ala Val Asp Leu
65                  70                  75                  80

Ala Asn Val Trp Arg Phe Pro Tyr Leu Cys Tyr Lys Asn Gly Gly Gly
                85                  90                  95

Ala Phe Leu Val Pro Tyr Leu Leu Phe Met Val Ile Ala Gly Met Pro
            100                 105                 110

Leu Phe Tyr Met Glu Leu Ala Leu Gly Gln Phe Asn Arg Glu Gly Ala
            115                 120                 125

Ala Gly Val Trp Lys Ile Cys Pro Ile Leu Lys Gly Val Gly Phe Thr
        130                 135                 140

Val Ile Leu Ile Ser Leu Tyr Val Gly Phe Phe Tyr Asn Val Ile Ile
145                 150                 155                 160

Ala Trp Ala Leu His Tyr Leu Phe Ser Ser Phe Thr Thr Glu Leu Pro
                165                 170                 175

Trp Ile His Cys Asn Asn Ser Trp Asn Ser Pro Asn Cys Ser Asp Ala
            180                 185                 190

His Pro Gly Asp Ser Ser Gly Asp Ser Ser Gly Leu Asn Asp Thr Phe
        195                 200                 205

Gly Thr Thr Pro Ala Ala Glu Tyr Phe Glu Arg Gly Val Leu His Leu
210                 215                 220

His Gln Ser His Gly Ile Asp Asp Leu Gly Pro Pro Arg Trp Gln Leu
225                 230                 235                 240

Thr Ala Cys Leu Val Leu Val Ile Val Leu Leu Tyr Phe Ser Leu Trp
                245                 250                 255

Lys Gly Val Lys Thr Ser Gly Lys Val Val Trp Ile Thr Ala Thr Met
            260                 265                 270

Pro Tyr Val Val Leu Thr Ala Leu Leu Leu Arg Gly Val Thr Leu Pro
            275                 280                 285

Gly Ala Ile Asp Gly Ile Arg Ala Tyr Leu Ser Val Asp Phe Tyr Arg
        290                 295                 300

Leu Cys Glu Ala Ser Val Trp Ile Asp Ala Ala Thr Gln Val Cys Phe
305                 310                 315                 320

Ser Leu Gly Val Gly Phe Gly Val Leu Ile Ala Phe Ser Ser Tyr Asn
                325                 330                 335

Lys Phe Thr Asn Asn Cys Tyr Arg Asp Ala Ile Val Thr Thr Ser Ile
            340                 345                 350

Asn Ser Leu Thr Ser Phe Ser Ser Gly Phe Val Val Phe Ser Phe Leu
        355                 360                 365

Gly Tyr Met Ala Gln Lys His Ser Val Pro Ile Gly Asp Val Ala Lys
    370                 375                 380

Asp Gly Pro Gly Leu Ile Phe Ile Ile Tyr Pro Glu Ala Ile Ala Thr
385                 390                 395                 400
```

```
Leu Pro Leu Ser Ser Ala Trp Ala Val Val Phe Phe Ile Met Leu Leu
                405                 410                 415

Thr Leu Gly Ile Asp Ser Ala Met Gly Gly Met Glu Ser Val Ile Thr
            420                 425                 430

Gly Leu Ile Asp Glu Phe Gln Leu Leu His Arg His Arg Glu Leu Phe
        435                 440                 445

Thr Leu Phe Ile Val Leu Ala Thr Phe Leu Leu Ser Leu Phe Cys Val
    450                 455                 460

Thr Asn Gly Gly Ile Tyr Val Phe Thr Leu Leu Asp His Phe Ala Ala
465                 470                 475                 480

Gly Thr Ser Ile Leu Phe Gly Val Leu Ile Glu Ala Ile Gly Val Ala
                485                 490                 495

Trp Phe Tyr Gly Val Gly Gln Phe Ser Asp Asp Ile Gln Gln Met Thr
            500                 505                 510

Gly Gln Arg Pro Ser Leu Tyr Trp Arg Leu Cys Trp Lys Leu Val Ser
        515                 520                 525

Pro Cys Phe Leu Leu Phe Val Val Val Ser Ile Val Thr Phe Arg
    530                 535                 540

Pro Pro His Tyr Gly Ala Tyr Ile Phe Pro Asp Trp Ala Asn Ala Leu
545                 550                 555                 560

Gly Trp Val Ile Ala Thr Ser Ser Met Ala Met Val Pro Ile Tyr Ala
                565                 570                 575

Ala Tyr Lys Phe Cys Ser Leu Pro Gly Ser Phe Arg Glu Lys Leu Ala
            580                 585                 590

Tyr Ala Ile Ala Pro Glu Lys Asp Arg Glu Leu Val Asp Arg Gly Glu
        595                 600                 605

Val Arg Gln Phe Thr Leu Arg His Trp Leu Lys Val
    610                 615                 620

<210> SEQ ID NO 19
<211> LENGTH: 398
<212> TYPE: PRT
<213> ORGANISM: Homo sapiens

<400> SEQUENCE: 19

Met His Thr Val Ala Thr Ser Gly Pro Asn Ala Ser Trp Gly Ala Pro
1               5                   10                  15

Ala Asn Ala Ser Gly Cys Pro Gly Cys Gly Ala Asn Ala Ser Asp Gly
            20                  25                  30

Pro Val Pro Ser Pro Arg Ala Val Asp Ala Trp Leu Val Pro Leu Phe
        35                  40                  45

Phe Ala Ala Leu Met Leu Leu Gly Leu Val Gly Asn Ser Leu Val Ile
    50                  55                  60

Tyr Val Ile Cys Arg His Lys Pro Met Arg Thr Val Thr Asn Phe Tyr
65                  70                  75                  80

Ile Ala Asn Leu Ala Ala Thr Asp Val Thr Phe Leu Leu Cys Cys Val
                85                  90                  95

Pro Phe Thr Ala Leu Leu Tyr Pro Leu Pro Gly Trp Val Leu Gly Asp
            100                 105                 110

Phe Met Cys Lys Phe Val Asn Tyr Ile Gln Gln Val Ser Val Gln Ala
        115                 120                 125

Thr Cys Ala Thr Leu Thr Ala Met Ser Val Asp Arg Trp Tyr Val Thr
    130                 135                 140

Val Phe Pro Leu Arg Ala Leu His Arg Arg Thr Pro Arg Leu Ala Leu
145                 150                 155                 160
```

```
Ala Val Ser Leu Ser Ile Trp Val Gly Ser Ala Val Ser Ala Pro
            165                 170                 175

Val Leu Ala Leu His Arg Leu Ser Pro Gly Pro Arg Ala Tyr Cys Ser
        180                 185                 190

Glu Ala Phe Pro Ser Arg Ala Leu Glu Arg Ala Phe Ala Leu Tyr Asn
    195                 200                 205

Leu Leu Ala Leu Tyr Leu Leu Pro Leu Leu Ala Thr Cys Ala Cys Tyr
210                 215                 220

Ala Ala Met Leu Arg His Leu Gly Arg Val Ala Val Arg Pro Ala Pro
225                 230                 235                 240

Ala Asp Ser Ala Leu Gln Gly Gln Val Leu Ala Glu Arg Ala Gly Ala
            245                 250                 255

Val Arg Ala Lys Val Ser Arg Leu Val Ala Ala Val Leu Leu Phe
        260                 265                 270

Ala Ala Cys Trp Gly Pro Ile Gln Leu Phe Leu Val Leu Gln Ala Leu
    275                 280                 285

Gly Pro Ala Gly Ser Trp His Pro Arg Ser Tyr Ala Ala Tyr Ala Leu
    290                 295                 300

Lys Thr Trp Ala His Cys Met Ser Tyr Ser Asn Ser Ala Leu Asn Pro
305                 310                 315                 320

Leu Leu Tyr Ala Phe Leu Gly Ser His Phe Arg Gln Ala Phe Arg Arg
            325                 330                 335

Val Cys Pro Cys Ala Pro Arg Arg Pro Arg Arg Pro Arg Pro Gly
        340                 345                 350

Pro Ser Asp Pro Ala Ala Pro His Ala Glu Leu Leu Arg Leu Gly Ser
    355                 360                 365

His Pro Ala Pro Ala Arg Ala Gln Lys Pro Gly Ser Ser Gly Leu Ala
370                 375                 380

Ala Arg Gly Leu Cys Val Leu Gly Glu Asp Asn Ala Pro Leu
385                 390                 395

<210> SEQ ID NO 20
<211> LENGTH: 431
<212> TYPE: PRT
<213> ORGANISM: Homo sapiens

<400> SEQUENCE: 20

Met Gln Ala Leu Asn Ile Thr Pro Glu Gln Phe Ser Arg Leu Leu Arg
1               5                   10                  15

Asp His Asn Leu Thr Arg Glu Gln Phe Ile Ala Leu Tyr Arg Leu Arg
            20                  25                  30

Pro Leu Val Tyr Thr Pro Glu Leu Pro Gly Arg Ala Lys Leu Ala Leu
        35                  40                  45

Val Leu Thr Gly Val Leu Ile Phe Ala Leu Ala Leu Phe Gly Asn Ala
    50                  55                  60

Leu Val Phe Tyr Val Val Thr Arg Ser Lys Ala Met Arg Thr Val Thr
65                  70                  75                  80

Asn Ile Phe Ile Cys Ser Leu Ala Leu Ser Asp Leu Leu Ile Thr Phe
            85                  90                  95

Phe Cys Ile Pro Val Thr Met Leu Gln Asn Ile Ser Asp Asn Trp Leu
        100                 105                 110

Gly Gly Ala Phe Ile Cys Lys Met Val Pro Phe Val Gln Ser Thr Ala
    115                 120                 125

Val Val Thr Glu Ile Leu Thr Met Thr Cys Ile Ala Val Glu Arg His
```

```
            130                 135                 140
Gln Gly Leu Val His Pro Phe Lys Met Lys Trp Gln Tyr Thr Asn Arg
145                 150                 155                 160

Arg Ala Phe Thr Met Leu Gly Val Val Trp Leu Val Ala Val Ile Val
                    165                 170                 175

Gly Ser Pro Met Trp His Val Gln Gln Leu Glu Ile Lys Tyr Asp Phe
                180                 185                 190

Leu Tyr Glu Lys Glu His Ile Cys Cys Leu Glu Trp Thr Ser Pro
            195                 200                 205

Val His Gln Lys Ile Tyr Thr Thr Phe Ile Leu Val Ile Leu Phe Leu
        210                 215                 220

Leu Pro Leu Met Val Met Leu Ile Leu Tyr Ser Lys Ile Gly Tyr Glu
225                 230                 235                 240

Leu Trp Ile Lys Lys Arg Val Gly Asp Gly Ser Val Leu Arg Thr Ile
                245                 250                 255

His Gly Lys Glu Met Ser Lys Ile Ala Arg Lys Lys Arg Ala Val
            260                 265                 270

Ile Met Met Val Thr Val Val Ala Leu Phe Ala Val Cys Trp Ala Pro
                275                 280                 285

Phe His Val Val His Met Met Ile Glu Tyr Ser Asn Phe Glu Lys Glu
        290                 295                 300

Tyr Asp Asp Val Thr Ile Lys Met Ile Phe Ala Ile Val Gln Ile Ile
305                 310                 315                 320

Gly Phe Ser Asn Ser Ile Cys Asn Pro Ile Val Tyr Ala Phe Met Asn
                325                 330                 335

Glu Asn Phe Lys Lys Asn Val Leu Ser Ala Val Cys Tyr Cys Ile Val
                340                 345                 350

Asn Lys Thr Phe Ser Pro Ala Gln Arg His Gly Asn Ser Gly Ile Thr
            355                 360                 365

Met Met Arg Lys Lys Ala Lys Phe Ser Leu Arg Glu Asn Pro Val Glu
        370                 375                 380

Glu Thr Lys Gly Glu Ala Phe Ser Asp Gly Asn Ile Glu Val Lys Leu
385                 390                 395                 400

Cys Glu Gln Thr Glu Glu Lys Lys Lys Leu Lys Arg His Leu Ala Leu
                405                 410                 415

Phe Arg Ser Glu Leu Ala Glu Asn Ser Pro Leu Asp Ser Gly His
            420                 425                 430

<210> SEQ ID NO 21
<211> LENGTH: 335
<212> TYPE: PRT
<213> ORGANISM: Homo sapiens

<400> SEQUENCE: 21

Met Glu Ser Ser Phe Ser Phe Gly Val Ile Leu Ala Val Leu Ala Ser
1               5                   10                  15

Leu Ile Ile Ala Thr Asn Thr Leu Val Ala Val Ala Val Leu Leu Leu
                20                  25                  30

Ile His Lys Asn Asp Gly Val Ser Leu Cys Phe Thr Leu Asn Leu Ala
            35                  40                  45

Val Ala Asp Thr Leu Ile Gly Val Ala Ile Ser Gly Leu Leu Thr Asp
        50                  55                  60

Gln Leu Ser Ser Pro Ser Arg Pro Thr Gln Lys Thr Leu Cys Ser Leu
65                  70                  75                  80
```

```
Arg Met Ala Phe Val Thr Ser Ser Ala Ala Ser Val Leu Thr Val
             85                  90                  95

Met Leu Ile Thr Phe Asp Arg Tyr Leu Ala Ile Lys Gln Pro Phe Arg
            100                 105                 110

Tyr Leu Lys Ile Met Ser Gly Phe Val Ala Gly Ala Cys Ile Ala Gly
            115                 120                 125

Leu Trp Leu Val Ser Tyr Leu Ile Gly Phe Leu Pro Leu Gly Ile Pro
            130                 135                 140

Met Phe Gln Gln Thr Ala Tyr Lys Gly Gln Cys Ser Phe Phe Ala Val
145                 150                 155                 160

Phe His Pro His Phe Val Leu Thr Leu Ser Cys Val Gly Phe Phe Pro
                165                 170                 175

Ala Met Leu Leu Phe Val Phe Phe Tyr Cys Asp Met Leu Lys Ile Ala
                180                 185                 190

Ser Met His Ser Gln Gln Ile Arg Lys Met Glu His Ala Gly Ala Met
            195                 200                 205

Ala Gly Gly Tyr Arg Ser Pro Arg Thr Pro Ser Asp Phe Lys Ala Leu
            210                 215                 220

Arg Thr Val Ser Val Leu Ile Gly Ser Phe Ala Leu Ser Trp Thr Pro
225                 230                 235                 240

Phe Leu Ile Thr Gly Ile Val Gln Val Ala Cys Gln Glu Cys His Leu
                245                 250                 255

Tyr Leu Val Leu Glu Arg Tyr Leu Trp Leu Leu Gly Val Gly Asn Ser
                260                 265                 270

Leu Leu Asn Pro Leu Ile Tyr Ala Tyr Trp Gln Lys Glu Val Arg Leu
            275                 280                 285

Gln Leu Tyr His Met Ala Leu Gly Val Lys Lys Val Leu Thr Ser Phe
            290                 295                 300

Leu Leu Phe Leu Ser Ala Arg Asn Cys Gly Pro Glu Arg Pro Arg Glu
305                 310                 315                 320

Ser Ser Cys His Ile Val Thr Ile Ser Ser Glu Phe Asp Gly
                325                 330                 335

<210> SEQ ID NO 22
<211> LENGTH: 220
<212> TYPE: PRT
<213> ORGANISM: Homo sapiens

<400> SEQUENCE: 22

Met Ala Ser Ala Gly Met Gln Ile Leu Gly Val Val Leu Thr Leu Leu
1               5                   10                  15

Gly Trp Val Asn Gly Leu Val Ser Cys Ala Leu Pro Met Trp Lys Val
            20                  25                  30

Thr Ala Phe Ile Gly Asn Ser Ile Val Ala Gln Val Trp Glu
            35                  40                  45

Gly Leu Trp Met Ser Cys Val Val Gln Ser Thr Gly Gln Met Gln Cys
            50                  55                  60

Lys Val Tyr Asp Ser Leu Leu Ala Leu Pro Gln Asp Leu Gln Ala Ala
65                  70                  75                  80

Arg Ala Leu Cys Val Ile Ala Leu Leu Val Ala Leu Phe Gly Leu Leu
                85                  90                  95

Val Tyr Leu Ala Gly Ala Lys Cys Thr Thr Cys Val Glu Glu Lys Asp
            100                 105                 110

Ser Lys Ala Arg Leu Val Leu Thr Ser Gly Ile Val Phe Val Ile Ser
            115                 120                 125
```

```
Gly Val Leu Thr Leu Ile Pro Val Cys Trp Thr Ala His Ala Ile Ile
           130                 135                 140

Arg Asp Phe Tyr Asn Pro Leu Val Ala Glu Ala Gln Lys Arg Glu Leu
145                 150                 155                 160

Gly Ala Ser Leu Tyr Leu Gly Trp Ala Ala Ser Gly Leu Leu Leu
                165                 170                 175

Gly Gly Gly Leu Leu Cys Cys Thr Cys Pro Ser Gly Ser Gln Gly
                180                 185                 190

Pro Ser His Tyr Met Ala Arg Tyr Ser Thr Ser Ala Pro Ala Ile Ser
        195                 200                 205

Arg Gly Pro Ser Glu Tyr Pro Thr Lys Asn Tyr Val
    210                 215                 220

<210> SEQ ID NO 23
<211> LENGTH: 21
<212> TYPE: PRT
<213> ORGANISM: Artificial Sequence
<220> FEATURE:
<223> OTHER INFORMATION: Synthesized

<400> SEQUENCE: 23

Met Ala Leu Pro Val Thr Ala Leu Leu Leu Pro Leu Ala Leu Leu Leu
1               5                   10                  15

His Ala Ala Arg Pro
            20

<210> SEQ ID NO 24
<211> LENGTH: 15
<212> TYPE: PRT
<213> ORGANISM: Artificial Sequence
<220> FEATURE:
<223> OTHER INFORMATION: Synthesized

<400> SEQUENCE: 24

Gly Gly Gly Gly Ser Gly Gly Gly Gly Ser Gly Gly Gly Gly Ser
1               5                   10                  15

<210> SEQ ID NO 25
<211> LENGTH: 45
<212> TYPE: PRT
<213> ORGANISM: Artificial Sequence
<220> FEATURE:
<223> OTHER INFORMATION: Synthesized

<400> SEQUENCE: 25

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
                20                  25                  30

Gly Ala Val His Thr Arg Gly Leu Asp Phe Ala Cys Asp
            35                  40                  45

<210> SEQ ID NO 26
<211> LENGTH: 23
<212> TYPE: PRT
<213> ORGANISM: Artificial Sequence
<220> FEATURE:
<223> OTHER INFORMATION: Synthesized

<400> SEQUENCE: 26

Tyr Ile Trp Ala Pro Leu Ala Gly Thr Cys Gly Val Leu Leu Leu Ser
1               5                   10                  15
```

```
Leu Val Ile Thr Leu Tyr Cys
            20

<210> SEQ ID NO 27
<211> LENGTH: 42
<212> TYPE: PRT
<213> ORGANISM: Artificial Sequence
<220> FEATURE:
<223> OTHER INFORMATION: Synthesized

<400> SEQUENCE: 27

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
            35                  40

<210> SEQ ID NO 28
<211> LENGTH: 112
<212> TYPE: PRT
<213> ORGANISM: Artificial Sequence
<220> FEATURE:
<223> OTHER INFORMATION: Synthesized

<400> SEQUENCE: 28

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
        50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 29
<211> LENGTH: 485
<212> TYPE: PRT
<213> ORGANISM: Artificial Sequence
<220> FEATURE:
<223> OTHER INFORMATION: Synthesized

<400> SEQUENCE: 29

Met Ala Leu Pro Val Thr Ala Leu Leu Leu Pro Leu Ala Leu Leu Leu
1               5                   10                  15

His Ala Ala Arg Pro Gln Ile Val Leu Thr Gln Ser Pro Ala Ile Met
            20                  25                  30

Ser Ala Ser Leu Gly Glu Arg Val Thr Met Thr Cys Thr Ala Ser Ser
            35                  40                  45

Val Val Ile Ser Thr Tyr Leu His Trp Tyr Gln Gln Lys Pro Gly Ser
        50                  55                  60

Ser Pro Lys Leu Trp Ile Tyr Ser Thr Ser Asn Leu Ala Ser Gly Val
65                  70                  75                  80
```

-continued

```
Pro Val Arg Phe Ser Gly Ser Gly Ser Gly Thr Ser Tyr Ser Leu Thr
             85                  90                  95
Ile Ser Ser Met Glu Ala Glu Asp Ala Ala Thr Tyr Tyr Cys His Gln
            100                 105                 110
Tyr His Arg Ser Pro Trp Thr Phe Gly Gly Gly Thr Lys Leu Glu Ile
            115                 120                 125
Lys Gly Gly Gly Gly Ser Gly Gly Gly Gly Ser Gly Gly Gly Gly Ser
130                 135                 140
Glu Val Gln Leu Gln Gln Ser Gly Pro Glu Leu Val Lys Pro Gly Gly
145                 150                 155                 160
Ser Met Lys Ile Ser Cys Lys Ala Ser Gly Tyr Ser Phe Thr Gly Tyr
            165                 170                 175
Thr Met Asn Trp Val Lys Gln Ser His Gly Lys Asn Leu Glu Trp Ile
            180                 185                 190
Gly Leu Ile Asn Pro Tyr Asn Gly Gly Ile Ser Tyr Asn Gln Lys Phe
            195                 200                 205
Lys Asp Lys Ala Thr Leu Thr Met Asp Lys Ser Ser Thr Ala Tyr
            210                 215                 220
Met Glu Leu Leu Ser Leu Thr Ser Glu Asp Ser Ala Ile Tyr Phe Cys
225                 230                 235                 240
Ala Arg Asp Tyr Arg Tyr Glu Gly Phe Asp Tyr Trp Gly Gln Gly Thr
            245                 250                 255
Leu Val Thr Val Ser Ala Thr Thr Thr Pro Ala Pro Arg Pro Pro Thr
            260                 265                 270
Pro Ala Pro Thr Ile Ala Ser Gln Pro Leu Ser Leu Arg Pro Glu Ala
            275                 280                 285
Cys Arg Pro Ala Ala Gly Gly Ala Val His Thr Arg Gly Leu Asp Phe
290                 295                 300
Ala Cys Asp Ile Tyr Ile Trp Ala Pro Leu Ala Gly Thr Cys Gly Val
305                 310                 315                 320
Leu Leu Leu Ser Leu Val Ile Thr Leu Tyr Cys Lys Arg Gly Arg Lys
            325                 330                 335
Lys Leu Leu Tyr Ile Phe Lys Gln Pro Phe Met Arg Pro Val Gln Thr
            340                 345                 350
Thr Gln Glu Glu Asp Gly Cys Ser Cys Arg Phe Pro Glu Glu Glu Glu
            355                 360                 365
Gly Gly Cys Glu Leu Arg Val Lys Phe Ser Arg Ser Ala Asp Ala Pro
            370                 375                 380
Ala Tyr Lys Gln Gly Gln Asn Gln Leu Tyr Asn Glu Leu Asn Leu Gly
385                 390                 395                 400
Arg Arg Glu Glu Tyr Asp Val Leu Asp Lys Arg Arg Gly Arg Asp Pro
            405                 410                 415
Glu Met Gly Gly Lys Pro Arg Arg Lys Asn Pro Gln Glu Gly Leu Tyr
            420                 425                 430
Asn Glu Leu Gln Lys Asp Lys Met Ala Glu Ala Tyr Ser Glu Ile Gly
            435                 440                 445
Met Lys Gly Glu Arg Arg Arg Gly Lys Gly His Asp Gly Leu Tyr Gln
450                 455                 460
Gly Leu Ser Thr Ala Thr Lys Asp Thr Tyr Asp Ala Leu His Met Gln
465                 470                 475                 480
Ala Leu Pro Pro Arg
            485
```

<210> SEQ ID NO 30
<211> LENGTH: 241
<212> TYPE: PRT
<213> ORGANISM: Artificial Sequence
<220> FEATURE:
<223> OTHER INFORMATION: Synthesized

<400> SEQUENCE: 30

```
Gln Ile Val Leu Thr Gln Ser Pro Ala Ile Met Ser Ala Ser Leu Gly
1               5                  10                  15

Glu Arg Val Thr Met Thr Cys Thr Ala Ser Ser Val Val Ile Ser Thr
            20                  25                  30

Tyr Leu His Trp Tyr Gln Gln Lys Pro Gly Ser Ser Pro Lys Leu Trp
        35                  40                  45

Ile Tyr Ser Thr Ser Asn Leu Ala Ser Gly Val Pro Val Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys His Gln Tyr His Arg Ser Pro
                85                  90                  95

Trp Thr Phe Gly Gly Gly Thr Lys Leu Glu Ile Lys Gly Gly Gly Gly
            100                 105                 110

Ser Gly Gly Gly Gly Ser Gly Gly Gly Ser Glu Val Gln Leu Gln
        115                 120                 125

Gln Ser Gly Pro Glu Leu Val Lys Pro Gly Ser Met Lys Ile Ser
    130                 135                 140

Cys Lys Ala Ser Gly Tyr Ser Phe Thr Gly Tyr Thr Met Asn Trp Val
145                 150                 155                 160

Lys Gln Ser His Gly Lys Asn Leu Glu Trp Ile Gly Leu Ile Asn Pro
                165                 170                 175

Tyr Asn Gly Gly Ile Ser Tyr Asn Gln Lys Phe Lys Asp Lys Ala Thr
            180                 185                 190

Leu Thr Met Asp Lys Ser Ser Thr Ala Tyr Met Glu Leu Leu Ser
        195                 200                 205

Leu Thr Ser Glu Asp Ser Ala Ile Tyr Phe Cys Ala Arg Asp Tyr Arg
    210                 215                 220

Tyr Glu Gly Phe Asp Tyr Trp Gly Gln Gly Thr Leu Val Thr Val Ser
225                 230                 235                 240

Ala
```

<210> SEQ ID NO 31
<211> LENGTH: 108
<212> TYPE: PRT
<213> ORGANISM: Artificial Sequence
<220> FEATURE:
<223> OTHER INFORMATION: Synthesized

<400> SEQUENCE: 31

```
Gln Ile Val Leu Thr Gln Ser Pro Ala Ile Met Ser Ala Ser Leu Gly
1               5                  10                  15

Glu Arg Val Thr Met Thr Cys Thr Ala Ser Ser Val Val Ile Ser Thr
            20                  25                  30

Tyr Leu His Trp Tyr Gln Gln Lys Pro Gly Ser Ser Pro Lys Leu Trp
        35                  40                  45

Ile Tyr Ser Thr Ser Asn Leu Ala Ser Gly Val Pro Val Arg Phe Ser
    50                  55                  60

Gly Ser Gly Ser Gly Thr Ser Tyr Ser Leu Thr Ile Ser Ser Met Glu
```

```
                65                  70                  75                  80
Ala Glu Asp Ala Ala Thr Tyr Tyr Cys His Gln Tyr His Arg Ser Pro
                85                  90                  95

Trp Thr Phe Gly Gly Gly Thr Lys Leu Glu Ile Lys
            100                 105

<210> SEQ ID NO 32
<211> LENGTH: 118
<212> TYPE: PRT
<213> ORGANISM: Artificial Sequence
<220> FEATURE:
<223> OTHER INFORMATION: Synthesized

<400> SEQUENCE: 32

Glu Val Gln Leu Gln Gln Ser Gly Pro Glu Leu Val Lys Pro Gly Gly
1               5                   10                  15

Ser Met Lys Ile Ser Cys Lys Ala Ser Gly Tyr Ser Phe Thr Gly Tyr
                20                  25                  30

Thr Met Asn Trp Val Lys Gln Ser His Gly Lys Asn Leu Glu Trp Ile
            35                  40                  45

Gly Leu Ile Asn Pro Tyr Asn Gly Gly Ile Ser Tyr Asn Gln Lys Phe
    50                  55                  60

Lys Asp Lys Ala Thr Leu Thr Met Asp Lys Ser Ser Ser Thr Ala Tyr
65                  70                  75                  80

Met Glu Leu Leu Ser Leu Thr Ser Glu Asp Ser Ala Ile Tyr Phe Cys
                85                  90                  95

Ala Arg Asp Tyr Arg Tyr Glu Gly Phe Asp Tyr Trp Gly Gln Gly Thr
                100                 105                 110

Leu Val Thr Val Ser Ala
            115

<210> SEQ ID NO 33
<211> LENGTH: 488
<212> TYPE: PRT
<213> ORGANISM: Artificial Sequence
<220> FEATURE:
<223> OTHER INFORMATION: Synthesized

<400> SEQUENCE: 33

Met Ala Leu Pro Val Thr Ala Leu Leu Leu Pro Leu Ala Leu Leu Leu
1               5                   10                  15

His Ala Ala Arg Pro Glu Asn Val Leu Thr Gln Ser Pro Ala Ile Met
                20                  25                  30

Ser Ala Thr Leu Gly Glu Lys Val Thr Met Ser Cys Arg Ala Thr Ser
            35                  40                  45

Asn Val Lys Tyr Met Tyr Trp Tyr Gln Gln Lys Ser Gly Ala Ser Pro
    50                  55                  60

Lys Leu Trp Ile Tyr Tyr Thr Ser Asn Leu Ala Ser Gly Val Pro Ala
65                  70                  75                  80

Arg Phe Ser Gly Ser Gly Ser Gly Thr Ser Tyr Ser Leu Thr Ile Ser
                85                  90                  95

Ser Val Glu Ala Ala Asp Ala Ala Thr Tyr Tyr Cys Gln Gln Phe Thr
                100                 105                 110

Ser Ser Pro Ser Thr Phe Gly Ala Gly Thr Lys Leu Glu Leu Lys Gly
            115                 120                 125

Gly Gly Gly Ser Gly Gly Gly Gly Ser Gly Gly Gly Gly Ser Glu Val
    130                 135                 140
```

Gln Leu Gln Gln Ser Gly Pro Glu Leu Val Lys Pro Gly Ala Ser Val
145                 150                 155                 160

Lys Ile Ser Cys Lys Ala Ser Gly Tyr Ser Phe Thr Gly Tyr Phe Met
            165                 170                 175

Asn Trp Val Lys Gln Ser His Gly Lys Ser Leu Glu Trp Ile Gly Arg
        180                 185                 190

Ile Asn Pro Tyr Asn Gly Asp Thr Phe Tyr Asn Gln Lys Phe Lys Gly
    195                 200                 205

Lys Ala Thr Leu Thr Val Asp Lys Ser Ser Asn Thr Ala His Met Glu
210                 215                 220

Leu Arg Ser Leu Thr Ser Glu Asp Ser Ala Val Tyr Tyr Cys Ala Arg
225                 230                 235                 240

Val Leu Phe Leu Asp Phe Asp Pro Tyr Leu Met Asp Tyr Trp Gly
            245                 250                 255

Gln Gly Thr Ser Val Thr Val Ser Ser Thr Thr Pro Ala Pro Arg
            260                 265                 270

Pro Pro Thr Pro Ala Pro Thr Ile Ala Ser Gln Pro Leu Ser Leu Arg
        275                 280                 285

Pro Glu Ala Cys Arg Pro Ala Ala Gly Gly Ala Val His Thr Arg Gly
        290                 295                 300

Leu Asp Phe Ala Cys Asp Ile Tyr Ile Trp Ala Pro Leu Ala Gly Thr
305                 310                 315                 320

Cys Gly Val Leu Leu Leu Ser Leu Val Ile Thr Leu Tyr Cys Lys Arg
                325                 330                 335

Gly Arg Lys Lys Leu Leu Tyr Ile Phe Lys Gln Pro Phe Met Arg Pro
            340                 345                 350

Val Gln Thr Thr Gln Glu Glu Asp Gly Cys Ser Cys Arg Phe Pro Glu
            355                 360                 365

Glu Glu Glu Gly Gly Cys Glu Leu Arg Val Lys Phe Ser Arg Ser Ala
            370                 375                 380

Asp Ala Pro Ala Tyr Lys Gln Gly Gln Asn Gln Leu Tyr Asn Glu Leu
385                 390                 395                 400

Asn Leu Gly Arg Arg Glu Glu Tyr Asp Val Leu Asp Lys Arg Arg Gly
            405                 410                 415

Arg Asp Pro Glu Met Gly Gly Lys Pro Arg Arg Lys Asn Pro Gln Glu
            420                 425                 430

Gly Leu Tyr Asn Glu Leu Gln Lys Asp Lys Met Ala Glu Ala Tyr Ser
            435                 440                 445

Glu Ile Gly Met Lys Gly Glu Arg Arg Arg Gly Lys Gly His Asp Gly
        450                 455                 460

Leu Tyr Gln Gly Leu Ser Thr Ala Thr Lys Asp Thr Tyr Asp Ala Leu
465                 470                 475                 480

His Met Gln Ala Leu Pro Pro Arg
                485

<210> SEQ ID NO 34
<211> LENGTH: 244
<212> TYPE: PRT
<213> ORGANISM: Artificial Sequence
<220> FEATURE:
<223> OTHER INFORMATION: Synthesized

<400> SEQUENCE: 34

Glu Asn Val Leu Thr Gln Ser Pro Ala Ile Met Ser Ala Thr Leu Gly
1               5                   10                  15

```
Glu Lys Val Thr Met Ser Cys Arg Ala Thr Ser Asn Val Lys Tyr Met
                20                  25                  30
Tyr Trp Tyr Gln Gln Lys Ser Gly Ala Ser Pro Lys Leu Trp Ile Tyr
            35                  40                  45
Tyr Thr Ser Asn Leu Ala Ser Gly Val Pro Ala Arg Phe Ser Gly Ser
 50                  55                  60
Gly Ser Gly Thr Ser Tyr Ser Leu Thr Ile Ser Ser Val Glu Ala Ala
 65                  70                  75                  80
Asp Ala Ala Thr Tyr Tyr Cys Gln Gln Phe Thr Ser Ser Pro Ser Thr
                85                  90                  95
Phe Gly Ala Gly Thr Lys Leu Glu Leu Lys Gly Gly Gly Gly Ser Gly
                100                 105                 110
Gly Gly Gly Ser Gly Gly Gly Ser Glu Val Gln Leu Gln Gln Ser
            115                 120                 125
Gly Pro Glu Leu Val Lys Pro Gly Ala Ser Val Lys Ile Ser Cys Lys
            130                 135                 140
Ala Ser Gly Tyr Ser Phe Thr Gly Tyr Phe Met Asn Trp Val Lys Gln
145                 150                 155                 160
Ser His Gly Lys Ser Leu Glu Trp Ile Gly Arg Ile Asn Pro Tyr Asn
                165                 170                 175
Gly Asp Thr Phe Tyr Asn Gln Lys Phe Lys Gly Lys Ala Thr Leu Thr
            180                 185                 190
Val Asp Lys Ser Ser Asn Thr Ala His Met Glu Leu Arg Ser Leu Thr
            195                 200                 205
Ser Glu Asp Ser Ala Val Tyr Tyr Cys Ala Arg Val Leu Phe Leu Asp
210                 215                 220
Phe Asp Pro Tyr Leu Met Asp Tyr Trp Gly Gln Gly Thr Ser Val
225                 230                 235                 240
Thr Val Ser Ser

<210> SEQ ID NO 35
<211> LENGTH: 106
<212> TYPE: PRT
<213> ORGANISM: Artificial Sequence
<220> FEATURE:
<223> OTHER INFORMATION: Synthesized

<400> SEQUENCE: 35

Asn Val Leu Thr Gln Ser Pro Ala Ile Met Ser Ala Thr Leu Gly Glu
 1               5                  10                  15
Lys Val Thr Met Ser Cys Arg Ala Thr Ser Asn Val Lys Tyr Met Tyr
                20                  25                  30
Trp Tyr Gln Gln Lys Ser Gly Ala Ser Pro Lys Leu Trp Ile Tyr Tyr
            35                  40                  45
Thr Ser Asn Leu Ala Ser Gly Val Pro Ala Arg Phe Ser Gly Ser Gly
 50                  55                  60
Ser Gly Thr Ser Tyr Ser Leu Thr Ile Ser Ser Val Glu Ala Ala Asp
 65                  70                  75                  80
Ala Ala Thr Tyr Tyr Cys Gln Gln Phe Thr Ser Ser Pro Ser Thr Phe
                85                  90                  95
Gly Ala Gly Thr Lys Leu Glu Leu Lys Glu
            100                 105

<210> SEQ ID NO 36
<211> LENGTH: 123
<212> TYPE: PRT
```

<213> ORGANISM: Artificial Sequence
<220> FEATURE:
<223> OTHER INFORMATION: Synthesized

<400> SEQUENCE: 36

```
Glu Val Gln Leu Gln Gln Ser Gly Pro Glu Leu Val Lys Pro Gly Ala
1               5                   10                  15
Ser Val Lys Ile Ser Cys Lys Ala Ser Gly Tyr Ser Phe Thr Gly Tyr
            20                  25                  30
Phe Met Asn Trp Val Lys Gln Ser His Gly Lys Ser Leu Glu Trp Ile
        35                  40                  45
Gly Arg Ile Asn Pro Tyr Asn Gly Asp Thr Phe Tyr Asn Gln Lys Phe
    50                  55                  60
Lys Gly Lys Ala Thr Leu Thr Val Asp Lys Ser Ser Asn Thr Ala His
65                  70                  75                  80
Met Glu Leu Arg Ser Leu Thr Ser Glu Asp Ser Ala Val Tyr Tyr Cys
                85                  90                  95
Ala Arg Val Leu Phe Leu Asp Phe Asp Pro Tyr Leu Met Asp Tyr
            100                 105                 110
Trp Gly Gln Gly Thr Ser Val Thr Val Ser Ser
        115                 120
```

<210> SEQ ID NO 37
<211> LENGTH: 485
<212> TYPE: PRT
<213> ORGANISM: Artificial Sequence
<220> FEATURE:
<223> OTHER INFORMATION: Synthesized

<400> SEQUENCE: 37

```
Met Ala Leu Pro Val Thr Ala Leu Leu Leu Pro Leu Ala Leu Leu Leu
1               5                   10                  15
His Ala Ala Arg Pro Asp Ile Gln Met Thr Gln Ser Pro Ala Ser Leu
            20                  25                  30
Ser Ala Ser Val Gly Glu Thr Val Thr Ile Thr Cys Arg Ala Ser Glu
        35                  40                  45
Asn Ile Asp Ser Tyr Leu Ala Trp Tyr Gln Gln Lys Gln Gly Lys Ser
    50                  55                  60
Pro Gln Leu Leu Val Tyr Ala Ser Thr Leu Leu Val Asp Gly Val Pro
65                  70                  75                  80
Ser Arg Phe Ser Gly Ser Arg Ser Gly Thr Gln Phe Ser Leu Lys Ile
                85                  90                  95
Asn Ser Leu Gln Ser Glu Asp Val Ala Arg Tyr Tyr Cys Gln His Tyr
            100                 105                 110
Tyr Ser Ile Pro Tyr Thr Phe Gly Ser Gly Thr Lys Leu Glu Ile Lys
        115                 120                 125
Gly Gly Gly Gly Ser Gly Gly Gly Gly Ser Gly Gly Gly Gly Ser Glu
    130                 135                 140
Val Lys Leu Val Glu Ser Gly Gly Gly Leu Val Lys Pro Gly Gly Ser
145                 150                 155                 160
Leu Lys Leu Ser Cys Ala Ala Ser Gly Phe Thr Phe Asn Ser Tyr Thr
                165                 170                 175
Met Ser Trp Val Arg Gln Thr Pro Ala Lys Arg Leu Glu Trp Val Val
            180                 185                 190
Thr Ile Ser Ser Gly Gly Gly Arg Thr Tyr Tyr Pro Asp Ser Val Lys
        195                 200                 205
```

```
Gly Arg Phe Thr Ile Ser Arg Asp Asn Ala Arg Asn Thr Leu Tyr Leu
            210                 215                 220

Gln Met Ser Ser Leu Arg Ser Glu Asp Thr Ala Met Tyr Tyr Cys Ile
225                 230                 235                 240

Arg Gly Asp Tyr Arg Tyr Asp Gly Phe Ala Tyr Trp Gly Gln Gly Thr
                245                 250                 255

Leu Val Thr Val Ser Thr Thr Thr Pro Ala Pro Arg Pro Pro Thr
                260                 265                 270

Pro Ala Pro Thr Ile Ala Ser Gln Pro Leu Ser Leu Arg Pro Glu Ala
            275                 280                 285

Cys Arg Pro Ala Ala Gly Gly Ala Val His Thr Arg Gly Leu Asp Phe
290                 295                 300

Ala Cys Asp Ile Tyr Ile Trp Ala Pro Leu Ala Gly Thr Cys Gly Val
305                 310                 315                 320

Leu Leu Leu Ser Leu Val Ile Thr Leu Tyr Cys Lys Arg Gly Arg Lys
                325                 330                 335

Lys Leu Leu Tyr Ile Phe Lys Gln Pro Phe Met Arg Pro Val Gln Thr
            340                 345                 350

Thr Gln Glu Glu Asp Gly Cys Ser Cys Arg Phe Pro Glu Glu Glu Glu
            355                 360                 365

Gly Gly Cys Glu Leu Arg Val Lys Phe Ser Arg Ser Ala Asp Ala Pro
370                 375                 380

Ala Tyr Lys Gln Gly Gln Asn Gln Leu Tyr Asn Glu Leu Asn Leu Gly
385                 390                 395                 400

Arg Arg Glu Glu Tyr Asp Val Leu Asp Lys Arg Arg Gly Arg Asp Pro
                405                 410                 415

Glu Met Gly Gly Lys Pro Arg Arg Lys Asn Pro Gln Glu Gly Leu Tyr
            420                 425                 430

Asn Glu Leu Gln Lys Asp Lys Met Ala Glu Ala Tyr Ser Glu Ile Gly
                435                 440                 445

Met Lys Gly Glu Arg Arg Arg Gly Lys Gly His Asp Gly Leu Tyr Gln
            450                 455                 460

Gly Leu Ser Thr Ala Thr Lys Asp Thr Tyr Asp Ala Leu His Met Gln
465                 470                 475                 480

Ala Leu Pro Pro Arg
                485

<210> SEQ ID NO 38
<211> LENGTH: 241
<212> TYPE: PRT
<213> ORGANISM: Artificial Sequence
<220> FEATURE:
<223> OTHER INFORMATION: Synthesized

<400> SEQUENCE: 38

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Asp Ser Tyr
                20                  25                  30

Leu Ala Trp Tyr Gln Gln Lys Gln Gly Lys Ser Pro Gln Leu Leu Val
            35                  40                  45

Tyr Ala Ser Thr Leu Leu Val Asp Gly Val Pro Ser Arg Phe Ser Gly
        50                  55                  60

Ser Arg Ser Gly Thr Gln Phe Ser Leu Lys Ile Asn Ser Leu Gln Ser
65                  70                  75                  80
```

```
Glu Asp Val Ala Arg Tyr Tyr Cys Gln His Tyr Tyr Ser Ile Pro Tyr
             85                  90                  95

Thr Phe Gly Ser Gly Thr Lys Leu Glu Ile Lys Gly Gly Gly Gly Ser
            100                 105                 110

Gly Gly Gly Gly Ser Gly Gly Gly Ser Glu Val Lys Leu Val Glu
            115                 120                 125

Ser Gly Gly Gly Leu Val Lys Pro Gly Gly Ser Leu Lys Leu Ser Cys
130                 135                 140

Ala Ala Ser Gly Phe Thr Phe Asn Ser Tyr Thr Met Ser Trp Val Arg
145                 150                 155                 160

Gln Thr Pro Ala Lys Arg Leu Glu Trp Val Val Thr Ile Ser Ser Gly
                165                 170                 175

Gly Gly Arg Thr Tyr Tyr Pro Asp Ser Val Lys Gly Arg Phe Thr Ile
            180                 185                 190

Ser Arg Asp Asn Ala Arg Asn Thr Leu Tyr Leu Gln Met Ser Ser Leu
            195                 200                 205

Arg Ser Glu Asp Thr Ala Met Tyr Tyr Cys Ile Arg Gly Asp Tyr Arg
            210                 215                 220

Tyr Asp Gly Phe Ala Tyr Trp Gly Gln Gly Thr Leu Val Thr Val Ser
225                 230                 235                 240

Thr

<210> SEQ ID NO 39
<211> LENGTH: 107
<212> TYPE: PRT
<213> ORGANISM: Artificial Sequence
<220> FEATURE:
<223> OTHER INFORMATION: Synthesized

<400> SEQUENCE: 39

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Asp Ser Tyr
            20                  25                  30

Leu Ala Trp Tyr Gln Gln Lys Gln Gly Lys Ser Pro Gln Leu Leu Val
            35                  40                  45

Tyr Ala Ser Thr Leu Leu Val Asp Gly Val Pro Ser Arg Phe Ser Gly
        50                  55                  60

Ser Arg Ser Gly Thr Gln Phe Ser Leu Lys Ile Asn Ser Leu Gln Ser
65                  70                  75                  80

Glu Asp Val Ala Arg Tyr Tyr Cys Gln His Tyr Tyr Ser Ile Pro Tyr
            85                  90                  95

Thr Phe Gly Ser Gly Thr Lys Leu Glu Ile Lys
            100                 105

<210> SEQ ID NO 40
<211> LENGTH: 119
<212> TYPE: PRT
<213> ORGANISM: Artificial Sequence
<220> FEATURE:
<223> OTHER INFORMATION: Synthesized

<400> SEQUENCE: 40

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Asn Ser Tyr
            20                  25                  30
```

```
Thr Met Ser Trp Val Arg Gln Thr Pro Ala Lys Arg Leu Glu Trp Val
        35                  40                  45

Val Thr Ile Ser Ser Gly Gly Arg Thr Tyr Tyr Pro Asp Ser Val
 50                  55                  60

Lys Gly Arg Phe Thr Ile Ser Arg Asp Asn Ala Arg Asn Thr Leu Tyr
 65                  70                  75                  80

Leu Gln Met Ser Ser Leu Arg Ser Glu Asp Thr Ala Met Tyr Tyr Cys
                85                  90                  95

Ile Arg Gly Asp Tyr Arg Tyr Asp Gly Phe Ala Tyr Trp Gly Gln Gly
                100                 105                 110

Thr Leu Val Thr Val Ser Thr
        115
```

<210> SEQ ID NO 41
<211> LENGTH: 488
<212> TYPE: PRT
<213> ORGANISM: Artificial Sequence
<220> FEATURE:
<223> OTHER INFORMATION: Synthesized

<400> SEQUENCE: 41

```
Met Ala Leu Pro Val Thr Ala Leu Leu Leu Pro Leu Ala Leu Leu Leu
 1               5                  10                  15

His Ala Ala Arg Pro Glu Asn Val Leu Thr Gln Ser Pro Ala Ile Met
                20                  25                  30

Ser Ala Thr Leu Gly Glu Lys Val Thr Met Ser Cys Arg Ala Thr Ser
        35                  40                  45

Asn Val Lys Tyr Met Tyr Trp Tyr Gln Gln Lys Ser Gly Ala Ser Pro
 50                  55                  60

Lys Leu Trp Ile Tyr Tyr Thr Ser Asn Leu Ala Ser Gly Val Pro Ala
 65                  70                  75                  80

Arg Phe Ser Gly Ser Gly Ser Gly Thr Ser Tyr Ser Leu Thr Ile Ser
                85                  90                  95

Ser Val Glu Ala Ala Asp Ala Ala Thr Tyr Tyr Cys Gln Gln Phe Thr
                100                 105                 110

Ser Ser Pro Ser Thr Phe Gly Ala Gly Thr Lys Leu Glu Leu Lys Gly
        115                 120                 125

Gly Gly Gly Ser Gly Gly Gly Gly Ser Gly Gly Gly Gly Ser Glu Val
 130                 135                 140

Gln Leu Gln Gln Ser Gly Pro Glu Leu Val Lys Pro Gly Ala Ser Val
145                 150                 155                 160

Lys Ile Ser Cys Lys Ala Ser Gly Tyr Ser Phe Thr Gly Tyr Phe Met
                165                 170                 175

Asn Trp Val Lys Gln Ser His Gly Lys Ser Leu Glu Trp Ile Gly Arg
                180                 185                 190

Ile Asn Pro Tyr Asn Gly Asp Thr Phe Tyr Asn Gln Lys Phe Lys Gly
                195                 200                 205

Lys Ala Thr Leu Thr Val Asp Lys Ser Ser Ser Thr Ala His Met Glu
        210                 215                 220

Leu Arg Ser Leu Thr Ser Glu Asp Ser Ala Val Tyr Tyr Cys Ala Arg
225                 230                 235                 240

Val Leu Phe Leu Asp Phe Asp Pro Tyr Leu Met Asp Tyr Trp Gly
                245                 250                 255

Gln Gly Thr Ser Val Thr Val Ser Ser Thr Thr Thr Pro Ala Pro Arg
                260                 265                 270
```

```
Pro Pro Thr Pro Ala Pro Thr Ile Ala Ser Gln Pro Leu Ser Leu Arg
        275                 280                 285
Pro Glu Ala Cys Arg Pro Ala Ala Gly Gly Ala Val His Thr Arg Gly
    290                 295                 300
Leu Asp Phe Ala Cys Asp Ile Tyr Ile Trp Ala Pro Leu Ala Gly Thr
305                 310                 315                 320
Cys Gly Val Leu Leu Leu Ser Leu Val Ile Thr Leu Tyr Cys Lys Arg
                325                 330                 335
Gly Arg Lys Lys Leu Leu Tyr Ile Phe Lys Gln Pro Phe Met Arg Pro
            340                 345                 350
Val Gln Thr Thr Gln Glu Glu Asp Gly Cys Ser Cys Arg Phe Pro Glu
        355                 360                 365
Glu Glu Glu Gly Gly Cys Glu Leu Arg Val Lys Phe Ser Arg Ser Ala
    370                 375                 380
Asp Ala Pro Ala Tyr Lys Gln Gly Gln Asn Gln Leu Tyr Asn Glu Leu
385                 390                 395                 400
Asn Leu Gly Arg Arg Glu Glu Tyr Asp Val Leu Asp Lys Arg Arg Gly
                405                 410                 415
Arg Asp Pro Glu Met Gly Gly Lys Pro Arg Arg Lys Asn Pro Gln Glu
            420                 425                 430
Gly Leu Tyr Asn Glu Leu Gln Lys Asp Lys Met Ala Glu Ala Tyr Ser
        435                 440                 445
Glu Ile Gly Met Lys Gly Glu Arg Arg Arg Gly Lys Gly His Asp Gly
    450                 455                 460
Leu Tyr Gln Gly Leu Ser Thr Ala Thr Lys Asp Thr Tyr Asp Ala Leu
465                 470                 475                 480
His Met Gln Ala Leu Pro Pro Arg
                485

<210> SEQ ID NO 42
<211> LENGTH: 244
<212> TYPE: PRT
<213> ORGANISM: Artificial Sequence
<220> FEATURE:
<223> OTHER INFORMATION: Synthesized

<400> SEQUENCE: 42

Glu Asn Val Leu Thr Gln Ser Pro Ala Ile Met Ser Ala Thr Leu Gly
1               5                   10                  15
Glu Lys Val Thr Met Ser Cys Arg Ala Thr Ser Asn Val Lys Tyr Met
            20                  25                  30
Tyr Trp Tyr Gln Gln Lys Ser Gly Ala Ser Pro Lys Leu Trp Ile Tyr
        35                  40                  45
Tyr Thr Ser Asn Leu Ala Ser Gly Val Pro Ala Arg Phe Ser Gly Ser
    50                  55                  60
Gly Ser Gly Thr Ser Tyr Ser Leu Thr Ile Ser Ser Val Glu Ala Ala
65                  70                  75                  80
Asp Ala Ala Thr Tyr Tyr Cys Gln Gln Phe Thr Ser Ser Pro Ser Thr
                85                  90                  95
Phe Gly Ala Gly Thr Lys Leu Glu Leu Lys Gly Gly Gly Gly Ser Gly
            100                 105                 110
Gly Gly Gly Ser Gly Gly Gly Ser Glu Val Gln Leu Gln Gln Ser
        115                 120                 125
Gly Pro Glu Leu Val Lys Pro Gly Ala Ser Val Lys Ile Ser Cys Lys
    130                 135                 140
```

```
Ala Ser Gly Tyr Ser Phe Thr Gly Tyr Phe Met Asn Trp Val Lys Gln
145                 150                 155                 160

Ser His Gly Lys Ser Leu Glu Trp Ile Gly Arg Ile Asn Pro Tyr Asn
                165                 170                 175

Gly Asp Thr Phe Tyr Asn Gln Lys Phe Lys Gly Lys Ala Thr Leu Thr
            180                 185                 190

Val Asp Lys Ser Ser Ser Thr Ala His Met Glu Leu Arg Ser Leu Thr
        195                 200                 205

Ser Glu Asp Ser Ala Val Tyr Tyr Cys Ala Arg Val Leu Phe Leu Asp
    210                 215                 220

Phe Asp Asp Pro Tyr Leu Met Asp Tyr Trp Gly Gln Gly Thr Ser Val
225                 230                 235                 240

Thr Val Ser Ser

<210> SEQ ID NO 43
<211> LENGTH: 106
<212> TYPE: PRT
<213> ORGANISM: Artificial Sequence
<220> FEATURE:
<223> OTHER INFORMATION: Synthesized

<400> SEQUENCE: 43

Glu Asn Val Leu Thr Gln Ser Pro Ala Ile Met Ser Ala Thr Leu Gly
1               5                   10                  15

Glu Lys Val Thr Met Ser Cys Arg Ala Thr Ser Asn Val Lys Tyr Met
            20                  25                  30

Tyr Trp Tyr Gln Gln Lys Ser Gly Ala Ser Pro Lys Leu Trp Ile Tyr
        35                  40                  45

Tyr Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Val Glu Ala Ala
65                  70                  75                  80

Asp Ala Ala Thr Tyr Tyr Cys Gln Gln Phe Thr Ser Ser Pro Ser Thr
                85                  90                  95

Phe Gly Ala Gly Thr Lys Leu Glu Leu Lys
            100                 105

<210> SEQ ID NO 44
<211> LENGTH: 123
<212> TYPE: PRT
<213> ORGANISM: Artificial Sequence
<220> FEATURE:
<223> OTHER INFORMATION: Synthesized

<400> SEQUENCE: 44

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Gly Tyr
            20                  25                  30

Phe Met Asn Trp Val Lys Gln Ser His Gly Lys Ser Leu Glu Trp Ile
        35                  40                  45

Gly Arg Ile Asn Pro Tyr Asn Gly Asp Thr Phe Tyr Asn Gln Lys Phe
    50                  55                  60

Lys Gly Lys Ala Thr Leu Thr Val Asp Lys Ser Ser Ser Thr Ala His
65                  70                  75                  80

Met Glu Leu Arg Ser Leu Thr Ser Glu Asp Ser Ala Val Tyr Tyr Cys
                85                  90                  95
```

```
Ala Arg Val Leu Phe Leu Asp Phe Asp Asp Pro Tyr Leu Met Asp Tyr
            100                 105                 110

Trp Gly Gln Gly Thr Ser Val Thr Val Ser Ser
        115                 120
```

<210> SEQ ID NO 45
<211> LENGTH: 482
<212> TYPE: PRT
<213> ORGANISM: Artificial Sequence
<220> FEATURE:
<223> OTHER INFORMATION: Synthesized

<400> SEQUENCE: 45

```
Met Ala Leu Pro Val Thr Ala Leu Leu Leu Pro Leu Ala Leu Leu Leu
1               5                   10                  15

His Ala Ala Arg Pro Ser Ser Glu Leu Thr Gln Asp Pro Ala Val Ser
            20                  25                  30

Val Ala Leu Gly Gln Thr Val Arg Ile Thr Cys Arg Gly Asp Ser Leu
        35                  40                  45

Arg Lys Tyr Tyr Ala Ser Trp Tyr Gln Gln Lys Pro Arg Gln Ala Pro
50              55                  60

Gln Leu Val Ile Tyr His Lys Asn Asn Arg Ala Ser Gly Ile Pro Asp
65                  70                  75                  80

Arg Phe Ser Gly Ser Ile Ser Gly Asn Thr Ala Ser Leu Thr Ile Thr
                85                  90                  95

Gly Ala Gln Ala Glu Asp Glu Ala Ala Tyr Phe Cys Asn Ser Arg Asp
            100                 105                 110

Thr Ser Gly Asn Tyr Leu Val Phe Gly Gly Gly Thr Lys Val Thr Val
        115                 120                 125

Leu Gly Gly Gly Gly Ser Gly Gly Gly Ser Gly Gly Gly Gly
130                 135                 140

Ser Gln Leu Gln Leu Gln Glu Ser Gly Pro Gly Leu Val Lys Pro Ser
145                 150                 155                 160

Glu Thr Leu Ser Leu Thr Cys Ala Val Ser Gly Ala Ser Ile Ser Asn
                165                 170                 175

Trp Trp Ser Trp Val Arg Gln Pro Pro Gly Lys Gly Leu Glu Trp Ile
            180                 185                 190

Gly Glu Val His His Ser Gly Val Thr Thr Tyr Lys Pro Ser Leu Lys
        195                 200                 205

Ser Arg Val Thr Ile Ser Val Asp Asn Ser Lys Asn Gln Leu Ser Leu
210                 215                 220

Lys Leu Thr Ser Val Thr Ala Ala Asp Thr Ala Val Tyr Tyr Cys Ala
225                 230                 235                 240

Arg Glu Phe Ala Asp Asp Ala Phe Asp Ile Trp Gly Arg Gly Thr Met
                245                 250                 255

Val Thr Val Thr Thr Pro Ala Pro Arg Pro Pro Thr Pro Ala Pro
            260                 265                 270

Thr Ile Ala Ser Gln Pro Leu Ser Leu Arg Pro Glu Ala Cys Arg Pro
        275                 280                 285

Ala Ala Gly Gly Ala Val His Thr Arg Gly Leu Asp Phe Ala Cys Asp
    290                 295                 300

Ile Tyr Ile Trp Ala Pro Leu Ala Gly Thr Cys Gly Val Leu Leu Leu
305                 310                 315                 320

Ser Leu Val Ile Thr Leu Tyr Cys Lys Arg Gly Arg Lys Lys Leu Leu
                325                 330                 335
```

```
Tyr Ile Phe Lys Gln Pro Phe Met Arg Pro Val Gln Thr Thr Gln Glu
            340                 345                 350

Glu Asp Gly Cys Ser Cys Arg Phe Pro Glu Glu Glu Gly Gly Cys
        355                 360                 365

Glu Leu Arg Val Lys Phe Ser Arg Ser Ala Asp Ala Pro Ala Tyr Lys
    370                 375                 380

Gln Gly Gln Asn Gln Leu Tyr Asn Glu Leu Asn Leu Gly Arg Arg Glu
385                 390                 395                 400

Glu Tyr Asp Val Leu Asp Lys Arg Gly Arg Asp Pro Glu Met Gly
            405                 410                 415

Gly Lys Pro Arg Arg Lys Asn Pro Gln Glu Gly Leu Tyr Asn Glu Leu
            420                 425                 430

Gln Lys Asp Lys Met Ala Glu Ala Tyr Ser Glu Ile Gly Met Lys Gly
            435                 440                 445

Glu Arg Arg Arg Gly Lys Gly His Asp Gly Leu Tyr Gln Gly Leu Ser
        450                 455                 460

Thr Ala Thr Lys Asp Thr Tyr Asp Ala Leu His Met Gln Ala Leu Pro
465                 470                 475                 480

Pro Arg

<210> SEQ ID NO 46
<211> LENGTH: 238
<212> TYPE: PRT
<213> ORGANISM: Artificial Sequence
<220> FEATURE:
<223> OTHER INFORMATION: Synthesized

<400> SEQUENCE: 46

Ser Ser Glu Leu Thr Gln Asp Pro Ala Val Ser Val Ala Leu Gly Gln
1               5                   10                  15

Thr Val Arg Ile Thr Cys Arg Gly Asp Ser Leu Arg Lys Tyr Tyr Ala
            20                  25                  30

Ser Trp Tyr Gln Gln Lys Pro Arg Gln Ala Pro Gln Leu Val Ile Tyr
        35                  40                  45

His Lys Asn Asn Arg Ala Ser Gly Ile Pro Asp Arg Phe Ser Gly Ser
    50                  55                  60

Ile Ser Gly Asn Thr Ala Ser Leu Thr Ile Thr Gly Ala Gln Ala Glu
65                  70                  75                  80

Asp Glu Ala Ala Tyr Phe Cys Asn Ser Arg Asp Thr Ser Gly Asn Tyr
                85                  90                  95

Leu Val Phe Gly Gly Gly Thr Lys Val Thr Val Leu Gly Gly Gly Gly
            100                 105                 110

Gly Ser Gly Gly Gly Gly Ser Gly Gly Gly Ser Gln Leu Gln Leu
        115                 120                 125

Gln Glu Ser Gly Pro Gly Leu Val Lys Pro Ser Glu Thr Leu Ser Leu
130                 135                 140

Thr Cys Ala Val Ser Gly Ala Ser Ile Ser Asn Trp Trp Ser Trp Val
145                 150                 155                 160

Arg Gln Pro Pro Gly Lys Gly Leu Glu Trp Ile Gly Glu Val His His
            165                 170                 175

Ser Gly Val Thr Thr Tyr Lys Pro Ser Leu Lys Ser Arg Val Thr Ile
            180                 185                 190

Ser Val Asp Asn Ser Lys Asn Gln Leu Ser Leu Lys Leu Thr Ser Val
        195                 200                 205

Thr Ala Ala Asp Thr Ala Val Tyr Tyr Cys Ala Arg Glu Phe Ala Asp
```

```
                    210                 215                 220
Asp Ala Phe Asp Ile Trp Gly Arg Gly Thr Met Val Thr Val
225                 230                 235

<210> SEQ ID NO 47
<211> LENGTH: 109
<212> TYPE: PRT
<213> ORGANISM: Artificial Sequence
<220> FEATURE:
<223> OTHER INFORMATION: Synthesized

<400> SEQUENCE: 47

Ser Ser Glu Leu Thr Gln Asp Pro Ala Val Ser Val Ala Leu Gly Gln
1               5                   10                  15

Thr Val Arg Ile Thr Cys Arg Gly Asp Ser Leu Arg Lys Tyr Tyr Ala
            20                  25                  30

Ser Trp Tyr Gln Gln Lys Pro Arg Gln Ala Pro Gln Leu Val Ile Tyr
        35                  40                  45

His Lys Asn Asn Arg Ala Ser Gly Ile Pro Asp Arg Phe Ser Gly Ser
    50                  55                  60

Ile Ser Gly Asn Thr Ala Ser Leu Thr Ile Thr Gly Ala Gln Ala Glu
65                  70                  75                  80

Asp Glu Ala Ala Tyr Phe Cys Asn Ser Arg Asp Thr Ser Gly Asn Tyr
                85                  90                  95

Leu Val Phe Gly Gly Gly Thr Lys Val Thr Val Leu Gly
            100                 105

<210> SEQ ID NO 48
<211> LENGTH: 114
<212> TYPE: PRT
<213> ORGANISM: Artificial Sequence
<220> FEATURE:
<223> OTHER INFORMATION: Synthesized

<400> SEQUENCE: 48

Gln Leu Gln Leu Gln Glu Ser Gly Pro Gly Leu Val Lys Pro Ser Glu
1               5                   10                  15

Thr Leu Ser Leu Thr Cys Ala Val Ser Gly Ala Ser Ile Ser Asn Trp
            20                  25                  30

Trp Ser Trp Val Arg Gln Pro Pro Gly Lys Gly Leu Glu Trp Ile Gly
        35                  40                  45

Glu Val His His Ser Gly Val Thr Thr Tyr Lys Pro Ser Leu Lys Ser
    50                  55                  60

Arg Val Thr Ile Ser Val Asp Asn Ser Lys Asn Gln Leu Ser Leu Lys
65                  70                  75                  80

Leu Thr Ser Val Thr Ala Ala Asp Thr Ala Val Tyr Tyr Cys Ala Arg
                85                  90                  95

Glu Phe Ala Asp Asp Ala Phe Asp Ile Trp Gly Arg Gly Thr Met Val
            100                 105                 110

Thr Val

<210> SEQ ID NO 49
<211> LENGTH: 250
<212> TYPE: PRT
<213> ORGANISM: Artificial Sequence
<220> FEATURE:
<223> OTHER INFORMATION: Synthesized

<400> SEQUENCE: 49
```

Asp Ile Val Met Thr Gln Ser Pro Leu Ser Leu Pro Val Thr Pro Gly
1               5                   10                  15

Glu Pro Ala Ser Ile Ser Cys Arg Ser Thr Lys Ser Leu Leu His Ser
            20                  25                  30

Asn Gly Asn Thr Tyr Leu Tyr Trp Tyr Leu Gln Lys Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Asp Phe Thr Leu Lys Ile
65              70                  75                  80

Ser Arg Val Glu Ala Glu Asp Val Gly Val Tyr Tyr Cys Met Gln His
                85                  90                  95

Leu Glu Tyr Pro Phe Thr Phe Gly Gly Gly Thr Lys Val Glu Ile Lys
            100                 105                 110

Gly Gly Gly Gly Ser Gly Gly Gly Gly Ser Gly Gly Gly Gly Ser Glu
        115                 120                 125

Ile Gln Leu Gln Gln Ser Gly Ala Glu Val Lys Lys Pro Gly Ser Ser
    130                 135                 140

Val Lys Val Ser Cys Lys Ala Ser Gly Tyr Thr Phe Thr Asp Tyr Asp
145                 150                 155                 160

Met His Trp Val Arg Gln Ala Pro Gly Gln Gly Leu Glu Trp Met Gly
                165                 170                 175

Thr Ile Asp Pro Glu Thr Gly Gly Thr Ala Tyr Asn Gln Lys Phe Lys
            180                 185                 190

Gly Arg Val Thr Ile Thr Ala Asp Lys Ser Thr Ser Thr Ala Tyr Met
        195                 200                 205

Glu Leu Ser Ser Leu Arg Ser Glu Asp Thr Ala Val Tyr Tyr Cys Thr
    210                 215                 220

Ser Phe Tyr Tyr Thr Tyr Ser Asn Tyr Asp Val Gly Phe Ala Tyr Trp
225                 230                 235                 240

Gly Gln Gly Thr Leu Val Thr Val Ser Ser
            245                 250

<210> SEQ ID NO 50
<211> LENGTH: 250
<212> TYPE: PRT
<213> ORGANISM: Artificial Sequence
<220> FEATURE:
<223> OTHER INFORMATION: Synthesized

<400> SEQUENCE: 50

Asp Ile Val Met Thr Gln Ser Pro Leu Ser Leu Pro Val Thr Pro Gly
1               5                   10                  15

Glu Pro Ala Ser Ile Ser Cys Arg Ser Thr Lys Ser Leu Leu His Ser
            20                  25                  30

Asn Gly Asn Thr Tyr Leu Tyr Trp Tyr Leu Gln Lys Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Asp Phe Thr Leu Lys Ile
65              70                  75                  80

Ser Arg Val Glu Ala Glu Asp Val Gly Val Tyr Tyr Cys Met Gln His
                85                  90                  95

Leu Glu Tyr Pro Phe Thr Phe Gly Gly Gly Thr Lys Val Glu Ile Lys
            100                 105                 110

Gly Gly Gly Gly Ser Gly Gly Gly Ser Gly Gly Gly Ser Glu
            115                 120                 125

Ile Gln Leu Gln Gln Ser Gly Ala Glu Val Lys Lys Pro Gly Ser Ser
        130                 135                 140

Val Lys Val Ser Cys Lys Ala Ser Gly Tyr Thr Phe Thr Asp Tyr Asp
145                 150                 155                 160

Met His Trp Val Arg Gln Ala Pro Gln Gly Leu Glu Trp Ile Gly
                165                 170                 175

Thr Ile Asp Pro Glu Thr Gly Gly Thr Ala Tyr Asn Gln Lys Phe Lys
            180                 185                 190

Gly Arg Ala Thr Leu Thr Ala Asp Arg Ser Thr Ser Thr Ala Tyr Met
    195                 200                 205

Glu Leu Ser Ser Leu Arg Ser Glu Asp Thr Ala Val Tyr Tyr Cys Thr
    210                 215                 220

Ser Phe Tyr Tyr Thr Tyr Ser Asn Tyr Asp Val Gly Phe Ala Tyr Trp
225                 230                 235                 240

Gly Gln Gly Thr Leu Val Thr Val Ser Ser
            245                 250

<210> SEQ ID NO 51
<211> LENGTH: 250
<212> TYPE: PRT
<213> ORGANISM: Artificial Sequence
<220> FEATURE:
<223> OTHER INFORMATION: Synthesized

<400> SEQUENCE: 51

Asp Ile Val Met Thr Gln Ser Pro Leu Ser Leu Pro Val Thr Pro Gly
1               5                   10                  15

Glu Pro Ala Ser Ile Ser Cys Arg Ser Thr Lys Ser Leu Leu His Ser
            20                  25                  30

Asn Gly Asn Thr Tyr Leu Tyr Trp Tyr Leu Gln Lys Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Gly Gly Thr Lys Val Glu Ile Lys
            100                 105                 110

Gly Gly Gly Gly Ser Gly Gly Gly Ser Gly Gly Gly Ser Glu
            115                 120                 125

Ile Gln Leu Gln Gln Ser Gly Ala Glu Val Lys Lys Pro Gly Ser Ser
        130                 135                 140

Val Lys Val Ser Cys Lys Ala Ser Gly Tyr Thr Phe Thr Asp Tyr Asp
145                 150                 155                 160

Met His Trp Val Lys Gln Ala Pro Gly Gln Gly Leu Glu Trp Ile Gly
                165                 170                 175

Thr Ile Asp Pro Glu Thr Gly Gly Thr Ala Tyr Asn Gln Lys Phe Lys
            180                 185                 190

Gly Lys Ala Thr Leu Thr Ala Asp Arg Ser Thr Ser Thr Ala Tyr Met
    195                 200                 205

Glu Leu Ser Ser Leu Arg Ser Glu Asp Thr Ala Val Tyr Tyr Cys Thr
    210                 215                 220

```
Ser Phe Tyr Tyr Thr Tyr Ser Asn Tyr Asp Val Gly Phe Ala Tyr Trp
225                 230                 235                 240

Gly Gln Gly Thr Leu Val Thr Val Ser Ser
            245                 250
```

<210> SEQ ID NO 52
<211> LENGTH: 250
<212> TYPE: PRT
<213> ORGANISM: Artificial Sequence
<220> FEATURE:
<223> OTHER INFORMATION: Synthesized

<400> SEQUENCE: 52

```
Asp Ile Val Met Thr Gln Ser Pro Leu Ser Leu Pro Val Thr Pro Gly
1               5                   10                  15

Glu Pro Ala Ser Ile Ser Cys Arg Ser Thr Lys Ser Leu Leu His Ser
            20                  25                  30

Asn Gly Asn Thr Tyr Leu Tyr Trp Tyr Leu Gln Lys Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Gly Gly Thr Lys Val Glu Ile Lys
            100                 105                 110

Gly Gly Gly Gly Ser Gly Gly Gly Ser Gly Gly Gly Gly Ser Glu
        115                 120                 125

Ile Gln Leu Gln Gln Ser Gly Ala Glu Val Lys Lys Pro Gly Ser Ser
    130                 135                 140

Val Lys Val Ser Cys Lys Ala Ser Gly Tyr Thr Phe Thr Asp Tyr Asp
145                 150                 155                 160

Met His Trp Val Lys Gln Ala Pro Gly His Gly Leu Glu Trp Ile Gly
                165                 170                 175

Thr Ile Asp Pro Glu Thr Gly Gly Thr Ala Tyr Asn Gln Lys Phe Lys
            180                 185                 190

Gly Lys Ala Thr Leu Thr Ala Asp Arg Ser Thr Ser Thr Ala Tyr Met
        195                 200                 205

Glu Leu Ser Ser Leu Thr Ser Glu Asp Thr Ala Val Tyr Tyr Cys Thr
    210                 215                 220

Ser Phe Tyr Tyr Thr Tyr Ser Asn Tyr Asp Val Gly Phe Ala Tyr Trp
225                 230                 235                 240

Gly Gln Gly Thr Leu Val Thr Val Ser Ser
            245                 250
```

<210> SEQ ID NO 53
<211> LENGTH: 250
<212> TYPE: PRT
<213> ORGANISM: Artificial Sequence
<220> FEATURE:
<223> OTHER INFORMATION: Synthesized

<400> SEQUENCE: 53

```
Asp Ile Val Met Thr Gln Ser Pro Leu Ser Leu Pro Val Thr Pro Gly
1               5                   10                  15

Glu Pro Ala Ser Ile Ser Cys Arg Ser Thr Lys Ser Leu Leu His Ser
            20                  25                  30
```

Asn Gly Asn Thr Tyr Leu Tyr Trp Phe Leu Gln Lys Pro Gly Gln Ser
            35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Gly Gly Thr Lys Val Glu Ile Lys
            100                 105                 110

Gly Gly Gly Gly Ser Gly Gly Gly Gly Ser Gly Gly Gly Gly Ser Glu
            115                 120                 125

Ile Gln Leu Gln Gln Ser Gly Ala Glu Val Lys Lys Pro Gly Ser Ser
    130                 135                 140

Val Lys Val Ser Cys Lys Ala Ser Gly Tyr Thr Phe Thr Asp Tyr Asp
145                 150                 155                 160

Met His Trp Val Arg Gln Ala Pro Gly Gln Gly Leu Glu Trp Met Gly
                165                 170                 175

Thr Ile Asp Pro Glu Thr Gly Gly Thr Ala Tyr Asn Gln Lys Phe Lys
            180                 185                 190

Gly Arg Val Thr Ile Thr Ala Asp Lys Ser Thr Ser Thr Ala Tyr Met
            195                 200                 205

Glu Leu Ser Ser Leu Arg Ser Glu Asp Thr Ala Val Tyr Tyr Cys Thr
    210                 215                 220

Ser Phe Tyr Tyr Thr Tyr Ser Asn Tyr Asp Val Gly Phe Ala Tyr Trp
225                 230                 235                 240

Gly Gln Gly Thr Leu Val Thr Val Ser Ser
            245                 250

<210> SEQ ID NO 54
<211> LENGTH: 250
<212> TYPE: PRT
<213> ORGANISM: Artificial Sequence
<220> FEATURE:
<223> OTHER INFORMATION: Synthesized

<400> SEQUENCE: 54

Asp Ile Val Met Thr Gln Ser Pro Leu Ser Leu Pro Val Thr Pro Gly
1               5                   10                  15

Glu Pro Ala Ser Ile Ser Cys Arg Ser Thr Lys Ser Leu Leu His Ser
            20                  25                  30

Asn Gly Asn Thr Tyr Leu Tyr Trp Phe Leu Gln Lys Pro Gly Gln Ser
            35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Gly Gly Thr Lys Val Glu Ile Lys
            100                 105                 110

Gly Gly Gly Gly Ser Gly Gly Gly Gly Ser Gly Gly Gly Gly Ser Glu
            115                 120                 125

Ile Gln Leu Gln Gln Ser Gly Ala Glu Val Lys Lys Pro Gly Ser Ser
    130                 135                 140

```
Val Lys Val Ser Cys Lys Ala Ser Gly Tyr Thr Phe Thr Asp Tyr Asp
145                 150                 155                 160

Met His Trp Val Arg Gln Ala Pro Gly Gln Gly Leu Glu Trp Ile Gly
                165                 170                 175

Thr Ile Asp Pro Glu Thr Gly Gly Thr Ala Tyr Asn Gln Lys Phe Lys
            180                 185                 190

Gly Arg Ala Thr Leu Thr Ala Asp Arg Ser Thr Ser Thr Ala Tyr Met
        195                 200                 205

Glu Leu Ser Ser Leu Arg Ser Glu Asp Thr Ala Val Tyr Tyr Cys Thr
    210                 215                 220

Ser Phe Tyr Tyr Thr Tyr Ser Asn Tyr Asp Val Gly Phe Ala Tyr Trp
225                 230                 235                 240

Gly Gln Gly Thr Leu Val Thr Val Ser Ser
            245                 250

<210> SEQ ID NO 55
<211> LENGTH: 250
<212> TYPE: PRT
<213> ORGANISM: Artificial Sequence
<220> FEATURE:
<223> OTHER INFORMATION: Synthesized

<400> SEQUENCE: 55

Asp Ile Val Met Thr Gln Ser Pro Leu Ser Leu Pro Val Thr Pro Gly
1               5                   10                  15

Glu Pro Ala Ser Ile Ser Cys Arg Ser Thr Lys Ser Leu Leu His Ser
            20                  25                  30

Asn Gly Asn Thr Tyr Leu Tyr Trp Phe Leu Gln Lys Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Gly Gly Thr Lys Val Glu Ile Lys
            100                 105                 110

Gly Gly Gly Gly Ser Gly Gly Gly Ser Gly Gly Gly Gly Ser Glu
        115                 120                 125

Ile Gln Leu Gln Gln Ser Gly Ala Glu Val Lys Lys Pro Gly Ser Ser
    130                 135                 140

Val Lys Val Ser Cys Lys Ala Ser Gly Tyr Thr Phe Thr Asp Tyr Asp
145                 150                 155                 160

Met His Trp Val Lys Gln Ala Pro Gly Gln Gly Leu Glu Trp Ile Gly
                165                 170                 175

Thr Ile Asp Pro Glu Thr Gly Gly Thr Ala Tyr Asn Gln Lys Phe Lys
            180                 185                 190

Gly Lys Ala Thr Leu Thr Ala Asp Arg Ser Thr Ser Thr Ala Tyr Met
        195                 200                 205

Glu Leu Ser Ser Leu Arg Ser Glu Asp Thr Ala Val Tyr Tyr Cys Thr
    210                 215                 220

Ser Phe Tyr Tyr Thr Tyr Ser Asn Tyr Asp Val Gly Phe Ala Tyr Trp
225                 230                 235                 240

Gly Gln Gly Thr Leu Val Thr Val Ser Ser
            245                 250
```

<210> SEQ ID NO 56
<211> LENGTH: 250
<212> TYPE: PRT
<213> ORGANISM: Artificial Sequence
<220> FEATURE:
<223> OTHER INFORMATION: Synthesized

<400> SEQUENCE: 56

```
Asp Ile Val Met Thr Gln Ser Pro Leu Ser Leu Pro Val Thr Pro Gly
1               5                   10                  15

Glu Pro Ala Ser Ile Ser Cys Arg Ser Thr Lys Ser Leu Leu His Ser
            20                  25                  30

Asn Gly Asn Thr Tyr Leu Tyr Trp Phe Leu Gln Lys Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Gly Gly Thr Lys Val Glu Ile Lys
            100                 105                 110

Gly Gly Gly Gly Ser Gly Gly Gly Ser Gly Gly Gly Gly Ser Glu
            115                 120                 125

Ile Gln Leu Gln Gln Ser Gly Ala Glu Val Lys Lys Pro Gly Ser Ser
    130                 135                 140

Val Lys Val Ser Cys Lys Ala Ser Gly Tyr Thr Phe Thr Asp Tyr Asp
145                 150                 155                 160

Met His Trp Val Lys Gln Ala Pro Gly His Gly Leu Glu Trp Ile Gly
                165                 170                 175

Thr Ile Asp Pro Glu Thr Gly Gly Thr Ala Tyr Asn Gln Lys Phe Lys
            180                 185                 190

Gly Lys Ala Thr Leu Thr Ala Asp Arg Ser Thr Ser Thr Ala Tyr Met
        195                 200                 205

Glu Leu Ser Ser Leu Thr Ser Glu Asp Thr Ala Val Tyr Tyr Cys Thr
    210                 215                 220

Ser Phe Tyr Tyr Thr Tyr Ser Asn Tyr Asp Val Gly Phe Ala Tyr Trp
225                 230                 235                 240

Gly Gln Gly Thr Leu Val Thr Val Ser Ser
                245                 250
```

<210> SEQ ID NO 57
<211> LENGTH: 112
<212> TYPE: PRT
<213> ORGANISM: Artificial Sequence
<220> FEATURE:
<223> OTHER INFORMATION: Synthesized

<400> SEQUENCE: 57

```
Asp Ile Val Met Thr Gln Ser Pro Leu Ser Leu Pro Val Thr Pro Gly
1               5                   10                  15

Glu Pro Ala Ser Ile Ser Cys Arg Ser Thr Lys Ser Leu Leu His Ser
            20                  25                  30

Asn Gly Asn Thr Tyr Leu Tyr Trp Tyr Leu Gln Lys Pro Gly Gln Ser
        35                  40                  45

Pro Gln Leu Leu Ile Tyr Arg Met Ser Asn Leu Ala Ser Gly Val Pro
```

```
                    50                  55                  60
Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln His
                     85                  90                  95

Leu Glu Tyr Pro Phe Thr Phe Gly Gly Gly Thr Lys Val Glu Ile Lys
                100                 105                 110
```

<210> SEQ ID NO 58
<211> LENGTH: 112
<212> TYPE: PRT
<213> ORGANISM: Artificial Sequence
<220> FEATURE:
<223> OTHER INFORMATION: Synthesized

<400> SEQUENCE: 58

```
Asp Ile Val Met Thr Gln Ser Pro Leu Ser Leu Pro Val Thr Pro Gly
 1               5                  10                  15

Glu Pro Ala Ser Ile Ser Cys Arg Ser Thr Lys Ser Leu Leu His Ser
                 20                  25                  30

Asn Gly Asn Thr Tyr Leu Tyr Trp Phe Leu Gln Lys Pro Gly Gln Ser
             35                  40                  45

Pro Gln Leu Leu Ile Tyr Arg Met Ser Asn Leu Ala Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln His
                     85                  90                  95

Leu Glu Tyr Pro Phe Thr Phe Gly Gly Gly Thr Lys Val Glu Ile Lys
                100                 105                 110
```

<210> SEQ ID NO 59
<211> LENGTH: 123
<212> TYPE: PRT
<213> ORGANISM: Artificial Sequence
<220> FEATURE:
<223> OTHER INFORMATION: Synthesized

<400> SEQUENCE: 59

```
Glu Ile Gln Leu Gln Gln Ser Gly Ala Glu Val Lys Lys Pro Gly Ser
 1               5                  10                  15

Ser Val Lys Val Ser Cys Lys Ala Ser Gly Tyr Thr Phe Thr Asp Tyr
                 20                  25                  30

Asp Met His Trp Val Arg Gln Ala Pro Gly Gln Gly Leu Glu Trp Met
             35                  40                  45

Gly Thr Ile Asp Pro Glu Thr Gly Gly Thr Ala Tyr Asn Gln Lys Phe
 50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                     85                  90                  95

Thr Ser Phe Tyr Tyr Thr Tyr Ser Asn Tyr Asp Val Gly Phe Ala Tyr
                100                 105                 110

Trp Gly Gln Gly Thr Leu Val Thr Val Ser Ser
                115                 120
```

<210> SEQ ID NO 60
<211> LENGTH: 123

```
<212> TYPE: PRT
<213> ORGANISM: Artificial Sequence
<220> FEATURE:
<223> OTHER INFORMATION: Synthesized

<400> SEQUENCE: 60

Glu Ile Gln Leu Gln Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
                20                  25                  30

Asp Met His Trp Val Arg Gln Ala Pro Gly Gln Gly Leu Glu Trp Ile
            35                  40                  45

Gly Thr Ile Asp Pro Glu Thr Gly Gly Thr Ala Tyr Asn Gln Lys Phe
    50                  55                  60

Lys Gly Arg Ala Thr Leu Thr Ala Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Ser Phe Tyr Tyr Thr Tyr Ser Asn Tyr Asp Val Gly Phe Ala Tyr
                100                 105                 110

Trp Gly Gln Gly Thr Leu Val Thr Val Ser Ser
            115                 120

<210> SEQ ID NO 61
<211> LENGTH: 123
<212> TYPE: PRT
<213> ORGANISM: Artificial Sequence
<220> FEATURE:
<223> OTHER INFORMATION: Synthesized

<400> SEQUENCE: 61

Glu Ile Gln Leu Gln Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
                20                  25                  30

Asp Met His Trp Val Lys Gln Ala Pro Gly Gln Gly Leu Glu Trp Ile
            35                  40                  45

Gly Thr Ile Asp Pro Glu Thr Gly Gly Thr Ala Tyr Asn Gln Lys Phe
    50                  55                  60

Lys Gly Lys Ala Thr Leu Thr Ala Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Ser Phe Tyr Tyr Thr Tyr Ser Asn Tyr Asp Val Gly Phe Ala Tyr
                100                 105                 110

Trp Gly Gln Gly Thr Leu Val Thr Val Ser Ser
            115                 120

<210> SEQ ID NO 62
<211> LENGTH: 123
<212> TYPE: PRT
<213> ORGANISM: Artificial Sequence
<220> FEATURE:
<223> OTHER INFORMATION: Synthesized

<400> SEQUENCE: 62

Glu Ile Gln Leu Gln Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
                20                  25                  30
```

```
                    20                  25                  30
Asp Met His Trp Val Lys Gln Ala Pro Gly His Gly Leu Glu Trp Ile
                35                  40                  45

Gly Thr Ile Asp Pro Glu Thr Gly Gly Thr Ala Tyr Asn Gln Lys Phe
            50                  55                  60

Lys Gly Lys Ala Thr Leu Thr Ala Asp Arg Ser Thr Ser Thr Ala Tyr
 65                 70                  75                  80

Met Glu Leu Ser Ser Leu Thr Ser Glu Asp Thr Ala Val Tyr Tyr Cys
                85                  90                  95

Thr Ser Phe Tyr Tyr Thr Tyr Ser Asn Tyr Asp Val Gly Phe Ala Tyr
                100                 105                 110

Trp Gly Gln Gly Thr Leu Val Thr Val Ser Ser
                115                 120

<210> SEQ ID NO 63
<211> LENGTH: 482
<212> TYPE: PRT
<213> ORGANISM: Artificial Sequence
<220> FEATURE:
<223> OTHER INFORMATION: Synthesized

<400> SEQUENCE: 63

Met Ala Leu Pro Val Thr Ala Leu Leu Leu Pro Leu Ala Leu Leu Leu
 1               5                  10                  15

His Ala Ala Arg Pro Asp Ile Gln Met Thr Gln Ser Pro Ser Ser Leu
                20                  25                  30

Ser Ala Ser Val Gly Asp Arg Val Thr Ile Thr Cys Lys Ala Ser Asp
                35                  40                  45

Leu Ile His Asn Trp Leu Ala Trp Tyr Gln Gln Lys Pro Gly Lys Ala
            50                  55                  60

Pro Lys Leu Leu Ile Tyr Gly Ala Thr Ser Leu Glu Thr Gly Val Pro
 65                 70                  75                  80

Ser Arg Phe Ser Gly Ser Gly Ser Gly Thr Asp Phe Thr Leu Thr Ile
                85                  90                  95

Ser Ser Leu Gln Pro Glu Asp Phe Ala Thr Tyr Tyr Cys Gln Gln Tyr
                100                 105                 110

Trp Thr Thr Pro Phe Thr Phe Gly Gln Gly Thr Lys Val Glu Ile Lys
                115                 120                 125

Gly Gly Gly Gly Ser Gly Gly Gly Ser Gly Gly Gly Gly Ser Glu
            130                 135                 140

Val Gln Leu Val Glu Ser Gly Gly Leu Val Gln Pro Gly Gly Ser
145                 150                 155                 160

Leu Arg Leu Ser Cys Ala Ala Ser Gly Tyr Ser Ile Thr Asn Asp Tyr
                165                 170                 175

Ala Trp Asn Trp Val Arg Gln Ala Pro Gly Lys Gly Leu Glu Trp Val
            180                 185                 190

Gly Tyr Ile Ser Tyr Ser Gly Tyr Thr Thr Tyr Asn Pro Ser Leu Lys
            195                 200                 205

Ser Arg Phe Thr Ile Ser Arg Asp Thr Ser Lys Asn Thr Leu Tyr Leu
            210                 215                 220

Gln Met Asn Ser Leu Arg Ala Glu Asp Thr Ala Val Tyr Tyr Cys Ala
225                 230                 235                 240

Arg Trp Thr Ser Gly Leu Asp Tyr Trp Gly Gln Gly Thr Leu Val Thr
                245                 250                 255

Val Ser Ser Thr Thr Thr Pro Ala Pro Arg Pro Pro Thr Pro Ala Pro
```

```
            260                 265                 270
Thr Ile Ala Ser Gln Pro Leu Ser Leu Arg Pro Glu Ala Cys Arg Pro
            275                 280                 285

Ala Ala Gly Gly Ala Val His Thr Arg Gly Leu Asp Phe Ala Cys Asp
        290                 295                 300

Ile Tyr Ile Trp Ala Pro Leu Ala Gly Thr Cys Gly Val Leu Leu Leu
305                 310                 315                 320

Ser Leu Val Ile Thr Leu Tyr Cys Lys Arg Gly Arg Lys Lys Leu Leu
                325                 330                 335

Tyr Ile Phe Lys Gln Pro Phe Met Arg Pro Val Gln Thr Thr Gln Glu
                340                 345                 350

Glu Asp Gly Cys Ser Cys Arg Phe Pro Glu Glu Glu Glu Gly Gly Cys
            355                 360                 365

Glu Leu Arg Val Lys Phe Ser Arg Ser Ala Asp Ala Pro Ala Tyr Lys
        370                 375                 380

Gln Gly Gln Asn Gln Leu Tyr Asn Glu Leu Asn Leu Gly Arg Arg Glu
385                 390                 395                 400

Glu Tyr Asp Val Leu Asp Lys Arg Arg Gly Arg Asp Pro Glu Met Gly
                405                 410                 415

Gly Lys Pro Arg Arg Lys Asn Pro Gln Glu Gly Leu Tyr Asn Glu Leu
                420                 425                 430

Gln Lys Asp Lys Met Ala Glu Ala Tyr Ser Glu Ile Gly Met Lys Gly
            435                 440                 445

Glu Arg Arg Arg Gly Lys Gly His Asp Gly Leu Tyr Gln Gly Leu Ser
        450                 455                 460

Thr Ala Thr Lys Asp Thr Tyr Asp Ala Leu His Met Gln Ala Leu Pro
465                 470                 475                 480

Pro Arg

<210> SEQ ID NO 64
<211> LENGTH: 238
<212> TYPE: PRT
<213> ORGANISM: Artificial Sequence
<220> FEATURE:
<223> OTHER INFORMATION: Synthesized

<400> SEQUENCE: 64

Asp Ile Gln Met Thr Gln Ser Pro Ser Ser Leu Ser Ala Ser Val Gly
1               5                   10                  15

Asp Arg Val Thr Ile Thr Cys Lys Ala Ser Asp Leu Ile His Asn Trp
            20                  25                  30

Leu Ala Trp Tyr Gln Gln Lys Pro Gly Lys Ala Pro Lys Leu Leu Ile
        35                  40                  45

Tyr Gly Ala Thr Ser Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Trp Thr Thr Pro Phe
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Ser Glu Val Gln Leu Val Glu
        115                 120                 125

Ser Gly Gly Gly Leu Val Gln Pro Gly Gly Ser Leu Arg Leu Ser Cys
    130                 135                 140
```

```
Ala Ala Ser Gly Tyr Ser Ile Thr Asn Asp Tyr Ala Trp Asn Trp Val
145                 150                 155                 160

Arg Gln Ala Pro Gly Lys Gly Leu Glu Trp Val Gly Tyr Ile Ser Tyr
                165                 170                 175

Ser Gly Tyr Thr Thr Tyr Asn Pro Ser Leu Lys Ser Arg Phe Thr Ile
            180                 185                 190

Ser Arg Asp Thr Ser Lys Asn Thr Leu Tyr Leu Gln Met Asn Ser Leu
        195                 200                 205

Arg Ala Glu Asp Thr Ala Val Tyr Tyr Cys Ala Arg Trp Thr Ser Gly
    210                 215                 220

Leu Asp Tyr Trp Gly Gln Gly Thr Leu Val Thr Val Ser Ser
225                 230                 235
```

<210> SEQ ID NO 65
<211> LENGTH: 107
<212> TYPE: PRT
<213> ORGANISM: Artificial Sequence
<220> FEATURE:
<223> OTHER INFORMATION: Synthesized

<400> SEQUENCE: 65

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Asp Leu Ile His Asn Trp
            20                  25                  30

Leu Ala Trp Tyr Gln Gln Lys Pro Gly Lys Ala Pro Lys Leu Leu Ile
        35                  40                  45

Tyr Gly Ala Thr Ser Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Trp Thr Thr Pro Phe
                85                  90                  95

Thr Phe Gly Gln Gly Thr Lys Val Glu Ile Lys
            100                 105
```

<210> SEQ ID NO 66
<211> LENGTH: 116
<212> TYPE: PRT
<213> ORGANISM: Artificial Sequence
<220> FEATURE:
<223> OTHER INFORMATION: Synthesized

<400> SEQUENCE: 66

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Ile Thr Asn Asp
            20                  25                  30

Tyr Ala Trp Asn Trp Val Arg Gln Ala Pro Gly Lys Gly Leu Glu Trp
        35                  40                  45

Val Gly Tyr Ile Ser Tyr Ser Gly Tyr Thr Thr Tyr Asn Pro Ser Leu
    50                  55                  60

Lys Ser Arg Phe Thr Ile Ser Arg Asp Thr Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Thr Ser Gly Leu Asp Tyr Trp Gly Gln Gly Thr Leu Val
```

```
              100                 105                 110
Thr Val Ser Ser
            115
```

<210> SEQ ID NO 67
<211> LENGTH: 482
<212> TYPE: PRT
<213> ORGANISM: Artificial Sequence
<220> FEATURE:
<223> OTHER INFORMATION: Synthesized

<400> SEQUENCE: 67

```
Met Ala Leu Pro Val Thr Ala Leu Leu Pro Leu Ala Leu Leu Leu
1               5                   10                  15

His Ala Ala Arg Pro Asp Ile Gln Met Thr Gln Ser Ser Phe Leu
            20                  25                  30

Ser Val Ser Leu Gly Gly Arg Val Thr Ile Thr Cys Lys Ala Ser Asp
        35                  40                  45

Leu Ile His Asn Trp Leu Ala Trp Tyr Gln Gln Lys Pro Gly Asn Ala
    50                  55                  60

Pro Arg Leu Leu Ile Ser Gly Ala Thr Ser Leu Glu Thr Gly Val Pro
65                  70                  75                  80

Ser Arg Phe Ser Gly Ser Gly Ser Gly Asn Asp Tyr Thr Leu Ser Ile
                85                  90                  95

Ala Ser Leu Gln Thr Glu Asp Ala Ala Thr Tyr Tyr Cys Gln Gln Tyr
            100                 105                 110

Trp Thr Thr Pro Phe Thr Phe Gly Ser Gly Thr Lys Val Glu Ile Lys
        115                 120                 125

Gly Gly Gly Gly Ser Gly Gly Gly Gly Ser Gly Gly Gly Gly Ser Asp
    130                 135                 140

Val Gln Leu Gln Glu Ser Gly Pro Gly Leu Val Asn Pro Ser Gln Ser
145                 150                 155                 160

Leu Ser Leu Thr Cys Thr Val Thr Gly Tyr Ser Ile Thr Asn Asp Tyr
                165                 170                 175

Ala Trp Asn Trp Ile Arg Gln Phe Pro Gly Asn Lys Leu Glu Trp Met
            180                 185                 190

Gly Tyr Ile Asn Tyr Ser Gly Tyr Thr Thr Tyr Asn Pro Ser Leu Lys
        195                 200                 205

Ser Arg Ile Ser Ile Thr Arg Asp Thr Ser Lys Asn Gln Phe Phe Leu
    210                 215                 220

His Leu Asn Ser Val Thr Thr Glu Asp Thr Ala Thr Tyr Tyr Cys Ala
225                 230                 235                 240

Arg Trp Asp Gly Gly Leu Thr Tyr Trp Gly Gln Gly Thr Leu Val Thr
                245                 250                 255

Val Ser Ala Thr Thr Thr Pro Ala Pro Arg Pro Pro Thr Pro Ala Pro
            260                 265                 270

Thr Ile Ala Ser Gln Pro Leu Ser Leu Arg Pro Glu Ala Cys Arg Pro
        275                 280                 285

Ala Ala Gly Gly Ala Val His Thr Arg Gly Leu Asp Phe Ala Cys Asp
    290                 295                 300

Ile Tyr Ile Trp Ala Pro Leu Ala Gly Thr Cys Gly Val Leu Leu Leu
305                 310                 315                 320

Ser Leu Val Ile Thr Leu Tyr Cys Lys Arg Gly Arg Lys Lys Leu Leu
                325                 330                 335

Tyr Ile Phe Lys Gln Pro Phe Met Arg Pro Val Gln Thr Thr Gln Glu
```

```
             340                 345                 350
Glu Asp Gly Cys Ser Cys Arg Phe Pro Glu Glu Glu Gly Gly Cys
            355                 360                 365

Glu Leu Arg Val Lys Phe Ser Arg Ser Ala Asp Ala Pro Ala Tyr Lys
    370                 375                 380

Gln Gly Gln Asn Gln Leu Tyr Asn Glu Leu Asn Leu Gly Arg Arg Glu
385                 390                 395                 400

Glu Tyr Asp Val Leu Asp Lys Arg Arg Gly Arg Asp Pro Glu Met Gly
                405                 410                 415

Gly Lys Pro Arg Arg Lys Asn Pro Gln Glu Gly Leu Tyr Asn Glu Leu
            420                 425                 430

Gln Lys Asp Lys Met Ala Glu Ala Tyr Ser Glu Ile Gly Met Lys Gly
        435                 440                 445

Glu Arg Arg Arg Gly Lys Gly His Asp Gly Leu Tyr Gln Gly Leu Ser
    450                 455                 460

Thr Ala Thr Lys Asp Thr Tyr Asp Ala Leu His Met Gln Ala Leu Pro
465                 470                 475                 480

Pro Arg

<210> SEQ ID NO 68
<211> LENGTH: 238
<212> TYPE: PRT
<213> ORGANISM: Artificial Sequence
<220> FEATURE:
<223> OTHER INFORMATION: Synthesized

<400> SEQUENCE: 68

Asp Ile Gln Met Thr Gln Ser Ser Ser Phe Leu Ser Val Ser Leu Gly
1               5                   10                  15

Gly Arg Val Thr Ile Thr Cys Lys Ala Ser Asp Leu Ile His Asn Trp
            20                  25                  30

Leu Ala Trp Tyr Gln Gln Lys Pro Gly Asn Ala Pro Arg Leu Leu Ile
        35                  40                  45

Ser Gly Ala Thr Ser Leu Glu Thr Gly Val Pro Ser Arg Phe Ser Gly
    50                  55                  60

Ser Gly Ser Gly Asn Asp Tyr Thr Leu Ser Ile Ala Ser Leu Gln Thr
65                  70                  75                  80

Glu Asp Ala Ala Thr Tyr Tyr Cys Gln Gln Tyr Trp Thr Thr Pro Phe
                85                  90                  95

Thr Phe Gly Ser Gly Thr Lys Val Glu Ile Lys Gly Gly Gly Gly Ser
            100                 105                 110

Gly Gly Gly Gly Ser Gly Gly Gly Ser Asp Val Gln Leu Gln Glu
        115                 120                 125

Ser Gly Pro Gly Leu Val Asn Pro Ser Gln Ser Leu Ser Leu Thr Cys
    130                 135                 140

Thr Val Thr Gly Tyr Ser Ile Thr Asn Asp Tyr Ala Trp Asn Trp Ile
145                 150                 155                 160

Arg Gln Phe Pro Gly Asn Lys Leu Glu Trp Met Gly Tyr Ile Asn Tyr
                165                 170                 175

Ser Gly Tyr Thr Thr Tyr Asn Pro Ser Leu Lys Ser Arg Ile Ser Ile
            180                 185                 190

Thr Arg Asp Thr Ser Lys Asn Gln Phe Phe Leu His Leu Asn Ser Val
        195                 200                 205

Thr Thr Glu Asp Thr Ala Thr Tyr Tyr Cys Ala Arg Trp Asp Gly Gly
    210                 215                 220
```

```
Leu Thr Tyr Trp Gly Gln Gly Thr Leu Val Thr Val Ser Ala
225                 230                 235

<210> SEQ ID NO 69
<211> LENGTH: 107
<212> TYPE: PRT
<213> ORGANISM: Artificial Sequence
<220> FEATURE:
<223> OTHER INFORMATION: Synthesized

<400> SEQUENCE: 69

Asp Ile Gln Met Thr Gln Ser Ser Ser Phe Leu Ser Val Ser Leu Gly
1               5                   10                  15

Gly Arg Val Thr Ile Thr Cys Lys Ala Ser Asp Leu Ile His Asn Trp
            20                  25                  30

Leu Ala Trp Tyr Gln Gln Lys Pro Gly Asn Ala Pro Arg Leu Leu Ile
        35                  40                  45

Ser Gly Ala Thr Ser Leu Glu Thr Gly Val Pro Ser Arg Phe Ser Gly
    50                  55                  60

Ser Gly Ser Gly Asn Asp Tyr Thr Leu Ser Ile Ala Ser Leu Gln Thr
65                  70                  75                  80

Glu Asp Ala Ala Thr Tyr Tyr Cys Gln Gln Tyr Trp Thr Thr Pro Phe
                85                  90                  95

Thr Phe Gly Ser Gly Thr Lys Val Glu Ile Lys
            100                 105

<210> SEQ ID NO 70
<211> LENGTH: 116
<212> TYPE: PRT
<213> ORGANISM: Artificial Sequence
<220> FEATURE:
<223> OTHER INFORMATION: Synthesized

<400> SEQUENCE: 70

Asp Val Gln Leu Gln Glu Ser Gly Pro Gly Leu Val Asn Pro Ser Gln
1               5                   10                  15

Ser Leu Ser Leu Thr Cys Thr Val Thr Gly Tyr Ser Ile Thr Asn Asp
            20                  25                  30

Tyr Ala Trp Asn Trp Ile Arg Gln Phe Pro Gly Asn Lys Leu Glu Trp
        35                  40                  45

Met Gly Tyr Ile Asn Tyr Ser Gly Tyr Thr Thr Tyr Asn Pro Ser Leu
    50                  55                  60

Lys Ser Arg Ile Ser Ile Thr Arg Asp Thr Ser Lys Asn Gln Phe Phe
65                  70                  75                  80

Leu His Leu Asn Ser Val Thr Thr Glu Asp Thr Ala Thr Tyr Tyr Cys
                85                  90                  95

Ala Arg Trp Asp Gly Gly Leu Thr Tyr Trp Gly Gln Gly Thr Leu Val
            100                 105                 110

Thr Val Ser Ala
        115

<210> SEQ ID NO 71
<211> LENGTH: 298
<212> TYPE: PRT
<213> ORGANISM: Artificial Sequence
<220> FEATURE:
<223> OTHER INFORMATION: Synthesized

<400> SEQUENCE: 71
```

Met Ala Leu Pro Val Thr Ala Leu Leu Leu Pro Leu Ala Leu Leu Leu
1               5                   10                  15

His Ala Ala Arg Pro Gly Thr Ser Leu Ser Pro Pro Glu Ser Ser
            20                  25                  30

Gly Ser Pro Gln Gln Pro Gly Leu Ser Ala Pro His Ser Arg Gln Ile
        35                  40                  45

Pro Ala Pro Gln Gly Ala Val Leu Val Gln Arg Glu Lys Asp Leu Pro
50                  55                  60

Asn Tyr Asn Trp Asn Ser Phe Gly Leu Arg Phe Thr Thr Thr Pro Ala
65                  70                  75                  80

Pro Arg Pro Pro Thr Pro Ala Pro Thr Ile Ala Ser Gln Pro Leu Ser
                85                  90                  95

Leu Arg Pro Glu Ala Cys Arg Pro Ala Ala Gly Gly Ala Val His Thr
            100                 105                 110

Arg Gly Leu Asp Phe Ala Cys Asp Ile Tyr Ile Trp Ala Pro Leu Ala
        115                 120                 125

Gly Thr Cys Gly Val Leu Leu Leu Ser Leu Val Ile Thr Leu Tyr Cys
    130                 135                 140

Lys Arg Gly Arg Lys Lys Leu Leu Tyr Ile Phe Lys Gln Pro Phe Met
145                 150                 155                 160

Arg Pro Val Gln Thr Thr Gln Glu Glu Asp Gly Cys Ser Cys Arg Phe
                165                 170                 175

Pro Glu Glu Glu Glu Gly Gly Cys Glu Leu Arg Val Lys Phe Ser Arg
            180                 185                 190

Ser Ala Asp Ala Pro Ala Tyr Lys Gln Gly Gln Asn Gln Leu Tyr Asn
        195                 200                 205

Glu Leu Asn Leu Gly Arg Arg Glu Glu Tyr Asp Val Leu Asp Lys Arg
    210                 215                 220

Arg Gly Arg Asp Pro Glu Met Gly Gly Lys Pro Arg Arg Lys Asn Pro
225                 230                 235                 240

Gln Glu Gly Leu Tyr Asn Glu Leu Gln Lys Asp Lys Met Ala Glu Ala
                245                 250                 255

Tyr Ser Glu Ile Gly Met Lys Gly Glu Arg Arg Arg Gly Lys Gly His
            260                 265                 270

Asp Gly Leu Tyr Gln Gly Leu Ser Thr Ala Thr Lys Asp Thr Tyr Asp
        275                 280                 285

Ala Leu His Met Gln Ala Leu Pro Pro Arg
    290                 295

<210> SEQ ID NO 72
<211> LENGTH: 54
<212> TYPE: PRT
<213> ORGANISM: Artificial Sequence
<220> FEATURE:
<223> OTHER INFORMATION: Synthesized

<400> SEQUENCE: 72

Gly Thr Ser Leu Ser Pro Pro Glu Ser Ser Gly Ser Pro Gln Gln
1               5                   10                  15

Pro Gly Leu Ser Ala Pro His Ser Arg Gln Ile Pro Ala Pro Gln Gly
            20                  25                  30

Ala Val Leu Val Gln Arg Glu Lys Asp Leu Pro Asn Tyr Asn Trp Asn
        35                  40                  45

Ser Phe Gly Leu Arg Phe
    50

<210> SEQ ID NO 73
<211> LENGTH: 330
<212> TYPE: DNA
<213> ORGANISM: Artificial Sequence
<220> FEATURE:
<223> OTHER INFORMATION: synthesized

<400> SEQUENCE: 73

| | | | | | |
|---|---|---|---|---|---|
| cagagcgtgc | tgacacaacc | cgccagcgtg | agcggcagcc | ccggccaatc | cgtgacaatc | 60 |
| agctgcaccg | gaaccagctc | cgatgtgggc | ggctacaact | atgtcagctg | gtaccagcag | 120 |
| caccccggca | agccccctaa | gctcatgatc | tacgaggtca | gcaagagacc | ctccggagtg | 180 |
| cccgacagat | tctccggctc | caaatccggc | aacaccgctt | ccctcaccat | cagcggactc | 240 |
| caagccgaag | atgaggccga | ctactactgc | tccagccaca | ccagcagcaa | cacactgatc | 300 |
| tttggcggcg | gcaccaaagt | gacagtgctg | | | | 330 |

<210> SEQ ID NO 74
<211> LENGTH: 354
<212> TYPE: DNA
<213> ORGANISM: Artificial Sequence
<220> FEATURE:
<223> OTHER INFORMATION: synthesized

<400> SEQUENCE: 74

| | | | | | |
|---|---|---|---|---|---|
| gaagtgcagc | tggtgcaatc | cggcgctgag | gtgaagaagc | ccggcgaatc | tctgaagatt | 60 |
| agctgcaaag | gctccggcta | caccttcaca | aactactgga | tcggctgggt | gagacagatg | 120 |
| cccggcaagg | gactggagtg | gatgggaaga | atctaccccg | cgactccta | caccaactac | 180 |
| tcccccctcct | tccaaggcca | agtgaccatt | agcgccgaca | agagcatctc | caccgcctat | 240 |
| ctgcagtggt | ccagcctcaa | ggccagcgat | acagccatgt | actactgcgc | cagagaccte | 300 |
| gagcctaccc | atcattacag | ctggggccaa | ggcacactcg | tgacagtgag | ctcc | 354 |

<210> SEQ ID NO 75
<211> LENGTH: 330
<212> TYPE: DNA
<213> ORGANISM: Artificial Sequence
<220> FEATURE:
<223> OTHER INFORMATION: synthesized

<400> SEQUENCE: 75

| | | | | | |
|---|---|---|---|---|---|
| ctccccgtgc | tgacacagcc | tccttccgcc | tccggaacac | ccggccagag | agtgaccatc | 60 |
| agctgcagcg | gctccagctc | caacatcggc | agcaacgccg | tggactggta | tcagcaactg | 120 |
| cccggcacag | ctcccaagct | gctgatctac | accaacaaca | gaaggcccag | cggcgtgccc | 180 |
| gatagattca | gcggcagcaa | atccggcaca | agcggctctc | tggccatttc | cggactgcag | 240 |
| ttcgaggacg | aggctgacta | ctactgcgct | gcttgggatg | actctctgtc | cggcgtgatc | 300 |
| tttggcggag | gcaccaaggt | cacagtgctg | | | | 330 |

<210> SEQ ID NO 76
<211> LENGTH: 363
<212> TYPE: DNA
<213> ORGANISM: Artificial Sequence
<220> FEATURE:
<223> OTHER INFORMATION: synthesized

<400> SEQUENCE: 76

| | | | | | |
|---|---|---|---|---|---|
| caagtgcaac | tggtgcagag | cggcgctgag | gtgaagaagc | ccggcagcag | cgtgaaggtc | 60 |
| agctgcaagg | ccagcgaaga | cacattcagc | tcctacgtga | tcagctgggt | gagacaagct | 120 |

```
cccggccaag gactggagtg gatgggagcc ttcatccctc tgctgggcag agtgcactat    180
gcccaagagt tccaaggcag actgacaatc accgccgacg agtccaccgg caccgcttac    240
atggagctga aaggactgag gagcgacgac accgccatgt actactgcgc cagagatcaa    300
ggcttcgccg gcgatgacgc cttcgatatc tggggccaag gcacaatggt gacagtgagc    360
agc                                                                  363

<210> SEQ ID NO 77
<211> LENGTH: 324
<212> TYPE: DNA
<213> ORGANISM: Artificial Sequence
<220> FEATURE:
<223> OTHER INFORMATION: synthesized

<400> SEQUENCE: 77
cagcccgtgc tgacccaaga ccccgtggtg tccgtggctc tgggacagac cgtgaggatc     60
acatgccaag gcgattctct gaggagctac tatgccacat ggtaccagca gaaacccgga    120
ctggcccccg tgagtcat cttcggaaag aactctaggc ccagcggcat ccccgataga    180
ttcagcggca gcagcagcgg caataccgcc tccctcacca tcaccggcgc caagccgag    240 gacgaagccg actactactg caacagctgg gacaacagcg ccaaccatcc cgtgttcggc    300
ggcggcacaa agctgacagt gctc                                          324

<210> SEQ ID NO 78
<211> LENGTH: 366
<212> TYPE: DNA
<213> ORGANISM: Artificial Sequence
<220> FEATURE:
<223> OTHER INFORMATION: synthesized

<400> SEQUENCE: 78
gaggtgcagc tcgtgcagtc cggcgccgaa gtgaggaagc ccggcagctc cgtgaaggtg     60
agctgtaagg ccagcggcga caacttcaac aactacggca tcacatgggt gagacaagcc    120
cccggccaag gactggagtg gatgggaaga ctgatcaccg tgctgggact ggacaactac    180
gcccagaagt tccaaggaag actgacaatc accgctgacg agtccaccgg caccgcctat    240
atggaactga ccggactgga gcccgaggat accgccgtgt actattgcgc tagagacatc    300
atgtcccccg aggccatcga tgccttcgac gtgtggggac aaggcacact ggtgaccgtg    360
agctcc                                                              366

<210> SEQ ID NO 79
<211> LENGTH: 321
<212> TYPE: DNA
<213> ORGANISM: Artificial Sequence
<220> FEATURE:
<223> OTHER INFORMATION: synthesized

<400> SEQUENCE: 79
gacatccaga tgacacagag ccccttcctct ctgagcgcct ccgtcggaga tagagtgacc     60
atcacatgca gagcctccca agacgtcagc aactatctga actggtacca gcagaagccc    120
ggcaaggccc ctaaactgct gatctatggc gccagcaata gacagaccgg cgtgccttcc    180
agattctccg gcagcggaag cggcaccgat ttcacactga caatttcctc tctgcagccc    240
gaggactttg ccacctacta ctgccagcaa gaggacagat ccctacaac cttcggccaa    300 ggcacaaagg tggagatcaa a                                             321
```

<210> SEQ ID NO 80
<211> LENGTH: 366
<212> TYPE: DNA
<213> ORGANISM: Artificial Sequence
<220> FEATURE:
<223> OTHER INFORMATION: synthesized

<400> SEQUENCE: 80

```
gaagtgcagc tggtgcagag cggagctgag gtgagaaagc ccggcagcag cgtcaaggtg      60
agctgtaagg ccagcggcga caacttcaac aactacggca tcacatgggt gaggcaagcc     120
cccggccaag gcctcgagtg gatgggaaga ctgatcaccg tgctcggact ggacaactac     180
gcccagaagt tccaaggcag actgacaatc accgccgatg agtccaccgg aacagcctac     240
atggagctga ccggactgga gcccgaagac acagctgtgt actactgcgc tagagacatc     300
atgtcccccg aggccatcga tgcctttgac gtgtggggcc aaggcacact ggtgacagtc     360
agcagc                                                                366
```

<210> SEQ ID NO 81
<211> LENGTH: 45
<212> TYPE: DNA
<213> ORGANISM: Artificial Sequence
<220> FEATURE:
<223> OTHER INFORMATION: synthesized

<400> SEQUENCE: 81

```
ggaggaggag gcagcggagg cggaggcagc ggaggaggcg gcagc                      45
```

<210> SEQ ID NO 82
<211> LENGTH: 110
<212> TYPE: PRT
<213> ORGANISM: Artificial Sequence
<220> FEATURE:
<223> OTHER INFORMATION: synthesized

<400> SEQUENCE: 82

```
Gln Ser Val Leu Thr Gln Pro Ala Ser Val Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Pro Pro Lys Leu
        35                  40                  45

Met Ile Tyr Glu Val Ser Lys Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser His Thr Ser Ser
                85                  90                  95

Asn Thr Leu Ile Phe Gly Gly Gly Thr Lys Val Thr Val Leu
            100                 105                 110
```

<210> SEQ ID NO 83
<211> LENGTH: 118
<212> TYPE: PRT
<213> ORGANISM: Artificial Sequence
<220> FEATURE:
<223> OTHER INFORMATION: synthesized

<400> SEQUENCE: 83

```
Glu Val Gln Leu Val Gln Ser Gly Ala Glu Val Lys Lys Pro Gly Glu
1               5                   10                  15
```

```
Ser Leu Lys Ile Ser Cys Lys Gly Ser Gly Tyr Thr Phe Thr Asn Tyr
            20                  25                  30

Trp Ile Gly Trp Val Arg Gln Met Pro Gly Lys Gly Leu Glu Trp Met
        35                  40                  45

Gly Arg Ile Tyr Pro Ser Asp Ser Tyr Thr Asn Tyr Ser Pro Ser Phe
 50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                85                  90                  95

Ala Arg Asp Leu Glu Pro Thr His His Tyr Ser Trp Gly Gln Gly Thr
                100                 105                 110

Leu Val Thr Val Ser Ser
            115
```

<210> SEQ ID NO 84
<211> LENGTH: 110
<212> TYPE: PRT
<213> ORGANISM: Artificial Sequence
<220> FEATURE:
<223> OTHER INFORMATION: synthesized

<400> SEQUENCE: 84

```
Leu Pro Val Leu Thr Gln Pro Pro Ser Ala Ser Gly Thr Pro Gly Gln
 1               5                  10                  15

Arg Val Thr Ile Ser Cys Ser Gly Ser Ser Asn Ile Gly Ser Asn
            20                  25                  30

Ala Val Asp Trp Tyr Gln Gln Leu Pro Gly Thr Ala Pro Lys Leu Leu
        35                  40                  45

Ile Tyr Thr Asn Asn Arg Arg Pro Ser Gly Val Pro Asp Arg Phe Ser
 50                  55                  60

Gly Ser Lys Ser Gly Thr Ser Gly Ser Leu Ala Ile Ser Gly Leu Gln
 65                  70                  75                  80

Phe Glu Asp Glu Ala Asp Tyr Tyr Cys Ala Ala Trp Asp Asp Ser Leu
                85                  90                  95

Ser Gly Val Ile Phe Gly Gly Gly Thr Lys Val Thr Val Leu
                100                 105                 110
```

<210> SEQ ID NO 85
<211> LENGTH: 121
<212> TYPE: PRT
<213> ORGANISM: Artificial Sequence
<220> FEATURE:
<223> OTHER INFORMATION: synthesized

<400> SEQUENCE: 85

```
Gln Val Gln Leu Val Gln Ser Gly Ala Glu Val Lys Lys Pro Gly Ser
 1               5                  10                  15

Ser Val Lys Val Ser Cys Lys Ala Ser Glu Asp Thr Phe Ser Ser Tyr
            20                  25                  30

Val Ile Ser Trp Val Arg Gln Ala Pro Gly Gln Gly Leu Glu Trp Met
        35                  40                  45

Gly Ala Phe Ile Pro Leu Leu Gly Arg Val His Tyr Ala Gln Glu Phe
 50                  55                  60

Gln Gly Arg Leu Thr Ile Thr Ala Asp Glu Ser Thr Gly Thr Ala Tyr
 65                  70                  75                  80

Met Glu Leu Lys Gly Leu Arg Ser Asp Asp Thr Ala Met Tyr Tyr Cys
```

```
                    85                  90                  95
Ala Arg Asp Gln Gly Phe Ala Gly Asp Asp Ala Phe Asp Ile Trp Gly
                100                 105                 110
Gln Gly Thr Met Val Thr Val Ser Ser
        115                 120

<210> SEQ ID NO 86
<211> LENGTH: 108
<212> TYPE: PRT
<213> ORGANISM: Artificial Sequence
<220> FEATURE:
<223> OTHER INFORMATION: synthesized

<400> SEQUENCE: 86

Gln Pro Val Leu Thr Gln Asp Pro Val Ser Val Ala Leu Gly Gln
1               5                   10                  15

Thr Val Arg Ile Thr Cys Gln Gly Asp Ser Leu Arg Ser Tyr Tyr Ala
                20                  25                  30

Thr Trp Tyr Gln Gln Lys Pro Gly Leu Ala Pro Val Arg Val Ile Phe
            35                  40                  45

Gly Lys Asn Ser Arg Pro Ser Gly Ile Pro Asp Arg Phe Ser Gly Ser
50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Trp Asp Ser Ala Asn His
                85                  90                  95

Pro Val Phe Gly Gly Gly Thr Lys Leu Thr Val Leu
            100                 105

<210> SEQ ID NO 87
<211> LENGTH: 122
<212> TYPE: PRT
<213> ORGANISM: Artificial Sequence
<220> FEATURE:
<223> OTHER INFORMATION: synthesized

<400> SEQUENCE: 87

Glu Val Gln Leu Val Gln Ser Gly Ala Glu Val Arg Lys Pro Gly Ser
1               5                   10                  15

Ser Val Lys Val Ser Cys Lys Ala Ser Gly Asp Asn Phe Asn Asn Tyr
                20                  25                  30

Gly Ile Thr Trp Val Arg Gln Ala Pro Gly Gln Gly Leu Glu Trp Met
            35                  40                  45

Gly Arg Leu Ile Thr Val Leu Gly Leu Asp Asn Tyr Ala Gln Lys Phe
50                  55                  60

Gln Gly Arg Leu Thr Ile Thr Ala Asp Glu Ser Thr Gly Thr Ala Tyr
65                  70                  75                  80

Met Glu Leu Thr Gly Leu Glu Pro Glu Asp Thr Ala Val Tyr Tyr Cys
                85                  90                  95

Ala Arg Asp Ile Met Ser Pro Glu Ala Ile Asp Ala Phe Asp Val Trp
                100                 105                 110

Gly Gln Gly Thr Leu Val Thr Val Ser Ser
        115                 120

<210> SEQ ID NO 88
<211> LENGTH: 107
<212> TYPE: PRT
<213> ORGANISM: Artificial Sequence
<220> FEATURE:
```

<223> OTHER INFORMATION: synthesized

<400> SEQUENCE: 88

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Asn Tyr
            20                  25                  30

Leu Asn Trp Tyr Gln Gln Lys Pro Gly Lys Ala Pro Lys Leu Leu Ile
        35                  40                  45

Tyr Gly Ala Ser Asn Arg Gln Thr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Glu Asp Arg Phe Pro Thr
                85                  90                  95

Thr Phe Gly Gln Gly Thr Lys Val Glu Ile Lys
            100                 105
```

<210> SEQ ID NO 89
<211> LENGTH: 122
<212> TYPE: PRT
<213> ORGANISM: Artificial Sequence
<220> FEATURE:
<223> OTHER INFORMATION: synthesized

<400> SEQUENCE: 89

```
Glu Val Gln Leu Val Gln Ser Gly Ala Glu Val Arg Lys Pro Gly Ser
1               5                   10                  15

Ser Val Lys Val Ser Cys Lys Ala Ser Gly Asp Asn Phe Asn Asn Tyr
            20                  25                  30

Gly Ile Thr Trp Val Arg Gln Ala Pro Gly Gln Gly Leu Glu Trp Met
        35                  40                  45

Gly Arg Leu Ile Thr Val Leu Gly Leu Asp Asn Tyr Ala Gln Lys Phe
50                  55                  60

Gln Gly Arg Leu Thr Ile Thr Ala Asp Glu Ser Thr Gly Thr Ala Tyr
65                  70                  75                  80

Met Glu Leu Thr Gly Leu Glu Pro Glu Asp Thr Ala Val Tyr Tyr Cys
                85                  90                  95

Ala Arg Asp Ile Met Ser Pro Glu Ala Ile Asp Ala Phe Asp Val Trp
            100                 105                 110

Gly Gln Gly Thr Leu Val Thr Val Ser Ser
        115                 120
```

<210> SEQ ID NO 90
<211> LENGTH: 15
<212> TYPE: PRT
<213> ORGANISM: Artificial Sequence
<220> FEATURE:
<223> OTHER INFORMATION: Sythesized

<400> SEQUENCE: 90

```
Gly Gly Gly Gly Ser Gly Gly Gly Ser Gly Gly Gly Gly Ser
1               5                   10                  15
```

<210> SEQ ID NO 91
<211> LENGTH: 717
<212> TYPE: DNA
<213> ORGANISM: Artificial Sequence
<220> FEATURE:
<223> OTHER INFORMATION: Synthesized -continued

<400> SEQUENCE: 91

```
gaggtccaac tgcagcagtc tggagctgag ctgatgaagc ctgggacttc agtgaagatg    60
tcctgcaagg ctgctggata caccttcact aagtactgga taggttgggt aaagcagagg   120
cctggacatg gccttgagtg gattggagat atttaccctg aggtggtta tactctcttc    180
aatgagaagt tcaagggcaa ggccacactg actgcagaca catcctccag cacagcctac   240
atgcagctca gcagcctgac atctgaggac tctgccatct attactgtgc aagagggaac   300
tactggggcc aaggcaccac tctcaccgtc tcctcaggtg gtggtggtag cggcggcggc   360
ggctctggtg gtggtggatc cgatgttgtg atgacccaaa ctccactcac tttgtcggtt   420
accattggac aaccagcctc catctcttgc aagtcaagtc agagcctctt agatagtgat   480
ggaaagacat atttgaattg gttgttacag aggccaggcc agtctccaaa gcgcctaatc   540
tatctggtgt ctaaactgga ctctggagtc cctgacaggt tcactggcag tggatcaggg   600
acagatttca cactgaaaat cagcagagtg gaggctgagg attgggagt ttattattgc    660
tggcaaggta cacattttcc tcacacgttc ggaggggca ccaagctgga aatgaaa       717
```

<210> SEQ ID NO 92
<211> LENGTH: 239
<212> TYPE: PRT
<213> ORGANISM: Artificial Sequence
<220> FEATURE:
<223> OTHER INFORMATION: Synthesized

<400> SEQUENCE: 92

```
Glu Val Gln Leu Gln Gln Ser Gly Ala Glu Leu Met Lys Pro Gly Thr
1               5                   10                  15
Ser Val Lys Met Ser Cys Lys Ala Ala Gly Tyr Thr Phe Thr Lys Tyr
            20                  25                  30
Trp Ile Gly Trp Val Lys Gln Arg Pro Gly His Gly Leu Glu Trp Ile
        35                  40                  45
Gly Asp Ile Tyr Pro Gly Gly Gly Tyr Thr Leu Phe Asn Glu Lys Phe
    50                  55                  60
Lys Gly Lys Ala Thr Leu Thr Ala Asp Thr Ser Ser Ser Thr Ala Tyr
65                  70                  75                  80
Met Gln Leu Ser Ser Leu Thr Ser Glu Asp Ser Ala Ile Tyr Tyr Cys
                85                  90                  95
Ala Arg Gly Asn Tyr Trp Gly Gln Gly Thr Thr Leu Thr Val Ser Ser
            100                 105                 110
Gly Gly Gly Gly Ser Gly Gly Gly Gly Ser Gly Gly Gly Gly Ser Asp
        115                 120                 125
Val Val Met Thr Gln Thr Pro Leu Thr Leu Ser Val Thr Ile Gly Gln
    130                 135                 140
Pro Ala Ser Ile Ser Cys Lys Ser Ser Gln Ser Leu Leu Asp Ser Asp
145                 150                 155                 160
Gly Lys Thr Tyr Leu Asn Trp Leu Leu Gln Arg Pro Gly Gln Ser Pro
                165                 170                 175
Lys Arg Leu Ile Tyr Leu Val Ser Lys Leu Asp Ser Gly Val Pro Asp
            180                 185                 190
Arg Phe Thr Gly Ser Gly Ser Gly Thr Asp Phe Thr Leu Lys Ile Ser
        195                 200                 205
Arg Val Glu Ala Glu Asp Leu Gly Val Tyr Tyr Cys Trp Gln Gly Thr
    210                 215                 220
```

His Phe Pro His Thr Phe Gly Gly Gly Thr Lys Leu Glu Met Lys
225                 230                 235

<210> SEQ ID NO 93
<211> LENGTH: 112
<212> TYPE: PRT
<213> ORGANISM: Artificial Sequence
<220> FEATURE:
<223> OTHER INFORMATION: Synthesized

<400> SEQUENCE: 93

Glu Val Gln Leu Gln Gln Ser Gly Ala Glu Leu Met Lys Pro Gly Thr
1               5                   10                  15

Ser Val Lys Met Ser Cys Lys Ala Ala Gly Tyr Thr Phe Thr Lys Tyr
            20                  25                  30

Trp Ile Gly Trp Val Lys Gln Arg Pro Gly His Gly Leu Glu Trp Ile
        35                  40                  45

Gly Asp Ile Tyr Pro Gly Gly Gly Tyr Thr Leu Phe Asn Glu Lys Phe
    50                  55                  60

Lys Gly Lys Ala Thr Leu Thr Ala Asp Thr Ser Ser Thr Ala Tyr
65                  70                  75                  80

Met Gln Leu Ser Ser Leu Thr Ser Glu Asp Ser Ala Ile Tyr Tyr Cys
                85                  90                  95

Ala Arg Gly Asn Tyr Trp Gly Gln Gly Thr Thr Leu Thr Val Ser Ser
            100                 105                 110

<210> SEQ ID NO 94
<211> LENGTH: 112
<212> TYPE: PRT
<213> ORGANISM: Artificial Sequence
<220> FEATURE:
<223> OTHER INFORMATION: Synthesized

<400> SEQUENCE: 94

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro His Thr Phe Gly Gly Gly Thr Lys Leu Glu Met Lys
            100                 105                 110

<210> SEQ ID NO 95
<211> LENGTH: 708
<212> TYPE: DNA
<213> ORGANISM: Artificial Sequence
<220> FEATURE:
<223> OTHER INFORMATION: Synthesized

<400> SEQUENCE: 95
caggtcaagc tgcaacagtc tgggcccgag ctggtgaggc ctggggcttc agtgaagatg      60
tcctgcaagg cttcaggcta taccttcacc acctactgga tgcactgggt gaaacagagg     120

```
ccaggacaag gccttgagtg gattggcatg attgatccct ccaatagtga cactaggtta    180
aatcagaagt tcaaggacaa ggccacattg aatgttgaca catcctccaa cacagcctac    240
atgcacctca gcagcctgac atctgaggac tctgcagtct attactgtac attaggtggg    300
actgagtatt ggggccaagg cgccactctc acagtctcct caggtggtgg tggtagcggc    360
ggcggcggct ctggtggtgg tggatccagt attgtgatga cccagtctcc agccaccctg    420
tctgtgactc caggagatag agtctctctt tcctgcaggg ccagccagag tattggcgac    480
tacctacact ggtttcaaca aaaatcacat gagtctccaa ggcttctcat caaatatgct    540
tcccaatcca tctctgggat cccctccagg ttcagtggca gtggatcagg gtcagatttc    600
actctcatta tcaacactat ggaacctgaa gatgttggag tgtattactg tcaaaatgct    660
cacacctatc cgtacacgtt cggaggggc accaagctgg aaatcaaa    708
```

```
<210> SEQ ID NO 96
<211> LENGTH: 236
<212> TYPE: PRT
<213> ORGANISM: Artificial Sequence
<220> FEATURE:
<223> OTHER INFORMATION: Synthesized

<400> SEQUENCE: 96

Gln Val Lys Leu Gln Gln Ser Gly Pro Glu Leu Val Arg Pro Gly Ala
1               5                   10                  15

Ser Val Lys Met Ser Cys Lys Ala Ser Gly Tyr Thr Phe Thr Thr Tyr
                20                  25                  30

Trp Met His Trp Val Lys Gln Arg Pro Gly Gln Gly Leu Glu Trp Ile
            35                  40                  45

Gly Met Ile Asp Pro Ser Asn Ser Asp Thr Arg Leu Asn Gln Lys Phe
        50                  55                  60

Lys Asp Lys Ala Thr Leu Asn Val Asp Thr Ser Ser Asn Thr Ala Tyr
65                  70                  75                  80

Met His Leu Ser Ser Leu Thr Ser Glu Asp Ser Ala Val Tyr Tyr Cys
                85                  90                  95

Thr Leu Gly Gly Thr Glu Tyr Trp Gly Gln Gly Ala Thr Leu Thr Val
                100                 105                 110

Ser Ser Gly Gly Gly Gly Ser Gly Gly Gly Gly Ser Gly Gly Gly Gly
            115                 120                 125

Ser Ser Ile Val Met Thr Gln Ser Pro Ala Thr Leu Ser Val Thr Pro
130                 135                 140

Gly Asp Arg Val Ser Leu Ser Cys Arg Ala Ser Gln Ser Ile Gly Asp
145                 150                 155                 160

Tyr Leu His Trp Phe Gln Gln Lys Ser His Glu Ser Pro Arg Leu Leu
                165                 170                 175

Ile Lys Tyr Ala Ser Gln Ser Ile Ser Gly Ile Pro Ser Arg Phe Ser
            180                 185                 190

Gly Ser Gly Ser Gly Ser Asp Phe Thr Leu Ile Ile Asn Thr Met Glu
        195                 200                 205

Pro Glu Asp Val Gly Val Tyr Tyr Cys Gln Asn Ala His Thr Tyr Pro
    210                 215                 220

Tyr Thr Phe Gly Gly Gly Thr Lys Leu Glu Ile Lys
225                 230                 235

<210> SEQ ID NO 97
<211> LENGTH: 114
<212> TYPE: PRT
```

<213> ORGANISM: Artificial Sequence
<220> FEATURE:
<223> OTHER INFORMATION: Synthesized

<400> SEQUENCE: 97

```
Gln Val Lys Leu Gln Gln Ser Gly Pro Glu Leu Val Arg Pro Gly Ala
1               5                   10                  15

Ser Val Lys Met Ser Cys Lys Ala Ser Gly Tyr Thr Phe Thr Thr Tyr
            20                  25                  30

Trp Met His Trp Val Lys Gln Arg Pro Gly Gln Gly Leu Glu Trp Ile
        35                  40                  45

Gly Met Ile Asp Pro Ser Asn Ser Asp Thr Arg Leu Asn Gln Lys Phe
    50                  55                  60

Lys Asp Lys Ala Thr Leu Asn Val Asp Thr Ser Ser Asn Thr Ala Tyr
65                  70                  75                  80

Met His Leu Ser Ser Leu Thr Ser Glu Asp Ser Ala Val Tyr Tyr Cys
                85                  90                  95

Thr Leu Gly Gly Thr Glu Tyr Trp Gly Gln Gly Ala Thr Leu Thr Val
            100                 105                 110

Ser Ser
```

<210> SEQ ID NO 98
<211> LENGTH: 107
<212> TYPE: PRT
<213> ORGANISM: Artificial Sequence
<220> FEATURE:
<223> OTHER INFORMATION: Synthesized

<400> SEQUENCE: 98

```
Ser Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Gly Asp Tyr
            20                  25                  30

Leu His Trp Phe Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Ser Asp Phe Thr Leu Ile Ile Asn Thr Met Glu Pro
65                  70                  75                  80

Glu Asp Val Gly Val Tyr Tyr Cys Gln Asn Ala His Thr Tyr Pro Tyr
                85                  90                  95

Thr Phe Gly Gly Gly Thr Lys Leu Glu Ile Lys
            100                 105
```

<210> SEQ ID NO 99
<211> LENGTH: 738
<212> TYPE: DNA
<213> ORGANISM: Artificial Sequence
<220> FEATURE:
<223> OTHER INFORMATION: Synthesized

<400> SEQUENCE: 99

```
gaagtgaagc tgaagcagtc tggggctgaa ctggtgaagc ctgggggcttc agtgaagttg      60 tcctgcaagg cttctggcta caccctcacc agttactata tttactgggt gaagcagagg     120
cctggacaag gccttgagtg gattgggggg attagtccta gcaatggtaa tacttacttc     180
actgagaagt tcaagaacat ggccacactg actgtagaca atcctccaa cacagcctac      240 atgcaactca gcagcctgac atctgaggac tctgcggtct attactgtgc aagaaactat     300
```

-continued

```
gattacgacg tggggtttgc ttactggggc caagggactc tggtcacagt ctcctcaggt      360
ggtggtggta gcggcggcgg cggctctggt ggtggtggat ccgatgttgt gatgacccaa      420
actccactct ccctgcctgt cagtcttgga gatcaagcct ccatctcttg cagatctagt      480
cagagcattg tacatagtaa tggaaacacc tatttagaat ggtacctgca gaaaccaggc      540
cagtctccaa agctcctgat ctacaaagtt ccaaccgat tttctggggt cccagacagg      600
ttcagtggca gtggatcagg gacagatttc acactcaaga tcagcagagt ggaggctgag      660
gatctgggag tttattactg ctttcaaggt tcacatgttc cattcacgtt cggctcgggg      720
accaagctgg aaatcaaa                                                    738
```

<210> SEQ ID NO 100
<211> LENGTH: 246
<212> TYPE: PRT
<213> ORGANISM: Artificial Sequence
<220> FEATURE:
<223> OTHER INFORMATION: Synthesized

<400> SEQUENCE: 100

```
Glu Val Lys Leu Lys Gln Ser Gly Ala Glu Leu Val Lys Pro Gly Ala
1               5                   10                  15

Ser Val Lys Leu Ser Cys Lys Ala Ser Gly Tyr Thr Leu Thr Ser Tyr
            20                  25                  30

Tyr Ile Tyr Trp Val Lys Gln Arg Pro Gly Gln Gly Leu Glu Trp Ile
        35                  40                  45

Gly Gly Ile Ser Pro Ser Asn Gly Asn Thr Tyr Phe Thr Glu Lys Phe
    50                  55                  60

Lys Asn Met Ala Thr Leu Thr Val Asp Lys Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Ala Arg Asn Tyr Asp Tyr Asp Val Gly Phe Ala Tyr Trp Gly Gln Gly
            100                 105                 110

Thr Leu Val Thr Val Ser Ser Gly Gly Gly Ser Gly Gly Gly Gly
        115                 120                 125

Ser Gly Gly Gly Gly Ser Asp Val Val Met Thr Gln Thr Pro Leu Ser
    130                 135                 140

Leu Pro Val Ser Leu Gly Asp Gln Ala Ser Ile Ser Cys Arg Ser Ser
145                 150                 155                 160

Gln Ser Ile Val His Ser Asn Gly Asn Thr Tyr Leu Glu Trp Tyr Leu
                165                 170                 175

Gln Lys Pro Gly Gln Ser Pro Lys Leu Leu Ile Tyr Lys Val Ser Asn
            180                 185                 190

Arg Phe Ser Gly Val Pro Asp Arg Phe Ser Gly Ser Gly Ser Gly Thr
        195                 200                 205

Asp Phe Thr Leu Lys Ile Ser Arg Val Glu Ala Glu Asp Leu Gly Val
    210                 215                 220

Tyr Tyr Cys Phe Gln Gly Ser His Val Pro Phe Thr Phe Gly Ser Gly
225                 230                 235                 240

Thr Lys Leu Glu Ile Lys
                245
```

<210> SEQ ID NO 101
<211> LENGTH: 119
<212> TYPE: PRT

<213> ORGANISM: Artificial Sequence
<220> FEATURE:
<223> OTHER INFORMATION: Synthesized

<400> SEQUENCE: 101

```
Glu Val Lys Leu Lys Gln Ser Gly Ala Glu Leu Val Lys Pro Gly Ala
1               5                   10                  15
Ser Val Lys Leu Ser Cys Lys Ala Ser Gly Tyr Thr Leu Thr Ser Tyr
            20                  25                  30
Tyr Ile Tyr Trp Val Lys Gln Arg Pro Gly Gln Gly Leu Glu Trp Ile
        35                  40                  45
Gly Gly Ile Ser Pro Ser Asn Gly Asn Thr Tyr Phe Thr Glu Lys Phe
    50                  55                  60
Lys Asn Met Ala Thr Leu Thr Val Asp Lys Ser Ser Asn Thr Ala Tyr
65                  70                  75                  80
Met Gln Leu Ser Ser Leu Thr Ser Glu Asp Ser Ala Val Tyr Tyr Cys
                85                  90                  95
Ala Arg Asn Tyr Asp Tyr Asp Val Gly Phe Ala Tyr Trp Gly Gln Gly
            100                 105                 110
Thr Leu Val Thr Val Ser Ser
        115
```

<210> SEQ ID NO 102
<211> LENGTH: 112
<212> TYPE: PRT
<213> ORGANISM: Artificial Sequence
<220> FEATURE:
<223> OTHER INFORMATION: Synthesized

<400> SEQUENCE: 102

```
Asp Val Val Met Thr Gln Thr Pro Leu Ser Leu Pro Val Ser Leu Gly
1               5                   10                  15
Asp Gln Ala Ser Ile Ser Cys Arg Ser Ser Gln Ser Ile Val His Ser
            20                  25                  30
Asn Gly Asn Thr Tyr Leu Glu Trp Tyr Leu Gln Lys Pro Gly Gln Ser
        35                  40                  45
Pro Lys Leu Leu Ile Tyr Lys Val Ser Asn Arg Phe Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Leu Gly Val Tyr Tyr Cys Phe Gln Gly
                85                  90                  95
Ser His Val Pro Phe Thr Phe Gly Ser Gly Thr Lys Leu Glu Ile Lys
            100                 105                 110
```

<210> SEQ ID NO 103
<211> LENGTH: 726
<212> TYPE: DNA
<213> ORGANISM: Artificial Sequence
<220> FEATURE:
<223> OTHER INFORMATION: Synthesized

<400> SEQUENCE: 103

```
caggtgcagc tgaaggagtc tgggggaggc ttagtgcagc ctggggagtc cctgaaactc      60
tcctgtgaat ccagtgaatt cccattccct tccatgaca tgtcttgggt ccgcaagact      120
ccggagaaga ggctggagtt ggtcgcagcc attaatagtg atggtggtag cacctactat     180
ccagacacca tggagagacg attcatcatc tccagagaca ataccaagaa gaccctgtac     240
```

-continued

```
ctgcaaatga gcagtctgag gtctgaggac acagccttgt attactgtgc aagcctaccc    300
acgtttgctt actggggcca agggactctg gtcactgtct ctgcaggtgg tggtggtagc    360
ggcggcggcg gctctggtgg tggtggatcc agtattgtga tgacccaaac tccactcact    420
ttgtcggtta ccattggaca accagcctct atctcttgca agtcaagtca gagcctctta    480
tatagtgatg acaaaccta tttgaattgg ttattacaga ggccaggcca gtctccaaag    540
cgcctaatct atctggtgtc taaactggac tctggagtcc ctgacaggtt cactggcagt    600
ggatcaggta cagattttac actgaaaatc agcagagtgg aggctgagga tttgggagtt    660
tattactgcg tgcaaactac acattttccg tacacgttcg gaggggggac caagctggaa    720
atgaaa                                                                726
```

<210> SEQ ID NO 104
<211> LENGTH: 242
<212> TYPE: PRT
<213> ORGANISM: Artificial Sequence
<220> FEATURE:
<223> OTHER INFORMATION: Synthesized

<400> SEQUENCE: 104

```
Gln Val Gln Leu Lys Glu Ser Gly Gly Gly Leu Val Gln Pro Gly Glu
 1               5                  10                  15

Ser Leu Lys Leu Ser Cys Glu Ser Ser Glu Phe Pro Phe Pro Ser His
            20                  25                  30

Asp Met Ser Trp Val Arg Lys Thr Pro Glu Lys Arg Leu Glu Leu Val
        35                  40                  45

Ala Ala Ile Asn Ser Asp Gly Ser Thr Tyr Tyr Pro Asp Thr Met
    50                  55                  60

Glu Arg Arg Phe Ile Ile Ser Arg Asp Asn Thr Lys Lys Thr Leu Tyr
 65                  70                  75                  80

Leu Gln Met Ser Ser Leu Arg Ser Glu Asp Thr Ala Leu Tyr Tyr Cys
                85                  90                  95

Ala Ser Leu Pro Thr Phe Ala Tyr Trp Gly Gln Gly Thr Leu Val Thr
            100                 105                 110

Val Ser Ala Gly Gly Gly Gly Ser Gly Gly Gly Gly Ser Gly Gly Gly
        115                 120                 125

Gly Ser Ser Ile Val Met Thr Gln Thr Pro Leu Thr Leu Ser Val Thr
130                 135                 140

Ile Gly Gln Pro Ala Ser Ile Ser Cys Lys Ser Ser Gln Ser Leu Leu
145                 150                 155                 160

Tyr Ser Asp Gly Gln Thr Tyr Leu Asn Trp Leu Leu Gln Arg Pro Gly
                165                 170                 175

Gln Ser Pro Lys Arg Leu Ile Tyr Leu Val Ser Lys Leu Asp Ser Gly
            180                 185                 190

Val Pro Asp Arg Phe Thr Gly Ser Gly Ser Gly Thr Asp Phe Thr Leu
        195                 200                 205

Lys Ile Ser Arg Val Glu Ala Glu Asp Leu Gly Val Tyr Tyr Cys Val
    210                 215                 220

Gln Thr Thr His Phe Pro Tyr Thr Phe Gly Gly Gly Thr Lys Leu Glu
225                 230                 235                 240

Met Lys
```

<210> SEQ ID NO 105
<211> LENGTH: 115
<212> TYPE: PRT

<213> ORGANISM: Artificial Sequence
<220> FEATURE:
<223> OTHER INFORMATION: Synthesized

<400> SEQUENCE: 105

```
Gln Val Gln Leu Lys Glu Ser Gly Gly Gly Leu Val Gln Pro Gly Glu
1               5                   10                  15

Ser Leu Lys Leu Ser Cys Glu Ser Ser Glu Phe Pro Phe Pro Ser His
            20                  25                  30

Asp Met Ser Trp Val Arg Lys Thr Pro Glu Lys Arg Leu Glu Leu Val
        35                  40                  45

Ala Ala Ile Asn Ser Asp Gly Gly Ser Thr Tyr Tyr Pro Asp Thr Met
    50                  55                  60

Glu Arg Arg Phe Ile Ile Ser Arg Asp Asn Thr Lys Lys Thr Leu Tyr
65                  70                  75                  80

Leu Gln Met Ser Ser Leu Arg Ser Glu Asp Thr Ala Leu Tyr Tyr Cys
                85                  90                  95

Ala Ser Leu Pro Thr Phe Ala Tyr Trp Gly Gln Gly Thr Leu Val Thr
            100                 105                 110

Val Ser Ala
        115
```

<210> SEQ ID NO 106
<211> LENGTH: 112
<212> TYPE: PRT
<213> ORGANISM: Artificial Sequence
<220> FEATURE:
<223> OTHER INFORMATION: Synthesized

<400> SEQUENCE: 106

```
Ser Ile Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Tyr Ser
            20                  25                  30

Asp Gly Gln Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Val Gln Thr
                85                  90                  95

Thr His Phe Pro Tyr Thr Phe Gly Gly Gly Thr Lys Leu Glu Met Lys
            100                 105                 110
```

<210> SEQ ID NO 107
<211> LENGTH: 720
<212> TYPE: DNA
<213> ORGANISM: Artificial Sequence
<220> FEATURE:
<223> OTHER INFORMATION: Synthesized

<400> SEQUENCE: 107

```
caggttcagc tgcagcagtc tggggcagag cttgtgaggt caggggcctc agtcaagttg    60
tcctgcacag attctggctt caacattaaa gactactata tgaactgggt gaaacagcgg   120
cctgaacagg gcctggagtg gattggatgg attgatcctg aaaatggtgt tactcaatat   180
gacccgaagt tccagggcaa ggccactgtg actgcagaca cattctccaa cacagcctac   240
```

```
ctgcagctca gcagcctgac atctgaggac actgccgtct attactgtaa tgcaaactat    300
aagtacgact ggtttggtta ctggggccaa gggactctgg tcactgtctc tgcaggtggt    360
ggtggtagcg gcggcggcgg ctctggtggt ggtggatcca acattgtaat gacccagtct    420
ccatcctcct tatctgcctc tctgggagaa agagtcagtc tcacttgtcg ggcaagtcag    480
gaaattagtg gttacttaag ctggcttcag cagaaaccag atggaactat taaacgcctg    540
atctacgccg catccacttt agattctggt gtcccagaaa ggttcagtgg cagtaggtct    600
gggtcagatt attctctcac catcagcagc cttgagtctg aagattttgc agactattac    660
tgtctacaat atgctagtta tccgtggacg ttcggtggag ggaccaagct ggaaatgaaa    720
```

<210> SEQ ID NO 108
<211> LENGTH: 240
<212> TYPE: PRT
<213> ORGANISM: Artificial Sequence
<220> FEATURE:
<223> OTHER INFORMATION: Synthesized

<400> SEQUENCE: 108

```
Gln Val Gln Leu Gln Gln Ser Gly Ala Glu Leu Val Arg Ser Gly Ala
1               5                   10                  15

Ser Val Lys Leu Ser Cys Thr Asp Ser Gly Phe Asn Ile Lys Asp Tyr
            20                  25                  30

Tyr Met Asn Trp Val Lys Gln Arg Pro Glu Gln Gly Leu Glu Trp Ile
        35                  40                  45

Gly Trp Ile Asp Pro Glu Asn Gly Val Thr Gln Tyr Asp Pro Lys Phe
    50                  55                  60

Gln Gly Lys Ala Thr Val Thr Ala Asp Thr Phe Ser Asn Thr Ala Tyr
65                  70                  75                  80

Leu Gln Leu Ser Ser Leu Thr Ser Glu Asp Thr Ala Val Tyr Tyr Cys
                85                  90                  95

Asn Ala Asn Tyr Lys Tyr Asp Trp Phe Gly Tyr Trp Gly Gln Gly Thr
            100                 105                 110

Leu Val Thr Val Ser Ala Gly Gly Gly Ser Gly Gly Gly Gly Ser
        115                 120                 125

Gly Gly Gly Gly Ser Asn Ile Val Met Thr Gln Ser Pro Ser Ser Leu
    130                 135                 140

Ser Ala Ser Leu Gly Glu Arg Val Ser Leu Thr Cys Arg Ala Ser Gln
145                 150                 155                 160

Glu Ile Ser Gly Tyr Leu Ser Trp Leu Gln Gln Lys Pro Asp Gly Thr
                165                 170                 175

Ile Lys Arg Leu Ile Tyr Ala Ala Ser Thr Leu Asp Ser Gly Val Pro
            180                 185                 190

Glu Arg Phe Ser Gly Ser Arg Ser Gly Ser Asp Tyr Ser Leu Thr Ile
        195                 200                 205

Ser Ser Leu Glu Ser Glu Asp Phe Ala Asp Tyr Tyr Cys Leu Gln Tyr
    210                 215                 220

Ala Ser Tyr Pro Trp Thr Phe Gly Gly Gly Thr Lys Leu Glu Met Lys
225                 230                 235                 240
```

<210> SEQ ID NO 109
<211> LENGTH: 118
<212> TYPE: PRT
<213> ORGANISM: Artificial Sequence
<220> FEATURE:
<223> OTHER INFORMATION: Synthesized -continued

<400> SEQUENCE: 109

Gln Val Gln Leu Gln Gln Ser Gly Ala Glu Leu Val Arg Ser Gly Ala
1               5                   10                  15

Ser Val Lys Leu Ser Cys Thr Asp Ser Gly Phe Asn Ile Lys Asp Tyr
            20                  25                  30

Tyr Met Asn Trp Val Lys Gln Arg Pro Glu Gln Gly Leu Glu Trp Ile
        35                  40                  45

Gly Trp Ile Asp Pro Glu Asn Gly Val Thr Gln Tyr Asp Pro Lys Phe
    50                  55                  60

Gln Gly Lys Ala Thr Val Thr Ala Asp Thr Phe Ser Asn Thr Ala Tyr
65                  70                  75                  80

Leu Gln Leu Ser Ser Leu Thr Ser Glu Asp Thr Ala Val Tyr Tyr Cys
                85                  90                  95

Asn Ala Asn Tyr Lys Tyr Asp Trp Phe Gly Tyr Trp Gly Gln Gly Thr
            100                 105                 110

Leu Val Thr Val Ser Ala
        115

<210> SEQ ID NO 110
<211> LENGTH: 107
<212> TYPE: PRT
<213> ORGANISM: Artificial Sequence
<220> FEATURE:
<223> OTHER INFORMATION: Synthesized

<400> SEQUENCE: 110

Asn Ile Val Met Thr Gln Ser Pro Ser Ser Leu Ser Ala Ser Leu Gly
1               5                   10                  15

Glu Arg Val Ser Leu Thr Cys Arg Ala Ser Gln Glu Ile Ser Gly Tyr
            20                  25                  30

Leu Ser Trp Leu Gln Gln Lys Pro Asp Gly Thr Ile Lys Arg Leu Ile
        35                  40                  45

Tyr Ala Ala Ser Thr Leu Asp Ser Gly Val Pro Glu Arg Phe Ser Gly
    50                  55                  60

Ser Arg Ser Gly Ser Asp Tyr Ser Leu Thr Ile Ser Ser Leu Glu Ser
65                  70                  75                  80

Glu Asp Phe Ala Asp Tyr Tyr Cys Leu Gln Tyr Ala Ser Tyr Pro Trp
                85                  90                  95

Thr Phe Gly Gly Gly Thr Lys Leu Glu Met Lys
            100                 105

<210> SEQ ID NO 111
<211> LENGTH: 723
<212> TYPE: DNA
<213> ORGANISM: Artificial Sequence
<220> FEATURE:
<223> OTHER INFORMATION: Synthesized

<400> SEQUENCE: 111
caggtgcagc tgaagcagtc tgggcctggg ctggtgaggc tggggcttc  agtgacgatg      60 tcctgcaagg cttcaggcta taccttcacc agcaactgga tgcactgggt taaacagagg     120
cctggacaag gccttgattg gattggcatg attgatcctt ccaatagtga cactaggtta     180
aatcagaagt tcaaggacaa ggccacattg aatgtagaca atcctccaa  cacagcctac     240 atgcagctca gcagcctgac gtctgatgac tctgcagtct attactgtat gagagggggc     300
ggcgactact ggggccaagg caccactctc acagtctcct caggtggtgg tggtagcggc     360

```
ggcggctctg gtggtggtgg atccgacatt gtgatgtcac agtctccatc ctccctagct    420
gtgtcagttg gagagaaggt tactatgagc tgcaagtcca gtcagagcct tttatatagt    480
agcaatcaaa agaactactt ggcctggtac cagcagaaac agggcagtc tcctaaactg     540 ctgatttact gggcatccac tagggaatct ggggtccctg atcgcttcac aggcagtgga    600
tctgggacag atttcactct caccatcagc agtgtgaagg ctgaagacct ggcagtttat    660
tactgtcagc aatattatag ctatccgtac acgttcggag gggggaccaa gctggaaatg    720
aaa                                                                  723
```

<210> SEQ ID NO 112
<211> LENGTH: 242
<212> TYPE: PRT
<213> ORGANISM: Artificial Sequence
<220> FEATURE:
<223> OTHER INFORMATION: Synthesized

<400> SEQUENCE: 112

Gln Val Gln Leu Lys Gln Ser Gly Pro Gly Leu Val Arg Pro Gly Ala
1               5                   10                  15

Ser Val Thr Met Ser Cys Lys Ala Ser Gly Tyr Thr Phe Thr Ser Asn
            20                  25                  30

Trp Met His Trp Val Lys Gln Arg Pro Gly Gln Gly Leu Asp Trp Ile
        35                  40                  45

Gly Met Ile Asp Pro Ser Asn Ser Asp Thr Arg Leu Asn Gln Lys Phe
    50                  55                  60

Lys Asp Lys Ala Thr Leu Asn Val Asp Lys Ser Ser Asn Thr Ala Tyr
65                  70                  75                  80

Met Gln Leu Ser Ser Leu Thr Ser Asp Ser Ala Val Tyr Tyr Cys
                85                  90                  95

Met Arg Gly Gly Gly Asp Tyr Trp Gly Gln Gly Thr Thr Leu Thr Val
            100                 105                 110

Ser Ser Gly Gly Gly Gly Ser Gly Gly Gly Gly Ser Gly Gly Gly Gly
        115                 120                 125

Ser Asp Ile Val Met Ser Gln Ser Pro Ser Ser Leu Ala Val Ser Val
    130                 135                 140

Gly Glu Lys Val Thr Met Ser Cys Lys Ser Ser Gln Ser Leu Leu Tyr
145                 150                 155                 160

Ser Ser Asn Gln Lys Asn Tyr Leu Ala Trp Tyr Gln Gln Lys Pro Gly
                165                 170                 175

Gln Ser Pro Lys Leu Leu Ile Tyr Trp Ala Ser Thr Arg Glu Ser Gly
            180                 185                 190

Val Pro Asp Arg Phe Thr Gly Ser Gly Ser Gly Thr Asp Phe Thr Leu
        195                 200                 205

Thr Ile Ser Ser Val Lys Ala Glu Asp Leu Ala Val Tyr Tyr Cys Gln
    210                 215                 220

Gln Tyr Tyr Ser Tyr Pro Tyr Thr Phe Gly Gly Gly Thr Lys Leu Glu
225                 230                 235                 240

Met Lys

<210> SEQ ID NO 113
<211> LENGTH: 114
<212> TYPE: PRT
<213> ORGANISM: Artificial Sequence
<220> FEATURE:
<223> OTHER INFORMATION: Synthesized

<400> SEQUENCE: 113

Gln Val Gln Leu Lys Gln Ser Gly Pro Gly Leu Val Arg Pro Gly Ala
1               5                   10                  15

Ser Val Thr Met Ser Cys Lys Ala Ser Gly Tyr Thr Phe Thr Ser Asn
            20                  25                  30

Trp Met His Trp Val Lys Gln Arg Pro Gly Gln Gly Leu Asp Trp Ile
        35                  40                  45

Gly Met Ile Asp Pro Ser Asn Ser Asp Thr Arg Leu Asn Gln Lys Phe
    50                  55                  60

Lys Asp Lys Ala Thr Leu Asn Val Asp Lys Ser Ser Asn Thr Ala Tyr
65                  70                  75                  80

Met Gln Leu Ser Ser Leu Thr Ser Asp Asp Ser Ala Val Tyr Tyr Cys
                85                  90                  95

Met Arg Gly Gly Gly Asp Tyr Trp Gly Gln Gly Thr Thr Leu Thr Val
            100                 105                 110

Ser Ser

<210> SEQ ID NO 114
<211> LENGTH: 113
<212> TYPE: PRT
<213> ORGANISM: Artificial Sequence
<220> FEATURE:
<223> OTHER INFORMATION: Synthesized

<400> SEQUENCE: 114

Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Pro Tyr Thr Phe Gly Gly Gly Thr Lys Leu Glu Met
            100                 105                 110

Lys

<210> SEQ ID NO 115
<211> LENGTH: 720
<212> TYPE: DNA
<213> ORGANISM: Artificial Sequence
<220> FEATURE:
<223> OTHER INFORMATION: Synthesized

<400> SEQUENCE: 115
gaggtgcagc tgaaggagtc tggggcagag cttgtgaggt caggggcctc agtcaagttg      60
tcctgcacag cttctgcctt caacattaaa gactactata tgaactggat gaagcagagg     120
cctgaacagg gcctggagtg gattggatgg attgatcctg agaatggtga tactaaatat     180
gccccgaagt tccagggcaa ggccactatc actgcagaca catcctccag cacagcctac     240
ctgcagctca ccagcctgac atctgaggac tctgccgtct ctattgtaa tgtaaactat      300 aagtacgact ggtttgctta ctggggccaa gggactctgg tcactgtctc tgcaggtggt     360

```
ggtggtagcg gcggcggcgg ctctggtggt ggtggatccg atgttgtgat gacccagtcc    420
caaaaattca tgtccacatc agtaggagac agggtcagcg tcacctgcaa ggccagtcag    480
aatgtgggta ctaatgtagc ctggtatcaa cagaaaccag ggcaatctcc tagagcactg    540
atttactcgg catcctaccg gtacagtgga gtccctgatc gcttcacagg cagtggatct    600
gggacagatt tcactctcac catcagcaat gtgcagtctg aagacttggc agagtatttc    660
tgtcagcaat ataacaccta tccgtggacg ttcggtgggg gacaaagct  ggaaataaaa    720
```

<210> SEQ ID NO 116
<211> LENGTH: 240
<212> TYPE: PRT
<213> ORGANISM: Artificial Sequence
<220> FEATURE:
<223> OTHER INFORMATION: Synthesized
<400> SEQUENCE: 116

```
Glu Val Gln Leu Lys Glu Ser Gly Ala Glu Leu Val Arg Ser Gly Ala
1               5                   10                  15

Ser Val Lys Leu Ser Cys Thr Ala Ser Ala Phe Asn Ile Lys Asp Tyr
            20                  25                  30

Tyr Met Asn Trp Met Lys Gln Arg Pro Glu Gln Gly Leu Glu Trp Ile
        35                  40                  45

Gly Trp Ile Asp Pro Glu Asn Gly Asp Thr Lys Tyr Ala Pro Lys Phe
    50                  55                  60

Gln Gly Lys Ala Thr Ile Thr Ala Asp Thr Ser Ser Ser Thr Ala Tyr
65                  70                  75                  80

Leu Gln Leu Thr Ser Leu Thr Ser Glu Asp Ser Ala Val Phe Tyr Cys
                85                  90                  95

Asn Val Asn Tyr Lys Tyr Asp Trp Phe Ala Tyr Trp Gly Gln Gly Thr
            100                 105                 110

Leu Val Thr Val Ser Ala Gly Gly Gly Ser Gly Gly Gly Gly Ser
        115                 120                 125

Gly Gly Gly Gly Ser Asp Val Val Met Thr Gln Ser Gln Lys Phe Met
    130                 135                 140

Ser Thr Ser Val Gly Asp Arg Val Ser Val Thr Cys Lys Ala Ser Gln
145                 150                 155                 160

Asn Val Gly Thr Asn Val Ala Trp Tyr Gln Gln Lys Pro Gly Gln Ser
                165                 170                 175

Pro Arg Ala Leu Ile Tyr Ser Ala Ser Tyr Arg Tyr Ser Gly Val Pro
            180                 185                 190

Asp Arg Phe Thr Gly Ser Gly Ser Gly Thr Asp Phe Thr Leu Thr Ile
        195                 200                 205

Ser Asn Val Gln Ser Glu Asp Leu Ala Glu Tyr Phe Cys Gln Gln Tyr
    210                 215                 220

Asn Thr Tyr Pro Trp Thr Phe Gly Gly Gly Thr Lys Leu Glu Ile Lys
225                 230                 235                 240
```

<210> SEQ ID NO 117
<211> LENGTH: 118
<212> TYPE: PRT
<213> ORGANISM: Artificial Sequence
<220> FEATURE:
<223> OTHER INFORMATION: Synthesized
<400> SEQUENCE: 117

Glu Val Gln Leu Lys Glu Ser Gly Ala Glu Leu Val Arg Ser Gly Ala

```
                1               5                   10                  15
Ser Val Lys Leu Ser Cys Thr Ala Ser Ala Phe Asn Ile Lys Asp Tyr
            20                  25                  30

Tyr Met Asn Trp Met Lys Gln Arg Pro Glu Gln Gly Leu Glu Trp Ile
            35                  40                  45

Gly Trp Ile Asp Pro Glu Asn Gly Asp Thr Lys Tyr Ala Pro Lys Phe
        50                  55                  60

Gln Gly Lys Ala Thr Ile Thr Ala Asp Thr Ser Ser Ser Thr Ala Tyr
65                  70                  75                  80

Leu Gln Leu Thr Ser Leu Thr Ser Glu Asp Ser Ala Val Phe Tyr Cys
                85                  90                  95

Asn Val Asn Tyr Lys Tyr Asp Trp Phe Ala Tyr Trp Gly Gln Gly Thr
                100                 105                 110

Leu Val Thr Val Ser Ala
            115

<210> SEQ ID NO 118
<211> LENGTH: 107
<212> TYPE: PRT
<213> ORGANISM: Artificial Sequence
<220> FEATURE:
<223> OTHER INFORMATION: Synthesized

<400> SEQUENCE: 118

Asp Val Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Arg Ala Leu Ile
            35                  40                  45

Tyr Ser Ala Ser Tyr Arg Tyr Ser Gly Val Pro Asp Arg Phe Thr Gly
        50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Thr Tyr Pro Trp
                85                  90                  95

Thr Phe Gly Gly Gly Thr Lys Leu Glu Ile Lys
            100                 105

<210> SEQ ID NO 119
<211> LENGTH: 720
<212> TYPE: DNA
<213> ORGANISM: Artificial Sequence
<220> FEATURE:
<223> OTHER INFORMATION: Synthesized

<400> SEQUENCE: 119
caggtccaac tgcagcagtc tgggcctgag ctggtgaggc ctggggcttc agtgacgatg      60
tcctgcaagg cttcaggcta taccttcacc agcaactgga tgcactgggt aaacagagg     120 cctggacaag gccttgattg gattggcatg attgatcctt ccaatagtga cactaggtta    180
aatcagaagt tcaaggacaa ggccacattg aatgtagaca atcctccaa cacagcctac     240 atgcagctca gcagcctgac gtctgaggac tctgcagtct attactgtat gagagggggc    300
ggcgactact ggggccaagg caccactctc acagtctcct caggtggtgg tggtagcggc    360
ggcggcggct ctggtggtgg tggatccgac attgtgatga cccagtctcc agcttctttg    420
gctgtgtctc tagggcagag ggccaccatc tcctgcaagg ccagccaaag tgttgattat    480
```

```
gatggtgata gttatatgaa ctggtaccaa cagaaaccag gacagccacc caaactcctc    540
atctatgctg catccaatct agaatctggg atcccagcca ggtttagtgg cagtgggtct    600
gggacagact tcaccctcaa catccatcct gtggaggagg aggatgctgc aacctattac    660
tgtcagcaca gttgggagat tccgtacacg ttcggagggg gcaccaagct ggaaatgaaa    720
```

<210> SEQ ID NO 120
<211> LENGTH: 240
<212> TYPE: PRT
<213> ORGANISM: Artificial Sequence
<220> FEATURE:
<223> OTHER INFORMATION: Synthesized

<400> SEQUENCE: 120

```
Gln Val Gln Leu Gln Gln Ser Gly Pro Glu Leu Val Arg Pro Gly Ala
1               5                   10                  15

Ser Val Thr Met Ser Cys Lys Ala Ser Gly Tyr Thr Phe Thr Ser Asn
            20                  25                  30

Trp Met His Trp Val Lys Gln Arg Pro Gly Gln Gly Leu Asp Trp Ile
        35                  40                  45

Gly Met Ile Asp Pro Ser Asn Ser Asp Thr Arg Leu Asn Gln Lys Phe
    50                  55                  60

Lys Asp Lys Ala Thr Leu Asn Val Asp Lys Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Met Arg Gly Gly Gly Asp Tyr Trp Gly Gln Gly Thr Thr Leu Thr Val
            100                 105                 110

Ser Ser Gly Gly Gly Gly Ser Gly Gly Gly Ser Gly Gly Gly Gly
        115                 120                 125

Ser Asp Ile Val Met Thr Gln Ser Pro Ala Ser Leu Ala Val Ser Leu
    130                 135                 140

Gly Gln Arg Ala Thr Ile Ser Cys Lys Ala Ser Gln Ser Val Asp Tyr
145                 150                 155                 160

Asp Gly Asp Ser Tyr Met Asn Trp Tyr Gln Gln Lys Pro Gly Gln Pro
                165                 170                 175

Pro Lys Leu Leu Ile Tyr Ala Ala Ser Asn Leu Glu Ser Gly Ile Pro
            180                 185                 190

Ala Arg Phe Ser Gly Ser Gly Ser Gly Thr Asp Phe Thr Leu Asn Ile
        195                 200                 205

His Pro Val Glu Glu Glu Asp Ala Ala Thr Tyr Tyr Cys Gln His Ser
    210                 215                 220

Trp Glu Ile Pro Tyr Thr Phe Gly Gly Gly Thr Lys Leu Glu Met Lys
225                 230                 235                 240
```

<210> SEQ ID NO 121
<211> LENGTH: 114
<212> TYPE: PRT
<213> ORGANISM: Artificial Sequence
<220> FEATURE:
<223> OTHER INFORMATION: Synthesized

<400> SEQUENCE: 121

```
Gln Val Gln Leu Gln Gln Ser Gly Pro Glu Leu Val Arg Pro Gly Ala
1               5                   10                  15

Ser Val Thr Met Ser Cys Lys Ala Ser Gly Tyr Thr Phe Thr Ser Asn
            20                  25                  30
```

```
Trp Met His Trp Val Lys Gln Arg Pro Gly Gln Gly Leu Asp Trp Ile
            35                  40                  45

Gly Met Ile Asp Pro Ser Asn Ser Asp Thr Arg Leu Asn Gln Lys Phe
        50                  55                  60

Lys Asp Lys Ala Thr Leu Asn Val Asp Lys Ser Ser Asn Thr Ala Tyr
 65                  70                  75                  80

Met Gln Leu Ser Ser Leu Thr Ser Glu Asp Ser Ala Val Tyr Tyr Cys
                85                  90                  95

Met Arg Gly Gly Gly Asp Tyr Trp Gly Gln Gly Thr Thr Leu Thr Val
            100                 105                 110

Ser Ser
```

<210> SEQ ID NO 122
<211> LENGTH: 111
<212> TYPE: PRT
<213> ORGANISM: Artificial Sequence
<220> FEATURE:
<223> OTHER INFORMATION: Synthesized

<400> SEQUENCE: 122

```
Asp Ile Val Met Thr Gln Ser Pro Ala Ser Leu Ala Val Ser Leu Gly
 1               5                  10                  15

Gln Arg Ala Thr Ile Ser Cys Lys Ala Ser Gln Ser Val Asp Tyr Asp
            20                  25                  30

Gly Asp Ser Tyr Met Asn Trp Tyr Gln Gln Lys Pro Gly Gln Pro Pro
        35                  40                  45

Lys Leu Leu Ile Tyr Ala Ala Ser Asn Leu Glu Ser Gly Ile Pro Ala
 50                  55                  60

Arg Phe Ser Gly Ser Gly Ser Gly Thr Asp Phe Thr Leu Asn Ile His
 65                  70                  75                  80

Pro Val Glu Glu Glu Asp Ala Ala Thr Tyr Tyr Cys Gln His Ser Trp
                85                  90                  95

Glu Ile Pro Tyr Thr Phe Gly Gly Gly Thr Lys Leu Glu Met Lys
            100                 105                 110
```

<210> SEQ ID NO 123
<211> LENGTH: 499
<212> TYPE: PRT
<213> ORGANISM: Artificial Sequence
<220> FEATURE:
<223> OTHER INFORMATION: Synthesized

<400> SEQUENCE: 123

```
Gln Val Gln Leu Gln Gln Ser Asp Ala Glu Leu Val Lys Pro Gly Ser
 1               5                  10                  15

Ser Val Lys Ile Ser Cys Lys Ala Ser Gly Tyr Thr Phe Thr Asp His
            20                  25                  30

Ala Ile His Trp Val Lys Gln Lys Pro Glu Gln Gly Leu Glu Trp Ile
            35                  40                  45

Gly His Phe Ser Pro Gly Asn Thr Asp Ile Lys Tyr Asn Asp Lys Phe
        50                  55                  60

Lys Gly Lys Ala Thr Leu Thr Val Asp Arg Ser Ser Ser Thr Ala Tyr
 65                  70                  75                  80

Met Gln Leu Asn Ser Leu Thr Ser Glu Asp Ser Ala Val Tyr Phe Cys
                85                  90                  95

Lys Thr Ser Thr Phe Phe Asp Tyr Trp Gly Gln Gly Thr Thr Leu
            100                 105                 110
```

Thr Val Ser Ser Gly Gly Gly Ser Gly Gly Gly Ser Gly Gly
            115                 120                 125
Gly Gly Ser Asp Ile Val Met Thr Gln Ser Pro Ser Ser Leu Thr Val
        130                 135                 140
Thr Ala Gly Glu Lys Val Thr Met Ile Cys Lys Ser Ser Gln Ser Leu
145                 150                 155                 160
Leu Asn Ser Gly Asp Gln Lys Asn Tyr Leu Thr Trp Tyr Gln Gln Lys
                165                 170                 175
Pro Gly Gln Pro Pro Lys Leu Leu Ile Phe Trp Ala Ser Thr Arg Glu
            180                 185                 190
Ser Gly Val Pro Asp Arg Phe Thr Gly Ser Gly Ser Gly Thr Asp Phe
        195                 200                 205
Thr Leu Thr Ile Ser Ser Val Gln Ala Glu Asp Leu Ala Val Tyr Tyr
    210                 215                 220
Cys Gln Asn Asp Tyr Ser Tyr Pro Leu Thr Phe Gly Ala Gly Thr Lys
225                 230                 235                 240
Leu Glu Leu Lys Ser Gly Gly Gly Ser Glu Val Gln Leu Val Glu
                245                 250                 255
Ser Gly Gly Gly Leu Val Gln Pro Gly Gly Ser Leu Lys Leu Ser Cys
            260                 265                 270
Ala Ala Ser Gly Phe Thr Phe Asn Lys Tyr Ala Met Asn Trp Val Arg
        275                 280                 285
Gln Ala Pro Gly Lys Gly Leu Glu Trp Val Ala Arg Ile Arg Ser Lys
    290                 295                 300
Tyr Asn Asn Tyr Ala Thr Tyr Tyr Ala Asp Ser Val Lys Asp Arg Phe
305                 310                 315                 320
Thr Ile Ser Arg Asp Asp Ser Lys Asn Thr Ala Tyr Leu Gln Met Asn
                325                 330                 335
Asn Leu Lys Thr Glu Asp Thr Ala Val Tyr Tyr Cys Val Arg His Gly
            340                 345                 350
Asn Phe Gly Asn Ser Tyr Ile Ser Tyr Trp Ala Tyr Trp Gly Gln Gly
        355                 360                 365
Thr Leu Val Thr Val Ser Ser Gly Gly Gly Gly Ser Gly Gly Gly Gly
    370                 375                 380
Ser Gly Gly Gly Gly Ser Gln Thr Val Val Thr Gln Glu Pro Ser Leu
385                 390                 395                 400
Thr Val Ser Pro Gly Gly Thr Val Thr Leu Thr Cys Gly Ser Ser Thr
                405                 410                 415
Gly Ala Val Thr Ser Gly Asn Tyr Pro Asn Trp Val Gln Gln Lys Pro
            420                 425                 430
Gly Gln Ala Pro Arg Gly Leu Ile Gly Gly Thr Lys Phe Leu Ala Pro
        435                 440                 445
Gly Thr Pro Ala Arg Phe Ser Gly Ser Leu Leu Gly Gly Lys Ala Ala
    450                 455                 460
Leu Thr Leu Ser Gly Val Gln Pro Glu Asp Glu Ala Glu Tyr Tyr Cys
465                 470                 475                 480
Val Leu Trp Tyr Ser Asn Arg Trp Val Phe Gly Gly Gly Thr Lys Leu
                485                 490                 495
Thr Val Leu

<210> SEQ ID NO 124
<211> LENGTH: 501
<212> TYPE: PRT

<213> ORGANISM: Artificial Sequence
<220> FEATURE:
<223> OTHER INFORMATION: Synthesized

<400> SEQUENCE: 124

```
Glu Val Lys Leu Val Glu Ser Gly Gly Gly Leu Val Gln Pro Gly Gly
1               5                   10                  15

Ser Met Lys Leu Ser Cys Val Ala Ser Gly Phe Thr Phe Ser Asn Tyr
            20                  25                  30

Trp Met Asn Trp Val Arg Gln Ser Pro Glu Lys Gly Leu Glu Trp Val
        35                  40                  45

Ala Glu Ile Arg Leu Lys Ser Asn Asn Tyr Thr Thr His Tyr Ala Glu
    50                  55                  60

Ser Val Lys Gly Arg Phe Thr Ile Ser Arg Asp Asp Ser Lys Ser Ser
65                  70                  75                  80

Val Ser Leu Gln Met Asn Asn Leu Arg Val Glu Asp Thr Gly Ile Tyr
                85                  90                  95

Tyr Cys Thr Arg His Tyr Tyr Phe Asp Tyr Trp Gly Gln Gly Thr Thr
            100                 105                 110

Leu Thr Val Ser Ser Gly Gly Gly Gly Ser Gly Gly Gly Gly Ser Gly
        115                 120                 125

Gly Gly Gly Ser Asp Ile Val Met Thr Gln Ala Ala Phe Ser Asn Pro
    130                 135                 140

Val Thr Leu Gly Thr Ser Ala Ser Ile Ser Cys Arg Ser Ser Lys Ser
145                 150                 155                 160

Leu Leu His Ser Asn Gly Ile Thr Tyr Phe Phe Trp Tyr Leu Gln Lys
                165                 170                 175

Pro Gly Leu Ser Pro Gln Leu Leu Ile Tyr Gln Met Ser Asn Leu Ala
            180                 185                 190

Ser Gly Val Pro Asp Arg Phe Ser Ser Gly Ser Gly Thr Asp Phe
        195                 200                 205

Thr Leu Arg Ile Ser Arg Val Glu Ala Glu Asp Val Gly Val Tyr Tyr
    210                 215                 220

Cys Ala Gln Asn Leu Glu Leu Pro Pro Thr Phe Gly Gly Gly Thr Lys
225                 230                 235                 240

Leu Glu Ile Lys Arg Ala Ser Gly Gly Gly Ser Glu Val Gln Leu
                245                 250                 255

Val Glu Ser Gly Gly Gly Leu Val Gln Pro Gly Gly Ser Leu Lys Leu
            260                 265                 270

Ser Cys Ala Ala Ser Gly Phe Thr Phe Asn Lys Tyr Ala Met Asn Trp
    275                 280                 285

Val Arg Gln Ala Pro Gly Lys Gly Leu Glu Trp Val Ala Arg Ile Arg
290                 295                 300

Ser Lys Tyr Asn Asn Tyr Ala Thr Tyr Tyr Ala Asp Ser Val Lys Asp
305                 310                 315                 320

Arg Phe Thr Ile Ser Arg Asp Asp Ser Lys Asn Thr Ala Tyr Leu Gln
                325                 330                 335

Met Asn Asn Leu Lys Thr Glu Asp Thr Ala Val Tyr Tyr Cys Val Arg
            340                 345                 350

His Gly Asn Phe Gly Asn Ser Tyr Ile Ser Tyr Trp Ala Tyr Trp Gly
        355                 360                 365

Gln Gly Thr Leu Val Thr Val Ser Ser Gly Gly Gly Gly Ser Gly Gly
    370                 375                 380

Gly Gly Ser Gly Gly Gly Gly Ser Gln Thr Val Val Thr Gln Glu Pro
```

```
385                 390                 395                 400
Ser Leu Thr Val Ser Pro Gly Thr Val Thr Leu Thr Cys Gly Ser
                405                 410                 415

Ser Thr Gly Ala Val Thr Ser Gly Asn Tyr Pro Asn Trp Val Gln Gln
                420                 425                 430

Lys Pro Gly Gln Ala Pro Arg Gly Leu Ile Gly Thr Lys Phe Leu
                435                 440                 445

Ala Pro Gly Thr Pro Ala Arg Phe Ser Gly Ser Leu Leu Gly Gly Lys
    450                 455                 460

Ala Ala Leu Thr Leu Ser Gly Val Gln Pro Glu Asp Glu Ala Glu Tyr
465                 470                 475                 480

Tyr Cys Val Leu Trp Tyr Ser Asn Arg Trp Val Phe Gly Gly Thr
                485                 490                 495

Lys Leu Thr Val Leu
                500

<210> SEQ ID NO 125
<211> LENGTH: 492
<212> TYPE: PRT
<213> ORGANISM: Artificial Sequence
<220> FEATURE:
<223> OTHER INFORMATION: Synthesized

<400> SEQUENCE: 125

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Asn Asp Thr
                20                  25                  30

Tyr Met His Trp Val Lys Gln Arg Pro Glu Gln Gly Leu Glu Trp Ile
            35                  40                  45

Gly Arg Ile Asp Pro Ala Asn Gly Asn Thr Lys Tyr Asp Pro Lys Phe
        50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Arg Gly Ala Arg Gly Ser Arg Phe Ala Tyr Trp Gly Gln Gly Thr
            100                 105                 110

Leu Val Thr Val Ser Ala Gly Gly Gly Gly Ser Gly Gly Gly Gly Ser
        115                 120                 125

Gly Gly Gly Gly Ser Asp Ile Gln Met Thr Gln Ser Pro Ala Ser Leu
    130                 135                 140

Ser Val Ser Val Gly Glu Thr Val Thr Ile Thr Cys Arg Ala Ser Glu
145                 150                 155                 160

Asn Ile Tyr Ser Asn Leu Ala Trp Tyr Gln Gln Lys Gln Gly Lys Ser
                165                 170                 175

Pro Gln Leu Leu Val Tyr Val Ala Thr Asn Leu Ala Asp Gly Val Pro
            180                 185                 190

Ser Arg Phe Ser Gly Ser Gly Ser Gly Thr Gln Tyr Ser Leu Lys Ile
        195                 200                 205

Asn Ser Leu Gln Ser Glu Asp Phe Gly Ser Tyr Tyr Cys Gln His Phe
    210                 215                 220

Trp Gly Thr Pro Tyr Thr Phe Gly Gly Gly Thr Lys Leu Ser Gly Gly
225                 230                 235                 240

Gly Gly Ser Glu Val Gln Leu Val Glu Ser Gly Gly Gly Leu Val Gln
```

245                 250                 255
Pro Gly Gly Ser Leu Lys Leu Ser Cys Ala Ala Ser Gly Phe Thr Phe
                260                 265                 270

Asn Lys Tyr Ala Met Asn Trp Val Arg Gln Ala Pro Gly Lys Gly Leu
            275                 280                 285

Glu Trp Val Ala Arg Ile Arg Ser Lys Tyr Asn Asn Tyr Ala Thr Tyr
        290                 295                 300

Tyr Ala Asp Ser Val Lys Asp Arg Phe Thr Ile Ser Arg Asp Asp Ser
305                 310                 315                 320

Lys Asn Thr Ala Tyr Leu Gln Met Asn Asn Leu Lys Thr Glu Asp Thr
                325                 330                 335

Ala Val Tyr Tyr Cys Val Arg His Gly Asn Phe Gly Asn Ser Tyr Ile
            340                 345                 350

Ser Tyr Trp Ala Tyr Trp Gly Gln Gly Thr Leu Val Thr Val Ser Ser
        355                 360                 365

Gly Gly Gly Gly Ser Gly Gly Gly Ser Gly Gly Gly Ser Gln
        370                 375                 380

Thr Val Val Thr Gln Glu Pro Ser Leu Thr Val Ser Pro Gly Gly Thr
385                 390                 395                 400

Val Thr Leu Thr Cys Gly Ser Ser Thr Gly Ala Val Thr Ser Gly Asn
                405                 410                 415

Tyr Pro Asn Trp Val Gln Gln Lys Pro Gly Gln Ala Pro Arg Gly Leu
            420                 425                 430

Ile Gly Gly Thr Lys Phe Leu Ala Pro Gly Thr Pro Ala Arg Phe Ser
        435                 440                 445

Gly Ser Leu Leu Gly Gly Lys Ala Ala Leu Thr Leu Ser Gly Val Gln
        450                 455                 460

Pro Glu Asp Glu Ala Glu Tyr Tyr Cys Val Leu Trp Tyr Ser Asn Arg
465                 470                 475                 480

Trp Val Phe Gly Gly Gly Thr Lys Leu Thr Val Leu
                485                 490

<210> SEQ ID NO 126
<211> LENGTH: 499
<212> TYPE: PRT
<213> ORGANISM: Artificial Sequence
<220> FEATURE:
<223> OTHER INFORMATION: Synthesized

<400> SEQUENCE: 126

Glu Val Gln Leu Val Gln Ser Gly Ala Glu Val Lys Lys Pro Gly Gln
1               5                   10                  15

Ser Leu Lys Ile Ser Cys Lys Ala Ser Gly Tyr Ser Leu Thr Asp Asn
            20                  25                  30

Trp Ile Gly Trp Val Arg Gln Lys Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Asn Thr Ala Tyr
65                  70                  75                  80

Leu Gln Trp Ser Ser Leu Lys Ala Ser Asp Thr Ala Ile Tyr Tyr Cys
                85                  90                  95

Val Gly Leu Asp Trp Asn Tyr Asn Pro Leu Arg Tyr Trp Gly Pro Gly
            100                 105                 110

Thr Leu Val Thr Val Ser Ser Gly Gly Gly Gly Ser Gly Gly Gly Gly

```
            115                 120                 125
Ser Gly Gly Gly Gly Ser Gln Ser Val Leu Thr Gln Pro Pro Ser Val
    130                 135                 140

Ser Ala Ala Pro Gly Gln Lys Val Thr Ile Ser Cys Ser Gly Ser Ser
145                 150                 155                 160

Ser Asp Ile Gly Ser Asn Tyr Val Ser Trp Tyr Gln Gln Phe Pro Gly
                165                 170                 175

Thr Ala Pro Lys Leu Leu Ile Tyr Asp Asn Asn Lys Arg Pro Ser Ala
            180                 185                 190

Ile Pro Asp Arg Phe Ser Gly Ser Lys Ser Gly Thr Ser Ala Thr Leu
        195                 200                 205

Gly Ile Thr Gly Leu Gln Thr Gly Asp Glu Ala Asp Tyr Tyr Cys Gly
    210                 215                 220

Thr Trp Asp Ser Arg Leu Gly Ile Ala Val Phe Gly Gly Gly Thr Gln
225                 230                 235                 240

Leu Thr Val Leu Ser Gly Gly Gly Ser Glu Val Gln Leu Val Glu
                245                 250                 255

Ser Gly Gly Gly Leu Val Gln Pro Gly Gly Ser Leu Lys Leu Ser Cys
            260                 265                 270

Ala Ala Ser Gly Phe Thr Phe Asn Lys Tyr Ala Met Asn Trp Val Arg
        275                 280                 285

Gln Ala Pro Gly Lys Gly Leu Glu Trp Val Ala Arg Ile Arg Ser Lys
    290                 295                 300

Tyr Asn Asn Tyr Ala Thr Tyr Tyr Ala Asp Ser Val Lys Asp Arg Phe
305                 310                 315                 320

Thr Ile Ser Arg Asp Asp Ser Lys Asn Thr Ala Tyr Leu Gln Met Asn
                325                 330                 335

Asn Leu Lys Thr Glu Asp Thr Ala Val Tyr Tyr Cys Val Arg His Gly
            340                 345                 350

Asn Phe Gly Asn Ser Tyr Ile Ser Tyr Trp Ala Tyr Trp Gly Gln Gly
        355                 360                 365

Thr Leu Val Thr Val Ser Ser Gly Gly Gly Ser Gly Gly Gly Gly
    370                 375                 380

Ser Gly Gly Gly Gly Ser Gln Thr Val Val Thr Gln Glu Pro Ser Leu
385                 390                 395                 400

Thr Val Ser Pro Gly Gly Thr Val Thr Leu Thr Cys Gly Ser Ser Thr
                405                 410                 415

Gly Ala Val Thr Ser Gly Asn Tyr Pro Asn Trp Val Gln Gln Lys Pro
            420                 425                 430

Gly Gln Ala Pro Arg Gly Leu Ile Gly Gly Thr Lys Phe Leu Ala Pro
        435                 440                 445

Gly Thr Pro Ala Arg Phe Ser Gly Ser Leu Leu Gly Gly Lys Ala Ala
    450                 455                 460

Leu Thr Leu Ser Gly Val Gln Pro Glu Asp Glu Ala Glu Tyr Tyr Cys
465                 470                 475                 480

Val Leu Trp Tyr Ser Asn Arg Trp Val Phe Gly Gly Gly Thr Lys Leu
                485                 490                 495

Thr Val Leu

<210> SEQ ID NO 127
<211> LENGTH: 507
<212> TYPE: PRT
<213> ORGANISM: Artificial Sequence
<220> FEATURE:
```

<223> OTHER INFORMATION: Synthesized

<400> SEQUENCE: 127

```
Glu Val Gln Leu Val Glu Ser Gly Gly Asp Leu Val Lys Pro Gly Gly
1               5                   10                  15
Ser Leu Lys Leu Ser Cys Ala Val Ser Gly Phe Thr Phe Ser Ser Tyr
            20                  25                  30
Gly Met Ser Trp Val Arg Gln Thr Pro Asp Lys Arg Leu Glu Trp Val
        35                  40                  45
Ala Thr Val Ser Ser Gly Gly Thr Tyr Thr Tyr Tyr Pro Asp Ser Val
    50                  55                  60
Lys Gly Arg Phe Thr Ile Ser Arg Asp Asn Ala Lys Asn Thr Leu Tyr
65                  70                  75                  80
Leu Gln Met Ser Ser Leu Lys Ser Glu Asp Ser Ala Met Tyr Tyr Cys
            85                  90                  95
Ala Arg His Arg Gly Asn Tyr Tyr Ala Thr Tyr Tyr Ala Met Asp
        100                 105                 110
Tyr Trp Gly Gln Gly Thr Ser Val Thr Val Ser Ser Gly Gly Gly Gly
            115                 120                 125
Ser Gly Gly Gly Ser Gly Gly Gly Ser Asp Ile Val Leu Thr
130                 135                 140
Gln Ser Pro Ala Ser Leu Ala Val Ser Leu Gly Gln Gly Ala Thr Ile
145                 150                 155                 160
Ser Cys Arg Ala Ser Lys Ser Val Ser Thr Ser Gly Tyr Thr Tyr Met
            165                 170                 175
His Trp Tyr Gln Gln Lys Pro Gly Gln Pro Pro Lys Leu Leu Ile Tyr
        180                 185                 190
Leu Ala Ser Asn Leu Glu Ser Gly Val Pro Ala Arg Phe Ser Gly Ser
    195                 200                 205
Gly Ser Gly Thr Asp Phe Thr Leu Asn Ile His Pro Val Glu Glu Glu
210                 215                 220
Asp Ala Ala Thr Tyr Tyr Cys Gln His Ser Gly Glu Leu Pro Pro Ser
225                 230                 235                 240
Phe Gly Gly Gly Thr Lys Leu Glu Ile Lys Arg Ala Ser Gly Gly Gly
            245                 250                 255
Gly Ser Glu Val Gln Leu Val Glu Ser Gly Gly Gly Leu Val Gln Pro
        260                 265                 270
Gly Gly Ser Leu Lys Leu Ser Cys Ala Ala Ser Gly Phe Thr Phe Asn
    275                 280                 285
Lys Tyr Ala Met Asn Trp Val Arg Gln Ala Pro Gly Lys Gly Leu Glu
290                 295                 300
Trp Val Ala Arg Ile Arg Ser Lys Tyr Asn Asn Tyr Ala Thr Tyr Tyr
305                 310                 315                 320
Ala Asp Ser Val Lys Asp Arg Phe Thr Ile Ser Arg Asp Asp Ser Lys
            325                 330                 335
Asn Thr Ala Tyr Leu Gln Met Asn Asn Leu Lys Thr Glu Asp Thr Ala
        340                 345                 350
Val Tyr Tyr Cys Val Arg His Gly Asn Phe Gly Asn Ser Tyr Ile Ser
    355                 360                 365
Tyr Trp Ala Tyr Trp Gly Gln Gly Thr Leu Val Thr Val Ser Ser Gly
370                 375                 380
Gly Gly Gly Ser Gly Gly Gly Ser Gly Gly Gly Ser Gln Thr
385                 390                 395                 400
```

```
Val Val Thr Gln Glu Pro Ser Leu Thr Val Ser Pro Gly Gly Thr Val
                405                 410                 415
Thr Leu Thr Cys Gly Ser Ser Thr Gly Ala Val Thr Ser Gly Asn Tyr
                420                 425                 430
Pro Asn Trp Val Gln Gln Lys Pro Gly Gln Ala Pro Arg Gly Leu Ile
                435                 440                 445
Gly Gly Thr Lys Phe Leu Ala Pro Gly Thr Pro Ala Arg Phe Ser Gly
                450                 455                 460
Ser Leu Leu Gly Gly Lys Ala Ala Leu Thr Leu Ser Gly Val Gln Pro
465                 470                 475                 480
Glu Asp Glu Ala Glu Tyr Tyr Cys Val Leu Trp Tyr Ser Asn Arg Trp
                485                 490                 495
Val Phe Gly Gly Gly Thr Lys Leu Thr Val Leu
                500                 505

<210> SEQ ID NO 128
<211> LENGTH: 498
<212> TYPE: PRT
<213> ORGANISM: Artificial Sequence
<220> FEATURE:
<223> OTHER INFORMATION: Synthesized

<400> SEQUENCE: 128

Gln Val Gln Leu Gln Gln Pro Gly Ala Glu Leu Val Arg Pro Gly Ala
1               5                   10                  15
Ser Val Lys Leu Ser Cys Lys Ala Ser Gly Tyr Thr Phe Thr Thr Tyr
                20                  25                  30
Trp Met Asn Trp Val Lys Gln Arg Pro Glu Gln Gly Leu Glu Trp Ile
                35                  40                  45
Gly Arg Ile Asp Pro Tyr Asp Ser Glu Thr His Tyr Asn Gln Lys Phe
            50                  55                  60
Lys Asp Lys Ala Ile Leu Thr Val Asp Lys Ser Ser Ser Thr Ala Tyr
65                  70                  75                  80
Met Gln Leu Ser Ser Leu Thr Ser Glu Asp Ser Ala Val Tyr Tyr Cys
                85                  90                  95
Ala Arg Gly Pro Tyr Tyr Gly Thr Asn Pro Trp Phe Pro Tyr Trp Gly
                100                 105                 110
Gln Gly Thr Leu Val Thr Val Ser Ser Gly Gly Gly Ser Gly Gly
                115                 120                 125
Gly Gly Ser Gly Gly Gly Ser Asp Val Gln Ile Thr Gln Ser Pro
            130                 135                 140
Ser Tyr Leu Ala Ala Ser Pro Gly Glu Thr Ile Thr Ile Asn Cys Arg
145                 150                 155                 160
Ala Ser Lys Ser Ile Ser Lys Tyr Leu Ala Trp Tyr Gln Glu Lys Pro
                165                 170                 175
Gly Lys Thr Asn Lys Leu Leu Ile Tyr Ser Gly Ser Thr Leu Gln Ser
                180                 185                 190
Gly Ile Pro Ser Arg Phe Ser Gly Ser Gly Ser Gly Thr Asp Phe Thr
                195                 200                 205
Leu Thr Ile Ser Ser Leu Glu Pro Glu Asp Phe Ala Met Tyr Tyr Cys
            210                 215                 220
Gln Gln His His Glu Tyr Pro Tyr Thr Phe Gly Gly Thr Lys Leu
225                 230                 235                 240
Glu Ile Lys Ser Gly Gly Gly Gly Ser Glu Val Gln Leu Val Glu Ser
                245                 250                 255
```

```
Gly Gly Gly Leu Val Gln Pro Gly Gly Ser Leu Lys Leu Ser Cys Ala
            260                 265                 270

Ala Ser Gly Phe Thr Phe Asn Lys Tyr Ala Met Asn Trp Val Arg Gln
            275                 280                 285

Ala Pro Gly Lys Gly Leu Glu Trp Val Ala Arg Ile Arg Ser Lys Tyr
    290                 295                 300

Asn Asn Tyr Ala Thr Tyr Tyr Ala Asp Ser Val Lys Asp Arg Phe Thr
305                 310                 315                 320

Ile Ser Arg Asp Asp Ser Lys Asn Thr Ala Tyr Leu Gln Met Asn Asn
                325                 330                 335

Leu Lys Thr Glu Asp Thr Ala Val Tyr Tyr Cys Val Arg His Gly Asn
            340                 345                 350

Phe Gly Asn Ser Tyr Ile Ser Tyr Trp Ala Tyr Trp Gly Gln Gly Thr
            355                 360                 365

Leu Val Thr Val Ser Ser Gly Gly Gly Gly Ser Gly Gly Gly Gly Ser
            370                 375                 380

Gly Gly Gly Gly Ser Gln Thr Val Val Thr Gln Glu Pro Ser Leu Thr
385                 390                 395                 400

Val Ser Pro Gly Gly Thr Val Thr Leu Thr Cys Gly Ser Ser Thr Gly
            405                 410                 415

Ala Val Thr Ser Gly Asn Tyr Pro Asn Trp Val Gln Gln Lys Pro Gly
            420                 425                 430

Gln Ala Pro Arg Gly Leu Ile Gly Gly Thr Lys Phe Leu Ala Pro Gly
            435                 440                 445

Thr Pro Ala Arg Phe Ser Gly Ser Leu Leu Gly Lys Ala Ala Leu
    450                 455                 460

Thr Leu Ser Gly Val Gln Pro Glu Asp Glu Ala Glu Tyr Tyr Cys Val
465                 470                 475                 480

Leu Trp Tyr Ser Asn Arg Trp Val Phe Gly Gly Thr Lys Leu Thr
                485                 490                 495

Val Leu

<210> SEQ ID NO 129
<211> LENGTH: 496
<212> TYPE: PRT
<213> ORGANISM: Artificial Sequence
<220> FEATURE:
<223> OTHER INFORMATION: Synthesized

<400> SEQUENCE: 129

Gln Val Gln Leu Gln Gln Trp Gly Ala Gly Leu Leu Lys Pro Ser Glu
1               5                   10                  15

Thr Leu Ser Leu Thr Cys Ala Val Phe Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Arg Gly Asn Thr Asn Asp Asn Pro Ser Leu Lys
    50                  55                  60

Ser Arg Val Thr Ile Ser Val Asp Thr Ser Lys Asn Gln Phe Ala Leu
65                  70                  75                  80

Lys Leu Ser Ser Val Thr Ala Ala Asp Thr Ala Val Tyr Tyr Cys Ala
                85                  90                  95

Arg Glu Arg Gly Tyr Thr Tyr Gly Asn Phe Asp His Trp Gly Gln Gly
            100                 105                 110

Thr Leu Val Thr Val Ser Ser Gly Gly Gly Gly Ser Gly Gly Gly Gly
```

```
            115                 120                 125
Ser Gly Gly Gly Ser Glu Ile Val Met Thr Gln Ser Pro Ala Thr
    130                 135                 140

Leu Ser Val Ser Pro Gly Glu Arg Ala Thr Leu Ser Cys Arg Ala Ser
145                 150                 155                 160

Gln Ser Val Ser Arg Asn Leu Ala Trp Tyr Gln Gln Lys Pro Gly Gln
                165                 170                 175

Ala Pro Arg Leu Leu Ile Tyr Gly Ala Ser Thr Arg Ala Thr Gly Ile
            180                 185                 190

Pro Ala Arg Phe Ser Gly Ser Gly Ser Gly Thr Glu Phe Thr Leu Thr
            195                 200                 205

Ile Gly Ser Leu Gln Ser Glu Asp Phe Ala Val Tyr Tyr Cys Gln Gln
    210                 215                 220

Tyr Lys Thr Trp Pro Arg Thr Phe Gly Gln Gly Thr Asn Val Glu Ile
225                 230                 235                 240

Lys Ser Gly Gly Gly Gly Ser Glu Val Gln Leu Val Glu Ser Gly Gly
                245                 250                 255

Gly Leu Val Gln Pro Gly Gly Ser Leu Lys Leu Ser Cys Ala Ala Ser
            260                 265                 270

Gly Phe Thr Phe Asn Lys Tyr Ala Met Asn Trp Val Arg Gln Ala Pro
            275                 280                 285

Gly Lys Gly Leu Glu Trp Val Ala Arg Ile Arg Ser Lys Tyr Asn Asn
            290                 295                 300

Tyr Ala Thr Tyr Tyr Ala Asp Ser Val Lys Asp Arg Phe Thr Ile Ser
305                 310                 315                 320

Arg Asp Asp Ser Lys Asn Thr Ala Tyr Leu Gln Met Asn Asn Leu Lys
                325                 330                 335

Thr Glu Asp Thr Ala Val Tyr Tyr Cys Val Arg His Gly Asn Phe Gly
            340                 345                 350

Asn Ser Tyr Ile Ser Tyr Trp Ala Tyr Trp Gly Gln Gly Thr Leu Val
            355                 360                 365

Thr Val Ser Ser Gly Gly Gly Ser Gly Gly Gly Ser Gly Gly
    370                 375                 380

Gly Gly Ser Gln Thr Val Val Thr Gln Glu Pro Ser Leu Thr Val Ser
385                 390                 395                 400

Pro Gly Gly Thr Val Thr Leu Thr Cys Gly Ser Ser Thr Gly Ala Val
                405                 410                 415

Thr Ser Gly Asn Tyr Pro Asn Trp Val Gln Gln Lys Pro Gly Gln Ala
            420                 425                 430

Pro Arg Gly Leu Ile Gly Gly Thr Lys Phe Leu Ala Pro Gly Thr Pro
            435                 440                 445

Ala Arg Phe Ser Gly Ser Leu Leu Gly Gly Lys Ala Ala Leu Thr Leu
    450                 455                 460

Ser Gly Val Gln Pro Glu Asp Glu Ala Glu Tyr Tyr Cys Val Leu Trp
465                 470                 475                 480

Tyr Ser Asn Arg Trp Val Phe Gly Gly Gly Thr Lys Leu Thr Val Leu
                485                 490                 495

<210> SEQ ID NO 130
<211> LENGTH: 501
<212> TYPE: PRT
<213> ORGANISM: Artificial Sequence
<220> FEATURE:
<223> OTHER INFORMATION: Synthesized
```

```
<400> SEQUENCE: 130

Gln Val Gln Leu Arg Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Val Ile Ser Trp Val Lys Gln Arg Thr Gly Gln Gly Leu Glu Trp Ile
        35                  40                  45

Gly Asp Ile Tyr Pro Gly Ser Gly Tyr Ser Phe Tyr Asn Glu Asn Phe
    50                  55                  60

Lys Gly Lys Ala Thr Leu Thr Ala Asp Lys Ser Ser Thr Thr Ala Tyr
65                  70                  75                  80

Met Gln Leu Ser Ser Leu Thr Ser Glu Asp Ser Ala Val Tyr Phe Cys
                85                  90                  95

Ala Thr Tyr Tyr Asn Tyr Pro Phe Ala Tyr Trp Gly Gln Gly Thr Leu
            100                 105                 110

Val Thr Val Ser Ala Gly Gly Gly Ser Gly Gly Gly Gly Ser Gly
        115                 120                 125

Gly Gly Gly Ser Asp Val Val Met Thr Gln Thr Pro Leu Ser Leu Pro
    130                 135                 140

Val Arg Leu Gly Asp Gln Ala Ser Ile Ser Cys Arg Ser Ser Gln Ser
145                 150                 155                 160

Leu Val His Ser Asn Gly Asn Thr Tyr Leu His Trp Tyr Leu Gln Lys
                165                 170                 175

Pro Gly Gln Ser Pro Lys Leu Leu Ile Tyr Lys Val Ser Asn Arg Phe
            180                 185                 190

Ser Gly Val Pro Asp Arg Phe Ser Gly Ser Gly Ser Gly Thr Asn Phe
        195                 200                 205

Thr Leu Lys Ile Ser Arg Val Glu Ala Glu Asp Leu Gly Leu Tyr Phe
    210                 215                 220

Cys Ser Gln Ser Thr His Val Pro Tyr Thr Phe Gly Gly Gly Thr Lys
225                 230                 235                 240

Leu Glu Ile Lys Arg Ala Ser Gly Gly Gly Gly Ser Glu Val Gln Leu
                245                 250                 255

Val Glu Ser Gly Gly Gly Leu Val Gln Pro Gly Gly Ser Leu Lys Leu
            260                 265                 270

Ser Cys Ala Ala Ser Gly Phe Thr Phe Asn Lys Tyr Ala Met Asn Trp
        275                 280                 285

Val Arg Gln Ala Pro Gly Lys Gly Leu Glu Trp Val Ala Arg Ile Arg
    290                 295                 300

Ser Lys Tyr Asn Asn Tyr Ala Thr Tyr Tyr Ala Asp Ser Val Lys Asp
305                 310                 315                 320

Arg Phe Thr Ile Ser Arg Asp Asp Ser Lys Asn Thr Ala Tyr Leu Gln
                325                 330                 335

Met Asn Asn Leu Lys Thr Glu Asp Thr Ala Val Tyr Tyr Cys Val Arg
            340                 345                 350

His Gly Asn Phe Gly Asn Ser Tyr Ile Ser Tyr Trp Ala Tyr Trp Gly
        355                 360                 365

Gln Gly Thr Leu Val Thr Val Ser Ser Gly Gly Gly Gly Ser Gly Gly
    370                 375                 380

Gly Gly Ser Gly Gly Gly Gly Ser Gln Thr Val Val Thr Gln Glu Pro
385                 390                 395                 400

Ser Leu Thr Val Ser Pro Gly Gly Thr Val Thr Leu Thr Cys Gly Ser
                405                 410                 415
```

```
Ser Thr Gly Ala Val Thr Ser Gly Asn Tyr Pro Asn Trp Val Gln Gln
            420                 425                 430

Lys Pro Gly Gln Ala Pro Arg Gly Leu Ile Gly Thr Lys Phe Leu
            435                 440                 445

Ala Pro Gly Thr Pro Ala Arg Phe Ser Gly Ser Leu Leu Gly Gly Lys
450                 455                 460

Ala Ala Leu Thr Leu Ser Gly Val Gln Pro Glu Asp Glu Ala Glu Tyr
465                 470                 475                 480

Tyr Cys Val Leu Trp Tyr Ser Asn Arg Trp Val Phe Gly Gly Thr
                485                 490                 495

Lys Leu Thr Val Leu
            500
```

<210> SEQ ID NO 131
<211> LENGTH: 501
<212> TYPE: PRT
<213> ORGANISM: Artificial Sequence
<220> FEATURE:
<223> OTHER INFORMATION: Synthesized

<400> SEQUENCE: 131

```
Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Ser Tyr
            20                  25                  30

Trp Ile Asn Trp Val Lys Gln Arg Pro Gly Gln Gly Leu Glu Trp Ile
            35                  40                  45

Gly Asn Ile Tyr Pro Ser Asp Ser Tyr Thr Asn Tyr Asn Gln Lys Phe
50                  55                  60

Lys Asp Lys Ala Thr Leu Thr Val Asp Lys Ser Ser Ser Thr Ala Tyr
65                  70                  75                  80

Met Gln Leu Ser Ser Pro Thr Ser Glu Asp Ser Ala Val Tyr Tyr Cys
                85                  90                  95

Thr Arg Ser Trp Arg Gly Asn Ser Phe Asp Tyr Trp Gly Gln Gly Thr
            100                 105                 110

Thr Leu Thr Val Ser Ser Gly Gly Gly Gly Ser Gly Gly Gly Gly Ser
            115                 120                 125

Gly Gly Gly Gly Ser Asp Ile Val Met Thr Gln Ser Pro Ser Ser Leu
130                 135                 140

Thr Val Thr Ala Gly Glu Lys Val Thr Met Ser Cys Lys Ser Ser Gln
145                 150                 155                 160

Ser Leu Leu Asn Ser Gly Asn Gln Lys Asn Tyr Leu Thr Trp Tyr Gln
                165                 170                 175

Gln Lys Pro Gly Gln Pro Pro Lys Leu Leu Ile Tyr Trp Ala Ser Thr
            180                 185                 190

Arg Glu Ser Gly Val Pro Asp Arg Phe Thr Gly Ser Gly Ser Gly Thr
            195                 200                 205

Asp Phe Thr Leu Thr Ile Ser Ser Val Gln Ala Glu Asp Leu Ala Val
            210                 215                 220

Tyr Tyr Cys Gln Asn Asp Tyr Ser Tyr Pro Phe Thr Phe Gly Ser Gly
225                 230                 235                 240

Thr Lys Leu Glu Ile Lys Ser Gly Gly Gly Gly Ser Glu Val Gln Leu
                245                 250                 255

Val Glu Ser Gly Gly Gly Leu Val Gln Pro Gly Gly Ser Leu Lys Leu
            260                 265                 270
```

```
Ser Cys Ala Ala Ser Gly Phe Thr Phe Asn Lys Tyr Ala Met Asn Trp
            275                 280                 285

Val Arg Gln Ala Pro Gly Lys Gly Leu Glu Trp Val Ala Arg Ile Arg
        290                 295                 300

Ser Lys Tyr Asn Asn Tyr Ala Thr Tyr Tyr Ala Asp Ser Val Lys Asp
305                 310                 315                 320

Arg Phe Thr Ile Ser Arg Asp Asp Ser Lys Asn Thr Ala Tyr Leu Gln
                325                 330                 335

Met Asn Asn Leu Lys Thr Glu Asp Thr Ala Val Tyr Tyr Cys Val Arg
            340                 345                 350

His Gly Asn Phe Gly Asn Ser Tyr Ile Ser Tyr Trp Ala Tyr Trp Gly
        355                 360                 365

Gln Gly Thr Leu Val Thr Val Ser Ser Gly Gly Gly Ser Gly Gly
        370                 375                 380

Gly Gly Ser Gly Gly Gly Ser Gln Thr Val Val Thr Gln Glu Pro
385                 390                 395                 400

Ser Leu Thr Val Ser Pro Gly Gly Thr Val Thr Leu Thr Cys Gly Ser
                405                 410                 415

Ser Thr Gly Ala Val Thr Ser Gly Asn Tyr Pro Asn Trp Val Gln Gln
            420                 425                 430

Lys Pro Gly Gln Ala Pro Arg Gly Leu Ile Gly Gly Thr Lys Phe Leu
        435                 440                 445

Ala Pro Gly Thr Pro Ala Arg Phe Ser Gly Ser Leu Leu Gly Gly Lys
    450                 455                 460

Ala Ala Leu Thr Leu Ser Gly Val Gln Pro Glu Asp Glu Ala Glu Tyr
465                 470                 475                 480

Tyr Cys Val Leu Trp Tyr Ser Asn Arg Trp Val Phe Gly Gly Gly Thr
                485                 490                 495

Lys Leu Thr Val Leu
            500

<210> SEQ ID NO 132
<211> LENGTH: 496
<212> TYPE: PRT
<213> ORGANISM: Artificial Sequence
<220> FEATURE:
<223> OTHER INFORMATION: Synthesized

<400> SEQUENCE: 132

Glu Val Gln Leu Gln Gln Ser Gly Pro Glu Leu Val Lys Pro Gly Gly
1               5                   10                  15

Ser Met Lys Ile Ser Cys Lys Ala Ser Gly Tyr Ser Phe Thr Gly Tyr
            20                  25                  30

Thr Met Asn Trp Val Lys Gln Ser His Gly Lys Asn Leu Glu Trp Ile
        35                  40                  45

Gly Leu Ile Asn Pro Tyr Asn Gly Gly Ile Ser Tyr Asn Gln Lys Phe
    50                  55                  60

Lys Asp Lys Ala Thr Leu Thr Met Asp Lys Ser Ser Ser Thr Ala Tyr
65                  70                  75                  80

Met Glu Leu Leu Ser Leu Thr Ser Glu Asp Ser Ala Ile Tyr Phe Cys
                85                  90                  95

Ala Arg Asp Tyr Arg Tyr Glu Gly Phe Asp Tyr Trp Gly Gln Gly Thr
            100                 105                 110

Leu Val Thr Val Ser Ala Gly Gly Gly Gly Ser Gly Gly Gly Gly Ser
        115                 120                 125
```

Gly Gly Gly Gly Ser Gln Ile Val Leu Thr Gln Ser Pro Ala Ile Met
            130                 135                 140

Ser Ala Ser Leu Gly Glu Arg Val Thr Met Thr Cys Thr Ala Ser Ser
145                 150                 155                 160

Val Val Ile Ser Thr Tyr Leu His Trp Tyr Gln Gln Lys Pro Gly Ser
                165                 170                 175

Ser Pro Lys Leu Trp Ile Tyr Ser Thr Ser Asn Leu Ala Ser Gly Val
            180                 185                 190

Pro Val Arg Phe Ser Gly Ser Gly Ser Gly Thr Ser Tyr Ser Leu Thr
        195                 200                 205

Ile Ser Ser Met Glu Ala Glu Asp Ala Ala Thr Tyr Tyr Cys His Gln
210                 215                 220

Tyr His Arg Ser Pro Trp Thr Phe Gly Gly Gly Thr Lys Leu Glu Ile
225                 230                 235                 240

Lys Ser Gly Gly Gly Gly Ser Glu Val Gln Leu Val Glu Ser Gly Gly
                245                 250                 255

Gly Leu Val Gln Pro Gly Gly Ser Leu Lys Leu Ser Cys Ala Ala Ser
            260                 265                 270

Gly Phe Thr Phe Asn Lys Tyr Ala Met Asn Trp Val Arg Gln Ala Pro
        275                 280                 285

Gly Lys Gly Leu Glu Trp Val Ala Arg Ile Arg Ser Lys Tyr Asn Asn
290                 295                 300

Tyr Ala Thr Tyr Tyr Ala Asp Ser Val Lys Asp Arg Phe Thr Ile Ser
305                 310                 315                 320

Arg Asp Asp Ser Lys Asn Thr Ala Tyr Leu Gln Met Asn Asn Leu Lys
                325                 330                 335

Thr Glu Asp Thr Ala Val Tyr Tyr Cys Val Arg His Gly Asn Phe Gly
            340                 345                 350

Asn Ser Tyr Ile Ser Tyr Trp Ala Tyr Trp Gly Gln Gly Thr Leu Val
        355                 360                 365

Thr Val Ser Ser Gly Gly Gly Gly Ser Gly Gly Gly Gly Ser Gly Gly
370                 375                 380

Gly Gly Ser Gln Thr Val Val Thr Gln Glu Pro Ser Leu Thr Val Ser
385                 390                 395                 400

Pro Gly Gly Thr Val Thr Leu Thr Cys Gly Ser Ser Thr Gly Ala Val
                405                 410                 415

Thr Ser Gly Asn Tyr Pro Asn Trp Val Gln Gln Lys Pro Gly Gln Ala
            420                 425                 430

Pro Arg Gly Leu Ile Gly Gly Thr Lys Phe Leu Ala Pro Gly Thr Pro
        435                 440                 445

Ala Arg Phe Ser Gly Ser Leu Leu Gly Gly Lys Ala Ala Leu Thr Leu
450                 455                 460

Ser Gly Val Gln Pro Glu Asp Glu Ala Glu Tyr Tyr Cys Val Leu Trp
465                 470                 475                 480

Tyr Ser Asn Arg Trp Val Phe Gly Gly Gly Thr Lys Leu Thr Val Leu
                485                 490                 495

<210> SEQ ID NO 133
<211> LENGTH: 505
<212> TYPE: PRT
<213> ORGANISM: Artificial Sequence
<220> FEATURE:
<223> OTHER INFORMATION: Synthesized

<400> SEQUENCE: 133

```
Glu Ile Gln Leu Gln Gln Ser Gly Ala Glu Lys Lys Pro Gly Ser
1               5                   10                  15

Ser Val Lys Val Ser Cys Lys Ala Ser Gly Tyr Thr Phe Thr Asp Tyr
            20                  25                  30

Asp Met His Trp Val Arg Gln Ala Pro Gly Gln Gly Leu Glu Trp Met
            35                  40                  45

Gly Thr Ile Asp Pro Glu Thr Gly Gly Thr Ala Tyr Asn Gln Lys Phe
        50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Ser Phe Tyr Tyr Thr Tyr Ser Asn Tyr Asp Val Gly Phe Ala Tyr
            100                 105                 110

Trp Gly Gln Gly Thr Leu Val Thr Val Ser Ser Gly Gly Gly Gly Ser
            115                 120                 125

Gly Gly Gly Gly Ser Gly Gly Gly Ser Asp Ile Val Met Thr Gln
130                 135                 140

Ser Pro Leu Ser Leu Pro Val Thr Pro Gly Glu Pro Ala Ser Ile Ser
145                 150                 155                 160

Cys Arg Ser Thr Lys Ser Leu Leu His Ser Asn Gly Asn Thr Tyr Leu
                165                 170                 175

Tyr Trp Tyr Leu Gln Lys Pro Gly Gln Ser Pro Gln Leu Leu Ile Tyr
            180                 185                 190

Arg Met Ser Asn Leu Ala Ser Gly Val Pro Asp Arg Phe Ser Gly Ser
                195                 200                 205

Gly Ser Gly Thr Asp Phe Thr Leu Lys Ile Ser Arg Val Glu Ala Glu
            210                 215                 220

Asp Val Gly Val Tyr Tyr Cys Met Gln His Leu Glu Tyr Pro Phe Thr
225                 230                 235                 240

Phe Gly Gly Gly Thr Lys Val Glu Ile Lys Ser Gly Gly Gly Gly Ser
            245                 250                 255

Glu Val Gln Leu Val Glu Ser Gly Gly Gly Leu Val Gln Pro Gly Gly
            260                 265                 270

Ser Leu Lys Leu Ser Cys Ala Ala Ser Gly Phe Thr Phe Asn Lys Tyr
            275                 280                 285

Ala Met Asn Trp Val Arg Gln Ala Pro Gly Lys Gly Leu Glu Trp Val
            290                 295                 300

Ala Arg Ile Arg Ser Lys Tyr Asn Asn Tyr Ala Thr Tyr Tyr Ala Asp
305                 310                 315                 320

Ser Val Lys Asp Arg Phe Thr Ile Ser Arg Asp Asp Ser Lys Asn Thr
                325                 330                 335

Ala Tyr Leu Gln Met Asn Asn Leu Lys Thr Glu Asp Thr Ala Val Tyr
            340                 345                 350

Tyr Cys Val Arg His Gly Asn Phe Gly Asn Ser Tyr Ile Ser Tyr Trp
            355                 360                 365

Ala Tyr Trp Gly Gln Gly Thr Leu Val Thr Val Ser Ser Gly Gly Gly
        370                 375                 380

Gly Ser Gly Gly Gly Gly Ser Gly Gly Gly Gly Ser Gln Thr Val Val
385                 390                 395                 400

Thr Gln Glu Pro Ser Leu Thr Val Ser Pro Gly Gly Thr Val Thr Leu
                405                 410                 415
```

```
Thr Cys Gly Ser Ser Thr Gly Ala Val Thr Ser Gly Asn Tyr Pro Asn
                420                 425                 430

Trp Val Gln Gln Lys Pro Gly Gln Ala Pro Arg Gly Leu Ile Gly Gly
                435                 440                 445

Thr Lys Phe Leu Ala Pro Gly Thr Pro Ala Arg Phe Ser Gly Ser Leu
                450                 455                 460

Leu Gly Gly Lys Ala Ala Leu Thr Leu Ser Gly Val Gln Pro Glu Asp
465                 470                 475                 480

Glu Ala Glu Tyr Tyr Cys Val Leu Trp Tyr Ser Asn Arg Trp Val Phe
                485                 490                 495

Gly Gly Gly Thr Lys Leu Thr Val Leu
                500                 505

<210> SEQ ID NO 134
<211> LENGTH: 493
<212> TYPE: PRT
<213> ORGANISM: Artificial Sequence
<220> FEATURE:
<223> OTHER INFORMATION: Synthesized

<400> SEQUENCE: 134

Glu Val Gln Leu Val Glu Ser Gly Gly Leu Val Gln Pro Gly Gly
1               5                   10                  15

Ser Leu Arg Leu Ser Cys Ala Ala Ser Gly Tyr Ser Ile Thr Asn Asp
                20                  25                  30

Tyr Ala Trp Asn Trp Val Arg Gln Ala Pro Gly Lys Gly Leu Glu Trp
                35                  40                  45

Val Gly Tyr Ile Ser Tyr Ser Gly Tyr Thr Thr Tyr Asn Pro Ser Leu
                50                  55                  60

Lys Ser Arg Phe Thr Ile Ser Arg Asp Thr Ser Lys Asn Thr Leu Tyr
65              70                  75                  80

Leu Gln Met Asn Ser Leu Arg Ala Glu Asp Thr Ala Val Tyr Tyr Cys
                85                  90                  95

Ala Arg Trp Thr Ser Gly Leu Asp Tyr Trp Gly Gln Gly Thr Leu Val
                100                 105                 110

Thr Val Ser Ser Gly Gly Gly Gly Ser Gly Gly Gly Gly Ser Gly Gly
                115                 120                 125

Gly Gly Ser Asp Ile Gln Met Thr Gln Ser Pro Ser Ser Leu Ser Ala
                130                 135                 140

Ser Val Gly Asp Arg Val Thr Ile Thr Cys Lys Ala Ser Asp Leu Ile
145                 150                 155                 160

His Asn Trp Leu Ala Trp Tyr Gln Gln Lys Pro Gly Lys Ala Pro Lys
                165                 170                 175

Leu Leu Ile Tyr Gly Ala Thr Ser Leu Glu Thr Gly Val Pro Ser Arg
                180                 185                 190

Phe Ser Gly Ser Gly Ser Gly Thr Asp Phe Thr Leu Thr Ile Ser Ser
                195                 200                 205

Leu Gln Pro Glu Asp Phe Ala Thr Tyr Tyr Cys Gln Gln Tyr Trp Thr
                210                 215                 220

Thr Pro Phe Thr Phe Gly Gln Gly Thr Lys Val Glu Ile Lys Ser Gly
225                 230                 235                 240

Gly Gly Gly Ser Glu Val Gln Leu Val Glu Ser Gly Gly Gly Leu Val
                245                 250                 255

Gln Pro Gly Gly Ser Leu Lys Leu Ser Cys Ala Ala Ser Gly Phe Thr
                260                 265                 270
```

```
Phe Asn Lys Tyr Ala Met Asn Trp Val Arg Gln Ala Pro Gly Lys Gly
            275                 280                 285

Leu Glu Trp Val Ala Arg Ile Arg Ser Lys Tyr Asn Asn Tyr Ala Thr
        290                 295                 300

Tyr Tyr Ala Asp Ser Val Lys Asp Arg Phe Thr Ile Ser Arg Asp Asp
305                 310                 315                 320

Ser Lys Asn Thr Ala Tyr Leu Gln Met Asn Asn Leu Lys Thr Glu Asp
                325                 330                 335

Thr Ala Val Tyr Tyr Cys Val Arg His Gly Asn Phe Gly Asn Ser Tyr
            340                 345                 350

Ile Ser Tyr Trp Ala Tyr Trp Gly Gln Gly Thr Leu Val Thr Val Ser
        355                 360                 365

Ser Gly Gly Gly Gly Ser Gly Gly Gly Gly Ser Gly Gly Gly Gly Ser
    370                 375                 380

Gln Thr Val Val Thr Gln Glu Pro Ser Leu Thr Val Ser Pro Gly Gly
385                 390                 395                 400

Thr Val Thr Leu Thr Cys Gly Ser Ser Thr Gly Ala Val Thr Ser Gly
                405                 410                 415

Asn Tyr Pro Asn Trp Val Gln Gln Lys Pro Gly Gln Ala Pro Arg Gly
            420                 425                 430

Leu Ile Gly Gly Thr Lys Phe Leu Ala Pro Gly Thr Pro Ala Arg Phe
        435                 440                 445

Ser Gly Ser Leu Leu Gly Gly Lys Ala Ala Leu Thr Leu Ser Gly Val
    450                 455                 460

Gln Pro Glu Asp Glu Ala Glu Tyr Tyr Cys Val Leu Trp Tyr Ser Asn
465                 470                 475                 480

Arg Trp Val Phe Gly Gly Gly Thr Lys Leu Thr Val Leu
                485                 490

<210> SEQ ID NO 135
<211> LENGTH: 109
<212> TYPE: PRT
<213> ORGANISM: Artificial Sequence
<220> FEATURE:
<223> OTHER INFORMATION: Synthesized

<400> SEQUENCE: 135

Gln Thr Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Ser Gly
            20                  25                  30

Asn Tyr Pro Asn Trp Val Gln Gln Lys Pro Gly Gln Ala Pro Arg Gly
        35                  40                  45

Leu Ile Gly Gly Thr Lys Phe Leu Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Val Leu Trp Tyr Ser Asn
                85                  90                  95

Arg Trp Val Phe Gly Gly Gly Thr Lys Leu Thr Val Leu
            100                 105

<210> SEQ ID NO 136
<211> LENGTH: 244
<212> TYPE: PRT
<213> ORGANISM: Artificial Sequence
<220> FEATURE:
```

<223> OTHER INFORMATION: Synthesized

<400> SEQUENCE: 136

```
Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asp Ile Gly Ser Asn
            20                  25                  30

Tyr Val Ser Trp Tyr Gln Gln Phe Pro Gly Thr Ala Pro Lys Leu Leu
        35                  40                  45

Ile Tyr Asp Asn Asn Lys Arg Pro Ser Ala Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Arg Leu
                85                  90                  95

Gly Ile Ala Val Phe Gly Gly Gly Thr Gln Leu Thr Val Leu Gly Gly
            100                 105                 110

Gly Gly Ser Gly Gly Gly Gly Ser Gly Gly Gly Gly Ser Glu Val Gln
        115                 120                 125

Leu Val Gln Ser Gly Ala Glu Val Lys Lys Pro Gly Gln Ser Leu Lys
    130                 135                 140

Ile Ser Cys Lys Ala Ser Gly Tyr Ser Leu Thr Asp Asn Trp Ile Gly
145                 150                 155                 160

Trp Val Arg Gln Lys Pro Gly Lys Gly Leu Glu Trp Met Gly Ile Ile
                165                 170                 175

Tyr Pro Gly Asp Ser Asp Thr Arg Tyr Ser Pro Ser Phe Gln Gly Gln
            180                 185                 190

Val Thr Ile Ser Ala Asp Lys Ser Ile Asn Thr Ala Tyr Leu Gln Trp
        195                 200                 205

Ser Ser Leu Lys Ala Ser Asp Thr Ala Ile Tyr Tyr Cys Val Gly Leu
    210                 215                 220

Asp Trp Asn Tyr Asn Pro Leu Arg Tyr Trp Gly Pro Gly Thr Leu Val
225                 230                 235                 240

Thr Val Ser Ser
```

<210> SEQ ID NO 137
<211> LENGTH: 252
<212> TYPE: PRT
<213> ORGANISM: Artificial Sequence
<220> FEATURE:
<223> OTHER INFORMATION: Synthesized

<400> SEQUENCE: 137

```
Asp Ile Val Leu Thr Gln Ser Pro Ala Ser Leu Ala Val Ser Leu Gly
1               5                   10                  15

Gln Gly Ala Thr Ile Ser Cys Arg Ala Ser Lys Ser Val Ser Thr Ser
            20                  25                  30

Gly Tyr Thr Tyr Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Gly
                85                  90                  95
```

Glu Leu Pro Pro Ser Phe Gly Gly Thr Lys Leu Glu Ile Lys Arg
                100                 105                 110

Ala Gly Gly Gly Ser Gly Gly Gly Ser Gly Gly Gly Ser
            115                 120                 125

Glu Val Gln Leu Val Glu Ser Gly Gly Asp Leu Val Lys Pro Gly Gly
        130                 135                 140

Ser Leu Lys Leu Ser Cys Ala Val Ser Gly Phe Thr Phe Ser Ser Tyr
145                 150                 155                 160

Gly Met Ser Trp Val Arg Gln Thr Pro Asp Lys Arg Leu Glu Trp Val
                165                 170                 175

Ala Thr Val Ser Ser Gly Gly Thr Tyr Thr Tyr Tyr Pro Asp Ser Val
            180                 185                 190

Lys Gly Arg Phe Thr Ile Ser Arg Asp Asn Ala Lys Asn Thr Leu Tyr
        195                 200                 205

Leu Gln Met Ser Ser Leu Lys Ser Glu Asp Ser Ala Met Tyr Tyr Cys
    210                 215                 220

Ala Arg His Arg Gly Asn Tyr Tyr Ala Thr Tyr Tyr Ala Met Asp
225                 230                 235                 240

Tyr Trp Gly Gln Gly Thr Ser Val Thr Val Ser Ser
                245                 250

<210> SEQ ID NO 138
<211> LENGTH: 243
<212> TYPE: PRT
<213> ORGANISM: Artificial Sequence
<220> FEATURE:
<223> OTHER INFORMATION: Synthesized

<400> SEQUENCE: 138

Asp Val Gln Ile Thr Gln Ser Pro Ser Tyr Leu Ala Ala Ser Pro Gly
1               5                   10                  15

Glu Thr Ile Thr Ile Asn Cys Arg Ala Ser Lys Ser Ile Ser Lys Tyr
            20                  25                  30

Leu Ala Trp Tyr Gln Glu Lys Pro Gly Lys Thr Asn Lys Leu Leu Ile
        35                  40                  45

Tyr Ser Gly Ser Thr Leu Gln Ser Gly Ile Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln His His Glu Tyr Pro Tyr
                85                  90                  95

Thr Phe Gly Gly Gly Thr Lys Leu Glu Ile Lys Gly Gly Gly Gly Ser
            100                 105                 110

Gly Gly Gly Gly Ser Gly Gly Gly Ser Gln Val Gln Leu Gln Gln
        115                 120                 125

Pro Gly Ala Glu Leu Val Arg Pro Gly Ala Ser Val Lys Leu Ser Cys
    130                 135                 140

Lys Ala Ser Gly Tyr Thr Phe Thr Thr Tyr Trp Met Asn Trp Val Lys
145                 150                 155                 160

Gln Arg Pro Glu Gln Gly Leu Glu Trp Ile Gly Arg Ile Asp Pro Tyr
                165                 170                 175

Asp Ser Glu Thr His Tyr Asn Gln Lys Phe Lys Asp Lys Ala Ile Leu
            180                 185                 190

Thr Val Asp Lys Ser Ser Ser Thr Ala Tyr Met Gln Leu Ser Ser Leu
        195                 200                 205

Thr Ser Glu Asp Ser Ala Val Tyr Tyr Cys Ala Arg Gly Pro Tyr Tyr
210                 215                 220

Gly Thr Asn Pro Trp Phe Pro Tyr Trp Gly Gln Gly Thr Leu Val Thr
225                 230                 235                 240

Val Ser Ser

<210> SEQ ID NO 139
<211> LENGTH: 241
<212> TYPE: PRT
<213> ORGANISM: Artificial Sequence
<220> FEATURE:
<223> OTHER INFORMATION: Synthesized

<400> SEQUENCE: 139

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Arg Asn
                20                  25                  30

Leu Ala Trp Tyr Gln Gln Lys Pro Gly Gln Ala Pro Arg Leu Leu Ile
            35                  40                  45

Tyr Gly Ala Ser Thr Arg Ala Thr Gly Ile Pro Ala Arg Phe Ser Gly
50                  55                  60

Ser Gly Ser Gly Thr Glu Phe Thr Leu Thr Ile Gly Ser Leu Gln Ser
65                  70                  75                  80

Glu Asp Phe Ala Val Tyr Tyr Cys Gln Gln Tyr Lys Thr Trp Pro Arg
                85                  90                  95

Thr Phe Gly Gln Gly Thr Asn Val Glu Ile Lys Gly Gly Gly Gly Ser
            100                 105                 110

Gly Gly Gly Gly Ser Gly Gly Gly Ser Gln Val Gln Leu Gln Gln
            115                 120                 125

Trp Gly Ala Gly Leu Leu Lys Pro Ser Glu Thr Leu Ser Leu Thr Cys
130                 135                 140

Ala Val Phe Gly Gly Ser Phe Ser Gly Tyr Tyr Trp Ser Trp Ile Arg
145                 150                 155                 160

Gln Pro Pro Gly Lys Gly Leu Glu Trp Ile Gly Glu Ile Asn His Arg
                165                 170                 175

Gly Asn Thr Asn Asp Asn Pro Ser Leu Lys Ser Arg Val Thr Ile Ser
            180                 185                 190

Val Asp Thr Ser Lys Asn Gln Phe Ala Leu Lys Leu Ser Ser Val Thr
195                 200                 205

Ala Ala Asp Thr Ala Val Tyr Tyr Cys Ala Arg Glu Arg Gly Tyr Thr
210                 215                 220

Tyr Gly Asn Phe Asp His Trp Gly Gln Gly Thr Leu Val Thr Val Ser
225                 230                 235                 240

Ser

<210> SEQ ID NO 140
<211> LENGTH: 246
<212> TYPE: PRT
<213> ORGANISM: Artificial Sequence
<220> FEATURE:
<223> OTHER INFORMATION: Synthesized

<400> SEQUENCE: 140

Asp Val Val Met Thr Gln Thr Pro Leu Ser Leu Pro Val Arg Leu Gly
1               5                   10                  15

Asp Gln Ala Ser Ile Ser Cys Arg Ser Ser Gln Ser Leu Val His Ser

```
                 20                  25                  30
Asn Gly Asn Thr Tyr Leu His Trp Tyr Leu Gln Lys Pro Gly Gln Ser
            35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asn Phe Thr Leu Lys Ile
 65                  70                  75                  80

Ser Arg Val Glu Ala Glu Asp Leu Gly Leu Tyr Phe Cys Ser Gln Ser
                85                  90                  95

Thr His Val Pro Tyr Thr Phe Gly Gly Gly Thr Lys Leu Glu Ile Lys
            100                 105                 110

Arg Ala Gly Gly Gly Gly Ser Gly Gly Gly Gly Ser Gly Gly Gly Gly
        115                 120                 125

Ser Gln Val Gln Leu Arg Gln Ser Gly Pro Glu Leu Val Lys Pro Gly
    130                 135                 140

Ala Ser Val Lys Met Ser Cys Lys Ala Ser Gly Tyr Thr Phe Thr Asp
145                 150                 155                 160

Tyr Val Ile Ser Trp Val Lys Gln Arg Thr Gly Gln Gly Leu Glu Trp
                165                 170                 175

Ile Gly Asp Ile Tyr Pro Gly Ser Gly Tyr Ser Phe Tyr Asn Glu Asn
            180                 185                 190

Phe Lys Gly Lys Ala Thr Leu Thr Ala Asp Lys Ser Ser Thr Thr Ala
        195                 200                 205

Tyr Met Gln Leu Ser Ser Leu Thr Ser Glu Asp Ser Ala Val Tyr Phe
    210                 215                 220

Cys Ala Thr Tyr Tyr Asn Tyr Pro Phe Ala Tyr Trp Gly Gln Gly Thr
225                 230                 235                 240

Leu Val Thr Val Ser Ala
                245

<210> SEQ ID NO 141
<211> LENGTH: 199
<212> TYPE: PRT
<213> ORGANISM: Artificial Sequence
<220> FEATURE:
<223> OTHER INFORMATION: Synthesized

<400> SEQUENCE: 141

Leu Pro Ile Cys Pro Gly Gly Ala Ala Arg Cys Gln Val Thr Leu Arg
 1               5                  10                  15

Asp Leu Phe Asp Arg Ala Val Val Leu Ser His Tyr Ile His Asn Leu
            20                  25                  30

Ser Ser Glu Met Phe Ser Glu Phe Asp Lys Arg Tyr Thr His Gly Arg
        35                  40                  45

Gly Phe Ile Thr Lys Ala Ile Asn Ser Cys His Thr Ser Ser Leu Ala
    50                  55                  60

Thr Pro Glu Asp Lys Glu Gln Ala Gln Gln Met Asn Gln Lys Asp Phe
 65                  70                  75                  80

Leu Ser Leu Ile Val Ser Ile Leu Arg Ser Trp Asn Glu Pro Leu Tyr
                85                  90                  95

His Leu Val Thr Glu Val Arg Gly Met Gln Glu Ala Pro Glu Ala Ile
            100                 105                 110

Leu Ser Lys Ala Val Glu Ile Glu Glu Gln Thr Lys Arg Leu Leu Glu
        115                 120                 125

Gly Met Glu Leu Ile Val Ser Gln Val His Pro Glu Thr Lys Glu Asn
```

130                 135                 140
Glu Ile Tyr Pro Val Trp Ser Gly Leu Pro Ser Leu Gln Met Ala Asp
145                 150                 155                 160

Glu Glu Ser Arg Leu Ser Ala Tyr Tyr Asn Leu Leu His Cys Leu Arg
                165                 170                 175

Arg Asp Ser His Lys Ile Asp Asn Tyr Leu Lys Leu Leu Lys Cys Arg
                180                 185                 190

Ile Ile His Asn Asn Asn Cys
                195

<210> SEQ ID NO 142
<211> LENGTH: 240
<212> TYPE: PRT
<213> ORGANISM: Artificial Sequence
<220> FEATURE:
<223> OTHER INFORMATION: Synthesized

<400> SEQUENCE: 142

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
                20                  25                  30

Arg Thr Arg Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Thr Gln
                85                  90                  95

Ser Phe Ile Leu Arg Thr Phe Gly Gln Gly Thr Lys Val Glu Ile Lys
                100                 105                 110

Gly Gly Gly Gly Gly Ser Gly Gly Gly Ser Gly Gly Gly Gly Gly Ser
                115                 120                 125

Asp Ile Val Met Thr Gln Ser Pro Asp Ser Leu Ala Val Ser Leu Gly
            130                 135                 140

Glu Arg Ala Thr Ile Asn Cys Lys Ser Ser Gln Ser Leu Leu Asn Ser
145                 150                 155                 160

Arg Thr Arg Lys Asn Tyr Leu Ala Trp Tyr Gln Gln Lys Pro Gly Gln
                165                 170                 175

Pro Pro Lys Leu Leu Ile Tyr Trp Ala Ser Thr Arg Glu Ser Gly Val
                180                 185                 190

Pro Asp Arg Phe Ser Gly Ser Gly Ser Gly Thr Asp Phe Thr Leu Thr
            195                 200                 205

Ile Ser Ser Leu Gln Ala Glu Asp Val Ala Val Tyr Tyr Cys Thr Gln
        210                 215                 220

Ser Phe Ile Leu Arg Thr Phe Gly Gln Gly Thr Lys Val Glu Ile Lys
225                 230                 235                 240

<210> SEQ ID NO 143
<211> LENGTH: 281
<212> TYPE: PRT
<213> ORGANISM: Artificial Sequence
<220> FEATURE:
<223> OTHER INFORMATION: Synthesized

<400> SEQUENCE: 143

Met Asn Val Pro Thr Gln Leu Leu Gly Leu Leu Leu Trp Leu Thr
1               5                   10                  15

Gly Gly Lys Cys Asp Ile Gln Met Thr Gln Ser Pro Ala Ser Leu Ser
            20                  25                  30

Ala Ser Leu Glu Glu Ile Val Thr Ile Thr Cys Lys Ala Ser Gln Ala
        35                  40                  45

Ile Asp Ala Tyr Leu Ser Trp Tyr Gln Gln Lys Pro Gly Lys Ser Pro
50                  55                  60

Gln Leu Leu Ile Tyr Asp Ala Thr Ser Leu Ala Asp Gly Val Pro Ser
65                  70                  75                  80

Arg Phe Ser Gly Ser Arg Ser Gly Thr Gln Tyr Ser Leu Lys Ile Ser
                85                  90                  95

Arg Pro Gln Val Asp Asp Ser Gly Ile Tyr Tyr Cys Leu Gln Ser Tyr
            100                 105                 110

Ser Thr Pro Phe Thr Phe Gly Ser Gly Thr Lys Leu Glu Ile Lys Gly
        115                 120                 125

Gly Gly Gly Gly Ser Gly Gly Gly Ser Gly Gly Gly Gly Ser Met
130                 135                 140

Ala Val Leu Val Leu Leu Leu Cys Leu Leu Ile Phe Pro Ser Cys Val
145                 150                 155                 160

Leu Ser Gln Val Gln Leu Lys Glu Ser Gly Pro Gly Leu Val Gln Pro
                165                 170                 175

Ser Gln Thr Leu Ser Leu Thr Cys Thr Val Ser Gly Ser Ser Leu Thr
            180                 185                 190

Ser Asn Ser Val Ser Trp Ile Arg Gln Pro Pro Gly Lys Gly Leu Glu
        195                 200                 205

Trp Met Gly Val Ile Trp Ser Asn Gly Asp Ala Asp Tyr Asn Ser Ala
210                 215                 220

Ile Lys Ser Arg Leu Ser Ile Ser Arg Asp Thr Ser Lys Ser Gln Val
225                 230                 235                 240

Phe Leu Lys Met Asn Ser Leu Gln Thr Glu Asp Thr Ala Met Tyr Phe
                245                 250                 255

Cys Ala Ser Pro Tyr Tyr Gly Tyr Tyr Phe Pro Phe Asp Tyr Trp Gly
            260                 265                 270

Gln Gly Val Met Val Thr Val Ser Ser
        275                 280

<210> SEQ ID NO 144
<211> LENGTH: 285
<212> TYPE: PRT
<213> ORGANISM: Artificial Sequence
<220> FEATURE:
<223> OTHER INFORMATION: Synthesized

<400> SEQUENCE: 144

Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Ala Leu Ala Val
            20                  25                  30

Ser Leu Gly Gln Arg Ala Thr Ile Ser Cys Arg Ala Ser Gln Ser Val
        35                  40                  45

Ser Ile Ser Ser His Asp Leu Met Gln Trp Tyr Gln Gln Lys Pro Gly
    50                  55                  60

Gln Gln Pro Lys Leu Leu Ile Tyr Asp Ala Phe Asn Leu Ala Ser Gly
65                  70                  75                  80

```
Ile Pro Val Arg Phe Ser Gly Ser Gly Ser Gly Thr Asp Phe Thr Leu
                85                  90                  95

Thr Ile Asp Pro Val Gln Ala Asp Asp Ile Ala Thr Tyr Tyr Cys Gln
            100                 105                 110

Gln Ser Lys Asp Asp Pro Tyr Thr Phe Gly Ala Gly Thr Lys Leu Glu
            115                 120                 125

Leu Lys Gly Gly Gly Gly Ser Gly Gly Gly Ser Gly Gly Gly
130                 135                 140

Gly Ser Met Asp Ile Arg Leu Ser Leu Ala Phe Leu Val Leu Phe Ile
145                 150                 155                 160

Lys Gly Val Gln Cys Glu Val Gln Leu Val Glu Ser Gly Gly Gly Leu
                165                 170                 175

Val Gln Pro Gly Arg Ser Met Lys Leu Ser Cys Ala Ala Ser Gly Phe
            180                 185                 190

Thr Phe Ser Asn Tyr Gly Met Ala Trp Val Arg Gln Ala Pro Thr Lys
            195                 200                 205

Gly Leu Glu Trp Val Ala Thr Ile Ser Tyr Asp Gly Ser Ile Thr Tyr
            210                 215                 220

Tyr Arg Asp Ser Val Lys Gly Arg Phe Thr Ile Ser Arg Asp His Ala
225                 230                 235                 240

Lys Ser Thr Leu Tyr Leu Gln Met Asn Ser Leu Arg Ser Glu Asp Thr
                245                 250                 255

Ala Thr Tyr Tyr Cys Thr Arg Glu Glu Gln Tyr Ser Ser Trp Tyr Phe
            260                 265                 270

Asp Phe Trp Gly Pro Gly Ile Met Val Thr Val Ser Ser
            275                 280                 285

<210> SEQ ID NO 145
<211> LENGTH: 242
<212> TYPE: PRT
<213> ORGANISM: Artificial Sequence
<220> FEATURE:
<223> OTHER INFORMATION: Synthesized

<400> SEQUENCE: 145

Asn Ile Val Met Thr Gln Ser Pro Ser Ser Leu Ser Ala Ser Val Gly
1               5                   10                  15

Asp Arg Val Thr Ile Thr Cys Gln Ala Ser Gln Asp Val Gly Thr Ala
            20                  25                  30

Val Ala Trp Tyr Gln Gln Lys Pro Asp Gln Ser Pro Lys Leu Leu Ile
        35                  40                  45

Tyr Trp Thr Ser Thr Arg His Thr Gly Val Pro Asp Arg Phe Thr Gly
    50                  55                  60

Ser Gly Ser Gly Thr Asp Phe Thr Leu Thr Ile Ser Ser Leu Gln Pro
65                  70                  75                  80

Glu Asp Ile Ala Thr Tyr Phe Cys His Gln Tyr Asn Ser Tyr Asn Thr
                85                  90                  95

Phe Gly Ser Gly Thr Lys Leu Glu Ile Lys Gly Gly Gly Gly Ser
            100                 105                 110

Gly Gly Gly Gly Ser Gly Gly Gly Ser Gln Val Thr Leu Lys Glu
            115                 120                 125

Ser Gly Pro Val Leu Val Lys Pro Thr Glu Thr Leu Thr Leu Thr Cys
            130                 135                 140

Thr Phe Ser Gly Phe Ser Leu Ser Thr Ser Gly Met Gly Val Gly Trp
145                 150                 155                 160
```

Ile Arg Gln Ala Pro Gly Lys Gly Leu Glu Trp Val Ala His Ile Trp
            165                 170                 175

Trp Asp Asp Val Tyr Tyr Asn Pro Ser Leu Lys Ser Arg Leu Thr
        180                 185                 190

Ile Thr Lys Asp Ala Ser Lys Asp Gln Val Ser Leu Lys Leu Ser Ser
        195                 200                 205

Val Thr Ala Ala Asp Thr Ala Val Tyr Tyr Cys Val Arg Arg Ala
210                 215                 220

Thr Gly Thr Gly Phe Asp Tyr Trp Gly Gln Gly Thr Leu Val Thr Val
225                 230                 235                 240

Ser Ser

<210> SEQ ID NO 146
<211> LENGTH: 246
<212> TYPE: PRT
<213> ORGANISM: Artificial Sequence
<220> FEATURE:
<223> OTHER INFORMATION: Synthesized

<400> SEQUENCE: 146

Glu Ile Val Leu Thr Gln Ser Pro Gly Ser Leu Ala Val Ser Pro Gly
1               5                   10                  15

Glu Arg Val Thr Met Ser Cys Lys Ser Ser Gln Ser Val Phe Phe Ser
            20                  25                  30

Ser Ser Gln Lys Asn Tyr Leu Ala Trp Tyr Gln Gln Ile Pro Gly Gln
        35                  40                  45

Ser Pro Arg Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Pro Glu Asp Leu Ala Ile Tyr Tyr Cys His Gln
                85                  90                  95

Tyr Leu Ser Ser Arg Thr Phe Gly Gln Gly Thr Lys Leu Glu Ile Lys
            100                 105                 110

Arg Gly Gly Gly Gly Ser Gly Gly Gly Gly Ser Gly Gly Gly Gly Ser
        115                 120                 125

Gln Val Gln Leu Gln Gln Pro Gly Ala Glu Val Val Lys Pro Gly Ala
    130                 135                 140

Ser Val Lys Met Ser Cys Lys Ala Ser Gly Tyr Thr Phe Thr Ser Tyr
145                 150                 155                 160

Tyr Ile His Trp Ile Lys Gln Thr Pro Gly Gln Gly Leu Glu Trp Val
                165                 170                 175

Gly Val Ile Tyr Pro Gly Asn Asp Asp Ile Ser Tyr Asn Gln Lys Phe
            180                 185                 190

Gln Gly Lys Ala Thr Leu Thr Ala Asp Lys Ser Ser Thr Thr Ala Tyr
        195                 200                 205

Met Gln Leu Ser Ser Leu Thr Ser Glu Asp Ser Ala Val Tyr Tyr Cys
    210                 215                 220

Ala Arg Glu Val Arg Leu Arg Tyr Phe Asp Val Trp Gly Gln Gly Thr
225                 230                 235                 240

Thr Val Thr Val Ser Ser
                245

<210> SEQ ID NO 147
<211> LENGTH: 255
<212> TYPE: PRT

<213> ORGANISM: Artificial Sequence
<220> FEATURE:
<223> OTHER INFORMATION: Synthesized

<400> SEQUENCE: 147

Met Ala Asp Tyr Lys Asp Ile Val Met Thr Gln Ser Pro Ser Ser Val
1               5                   10                  15

Ser Ala Ser Val Gly Asp Arg Val Thr Ile Thr Cys Arg Ala Ser Gln
            20                  25                  30

Asn Val Asp Ser Ala Val Ala Trp Tyr Gln Gln Lys Pro Gly Lys Ala
        35                  40                  45

Pro Lys Ala Leu Ile Tyr Ser Ala Ser Tyr Arg Tyr Ser Gly Val Pro
50                  55                  60

Ser Arg Phe Ser Gly Arg Gly Ser Gly Thr Asp Phe Thr Leu Thr Ile
65                  70                  75                  80

Ser Ser Leu Gln Pro Glu Asp Phe Ala Thr Tyr Tyr Cys Gln Gln Tyr
                85                  90                  95

Tyr Ser Thr Pro Trp Thr Phe Gly Gln Gly Thr Lys Val Glu Ile Lys
            100                 105                 110

Arg Gly Gly Gly Gly Ser Gly Gly Gly Ser Gly Gly Gly Gly Ser
        115                 120                 125

Glu Val Lys Leu Val Glu Ser Gly Gly Leu Val Gln Pro Gly Arg
130                 135                 140

Ser Leu Arg Leu Ser Cys Thr Ala Ser Gly Phe Thr Phe Thr Asp Tyr
145                 150                 155                 160

Tyr Met Ser Trp Val Arg Gln Ala Pro Gly Lys Gly Leu Glu Trp Val
                165                 170                 175

Gly Leu Ile Arg Ser Lys Ala Asp Gly Tyr Thr Thr Glu Tyr Ser Ala
            180                 185                 190

Ser Val Lys Gly Arg Phe Thr Ile Ser Arg Asp Asp Ser Lys Ser Ile
        195                 200                 205

Leu Tyr Leu Gln Met Asn Ser Leu Lys Thr Glu Asp Thr Ala Val Tyr
    210                 215                 220

Tyr Cys Ala Arg Asp Ala Ala Tyr Tyr Ser Tyr Tyr Ser Pro Glu Gly
225                 230                 235                 240

Ala Met Asp Tyr Trp Gly Gln Gly Thr Leu Val Thr Val Ser Ser
                245                 250                 255

<210> SEQ ID NO 148
<211> LENGTH: 244
<212> TYPE: PRT
<213> ORGANISM: Artificial Sequence
<220> FEATURE:
<223> OTHER INFORMATION: Synthesized

<400> SEQUENCE: 148

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ile Asn
            20                  25                  30

Thr Val Asn Trp Tyr Gln Gln Leu Pro Gly Thr Ala Pro Lys Leu Leu
        35                  40                  45

Ile Tyr Asp Asn Asn Lys Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Asp Ser Leu
            85                  90                  95

Ser Gly Trp Val Phe Gly Gly Thr Lys Leu Thr Val Leu Gly Gly
            100                 105                 110

Gly Gly Ser Gly Gly Gly Ser Gly Gly Gly Ser Glu Val Gln
            115                 120                 125

Leu Leu Glu Ser Gly Gly Leu Val Gln Pro Gly Gly Ser Leu Arg
130                 135                 140

Leu Ser Cys Ala Ala Ser Gly Phe Thr Phe Ser Asp Tyr Tyr Met Ser
145                 150                 155                 160

Trp Ile Arg Gln Ala Pro Gly Lys Gly Leu Glu Trp Val Ser Ala Ile
            165                 170                 175

Ser Gly Ser Gly Gly Ser Thr Tyr Tyr Ala Asp Ser Val Lys Gly Arg
            180                 185                 190

Phe Thr Ile Ser Arg Asp Asn Ser Lys Asn Thr Leu Tyr Leu Gln Met
            195                 200                 205

Asn Ser Leu Arg Ala Glu Asp Thr Ala Val Tyr Tyr Cys Ala Lys Glu
            210                 215                 220

Asp Trp Glu Gly Ala Ser Phe Asp Tyr Trp Gly Gln Gly Thr Leu Val
225                 230                 235                 240

Thr Val Ser Ser

<210> SEQ ID NO 149
<211> LENGTH: 245
<212> TYPE: PRT
<213> ORGANISM: Artificial Sequence
<220> FEATURE:
<223> OTHER INFORMATION: Synthesized

<400> SEQUENCE: 149

Asp Ile Val Met Thr Gln Ser Pro Asp Ser Leu Ala Val Ser Leu Gly
1               5                   10                  15

Glu Arg Ala Thr Ile Asn Cys Arg Ala Ser Lys Ser Val Ser Thr Ser
            20                  25                  30

Gly Tyr Ser Phe Met His Trp Tyr Gln Gln Lys Pro Gly Gln Pro Pro
            35                  40                  45

Lys Leu Leu Ile Tyr Leu Ala Ser Asn Leu Glu Ser Gly Val Pro Asp
        50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ser Arg
            85                  90                  95

Glu Val Pro Trp Thr Phe Gly Gln Gly Thr Lys Val Glu Ile Lys Arg
            100                 105                 110

Gly Gly Gly Gly Ser Gly Gly Gly Gly Ser Gly Gly Gly Gly Ser Gln
            115                 120                 125

Val Gln Leu Val Gln Ser Gly Ala Glu Val Lys Lys Pro Gly Ala Ser
130                 135                 140

Val Lys Val Ser Cys Lys Ala Ser Gly Tyr Thr Phe Thr Asn Tyr Gly
145                 150                 155                 160

Met Asn Trp Val Arg Gln Ala Pro Gly Gln Gly Leu Glu Trp Met Gly
            165                 170                 175

Trp Ile Asn Thr Tyr Thr Gly Glu Pro Thr Tyr Ala Asp Ala Phe Lys
            180                 185                 190

Gly Arg Val Thr Met Thr Thr Asp Thr Ser Thr Ser Thr Ala Tyr Met

```
                195                 200                 205
Glu Leu Arg Ser Leu Arg Ser Asp Asp Thr Ala Val Tyr Tyr Cys Ala
    210                 215                 220
Arg Asp Tyr Gly Asp Tyr Gly Met Asp Tyr Trp Gly Gln Gly Thr Thr
225                 230                 235                 240
Val Thr Val Ser Ser
                245

<210> SEQ ID NO 150
<211> LENGTH: 263
<212> TYPE: PRT
<213> ORGANISM: Artificial Sequence
<220> FEATURE:
<223> OTHER INFORMATION: Synthesized

<400> SEQUENCE: 150

Ala Gln Ala Ala Glu Leu Asp Ile Val Leu Ser Gln Ser Pro Ala Ile
1               5                   10                  15
Met Ser Ala Ser Pro Gly Glu Lys Val Thr Ile Ser Cys Ser Ala Ser
            20                  25                  30
Ser Ser Val Ser Tyr Met Tyr Trp Tyr Gln Gln Lys Pro Gly Ser Ser
        35                  40                  45
Pro Lys Pro Trp Ile Tyr Arg Thr Ser Asn Leu Ala Ser Gly Val Pro
    50                  55                  60
Ala Arg Phe Ser Gly Ser Gly Ser Gly Thr Ser Tyr Ser Leu Thr Ile
65                  70                  75                  80
Ser Ser Met Glu Ala Glu Asp Ala Ala Thr Tyr Tyr Cys Gln Gln Tyr
                85                  90                  95
His Ser Tyr Pro Pro Thr Phe Gly Ala Gly Thr Lys Leu Glu Leu Lys
            100                 105                 110
Ser Ser Gly Gly Gly Ser Gly Gly Gly Gly Ser Ser Arg
        115                 120                 125
Ser Ser Leu Glu Val Lys Leu Val Glu Ser Gly Pro Glu Leu Lys Lys
    130                 135                 140
Pro Gly Glu Thr Val Lys Ile Ser Cys Lys Ala Ser Gly Tyr Thr Phe
145                 150                 155                 160
Thr Asp Tyr Ser Met His Trp Val Asn Gln Ala Pro Gly Lys Gly Leu
                165                 170                 175
Lys Trp Met Gly Trp Ile Asn Thr Glu Thr Gly Glu Pro Ser Tyr Ala
            180                 185                 190
Asp Asp Phe Lys Gly Arg Phe Ala Phe Ser Leu Glu Thr Ser Ala Ser
        195                 200                 205
Thr Ala Tyr Leu Gln Ile Asn Asn Leu Lys Asn Glu Asp Thr Ala Thr
    210                 215                 220
Tyr Phe Cys Ala Thr Asp Tyr Gly Asp Tyr Phe Asp Tyr Trp Gly Gln
225                 230                 235                 240
Gly Thr Thr Leu Thr Val Ser Ser Ala Lys Thr Thr Pro Pro Ser Val
                245                 250                 255
Thr Ser Gly Gln Ala Gly Gln
            260

<210> SEQ ID NO 151
<211> LENGTH: 239
<212> TYPE: PRT
<213> ORGANISM: Artificial Sequence
<220> FEATURE:
<223> OTHER INFORMATION: Synthesized
```

<400> SEQUENCE: 151

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Thr Ile Gln Lys Gln Gly Leu Pro Thr Glu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asn Arg Ala Lys Phe Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Thr Asp Ile Gln Met Thr Gln Ser Pro Ser Ser Leu Ser
130                 135                 140

Ala Ser Val Gly Asp Arg Val Thr Ile Thr Cys Arg Ala Ser Gln Ser
145                 150                 155                 160

Ile Ser Ser Tyr Leu Asn Trp Tyr Gln Gln Lys Pro Gly Lys Ala Pro
                165                 170                 175

Lys Leu Leu Ile Tyr Asn Ala Ser Met Leu Gln Ser Gly Val Pro Ser
            180                 185                 190

Arg Phe Ser Gly Ser Gly Ser Gly Thr Asp Phe Thr Leu Thr Ile Ser
        195                 200                 205

Ser Leu Gln Pro Glu Asp Phe Ala Thr Tyr Tyr Cys Gln Gln Asn Arg
    210                 215                 220

Gly Phe Pro Leu Thr Phe Gly Gln Gly Thr Lys Val Glu Ile Lys
225                 230                 235

<210> SEQ ID NO 152
<211> LENGTH: 239
<212> TYPE: PRT
<213> ORGANISM: Artificial Sequence
<220> FEATURE:
<223> OTHER INFORMATION: Synthesized

<400> SEQUENCE: 152

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Ile Ile
        35                  40                  45

Tyr Gly Ala Ser Thr Thr Ala Ser Gly Ile Pro Ala Arg Phe Ser Ala
    50                  55                  60

Ser Gly Ser Gly Thr Asp Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Pro
                85                  90                  95

Ala Tyr Thr Phe Gly Gln Gly Thr Lys Leu Glu Ile Lys Gly Gly Gly
            100                 105                 110

```
Gly Ser Gly Gly Gly Ser Gly Gly Gly Ser Gln Val Gln Leu
        115                 120                 125

Val Gln Ser Gly Ala Glu Val Lys Lys Pro Gly Ser Ser Val Lys Val
130                 135                 140

Ser Cys Lys Ala Ser Gly Gly Thr Phe Ser Ser Tyr Ala Ile Ser Trp
145                 150                 155                 160

Val Arg Gln Ala Pro Gly Gln Gly Leu Glu Trp Met Gly Gly Ile Ile
                165                 170                 175

Pro Ile Phe Gly Thr Ala Asn Tyr Ala Gln Lys Phe Gln Gly Arg Val
            180                 185                 190

Thr Ile Thr Ala Asp Glu Ser Thr Ser Thr Ala Tyr Met Glu Leu Ser
        195                 200                 205

Ser Leu Arg Ser Glu Asp Thr Ala Val Tyr Tyr Cys Ala Arg Gly Leu
    210                 215                 220

Leu Trp Asn Tyr Trp Gly Gln Gly Thr Leu Val Thr Val Ser Ser
225                 230                 235

<210> SEQ ID NO 153
<211> LENGTH: 246
<212> TYPE: PRT
<213> ORGANISM: Artificial Sequence
<220> FEATURE:
<223> OTHER INFORMATION: Synthesized

<400> SEQUENCE: 153

Ser Thr Val Met Thr Gln Ser Pro Ser Phe Leu Ser Ala Ser Val Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Cys Gln Ser Pro Lys Val Leu Ile
        35                  40                  45

Tyr Phe Ala Ser Asn Arg Tyr Thr Gly Val Pro Asp Arg Phe Ser Gly
    50                  55                  60

Ser Gly Tyr Gly Thr Asp Phe Thr Leu Thr Ile Ser Ser Leu Gln Ala
65                  70                  75                  80

Glu Asp Val Ala Val Tyr Phe Cys Gln Gln Asp Tyr Ser Ser Pro Leu
                85                  90                  95

Thr Phe Gly Ala Gly Thr Lys Leu Glu Ile Lys Gly Gly Gly Gly Ser
            100                 105                 110

Gly Gly Gly Gly Ser Gly Gly Gly Ser Gln Ile Gln Leu Val Gln
        115                 120                 125

Ser Gly Ser Glu Leu Lys Lys Pro Gly Ala Ser Val Lys Val Ser Cys
130                 135                 140

Lys Ala Ser Gly Tyr Thr Phe Thr Asn Phe Phe Val Asn Trp Val Lys
145                 150                 155                 160

Gln Ala Pro Gly Lys Gly Leu Lys Trp Met Gly Trp Ile Asn Thr Tyr
                165                 170                 175

Thr Gly Glu Pro Ser Tyr Ala Asp Asp Phe Lys Gly Arg Phe Ala Phe
            180                 185                 190

Ser Leu Asp Ala Ser Ala Ser Thr Ala Tyr Leu Gln Ile Ser Ser Leu
        195                 200                 205

Lys Ala Glu Asp Met Ala Thr Tyr Phe Cys Thr Arg Arg Thr Asn Tyr
    210                 215                 220

Tyr Gly Thr Ser Tyr Tyr Tyr Ala Met Asp Tyr Trp Gly Gln Gly Thr
225                 230                 235                 240
```

```
Thr Val Thr Val Ser Ser
            245

<210> SEQ ID NO 154
<211> LENGTH: 458
<212> TYPE: PRT
<213> ORGANISM: Artificial Sequence
<220> FEATURE:
<223> OTHER INFORMATION: Synthesized

<400> SEQUENCE: 154

Arg Ile Val Met Thr Gln Ser Pro Gly Thr Leu Ser Val Ser Pro Gly
1               5                   10                  15

Glu Thr Ala Thr Leu Ser Cys Arg Ala Ser Gln Ser Phe Ser Asn Met
            20                  25                  30

Leu Ala Trp Tyr Gln Gln Lys Ser Gly Gln Pro Pro Arg Leu Leu Ile
        35                  40                  45

Tyr Gly Val Ser Thr Arg Ala Ala Gly Val Pro Ala Arg Phe Ser Gly
    50                  55                  60

Ser Gly Ser Gly Thr Glu Phe Thr Leu Thr Ile Ser Asn Leu Gln Ser
65                  70                  75                  80

Glu Asp Phe Ala Val Tyr Tyr Cys Gln Gln Tyr Gly Asp Trp Pro Arg
                85                  90                  95

Tyr Thr Phe Gly Gln Gly Thr Lys Val Glu Arg Lys Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys Gly Gly Gly Ser Gly Gly Gly Gly
    210                 215                 220

Ser Gly Gly Gly Gly Ser Glu Val Gln Leu Val Gln Ser Gly Gly Gly
225                 230                 235                 240

Val Val Arg Pro Gly Gly Ser Leu Arg Leu Pro Cys Ala Ala Ser Gly
                245                 250                 255

Phe Thr Phe Asp Asp Tyr Gly Met Ser Trp Val Arg Gln Ala Pro Gly
            260                 265                 270

Lys Gly Leu Glu Trp Val Ser Gly Ile Asn Trp Asn Gly Gly Ser Thr
        275                 280                 285

Gly Tyr Ala Asp Ser Val Lys Gly Arg Phe Thr Ile Ser Arg Asp Asn
    290                 295                 300

Ala Lys Asn Ser Leu Tyr Leu Gln Met Asn Ser Leu Arg Ala Glu Asp
305                 310                 315                 320

Thr Ala Leu Tyr His Cys Ala Arg Gly Gly Asp Ala Phe Asp Ile
                325                 330                 335

Trp Gly Gln Gly Thr Met Val Thr Val Ser Ser Ala Ser Thr Lys Gly
            340                 345                 350
```

Pro Ser Val Phe Pro Leu Ala Pro Ser Ser Lys Ser Thr Ser Gly Gly
            355                 360                 365

Thr Ala Ala Leu Gly Cys Leu Val Lys Asp Tyr Phe Pro Glu Pro Val
    370                 375                 380

Thr Val Ser Trp Asn Ser Gly Ala Leu Thr Ser Gly Val His Thr Phe
385                 390                 395                 400

Pro Ala Val Leu Gln Ser Ser Gly Leu Tyr Ser Leu Ser Ser Val Val
                405                 410                 415

Thr Val Pro Ser Ser Leu Gly Thr Gln Thr Tyr Ile Cys Asn Val
            420                 425                 430

Asn His Lys Pro Ser Asn Thr Lys Val Asp Lys Lys Val Glu Pro Lys
            435                 440                 445

Ser Cys Asp Lys Thr Ser Gly Gln Ala Gly
    450                 455

<210> SEQ ID NO 155
<211> LENGTH: 239
<212> TYPE: PRT
<213> ORGANISM: Artificial Sequence
<220> FEATURE:
<223> OTHER INFORMATION: Synthesized

<400> SEQUENCE: 155

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys Gly Gly Gly Gly
            100                 105                 110

Ser Gly Gly Gly Gly Ser Gly Gly Gly Gly Ser Glu Val Gln Leu Val
        115                 120                 125

Glu Ser Gly Gly Gly Leu Val Gln Pro Gly Gly Ser Leu Arg Leu Ser
130                 135                 140

Cys Val Ala Ser Gly Phe Thr Phe Ser Asn Ser Trp Met Ser Trp Val
145                 150                 155                 160

Arg Gln Ala Pro Gly Lys Gly Leu Glu Trp Val Ala Asn Ile Asn Glu
                165                 170                 175

Asp Gly Ser Glu Lys Phe Tyr Val Asp Ser Val Lys Gly Arg Phe Thr
            180                 185                 190

Phe Ser Arg Asp Asn Ala Glu Asn Ser Leu Tyr Leu Gln Met Asn Ser
        195                 200                 205

Leu Arg Ala Glu Asp Thr Ala Val Tyr Tyr Cys Ala Arg Val His Trp
    210                 215                 220

Tyr Phe His Leu Trp Gly Arg Gly Thr Leu Val Thr Val Ser Ser
225                 230                 235

<210> SEQ ID NO 156
<211> LENGTH: 242

```
<212> TYPE: PRT
<213> ORGANISM: Artificial Sequence
<220> FEATURE:
<223> OTHER INFORMATION: Synthesized

<400> SEQUENCE: 156

Asn Ile Val Met Thr Gln Ser Pro Ser Ser Leu Ser Ala Ser Val Gly
1               5                   10                  15

Asp Arg Val Thr Ile Thr Cys Gln Ala Ser Gln Asp Val Gly Thr Ala
            20                  25                  30

Val Ala Trp Tyr Gln Gln Lys Pro Asp Gln Ser Pro Lys Leu Leu Ile
        35                  40                  45

Tyr Trp Thr Ser Thr Arg His Thr Gly Val Pro Asp Arg Phe Thr Gly
    50                  55                  60

Ser Gly Ser Gly Thr Asp Phe Thr Leu Thr Ile Ser Ser Leu Gln Pro
65                  70                  75                  80

Glu Asp Ile Ala Thr Tyr Phe Cys His Gln Tyr Asn Ser Tyr Asn Thr
                85                  90                  95

Phe Gly Ser Gly Thr Lys Leu Glu Ile Lys Gly Gly Gly Gly Ser
            100                 105                 110

Gly Gly Gly Gly Ser Gly Gly Gly Ser Gln Val Thr Leu Lys Glu
        115                 120                 125

Ser Gly Pro Val Leu Val Lys Pro Thr Glu Thr Leu Thr Leu Thr Cys
130                 135                 140

Thr Phe Ser Gly Phe Ser Leu Ser Thr Ser Gly Met Gly Val Gly Trp
145                 150                 155                 160

Ile Arg Gln Ala Pro Gly Lys Gly Leu Glu Trp Val Ala His Ile Trp
                165                 170                 175

Trp Asp Asp Val Tyr Tyr Asn Pro Ser Leu Lys Ser Arg Leu Thr
            180                 185                 190

Ile Thr Lys Asp Ala Ser Lys Asp Gln Val Ser Leu Lys Leu Ser Ser
        195                 200                 205

Val Thr Ala Ala Asp Thr Ala Val Tyr Tyr Cys Val Arg Arg Arg Ala
    210                 215                 220

Thr Gly Thr Gly Phe Asp Tyr Trp Gly Gln Gly Thr Leu Val Thr Val
225                 230                 235                 240

Ser Ser

<210> SEQ ID NO 157
<211> LENGTH: 679
<212> TYPE: PRT
<213> ORGANISM: Artificial Sequence
<220> FEATURE:
<223> OTHER INFORMATION: Synthesized

<400> SEQUENCE: 157

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80
```

-continued

```
Glu Asp Phe Ala Thr Tyr Tyr Cys Gln Gln His Tyr Thr Thr Pro Pro
                 85                  90                  95
Thr Phe Gly Gln Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
            115                 120                 125
Thr Ala Ser Val Val Cys Leu Leu Asn Asn Phe Tyr Pro Arg Glu Ala
            130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
                180                 185                 190
Ala Cys Glu Val Thr His Gln Gly Leu Ser Ser Pro Val Thr Lys Ser
            195                 200                 205
Phe Asn Arg Gly Glu Cys Gly Gly Gly Ser Gly Gly Gly Gly Ser
210                 215                 220
Gly Gly Gly Gly Ser Glu Val Gln Leu Val Glu Ser Gly Gly Gly Leu
225                 230                 235                 240
Val Gln Pro Gly Gly Ser Leu Arg Leu Ser Cys Ala Ala Ser Gly Phe
                245                 250                 255
Asn Ile Lys Asp Thr Tyr Ile His Trp Val Arg Gln Ala Pro Gly Lys
            260                 265                 270
Gly Leu Glu Trp Val Ala Arg Ile Tyr Pro Thr Asn Gly Tyr Thr Arg
275                 280                 285
Tyr Ala Asp Ser Val Lys Gly Arg Phe Thr Ile Ser Ala Asp Thr Ser
            290                 295                 300
Lys Asn Thr Ala Tyr Leu Gln Met Asn Ser Leu Arg Ala Glu Asp Thr
305                 310                 315                 320
Ala Val Tyr Tyr Cys Ser Arg Trp Gly Gly Asp Gly Phe Tyr Ala Met
                325                 330                 335
Asp Tyr Trp Gly Gln Gly Thr Leu Val Thr Val Ser Ser Ala Ser Thr
            340                 345                 350
Lys Gly Pro Ser Val Phe Pro Leu Ala Pro Ser Ser Lys Ser Thr Ser
            355                 360                 365
Gly Gly Thr Ala Ala Leu Gly Cys Leu Val Lys Asp Tyr Phe Pro Glu
            370                 375                 380
Pro Val Thr Val Ser Trp Asn Ser Gly Ala Leu Thr Ser Gly Val His
385                 390                 395                 400
Thr Phe Pro Ala Val Leu Gln Ser Ser Gly Leu Tyr Ser Leu Ser Ser
                405                 410                 415
Val Val Thr Val Pro Ser Ser Ser Leu Gly Thr Gln Thr Tyr Ile Cys
            420                 425                 430
Asn Val Asn His Lys Pro Ser Asn Thr Lys Val Asp Lys Lys Val Glu
            435                 440                 445
Pro Lys Ser Cys Asp Lys Thr His Thr Cys Pro Pro Cys Pro Ala Pro
            450                 455                 460
Glu Leu Leu Gly Gly Pro Ser Val Phe Leu Phe Pro Pro Lys Pro Lys
465                 470                 475                 480
Asp Thr Leu Met Ile Ser Arg Thr Pro Glu Val Thr Cys Val Val Val
                485                 490                 495
Asp Val Ser His Glu Asp Pro Glu Val Lys Phe Asn Trp Tyr Val Asp
```

```
                500                 505                 510
Gly Val Glu Val His Asn Ala Lys Thr Lys Pro Arg Glu Glu Gln Tyr
            515                 520                 525

Asn Ser Thr Tyr Arg Val Val Ser Val Leu Thr Val Leu His Gln Asp
            530                 535                 540

Trp Leu Asn Gly Lys Glu Tyr Lys Cys Lys Val Ser Asn Lys Ala Leu
545                 550                 555                 560

Pro Ala Pro Ile Glu Lys Thr Ile Ser Lys Ala Lys Gly Gln Pro Arg
            565                 570                 575

Glu Pro Gln Val Tyr Thr Leu Pro Pro Ser Arg Asp Glu Leu Thr Lys
            580                 585                 590

Asn Gln Val Ser Leu Thr Cys Leu Val Lys Gly Phe Tyr Pro Ser Asp
            595                 600                 605

Ile Ala Val Glu Trp Glu Ser Asn Gly Gln Pro Glu Asn Asn Tyr Lys
            610                 615                 620

Thr Thr Pro Pro Val Leu Asp Ser Asp Gly Ser Phe Phe Leu Tyr Ser
625                 630                 635                 640

Lys Leu Thr Val Asp Lys Ser Arg Trp Gln Gln Gly Asn Val Phe Ser
            645                 650                 655

Cys Ser Val Met His Glu Ala Leu His Asn His Tyr Thr Gln Lys Ser
            660                 665                 670

Leu Ser Leu Ser Pro Gly Lys
            675

<210> SEQ ID NO 158
<211> LENGTH: 246
<212> TYPE: PRT
<213> ORGANISM: Artificial Sequence
<220> FEATURE:
<223> OTHER INFORMATION: Synthesized

<400> SEQUENCE: 158

Asp Ile Gln Met Thr Gln Ser Pro Ser Ser Leu Ser Ala Ser Val Gly
1               5                   10                  15

Asp Arg Val Thr Ile Thr Cys Lys Ala Ser Ala Ala Val Gly Thr Tyr
            20                  25                  30

Val Ala Trp Tyr Gln Gln Lys Pro Gly Lys Ala Pro Lys Leu Leu Ile
        35                  40                  45

Tyr Ser Ala Ser Tyr Arg Lys Arg Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys His Gln Tyr Tyr Thr Tyr Pro Leu
            85                  90                  95

Phe Thr Phe Gly Gln Gly Thr Lys Leu Glu Ile Lys Arg Thr Gly Gly
            100                 105                 110

Gly Gly Ser Gly Gly Gly Gly Ser Gly Gly Gly Ser Gln Val Gln
        115                 120                 125

Leu Val Gln Ser Gly Ser Glu Leu Lys Lys Pro Gly Ala Ser Val Lys
    130                 135                 140

Val Ser Cys Lys Ala Ser Gly Tyr Thr Phe Thr Glu Phe Gly Met Asn
145                 150                 155                 160

Trp Val Arg Gln Ala Pro Gly Gln Gly Leu Glu Trp Met Gly Trp Ile
            165                 170                 175

Asn Thr Lys Thr Gly Glu Ala Thr Tyr Val Glu Glu Phe Lys Gly Arg
```

```
                180               185               190
Phe Val Phe Ser Leu Asp Thr Ser Val Ser Thr Ala Tyr Leu Gln Ile
            195               200               205
Ser Ser Leu Lys Ala Glu Asp Thr Ala Val Tyr Tyr Cys Ala Arg Trp
            210               215               220
Asp Phe Tyr Asp Tyr Val Glu Ala Met Asp Tyr Trp Gly Gln Gly Thr
225               230               235               240
Thr Val Thr Val Ser Ser
                245

<210> SEQ ID NO 159
<211> LENGTH: 392
<212> TYPE: PRT
<213> ORGANISM: Artificial Sequence
<220> FEATURE:
<223> OTHER INFORMATION: Synthesized

<400> SEQUENCE: 159

Ser Arg Ala Ala Thr Met Glu Thr Asp Thr Leu Leu Leu Trp Val Leu
1               5                   10                  15
Leu Leu Trp Val Pro Gly Ser Thr Gly Asp Ile Gln Leu Thr Gln Ser
            20                  25                  30
Pro Ser Ser Leu Ser Ala Ser Val Gly Asp Arg Val Thr Ile Thr Cys
        35                  40                  45
Ser Ala Ser Ser Ser Val Arg Phe Ile His Trp Tyr Gln Gln Lys Pro
    50                  55                  60
Gly Lys Ala Pro Lys Arg Leu Ile Tyr Asp Thr Ser Lys Leu Ala Ser
65                  70                  75                  80
Gly Val Pro Ser Arg Pro Ser Gly Ser Gly Ser Gly Thr Asp Phe Thr
                85                  90                  95
Leu Thr Ile Ser Ser Leu Gln Pro Glu Asp Phe Ala Thr Tyr Tyr Cys
            100                 105                 110
Gln Gln Trp Ser Ser Ser Pro Phe Thr Phe Gly Gln Gly Thr Lys Val
        115                 120                 125
Glu Ile Lys Gly Ser Thr Ser Gly Gly Gly Ser Gly Gly Gly Ser Gly
    130                 135                 140
Gly Gly Gly Ser Ser Glu Val Gln Leu Val Glu Ser Gly Gly Gly Leu
145                 150                 155                 160
Val Gln Pro Gly Gly Ser Leu Arg Leu Ser Cys Ala Ala Ser Gly Phe
                165                 170                 175
Asn Ile Lys Asp Tyr Tyr Ile His Trp Val Arg Gln Ala Pro Gly Lys
            180                 185                 190
Gly Leu Glu Trp Val Ala Trp Ile Asp Pro Glu Asn Gly Asp Thr Glu
        195                 200                 205
Phe Val Pro Lys Phe Gln Gly Arg Ala Thr Ile Ser Ala Asp Thr Ser
    210                 215                 220
Lys Asn Thr Ala Tyr Leu Gln Met Asn Ser Leu Arg Ala Glu Asp Thr
225                 230                 235                 240
Ala Val Tyr Tyr Cys Lys Thr Gly Gly Phe Trp Gly Gln Gly Thr Leu
                245                 250                 255
Val Thr Val Ser Ser Glu Pro Lys Ser Cys Asp Lys Thr His Thr Cys
            260                 265                 270
Pro Pro Cys Gly Gly Gly Ser Gly Gly Gly Ser Gly Gly Gln Pro
        275                 280                 285
Arg Glu Pro Gln Val Tyr Thr Leu Pro Pro Ser Arg Asp Glu Leu Thr
```

```
                290                 295                 300
Lys Asn Gln Val Ser Leu Thr Cys Leu Val Lys Gly Phe Tyr Pro Ser
305                 310                 315                 320

Asp Ile Ala Val Glu Trp Glu Ser Asn Gly Gln Pro Glu Asn Asn Tyr
                325                 330                 335

Lys Thr Thr Pro Pro Val Leu Asp Ser Asp Gly Ser Phe Phe Leu Tyr
                340                 345                 350

Ser Lys Leu Thr Val Asp Lys Ser Arg Trp Gln Gln Gly Asn Val Phe
                355                 360                 365

Ser Cys Ser Val Met His Glu Ala Leu His Asn His Tyr Thr Gln Lys
                370                 375                 380

Ser Leu Ser Leu Ser Pro Gly Lys
385                 390

<210> SEQ ID NO 160
<211> LENGTH: 243
<212> TYPE: PRT
<213> ORGANISM: Artificial Sequence
<220> FEATURE:
<223> OTHER INFORMATION: Synthesized

<400> SEQUENCE: 160

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
                20                  25                  30

Ser Asn Asn Lys Asn Tyr Leu Ala Trp Tyr Gln Gln Lys Pro Gly Gln
                35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Tyr Pro Leu Thr Phe Gly Gly Gly Thr Lys Val Glu Ile
                100                 105                 110

Lys Gly Gly Gly Gly Ser Gly Gly Gly Gly Ser Gly Gly Gly Gly Ser
                115                 120                 125

Gln Val Gln Leu Val Gln Ser Gly Ala Glu Val Lys Lys Pro Gly Ala
                130                 135                 140

Ser Val Lys Val Ser Cys Lys Ala Ser Gly Tyr Thr Phe Thr Asp His
145                 150                 155                 160

Ala Ile His Trp Val Arg Gln Ala Pro Gly Gln Arg Leu Glu Trp Met
                165                 170                 175

Gly Tyr Phe Ser Pro Gly Asn Asp Asp Phe Lys Tyr Ser Gln Lys Phe
                180                 185                 190

Gln Gly Arg Val Thr Ile Thr Ala Asp Lys Ser Ala Ser Thr Ala Tyr
                195                 200                 205

Met Glu Leu Ser Ser Leu Arg Ser Glu Asp Thr Ala Val Tyr Tyr Cys
                210                 215                 220

Ala Arg Ser Leu Asn Met Ala Tyr Trp Gly Gln Gly Thr Leu Val Thr
225                 230                 235                 240

Val Ser Ser

<210> SEQ ID NO 161
```

<211> LENGTH: 243
<212> TYPE: PRT
<213> ORGANISM: Artificial Sequence
<220> FEATURE:
<223> OTHER INFORMATION: Synthesized

<400> SEQUENCE: 161

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys Gly Gly Gly Gly Ser
            100                 105                 110

Gly Gly Gly Gly Ser Gly Gly Gly Ser Gln Val Gln Leu Val Gln
        115                 120                 125

Ser Gly Ala Glu Val Lys Lys Pro Gly Ser Ser Val Lys Val Ser Cys
130                 135                 140

Lys Ala Phe Gly Gly Thr Phe Ser Ser Tyr Ala Ile Ser Trp Val Arg
145                 150                 155                 160

Gln Ala Pro Gly Gln Gly Leu Glu Trp Met Gly Arg Ile Ile Arg Phe
                165                 170                 175

Leu Gly Lys Thr Asn His Ala Gln Lys Phe Gln Gly Arg Val Thr Leu
            180                 185                 190

Thr Ala Asp Lys Ser Thr Asn Thr Ala Tyr Met Glu Leu Ser Ser Leu
        195                 200                 205

Arg Ser Glu Asp Thr Ala Val Tyr Tyr Cys Ala Gly Glu Pro Gly Asp
    210                 215                 220

Arg Asp Pro Asp Ala Val Asp Ile Trp Gly Gln Gly Thr Met Val Thr
225                 230                 235                 240

Val Ser Ser

<210> SEQ ID NO 162
<211> LENGTH: 249
<212> TYPE: PRT
<213> ORGANISM: Artificial Sequence
<220> FEATURE:
<223> OTHER INFORMATION: Synthesized

<400> SEQUENCE: 162

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Ser Trp Leu His Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Ala Phe Thr Leu Lys Ile
65                  70                  75                  80

```
Ser Arg Val Glu Ala Glu Asp Val Gly Val Tyr Tyr Cys Met Gln Ala
                85                  90                  95

Thr Gln Leu Pro Arg Thr Phe Gly Gln Gly Thr Lys Val Glu Ile Lys
            100                 105                 110

Arg Gly Gly Gly Gly Ser Gly Gly Gly Ser Gly Gly Gly Ser
        115                 120                 125

Gln Val Gln Leu Val Glu Ser Gly Gly Val Val Gln Pro Gly Arg
    130                 135                 140

Ser Leu Arg Leu Ser Cys Ala Ala Ser Gly Phe Thr Phe Ser Ser Tyr
145                 150                 155                 160

Gly Met His Trp Val Arg Gln Ala Pro Gly Lys Gly Leu Glu Trp Val
                165                 170                 175

Ala Val Ile Trp Tyr Asp Gly Ser Asn Lys Tyr Tyr Val Asp Ser Val
            180                 185                 190

Lys Gly Arg Phe Thr Ile Ser Arg Asp Asn Ser Lys Asn Thr Leu Tyr
            195                 200                 205

Leu Gln Met Asn Ser Leu Arg Ala Glu Asp Thr Ala Val Tyr Tyr Cys
    210                 215                 220

Ala Arg Asp Gly Trp Gln Gln Leu Ala Pro Phe Asp Tyr Trp Gly Gln
225                 230                 235                 240

Gly Thr Leu Val Thr Val Ser Ser Ala
                245

<210> SEQ ID NO 163
<211> LENGTH: 237
<212> TYPE: PRT
<213> ORGANISM: Artificial Sequence
<220> FEATURE:
<223> OTHER INFORMATION: Synthesized

<400> SEQUENCE: 163

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Asn Tyr
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Glu Asp Met Gly Ile Tyr Tyr Cys Leu Lys Tyr Asp Glu Phe Pro Tyr
                85                  90                  95

Thr Phe Gly Gly Gly Thr Lys Leu Glu Ile Lys Gly Gly Gly Gly Ser
            100                 105                 110

Gly Gly Gly Gly Ser Gly Gly Gly Ser Asp Val Lys Leu Val Glu
        115                 120                 125

Ser Gly Gly Gly Leu Val Lys Pro Gly Gly Ser Leu Lys Leu Ser Cys
    130                 135                 140

Ala Ala Ser Gly Phe Thr Phe Ser Ser Tyr Thr Met Ser Trp Val Arg
145                 150                 155                 160

Gln Thr Pro Glu Lys Arg Leu Glu Trp Val Ala Thr Ile Ser Ser Gly
                165                 170                 175

Gly Thr Tyr Thr Tyr Tyr Pro Asp Ser Val Lys Gly Arg Phe Thr Ile
            180                 185                 190
```

Ser Arg Asp Asn Ala Lys Asn Thr Leu Tyr Leu Gln Met Ser Ser Leu
            195                 200                 205

Lys Ser Glu Asp Thr Ala Met Tyr Tyr Cys Thr Arg Glu Ala Ile Phe
210                 215                 220

Thr Tyr Trp Gly Gln Gly Thr Leu Val Thr Val Ser Ala
225                 230                 235

<210> SEQ ID NO 164
<211> LENGTH: 239
<212> TYPE: PRT
<213> ORGANISM: Artificial Sequence
<220> FEATURE:
<223> OTHER INFORMATION: Synthesized

<400> SEQUENCE: 164

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Arg Ser
            20                  25                  30

Tyr Leu Ala Trp Tyr Gln Gln Lys Pro Gly Gln Ala Pro Arg Leu Leu
        35                  40                  45

Ile Ile Gly Ala Ser Thr Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Gln Val Ile Pro
                85                  90                  95

Pro Thr Phe Gly Gln Gly Thr Lys Val Glu Ile Gly Gly Gly Gly Ser
            100                 105                 110

Gly Gly Gly Gly Ser Gly Gly Gly Ser Glu Val Gln Leu Leu Glu
        115                 120                 125

Ser Gly Gly Gly Leu Val Gln Pro Gly Gly Ser Leu Arg Leu Ser Cys
130                 135                 140

Ala Ala Ser Gly Phe Thr Phe Ser Ser Tyr Ala Met Ser Trp Val Arg
145                 150                 155                 160

Gln Ala Pro Gly Lys Gly Leu Glu Trp Val Ser Ala Ile Ser Gly Ser
                165                 170                 175

Gly Gly Ser Thr Tyr Tyr Ala Asp Ser Val Lys Gly Arg Phe Thr Ile
            180                 185                 190

Ser Arg Asp Asn Ser Lys Asn Thr Leu Tyr Leu Gln Met Asn Ser Leu
        195                 200                 205

Arg Ala Glu Asp Thr Ala Val Tyr Tyr Cys Ala Lys Gly Trp Leu Gly
    210                 215                 220

Asn Phe Asp Tyr Trp Gly Gln Gly Thr Leu Val Thr Val Ser Ser
225                 230                 235

<210> SEQ ID NO 165
<211> LENGTH: 441
<212> TYPE: PRT
<213> ORGANISM: Artificial Sequence
<220> FEATURE:
<223> OTHER INFORMATION: Synthesized

<400> SEQUENCE: 165

Glu Ile Val Met Thr Gln Thr Pro Ala Thr Leu Ser Val Ser Ala Gly
1               5                   10                  15

Glu Arg Val Thr Ile Thr Cys Lys Ala Ser Gln Ser Val Ser Asn His

```
                20                  25                  30
Val Thr Trp Tyr Gln Gln Lys Pro Gly Gln Ala Pro Arg Leu Leu Ile
            35                  40                  45

Tyr Ser Ala Ser Asn Arg Tyr Ser Gly Val Pro Ala Arg Phe Ser Gly
        50                  55                  60

Ser Gly Tyr Gly Thr Glu Phe Thr Phe Thr Ile Ser Ser Val Gln Ser
65                  70                  75                  80

Glu Asp Phe Ala Val Tyr Phe Cys Gln Gln Asp Tyr Ser Ser Phe Gly
                85                  90                  95

Gln Gly Thr Lys Leu Glu Ile Lys Arg Thr Val Ala Ala Pro Ser Val
            100                 105                 110

Phe Ile Phe Pro Pro Ser Asp Glu Gln Leu Lys Ser Gly Thr Ala Ser
        115                 120                 125

Val Val Cys Tyr Glu Leu Leu Ala Glu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys Gly Gly Gly Ser Gly Gly Gly Gly
    210                 215                 220

Ser Gly Gly Gly Gly Ser Lys Ile Val Met Thr Gln Thr Pro Ala Thr
225                 230                 235                 240

Leu Ser Val Ser Ala Gly Glu Arg Val Thr Ile Thr Cys Lys Ala Ser
                245                 250                 255

Gln Ser Val Ser Asn His Val Thr Trp Tyr Gln Gln Lys Pro Gly Gln
            260                 265                 270

Ala Pro Arg Leu Leu Ile Tyr Ser Ala Ser Asn Arg Tyr Ser Gly Val
        275                 280                 285

Pro Ala Arg Phe Ser Gly Ser Gly Tyr Gly Thr Glu Phe Thr Phe Thr
    290                 295                 300

Ile Ser Ser Val Gln Ser Glu Asp Phe Ala Val Tyr Phe Cys Gln Gln
305                 310                 315                 320

Asp Tyr Ser Ser Phe Gly Gln Gly Thr Lys Leu Glu Ile Lys Arg Thr
                325                 330                 335

Val Ala Ala Pro Ser Val Phe Ile Phe Pro Pro Ser Asp Glu Gln Leu
            340                 345                 350

Lys Ser Gly Thr Ala Ser Val Val Cys Leu Leu Asn Asn Phe Tyr Pro
        355                 360                 365

Arg Glu Ala Lys Val Gln Trp Lys Val Asp Asn Ala Leu Gln Ser Gly
    370                 375                 380

Asn Ser Gln Glu Ser Val Thr Glu Gln Asp Ser Lys Asp Ser Thr Tyr
385                 390                 395                 400

Ser Leu Ser Ser Thr Leu Thr Leu Ser Lys Ala Asp Tyr Glu Lys His
                405                 410                 415

Lys Val Tyr Ala Cys Glu Val Thr His Gln Gly Leu Ser Ser Pro Val
            420                 425                 430

Thr Lys Ser Phe Asn Arg Gly Glu Cys
        435                 440
```

<210> SEQ ID NO 166
<211> LENGTH: 685
<212> TYPE: PRT
<213> ORGANISM: Artificial Sequence
<220> FEATURE:
<223> OTHER INFORMATION: Synthesized

<400> SEQUENCE: 166

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Asn Phe
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Gln Ser Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Lys Thr Leu Pro Tyr
                85                  90                  95

Thr Phe Gly Gly Gly Thr Lys Val Glu Ile Lys Asp Ile Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys Gly Gly Gly Ser Gly Gly Gly
210                 215                 220

Gly Ser Gly Gly Gly Ser Gln Val Gln Leu Val Glu Ser Gly Gly
225                 230                 235                 240

Gly Val Val Gln Pro Gly Arg Ser Leu Arg Leu Ser Cys Ala Ala Ser
                245                 250                 255

Gly Phe Thr Phe Ser Asn Phe Gly Met His Trp Val Arg Gln Ala Pro
            260                 265                 270

Gly Lys Gly Leu Glu Trp Val Ala Tyr Ile Ser Ser Gly Gly Ser Ser
        275                 280                 285

Ile Asn Tyr Ala Asp Thr Val Lys Gly Arg Phe Thr Ile Ser Arg Asp
290                 295                 300

Asn Ser Lys Asn Thr Leu Tyr Leu Gln Met Asn Ser Leu Arg Ala Glu
305                 310                 315                 320

Asp Thr Ala Val Tyr Tyr Cys Thr Arg Gly Gly Thr Gly Thr Arg Ser
                325                 330                 335

Leu Tyr Tyr Phe Asp Tyr Trp Gly Gln Gly Thr Thr Val Thr Val Ser
            340                 345                 350

Ser Asp Ile Pro Ser Thr Lys Gly Pro Ser Val Phe Pro Leu Ala Pro
        355                 360                 365
```

Ser Ser Lys Ser Thr Ser Gly Gly Thr Ala Ala Leu Gly Cys Leu Val
    370                 375                 380

Lys Asp Tyr Phe Pro Glu Pro Val Thr Val Ser Trp Asn Ser Gly Ala
385                 390                 395                 400

Leu Thr Ser Gly Val His Thr Phe Pro Ala Val Leu Gln Ser Ser Gly
                405                 410                 415

Leu Tyr Ser Leu Ser Ser Val Val Thr Val Pro Ser Ser Ser Leu Gly
                420                 425                 430

Thr Gln Thr Tyr Ile Cys Asn Val Asn His Lys Pro Ser Asn Thr Lys
            435                 440                 445

Val Asp Lys Lys Val Glu Pro Lys Ser Cys Asp Lys Thr His Thr Cys
    450                 455                 460

Pro Pro Cys Pro Ala Pro Glu Leu Leu Gly Gly Pro Ser Val Phe Leu
465                 470                 475                 480

Phe Pro Pro Lys Pro Lys Asp Thr Leu Met Ile Ser Arg Thr Pro Glu
                485                 490                 495

Val Thr Cys Val Val Val Asp Val Ser His Glu Asp Pro Glu Val Lys
                500                 505                 510

Phe Asn Trp Tyr Val Asp Gly Val Glu Val His Asn Ala Lys Thr Lys
            515                 520                 525

Pro Arg Glu Glu Gln Tyr Asn Ser Thr Tyr Arg Val Val Ser Val Leu
    530                 535                 540

Thr Val Leu His Gln Asp Trp Leu Asn Gly Lys Glu Tyr Lys Cys Lys
545                 550                 555                 560

Val Ser Asn Lys Ala Leu Pro Ala Pro Ile Glu Lys Thr Ile Ser Lys
                565                 570                 575

Ala Lys Gly Gln Pro Arg Glu Pro Gln Val Tyr Thr Leu Pro Pro Ser
            580                 585                 590

Arg Asp Glu Leu Thr Lys Asn Gln Val Ser Leu Thr Cys Leu Val Lys
    595                 600                 605

Gly Phe Tyr Pro Ser Asp Ile Ala Val Glu Trp Glu Ser Asn Gly Gln
610                 615                 620

Pro Glu Asn Asn Tyr Lys Thr Thr Pro Pro Val Leu Asp Ser Asp Gly
625                 630                 635                 640

Ser Phe Phe Leu Tyr Ser Lys Leu Thr Val Asp Lys Ser Arg Trp Gln
                645                 650                 655

Gln Gly Asn Val Phe Ser Cys Ser Val Met His Glu Ala Leu His Asn
            660                 665                 670

His Tyr Thr Gln Lys Ser Leu Ser Leu Ser Pro Gly Lys
    675                 680                 685

<210> SEQ ID NO 167
<211> LENGTH: 239
<212> TYPE: PRT
<213> ORGANISM: Artificial Sequence
<220> FEATURE:
<223> OTHER INFORMATION: Synthesized

<400> SEQUENCE: 167

Glu Ile Val Met Thr Gln Thr Pro Leu Ile Leu Ser Val Thr Ile Gly
1               5                   10                  15

Gln Pro Ala Ser Ile Ser Cys Lys Ser Ser Gln Ser Val Leu Tyr Ser
            20                  25                  30

Asn Gly Lys Thr Tyr Leu Asn Trp Leu Leu Gln Arg Pro Gly Gln Ser
        35                  40                  45

```
Pro Lys Arg Leu Ile Tyr Leu Val Ser Lys Leu Asp Ser Gly Val Pro
 50                  55                  60

Asp Arg Phe Thr Gly Ser Gly Ser Gly Thr Asp Phe Thr Leu Lys Ile
 65                  70                  75                  80

Ser Arg Val Glu Ala Glu Asp Leu Gly Val Tyr Tyr Cys Val Gln Gly
                 85                  90                  95

Ser His Phe Pro Tyr Thr Phe Gly Gly Gly Thr Lys Leu Glu Ile Lys
                100                 105                 110

Arg Ala Asp Ala Gly Gly Gly Ser Gly Gly Gly Ser Gly Gly
            115                 120                 125

Gly Gly Ser Gly Pro Glu Leu Lys Lys Pro Gly Glu Thr Val Lys Ile
130                 135                 140

Tyr Cys Lys Ala Ser Gly Tyr Ser Phe Arg Asp Tyr Ser Val His Trp
145                 150                 155                 160

Val Lys Gln Ala Pro Gly Lys Gly Leu Lys Trp Met Gly Trp Ile Asn
                165                 170                 175

Thr Glu Thr Gly Glu Pro Thr Tyr Val Asp Glu Phe Lys Gly Arg Phe
                180                 185                 190

Ala Phe Phe Leu Glu Ala Ser Ala Asn Thr Val Tyr Leu Gln Ile Ser
                195                 200                 205

Asn Leu Lys Asn Glu Asp Thr Ala Thr Tyr Phe Cys Asp Tyr Arg Phe
210                 215                 220

Thr Tyr Trp Gly Gln Gly Thr Leu Val Thr Val Ser Ala Ala Lys
225                 230                 235

<210> SEQ ID NO 168
<211> LENGTH: 243
<212> TYPE: PRT
<213> ORGANISM: Artificial Sequence
<220> FEATURE:
<223> OTHER INFORMATION: Synthesized

<400> SEQUENCE: 168

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Ser Trp
                 20                  25                  30

Leu Ala Trp Tyr Gln Gln Lys Pro Glu Lys Ala Pro Lys Ser Leu Ile
             35                  40                  45

Tyr Ala Ala Ser Ser Leu Gln Ser Gly Val Pro Ser Arg Glu Ser Gly
 50                  55                  60

Ser Gly Ser Gly Thr Asp Phe Thr Leu Thr Ile Ser Ser Leu Gln Pro
 65                  70                  75                  80

Glu Asp Glu Ala Thr Tyr Tyr Cys Gln Gln Tyr Asn Gly Tyr Pro Tyr
                 85                  90                  95

Thr Glu Gly Gln Gly Thr Lys Leu Glu Ile Lys Gly Gly Gly Gly Ser
                100                 105                 110

Gly Gly Gly Gly Ser Gly Gly Gly Ser Glu Val Gln Leu Val Glu
            115                 120                 125

Ser Gly Gly Gly Leu Val Lys Pro Gly Gly Ser Leu Arg Leu Ser Cys
130                 135                 140

Ala Ala Ser Gly Phe Thr Phe Ser Ser Tyr Ser Met Asn Trp Val Arg
145                 150                 155                 160

Gln Ala Pro Gly Lys Gly Leu Glu Trp Val Ser Ser Ile Thr Ser Ser
                165                 170                 175
```

-continued

```
Ser Ser Tyr Ile Tyr Tyr Ala Asp Ser Val Lys Gly Arg Phe Thr Ile
            180                 185                 190

Ser Arg Asp Asn Ala Lys Asn Ser Leu Tyr Leu Gln Met Asn Ser Leu
        195                 200                 205

Arg Ala Glu Asp Thr Ala Val Tyr Tyr Cys Ala Arg Asp Arg Arg Tyr
    210                 215                 220

Phe Asp Trp Phe Pro Ile Asp Tyr Arg Gly Gln Gly Thr Leu Val Thr
225                 230                 235                 240

Val Ser Ser

<210> SEQ ID NO 169
<211> LENGTH: 285
<212> TYPE: PRT
<213> ORGANISM: Artificial Sequence
<220> FEATURE:
<223> OTHER INFORMATION: Synthesized

<400> SEQUENCE: 169

Met Arg Val Pro Ala Gln Leu Leu Gly Leu Leu Leu Leu Cys Phe Pro
1               5                   10                  15

Gly Ala Arg Cys Asp Ile Gln Met Thr Gln Ser Pro Ser Ser Leu Ser
            20                  25                  30

Ala Ser Val Gly Asp Arg Val Thr Ile Thr Cys Arg Ala Ser Gln Gly
        35                  40                  45

Ile Thr Asn Tyr Leu Ala Trp Phe Gln Gln Lys Pro Gly Lys Ala Pro
    50                  55                  60

Lys Ser Leu Ile Tyr Ala Ala Ser Ser Leu Gln Ser Gly Val Pro Ser
65                  70                  75                  80

Lys Phe Ser Gly Ser Gly Ser Gly Thr Asp Phe Ser Leu Thr Ile Ser
                85                  90                  95

Ser Leu Gln Pro Glu Asp Phe Ala Thr Tyr Tyr Cys Gln Gln Tyr Asn
            100                 105                 110

Ser Tyr Pro Ile Thr Phe Gly Gln Gly Thr Arg Leu Glu Ile Lys Gly
        115                 120                 125

Gly Gly Gly Ser Gly Gly Gly Gly Ser Gly Gly Gly Gly Ser Met Glu
130                 135                 140

Leu Gly Leu Arg Trp Val Leu Leu Val Ala Leu Leu Arg Gly Val Gln
145                 150                 155                 160

Cys Gln Val Gln Leu Val Glu Ser Gly Gly Gly Val Val Gln Pro Gly
                165                 170                 175

Arg Ser Leu Arg Leu Ser Cys Ala Ala Ser Gly Phe Thr Phe Ser Asn
            180                 185                 190

Tyr Val Met His Trp Val Arg Gln Ala Pro Gly Lys Gly Leu Glu Trp
        195                 200                 205

Val Ala Ile Ile Trp Tyr Asp Gly Ser Asn Lys Tyr Tyr Ala Asp Ser
    210                 215                 220

Val Lys Gly Arg Phe Thr Ile Ser Arg Asp Asn Ser Lys Asn Thr Leu
225                 230                 235                 240

Tyr Leu Gln Met Asn Ser Leu Arg Ala Glu Asp Thr Ala Val Tyr Tyr
                245                 250                 255

Cys Ala Gly Gly Tyr Asn Trp Asn Tyr Glu Tyr His Tyr Tyr Gly Met
            260                 265                 270

Asp Val Trp Gly Gln Gly Thr Thr Val Thr Val Ser Ser
        275                 280                 285
```

<210> SEQ ID NO 170
<211> LENGTH: 279
<212> TYPE: PRT
<213> ORGANISM: Artificial Sequence
<220> FEATURE:
<223> OTHER INFORMATION: Synthesized

<400> SEQUENCE: 170

```
Met Asp Phe Gln Val Gln Ile Phe Ser Phe Leu Leu Ile Ser Ala Ser
1               5                   10                  15

Val Ile Leu Ser Ser Gly Gln Ile Gly Leu Thr Gln Ser Pro Ala Ile
            20                  25                  30

Met Ser Ala Ser Pro Gly Glu Lys Val Thr Met Thr Cys Ser Ala Ser
        35                  40                  45

Ser Ser Ile Ser Tyr Met His Trp Tyr Gln Gln Lys Pro Gly Thr Ser
    50                  55                  60

Pro Lys Thr Trp Ile Tyr Asp Thr Ser Lys Leu Ala Ser Gly Val Pro
65                  70                  75                  80

Ala Arg Phe Ser Gly Ser Gly Ser Gly Thr Ser Tyr Ser Leu Thr Ile
                85                  90                  95

Ser Ser Met Glu Ala Glu Asp Ala Ala Thr Tyr Tyr Cys His Gln Arg
            100                 105                 110

Ser Ser His His Thr Phe Gly Gly Gly Thr Lys Leu Glu Ile Lys Gly
        115                 120                 125

Gly Gly Gly Ser Gly Gly Gly Gly Ser Gly Gly Gly Ser Met Gly
    130                 135                 140

Trp Leu Trp Asn Leu Leu Phe Leu Met Ala Ala Ala Gln Ser Ala Gln
145                 150                 155                 160

Ala Gln Ile Gln Leu Val Gln Ser Gly Pro Glu Leu Lys Lys Pro Gly
                165                 170                 175

Glu Thr Val Lys Ile Ser Cys Lys Ala Ser Gly Tyr Thr Phe Thr Thr
            180                 185                 190

Tyr Gly Met Ser Trp Val Lys Gln Ala Pro Gly Arg Gly Leu Lys Trp
        195                 200                 205

Met Gly Trp Ile Asn Pro Tyr Ser Gly Val Pro Thr Tyr Ala Val Asp
    210                 215                 220

Phe Lys Gly Arg Phe Ala Phe Ser Leu Glu Thr Ser Ala Ser Thr Ala
225                 230                 235                 240

Tyr Leu Gln Ile Asn Asn Leu Lys Asn Glu Asp Thr Ala Thr Tyr Phe
                245                 250                 255

Cys Ala Arg Gly Gly Arg Arg Gly Asp Phe Gly Tyr Trp Gly Gln Gly
            260                 265                 270

Thr Thr Leu Thr Val Ser Ser
        275
```

<210> SEQ ID NO 171
<211> LENGTH: 244
<212> TYPE: PRT
<213> ORGANISM: Artificial Sequence
<220> FEATURE:
<223> OTHER INFORMATION: Synthesized

<400> SEQUENCE: 171

```
Asp Ile Val Met Thr Gln Ser Pro Ser Ser Leu Thr Val Thr Ala Gly
1               5                   10                  15

Glu Lys Val Thr Met Ile Cys Lys Ser Ser Gln Ser Leu Leu Asn Ser
            20                  25                  30
```

Gly Asp Gln Lys Asn Tyr Leu Thr Trp Tyr Gln Gln Lys Pro Gly Gln
            35                  40                  45

Pro Pro Lys Leu Leu Ile Phe Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Leu Thr Phe Gly Ala Gly Thr Lys Leu Glu Leu
            100                 105                 110

Lys Gly Gly Gly Gly Ser Gly Gly Gly Gly Ser Gly Gly Gly Gly Ser
            115                 120                 125

Gln Val Gln Leu Gln Gln Ser Asp Ala Glu Leu Val Lys Pro Gly Ser
    130                 135                 140

Ser Val Lys Ile Ser Cys Lys Ala Ser Gly Tyr Thr Phe Thr Asp His
145                 150                 155                 160

Ala Ile His Trp Val Lys Gln Lys Pro Glu Gln Gly Leu Glu Trp Ile
                165                 170                 175

Gly His Phe Ser Pro Gly Asn Thr Asp Ile Lys Tyr Asn Asp Lys Phe
            180                 185                 190

Lys Gly Lys Ala Thr Leu Thr Val Asp Arg Ser Ser Ser Thr Ala Tyr
            195                 200                 205

Met Gln Leu Asn Ser Leu Thr Ser Glu Asp Ser Ala Val Tyr Phe Cys
    210                 215                 220

Lys Thr Ser Thr Phe Phe Phe Asp Tyr Trp Gly Gln Gly Thr Thr Leu
225                 230                 235                 240

Thr Val Ser Ser

<210> SEQ ID NO 172
<211> LENGTH: 254
<212> TYPE: PRT
<213> ORGANISM: Artificial Sequence
<220> FEATURE:
<223> OTHER INFORMATION: Synthesized

<400> SEQUENCE: 172

Gln Val Gln Leu Glu Gln Ser Gly Leu Gly Leu Val Lys Pro Ser Gln
1               5                   10                  15

Thr Leu Ser Leu Thr Cys Ala Ile Ser Gly Asp Thr Val Ser Ser Asp
            20                  25                  30

Ser Ala Ala Trp Asn Trp Ile Arg Gln Ser Pro Ser Arg Gly Leu Glu
            35                  40                  45

Trp Leu Gly Arg Thr Tyr Tyr Arg Ser Lys Trp Phe Asn Asp Tyr Ala
    50                  55                  60

Val Ser Val Lys Gly Arg Ile Thr Ile Asn Ser Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Ser Asn Ser Tyr Tyr Tyr Ala Met Asp Val
            100                 105                 110

Trp Gly Gln Gly Thr Leu Val Thr Val Ser Ser Gly Gly Gly Gly Ser
            115                 120                 125

Gly Gly Gly Gly Ser Gly Gly Gly Gly Ser Gln Ala Val Leu Thr Gln
    130                 135                 140

```
Pro Ser Ser Leu Ser Ala Ser Pro Gly Ala Ser Ala Ser Leu Thr Cys
145                 150                 155                 160

Thr Leu Arg Ser Gly Ile Asn Val Gly Ile Tyr Arg Ile Tyr Trp Tyr
            165                 170                 175

Gln Gln Arg Pro Gly Ser Pro Gln Ile Leu Leu Thr Tyr Lys Ser
            180                 185                 190

Asp Ser Asp Lys Tyr Gln Gly Ser Gly Val Pro Ser Arg Phe Ser Gly
            195                 200                 205

Ser Lys Asp Ala Ser Ala Asn Ala Gly Ile Leu Leu Ile Ser Gly Leu
    210                 215                 220

Gln Ser Glu Asp Glu Ala Asp Tyr Tyr Cys Met Ile Trp His Ser Gly
225                 230                 235                 240

Gly Trp Val Phe Gly Gly Gly Thr Lys Val Thr Val Leu Gly
            245                 250
```

<210> SEQ ID NO 173
<211> LENGTH: 264
<212> TYPE: PRT
<213> ORGANISM: Artificial Sequence
<220> FEATURE:
<223> OTHER INFORMATION: Synthesized

<400> SEQUENCE: 173

```
Met Ala Leu Pro Val Thr Ala Leu Leu Leu Pro Leu Ala Leu Leu Leu
1               5                   10                  15

His Ala Ala Arg Pro Gln Ser Val Leu Thr Gln Pro Ala Ser Val Ser
            20                  25                  30

Gly Ser Pro Gly Gln Ser Val Thr Ile Ser Cys Thr Gly Thr Ser Ser
            35                  40                  45

Asp Val Gly Gly Tyr Asn Tyr Val Ser Trp Tyr Gln Gln His Pro Gly
    50                  55                  60

Lys Pro Pro Lys Leu Met Ile Tyr Glu Val Ser Lys Arg Pro Ser Gly
65                  70                  75                  80

Val Pro Asp Arg Phe Ser Gly Ser Lys Ser Gly Asn Thr Ala Ser Leu
                85                  90                  95

Thr Ile Ser Gly Leu Gln Ala Glu Asp Glu Ala Asp Tyr Tyr Cys Ser
            100                 105                 110

Ser His Thr Ser Ser Asn Thr Leu Ile Phe Gly Gly Gly Thr Lys Val
        115                 120                 125

Thr Val Leu Gly Gly Gly Gly Ser Gly Gly Gly Gly Ser Gly Gly Gly
130                 135                 140

Gly Ser Glu Val Gln Leu Val Gln Ser Gly Ala Glu Val Lys Lys Pro
145                 150                 155                 160

Gly Glu Ser Leu Lys Ile Ser Cys Lys Gly Ser Gly Tyr Thr Phe Thr
            165                 170                 175

Asn Tyr Trp Ile Gly Trp Val Arg Gln Met Pro Gly Lys Gly Leu Glu
            180                 185                 190

Trp Met Gly Arg Ile Tyr Pro Ser Asp Ser Tyr Thr Asn Tyr Ser Pro
            195                 200                 205

Ser Phe Gln Gly Gln Val Thr Ile Ser Ala Asp Lys Ser Ile Ser Thr
    210                 215                 220

Ala Tyr Leu Gln Trp Ser Ser Leu Lys Ala Ser Asp Thr Ala Met Tyr
225                 230                 235                 240

Tyr Cys Ala Arg Asp Leu Glu Pro Thr His His Tyr Ser Trp Gly Gln
            245                 250                 255
```

Gly Thr Leu Val Thr Val Ser Ser
        260

<210> SEQ ID NO 174
<211> LENGTH: 267
<212> TYPE: PRT
<213> ORGANISM: Artificial Sequence
<220> FEATURE:
<223> OTHER INFORMATION: Synthesized

<400> SEQUENCE: 174

Met Ala Leu Pro Val Thr Ala Leu Leu Leu Pro Leu Ala Leu Leu Leu
1               5                   10                  15

His Ala Ala Arg Pro Leu Pro Val Leu Thr Gln Pro Ser Ala Ser
            20                  25                  30

Gly Thr Pro Gly Gln Arg Val Thr Ile Ser Cys Ser Gly Ser Ser Ser
        35                  40                  45

Asn Ile Gly Ser Asn Ala Val Asp Trp Tyr Gln Gln Leu Pro Gly Thr
    50                  55                  60

Ala Pro Lys Leu Leu Ile Tyr Thr Asn Asn Arg Arg Pro Ser Gly Val
65                  70                  75                  80

Pro Asp Arg Phe Ser Gly Ser Lys Ser Gly Thr Ser Gly Ser Leu Ala
                85                  90                  95

Ile Ser Gly Leu Gln Phe Glu Asp Glu Ala Asp Tyr Tyr Cys Ala Ala
            100                 105                 110

Trp Asp Asp Ser Leu Ser Gly Val Ile Phe Gly Gly Gly Thr Lys Val
        115                 120                 125

Thr Val Leu Gly Gly Gly Gly Ser Gly Gly Gly Gly Ser Gly Gly Gly
    130                 135                 140

Gly Ser Gln Val Gln Leu Val Gln Ser Gly Ala Glu Val Lys Lys Pro
145                 150                 155                 160

Gly Ser Ser Val Lys Val Ser Cys Lys Ala Ser Glu Asp Thr Phe Ser
                165                 170                 175

Ser Tyr Val Ile Ser Trp Val Arg Gln Ala Pro Gly Gln Gly Leu Glu
            180                 185                 190

Trp Met Gly Ala Phe Ile Pro Leu Leu Gly Arg Val His Tyr Ala Gln
        195                 200                 205

Glu Phe Gln Gly Arg Leu Thr Ile Thr Ala Asp Glu Ser Thr Gly Thr
    210                 215                 220

Ala Tyr Met Glu Leu Lys Gly Leu Arg Ser Asp Asp Thr Ala Met Tyr
225                 230                 235                 240

Tyr Cys Ala Arg Asp Gln Gly Phe Ala Gly Asp Ala Phe Asp Ile
                245                 250                 255

Trp Gly Gln Gly Thr Met Val Thr Val Ser Ser
        260                 265

<210> SEQ ID NO 175
<211> LENGTH: 266
<212> TYPE: PRT
<213> ORGANISM: Artificial Sequence
<220> FEATURE:
<223> OTHER INFORMATION: Synthesized

<400> SEQUENCE: 175

Met Ala Leu Pro Val Thr Ala Leu Leu Leu Pro Leu Ala Leu Leu Leu
1               5                   10                  15

His Ala Ala Arg Pro Gln Pro Val Leu Thr Gln Asp Pro Val Val Ser
            20                  25                  30

Val Ala Leu Gly Gln Thr Val Arg Ile Thr Cys Gln Gly Asp Ser Leu
            35                  40                  45

Arg Ser Tyr Tyr Ala Thr Trp Tyr Gln Gln Lys Pro Gly Leu Ala Pro
    50                  55                  60

Val Arg Val Ile Phe Gly Lys Asn Ser Arg Pro Ser Gly Ile Pro Asp
65                  70                  75                  80

Arg Phe Ser Gly Ser Ser Ser Gly Asn Thr Ala Ser Leu Thr Ile Thr
                85                  90                  95

Gly Ala Gln Ala Glu Asp Glu Ala Asp Tyr Tyr Cys Asn Ser Trp Asp
            100                 105                 110

Asn Ser Ala Asn His Pro Val Phe Gly Gly Gly Thr Lys Leu Thr Val
        115                 120                 125

Leu Gly Gly Gly Ser Gly Gly Gly Ser Gly Gly Gly Gly Ser
130                 135                 140

Glu Val Gln Leu Val Gln Ser Gly Ala Glu Val Arg Lys Pro Gly Ser
145                 150                 155                 160

Ser Val Lys Val Ser Cys Lys Ala Ser Gly Asp Asn Phe Asn Asn Tyr
                165                 170                 175

Gly Ile Thr Trp Val Arg Gln Ala Pro Gly Gln Gly Leu Glu Trp Met
            180                 185                 190

Gly Arg Leu Ile Thr Val Leu Gly Leu Asp Asn Tyr Ala Gln Lys Phe
        195                 200                 205

Gln Gly Arg Leu Thr Ile Thr Ala Asp Glu Ser Thr Gly Thr Ala Tyr
    210                 215                 220

Met Glu Leu Thr Gly Leu Glu Pro Glu Asp Thr Ala Val Tyr Tyr Cys
225                 230                 235                 240

Ala Arg Asp Ile Met Ser Pro Glu Ala Ile Asp Ala Phe Asp Val Trp
                245                 250                 255

Gly Gln Gly Thr Leu Val Thr Val Ser Ser
            260                 265

<210> SEQ ID NO 176
<211> LENGTH: 265
<212> TYPE: PRT
<213> ORGANISM: Artificial Sequence
<220> FEATURE:
<223> OTHER INFORMATION: Synthesized

<400> SEQUENCE: 176

Met Ala Leu Pro Val Thr Ala Leu Leu Leu Pro Leu Ala Leu Leu Leu
1               5                   10                  15

His Ala Ala Arg Pro Asp Ile Gln Met Thr Gln Ser Pro Ser Ser Leu
            20                  25                  30

Ser Ala Ser Val Gly Asp Arg Val Thr Ile Thr Cys Arg Ala Ser Gln
        35                  40                  45

Asp Val Ser Asn Tyr Leu Asn Trp Tyr Gln Gln Lys Pro Gly Lys Ala
    50                  55                  60

Pro Lys Leu Leu Ile Tyr Gly Ala Ser Asn Arg Gln Thr Gly Val Pro
65                  70                  75                  80

Ser Arg Phe Ser Gly Ser Gly Ser Gly Thr Asp Phe Thr Leu Thr Ile
                85                  90                  95

Ser Ser Leu Gln Pro Glu Asp Phe Ala Thr Tyr Tyr Cys Gln Gln Glu
            100                 105                 110

Asp Arg Phe Pro Thr Thr Phe Gly Gln Gly Thr Lys Val Glu Ile Lys
        115                 120                 125

```
Gly Gly Gly Gly Ser Gly Gly Gly Ser Gly Gly Gly Ser Glu
        130                 135                 140
Val Gln Leu Val Gln Ser Gly Ala Glu Val Arg Lys Pro Gly Ser Ser
145                 150                 155                 160
Val Lys Val Ser Cys Lys Ala Ser Gly Asp Asn Phe Asn Asn Tyr Gly
                165                 170                 175
Ile Thr Trp Val Arg Gln Ala Pro Gly Gln Gly Leu Glu Trp Met Gly
            180                 185                 190
Arg Leu Ile Thr Val Leu Gly Leu Asp Asn Tyr Ala Gln Lys Phe Gln
        195                 200                 205
Gly Arg Leu Thr Ile Thr Ala Asp Glu Ser Thr Gly Thr Ala Tyr Met
    210                 215                 220
Glu Leu Thr Gly Leu Glu Pro Glu Asp Thr Ala Val Tyr Tyr Cys Ala
225                 230                 235                 240
Arg Asp Ile Met Ser Pro Glu Ala Ile Asp Ala Phe Asp Val Trp Gly
                245                 250                 255
Gln Gly Thr Leu Val Thr Val Ser Ser
            260                 265

<210> SEQ ID NO 177
<211> LENGTH: 270
<212> TYPE: PRT
<213> ORGANISM: Artificial Sequence
<220> FEATURE:
<223> OTHER INFORMATION: Synthesized

<400> SEQUENCE: 177

Met Ala Leu Pro Val Thr Ala Leu Leu Leu Pro Leu Ala Leu Leu Leu
1               5                   10                  15
His Ala Ala Arg Pro Glu Ile Val Leu Thr Gln Ser Ala Ser Ser Leu
            20                  25                  30
Ser Ala Ser Val Gly Asp Arg Val Thr Ile Thr Cys Arg Thr Ser Gln
        35                  40                  45
Asn Ile Tyr Arg Tyr Leu Asn Trp Tyr Gln Gln Lys Pro Gly Lys Ala
    50                  55                  60
Pro Lys Leu Leu Ile Phe Gly Ala Ser Thr Leu Gln Thr Gly Val Pro
65                  70                  75                  80
Ser Arg Phe Ser Gly Ser Gly Ser Gly Thr Asp Phe Thr Leu Thr Ile
                85                  90                  95
Thr Gly Leu Gln Pro Glu Asp Leu Ala Thr Tyr Tyr Cys Gln His Ser
            100                 105                 110
Phe Lys Leu Pro Phe Thr Phe Gly Gln Gly Thr Arg Leu Glu Ile Lys
        115                 120                 125
Gly Gly Gly Gly Ser Gly Gly Gly Ser Gly Gly Gly Ser Gln
    130                 135                 140
Met Leu Val Gln Ser Gly Ala Glu Val Lys Arg Pro Gly Ser Ser Val
145                 150                 155                 160
Thr Val Ser Cys Glu Thr Ser Gly Asp Thr Phe Ser Arg Tyr Ala Ile
                165                 170                 175
Ser Trp Leu Arg Gln Ala Pro Gly Gln Gly Leu Glu Trp Leu Gly Trp
            180                 185                 190
Ile Ser Gly Asn Ser Gly Arg Ala Asp Tyr Ala Gln Asn Phe Gln Gly
        195                 200                 205
Arg Val Thr Met Thr Thr Asp Arg Ser Thr Ser Thr Ala Tyr Leu Asn
    210                 215                 220
```

```
Leu Arg Ser Leu Arg Ser Asp Asp Thr Ala Val Tyr Tyr Cys Ala Arg
225                 230                 235                 240

Asp Ala Pro Met Leu Phe Gly Val Arg Gly Gly Tyr Tyr Phe Gly
            245                 250                 255

Met Asp Val Trp Gly Gln Gly Thr Thr Val Thr Val Ser Ser
            260                 265                 270

<210> SEQ ID NO 178
<211> LENGTH: 258
<212> TYPE: PRT
<213> ORGANISM: Artificial Sequence
<220> FEATURE:
<223> OTHER INFORMATION: Synthesized

<400> SEQUENCE: 178

Met Ala Leu Pro Val Thr Ala Leu Leu Leu Pro Leu Ala Leu Leu Leu
1               5                   10                  15

His Ala Ala Arg Pro Gln Pro Val Leu Thr Gln Asp Pro Ala Val Ser
                20                  25                  30

Val Ala Leu Gly Gln Thr Val Arg Ile Thr Cys Gln Gly Asp Ser Leu
            35                  40                  45

Arg Lys Tyr Tyr Ala Ser Trp Tyr Gln Gln Lys Pro Gly Gln Ala Pro
50                  55                  60

Arg Leu Val Met Tyr Asp Glu Asn Asp Arg Pro Ser Gly Ile Pro Asp
65                  70                  75                  80

Arg Phe Ser Gly Ser Ser Ser Gly Asn Thr Ala Ser Leu Thr Ile Thr
                85                  90                  95

Gly Ala Gln Ala Asp Asp Glu Ala Asp Tyr Tyr Cys Asn Ser Arg Asp
            100                 105                 110

Ser Ser Gly His His Val Val Phe Gly Gly Gly Thr Lys Val Thr Val
            115                 120                 125

Leu Gly Gly Gly Ser Gly Gly Gly Ser Gly Gly Gly Gly Ser
130                 135                 140

Gln Met Gln Leu Val Gln Ser Gly Ala Glu Val Arg Arg Pro Gly Ser
145                 150                 155                 160

Ser Val Lys Val Ser Cys Lys Thr Ser Gly Thr Leu Asn Asn Tyr
                165                 170                 175

Asp Ile Asn Trp Val Arg Gln Ala Pro Gly Gln Gly Leu Glu Trp Met
            180                 185                 190

Gly Trp Met Asn Pro Thr Ser Gly Gln Ala Asp Phe Ala Gln Lys Phe
            195                 200                 205

Gln Gly Arg Val Ser Met Thr Arg Asp Thr Ser Ile Asn Thr Ala Phe
    210                 215                 220

Met Glu Leu Asn Thr Leu Arg Ser Glu Asp Thr Ala Val Tyr Tyr Cys
225                 230                 235                 240

Val Arg Arg Gly Gly Lys Tyr Trp Gly Gln Gly Thr Leu Val Thr Val
                245                 250                 255

Ser Ser

<210> SEQ ID NO 179
<211> LENGTH: 267
<212> TYPE: PRT
<213> ORGANISM: Artificial Sequence
<220> FEATURE:
<223> OTHER INFORMATION: Synthesized

<400> SEQUENCE: 179
```

Met Ala Leu Pro Val Thr Ala Leu Leu Leu Pro Leu Ala Leu Leu Leu
1               5                   10                  15

His Ala Ala Arg Pro Ser Tyr Glu Leu Thr Gln Pro Pro Ser Val Ser
                20                  25                  30

Val Ala Pro Gly Gln Thr Ala Arg Ile Thr Cys Gly Gly Asp Ala Leu
            35                  40                  45

Pro Asn Asn Ser Val Arg Trp Tyr Gln Gln Lys Pro Gly Gln Ala Pro
    50                  55                  60

Val Leu Val Ile Tyr Gly Asn Ser Glu Arg Pro Ser Gly Ile Pro Glu
65                  70                  75                  80

Arg Phe Ser Gly Ser Asn Ser Gly Asn Thr Ala Thr Leu Thr Ile Ser
                85                  90                  95

Gly Thr Gln Ala Glu Asp Glu Ala Asp Tyr Tyr Cys Gln Val Ser Asp
            100                 105                 110

Lys Ser Thr Lys Tyr Ser Val Phe Gly Gly Gly Thr Lys Leu Thr Val
            115                 120                 125

Leu Gly Gly Gly Gly Ser Gly Gly Gly Ser Gly Gly Gly Gly Ser
    130                 135                 140

Glu Val Gln Leu Val Glu Ser Gly Gly Leu Val Gln Pro Gly Gly
145                 150                 155                 160

Ser Leu Arg Leu Ser Cys Ala Ala Ser Gly Phe Thr Phe Ser Asn Tyr
                165                 170                 175

Trp Met Ser Trp Val Arg Gln Ala Pro Gly Lys Gly Leu Glu Trp Val
                180                 185                 190

Ala Gly Ile Ser Ala Ser Gly Gly Asn Lys Tyr Tyr Ala Asp Ser Val
            195                 200                 205

Lys Gly Arg Phe Thr Ile Ser Arg Asp Asn Ser Lys Asn Thr Leu Tyr
    210                 215                 220

Leu Gln Met Asn Ser Leu Arg Ala Glu Asp Thr Ala Val Tyr Tyr Cys
225                 230                 235                 240

Ala Lys Gly Pro Ile Gln Leu Lys Arg His Lys Tyr Val Leu Asp Tyr
                245                 250                 255

Trp Gly Gln Gly Thr Leu Val Thr Val Ser Ser
                260                 265

<210> SEQ ID NO 180
<211> LENGTH: 108
<212> TYPE: PRT
<213> ORGANISM: Artificial Sequence
<220> FEATURE:
<223> OTHER INFORMATION: Synthesized

<400> SEQUENCE: 180

Gln Pro Val Leu Thr Gln Asp Pro Val Val Ser Val Ala Leu Gly Gln
1               5                   10                  15

Thr Val Arg Ile Thr Cys Gln Gly Asp Ser Leu Arg Ser Tyr Tyr Ala
                20                  25                  30

Thr Trp Tyr Gln Gln Lys Pro Gly Leu Ala Pro Val Arg Val Ile Phe
                35                  40                  45

Gly Lys Asn Ser Arg Pro Ser Gly Ile Pro Asp Arg Phe Ser Gly Ser
            50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Trp Asp Asn Ser Ala Asn His
                85                  90                  95

```
Pro Val Phe Gly Gly Gly Thr Lys Leu Thr Val Leu
            100                 105

<210> SEQ ID NO 181
<211> LENGTH: 122
<212> TYPE: PRT
<213> ORGANISM: Artificial Sequence
<220> FEATURE:
<223> OTHER INFORMATION: Synthesized

<400> SEQUENCE: 181

Glu Val Gln Leu Val Gln Ser Gly Ala Glu Val Arg Lys Pro Gly Ser
1               5                   10                  15

Ser Val Lys Val Ser Cys Lys Ala Ser Gly Asp Asn Phe Asn Asn Tyr
            20                  25                  30

Gly Ile Thr Trp Val Arg Gln Ala Pro Gly Gln Gly Leu Glu Trp Met
        35                  40                  45

Gly Arg Leu Ile Thr Val Leu Gly Leu Asp Asn Tyr Ala Gln Lys Phe
    50                  55                  60

Gln Gly Arg Leu Thr Ile Thr Ala Asp Glu Ser Thr Gly Thr Ala Tyr
65                  70                  75                  80

Met Glu Leu Thr Gly Leu Glu Pro Glu Asp Thr Ala Val Tyr Tyr Cys
                85                  90                  95

Ala Arg Asp Ile Met Ser Pro Glu Ala Ile Asp Ala Phe Asp Val Trp
            100                 105                 110

Gly Gln Gly Thr Leu Val Thr Val Ser Ser
        115                 120

<210> SEQ ID NO 182
<211> LENGTH: 127
<212> TYPE: PRT
<213> ORGANISM: Artificial Sequence
<220> FEATURE:
<223> OTHER INFORMATION: Synthesized

<400> SEQUENCE: 182

Gln Met Leu Val Gln Ser Gly Ala Glu Val Lys Arg Pro Gly Ser Ser
1               5                   10                  15

Val Thr Val Ser Cys Glu Thr Ser Gly Asp Thr Phe Ser Arg Tyr Ala
            20                  25                  30

Ile Ser Trp Leu Arg Gln Ala Pro Gly Gln Gly Leu Glu Trp Leu Gly
        35                  40                  45

Trp Ile Ser Gly Asn Ser Gly Arg Ala Asp Tyr Ala Gln Asn Phe Gln
    50                  55                  60

Gly Arg Val Thr Met Thr Thr Asp Arg Ser Thr Ser Thr Ala Tyr Leu
65                  70                  75                  80

Asn Leu Arg Ser Leu Arg Ser Asp Asp Thr Ala Val Tyr Tyr Cys Ala
                85                  90                  95

Arg Asp Ala Pro Met Leu Phe Gly Val Arg Gly Gly Tyr Tyr Phe
            100                 105                 110

Gly Met Asp Val Trp Gly Gln Gly Thr Thr Val Thr Val Ser Ser
        115                 120                 125

<210> SEQ ID NO 183
<211> LENGTH: 107
<212> TYPE: PRT
<213> ORGANISM: Artificial Sequence
<220> FEATURE:
<223> OTHER INFORMATION: Synthesized
```

<400> SEQUENCE: 183

Glu Ile Val Leu Thr Gln Ser Ala Ser Ser Leu Ser Ala Ser Val Gly
1               5                   10                  15

Asp Arg Val Thr Ile Thr Cys Arg Thr Ser Gln Asn Ile Tyr Arg Tyr
            20                  25                  30

Leu Asn Trp Tyr Gln Gln Lys Pro Gly Lys Ala Pro Lys Leu Leu Ile
        35                  40                  45

Phe Gly Ala Ser Thr Leu Gln Thr Gly Val Pro Ser Arg Phe Ser Gly
50                  55                  60

Ser Gly Ser Gly Thr Asp Phe Thr Leu Thr Ile Thr Gly Leu Gln Pro
65                  70                  75                  80

Glu Asp Leu Ala Thr Tyr Tyr Cys Gln His Ser Phe Lys Leu Pro Phe
                85                  90                  95

Thr Phe Gly Gln Gly Thr Arg Leu Glu Ile Lys
            100                 105

<210> SEQ ID NO 184
<211> LENGTH: 114
<212> TYPE: PRT
<213> ORGANISM: Artificial Sequence
<220> FEATURE:
<223> OTHER INFORMATION: Synthesized

<400> SEQUENCE: 184

Gln Met Gln Leu Val Gln Ser Gly Ala Glu Val Arg Arg Pro Gly Ser
1               5                   10                  15

Ser Val Lys Val Ser Cys Lys Thr Ser Gly Gly Thr Leu Asn Asn Tyr
            20                  25                  30

Asp Ile Asn Trp Val Arg Gln Ala Pro Gly Gln Gly Leu Glu Trp Met
        35                  40                  45

Gly Trp Met Asn Pro Thr Ser Gly Gln Ala Asp Phe Ala Gln Lys Phe
50                  55                  60

Gln Gly Arg Val Ser Met Thr Arg Asp Thr Ser Ile Asn Thr Ala Phe
65                  70                  75                  80

Met Glu Leu Asn Thr Leu Arg Ser Glu Asp Thr Ala Val Tyr Tyr Cys
                85                  90                  95

Val Arg Arg Gly Gly Lys Tyr Trp Gly Gln Gly Thr Leu Val Thr Val
            100                 105                 110

Ser Ser

<210> SEQ ID NO 185
<211> LENGTH: 108
<212> TYPE: PRT
<213> ORGANISM: Artificial Sequence
<220> FEATURE:
<223> OTHER INFORMATION: Synthesized

<400> SEQUENCE: 185

Gln Pro Val Leu Thr Gln Asp Pro Ala Val Ser Val Ala Leu Gly Gln
1               5                   10                  15

Thr Val Arg Ile Thr Cys Gln Gly Asp Ser Leu Arg Lys Tyr Tyr Ala
            20                  25                  30

Ser Trp Tyr Gln Gln Lys Pro Gly Gln Ala Pro Arg Leu Val Met Tyr
        35                  40                  45

Asp Glu Asn Asp Arg Pro Ser Gly Ile Pro Asp Arg Phe Ser Gly Ser
50                  55                  60

Ser Ser Gly Asn Thr Ala Ser Leu Thr Ile Thr Gly Ala Gln Ala Asp
65                  70                  75                  80

Asp Glu Ala Asp Tyr Tyr Cys Asn Ser Arg Asp Ser Ser Gly His His
                85                  90                  95

Val Val Phe Gly Gly Gly Thr Lys Val Thr Val Leu
            100                 105

<210> SEQ ID NO 186
<211> LENGTH: 123
<212> TYPE: PRT
<213> ORGANISM: Artificial Sequence
<220> FEATURE:
<223> OTHER INFORMATION: Synthesized

<400> SEQUENCE: 186

Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Asn Tyr
                20                  25                  30

Trp Met Ser Trp Val Arg Gln Ala Pro Gly Lys Gly Leu Glu Trp Val
            35                  40                  45

Ala Gly Ile Ser Ala Ser Gly Gly Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Pro Ile Gln Leu Lys Arg His Lys Tyr Val Leu Asp Tyr
            100                 105                 110

Trp Gly Gln Gly Thr Leu Val Thr Val Ser Ser
        115                 120

<210> SEQ ID NO 187
<211> LENGTH: 108
<212> TYPE: PRT
<213> ORGANISM: Artificial Sequence
<220> FEATURE:
<223> OTHER INFORMATION: Synthesized

<400> SEQUENCE: 187

Ser Tyr Glu Leu Thr Gln Pro Pro Ser Val Ser Val Ala Pro Gly Gln
1               5                   10                  15

Thr Ala Arg Ile Thr Cys Gly Gly Asp Ala Leu Pro Asn Asn Ser Val
                20                  25                  30

Arg Trp Tyr Gln Gln Lys Pro Gly Gln Ala Pro Val Leu Val Ile Tyr
            35                  40                  45

Gly Asn Ser Glu Arg Pro Ser Gly Ile Pro Glu Arg Phe Ser Gly Ser
        50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Val Ser Asp Lys Ser Thr Lys Tyr
                85                  90                  95

Ser Val Phe Gly Gly Gly Thr Lys Leu Thr Val Leu
            100                 105

<210> SEQ ID NO 188
<211> LENGTH: 20
<212> TYPE: PRT
<213> ORGANISM: Artificial Sequence

```
<220> FEATURE:
<223> OTHER INFORMATION: Synthesized

<400> SEQUENCE: 188

Gly Gly Gly Gly Ser Gly Gly Gly Ser Gly Gly Gly Gly Ser Gly
1               5                   10                  15

Gly Gly Gly Ser
            20

<210> SEQ ID NO 189
<211> LENGTH: 19
<212> TYPE: DNA
<213> ORGANISM: Artificial Sequence
<220> FEATURE:
<223> OTHER INFORMATION: Syntheisized

<400> SEQUENCE: 189
tgcatttgaa ctccttgcc                                             19

<210> SEQ ID NO 190
<211> LENGTH: 20
<212> TYPE: DNA
<213> ORGANISM: Artificial Sequence
<220> FEATURE:
<223> OTHER INFORMATION: Syntheisized

<400> SEQUENCE: 190
ccatcaatct tccacttgac                                            20
```